(12) United States Patent
Grosveld et al.

(10) Patent No.: US 9,980,470 B2
(45) Date of Patent: May 29, 2018

(54) ANTIBODY PRODUCTION

(71) Applicants: ERASMUS UNIVERSITY MEDICAL CENTER, Rotterdam (NL); Roger Kingdon Craig, Cheshire (GB)

(72) Inventors: Franklin Gerardus Grosveld, Rotterdam (NL); Richard Wilhelm Janssens, Rotterdam (NL); Marinus Johannes Van Haperen, Prinsenbeek (NL); Roger Kingdon Craig, Cheshire (GB); Ernie De Boer, Rotterdam (NL)

(73) Assignee: Erasmus University Medical Center, Rotterdam (NL)

( * ) Notice: Subject to any disclaimer, the term of this patent is extended or adjusted under 35 U.S.C. 154(b) by 648 days.

(21) Appl. No.: 14/211,130

(22) Filed: Mar. 14, 2014

(65) Prior Publication Data

US 2014/0356907 A1  Dec. 4, 2014

Related U.S. Application Data

(60) Provisional application No. 61/851,974, filed on Mar. 14, 2013.

(51) Int. Cl.
| | | |
|---|---|---|
| *A01K 67/00* | (2006.01) | |
| *A01K 67/027* | (2006.01) | |
| *C12N 15/85* | (2006.01) | |
| *C12P 21/02* | (2006.01) | |

(52) U.S. Cl.
CPC .......... *A01K 67/0278* (2013.01); *C12N 15/85* (2013.01); *C12N 15/8509* (2013.01); *C12P 21/02* (2013.01); *A01K 2207/15* (2013.01); *A01K 2217/052* (2013.01); *A01K 2217/15* (2013.01); *A01K 2227/10* (2013.01); *A01K 2227/105* (2013.01); *A01K 2267/01* (2013.01); *C07K 2317/24* (2013.01); *C12N 2015/8518* (2013.01); *C12N 2830/46* (2013.01)

(58) Field of Classification Search
CPC .................. A01K 67/0278; C12N 15/8509
See application file for complete search history.

(56) References Cited

U.S. PATENT DOCUMENTS

| | | | |
|---|---|---|---|
| 5,591,669 A | 1/1997 | Krimpenfort | |
| 5,814,318 A | 9/1998 | Lonberg | |
| 5,877,397 A | 3/1999 | Lonberg | |
| 6,162,963 A | 12/2000 | Kucherlapati | |
| 6,596,541 B2 | 7/2003 | Murphy | |
| 8,502,018 B2 | 8/2013 | Murphy | |
| 9,131,669 B2 | 9/2015 | Craig | |
| 2003/0070185 A1 | 4/2003 | Jakobovits | |
| 2003/0144484 A1 | 7/2003 | Le | |
| 2006/0015949 A1 | 1/2006 | Lonberg | |
| 2006/0026703 A1 | 2/2006 | Lonberg | |
| 2009/0098134 A1 | 4/2009 | Buelow | |
| 2011/0314563 A1 | 12/2011 | Craig | |
| 2012/0192300 A1† | 7/2012 | Babb | |
| 2013/0330771 A1 | 12/2013 | Craig | |

FOREIGN PATENT DOCUMENTS

| | | |
|---|---|---|
| EP | 1399559 A2 | 3/2004 |
| EP | 1399559 B1 | 4/2008 |
| WO | 9004036 A1 | 4/1990 |
| WO | 1990010077 A1 | 9/1990 |
| WO | 9312227 A1 | 6/1993 |
| WO | 1994004667 A1 | 3/1994 |
| WO | 1998024893 A2 | 6/1998 |
| WO | 02/066630 A1 † | 8/2002 |
| WO | 03000737 A2 | 1/2003 |
| WO | 2006008548 A2 | 1/2006 |
| WO | 2006047367 A2 | 5/2006 |
| WO | 2007096779 A2 | 8/2007 |
| WO | 2007117410 | 10/2007 |
| WO | 2008035216 A2 | 3/2008 |
| WO | 2008151081 A1 | 12/2008 |
| WO | 2009013620 A2 | 1/2009 |
| WO | 2010070263 | 6/2010 |
| WO | 2010109165 A2 | 9/2010 |
| WO | 2011163311 | 12/2011 |

OTHER PUBLICATIONS

Naito et al. J Reprod Fert 113:137-143, 1998.*
Raina et al. Gene 96-100, 2015.*
Carlson et al. PNAS 109:17382-17387, 2012.*
Laible et al. Biotechnology Journal 10:109-120, 2015.*
Gao et al. Genome Biology 18:1-15, 2017.*
Babcock, JS. et al., "A Novel Strategy for generating monoclonal antibodies from single, isolated lymphocytes producing antibodies of defined specificities," PNAS, Jul. 1996, vol. 93, No. 15, pp. 7843-7848.
Bell, A. et al., 'The Protein CTCF Is Required for the Enhancer Blocking Activity of Vertebrate Insulators,' Cell, vol. 98, pp. 387-396 (1999).
Biburger, M., et al., "A Novel Bispecific Tetravalent Antibody Fusion Protein to Target Costimulatory Activity for T-cell Activation to Tumor Cells Overexpressing ErbB2/HER2", J. Mol. Biol., vol. 346, pp. 1299-1311, 2005.
Boder, E.T., et al., "Yeast surface display for screening combinatorial polypeptide libraries", Nat. Biotechnol., vol. 15, No. 6, pp. 553-557, 1997.

(Continued)

*Primary Examiner* — Marcia S Noble

(74) *Attorney, Agent, or Firm* — Saul Ewing Arnstein & Lehr LLP

(57) ABSTRACT

A transgenic non-human mammal containing a heterologous lambda light chain gene locus, and/or a heterologous kappa light chain gene locus, and/or a heterologous heavy chain gene locus, each of which can re-arrange so that immunoglobulin heavy and light chain genes are formed and expressed in B-cells following antigen challenge.

1 Claim, 92 Drawing Sheets (5 of 92 Drawing Sheet(s) Filed in Color)

(56) References Cited

OTHER PUBLICATIONS

Boland, M.J. et al., "Adult mice generated from induced pluripotent stem cells," Nature, vol. 461, No. 7260, pp. 91-94, 2009.
Bond, C.J., et al., "Contributions of CDR3 to Vi,H Domain Stability and the Design of Monobody Scaffolds for Naive Antibody Libraries", J. Mol. Biol, vol. 332, pp. 643-655, 2003.
Brandt, C.R., et al., Loss of a Consensus Splice Signal in a Mutant Immunoglobulin Gene Eliminates the CH, Domain Exon from the mRNA, Molecular and Cellular Biology, vol. 4, No. 7, pp. 1270-1277,1984.
Brezinschek, H. et al., 'Analysis of the Heavy Chain Repertoire of Human Peripheral B Cells Using Single-Cell Polymerase Chain Reaction,' J. Immunol., vol. 155, pp. 190-202 (1995).
Brophy, B., et al., "Cloned transgenic cattle produce milk with higher levels of b-casein and k-casein", Nature Biotechnology, vol. 21, pp. 157-162, 2003.
Bruggemann, M., et al., "A repertoire of monoclonal antibodies with human heavy chains from transgenic mice", Proc. Natl. Acad. Sci. USA, vol. 86, pp. 6709-6713,1989.
Bruggemann, M., et al., "Strategies for expressing human antibody repertoires in transgenic mice", Immunology Today, vol. 17, No. 8, pp. 391-397, 1996.
Carter, B et al., "Bispecific human IgG by design," Journal of Immunological Methods, vol. 248, Nos. 1-2, pp. 7-15, 2001.
Cheung et al., "A proteomics approach for the identification and cloning of monoclonal antibodies from serum," Nat Biotechnol., Mar. 25, 2012, vol. 30, No. 5, pp. 447-452.
Related U.S. Appl. No. 13/140,529, filed Sep. 6, 2011.
Co-pending U.S. Appl. No. 14/806,802, filed Jul. 23, 2015.
Colbere-Garapin, F. et al., "A new dominant hybrid selective marker for higher eukaryotic cells," J. Mol. Biol., vol. 150, pp. 1-14, 1981.
Damak, S., et al., "Improved Wool Production in Transgenic Sheep Expressing Insulin-like Growth Factor 1", Bio/technology, vol. 14, pp. 185-188,1996.
Davis, J.M. et al., "A simple, single-step technique for selecting and cloning hybridomas for the production of monoclonal antibodies," J. Immunol. Methods, vol. 50, No. 2, pp. 161-171,1982.
De Franco, A.L. et al., "Signal transduction by the B-cell antigen receptor," Ann. NY Acad. Sci., vol. 766, pp. 195-201, 1995.
De Genst, E., et al., "Strong in Vivo Maturation Compensates for Structurally Restricted H3 Loops in Antibody Repertoires", J. Biol. Chem., vol. 280, No. 14, pp. 14114-14121, 2005.
De Wildt, R. et al., "Analysis of Heavy and Light Chain Pairings Indicates that Receptor Editing Shapes the Human Antibody Repertoire," J. Mol. Biol., vol. 285, pp. 895-901 (1999).
Degner, S.C. et al., "CCCTC-binding factor (CTCF) and cohesin influence the genomic architecture of the Igh locus and antisense transcription in pro-B cells," PNAS, pp. 1-6, 2011.
Degner, S.C. et al., "Cutting Edge: Developmental stage-specific recruitment of cohesin to CTCF sites throughout immunoglobulin loci during B lymphocyte development," J. Immunol., vol. 182, pp. 44-48, 2009.
Ebert, A., et al., "The Distal VH Gene Cluster of the Igh Locus Contains Distinct Regulatory Elements with Pax5 Transcription Factor-Dependent Activity in Pro-B Cells," Immunity, vol. 34, pp. 175-187, 2011.
European Communication pursuant to Rule 114(2) dated Feb. 29, 2016 for European Application No. 09760275.9.
Festenstein, R. et al., Locus Control Region Function and Heterochromatin-Induced Position Effect Variegation,"Science, vol. 271, No. 5252, pp. 1123-1125, 1996."
Garrett, F.E. et al., "Chromatin Architecture near a Potential 3' End of the Igh Locus Involves Modular Regulation of Histone Modifications during B-Cell Development and in Vivo Occupancy at CTCF Sigtes," Mol. and Cellular Biol., vol. 25, No. 4, pp. 1511-1525, 2005.
Glick et al., "Molecular Biotechnology. Principles and Applications of Recombinant DNA," 2nd Ed., ASM Press, Washington, DC, pp. 117 (1998).

Goldsby et al., Immunology, 5th Edition, W.H. Freeman & Co NY, p. 79.
Gottweis, H. et al., "iPS cells and the politics of promise," Nature Biotechnology, vol. 26, No. 3, pp. 271-272, 2008.
Guglielmi, L. et al., "Combination of 3' and 5' IgH regulatory elements mimics the B-specific endogenous expression pattern of IgH genes from pro-B to mature B cells in a transgenic mouse model," Biochim. Biophys. Acta, vol. 1642, pp. 181-190, 2003.
Guo, C., et al., "CTCF-binding elements mediate control of V(D)J recombination," Nature, vol. 477, pp. 424-430, 2011.
Guo, C., et al., "Two Forms of Loops Generate the Chromatin Conformation of the Immunoglobulin Heavy-Chain Gene Locus," Cell, vol. 147, pp. 332-343, 2011.
Hartman, S. et al., "Two dominant-acting selectable markers for gene transfer studies in mammalian cells," Proc. Natl. Acad. Sci. USA, vol. 85, No. 21, pp. 8047-8051, 1988.
Heinrich, G. et al., "Characterization of a human T cell specific chimeric antibody (CD7) with human constant and mouse variable regions," J. Immunol., vol. 143, pp. 3589-3597, 1989.
IGKV3-20 Gene, Apr. 8, 2014, "IGKV3-20 immunoglobulin kappa variable 3-20 [*Homo sapiens*(human)]," NCBI, pp. 1-8.
IGVK1-33 Gene, Apr. 8, 2014, IGKV1-33 immunoglobulin kappa variable 1-33 [*Homo sapiens* (human)], NCBI, pp. 1-4.
IGVK1-39 Gene, Apr. 8, 2014, IGKV1-39 immunoglobulin kappa variable 1-39 (gene/pseudogene) [*Homo sapiens* (human0], NCBI, pp. 1-4.
International Search Report based on International Application No. PCT/GB2009/002781, dated Apr. 19, 2010.
Janssens, R. et al., "Generation of heavy-chain-only antibodies in mice," PNAS, vol. 103, No. 41, pp. 15130-15135, 2006.
Jaton, J. et al., "Recovery of Antibody Activity upon Reoxidation of Completely Reduced Polyalanyl Heavy Chain and Its Fd Fragment Derived from Anti-2,4-dinitrophenyl Antibody," Biochemistry, vol. 7, No. 12, pp. 4185-4195, Dec. 1968.
Jhunjhunwala, S. et al., "The 3D structure of the immunoglobulin heavy-chain locus: implications for long-range genomic interactions," Cell, vol. 133, No. 2, pp. 265-279, 2008.
Johnson, G. et al, "Kabat Database and its applications:30 years after the first variability plot," Nucleic Acids Research 2000, vol. 28, No. 1, pp. 214-218.
Kabat, E.A. et al., "Sequence of Proteins of Immunological Interest," U.S. Public Health Services publication No. 91, pp. 3242 (1991).
Karreman, C., "New positive/negative selectable markers for mammalian cells on the basis of Blasticidin deaminase-thymidine kinase fusions," NAR, vol. 26, No. 10, pp. 2508-2510, 1998.
Kellermann, S. et al., "Antibody discovery: the use of transgenic mice to generate human monoclonal antibodies for therapeutics," Current Opinion in Biotechnology, vol. 13, pp. 593-597, 2002.
Kim, et al., "Analysis of the vertebrate insulator protein CTCF binding sites in the human genome," Cell, vol. 128, No. 6, pp. 1231-1245, 2007.
Kitamura, D. et al., "A B cell-deficient mouse by targeted disruption of the membrane exon of the immunoglobulin Mu chain gene," Nature, vol. 350, pp. 423-426, 1991.
Li, et al., "Locus control regions: coming of age at a decade plus," Trends Genet., vol. 15, No. 10, pp. 403-408, 1999.
Lonberg, N., "Human antibodies from transgenic animals," Nature Biotechnology, vol. 23, No. 9, pp. 1117-1125, 2005.
Lonberg, N. et al., "Antigen-specific Human Antibodies from Mice Comprising Four Distinct Genetic Modifications", Nature, vol. 368, No. 6474, pp. 856-859, 1994.
Madisen, L. et al., "Identification of a locus control region in the immunoglobulin heavy-chain locus that deregulates c-myc expression in plasmacytoma and Burkitt's lymphoma cells," Genes & Development, vol. 8, pp. 2212-2226, 1994.
Male et al., "Immunology," 7th Ed., Elsevier Ltd, pp. 81 (2006).
Mendez, M.J. et al., "Functional Transplant of Megabase Human Immunoglobulin Loci Recapitulates Human Antibody Response in Mice," Nature Genetics, vol. 15, No. 2, pp. 146-156, 1997.
Mills, F.C. et al., "Enhancer complexes located downstream of both human immunoglobulin C-alpha genes," J. Exp. Med., vol. 186, pp. 845-858, 1997.

(56) References Cited

OTHER PUBLICATIONS

Milot, E. et al., "Heterochromatin Effects on the Frequency and Duration of LCR-Mediated Gene Transcription," Cell, vol. 87, pp. 105-114, 1996.
Morrison, S.L. et al., "Chimeric human antibody molecules: Mouse antigen-binding domains with human constant region domains," Proc. Natl. Acad. Sci. USA, vol. 81, pp. 6851-6855, Nov. 1984.
Neuberger, M.S. et al., 'A hapten-specific chimaeric IgE antibody with Human physiological effector function,' Nature, vol. 314, pp. 268-270, 1985.
Neuberger, M.S. et al., "Construction of novel antibodies by use of DNA transfection: design of plasmid vectors," Phil. Trans. R. Soc. Lond., A317, pp. 425-432, 1986.
Nicholson et al., "Antibody Repertoires of Four- and Five-Feature Translocus Mice Carrying Human Immunoglobulin Heavy Chain and Kappa and Lambda Light Chain Yeast Artificial Chromosomes," J. Immunol., vol. 163, pp. 6898-6906 (1999).
Nussenzweig, M.C. et al., "Allelic exclusion in transgenic mice that express the membrane form of immunoglobulin Mu," Science, vol. 236, No. 4803, pp. 816-819, 1987.
Office Action by Japanese Patent Office dated Feb. 27, 2015, regarding Japanese Patent Application No. 2011-541578, filed on Dec. 18, 2009.
Office Action dated Aug. 25, 2014 by Russian Patent Office, regarding Russian Patent Application No. 2011129459 filed on Nov. 30, 2009.
Official Action by Japanese Patent Office dated Jun. 6, 2014, regarding Japanese Patent Application No. 2011-541578, filed on Nov. 30, 2009.
Osborn, M.J. et al., "High-Affinity IgG Antibodies Develop Naturally in Ig-Knockout Rats Carrying Germline Human IgH/Igk/IgA Loci Bearing the Rat CH Region," The Journal of Immunology, pp. 1481-1490.
Pasqualini, R. & Arap, W. Hybridoma-free generation of monoclonal antibodies, Proc. Natl. Acad. Sci. USA, vol. 101, No. 1, 2004, pp. 257-259.
Pettersson, S., et al., "Temporal Control of IgH Gene Expression in Developing B Cells by the 3' Locus Control Region," Immunobiol., vol. 198, pp. 236-248, 1997.
Pinaud, E. et al., "Localization of the 3' IgH Locus Elements that Effect Long-Distance Regulation of Class Switch Recombination," Immunity, vol. 15. pp. 187-199 (2001).
Reddy, S.T. et al., "Monoclonal antibodies isolated without screening by analyzing the variable-gene repertoire of plasma cells," Nat. Biotechnol., vol. 28, No. 9, 2010, pp. 965-969.
Related U.S. Appl. No. 13/815,676, filed Mar. 14, 2013.
Ribeiro De Almeida, C. et al., "The DNA-Binding Protein CTCF Limits Proximal Vk Recombination and Restricts k Enhancer Interactions to the Immunoglobulin k Light Chain Locus," Immunity, vol. 35, No. 4, pp. 501-513, 2011.
Riele, H.T. et al., "Highly efficient gene targeting in embryonic stem cells through homologous recombination with isogenic DNA constructs," Proc. Natl. Acad. Sci, USA, vol. 89, No. 11, pp. 5128-5132, 1992.
Santerre, R.F. et al., "Expression of Prokaryotic Genes for Hygromycin B and G418 Resistance as Dominant-Selection Markers in Mouse L Cells," Gene, vol. 30, pp. 147-156, 1984.

Singh, N. et al., "Biallelic germline transcription at the kappa immunoglobulin locus," J Exp. Med., vol. 197, No. 6, pp. 743-750, 2003.
Slifka, M.K. et al., "Humoral immunity due to long-lived plasma cells," Immunity, vol. 8, No. 3, pp. 363-372, 1998.
Solter, D., "Dolly is a Clone—and No Longer Alone," Nature, vol. 394, pp. 315-316, 1998.
Splinter, E. et al., "CTCF mediates long-range chromatin looping and local histone modification in the beta-globin locus," Genes Dev., vol. 20, No. 17, pp. 2349-2354, 2006.
Steenbakkers PG, et al., "A new approach to the generation of human or murine antibody producing hybridomas," J. Immunol Methods, Jul. 31, 1992, vol. 152, No. 1, pp. 69-77.
Sun, L.K. et al., "Chimeric antibody with human constant regions and mouse variable regions directed against carcinoma-associated antigen 17-1A," Proc. Natl. Acad. Sci. USA, vol. 84, pp. 214-218, Jan. 1987.
Translation of Search Report by Taiwanese Patent Office dated Jul. 30, 2014, regarding Taiwan Patent Application No. 098141093, filed on Dec. 1, 2009.
Truffinet, V. et al., "The 3' IgH Locus Control Region is Sufficient to Deregulate a c-myc Transgene and Promote Mature B Cell Malignancies with a Predominant Burkitt-Like Phenotype," J. Immunol., vol. 179, pp. 6033-6042, 2007.
Tuaillon, N., "Repertoire analysis in human immunoglobulin heavy chain minilocus transgenic, muMT/muMT mice," Molecular Immunology, vol. 37, No. 5, pp. 221-231, 2000.
Vara, J.A. et al., "Expression in Mammalian Cells of a Gene from Streptomyces alboniger Conferring Puromycin Resistance," Nucleic Acids Research, vol. 14, No. 11, pp. 4617-4624, 1986.
Wendt, K.S. et al., "Cohesin mediates transcriptional insulation by CCCTC-binding factor," Nature, vol. 451, No. 7180, pp. 796-801, 2008.
Xu, J.L. et al., "Diversity in the CDR3 Region of Vh Is Sufficient for Most Antibody Specificities," Immunity, vol. 13, pp. 37-45, 2000.
Xu, L. et al., "Evidence that the Mouse 3' kappa Light Chain Enhancer Confers Position-Independent Transgene Expression in T- and B-Lineage Cells," Human Gene Therapy, vol. 14, pp. 1753-1764, 2003.
Zou, Y-R. et al., "Cre-loxP-mediated gene replacement: a mouse strain producing humanized antibodies," Current Biology, Current Science, GB, vol. 4, No. 12, pp. 1099-1103, 1994.
Navas, Patrick A., et al., "Developmental Specificity of the Interaction between the Locus Control Region and Embryonic or Fetal Globin Genes in Transgenic Mice with an HS3 Core Deletion," Molecular and Cellular Biology, Jul. 1998, vol. 18, No. 7, pp. 4188-4196.
Murphy, A. 2009. VelocImmune: Immunoglobulin Variable Region Humanized Mice. In M. Little (ed.), Recombinant Antibodies for Immunotherapy (pp. 100-107). New York, NY: Cambridge University Press.†
Lefranc, Marie-Paule, and Gérard Lefranc. Immunoglobulin Facts Book. London: Academic Press, 2001. Print. (pp. 3-44, 97-428).†

\* cited by examiner
† cited by third party

Fig. 4

```
STARTVHLOCUSSEQUENCEATCCCTAGCTGAAGCTTCTGATGGAATTAGAACTTGGCAAAACAATACTGAGAATGAA
GTGTATGTGGAACAGAGGCTGCTGATCTCGTTCTTCAGGCTATGAAACTGACACATTTGGAAACCACAGTACTTAGAA
CCACAAAGTGGGAATCAAGAGAAAAACAATGATCCCACGAGAGATCTATAGATCTATAGATCATGAGTGGGAGGAATG
AGCTGGCCCCTTAATTTGGTTTTTGCTTGTTTAAAATTATGATATCCAACTATGAAACATTATCATAAAGCAATAGTAAAG
AGCCTTCAGTAAAGAGCAGGCATTTATCTAATCCCACCCCACCCCCACCCCCGTAGCCTCCAATCCTTCCATTCAAAAT
GTAGGTACTCTGTTCTCACCCCTTCTTAACAAAGTATGACAGGAAAAACTTCCATTTTAGTGGACATCTTTATTGTTTA
ATAGATCATCAATTTCTCGATTTCTCGACTATTCCTTTGCCCTCGGACGAGTGCTGGGGCGTCGGTTTCCACTATCGG
CGAGTACTTCTACACAGCCATCGGTCCAGACGGCCGCGCTTCTGCGGGCGATTTGTGTACGCCCGACAGTCCCGGCTC
CGGATCGGACGATTGCGTCGCATCGACCCTGCGCCCAAGCTGCATCATCGAAATTGCCGTCAACCAAGCTCTGATAGA
GTTGGTCAAGACCAATGCGGAGCATATACGCCCGGAGCCGCGGCGATCCTGCAAGCTCCGGATGCCTCCGCTCGAAGT
AGCGCGTCTGCTGCTCCATACAAGCCAACCACGGCCTCCAGAAGAAGATGTTGGCGACCTCGTATTGGGAATCCCCGA
ACATCGCCTCGCTCCAGTCAATGACCGCTGTTATGCGGCCATTGTCCGTCAGGACATTGTTGGAGCCGAAATCCGCGT
GCACGAGGTGCCGGACTTCGGGGCAGTCCTCGGCCCAAAGCATCAGCTCATCGAGAGCCTGCGCGACGGACGCACTGA
CGGTGTCGTCCATCACAGTTTGCCAGTGATACACATGGGGATCAGCAATCGCGCATATGAAATCACGCCATGTAGTGT
ATTGACCGATTCCTTGCGGTCCGAATGGGCCGAACCCGCTCGTCTGGCTAAGATCGGCCGCAGCGATCGCATCCATGG
CCTCCGCGACCGGCTGCAGAACAGCGGGCAGTTCGGTTTCAGGCAGGTCTTGCAACGTGACACCCTGTGCACGGCGGG
AGATGCAATAGGTCAGGCTCTCGCTGAATTCCCCAATGTCAAGCACTTCCGGAATCGGGAGCGCGGCCGATGCAAAGT
GCCGATAAACATAACGATCTTTGTAGAAACCATCGGCGCAGCTATTTACCCGCAGGACATATCCACGCCCTCNTACAT
CGAAGCTGAAAGCACGAGATTCTTCGCCCTCCGAGAGCTGCATCAGGTCGGAGACGCTGTCGAACTTTTCGATCAGAA
ACTTCTCGACAGACGTCGCGGTGAGTTCAGGCTTTTTCATGGTGGCGGCTGGATCGGTCGGTCGAAAGGCCCGGAGAT
GAGGAAGAGGAGAACAGCGCGGCAGACGTGCGCTTTTGAAGCGTGCAGAATGCCGGGCCTCCGGAGGACCTTCGGGCG
CCCGCCCCGCCCCTGAGCCCGCCCCTGAGCCCGCCCCCGGACCCACCCCTTCCCAGCCTCTGAGCCCAGAAAGCGAAG
GAGCAAAGCTGCTATTGGCCGCTGCCCCAAAAGGCCTACCCGCTTCCATTGCTCAGCGGTGCTGTCCATCTGCACGAGA
CTAGTGAGACGTGCTACTTCCATTTGTCACGTCCTGCACGACGCGAGCTGCGGGGCGGGGGGGAACTTCCTGACTAGG
GGAGGAGTAGAAGGTGGCGCGAAGGGGCCACCAAAGAACGGAGCCGGTTGGCGCCTACCGGTGGATGTGGAATGTGTG
CGAGGCCAGAGGCCACTTGTGTAGCGCCAAGTGCCCAGCGGGGCTGCTAAAGCGCATGCTCCAGACTGCCTTGGGAAA
AGCGCCTCCCCTACCCGGTAGAATTCATCGCTCGAGCAATTGGCTAGATAACTTCGTATAATGTATGCTATACGAAGT
TATCTAGCTCTAGAGTCG░░░GATTGAAGAGTGTGATAAGTGCCCAGACCAAGCAGAACAGAAATCAGCATGTAAAGAT
hygro
GATGATCTATGGATATGATCTAAAACCATGTAAATACTTCAAATAATTCTATTTAATGCAGTTTGAAATAAAACACAA
ACTTATTCAAAATACAAATTACTTGGTAATTATTTTGGGAGCTATGAGTTCACCAAGAAACTCAAATTCCTATTTCTA
TTTCAACCCCTGATTCCTACTGTCAATGGGAGGGAAGTCTCAGAACCAATCACACATCAGACGGCAAATCTGTCAACC
AAGAGTCTTTCCACTGAAGGACCTGGGAGGTCAGGACCCTCAGGAAAGTGCTGGGGACCCTGTCTTGGGAGTGCCCAG
CAGATCTCAGAACTCTCCATGGGTCCTGCTGGACACTCATGTAGGGTAACGAGTGGCCACCTTTTCAGTGTTACCAGT
GAGCTCTGAGTGTTCCTAACGGGACCAGGATGGGTCTAGGTGCCTGCTCAATGTCAGAGACAGCAATGGTCCCACAAA
AAACCCAGGTAATCTTTAGGCCAATAAAATGTGGGTTCACAGTGAGGAGTGCATCCTGGGGTTGGGGTTTGTTCTGCA
GCGGGAAGAGCGCTGTGCACAGAAAGCTTAGAAATGGGGCAAGAGATGCTTTTCCTCAGGCAGGATTTAGGGCTTGGT
CTCTCAGCATCCCACACTTGTACAGCTGATGTGGCATCTGTGTTTTCTTTCTCATCCTAGATCAGGCTTTGAGCTGTG
AAATACCCTGCCTCATGCATATGCAAATAACCTGAGGTCTTCTGAGATAAATATAGATATATTGGTGCCCTGAGAGCA
TCACATAACAACCACATTCCTCCTCTGAAGAAGCCCCTGGGAGCACAGCTCATCACCATGGACTGGACCTGGAGGTTC
CTCTTTGTGGTGGCAGCAGCTACAGGTAAGGGGCTTCCTAGTCCTAAGGCTGAGGAAGGGATCCTGGTTTAGTTAAAG
AGGATTTTATTCACCCCTGTGTCCTCTCCACAGGTGTCCAGTCCCAGGTGCAGCTGGTGCAGTCTGGGGCTGAGGTGA
AGAAGCCTGGGTCCTCGGTGAAGGTCTCCTGCAAGGCTTCTGGAGGCACCTTCAGCAGCTATGCTATCAGCTGGGTGC
GACAGGCCCCTGGACAAGGGCTTGAGTGGATGGGAGGGATCATCCCTATCTTTGGTACAGCAAACTACGCACAGAAGT
TCCAGGGCAGAGTCACGATTACCGCGGACAAATCCACGAGCACAGCCTACATGGAGCTGAGCAGCCTGAGATCTGAGG
ACACGGCCGTGTATTACTGTGCGAGAGACACAG
VH 1-69
TGTGAAAACCCACATCCTGAGAGTGTCAGAAACCCTGAGGGAGAAGGCAGCTGTGCCGGGCTGAGGAGATGACAGGGG
TTATTAGGTTTAAGGCTGTTTACAAAATGGGTTATATATTTGAGAAAAAAAGAACAGTAGAAACAAGTACATACTCTA
ATTTTAAGATAAATATTCCATTCAAGAGTCGTAATATAAGCCAAATTCACAGAGTGGAAAAGGCCACACTCTATAACG
TTGATACAAACATTCCATGAAGGTGCTACTGTGAACAAGTTTTCAAATTGGATGAATACATGATTTGGAGCAAGGTTA
TTTGATCATGTGGTGAGACTAAGAATG░░░░░TCTGGACTTGAGTGTCATTGTCCAGCCATGTTGCACAAGTGTGTC
CTGTCAGGGAAGGATCAGAGTTCCTTGTGCTCTCAGAGGGAAGGGGTCACAGAGTTCCTCTCTGGTTCCCAGGAAAGG
TAATCGCACTAATCTTCATGATCTTCATGAGACTATCCTCCAGTGCTGACCTGTTATAGAGTTTTTGTCTGAAGTTCT
```

Fig. 4 (Cont.)

```
CACTGCAATCCCCAATCTACATATTTTCAATCAGAAGTGTTTAGAGGCCAGGACACATCTTCAAGGTCACACATTGAG
AAGGATGTAGATATGTCCCACTACCTTCTCCTGAGATCTCAGACAGAATCCCAGATTTCAAAAGGACACAGAAGGACA
GCTCTCAGGTGCTTTTAAAAAATGACCCACTTCCAGGGACAGGGAGCTTCCCTATAACCATGGTGGATGTTCTGAACT
ACAATAAACATTGGATGGATCCAGGATTGTTTGAAGTCACTGTCATTATTACATTCAGCTGCTGTTTCAATGTGTCTG
AAGTAGTAAATGACAATTTAGATGACAATTTATATGAATCTTCAAGGGTAGAACAATATTGACCATATTCCAAAATCT
GTCCTTGATCCATGATCACACTCATCTCCCAGACCAGGTCCTTCAGCACGTCTCTTTACCTGAAAGAAGAGGACTCTG
GGCTTGGAGAGGGGAGACCCCAAGAAGCAACTGAGTTCTCAAAGGGCACAGCCAGCATCCTACTCCCAGGGCGAGCC
CAAAAGACTGGGGCCTCCCTCCTCCTTTTTCACCTCTCCATACAAAGGCACCACCCACATGCAAATCCTCACTTAAGC
ACCCACAGGAAACCACCACACATTTCCTTAAATTCAGGTTCCAGCTCACATGGGAAATACTTTCTGAGAGTCCTGGAC
CTCCTGTGCAAGAACATGAAACATCTGTGGTTCTTCCTTCTCCTGGTGGCAGCTCCCAGATGTGAGTATCTCAGGGAT
CCAGACATGGGGATATGGGAGGTGCCTCTGATCCCAGGGCTCACTGTGGGTCTCTCTGTTCACAGGGGTCCTGTCCCA
GGTGCAGCTGCAGGAGTCGGGCCCAGGACTGGTGAAGCCTTCGGAGACCCTGTCCCTCACCTGCACTGTCTCTGGTGG
CTCCATCAGTAGTTACTACTGGAGCTGGATCCGGCAGCCCCCAGGGAAGGGACTGGAGTGGATTGGGTATATCTATTA
CAGTGGGAGCACCAACTACAACCCCTCCCTCAAGAGTCGAGTCACCATATCAGTAGACAAGTCCAAGAACCAGTTCTC
CCTGAAGCTGAGCTCTGTGACCGCTGCGGACACGGCCGTGTATTACTGTGCGAGAG
ACACAGTGAGGGGAGGTGAGTGTGAGCCCAGACAAAAACCTCCGTGCAGGGAGGCGGAGGGGACCGGCGCAGGTGCT
VH 4-59
GCTCAGAGCCAGCAGGGGGCGCGCGGGGCCCACAGAGCAGGAGGCCCGGTCAGGAGCAGGTGCAGGGAGGGCGGGGCT
TCCTCATCTGCTCAGTGGTCTCCCTCCTCGCCAGCACCTCAGCTGTCCCCAGGGGTCCTCTTTCTTTATTATCTGTGG
TTCTGCTTCCTCACATTCTTGTGCCAAGAAAGAAATGAGGAAGACAAATTTTCGTCTGTAGTTGAAGTTTCACCAAT
       ACGATGCGGATGTGATTTAAGTTTCAGAGGAATAAAAAAAAAGATTTAGGGATTAATTTAATTATTCAAAAGT
TGATTGAAGTGCCGAGTGAATGGCTGCAAACATAGTCTACATTTTTCAAATCATTCCCTATAAATTTGAATTAATTAT
TTATTTTTATACTTGAATAAAAGCAATAACAAAGAAATAAATGAATATTTTTGCTAAAATGGAGCAATAAAAAGACTGA
TATTGACAGAAGAAATATGACTGACTTCTGAAAATACACACACATGAGCCGTGGTTCTCTCTACATATTTAGATAAAT
TACAGAAAGTTGTCATAACTGATGGGGAATCCTGCAGACTTCACTAGGCATAGTCCACACTGCCCTGGAGTTGTCTCA
GGGGAGCTGCCTCCTCCAGTGGTTAGAGCACAGGCCCAGGTAATAGGACTCATTTTTTTAGATGTGTAATTTTAGACA
CACTGCACAACTGCTGTGTTCTCTGCGCAAATTATCTCCTGTAAAATGCAACATTGAAACCTGCCTTAAATATATTGT
GTAAATATGTAAAAATAAAATCAGATTGTGAGAGCTAAATGCTAATCAAGGCGCAATCACGTAATATACAATTATATT
TTCCTGAATGATGGAATTAATACCAATCTCCCCCAGGACACTTCATCTGCACGGAGCCCGGCCTCTCCTCAGATGTCC
CACCCCAGAGCTTGCTATATAGTCGGGGACATGCAAATAGGGCCCTCCCTCTGCTGATGAAAACCAGCCCAGCTGACC
CTGCAGCTCTGGGAGAGGAGCCCAGCACTGGGATTCCGAGGTGTTTCCATTCGGTGATCAGCACTGAACACAGAGGAC
TCACCATGGAGTTTTGGCTGAGCTGGGTTTTCCTTGTTGCTATTTCAAAAGGTGATTCATGGAGAACTAGAGATATCG
AGTGTGAGTGAACACGAGTGAGAGAAACAGTGGATATGTGTGGCAGTTTCTAACCAATGTCTCTGTGTTTGCAGGTGT
CCAGTGTGAGGTGCAGCTGGTGGAGACTGGAGGAGGCTTGATCCAGCCTGGGGGGTCCCTGAGACTCTCCTGTGCAGC
CTCTGGGTTCACCGTCAGTAGCAACTACATGAGCTGGGTCCGCCAGGCTCCAGGGAAGGGGCTGGAGTGGGTCTCAGT
TATTTATAGCGGTGGTAGCACATACTACGCAGACTCCGTGAAGGGCCGATTCACCATCTCCAGAGACAATTCCAAGAA
CACGCTGTATCTTCAAATGAACAGCCTGAGAGCCGAGGACACGGCCGTGTATTACTGTGCGAGAGACACAGTGAGGGG
AAGTCATTGTGCGCCCAGACACAAACCTCCCTGCAGGAACGCTGGGGGGAAATCAGC
VH 3-53
TGCAGGGGGCGCTCAGGAGCCACTGATCAGAGTCAGCCCCGGAGGCAGGTGCAGATGGAGGCTGATTTCCTGTCAGGA
TGTGGGACTCTGTCTTCTTCTGACGGTTCCCCAGGGAACCTCTCTAAGTTTAGCATTCTGTGCCTATGAACGTCTTCT
CTAAGTATTTGAAAGAGATTATTTTAATATGAAGAGCAGTTCTCACTC       CTCTTCTGAAGGACCATGAATGCC
TCAACCAACCATCTCCCCTGCCTCCATGACCAGAAATGCACCACGTGCCCACACGGATATTCATCCCTCATGGGGATA
AGACTCCATTGATGAGGCTGACTATTTTATCATATAAAATTACTAAAGACTGATTTAAGGGTTTCAAAAACTAATTGA
ACTCTGTTGTTCTATGTCCACCAGAGATTACAAATCTTCCAATGATGCCTTCTTTGTTTTTTGTCTGCTTGACTTTGT
CTCTTCAACTTGTTCTGTACCCCAGAGAATCTCTTTCAGCTCCCTCAGGTGCATTCAATTGTTTTATTTAACTGACAA
TTTCTAAATCAGTTAAAGACATTACGCTAAAGACTCCATATTCCTAGGTCCATATTCCTTTTTCCATATTCCTAGGAA
GGCATTGTGACCCAGAGTCTGGGCATGACCTTGTGAGTGTTCCTGACCCTCCTCCATATGAGATGCTGGTCTGGGTGT
TCTTGCCCCTTTCCCTGGGGTAGAGTCCTCCTGTTTTCCCCAGGTGCTCCCTCCCACAGCTCTAGTGTTCTCAATCAG
TGTCATCACCTTCCAGATCTTCTGCCCTGCCCTGCAGACTAAGGCTCTGATTCCATAAGCAAGATAGGGGAGCTGCTC
CTCAATAGATCTTTGGTGAGGATCTCTGTTCCCATCTCAATTCCTGTAGGGTGGAACCAGTGTTCCTAGGATTCTGGT
TTCAGTAGCTTGTCCCTGCAGAGTAAATTCTTAGTTCTGTAGGGGATTAAGGGAGTTGGGTCTGAATACATTTTAGA
TGTCGAGGATCTTGTTCTCTCCCAGAAAGACACTTCGGGAAAGTAAGACTTTGGTAACTGTCCCCTTTCTTGGGGAAA
GGGATTCAAGAGGATAGGTTGCTTTTGGGCATGTGGTCCCTTAAAATTTCACACTAAAAAGCGTTTCCCACACTCAAT
TTCAAGCAGCCCAATATATATTTGTATTTTTTCTTGGAACAGACAATATTTTATATTCCAGACTCTGCCTTAGGTAAT
TTCAAACCCCGGCTTTGTTACTCTCTACAAGAAATTGCTTCTCCATAAGCTTCAGATTTGTTGTGTGTTTTGAAATTT
```

Fig. 4 (Cont.)

```
TATCAGAAATATTAAAGAAAATTGGCAAAATTCCATCCTCCATGTTTATCTGTTATTGTTGATGCAGTTGTAAAAAAT
AAGAAAAATATATTCCTTTTTTCTGTACATTTCCAAGCTTAGTAGCAAATTTTTAGTAACACCCAGAATAATAAAAAA
TTCAAATATTGTTTAGCTGCTTAATAGGAAAACAAATTATAGTAAATTTGTTTGCTAGAATGCTACCCAGCATTTATA
ATAAGTAAACATTTGATATACCCAACTACAAGGTAAAATATCCATTTATGCTAACTAAAATAAGCCAAACAAATGAGA
ATATATACTGTTATTTCATTTTTATAAATTCTGAAAAATTAAAATGAATTTGCAGCAATGTAAAGATCAGTAGTTGCC
AGGGAAATGGTAGAAGAAAGAAAGGAAAAGGAGAAAGAATACAGAAAAACAAAAGGAAATGTTAAGAATTCTCTTGTC
CAACTTGATAAGGATGACGGTTACATCATTTTTATCAACTGTAATCTTTAAATATGTGAAAGTTTATTATCCGTAAAC
TAAACGTTATAAACTTTATTACAAGCAAAAATTGAAAGTTAGACAACAAGGAGTGATAGAAAGAGAAAATGTATATTA
AATTTCAGAAATATTTAAGAATGTATCTGCCTGAACCCTAGTTCTCACCATATCTTTAGGTGAATGCTAAAATGCAGC
AAAATCACGCATGTTCTCACTACAGAAAGTGGGTTCTACAAACCACACTCGGCACATTTAGCTTTGTCCTGGAGTTGG
TGCAGGGAGTTATTGGGGCCAGTGATGAGGAGCACAGGCCAAGATACCAGCGATTACTTATCCCAAACATGAGCTCTA
ACATACACACTTAGTCCCTTTTCCGTGTGTGGTTTACTTCCACATCTGTACATGGAGAGACCACTGACTGACAAAATA
TAATTTATACAAATATGTAAAATTAAATAGGGTGATCAGTTCAAGGTGTTTATCACAGCATAATTTTACAATAAGACA
GCATATTTCCCAAATACCATCATTGTCACCAAACTCCTTCAAGGCACAGTCATCTTATCTGGGCCCGTCCTCTCCTC
AGGTGTCCCACCCCAGAGCTTGGTATATAGTAGGAGACATGCAAATAAGGCCCTCCCTCTGCTGATGAAAATGAGCCC
AGCCCTGACCCTGCAGCTCTGGGAGAGGAGCCCCAGCCGTGAGATTCCCAGGAGTTTCCACTTGGTGATCAGCACTGA
ACACAGACCACCAACCATGGAGTTTGGGCTTAGCTGGGTTTTCCTTGTTGCTATTTTAAAAGGTAATTCATGGTGTAC
TAGAGATACTGAGTGTGAGGGGACATGAGTGGTAGAAACAGTGGATATGTGTGGCAGTTTCTGACCTTGGTGTTTCTG
TGTTTGCAGGTGTCCAATGTGAGGTGCAGCTGGTGGAGTCTGGGGGAGGCTTGGTACAGCCAGGGCGGTCCCTGAGAC
TCTCCTGTACAGCTTCTGGATTCACCTTTGGTGATTATGCTATGAGCTGGTTCCGCCAGGCTCCAGGGAAGGGGCTGG
AGTGGGTAGGTTTCATTAGAAGCAAAGCTTATGGTGGGACAACAGAATACGCCGCGTCTGTGAAAGGCAGATTCACCA
TCTCAAGAGATGATTCCAAAAGCATCGCCTATCTGCAAATGAACAGCCTGAAAACCGAGGACACAGCCGTGTATTACT
GTACTAGAGACACAGTGAGGGGAGGTCAATGTGAGCCC
```

VH 3-49

```
AGACACAAACCTCCCTGCAGGGGCGCACAGAGCCACCAGGGGGCGCTAGGGACCGACTGAGTACGGGACAGGTCCCAG
GAGCAGGTGCAGGGGGAGGTTTCCTTTTTCCTTGGCTGGAAAAGTCACCTTTATCTTCCCAGGA▓▓▓▓GATGAGAC
TATCCTCCAGTGCTGATGTACTATAGAGTTTTCATCTGAAGCTGTCACTGCTATCCCCAATGTACATCTTTTCACACA
GAAATGTTTAGAGGTCAGGCCATATTCTCAGGGTTACACATTGAGAAGGATGGAGATATATTCTACTACCTTCTCCTG
AGATCTCACACACAATCTCAAATTTCAAAAGGTCTCAGAAGGGCAGCTCTCAGGTACTATTTAAAAATAACCCACTTC
CTGGGACAGGTAGCATCCTTCTAACCATGATGGATGTTCTGAACTACAGTACACATTGCATGGATCCGGGTTTGTCTC
AATTCACTGTGATTATTACACTCAGCAGCTGTTTCAATATGTCTGAAGGGGTAAATGACAATTTAGGTGACCTGGGTG
TATGGTTGGTGTTTATGAATCTTTAAATGTAGAACAGTATTAACTGTATTCCAAAATCTGTCTTTGATCCATGATCA
CACTTGTCTCCCAGACCAGCTCCTTCAGCACATTTCCTACCTGGAAGAAGAGGACTCTGGGTTTGGTGAGGGGAGGCC
ACAGGAAGAGAACTGAGTTCTCAGAGGGCACAGCCAGCATACACCTCCCAGGGTGAGCCCAAAAGACTGGGGCCTCCC
TCATCCCTTTTTACCTATCCATACAAAAGGCACCACCCACATGCAAATCCTCACTTAGGCACCCACAGGAAATGACTAC
ACATTTCCTTAAATTCAGGGTCCAGCTCACATGGGAAGTGCTTTCTGAGAGTCATGGACCTCCTGCACAAGAACATGA
AACACCTGTGGTTCTTCCTCCTCCTGGTGGCAGCTCCCAGATGTGAGTGTCTCAGGAATGCGGATATGAAGATATGAG
ATGCTGCCTCTGATCCCAGGGCTCACTGTGGGTTTCTCTGTTCACAGGGGTCCTGTCCCAGGTGCAGCTACAGCAGTG
GGGCGCAGGACTGTTGAAGCCTTCGGAGACCCTGTCCCTCACCTGCGCTGTCTATGGTGGGTCCTTCAGTGGTTACTA
CTGGAGCTGGATCCGCCAGCCCCAGGGAAGGGGCTGGAGTGGATTGGGGAAATCAATCATAGTGGAAGCACCAACTA
CAACCCGTCCCTCAAGAGTCGAGTCACCATATCAGTAGACAAGTCCAAGAACCAGTTCTCCCTGAAGCTGAGCTCTGT
GACCGCCGCGGACACGGCTGTGTATTACTGTGCGAGAGGCACAGTGAGGGGAGGTGAGTG
```

VH 4-34

```
TGAGCCCAGACAAAAACCCCCCTGCAGGTAGGCAGAGGGGCGGGCGCAGGTACTGCTCAAGACCAGCAGGTGGCGCG
CGGCGCCCACAGATCCCGAGGCCGGGTCCGGAGCAGGTGCAAGGAGGGCGGGGCTTCCTCAACAGCTCAGTGGTCTGT
CTCCTCGCCAGCACCTCAGATGTCCCCAGGACTCTCTTTCTTTATTATCTGTGGTTCTGCTTCCTCACATCCTTGTGG
CAGGGAAGAAAGGAGGAAGACAATTTTTCTGTTTACTGTTGAGGTTTCACCAATTAC▓▓▓▓GTCTTGTTACACTTC
ATCAAGAATTAACCTCTGCTGTTTCCTCAAAGTGTTTAATTGGATAATGAATTTGTCTATAAATTGAAGAGTTGAAAT
ACATCAAATATTAATTTGTAATAATCTGGCACAAATTATCTAAGCAAATTCAATAACTAGATGTTTTTCATTTATTT
TTATTTAAAATCAGGATCTAAGCACTGACATGCTTTAATAACATCTGTGACCCTCTCAGCAGTTTTCTCTTCTGAGTA
TATGATCTGCTGTGGCAGTTTTCTTAGCTTCAATGTTACCTCTTTTGGCAATGACTACCGTCTTTATATTTGCCAGGA
ATCTGGGATAAGGGAGTGCTTCTAAGAGTTCCCTAACTTGCCCATTTTGGTGGGTGTTCCAGAACATATGAGATGCTC
TGTTGTTAACAAAGCATCCCAAAGCCATGCACTGCCCTAAAATGTGTTTGTTTCCTAGTTTGACAAATTGGAAGTTCT
AATAAAATACAATCACTTCTGCCATCTGGGCTGATTTTACATCAGATAGAGGGCTGTATTCCAAAGAAAAGCTTACATT
AGTAATAGCAATTCTAGTCAGAAACCTAGAGTTTTATCATTGAGGTGCAATTCATAACAAATAATATTAGGTCGAGGT
TCTCAGTGGCAGTGTCTAAATCTCTTAGGTGTACAGGGTCTTCCCTGTTAACATGAAGCATTTATAAGCACAGTCATA
```

Fig. 4 (Cont.)

```
GTTTCCAGCTATGCTTCTCCCTGTCTCATTATCACCACAAACTATGGCCTCACCTGGAACTTGGGTTAATTTCCAAAT
AAGTAATTTTTTAGTGTTTATGCCTCTAGATTATTATGTGAGAAAGTTAACATTCAGTAGAAAGTTAAAAAGAACATT
TGAACTGACTAAACAACACAGACAATCAAGAATAAAATTCAAAGCCTAGATGTGAGAGGCTCCAGGCCTGGATAATGC
AATAGTTCATGTATGCAGGCAGTTTCTTTGCCCAGTTCTACACTGATACACCCAGAATGTCAGCTTCATGCCAGATTT
GACTCCTATTATGTAGAGACATGGCAATACATTCTCAAGGGTCACATGAAATAATATGAAAATTGGTGGGAATAGGGG
AGGAGACAACTCTGCAATTCTCATCTGAAGGACCAGGAAAGCCTGGACAGACCATCTCCCCAGCCTCCGTGACTGCAC
CACGTGCCCACATGGACGCTCATCCCTGATAGGGTAAGAAGACTCCATTGATGGGGCTGAGCATTTTATGATAGAAAT
TACTAGAGACTGACGTGGAGGTTTCAACAACTAATATTTATAACCAAAATTTAATTACCCCCACATTGTTACCATTTT
CTTCAGTGAAAAATTGCTTGCCATGATTAAGTTTTAAGTAGATTTCCAATGTTCACAACTGAGCTTCCAAGAGAGTCT
TGAGAACAAAAACAATGAGGGCAGAGAAATCTACCTTTTCTGCATTCACCACTAAACTCAAGTGGACTCAGCACTGCC
TTTGATCACTGCTACTTCTCTGCAGAGTTCAGGTTTCTACTTCTCACAATTCTGACACACATTCTACCTCTCCTCAGA
TGTTTGGCCTCTGCTTCTTGTAAGGTCACCCTCTGTTCTTAACTTCTTCTCTGAGTCATTTTGTGAGGTGGTCATGAG
CCATTAAATGGATATTTTATATTTTCCCAACATGAATCACATGAGTGGTCATGAATTATACTTCTGATTATGGCAGTT
GATTTTCTTGGCATGTTCATGACTAGTAATATTTGAAGCCATTTCATTCAAATCTTCGGGGCTTCGTTTTGTTGCT
ATGACATTTTTTCTTCTATTGAGTCTTTCCACTAGTATTATAACATGACCTAGTATCCAGGCTCAGTTGTCATTAATA
ATAACCACATATGTCAAAAATCATGCATTCTTTTCACAGCAGACATAATTTCCTCTTTTCTGCAGATGAAGACACACT
GCTGAGCTACCCCCACTTACAAGAATATATGCACAATTATGATATCTTCATTTATTTGACTAATAAGCTATATCATTC
TCCCTTCAAATTCTTTACCCCCCAGAAGTCCTGGACAAATTTCTGCATCTGCTCAAACGATAAACTCAGAACTACATG
GTGAGTAAAAGTCACCTGGTTCTGGATATTGGGTCCATCTCTTCCCCTCCAATGTCCCAGAGCACCTCAGCACACCCG
TCCAGGTTCTATCAAGAAAGAGTAGCTCCTGCACACTGAAGGAAACAATTGAGTTAAGAGAGGACCTGCAGATGATAG
ACAATATTGAAAACTGTTAATATGACAAAGGATTACTACCAAGCATGTGAAATAAGCTCAACGGGTGCGGTGGTTCAT
GTCTGTAGTACCAGCAATTTGGGAGGCAAGTTGCGCAGATCACCTGAGGTTAGGAGCTCGACACCAGCCTGACCAACA
TAAAGAACACCCTGTCTCTACTAAAAGTACAAAATTAGCCGGGCATGGTGGCATGCGCCTGTAATCCCAGCTACTCGG
GAGGCTGAGGCAGGAGCATCACTTGAACCTGGGAAGTGGAGGTTGCGGTGAGCTGAGATGGCACCATTGCACTCCAGC
CTGGGCAACAAGAGGGAAACTCCATCTCAAAAAAAAAAATTACAAAAAATTAGCTGAGCGTGGTGGTGGGCGCCTGTAT
ACCCAGCTGCTAGGGAGACTGAGGCAGGAGAATGGCTTGAACCCAGGAGGTGAAGGTTGCAGTGAGCTGAGATTGCGC
CATTGCACTCCATCCTGGGCAACAAGAGTGAAACTCCATCTCAAAAAAAAAAAAGAGACTTGCAAAGGGCAAATAGA
TCATAGACAGACAGATAGATAGATAGACCTATTAGTATACATACATACATATATATACACTAATATTCAGGAAAATGC
AAATTCATAATGAGATGTCTTTTCACCCTTCATCTCTGCTAGAAAGTTTGTTATCTGAAAAACAAATACATACATACA
TACTTATTAAAAGCTGGCCAGGATGCCTAGAAAGTAAAACTCATAGACCACTGGTGGAAATGTAAATTAGTGCAGCCA
TCAAGGGAAAAAAATAGAACTACCATATATTCCAGCAATCCAACTGCTAAGTATATATCTATTTAAATATTTAAAAGA
AAAAACTAATATTGAAGAGATACCTGTACACCCATGTTTATTGCAGCACTAATCACAATTTCTAGGATATGAAATCAA
CATATGTGTCCATCAACAGATGAATGGATACATAAAATGTGATATATTTACACAATGGAATATTATTCAGCCTTAACA
ATGAAATTCTGCCGTTTGAAGCAACATGGATGGAATGGGACACCTCTATGTTGAGTGAAATGAGTCAGACACAGAAAA
ATAAATACCGCATTTCTCAGCGTTACTTCTAGAAGTAAATAGTAGAGTAGTGGTGATGAGATGCCAGGAATGAGAGAA
GGCTGAGATAAGAAGAGGTTTGTTAACAAACACACAATTACAGGTAGACAGGAGGGATGTGCTCTAGTGTTCTACAGC
ACAGTAGGGTGACTACAGTTAACAATATATTGTACGTTTTCTGTTTACAAGAAGCCAGAAGAGAGAATTTTCTATGCT
ACCAACACAAATAAATGTTAGTGTCTGAACTGACGAATTTGCTCATTGTTCTGATTTTAGTCATACCAAGTGGCACAC
ATGTATTCAAATATCACACTGTACCCCATAAACATAAGCAGTTATTATGTGCCAAATTTGAAAAATCCTTTAATTAGA
AGGAATTATATTGGCGTACATTACAAATGATTCAACACAGAGACAGGAATAAATACCATTTTTCTTTGAAATAGTTAA
TTAACTAACAATGTAGTTACATTCATTTGCACCAAATCGTGTATTTGATAATGGTATGCATAGACAGATTTATGCATA
GGATAATATCTTTTAATTTTAGACTACTACTTAATACTATAAATATAAATAATTTTAAAACAACTAAGTAAAAAGAAT
AAAGCTGAGAAAATGTGTGTGGTGTGTGATGTGTGAGCTTTTTCTTGTGCACCACTGTGTCCTTGGTGGATGTGTG
GTTCATGTGTTTGTTTTTATTTACTCTGTTTGGGGTTCTCTTTGCTTCTAGGATCGTAGTTCAGTTTCTTTCACAAA
ATTGGGAACATTCTTCGCTATTATCTTTTTCAAATAGTTTCTGTGTATTTATAATTTCTCCTTCTCAGATTTAAAATA
TACACATACTATAATTTTGATATTAATGTTTAGTTTCTTTCTTCACTCTCTTTTCGTTTGCAATTTACTTTGTGAAAT
TTCTAATGACATACTAATCACATGGTTTTATTGAAAAGCTGAGCCAGCTCTACTGAGGTGTGTGCCAAAAGATTGCTC
GATGTTTATACAGCATTGCTTTTGATTTCTTATGCATTTCCATTTGATTTATTCTTAGTATTTTCATATTTCAGTTCC
CTATCTATGTCCACGATTTCTTTAAGAGATTCTTGCGTGTGAATTATAGTTACTTTACATATCTTGTTTAATTAGATA
TTTATAACATCTGTTTCATCTACAAATCTCATGCTGATCATTTGTTTATTACAACTTTGGTACTTCTCATTAATGTAT
GTAATAATTGTTGATAGCCACAGATACTGGGATGGACAGTGGATACTGGCCTTATTATTTCATTTATGCATTTCTGC
CTGTATTTGACCACACTTTACCTTTGCCAGGCCTTTACTGTGGAAGTATCTGTGAATCTTCTCAGAACTATATTTGAC
ATTCACTTTTGCAGTGGACATCAAAGTTGAAGTCTGTTCTTCTGTGTCCACCAGAGACTTCAGTTCCTCCAGTGATAC
CTTGTTTTTCTTTCCTGCTTGGCTTTGTCTCTTCACCTGTTCCCTCCTCCAGAGAATCATGTTCAGCTCCCTCAGGTG
GATTAAAATGTTATCTAACTGACAATTGTGAAATTGGTGGAAAGCAATAGAATAAAGGGAGATTTTCTGACCTTTCTT
GGGTTCATATTGTGAACATGAGTCTGGGTGTGACCTTCCCAATGTTTCTGAACTTCCTCCAGATGAGATGTTGGTCTG
```

Fig. 4 (Cont.)

TGTGTTCTTGCTCTTTTCCCTGCTGTGGAGTCCTCTTGTTTCCCCCAGTTGTTCCCTCCCGCAGCTCCAATGTTCTCT
TTTTGTGTTATCACCTTACAGATTTGCTGACTAGAACTGCAGATTAGGGCTCTGATTAAATAAGAAGGAGGGGAGATA
CTTCTCAATGGAACTTAGGTGAAGACCTCTTTTCCCATCTCAGTTCTTAAGGGATTGCCCCAGTGNNNNNNNACTGGT
TTTGGTGGCTTGCCCCTCCAAAAAATTTCTTTGTTCTCCAGTGGGGATATGGAAGGTGGGTCTGAACACTTTTCAGAA
GGGTGGGCACTTTTTCTCTCCTAGACAGACACAATGGGACAGAACAATTTTGGTGACTGTCCCCATTTTGGGGAAAAA
GGATTCAATAGGATAGGAAAACTCTTCAGTCTGTGGTCCCTTAGAAATTCACCCTACAACACATTTACCACACTTGAC
TTCAAGAAATCCAATATATATGTGTGTTTTCATCTTGTAATAGCCTACATTTTACATGCCATACTCTGCCTCAGTTCA
GCTCATACCCCAGCTTTGTTACTCTTTACAAGAACTTGCCTCTCCCTAGATTTCACATTTGCTGTTTATCTTAAAACT
TCAAGTATCTAAAGTATTATTTTTAAAAAATGGCCAGTTGTGGTGGCTCACACCTGTAATCCCAACGCTTTGGGAGGC
TGAGGTATGTGGATCACCTGAGGTCAGGAGTTTGAGACCACCCTGGCCAACATGGTAAAACCTGTCTCTACTAAAAAT
ACAAAAAAAAAAAAATAGCTTGGCATGGTGGCAGGCACCTGTAATCCCAGCTACTCGGGAGGCTGATACTGGAGAATA
GCTTGAACCCACGAGGCAGAGTTTGCAAGTCGTACCATTGCACTCCAGCCTGGGCGACAGAGTGAGACTCTGTCTCAA
AAAAAAAAATTCCAAAATTCCAGCTCCTCTGTTTATCTATTTTTGTTGATACTGTTGTTGTAAAACATAAGTAAAATA
TATTATTCATCTATGTACATTTCCAAGCTGTGTAGAAGAATTTTTAATAAGACCCAGAGTAAAAAAAGAATGCAAATA
TGTAGGGGCCAGCCCTACAGGGTCTGTGGATCTTTCTCCCCATGTGCAGAGATGAGAGATCATAGAAATAAAGGCACA
AGACAAAGAGATAGAAGAAAAAACAGCCGGGCCCAGGGGACCACTACCACCAAGACACAGACTAGAAGTGGCCCCAAA
TGCCTGGCTCTGCTGTTATTTATTGGATACAAGGCAAAAGGGGAAGGGTAAGGAGTGTGAGTCATCTGCAATGATTGA
TAAGGTCATGTGTGTCACGTGTCCGCCAGACAGAGGGCACTTCCCTGTTTGGCAGCCGAGGCGGAGAGAGAGAGGA
CAGCTTAGGTCATTATTTCTTCCATTCTCTTCTCAGAAAGATCAAAGACTTTAATACTTTCACTAATTCTGCTACTGC
TATCTAGAGGGCGGAGCAAGTGTACAGAGTGGAACATGAGAGTGAAACAGGAGTGTGACCGCTGAAGCACAGCATCAC
AGAGAGACGTTTAGGCCTCTGGAGGGCTGCGGGCAGGTTTGACTGATGTCAGGCCTTCCACAAGAGGTGGTGGAGCAG
AGTCTTCTCTAACTCCCCCGGGGAAAGGGAGACTCCCTTTCCAGGTCTTCTAAGTAATGGGTGCCTTCCCAGGCACTG
GCGCTACCGCTAGACTGAGGAGCCCTCTAGTGGCCCTGTCCGGGCGTGACAGAGGCTCACACTCCTGTCTTCTGGTCA
CTTCTCACCGTGTCCCTTCAGCTCCTATTGCTGTATGGCCTGGTTTTTCCTAGGTTATAATTGTAGAGCAAGGATTGT
TATAATGTTGGAATAAAGAGTAATGCTACAGACTGATGATTAATGATATTCATATATAAACATATCTATAACCTATTA
CTAGTACAACTATTCTTATTTTACATATTCTCTTCATTACACTGGAACAGCTTGTGCCCTCAGTCTCTTGCCTCAGCA
CCTGGGTGGCTTGCCGCCCAGACAAATATTGTTAAGCTTCTTAATAGAAAAACAAATTATGGTAAATGTGTTCACTGG
AATACTACCCGTCATTTATAATAAATTAATGCCTGATACACAGAGCAACAAGGTAAAATATCTAAGTATTTATGTTGA
GTAAAATAAGCTAAACAAATAAGAATATATACTATGTAATTTCATTTTTATAAATTCTGATAAATAAAAATGCATCTG
AAGTAAAATAATGAAGATAAGTAGTTGCCTGGGGAAATGGTAGAAGAAGGGAGGGGGAGAGGAGGAGGAATACAGCAG
AACAAAGGGAAATGTTGAGAAGAATTCACTTGTCCACTTTCTTGATAATGATAGCAGTTACATCATTTTTATTAGTT
GTACATTTTAAATATGTGAAGTTTATCATCTTTCAATTAAGCCTCATAAAATGTCTTACAAGCAAACAAATGGAAACT
TAGACAAGGAAAGAGTAATAGAAAGATAGAAAAAATAAGTTCAATGTCAGAAGTACCTGAAAATTAATGTGCCTGGAT
CCTAGTTCTCTCCATATTTTCAGAAGAGGTGCTGGAGGGCAGCAAAACCACACATGCTCTTATTACGGAAAGTGGGTTC
TGATAAAAACACTAGACACATCCAGCTTTGTCCTGGAGTTGGTTTAGGGGGATGTCAGAGACAGTGATGAAGAGCACA
GGGCCAGATACCGGGGTTCACTCATCCCAGACATGAGCTCCTAGATGCATACAGAGCCCCCCCATGTGTGGGTTTACT
TCCACTTCTGTAAATGGAGAAAATATTGTCTCCTACAGAACATAGTTTACATGAATACTTAAAATGAAATAGGGTGAT
TAGTGCAAAGTGTTTATCACAGCACAATTTCATAATAAGACAGCATATTTTCCAAATGCAATCATTGCCAGCAAACTT
CTACAGGGCACCGTCGTCTTATCTGGGTACAGCCTACTCCTCAAGGGTCCCACCCTAGAGCTTGCTATATAGTAGGAG
ATATGCAAATAGGGCCCTCCCTCTACTGATGAAAACCAACCCAACCCTGACCCTGCAGCTCTCAGAGAGGTGCCTTAG
CCCTGGATTCCAAGGCATTTCCACTTGGTGATCAGCACTGAACACAGAGGACTCACCATGGAGTTGGGGCTGTGCTGG
GTTTTCCTTGTTGCTATTTTAGAAGGTGATTCACGGAAAACTAGAGAGATTTAGTGTGTGTGGATATGAGTGAGAGAA
ACAGTGGATATGTGTGGCAGTTTCTGACCTTGGTGTCTCTTTGTTTGCAGGTGTCCAGTGTGAGGTGCAGCTGGTGGA
GTCTGGGGGAGGCTTGGTACAGCCTGGGGGGTCCCTGAGACTCTCCTGTGCAGCCTCTGGATTCACCTTCAGTAGCTA
TAGCATGAACTGGGTCCGCCAGGCTCCAGGGAAGGGGCTGGAGTGGGTTTCATACATTAGTAGTAGTAGTAGTACCAT
ATATTACGCAGACTCTGTGAAGGGCCGATTCTCCATCTCCAGAGACAATGCCAAGAACTCACTGTATCTGCAAATGAA
CAGCCTGAGAGACGAGGACACGGCTGTGTATTACTGTGCGAGAGACACAGTGAGGGGAGGTCAGTGTGAGCCCAGACA
CAAACCTCCCTGCAGGGGTCCGCAGGACCACCAGGGGG
VH 3-48
CGACAGGACACTGAGCACGGGGCTGTCTCCAGGGCAGGTGCAGGTGCTGCTGAGGGCTGGCTTCCTGTCATGGCCTGG
GGCGGCCTCATTGTCAAGTTTCCCCAGGGAACTTCTCCAGATTTACAATCCTGTACTAATATTTGATGTCTCTAAATG
CAACCTTTTTTTCCTTTTTGTGTCTGTTTTTTTTTTTAAAAACAGGAGGACACATCCTCACCTCCACAGAAGCCA
CAGTGTCACTTTGGGGCGGAAATAATCCTTTCGTGGTCAACAGGGTGAGAGTTTTGAGGAATCCCAGGGAAACCTGG
GGAATGTTTTCCAATTAGACTCAGGGCAGAGACCTCCATGGGAATCCCTGATTAGAACAGGCTTTGAGTTCTGATGGG
AGCCAAAAGAGAGGCTCACCCAGGGTCAGGGTTCTTAAAACCTGATGGTTTTCACAGCAATCCCCCTTCATCTTGTGA
AACTGGGCACATCTGACTCAGACTGATTCAGTTGACCCTCTTTCTGCTAATCCATTTTCCTTCCCAGTAGACTTGATT

Fig. 4 (Cont.)

```
CTCACAGATCCCTTTCTTCTTCTCTTTCCTGAAAACAGAGGATGTGTTTTCTGTAGTC▓▓▓▓▓CCTTGATTGAAGTG
CTGAGTAAATGGTTGCAAACATAGGTCTACATTTTTCAAATCATTCACCATAAATTTGAATTATTTATTAATTACACT
CGAATAAAGCAATAAAGAAACTGATGAGATAATATTTGACTGAATTGCATCAATAAATAGATCGATATTAACACAAGG
AATATAACTGATTTCCAAAAACATACACATGAACCGTGGTTCACTCTGCGTATTTAGATAAATTACAGAAAGTTGTCA
TAACAGATGGGGAATCCTGCAGACTTCACTAGGCATGGGCCATGCTGCCCTGGAGTTGTCTCAGGGGAGCTGCCTCCT
CCAGAGGTTAGAGCACAGGCCCAGGTAATAGGACTAAATTTTTAGATGTGTTATCTTAGACACACTGCACAACTGCTG
TGTTCTCTATGTAAATTATCTCCTGTAAAATATAACATTGAAGCCTGCATTAAATATATTGTGTAAATATGTAAGAAT
AAAAGAAAGTTATGAGAGCTAAGTGTTAATCAAGGCACAAGCATATAAGATATAACTATATTTTCCTGAATGATGGAA
TTACTACCAGTCTCCCCCAGGACACTTCATCTGCCCTGAGCCCAGCCTCTCCTCAGATGTCCCACCCAGAGCTTGCTA
TATAGTGGGGGACATGCAAATAGGGCCCTCCCTCTACTGATGAAAACCAGCCCAGCCCTGACCCTGCAGCTCTGGGAG
AGGAGCCCAGCACTAGAAGTCGGCGGTGTTTCCATTCGGTGATCAGCACTGAACACAGAGGACTCACCATGGAGTTTG
GGCTGAGCTGGGTTTTCCTCGTTGCTCTTTTAAGAGGTGATTCATGGAGAAATAGAGAGACTGAGTGTGAGTGAACAT
GAGTGAGAAAAACTGGATTTGTGTGGCATTTTCTGATAACGGTGTCCTTCTGTTTGCAGGTGTCCAGTGTCAGGTGCA
GCTGGTGGAGTCTGGGGGAGGCGTGGTCCAGCCTGGGAGGTCCCTGAGACTCTCCTGTGCAGCGTCTGGATTCACCTT
CAGTAGCTATGGCATGCACTGGGTCCGCCAGGCTCCAGGCAAGGGGCTGGAGTGGGTGGCAGTTATATGGTATGATGG
AAGTAATAAATACTATGCAGACTCCGTGAAGGGCCGATTCACCATCTCCAGAGACAATTCCAAGAACACGCTGTATCT
GCAAATGAACAGCCTGAGAGCCGAGGACACGGCTGTGTATTACTGTGCGAGAGA
VH 3-30
CACAGTGAGGGGAGGTCATTGTGCGCCCAGACACAAACCTCCCTGCAGGAACGCTGGGGGGAAATCAGCTGCAGGGGG
CGCTCAGGAGCCACTGATCAGAGTCAGCCCTGGAGGCAGGTGCAGATGGAGGCTGTTTCCTGTCAGGATGTGGGACTT
TGTCTTCTTCTGACAGTTCCCCAGGGAACCTCTTAAATTTAGAAAACTGTGCCTAACAATGTCTTCTCTATGCATATG
AGGACCTTTTCTCCCTGGCACAAAATGCAGATTGACGCTGACACGGATG▓▓▓▓▓GCTGCTGACATTCCTAGATAACT
GCAGCTGTAGTTATGCCTGCTAAGGTTTGGGCGCATGGGCTTGGCTTTTGTCAGCTCCCTGGGATTTATTTTCCCAA
ACAAAGAAACCTCCAGGTTAGGGGCACCCTATTCATTCCCATCACCTGGCATGATTTAAAGGATAATTGCTTAGAATT
AAAATATTGATCCAGATTTTTTATATTCCCCATCGCTTTTTGTTTCTTCTGGGCTGTAGCCAGAGATCATTGATTGGC
GCTCAGGAATAAGCAGAGTTAGTCTAAAATGCAGGCAAATACTTAAACAACTGAAGAGATTAGAATTTAAAGACAAGT
GTATGATATGTTTTGAAATACAATGTTTCTCTTTCCAGTTTTGGTTTTTGTCAGCAGCAAATAATGATAAGACTGAGT
TGTTTGCAAAATAAACTTTAGTCTTAAACTTGGCCTGCATTATTTGCATAAAGTGCAGCAAGAATATTAATAATAATTC
TGTAGGAAAAGCCTGCAAGCACCAGGAGCTTCACAGTCTAACACTATGAGCACGTGCATCCTCACGCAACTCACTGAA
TATGTCCAAGTCAGCCTGTTCCGATCTTAAATGCCATCCAGTGGCATCTGCCCCAGGTACACTAATACATGGGTCCTG
CTTCTCTCTGCAGCCGCCTCTCTCCTCAGATTTCAGGTTTTGTGTATTGTTTGTTTTCTCTCTGACATCAACACAGAT
ATGTTGAAGGTTTTCTTTTTTTATTTGTAGTTGTTCAGCTTTGTTGTTAATGAGGTCAGAATAAGCTCATAGTTTAC
ACATTTTTACATTCCCATGCCGAGTAGCTGCTTTTCTCTATCAAATCCATTAACTGAGAGAACAATCACATTTCGTTA
CAGGTGAACAGTTAAATAGTTTGGCATATATTTCTGTGCTGGAATCTAATGCAGCTTGAAATCAAGTCATGCCTCACT
CATTGAAAAAAACATGGCTAAATTCTCAAAGAATTGTGCTGAGTGAAAGAAACTAAGGAATGAAGAGTAAATTTTATA
TGATACATTTGTAGAAATTTTAGAAGATGCCACTATTATAAATTAACATGGAGAAGATTTAAGTGTTTCTGAGAATAT
GCTATTGGGAGTAATGGGGATGTGAGTTAAATTTCAGAGGAATAAGAGAAAGATTTAGGGATTAATTTTTTCAAACCT
TGATTGAAGTGCTGAGTAAATGGTTGCAAACATAGGTCTACATTTTTCAAATCATTCACCATAAATTTGAATTATTTA
TTAATTACACTCGAATAAAGCAATAAAGAAACTGATGAGATAATATTTGACTGAATTGCATCAATAAATAGATCGATA
TTAACACAAGGAATATAACTGATTTCCAAAAACATACACATGAACCGTGGTTCACTCTGCGTATTTAGATAAATTACA
GAAAGTTGTCATAACAGATGGGGAATCCTGCAGACTTCACTAGGCATGGGCCATGCTGCCCTGGAGTTGTCTCAGGGG
AGCTGCCTCCTCCAGAGGTTAGAGCACAGGCCCAGGTAATAGGACTAAATTTTTAGATGTGTTATCTTAGACACACTG
CACAACTGCTGTGTTCTCTATGTAAATTATCTCCTGTAAAATATAACATTGAAGCCTGCATTAAATATATTGTGTAAA
TATGTAAGAATAAAAGAAAGTTATGAGAGCTAAGTGTTAATCAAGGCACAAGCATATAAGATATAACTATATTTTCCT
GAATGATGGAATTACTACCAGTCTCCCCCAGGACACTTCATCTGCCCTGAGCCCAGCCTCTCCTCAGATGTCCCACCC
AGAGCTTGCTATATAGTGGGGGACATGCAAATAGGGCCCTCCCTCTACTGATGAAAACCAGCCCAGCCCTGACCCTGC
AGCTCTGGGAGAGGAGCCCAGCACTAGAAGTCGGCGGTGTTTCCATTCGGTGATCAGCACTGAACACAGAGGACTCAC
CATGGAGTTTGGGCTGAGCTGGGTTTTCCTCGTTGCTCTTTTAAGAGGTGATTCATGGAGAAATAGAGAGACTGAGTG
TGAGTGAACATGAGTGAGAAAAACTGGATTTGTGTGGCATTTTCTGATAACGGTGTCCTTCTGTTTGCAGGTGTCCAG
TGTCAGGTGCAGCTGGTGGAGTCTGGGGGAGGCGTGGTCCAGCCTGGGAGGTCCCTGAGACTCTCCTGTGCAGCGTCT
GGATTCACCTTCAGTAGCTATGGCATGCACTGGGTCCGCCAGGCTCCAGGCAAGGGGCTGGAGTGGGTGGCAGTTATA
TGGTATGATGGAAGTAATAAATACTATGCAGACTCCGTGAAGGGCCGATTCACCATCTCCAGAGACAATTCCAAGAAC
ACGCTGTATCTGCAAATGAACAGCCTGAGAGCCGAGGACACGGCTGTGTATTACTGTGCGAGAGACACAGTGAGGGGA
GGTCATTGTGCGCCCAGACACAAACCTCCCTGCAGGAACGCT
VH 3-33
```

Fig. 4 (Cont.)

```
GGGGGGAAATCAGCTGCAGGGGGCGCTCAGGAGCCACTGATCAGAGTCAGCCCTGGAGGCAGGTGCAGATGGAGGCTG
TTTCCTGTCAGGATGTGGGACTTTGTCTTCTTCTGACAGTTCCCCAGGGAACCTCTTAAATTTAGAAAACTGTGCCTA
ACAATGTCTTCTCTATGCATATGAGGACCTTTTCTCCCTGGCACAAAATGCAGATTGACGCTGACACGGATGAAAATT
CCTCAACCATGGTCACAAGGATCAGAGTCCTGAGTAACCTCAGGGCTTCCTGGTGATTCTTCTCCAATCAGACCCAGG
ACAGGGACCTCCGTGAGATTCCCTGACTGGAACAGTCTTTATGGATCCTGGTCACAGACAATAGAGAGGCTGAACCAG
GGTCAGCGTCATGTAGAACGTCACAGATTTCACGTCTGATCCTTCTCCTGACACGAAAGTATGCAAATCAGTATCAGC
ACCGATCTG░░░░░GATGGAAAGATAATACCAACATGAGAAATGTATGACACTCAAGAAAATAAAACTGTAGGAAA
CTTGCTTTTCTTTATATTTGTTAGGTAATCACCACAGTGTGTACACATCACACCATGTTCCCATTACAGAGAAAGGT
TCTGCGAACCTCACGAGCTGTGACCCCTGTGTGCTGGGCTTGGTTCAGGGAGAAGTCAGGTCCAGTGGTGAGAAGCAC
AGGCCCAGATGCCCAGGCTCACTCTGACCAAAAGTGAGCACTGGGGACATTGTAAAACCCACCTGTGCTTTTGCTGAT
AATTTTTTCATCTTTAACATGGAAATAATATTGATACTATATACCATGGTTTCTCTGCGTATGTAAAAATAAAAGATGA
TTGGTGCTAACTTTAAAAATATGCAGTTTATGTAGATCTATGGTACCTCAATAAAACTGTTTTAAAATAAAAATTACA
AAATTATAAGATTTTTAGGTTTTAAGGTTTAAGTTTATCACAAAACAAACTGACAATAGGAAAGCACAATTTCCCAAT
GCTTTCAATATCACAGATCTCCCCGAGGACATTCTGACATGCTCTGAGCCCCACTATCTCCAAAGGCCTCTCACCCCA
GAGCTTACTATATAGTAGGAGATATGCAAATAGAGCCCTCCGTCTGCTGATGAAAACCAGCCCAGCCCTGACCCTGCA
GCTCTGAGAGAGGAGCCCAGCCCTGGGATTTTCAGGTGTTTTCATTTGGTGATCAGGACTGAACAGAGAGAACTCACC
ATGGAGTTTGGGCTGAGCTGGCTTTTTCTTGTGGCTATTTTAAAAGGTAATTCATGGAGAAATAGAAAAATTGAGTGT
GAATGGATAAGAGTGAGAGAAACAGTGGATACGTGTGGCAGTTTCTGACCAGGGTTTCTTTTTGTTTGCAGGTGTCCA
GTGTGAGGTGCAGCTGTTGGAGTCTGGGGGAGGCTTGGTACAGCCTGGGGGGTCCCTGAGACTCTCCTGTGCAGCCTC
TGGATTCACCTTTAGCAGCTATGCCATGAGCTGGGTCCGCCAGGCTCCAGGGAAGGGGCTGGAGTGGGTCTCAGCTAT
TAGTGGTAGTGGTGGTAGCACATACTACGCAGACTCCGTGAAGGGCCGGTTCACCATCTCCAGAGACAATTCCAAGAA
CACGCTGTATCTGCAAATGAACAGCCTGAGAGCCGAGGACACGGCCGTATATTACTGTGCGAAAGACACAGTGAGGGG
AAGTCATTGTGAGCCCAGACACAAACCTCCCTGCAGGAACGATGGGGGGGAAATC
VH 3-23
AGCGGCAGGGGCGCTCAGGACCCGCTGATCAGAGTCATCCGCAGAGGCAGGTGCAGATGGAGGCTGTTTCCTGTCAG
GGTGTGGGACTTCATCTTCTTCTGACAGTTTCTCTAGTGAACCTCTCTAACCTCAGAATTCTGTGCTTACTAATGTCA
TCTCTACGTATTTTTTAAAAGATCATTTTAATATGAGCACCTATTCTCACACGCACCAAATGCAGATTGACGCTTACA
GAGATG░░░░░CACTGGGATTCCTAAGGCCAATTCAGTATTTCAAAAGATGGTGTGAGAAGCACAGGCTGTCACTAA
AGGAGAATTCTGAGCCAGGGCACAGCCACTTTATACTTGGCTGGGGACACTGGTAGGAATATACTCTGTGAGATCAGA
CAGGAACCTCCTTGCAGGGGCAGGGCAGGGCTGCAGGGGGCGCTCAGGACACACAGAGCACAGGCTTCCGCCCCAGAG
CAGGTGAAGGAGGCTGGGGAGGGGTTCCTCTCAGGGCCTGGGACTTCCTTTAAAAAATCTAAAATAAGTATTTCACAA
GGACTGCCGATGTTTATATAAATATCCTATTCAATTGTGAGCATTTATGAAACTCGATGTTGTAATGAGAACCACTTT
TACAATGGGAATTTCAAACTTCCCTAGACATCTTAATAGTAAGCAGCTGGAGGTCAGGAGGAGATCCTTTCTTATAAA
TAAGTGCAATTTTTGGAGAAACACACTCATTCCCAAAATAGCACATTCACATATTAAGGTCTAGAAATGATTCGAGTT
GCCCCTGAGACAGTCAAATGTGGGTTCTAAGTGAGGTGCGTGTCCTGGGGGAGCTTGTTCTCCAGTGGGGAAGCTCT
GTCAACACAGAGTTCAGGGATGGATAGGGGATGCGTGGCCTCTAACAGGATTACGGCTTTAACCCTCAGCTTCTACAA
TTGTGTCGTCCATGTGTCATGTATTTGCTCTTTCTCATCCTGGGTCAGGAATTGGGCTATTAAATAGCATCCTTCATG
AATATGCAAATAACTGAGGTGAATATAGATATCTGTGTGCCCTGAGAGCATCACCCAAAAACCACACCCCTCCTTGGG
AGAATCCCCTAGATCACAGCTCCTCACCATGGACTGGACCTGGAGCATCCTTTTCTTGGTGGCAGCAGCAACAGGTAA
CGGACTCCCCAGTCCCAGGGCTGAGAGAGAAACCAGGCCAGTCATGTGAGACTTCACCCACTCCTGTGTCCTCTCCAC
AGGTGCCCACTCCCAGGTGCAGCTGGTGCAGTCTGGAGCTGAGGTGAAGAAGCCTAGAGCCTCAGTGAAGGTCTCCTG
CAAGGCTTCTGGTTACACCTTTACCAGCTACTATATCAGCTGGGTGTGACAGGCCCTGAACAAGGGCTTGAGTGGAT
GGGATGGATCAACACTTACAATGGTAACACAAACTACCCACAGAAGCTCCAGGGCAGAGTCACCATGACCAGAGACAC
ATCCACGAGCACAGCCTACATGGAGCTGAGCAGCCTGAGATCTGACGACATGGCCGTGTATTACTGTGCGAGAGACAC
AGTGTGAAAACCCACATCCTGAGGGTGTCAGAAACCCCAGGGAGGAGGCAGCTGCAG
VH 1-18
TGAATTTGAGGAGATTACAGGGCTTACAATGTTTAAAGTTGTTTAGAAAATGAGCTGAGCAACTGAGGAATGTAAGTA
ATAGAAACATGGATGCACTCTATATAGGAAATGTTTCTTTCAGCTGTCACCCTATATGCAAAATTCAGAGTGGTAAAG
ACAGCAATCAGTGAGGCTGATGCAAAGAATCCCATGGAGGCCTTGTGCAGACATATAGGTTTTAAAATCAGATAGATA
AATAATTTGGAACAAGATTGCTGGTAACGTGGCTAAGACTA░░░░░CACCTTGGTAACTAGGATGGTTACATCAGGT
TTATCAATTGTACACTTTAAATATGTGAAGTTTATTATCAGTAAACTGAAATTTATAAAATTTATTACCAGCAAACAA
ATGAAAACTTGCACAAGAAATAAGTGACATAAAGATAGAAAAAATATTAAATTTCAGAAACACCTAATAATTTATCTT
CGTGAACCCTAGTTCTCACCATATTTTTAGGTGAATGCTAGAATGCAGCAAAATTACACATGCTCTCAATACAGAAAG
TGGGTTTCACAAACCACACTAGGCATGCTCAGCTCTGTCCTGGAGTTGGGTTAGGGAGTAATATAGGGCCAGTGGATG
AGGAGCACAGGCCTAGATACTGGGCTCACTAACCTCAGGTATGAGCTCTTAGATACATACAAAGCCCCTCCACGCAT
GGGTTTACTTCCCCATCTGTAAATTGAGAAACCATTGACCCCTAAAAATATGATTTACACAAATATGTAAAAATGTAA
```

Fig. 4 (Cont.)

```
GAGAGTGATTAGTGCAAAGTGTTTATCACAGCACAATTTCATAACAAGACAGCAAGTTTTCCAAACAGCATCATTGTC
ATTAGATTCCTGCAGGGCATCATTACCTTATCTGGGCCCTGCCCTCTGTTCAGGCATCCCACCCCAGAGCTTGCTATA
TAGTAGGTGACATGCAAATAGGGCCCTCCCTCTCCTGATGAAAACCAGCCCAGTCCTGACCCTGCAGCTCTGGGAGAG
GAGCCCCAGCCTTGGGATTCCCAAGTGTTTTCATTCAGTGATCAGGACTGAACACAGAGGACTCACCATGGAGTTTGG
GCTGAGCTGGATTTTCCTTGCTGCTATTTTAAAAGGTGATTTATGGAGAACTAGAGAGATTAAGTGTGAGTGGACGTG
AGTGAGAGAAACAGTGGATATGTGTGGCAGTTTCTGATCTTAGTGTCTCTGTGTTTGCAGGTGTCCAGTGTGAGGTGC
AGCTGGTGGAGTCTGGGGGAGGCTTGGTAAAGCCTGGGGGGTCCCTTAGACTCTCCTGTGCAGCCTCTGGATTCACTT
TCAGTAACGCCTGGATGAGCTGGGTCCGCCAGGCTCCAGGGAAGGGGCTGGAGTGGGTTGGCCGTATTAAAAGCAAAA
CTGATGGTGGGACAACAGACTACGCTGCACCCGTGAAAGGCAGATTCACCATCTCAAGAGATGATTCAAAAAACACGC
TGTATCTGCAAATGAACAGCCTGAAAACCGAGGACACAGCCGTGTATTACTGTACCACAGACACAGTGAGGGGAGGTC
AGTGTGAGCCCGGACACAAACCTCCCTGCAGGGGCGCGCGGGGCCACCAGGGGGCGC
VH 3-15
TCGTGACCCACTGAGGGCGGGACAGGTCCCAGGAGCAGGTGCCGGGAGAGGTTTCCTTTCTCCTCAGCTGGAAAAGTC
AGGTTTATCTTCGCAGGACTCTGGAGTCTTCTAGGCTGTG░░░░░AGTGCAATGATATAGTTTAGATGTTTTCCCTT
CCAAATGTCATGGTGAAATGTGATTCTCAATGTTGGAGGTGGGACCGACTGGGAGGTTTTGGGTCATGGGGAAAGATC
CTTCAGGAATGGCTTGGGAACCACCCCATGGCACTTAGTGAATTCTTGCTGTGTTAGCTACTATGAGATCTGATTGTT
AAAAAGAGTCTGGCAACCCTTCTTGCCACTCATGTCCCAGCTCTCACCATGTGACATAGCCTGTTCCCCCTTTGCCTT
CCATCATGATTGTAAAGCAGATCCTGGTGCCATGCTTCTCACACAGCCTTCAGAACTGTAAGCCAAATGTGCCTCCTT
TCTTTGTAAATCACTTGGCCTCAGGTATTAATTTATAGGAATGCAAAAGAGACTAACACACCGTCCAAAGCATTACAC
AGATTCAACACTATTTTTATCAAATGACCAATATAATTGATTACATATTTAGAAAAAAAATACTAAAATTCCTACAGA
ATCAAAAAGAGTCTGAATAGCAAAAGCAATCCTAAGCAAAAAGACCGAAGCTGGAAGCACCACATTCTCTGACCTCA
AATTATACTACATGAATATAATAAGAAAGACAGCATGCTACTAGTAGAAAAAAACAGCCCAGAAAGAAAGCCAAATAT
CTAAAACCAACTGTTGTTTGACAAAACTGACAAAAATATACACTGGAGAAACAACCCTCTATTCAATAAGTGGTGCAG
GGAAAATTAGGTGGCTTATGTGGAAGAATAGAACGAGACTTCCATATCACCGTAGACACAAATTAACTGAATATGGAT
TCAGTGTTTAAATTTATAAACTAAAACTATAAAAATACTTGAATAAAATCTAAAAAGAGTCCTCTGGACATTGGTCTA
AGCAAACAATATACGACTAAGACTTCAAAAGCAAATGCAATAAAAACAGAAGTAGACAAACAGGATTTAGTTGAACTA
AAGGTCTTCTGCACAGCAAAAGAAATAACCAACATGGTGACCAGACAATCTGCAAATGGAAAAAATATCTGGAATCTA
TTCATCTTGCAAAGGGCTAATATATAGAATCTACAAGTAACTCAAATAAGTCAACTAAAAATTACAAATAACTTCATT
AAAGAATAGACATAAACAGACATTTATCAAAAGAATACACAGAAGTGGCCAACACAAATAAGAAAATATACTCAGCAT
CACCAATCATCTGATAAATGTAAATTAGAAACAACGTGATACGGCATCTTCCACCAGTCAGAATGGCTGTTATTACAA
ATAAAAACAGCAGGTTTTTGCAGACAAACATAGGAAAAATAATGATTTATATATGCTTGGTGAGAATGTAAATTAGTA
CAACCTCCATGAAAAACAACATAGAAATTTCTCAAAGAACTAAAATTAGAATTACCATTTCTTCCAGTGAGCTGTCCC
AGTAGGCATGTTCCTCCCAAACTTTTATATCAGAGAATGTTGCCTGCACTCATATGTTTATTTCAACACCATTTTCAA
TAGAAAAGTCAAATAATCTAAGTGTCAATCAGTGGATGATTAGATAAAATATGATATATGTAAATCATGGAATACTAT
GCAGCCAGTATGGTATGAATTCAGTGTGACCAGCCCCTGGACAAGGGCTTGAGTGGATGGGATGGATCATCACCTACA
CTGGGAACCCAACATATACCAACGGCTTCACAGGACGGTTTCTATTCTCCATGGACACCTCTGTCAGCATGGCGTATC
TGCAGATCAGCAGCCTAAAGGCTGAGGACACGGCCGTGTATGACTGTATGAGAGACACAGTGTGGAGACCCACATCCC
GAGGGAGTCAGAAACCCCGAGGGAGGAGGCAGCTGTGCTGAGCTGAGGCAGTGGTGCAGCAGTTTCTTTAACTTCCAT
ATGATCTCATTTTGCATCATCTTCTACTTTTATATTAGCTAAGAACTTGGGGTAGACAGGTGCTCCTAAGAGATCCTT
AACTTGCCCATTTTGATGGTTTTCCAGAAGACGTGAGAAGCCACTTTGTTAGCAAAGCATCCCAAATCCATGCCCTGT
TCTAGATACATGTGAGCCCATTTCCTGGTCTTTGCTTAACTGACAAGCTCTCATCAGTGCACCTGGGCTAATTTCACA
TCAGGTAGAGGAACGCGTTATAAAGGAAAGCTAATGTTGTAATGGCAATTCCTGCTTAAAAACCTTCAGCTTCATTGT
TTTTGTGTAATCCATCAGCAAATTATGTTAGTTCAAGGTTCTCAATGGGAGTTTCTAATAAATAGAAAGGTTGTATAG
AGCTTCCCCTAATTAAAATGAAACAATTGTGAACTCAACCTCGGTATTCAGCCATGTCTCCACCCTTCACACCCTTCG
CCACAAAGGAATTTTCACCTCTCCTGGAAGCTGGGTTCATTTTCAAATTAGTTATTTTTTCAATGTAATATCTCAAG
ATTATCGTATATGACTATTTTAGCAGAAAGTGAATTATGGGAACTTGAACTAAACAACTGAAAACAAATTCACAACTA
ATTAAACAAGATGCCAGAATGTGATTGGCTCCAGGCTTTGTAATTCAGCAGTTCATGTACCCAGACTGGAAATTTACA
TGTCTTCTTGTTACCTTCACAGCACAGTCAACTCCCATTATGTAAGAAATGGTGACTGCATTCCCAAGGGTTATGCAT
AGATATGAAAATAGACTGGGTAAGGTGAGGAGTTGATTGTTTAAATTCCCCTCTGAAGAAGCAGCATCAACTCAACAA
ACCACCTCTCTTCACTCTGTGACTAGAGCTATGTCACAGGCCACATGGACCTAAATCCTTGATGGATATAACATGACT
ACATAAATTGGGCTGATCATTTTTATGCTATAAAATTAATAGATGACACTGCACTCCAGCCTGCACAACCAAGCAAGT
CTTCATCTGTAAAATCTAAAAAAGAAAAATTAGTAGGTACTGACTTCGAAATTTTTGATAATAATATTTTCACCACCC
AAATTTAATCACACCCACATGTTACCTGCATCTTCACTGAAAAGTTCCCAGTCACGATGAGTTCCTTCAATGCTCCAT
GTGTTCAAATCTGGACATCAAGAGAGTCCAGAATAAAACACAATGACGGCAGTGAAACTGATATATATTCAGCACC
TCTTAACTCAGGAGGACTCCATACACCCTGGCACACAGCTGCTTTTCTAAATGGCTCACAATGACTCCAGCTCACTCA
CAGAGCTCAGACAGAAACCTCCCTTCAGGGTGGGAGCTGGGTGGCAGGGGGCACTCAGTACCCGCAGAGGTGAAAATG
```

Fig. 4 (Cont.)

AGTTTCAGATGGAACTTCCCTGTCACCTCAACATGGAATTTATTGTTCCATTTCATTACCTCTCTTTCCATAATGGTT
CATTTCTTTTGGCCTGTTCATTACTGATATTTTTCAGAGCAATCTCACTTGAATCTTTACTCTTTTGCATTTTGTCTC
CTTGACAATGTTGGGAAGTTTTACCTCCAGCATCATAACATGATCTAGTGATCTGACACATTGTGCAAACAATACCTA
CAAATTCAGAACCTCTTTGTTTTTCTTTCCACAAAATATAATTCTTTCTGTTCTGTGTATGAGCATGTCTTAGCAACC
CTGTACACACCCACATAGATGTCTACAAGCCTATGAATTGTTCTCTGTAAATAAAAATTTATCTCAAATTCCTTCAAT
GTTCATAATTCTGAGAGTGAGGAAGGTCCTTCTCAATCTGTTCAAACAAAATGCCCAGAGACCATCCAGTAGGTAAGG
AGTTCACCTGGCTCTGGTGTGGGGTCTGTCTCTTTCCCTCTGTTGTCCCACAGGTCAGCCCAGTTGTTCACGTCCTAA
CAAGAAAGCCCAGGTTTGTCCTGATTTTAAAACACATCAAACTTCTGATGACTCTCCTGTTACCCACATCCATGGAGA
TAGATTATTTATTATATAATTCAGCAAACTAATGTCAAATGCCCAAGTTGCAATACCGCACATCCTAGGGTATGTTCA
TGCAATTCAATGGAGGAGAAAATCTTTCAGAGACAGATGGATCTGAAATGATAAATATGTGGGTAAGGACTCTGGGCT
TGAGTATCATTGTCCAGCCATGTTTCACAAGTGTGTCCTGTCAGGGAAGGATCAGAGTTCCTTGTGCTCTCAGAGGGA
AGGGGTCACAGAGTTCCTCTCTGGTTCCCAGGAAAGGTAATCGCACTAATCTTCATGATCTTCATGAGACTATCCTCC
AGTGCTGACCTGTTACGGAGTTTTTGTCTGAAGTTCTCACTGCAATCCCCAATCTACATATTTTCAATCAGAAGTGTT
TAGAGGGCAGGACACATCTTCAAGGTCACACATTGAGAAGGATGGAGATATGTCCCACTACCTTCTCCTACGATCTCA
GACAGAATCCCAAATTTCAAAAGGACACAGAAGGACAGCTCTCAGGTGCTTTTAAAAAATGACCCACTTCCAGGGACA
GTGAGCTTCCCTGTAACCATGGTGGATGTTCTGAACTACAATAAACATTGGATGGATCCAGTATTGTTTGAAGTCACT
GTCATTATTACATTCAGCTGTTGTTTCAATGTGTCTGAAAGGGTAAATGACTATTTAGATGGCCTGGGTGTGTGGTTG
GTTTTATATGAATCTTTAAGGGTTGAACAGTATTGACCCTATTCCACAATCTGTCCTTGATCCATGATCACACTCATC
TCTCAGACAAGCTCCTTCAGCACATCTCTTTACCTGGAAGAAGAGCACTCTGGGCTTGGCGAGGGGAGCCCCAAGAAG
AGAACTGAGTTCTCAAAGGGCACAGCCAGCATTCTACTCCCAGGGTGAGCCCAAAAGACCGGCGCCTCTCTCATCCCT
TTTCACTGCTCCGTACAAAGGCACCACCCACATGCAAATCCTCACTTAGGCGCCCACAGGAAGCCACAACACATTTCC
TTAAATTCAGGTCCAACTCATAAGGGAAATGCTTTCTGAGAGTCATGGACCTCCTGTGCAAGAACATGAAGCACCTGT
GGTTTTTCCTCCTGCTGGTGGCAGCTCCCAGATGTGAGTGTTTCACGNNNNNNGATATGAAGATATGAGAAACTGCCT
CTGATCCCAGGGCTCACCGAGGGTTTTTCTGTTCACAGGGGTCCTGCCCCAGGTGCAGCTGCAGGAGTCGGGCCCAGG
ACTGGTGAAGCCTTCGGAGACCCTGTCCCTCACCTGCACTGTCTCTGGTGGCTCCATCAGCAGTAGTAATTACTACTG
GGGCTGGATCCGCCAGCCCCCAGGGAAGGGGCTGGAGTGGATTGGAGTATCTATCATAGTGGGAGCACCTACTACAA
CCCGTCCCTCAAGAGTCGAGTCACCATATCCGTAGACAAGTCCAAGAACCAGTTCTCCCTGAAGCTGAGCTCTGTGAC
CGCCGCAGACACGGCCGTGTATTACTGTGCGAGACACACAGTGAGGGGAGGTGAGTGTGAGCCCAGACAAAAACCTCC
CTGCA
VH 4-b
GGGAGGCTGAGGGGACCGGCGCAGGTGCAGCTCACGGCCAGCAGGGGCGCGCGGAGCTCACGGAATACAAGGCCGGG
TCAGGAGCAGGTGCAGGGTGAGCGGGGCTTGCTCATCTTCTCAAACATCTCCCTCCTCGCCAGCACCTCAGCTTTCCG
TAGAGGTCCTCTTTCTTTATTGTCTGTGGTTCTACTTCCTCACATCCTTGTGCCAGGAAAGAAAGGAGTAAGGCAAAT
TTTCCTGTTACAATTGAAGTTTCACCAATTACTAAAAACTTTCCTGCAAGTACCTGCACAGCCCATTATACCTTATTT
ATATATATATATATTCTAATGCTTCTCACCATCTCTTGATTTGTGTCATCAATTTAATTGTGCCCTTTTTGAAATTCA
TATGCTGAAACTTTAAATCCAATGGATCTATATCGGAATTTTAATGGTATAATTAACGTTAAATGTGGTCATAAGTGA
GACCCTAATGCAATAGACCTGTTGTCTTTATAAGAAGAGGAAGAGACACCAGAGACCTCTCACTTCTCACATGCACAC
AGAGAAGAGGCCACGTGGAGACATAGTGCACTAGAAGGTGGGCCTCTGCAAGCCAGGAAGAAGCCGCACCAAGAACCA
ACCCTGCCAGCACCTTGATCTTCTACATTCAGACTGCAGAATTGTAAGAAAACCAATATTTGTTGTTTAAGCCACCCA
CTCCTTTTGTCTTCTTACGAAGACCCAGACAGGCTAATACCACACAACTCTGTTAGCTCCATCTCCTGGAGGGAGAAG
CAGCCCCCTGAGGCTGGGCACATCGCTCAGATTTTCACATGAATTAGGCAAAAACAGTAGCTCTCATATAAAAACTGT
CACGTCCCTGTTGGGACAAGGTCTTCTAAACAACCCCTGGGGCTTTGTCACAAATGTTGCATTTTATCCTTTATTAGG
ACTTAACTAATTGACAATGAGTACCAGCTGGATGGAAACTGACCACTGACCATCTTCTGCTGTCTCCTTATTATATCA
CAGAAAACCACAGCAACATTACTCTATGTCTTCAACTTTCTAAATTTGTACTGAATCTATTGCTAAATGAGGAGCTAC
ATGGGGTCTGAGTTTTGTTATCTTCTCCCAGTCTTCCCCAATTACCAAGCACAGAAGATACTTTCAGTGAAATTTAG
CTGTCAATGCCCCCAACACCACATCATGTTTTAAGGTCCAAGGACTTTCTTTGGGGGCTATTTAAAAACACTTTTGA
ATGGAAAATCCTAAAGCATACAACAGCTGAAAGAATGGCCCCTGTGCACGTGAAGGCTGAAGGGATGGATGATAGGGT
ACGTTCCTCCAAGGTGTTCCTGGGCATGTGATGGTTGGATACCTCATG░░░░░░░CTATGGATGTGAACTACAAGTATG
TAAGTACTTCAAGTAATTCTATTTAATGGAGTTTGAAATAAAACTCAAACTTATTCAAAACACTAATTACTTGGTATT
TATTTTGAGATCTATGAGTTTATCAAGAAATTCAAATTCCTATTTCTATTTAAACTCCCGATTCCTACTCTCAGTGGG
AGGGAAAACTCACAGCCAATCACACATCACAGGACAAATCTGTAAACGAAGAGTCATTCCTCTGAAGGTCCTGGGTGT
TCAGGACTCTCAGGCAGGTGCTGAGGACCCTGTCTTGGGAGTGCCCAGCAGATCTCAGAACCCTACATGGGCCTGCT
GGACACTCATGTGGGATAACTAGTCGCCACTTATTCAGAGTTACCAGTGAGCTTTGACTGTTCCGAATGGGACCAGCA
TGGAGTCAAGGTGCCTGCTCAATGTCAGAGACAGCGATGGTCTCAGAAACAATCCAGGTAATCTCTAGGCCAATAAAA
TGTGGATTCACAGTGAGAAGTACATCCTGGAGGTGGAGCTTGTTCTTCAGTGGGAAGAGTGCTGTGCACAGAAAGCTT
AGAAATGGGGAAGGGGGTGCGTTTCCTCAGGCAGGATTAGGGCTTCGTCCCTCAGCGTCCCACTCTTGTATGGCTGAT

Fig. 4 (Cont.)

```
GTGGCATCTGTGTTTTCTTTTTCATACTAGATAAGGCTTTGAGCTGTGAAATACCCTGCCTCATGAATATGCAAATAA
CCTGAGCTCTTCTGAGGTAAATATAGGTATATTGGTGCCCTGAGAGCATCACTCAACAACCACATCTGTCCTCTAGAG
AAAACCCTGTGAGCACAGCTCCTCACCATGGACTGGACCTGGAGGATCCTCTTCTTGGTGGCAGCAGCTACAAGTAAG
GGGCTTCCTAGTCTCAAAGCTGAGGAACGGATCCTGGTTCAGTCAAAGAGGATTTTATTCTCTCCTGTGTTCTCTCCA
CAGGTGCCCACTCCCAGGTGCAGCTGGTGCAGTCTGGGGCTGAGGTGAAGAAGCCTGGGGCCTCAGTGAAGGTCTCCT
GCAAGGCTTCTGGATACACCTTCACCAGTTATGATATCAACTGGGTGCGACAGGCCACTGGACAAGGGCTTGAGTGGA
TGGGATGGATGAACCCTAACAGTGGTAACACAGGCTATGCACAGAAGTTCCAGGGCAGAGTCACCATGACCAGGAACA
CCTCCATAAGCACAGCCTACATGGAGCTGAGCAGCCTGAGATCTGAGGACACGGCCGTGTATTACTGTGCGAGAGGCA
CAGTGTGAAAAACCACATCCTCAGAGAGTCAGAAACCCTAGGG
VH 1-8
GAGAAGGCAGCTGTGCTGGGCTGAGGAGATGACAGGGGTTATCAGGTTTAAGGCTTTTTTGAAAATGGGTTATATATT
TGAGAAAAAAATAACAATAGAAACAAGTACACACTCTAATTTTAAGAGATATATTCAATTCAAGAATTGTAGAAGCCG
AATTCACAGTGGGAAAGGCCACACTCAATAAAGTTGATAAAAACATTCCAGGAAGGTGCTACTG       CCTGTGTT
TATCTGTTATGTTGATGCTGTAAAACAGTAAGTAAAATATACTCCTCATCTATGTACATTTTGAAGCTGAGTTGCAGG
TTTTTTGGTAAGACCCAGAGTCACAGAGAATTCAAATATTGTTAAGCTGCTTAATAGAAAAACAAATTATGGTAAATG
TGTTCACTGGAATACTACCCATGATTTATAATAAATAAATGCCTGACACACAGAACAGCAGCAAAACCACACATGCTC
TTATTACAGAAAGTGGCTTCTGAAAACCACACCGGGCACGTACAGCTTTGTCCTGGAGTTGGTTTAGGGGATGTCAG
AGCCAGTGACGAGAAGCACAGGGCCAGATGGCAGCGTTCACTCATCCCAGACATGAGCTCCTGGATGCATACAGAGCC
CCCCCATGTGTGGGTTTACTTCCACTTCTGTAAAAGGAGAAAATACTGACTCCTACAGAGCATAATTTACACATTTTT
TAAAAAATGTAATAGGGTGATCAGGGCAAAGTGTTTATCACAGCACAATTTCATAAGACAGCATATTTTCCAAATACC
ATCATTGTCAGCAAACTTCTGCAGAGCACCGTCTTCTTATATGGGTACAGCCTATTCCTCCAGCATCCCACTAGAGCT
TCTTATATAGTAGGAGACATGCAAATAGGGCCCTCCCTCTACTGATGAAAACCAACCCAACCCTGACCCTGCAGGTCT
CAGAGAGGAGCCTTAGCCCTGGACTCCAAGGCCTTTCCACTTGGTGATCAGCACTGAGCACAGAGGACTCACTATGGA
ATTGGGGCTGAGCTGGGTTTTCCTTGTTGCTATTTTAGAAGGTGATTCATGGAAAACTAGGAAGATTGAGTGTGTGTG
GATATGAGTGTGAGAAACAGTGGATTTGTGTGGCAGTTTCTGACCTTGGTGTCTCTTTGTTTGCAGGTGTCCAGTGTG
AGGTGCAGCTGGTGGAGTCTGGGGGAGGCTTGGTCCAGCCTGGGGGGTCCCTGAGACTCTCCTGTGCAGCCTCTGGAT
TCACCTTTAGTAGCTATTGGATGAGCTGGGTCCGCCAGGCTCCAGGGAAGGGGCTGGAGTGGGTGGCCAACATAAAGC
AAGATGGAAGTGAGAAATACTATGTGGACTCTGTGAAGGGCCGATTCACCATCTCCAGAGACAACGCCAAGAACTCAC
TGTATCTGCAAATGAACAGCCTGAGAGCCGAGGACACGGCTGTGTATTACTGTGCGAGAGACACAGTGAGGGGAAGTC
AGTGTGAGCCCAGACACAAACCTCCCTGCAGGGGTCCCTTGGGACCACCAGGGGCGA
VH 3-7
CAGGGCATTGAGCACTGGGCTGTCTCCAGGGCAGGTGCAGGTGCTGCTGAGGGCTGGCTTCCTGTCGCGGTCTGGGGC
TGCCTCGTCGTCAAATTTCCCCAGGAACTTCTCCAGATTTACAATTCTGTACTGACATTTCATGTCTCTAAATGCAAT
ACTTTTTTTGTCCTTTTTGTTTCTTTGTTTTTTTGCAACAGGAGTACATATCCTCAGCTCCACAGAAGCCAGGG
    CATGGTCAGTGTCATATAGAATATGGGGACCCTCACAAGTTTTTTGTCTGACCCTTCTCCTGACACTAAATTATGC
AAATTAATAACACTGATCTGGTGCTTCTTTTGATTCTAATTTATTTTATTTTTAGTTGTCGTTCTCACTTTTCCTTTG
GATTTTCCTGCTCCCTGGAAAAGGTAAATGTGGTCTCCGTGACCTCAATTCAAGGGCTGAAGCCCTTTCCCTGTAGCT
CAGCTGGGGCTCAGGCTGTGGCTACTGCAGCCATGTGGAAGAGGCTGAAGGGACTTTCTTCACTCTCCTTGCTCAGGA
CCATCCACTGTATTGTGTATAGGCTTCTCTGGAAATGCAAGTGGCCATTTGTAGTGAAAGAAATATGTTTGTCTGGTT
AAAATGGGAGGTGGATGTAGAGTTAATTGGCTGCTACATAAACTGTCCTTCTCCACCAGTGCTTTTAGGATGAGATTG
TGAAATTTGTAAGAATCAAAATGGAGTCACATATGTTAAAACCCTGACAAATGGATTCAGGAAGTGTAGGGAGAATTC
TTACACACATATCCCTGACAACAAGAACTATCATAAAATAGTTCTTGCAAAAAGACCAACATGACCTCATAATCATGA
CTTCTGCAAAGACTTCTACTCAGAATCTACTTGCCCAGCCTTAGATTAATGCCATCTGAATTACACTGATCATGTTAC
TATCACTGCTCCTCACCACAGATGCAACACCCTCCTGAGTCCTGAAACCTGACTCCATCCCATAGAGTAGGGCACAGA
TGAGGGGAATGCAAATCTCCACCAGCTCCACCCTCCTCTGGGTTGAAAAAGCCGAGCACAGGTCCCAGCTCAGTGACT
CCTGTGCCCCACCATGGACACACTTTGCTCCACGCTCCTGCTGCTGACCATCCCTTCATGTGAGTGCTGTGGTCAGGG
ACTCCTTCACGGGTGAAACATCAGTTTTCTTGTTTGTGGGCTTCATCTTCTTATGCTTTCTCCACAGGGGTCTTGTCC
CAGATCACCTTGAAGGAGTCTGGTCCTACGCTGGTGAAACCCACACAGACCCTCACGCTGACCTGCACCTTCTCTGGG
TTCTCACTCAGCACTAGTGGAGTGGGTGTGGGCTGGATCCGTCAGCCCCCAGGAAAGGCCCTGGAGTGGCTTTCACTC
ATTTATTGGAATGATGATAAGCGCTACAGCCCATCTCTGAAGAGCAGGCTCACCATCACCAAGGACACCTCCAAAAAC
CAGGTGGTCCTTACAATGACCAACATGGACCCTGTGGACACAGCCACATATTACTGTGCACACAGACCACAAAGACAC
AGCCCAGGGCACCTCCTGTACAAAAACCCAGGCTGCTTCTCATTGGTGCTCCCTCCC
VH 2-5
CACCTTTGCAGAACAGGAAAGTGCAGCTGAGATACGTTTTCCTGCCAGGGCCTGCATTTCCCATCCCCATTAGACTCA
GAGCCCTGTCTTCCTCCTTCTTCTTTAATAATAAATGGCATGACTCCTGTTAATAGTTCATAGAAGCAGAAGCTGAGT
CCTGTTTGTCAAACATTCAGCATGAAATGTTCATGTTACCTGGGCCAGATGCATCACTGGTATGTGGCCGCCAG
```

Fig. 4 (Cont.)

```
▓GGTCACACATTGAGAATGATGAAGATATGTCCCACGAGTTTTTCCTAAGGTCTCAGAAAGAATTCCAGGACTCAAA
AGGTCTCAGAGGGCAGCTCCCAGTGCCTTAATTAAAATGGTGGCTCAGGCCTGTAATCCCAGCATTTTGGGAGGCTAA
GGCAAGTGGATCACCTGAGGTCGGGACATTGAGACTAGCTTGGCCAACATGGTGAAACCTTATCTCTACTAAAAATAT
AAAAATTAGACGGGGGTGGTTGTGCGTGCCTGTACTCCCAGCTACTCGGGAGGCTGAGGCAGGAGAATCACTTGAACC
CAGGAGGCGGAGGTTGCGGTGAGCCGAGATCGGGACACTGCACTCTAGCCTGGGCAAAGGAGCAAAAGTTCATCTAAA
AAATTTATTTTAATTTAAAAATTTTGAAAAAATGGCCCACTCCCTAGAACAGAGAGATTCCCTCTAAACATGATGGAG
GTCCCGAACTATACATTAAGTGAATCCTGGTGTGTCTGAACTCACATGATTATTACGTTAAGCTGCTGTTCCAATCTA
CTTCCTCACCTGGGAAAAGAGGAGCCAGGGCATGGCTAGTTGAGGCCCCAGGAAGAGAACTGAGTTCTCAAAGGACAA
AGCAAGCATCCTCATCCCAGGGCGAGCCTAAAAGACTGGGGCCTCCCTCATCCCTTTTCACCTCTTTATACAAAGGCA
CCACCTACATGCAAATCCTCACTTAGGCACCCACAGGAAACCACCACACATTTCCTTAAATTCAGGGTCCAGCTCACA
TGGGAAATACTTTCTGAGAGTCATGGACCTCCTGCACAAGAACATGAAACACCTGTGGTTTTTCCTCCTGCTGGTGGC
AGCTCCCAGATGTGAGTGTCTCAAGGCTGCAGACATGGGGATATGGGAGGTGCCTCTGATCCCAGGGCTCACTGTGGG
TCTCTCTGTTCACAGGGGTCCTGTCCCAGGTGCAGCTGCAGGAGTCGGGCCCAGGACTGGTGAAGCCTTCGGAGACCC
TGTCCCTCACCTGCACTGTCTCTGGTGGCTCCATCAGTAGTTACTACTGGAGCTGGATCCGGCAGCCCCCAGGGAAGG
GACTGGAGTGGATTGGGTATATCTATTACAGTGGGAGCACCAACTACAACCCCTCCCTCAAGAGTCGAGTCACCATGT
CAGTAGACAAGTCCAAGAACCAGTTCTCCCTGAAGCTGAGCTCTGTGACCGCCGCAGACACGGCCGTGTATTACTGTG
CGAGAGACACAGTGAGGGGAGGTGAGTGTGAGCCCAGACACAAACCTCCCTGCAGGGA
VH 4-4
GGCTGAGGGGACCGGCGCAGGTGCAGCTCAAAGCCAGCAGGGGGCGCGCGGGGCCCACAGAGCAAGAGGCCGGGTCTG
GAGCAGGTGCAGGGAGGGCGGGGCTTCCTCATCAGCTCAGTGCTCTCCCTCCTCGCCAGGACCTCAGCTGTCCCCAGG
CCTCCTCTTTCTTTATTATCTGTGGTTCTGCTTCCTCAC▓▓▓▓▓GTCACTGAAGGAGCATTCTGAGCCAGGGCACAG
TCACTTCCTAGTGAGCTACAGAGGCTGAGAGAAAAATGCTCTGTGAGACCCAATGGGAAGCTCCCTGCAGTGCAAGGT
CTGGGTGGCAGGGAGCGCTAGGGCCTCGCCCAGCACAGGCTGCAGCCCTGGAGCAGGTGCAAGGGAGGCTGGGGAGGG
GTTCCTCCCAGGGTCTGATGTCTTCCTTTTCTCGGACAAACATGCTTTAATAAGTTAAACAAGACTTTAGTAAAGACT
ATTGATGTGTCTTTGTGTCTTTCAGTATACAGTTCTATTTGTAGGATTTATCTAACCTAACAAGTCAATGAGAATCAC
ATGTAAAAGGAGAAATTTCTAGGATTTTCAGATATCTTAATAGGTAGGAGATGGAGAAAAGGGATGGTTTTATTAATT
CAGTGCTTGCCAATCTTAACAGAGACAGTAGTAAGACATGCAGAAAGCAAAGCCCAGAAAAGTATGAAGGTGTCAAAG
TGCCATTTAAGTATGGGTTCACTTGGAGGACCATGTTCTGCGGGAACTTGTTTTCAGCAGACAATCTATTTTAGCAGA
GTTCTGGGCATACAAGGGGACACACATCATTAAACAAGGATTGGGACAGGGACTTCAGCGTCCCACTGTTGCATGGCC
CATAAATTATGTGTGTTCTCTTTCTCATCTTGGATCAAGTCTAGAGCTATGAAATAGTATCCCTCATGAATATGCAAA
TAACCTGAGATTTACTGAAGTAAATACAGACCTGTCCTGTGCCCTGAGAGCATCACCCAGCAACCACATCTGTCCTCT
AGAGAATCCCCTGAGAGCTCCGTTCCTCACCATGGACTGGACCTGGAGGATCCTCTTCTTGGTGGCAGCAGCCACAGG
TAAGAGGCTCCCTAGTCCCAGTGATGAGAAAGAGATTGAGTCCAGTCCAGGGAGATCTCATCCACTTCTGTGTTCTCT
CCACAGGAGCCCACTCCCAGGTGCAGCTGGTGCAGTCTGGGGCTGAGGTGAAGAAGCCTGGGGCCTCAGTGAAGGTCT
CCTGCAAGGCTTCTGGATACACCTTCACCGGCTACTATATGCACTGGGTGTGACAGGCCCCTGAACAAGGGCTTGAGT
GGATGGGATGGATCAACCCTAACAGTGGTGGCACAAACTATGCACAGAAGTTTCAGGGCAGGGTCACCATGACCAGGG
ACACGTCCATCAGCACAGCCTACATGGAGCTGAGCAGGCTGAGATCTGACGACATGGCCGTGTATTACTGTGCGAGAG
ACACAGTGTGAAAACCCACATCCTGAGGGTGTCAGAAACCCAAGGGAGGAGGCAGCTG
VH 1-2
TGCTGGGGCTGAGAAATGAAAGGGATTATTATTTTTAATGTTGTTTACAGTATGTCATTAATAAATTGAAAAAAAGTA
ACAATAGAAGTATATACTCTAATTATATGGGAACTTTGTTTTTTCAGTTTTTTCATTTTTTTTTTTTTTTTGGTTTG
TTTGTGACAGAGTCTCACTCTGCCACCCAGGCTGGAGTGTAACGGCACAAT▓▓▓▓▓GAGCATGTGCACATTTCATTA
AACCCACTGTGTATGCAGCCCCTCCCAAGTGCTGGCAGGCCACTGTACATGTGGGCAGCCCACTCCAAGGGAAGAATC
AAGGGAGAAGAAATACAAACCCCAGAACCATGTCAATGTATAAAACCCCAAGTCAAGGGCCGGACAGAGCACTTAGAT
CTCTCAAGTCGCCCACTTAGCCCTCTTCCAAGTGTACTTTACTTCCTTTAGTTCCCACTTTAAAACTTTAATAAACAT
TTACTCCTGCTCTAAAACTTGCTTGGGTCTCTCACTCTTCTGTATGCCCCTTGGCCAAATTCTTTCCTCCAAGGAGGC
GAGAATCAAGTTGCTGCAGACCTGTATGGATTCGCTCCTGCTAACAGATAGCTGGATGGGTGGACAGATGCATGAATT
AGTGGATGGACGTTTGGATGTGTGGGTGGGTGGGTGGATTGTGGGATGGCTGGATGAATGCATGGCTGGATGGGTGGA
CAGATGCATGAATTAGTGGATGGATGTTTGGATGTGTGAGTGGGTGGGTGGATTGTGGGATGGCTGGATGAATGCATG
GCTGGATGGGTGGACAGATGCATGAATTCGTGGATGGACGTTTGGATGTGTGGGTGGGTGGTTGTGGGATGGC
TGGATGAATGCATGGCTGGATGGGTGGACAGATGCATGAATTCGTGGATGGACGTTTGGATGTGTGGGTGGGTGGGTG
GATTGTGGGATGGCTGGATGAATGCATGGCTGGATGGGTGGACAGATGCATGAATTCGTGGATGGACGTTTGGATGTG
TGGGTGGGTGGGTGGATTGTGGGATGGCTGGATGAATGCATGGCTGGGTGGGTGGATGGATGCATGGATAAGTGGTGG
ACGGATGGACGGGTGAGTGGATGGGTGGATGTGTGTGGATGGGTGGATAGGAAAGCCCTCTAATTGATTACAGGGC
TCAGTGTGTGCTTCAACATCATGATGGCATCATCACATTGGTCCCTGTATGAAGCAGTGGGGAGGAGAGTGTACCAG
GGGAGCAGGAATGACTCTTCTCCAGAATCGACCTCTCCCACCCTGCAGCCTGGGCTGTGCAGGCCACATTGGAGAAGG
```

Fig. 4 (Cont.)

```
TGCGGTCGACTACTCCTAAATGTTGTTGTGTCCAATGGCTTTTTGACGTTGATGTAGGAATGAGCCTACATCTCCACC
ATAGATGGAACTGTTTGGGTCCCCAAAGCAGAAAGCCTCTTCTGTTGCAGGTGCTGAAGTTTCCATCTTCTTCTGCTT
ATACGGAAGCTCACGCATCCCTTGGATGGCAGGCGTCAGGTTCCTGTGCGCACTGAGTTCCCCCCTTACATGCTTTGG
ACAGAAGTGTGAGACACACAAGATTGCTGCAGGAAGTCCACCTGTGGGGATGCTGCGACTTCTCCAGCAAGAACACGA
GTCTGCTCATTGACCATCACCACACATAACAAATTAAGTGTCCCTTTTTTGATAACACGTCATTGTTTCACAGAGTAT
TCTTTTAAAGTGTATAAGTTGACTGCAGTTATTATTTTTTACTTCTGTTACTAATTTACTCATAATTAGGCACAATTT
ACACTTAAGAAATTTCTTAATAGTTTTTTCCTCCTTAAGGTGAACTACAGTCAGATAACATACTTATCAATTGTCTCT
AGCTCTTGTCAGAAAAGCATATAGATGTGTGTGTGCGTGTGTCTTGGCCTTTCCAATGATGAATTAAGATGTGCATTG
AGAAGGCATTCACTTTATTTGACGTTAAGGAAGTACCAAGAAGACGCTCTCCACAGACCCTGGGAAAGCCAGCAGCTG
CACCCCGAGGCTGTGCCAGGCAGGGAACAAGGAGGCAGCACCACCTGCTGGGCAGGGAAAATGTCCTCCCAGTCCCTG
CCGCTTCTCTGCAGAGGCACAAAGAGCTGCCCCTTCTCCTGGGCCTTCTCCTGGGCTGATGAGATTGCTCCCCGATAT
GCCAAATCAGGGTTGTGCATCTGAGGCTCTGTCTAGACTCTCAGCTCCTTCCTACTCCTGCAAAGTGAAGAAAACAAT
GCCAAGGGGTCCTGGAGGCGTCTCTACCCCTGGAGAGTTTTGACTCTCTTCAATAGTCTCCACTACCCTGCCCTCACT
CCATGTCCTCCGTTTCTCCCTAAAGCGGTGCCCAGTCTGATTGCACTGTGGCAGGGATAACGAGGGGCCAGGACATCA
GGGGAGAGAAGTTTCTACCTGAGTCACAGCAGCGGCTGCCCTGCAGACTCCTGAAGACACAAGACACATTTCCATCCC
AGAGACCCAGCGAAATGCAACCTCAGGCTAGAGACAGCCAGTTATTTTTTCTTGTTCTGTCCTGGAGAGGCCACTGAG
AAAGTCGAGCCCCTTGTTGAGGAAAACATGAGATCTCTGTGTGTCGTCCTCTGCCTGATGGCTGTACCTCCATGTGAG
TGTCTCAGAGATTTCAGAACGGGGGCTGTGGGCTGTGGTGTCCGCTTGTGACTCATCTCTTTGCTTCTTGTCCCTGAG
TGTCCTGCATCAGATGCAGCTACTGGAGTCATGCCCAGGGCTGGTGAGGTCCTCACAGACCTCTGGGCCTGGACCCAG
CAGCCCTCTGGGAAGGCGCTGGGGCACCTCAGCTCCAGGGGCAGCACACACTTCAGCCCAGCCTTTCTGGGCCAACTC
TCCATCTGTAGAGACACATCCAAGGCCCAGTTATCCCTGCAGCTGAGCTCCGTGATGGCCAAGGGCAGGGCCGCACAT
TCCCGTGGGAGACAGAATGGGGACCTCAGCGTGAGCCCAGACACAAACCTCCCTGCAGGGAAGCACAAGACCACCAGG
CGGCGCTCCAGACCACACAGCGGCCCCAGAAGCAGGTTTTAGGGGCGGGGCAGACGTGTCCGCGTTGAGTCAGGTCA
CTGGTTTTACTTTCCCTGAACAAACGGCCTCTGCCAAGGACTCACTGCACCTCTCACCTTCACAGTTGTTTTTTTTTT
TTTTTTAATCACCCTGTAGGGTTTTGCTAGCTAATTTAGATATTGAGGAGTGCTTCATACTTCCTTGGGCCTCTGCTT
GCAGAAACATAGCAATTGTAAGGAGGCACGTGGGAAAGCCCCGGCTCGGTGACCCGGGGGATGCTGCTGTAGCCCTGG
CAAGAGGGCGTCGGGCCGCAGTAACAAAGGTGCAGACGGCTCTCAGCCTGCGCCCGCGGAGTACAACACATAAGGGCT
GTAACCTAACGAAAAAAGAATCGCAGTGCAACTGTCCTGCATTTGAGTTTGTGATCAGTTTTGCCCTTTGTCTTTAAC
AGGTTCTAACATAAAATTTTGAATGCTGGTTCAAGCCCTGTGGGTAAAATGCACTTACCCACATTCCTTAAACAAATA
GAACACTGAGGTGGAAATGTTTTGAAAAAGTAGTTTTCAGACATTTGGAAACAAGCATCACAGGATCATAACCCCTGA
GAAAAGAAAACAAATGAACGAATCCTGCTATTGCCTGAAAGCAGCTGCCAGGACACACGGAAAGGCTTAGTGAGCTG
AGCGGACAGAGAGCAGAGTTCAAGGCAGCAGCAGCCCGAGGGGAGGAGCACCGGGGAGCAGGCTGCTGTGCAGCCAGG
ATGGGCCGGGGTGGGGCGGGGGGAGAACAGCTGGAGACTTGCCGCAGGGAGGGGATCCCTCAGGTTTGGGGCTGAGA
ACTGACTTATGCCTGACTTATGCCTGCATGAAAAGAAACTACTCGATATCAGGGGGAAATCACCAGAAACCTGTGGAC
CCAAAACTACACAGAGCCTACACAAGGAAAGCATTGTTTGTGTTCTCCCAGCCAGGGTGGAAAGACCTTGAGATATGT
AAAGCTTCAAGCAATCTTCCGAAGTAATCTCGTGAGTAGTGGTGCCACATTAATTCAGGACTAAAGACTGCTCTGAAC
TGAACCTAAGAAATGCTTCAAGTGTAGCCTGGAGCCCGGGTGCAGTGGCTCACACCTGTAATCCCAGCACTGTGGGAG
GCCGAGGCAGGCGGATCACTTGAGGTCAGGACTTTGAGACCAGCCTGGCCAACATGGCAAAACCTGTCTCTACTAAAA
ACACAAAAATTAGCTGGGCATGGTGGCAGATGCCTGTAATCACCTCCCACCTGGACCCTTCCTTGATACATCAGAATT
ACAACTAGAGATGAGATTGGGGTGGGGACACAGAGCCAGACCGTATCACATAGGAACCTAAAAGGATAATAAAGTAGG
AAAACTTCCCACATCAGTAACCCTTTATCCGATAGTAATCCCAATCTGCAAAGTAAAACTGTGTGATTTTACTAAGAT
AACGGAATCTTCTCTACAGAAGGACTTTCCAGTGCAAAAGCTCCCCACCCTCACCATGAAATGCACGTGACCATTTCC
AATTTGTGTAAAGTCCTCAGTTAGTACTGAGACTTCGGAAGGTTAGAAATCCCTTTGCTCATGCTGCATGGTCCGGAT
GAGATGTAAGAATCATTAGCTAATAGACATGCAACAGCTTTTGTGCGAAAGATGTTATGAGACATTTAAGGTATTTGC
TTGTGCTTACTAAGCATTCATTGTATCATTGGAGCACATGTGCTTTTATACCCTGGAGAAATTCCAGTAATTGAATTG
CTGGGTTGAATGGGATTTTGATTTGGATTAAATTTAAACTATAGATTTTATTTAGGGAAAACTGGCATCTTAATTATG
TTATTGGGGGGCCCTTGCTCCCAGAGCTCCCAAGATGGTGGCAGGCCGCTTCCAAAATGACCGCAGGCCACTTCCAAG
ATGGTGGCAAGCCTCATGTTCTCTGACCTGGGGTTCTTGGCCTCACGGATTCCAAGGAATGGAAGCTTGGGCCATGCA
GTGAGTGTTATAGCTCTATTAGAAGCCGTGGGTCACGGAAGAGAACCGTGGAACCCAGTGACTAGTGTTCAGCTCGAT
TAGGACGAACCCAGGCACTTAGCCGTGCAGGAACAATGGCGAGCATTTGGCCCGATCGAGAGTGGCAATGGGCGCCTC
GCCGGATCAGGAGCACAGCGGATACCCTGATGGATCCGGAGGGATGGAAGCCAGCGGTGGGTCTCCCACGGGGCAAA
CAGCAGTGGTGGACGGTGAGCGAAAGCGAAGCTCGAGCCGTAACAAACATGGACCAGAAGAGTGCAGTTGCAAGATTT
AGTAGAGTGAAGACAGAGCTCCCATACAAAGGGAGGGGACCCAAAGAGGGTAGCTGTTACCGGCTCGAATGCCTGGGT
TTATATCCCGATCATTGTCCCTCCCGCTGTGCTCTCAGGTGATAGATGATTGGCTATTTCTTTACCTCCTGCTTTTGC
CTAATTAGCATTTTAGTGAACTCTCTTTACTATCTGATTGGTCGGGTGTGAGCTGAGTTGCAAGCCCCGTGTTTAAAG
GTGGAAGTGGTCACCTTCCCAGCTGGGCTTAGGGATTCTTAGTCGGCCTAGGAAATCCAGCTAGTCCTGTCTCTCAAT
```

Fig. 4 (Cont.)

```
TACACTGAGTTTTCCAATCCATGCATCCAATATGTGGTGTATCTCTTCATATGTTCATAGCCTCTGAGCAATGTTTTA
CAATTTTCTGTGTAAAGAACTCCACATCGTTTTATGTTTCTTCTAAGGTATATCCTGATTGCTTTTTATGTCTTCACA
AGTTTTTCCCTTTCAAAATTAATTTTCCAATTGTTTGGTGCTAATATGCTCAAATGTCCTTGATTTTCTTAGTTTGAA
CAGTCCGTTTTCGTTTTGGGGATTTATTTTTTTTTCAGATTCTTTAAGATTTTCTATGTCTATAACCATATAATCTCT
GAACAGAGACAGTTTTGCTTTTCCCTTTCAACTTGAGGTAGGTTTTCTGGGTAGTTCAGGACGCGCAGGCACTGGGTG
GGTGGTGTTAGCAGCTGCACGATGCCTTGGAGAGGACACTCTCGGGGGACTGTGGCCGCTGCTCAGCTGTGACTGTTC
TTATAGCACCAGCAGCTGCGGCCACCATTCTTATCCAATTTCCAAAGCCACACCACAGGCCCTCTCAAGAACGAGGCG
TGGAGGCTATGCCCTCTCCTGGACACATCATCATTCCCAAGCCCCACGATGTGGGCCCCATGGGACGCACACCTTTGT
CTGTCCAGACCTCAGCCCCACCTCCTCATCCTGCACCAGAACTCTTCAGAGCCCAGTGCATGAAATGGGCTACCAAGG
AAATGAGGGTAGGTTCCTGAGAGGAAACTGGCCCTGCATTTGGGAGCTAAGAGTCTGCTAATTCGCCTGGCAGCCCTG
TGCAGCCCTCCGTGGCTACAGTCCACCCGTGCCCATCAGTGCCTCCTTCCTGTGCAAGCCTGGACCTCGCCCTGGGC
TCAGGATGGGCTGTAGACCGAGAATGCAGGCGGGAAAGTCGTTGTCTATCGGGCCATAGTCAGGTTCTACAGTGAGT
CAGGGAAAGACCTGTGGAGGTGTGGATGAGGACAATGGGTCCACCATCAACAGGAGGACACGGGTTCGACCCCTTGCA
GAGGCACAGTCCCACATCACTGGGAGGCAGCCACACTCACTGCCTCGCCCTCTCCTCACACAGTGCAGTTTCCACGTT
CACAGCCCCAGCCAGTCACCAGGAATGCCCTGGGGCGGCCTTTCCCCAGTGCACCCCGAGCCCTCCCTTGGCTGTGC
GGTGAGCTCCATGCCCAGGAGATATCCACCCATAGTCCTCCGGAAAGCAGCTGACCTGCCATGCCCTGGAACCACAAA
TCCCCACAGATCAGCCAGCCTGCAGTGGGCCTTGGATGTGGTGAGGAGTGGTGGCACCCCGTTCCCACCCCACAGAT
GCAACGCCTGTGGGTGACGCATGTGAGTACTGAGGAGTGAGAGGGTAGAACTGTAGGCCCCGAGAACCACAGAAACTCG
GGTGTTACACTCTGGGGCCATGTAAGGAGAAAGTGTCACTGGACAGAAACAGGCCCCTCCTAGACACTGTGTGCGCCA
TAGTCACCTGTCATTAGCTCTCACTCTTGCAGATTCATGATTGAGGTGGTTAAAAAAAAAAAAGCTCCTACTCACCCA
TCCAACCCCATCCTGGGGTGTTTCCACCACCCTTGGGGTTTGGGATGAGCTGCCCTTGCCCACTGTGCTCTGTGGACC
TCCCTTTAGAAGCTCACAGCTCCCTGCACTCGGCTCCATCCTGCCCCACCACACAGAAGCAAAACCCCTCTCCTTTCC
ACTGCAGGCTTTTCCTGGACCAGAATGCTGACCTGCTGCCCTTCACTCCCGAAGTGGTGGGACTGCCTGGGGTGGTGT
GGGTGTTGAGCCTTCTTACTCTAGGGACCTGGCACCTGGCCCCAGGGGCACAGGGATGGTGCATCTGCCTAGGGATGC
CTCCTCATGCCAGGGGGTGGGGGTTAGTACCATCGGCCCTCAGGATTTGTTGCATGAATGAGTGAATGGGTGAATAAA
TGAAGGGGATCTGATCTATGAATAAGGGTATATGGACTTTGGTTGATGTAGGACGCCAAATGCTGGAATTTCGGAGTC
ATCACACCCAGGGGCCCTGCCTCTGAGCTCCTCTTTGCATCCAATCTGCTGAAGAACATGGCTCTAGGGAAACCCAGT
TGTAGACCTGAGGGCCCCGGCTCTTCAATGAGCCATCTCCGTCCCGGGGCCTTATATCAGCAAGTGACGCACACAGGC
AAATGCCAGGGTGTGGTTTCCTGTTTAAATGTAGCCTCCCCGCTGCAGAGCTGCAGAGCCTGCTGAATTCTGGCTGA
CCAGGGCAGTCACCCGAGCTCCAGACAATGTCTGTCTCCTTCCTCATCTTCCTGCCCGTGCTGGGCCTCCCATGGGGT
CAGTGTCAGGGAGATGCCGTATTCACAGCAGCATTCACAGACTGAGGGGTGTTTCACTTTGCTGTTTCCTTTTGTCTC
CAGGTGTCCTGTCACAGGTACAGCTGCAGCAGTCAGGTCCAGGACTGGTGAAGCCCTCGCAGACCCTCTCACTCACCT
GTGCCATCTCCGGGGACAGTGTCTCTAGCAACAGTGCTGCTTGGAACTGGATCAGGCAGTCCCCATCGAGAGGCCTTG
AGTGGCTGGGAAGGACATACTACAGGTCCAAGTGGTATAATGATTATGCAGTATCTGTGAAAAGTCGAATAACCATCA
ACCCAGACACATCCAAGAACCAGTTCTCCCTGCAGCTGAAACCCTGTGACTCCCGAGGACACGGCTGTGTATTACTGTG
CAAGAGACACAGTGAGGGGAAGTCAGTGTGAGCCCAGACACAAACC
VH 6-1
TCCCTGCAGGGATGCTCAGGACCCCAGAAGGCACCCAGCACTACCAGCGCAGGGCCCAGACCAGGAGCAGGTGTGGAG
TTAAGCAAAAATGGAACTTCTTGCTGTGTCTTAAACTGTTGTTGTTTTTTTTTTTTTTTGGCTCAGCAACAGAGATC
ATAGAAAACCCTTTTTCATATTTTTGAAATCTGTTCTTAGTCTAATGGAGATTCTCTGATATGTGACAATGTTTTTCT
CTTGCTGTTTTTGGAATTCTTTGTCTTTGACTTTTGACAACTTGACTTTTGACAGTGTGCCTCAAAGAAGTTCTATTT
TGGGTTCTGTGAACCTCCTGGATCTGGGAAGTTTTCAGCTATGATTTCATTAAACGTGTTTTCTACACCATTTCCCTA
CTCTTTTGGAATACCCATAATGCAAATATTTGTTCACTTAATTGTGTCCCATAAATGCTGGGGATTTTCTTCATTCCT
TTTTACTCTTTTTTTCTTTTATTCATCTGCCTGAATTATTTCAAAAGATCTGTCTTCAACTTCAGAAACTCTTTTGC
TTGGCCTAGTCTAATCTTGAAGGTCTCAATTGTACTTTTAATTTCATTCATTGAATTCTTCAACTCTGGAATTTCTGT
TGGTTCTTTTTTATGATACTTATCTCTTTGTTGAATTCCTCATTCAAATGATAAATTGTTTTCCTGATTTCACTGAAT
TTTCTATCTGTACACTATTGTATCTCCCTGAGTTTCTTAGAGATTATCCTTTTGAATTATTTTTCTGACATTCTGTAT
ATTTCCTTATGATTGGGGTCTGCTACTGGAGAATGACTGTTGTCTTTTTCAGGTGCCGTGTTTCCTGGCCTTTTCATG
TTTTATGTGTTCCTACGTTGATTTCTACACATCTGGCGGACCAGTCATCCCTTGCAATTTAATGGAGTAGGTTTTGCA
GGAAAAGACTTCCTAGTACAGACGGGTCTCAGGGTGTCAGTGTGGCGGGGCGTGCTGGCTTTAGTTCTAGGTTGACGC
AGTAGCGTAGTCTCCATGTCGTTTCTTCAGCTGCCGTCCACATTGGTGACGTTTGCGAGTGTCTCAGTGGCCTGGGCT
GAGAGGTTTGTGGCAGTGGAAGTGCAACGTTGCTAGAGGTGGACTCACCAGGCTGTTTCTGAGGTCGAGGCACATGCA
TGCACATGGTGGATTGACCAACTTGGTGCCAGGCTCACTAGGGTTGGGGACATGGGGCTGTTTCTCAGGCCCAGGATG
CAAACACAAGTCTCTTTGGCTGGCCTGGGGGTGTGGCTTCTGAGGGCAATCCACAGGGCTGTTTCTCAGGTTCAGGAC
ACAAGTGCATGGCCGCTCAACTGGCCTGGGCATGTGTCTCCCAGGGCCACCCCATGGGCTCTCTCTCAGACCCAGGAC
ATGGCCACATGGCTTCCTCAGCTGGCCTGGGTGTGTGTCTGCTTGGGGCCTGCAGGGGCACAGGGTTATTTCTCAGGC
```

Fig. 4 (Cont.)

```
CGGGGTCATGGGCGCACAGCTGCTTGCTGGCTTATAGGAGTGCCTGCCAGGGGTGGCCCATGATGCTGTTTCTCAGGC
C▓▓▓▓▓▓ACTGAATACATAAACAGGACACAGCATTTTGCTGCATAAAGCAAACACAGCGTTACTTTTTTTTTTCTAAA
TGACATTTTTTATTAGATATTGTCTTTATTGACATTTCAAATGTTATCCCCTTTCCTGGTTTACCCTCTGAAATCCCC
TATCTCCTCCCCCTCCCCCTGCTCACCAATCCACCCACTCCCACTTCCAGGCCCTGGCAATCCCCTATATTTGGGCAT
AGAGCCTTCACAGGACCAAGGTACTCTCCTTGCATTGATGACCAACTAGTCCATTCTCTGCTACAAATGCAGCTAGAT
CTATGAGTCCCACCATGTTTTCTTTTGTTGGTGGTTTCATGCCAGGGAGCTCTTGGAGTACTGATTGGTTCATATTGT
TGTTCTCCCTATGGGGTTACAAAACCCTTCAACTTCTTGGGTCCTTTCTCTGGCTGCCTCATTGGGGACCTTGTGCGA
AGTCCAATGGATGACTGTGAGCATCCACTTCTGTATTTGCCAGGCACTGGCAGAGCCTCTCAGAAGACAGCTATATCA
AGATCCTGGCAGCAAGCTCTTGTTGGTATCCACAAAAGTGTCTGGTGGTTGTCTATGGGATGGATCCCCAAAGGGGCA
GTCTCTGGATGGTCATTCCTTCAGTCTCTGTTCCACACTTTGTCTCTTTAACTCCTTCCATGACTATTTTATTCCTCC
CTCTAAGAAGGACCGAAGTATTCATACTTTGGTCTTCCTTCTTGAAATTCATGTGTTTTGTGAATTGTATCTTTGATA
TTCCGAACTTCTGGGCTAATATCCACTTATCAGTGAGTGAATATCATGTGTGTTCTTATGTGATTGAGTTACCTCACT
CAGGATGATATCCTCCAGAACCATCCATTTGTCTAAGAATTTAATGAATTCATTGTTTTTAATAGCTGAGGAGTACTC
CATTGTGTAAATGTACCACATTTTCTGTACCCATTGTTCTCTTGAGGGACATCTGGGTTCTTTAAAGCTTCTGGACAT
TAAATATAAGGCTGCTATGGAAATAGTGGAGAATGTGTCCTTATTACATGTTGGAGCATCTTCTGGGTATATGCCCAG
GAGTGCTATTGCTGGATCCTCTGATAGTACTATGTCCAATTTTCTGAGGAACTGCCAAACTGGTTTACAGAGTGGTTG
TGCCAGCTTGCAATTCCACCAGCAATGGAGAAATGTTCCCCTTCCTCCACATCCTCACCAACATCTGCTGTCACCTCA
ATTTGTTCTTAGTGATTCAGACAGGTGTGAGGTGGAATATCAGGGTTGTTTGGCATTTCCCTGATGACTAGTGATATT
GAAAAAAATTTTAAGTGTTTCTCAGCCATTCAGTATTCTTCAGTTGAGAATTCACTGTTTAGCTCTGTACTCAGGTTT
TTTTAATAGGGTTATTTGGTTTTCTGGAGTCTAACGTCTTGAATTCTTTCTATATATTGGATATTAGCCCTCTGTCAT
ATTTAGGATTGGTAAAGATCTTTCCCAATATGTTGGCTGCCTTTTTGTGTCCTTTGCCTTACAGAACCTTTTTAATTT
TATGAGGTCCCATTTGCTAATTCTTCATTTTACAGCAAAAGCCATTGGTGTTCTGTTCAAAAATCTTTCCCCCTGAAC
CCTATCTTCGAGGATCTTCCCCACTTTCTCCTCTATAAGTTTCAGTGTCTCTATTATTGTGCTGAGGTCCTTGATCCA
CTTGAACTTGAGCATTGTTCAAGGAGATAAGAATGGATCAATTCGAATTCTTCTACATGATAACAGCCAGTTGAGCCA
GCACCATTTGTTGAAAATTCTCTTTTTTGCACTGGATAGTTTTAGCACTTTTGTCAAAGATCAAGTGACTATGGCTCT
TCAACTATGGCTCATTCCATTGATCAACTTGTCTGTCACTGTACAAGCACCATGCAATTTTTATTGCAATTGCTTAGT
ATTACACCTTGAGGTCAAGGATGGTCATTCCACCAGAGGTTCTTCTATGGTTGAGAAGAGTTTTTGCTATCCTAGGTT
TTTGTTATTCCAGATGAATTTGCAAATGGCCCTTTCTAACTCAGTGAAGAATTGAGGTGGAATTTTGATGGGAATTTT
ATTGAATCTGTAGATTGCATTCAACAAGATAGCCATTTATAATACATTAATCCTGCCAGTCCATGAGCATGGGAGATC
TTTCCATCTTCCGAGATCTTCTTCGATTTCTTTCTTCAGAGACTTGAAGTTTTTATCATACAGATCTTTCACTTCCTT
AGTTAGAGTCACACCAAGGTATTTTATATTATTTGTGACTACTGTGAAGGTTGTTGTTTCCCTGATTTCTTCCTCAGC
CTGTTCATCCTTTGTGTAGAGAAAGGCCACTGATTTATTTGAGTTAATATTGTATCCAGCTAATTCACTGAAGTTGTT
TATCAGGTTTAGGAGTTCTCTTGTGGAATTTTTGGAATCACATGTGTATACTATTATATCATCTGCAATTAGTGATAT
TTTGACTTCTTCTTTCCCAAATTGTATCCCTTTGATCTCCTTTTGTTGTCTAATTGCCCACACTAGGACTCGGGCAGC
CTTAGTGCCTAGTCCCTGATTTTAGTGTGATTTGTTCAAGTTTCTCTCCACTTAGTCGGATGTTGGCTACTGATTTGC
TGTATATTGCTTTTATTATGTTTAGGTATGGGCCTTGAATTCCTGATCTTTCCAATACTTTTATCATGAATGGGTGTT
GAATTTTGTCAAATGCTTTCTCAACACCTACAAAGATGATCATGTAGATTTTGTCTTTCAGTTTGATTATATAGTGTA
TTATGTTGATGGATTTCCATATATTAAACCATCCCTGCATCCCTGGGATGAAGCCTACTTGGTCATGATAGACGATTG
TTTTGATGTGTTCTTGGATTCAGTTAGTGAGAAATATATTGAGTATTTTTACATCGATATTCATAAGGGAAATTGGTC
TGAAGTTCTCTTTCTTTGTTGGGTCTTTATGTGGTTTAGTTATCAGAGTCATCGTAGCTTCATAGAACAAATTGAGTA
GAGTACCTTCTGTCTCTATTTTGTGGTATAGTTTGAGGAGATTTGGAAATATGTCTTCTTGGGACGTCTGAGAGAATT
CTGCACTAAACCCATCTGATCCTGGGCTTCTTTGGGGGGGGGGACTATTAATGACTGCTTCTATTTCTTTAGGGGAA
ATGGGACTGTTTAGATTGTTAATATGATCCTGAATAGAAATCTGATCTGATCTAGAAAATTGTCCATTTTATTCAGGT
TTTCCAGTTTTGTTGAGTATTGCCTTTTGTGGTAGGGTCTGATGATGTTTTGGATTTCCTTAGGTTCTGTTGTTATGT
CTTCTTTTCCATTTCTCATTTTGTTAATTAGGATACTGTCCCTGTGTCCTCTAGTTACTCTGGCTAAGCGTTTATCTA
TCTTATTGATTTTCTCAAAGAACCAGCTCCTGGTTTGGTTGATTCTTTGTATAGTTCTTTTGTTTCCACTTGATTGA
TTTCTGCCCTAAGTTTGATTGTTTCCTGCTGTCTACTCCTCTTGGGTGAATTTGCTTCCTTTTGTTCTAGAGCTTTTA
GGTGTGCTGTCAAGCTGATAGGGTATGCTCTCTAGTTTCTTTTTGGCGGCACTCATAGCTAGGAGTTTTCCTCTTA
GCAGTGCTTTCATTACGTCCTGTAAGTTTGGGTATGTTGTGGCCTTCATTTGCATTAAATTCTAATAAGTCTTTAATCT
CTTTCCTTCTTTCTTCCTTGACCGAGTTATCATTGACTAGAGTGTTCATCAGCTTCCACATCAATGTTGGCTTTTAAT
TATTTATGTTTTATTGAGGATCAGCCTTTGTCGGTGGTGATCTTCTAGGATGCACGGGAAATTTTCAATATTTTTGT
ATCTATTGAGGCCTGTTTTGTGACCAATTATACGGTCAATTTTGGAGAAAGTACCGTGAGGTACTGAGAAGATGGTAT
ATCTTTTTGTTTTAGGATAAAATGTTCTGTAGATATCTGTTAAATCCATTTGTTTCATAACTTCTGTTAGTTTCACTG
TGTCTCTGCTTAGTTTCTGATTCCAGAATCTGTCCAATGATAAGAGTAGGGTATTAAATTCTCCCACTACTATTGTGT
GAGGTACAATGTGTGGTTTGAGCTTTAAAAGAGTTTCCTTAATGAATGTGGATGGCCTTGCATTTGGAGCATAGTTAT
TCAGAATTGAGAGTTCCTCTTGGAAGATTTTACCTTTGATGAGTATAAAATGCCCCTCCTTGTCTTTTTTGATACCTT
```

Fig. 4 (Cont.)

```
TGGGTTAGAAGTGGATTTTATTCGATATTAGAATGGCTAATCCATCTTGTTTCTTTGAGATGTTTGCTTGGAAAATTA
TTTTCCTGCCCTTTACTCGGTGGTAGTGTCTGTCTTAGTCCCTGAGGTGGGTTTCCTGTATACAGCAAAATGTTGGGT
CCTGGTTATGTAGCCAGTCTGTTAGTCTGTCTTTTTATCAGGTAATTGAGTCCATTGATATTAAGAGCTATTAAGGAA
AAGTAATTGGTGCTTCCTGTTATTTTGTTGTTAGACTTGGGATTCTGTTCTTGTGGCTATCTTCTTTTAGGTTTGTT
GAAGGATTACTTTCTTGCTTTTTTAGGGTGTAATTTCCCTCTTTGTGTTGGAGTTTTCTCTTTATTATCCTTTGAAG
GGCTGGATTCATGGAAAGATGTTGGGTGAATTTGGTTTTGTCATGGAATTCTTTGGTTTCTCCATCTATAATTGAGAG
TTTTGCTGGGTATAGTAGCCTAAGCTGGCATTTGTGCTCTCTTAGTGTCTATAACATCTGTCCAGGATCTTCTGGCTT
TCATAATCTCTGGTGAGAAGTCTGGTGTAATTCTGATAGGCCTGCCTTTATATGTTACTTGACCTTTTTCCCTTACTG
CTTTAAATATTCTATCTTCATTTAGTGCATTTTTTTCTGATTTTTTATGTGTCAGGAGGAATTTCTTTTCTGCTCCA
GTCTATTCGGATTCTGTAGGCTACTTCTATGTTCATGGGCATCTCCTTCTTTAGGTTACGGACGTTTTCTTCTATAAT
TTTGTTGAAGATATTTACTGGCCCTTTAAGTTGAAAATCTCCATTCTCATCTATACCTATTATCTTTAGGTTTGGTCT
TCTCATTGTGTCCTGGATTTCCTGGATGTTTTGAGTTAGGATCTTTTTGCATTTTGCATTTTTTTTATTGTTGTGC
CCATGTTTTCTACGGAATCTTATGCACCTGAGACTCTCTCTTCTACCTCTTGTATTCTATTGGCTGATGCTTCCACCT
ATGTTTCTCGATTTCTTTCCTAGGATTTCTATCCCCAGAGTTGTCTCCCTTTGTGATTTCTTTATTGTTTCTACTTCC
ATTTTTAGATTTTGAATGGTTCTGTTCGATTCCATCGCCTGTTGGGTTGTGTTTTCTGTATTTCTTTGAGGGATTTT
TGTGCTTCATCTTTAAGGTCTTCTACCTGTTTAGGAGTGTTTTCCTATAATTCTTTGAGGGATTTTGTGTTTTCTCT
TTAAGGGCTTCTAGCAATTTAGCAGTGTTCTCCTGTATTTCTTTAAGTGAGTTATTAATGCCCTTCTTAAAATCCTCT
ACCAACATCATTAGATATGATTTTAAATCCGAATCTTGCTTTTCAGGTGTGTTGGGGTATCCAGGACTCACTGTGGGG
GGAGTACTGGGTTCTGATGATGAAAACTGGTCTTGGTTTTTATTAGTAAGATTCCTACTTTTGCCTTCCACCATCTGA
TAATATCTGTTGTTAGATATTCTAGCTGTCTCTGGCTGGAGCTTGTTCCTCCTGTGATTCTGTCAGCCTCTGTCAGCA
CTCCTGGGAGTACAACTCTTTTCTGAGTCCAATGTTCAGAGCATTCTCTGCAGGCAAGCTCTCCTCTGGCAGGTAAG
GTGCCCAGAGCTCTTGAGCTCAGCTCCACCTCCTGACTGCAGATGAAGACCCAAAGGGACCCTGTCCAATAAGCTCTG
TTGCTTCTGCCACCCACATGCTCTCCTGTGCGAACTGGTCTCTGAGAGACCCGGGATACAAGATGGTACTCTCACCTG
AATCCCAGGGTCAAAGCCCTCCCTGGAGGCTGACTCTCCTCTTGTGGGAAGGTGCACAGAGGTCTGGAGCTCAGCTCT
GCCTCCTGGCTGAAGATGAAGGCCCGAAGGGACCCTGTCCAAGAAGCTTTGTTGCTTCTGGGACCCACATGCTCTCCT
ACATGGACTGGTCTCTGAGAGACCAGGGATTCAAGATGGTGCTCTCACCTGAGTCCCAGGGTCAGAGCCCTCTCTGGA
GGCCAACTCTCCTCAGTGATCCTAAGATCCTGGGTATGCTAGGGTGCCTATGGCATGGAGAGTCCTCTGAGGAATGTG
GGACTGTCTGCTGAGTTTCCACCCAAGGTGGTGCTGGGCTGGCTCCAGTCAGAATGAACCCAGACTCTGGTTGGGCAG
GTTTCCAGTCCTGTTGGCCCAAGCCCCTCTGGGTTGTTTTAGAACAGATGTTGCTTTCCACTCACCAGTGATCCCAAG
ATCCTGGGCGTGCTAGGGTGCCTGCTATGTGGAGAGTCCACTGGGGACCTTAGGAGCATACATCAAGTTCACACCCAT
GGTGGCAAGGAGCTGGTGCCTACCAGAACAAACCCCGGGCACTTTTACTGACCCTTTAAGTTGAAAATCTTCATTCTC
ATCTATACCTATTATCCTTAGGTTTGGTCTTCTCATTGTGTCCTGGATTTCCTGGATGTTTTGACTTAAGATCTTTTT
GCATTTTGCATTTTTTTGATTGTTGTGTCCATGTTCTCTGGAATCTTCTACACCTGAGATTCTCTCCTCTGTATCT
TGTATTCTGTTGGTGATGCTTGCATCTATTGCTCCTGATCTCTTTCCTAGGGTTTCTATCTCCAGAGTTTTCTCCCTT
TGTGATTTCTTTATTATTTCTACTTCCATTTTTAGATCCTAGATGATTTTGTTAAATTCCTTCACCTGTTTGGTTGTG
TGTTCCTGTAATTCTTTAAGGGATTTTTGTATTTCCTCTTTAAGGGCTTCTACCTGTTTAGCTGTGTTCTACTGTATT
TCTTTAAAGGACTTATGAATGTCCTTCTTAAAAACCTCTACCAGCATCATGAGATGTGATCTTAAATGTCAATCTTCC
CTTTCTGGTGTGTTGGGGTATCCAGGACTTGCTGTGGTTGGAGTTCTGGGTTCTGGTAAACCTGCCTTAGAGGGTCAC
CACACAGAGTAATGATAGCACTACTTTTAAACAGGGGAAGATGATGAAATAATTGCTGTGGGAAAATGCAAGGAAGGCTC
CAACACATGTAGGCATCTATGAAGGTCTCAAATCTTCAAAATCCAAAACCACCAAGAAAGAAAGAAAGAAAGAAAGAA
AGAAAGAAAGAAAGAAAGAAAGAAAGAAAGAAAGAAAGAAAGAAAGAAAGGAAGGAAGGAAGGAAGGAAGGAAGGAAG
GAAGGAAGGAAGGAAGGAAGGAAGGAAGGAAGGAAGGAAGGAAGATTCTAAAAGTAGTCACCTGCACCAGGTGCCTGG
GGAGTCACTCAGCAGCCCTAGACTGAGAAAGCTTGAAGAAAGTAGAAATAGAGAAAGTGTACAGCCAGTATCCTCTAG
CTACTCACATCCAAACAGGGCCTCCTGACTGCTCTGAGCCTGTCCTAAGAACAGCAATGATGCCACAGAAATTTTTAG
AGTGAACCCTGAAGGAACTTGAGGCCGATATGAGAAAGCCAGTCCCAGAGGAAAGGAAAACCCGTAGAGAGAAAACAG
GTGAGTTAGTGCATTAAAGGGGCTGAGCAGGCAACGCGCCGTCGACCGGAGGAGTTTCTTCCCTGTGCGGAGTCCACG
GGCCTCCTGTGAGTGTGTGCATGGGCACAAGTGTGTGTGGCTCTGCTGTGTGTCTGTACACACATATGTTTTGGGT
TTTTTTGTGTCTCAGACCACAGAGTCTGCCCCTCCCACCAAAGCCCAGGCAGAAGGATGAACCCACGCCCCTGGGGCC
CAGGCCTCAGCAGCCTCTGCGGGATCATTGTTCCCAGTTGTCACTTGCCTTTGCCACAGCCCTATTTCTCCACAATTC
CTTAAAGTCCTCAACATGCATTTAAGGCACAAAGGTGAAACTGCCCAGAAACATCTGACTCCGCCGTGGAACCCAGGA
GCAAGCTGGGTTAGCTAAGGAGCGGGCCGTTGGCAGAGGCTGGGGATCCAGGCTGAACTTTGGAGGAGGCATGTCCC
AGCATGGGCTCCTGACTATGTCCTCCTGGGACAAACCCAAACCCACTCTTTGAATATGGGAGGGACTTTGCTGGCCCC
GGCCCTGACCGCAGCACTTGGAAACTGAGGAGTGGTCCGCTCCTCCGTGTCACAGCTGCCCGTTCACCATCATAGAAG
CAACTCTGTCACCTCCATGGGCCCCTCTGTGGCTGCTGCCTGGGTCCAAGCTGAGCCCAGCTGCCCAGGCCCAGAAGG
AAAGCCCAGGCCAGGTGCCCAGCACAGAGGCAGTCACATACCCCGGGGAGAGCCACAGCAAGCAGCCAATATTGCCCA
GGAGAGGAGTAGCTGACAAGGCAGAACGTGAGCTGCCATCGGCTCGAGAGGCTTTGCTGGTCCTCCTGGGGCTCTGGA
```

Fig. 4 (Cont.)

```
CATGACCAGGAGGAGCGAGGGAAGAAGTCGCATGGTGGTCCCATCCTGGGTGGGGCCTGATGGCAGCTGGCCACCCGT
CCCAGAGTGGCAGCCAGATGCCAGCGCCATTCCCACAGTCACATCATTGGTCACAGAATGCAGGACATAGAGTGTCTT
CTTTCCATCACAGTGCTGTCCAGACCCATAGCCTAGGGTAGACCTGGAAGATTCAATGTCCACACCCGGGGCTGGAGC
GTAGCCATGAGCCACGCCCCCTGCCCGTGCATGGAAAGCCAGCCCAAGCTCTGCTCCATCCCTAGCCAAAGTCAGTGT
CCTTTCCCCTTCTCCCAAGTGAGCTCTAGCCACCTGCCTACCCTGCCATCTGAGGATGACAGCCTTCATTCCATTGGA
ACCTGGCTCTGCCACCAGCAGGCTTGCAGTCCTGGGCAGACTCCGTCACCTCTCTATGCCTCAGCCTTTCCATCTGCA
CAGGAGGAAGATGATGATGGTGGTGATGATGATGGCGATGGTTTCCTTTTGCATCTGAGGCAAGGACTAATTGAGATG
ATACACATCAGGCACTGGGTATGGTGCTGGTCCTTCCTGAGCACTCAATCTATGTGAGCTGTCCTTGTGAAATGGGTG
TCACCACATTTCCCCACGCAGAACATCCTTTGTCTGCCATACTTGAAACGTCTGCCCCAATACTAACAGCTCCTCATG
GAAGATGTGCCCACCCACCCACCCTCATACTCCCAAAGGTGCCCGTGCTTTATCAAGCCAAAGTCCAGCCAGGAACTT
TACAGCAGCATCCCTTTCCCTCTCCAAGCACCAAGGAGCAAGGCAAAGCACTACATCTTCCATCTGGAGGCAATGCCA
CCCTCTTCTCCCATTTTCACTGCCATCCCTAAGAGGCAGTGCTTCCCCAAAAGGTTCCATAGCAGCCTGCCTACAGCA
ACTCTGTTCACACGAGTTTCAGCATCCTTGCAGTGGCTCCCCTGCCATGCTGTGGCTCTTCATTCACCCTCTTCTCCT
GCTCCCCGTGACAGGCATAGATTCTGAGTGATCTGGATACATTGCTTTGTTTAATAACATTACAGCTTCTGTGCTGAA
AAAGATACAGCAGATAGAGAAGGCAATTGTTGAACACAAAATAGTGACAGCAGAGATGACGGCAAGTTGGCATTTTTC
TTTTCTAGCAATAAAACTTAAAGCTGACTCAAGGAGAAATGGAAATCATAATTGGAACAGTAATCCTCAAGAAAGCAT
TAAGATTATTAAATAATTGCCCTCACAGATGACTTCAGGCCAAGATGGCTTTATGGGTGAAGTTTAGACTTTCACAAA
ACTAATCAGTTCCCATAAGAACTGCTCCAGGATTTGGAGGAACATGGGAAAGTCTATTAAAGGGATCACAATTCACAG
TCCCCAGAGTAAAACATGGGCTAACTTGCATTTTGGCAAAGAGCCAAATGTTATAAATGACATCCTAGAAGGCCAAAT
TCTGTCCATCTCGTTGAACAAGGACTTACACCAGGAATTTAGAACTATTTATAGCTCATCCCACCACTCAGGCCAATG
ATGACCCATGATCATCTCACCAGAAATGGAAAGACTCAGATGATTAATAGAGTCTCAATTTCTCTGAGACATCTAAGA
GCCCAGCCCAAGCCCAGACCCAGGAGGGCACCCAGGCCTGGACAGAGAACACTGATATCACACCAGCCCTCCAGAGG
AAGCAGAGACTCCTTCAAGCTCTGGAAACACAGGCCCAGACAGCTGCCCAAAGTTGGGCAGGCTTCACTGCAAACCCA
AATCATGAAGCTAGGTAACACCTTTACAGATTCTTTACATTTAAAAATCATCAAAACAAGAGTAAATAATAAACTCAA
ATAATATTAATCTAATATGTAAAGGTCTTGTACCATTATTATGCAAACAACATACATAAGCTAATAAGAAAAAGAACA
AATCCCTTAAGAAATCAGCAAAAAGGATATAACACAATTTCTAAAAGAAAACAAATGGCTAGCACACATAAGGAAAAC
ACTTTGTGAACAGACATTCTTCAGAACATTATTTATAATTATAAAATAGTTGAAAGCAAGATAGTGCCTGAAGAAATT
ATGGTGCATACATTAGTGGGACTATTCTGCAAACATTCCCAATTATACTTGTCACATATCTGTGATAACGTGACAGCC
AGCATTCATGGGTGACCTCATTTGGTAAAAGGGTGCAAAGCTCAACACGCATTGTGAGATGACTGTGGTGTAAAATT
AGTGGGATTATTCCGCAAACATTCCCAATTATACTTACCGCATATCTGTGATAACATGACAGCATTCATGGGTGACC
TCATTTGGTAAAAGGGTGCAAAGCTCAACACGCATTGTGAGATGACTGGTGTAAATACAAAGACCAAACTGTGAAAAG
GAGTCCATCAATTAATCGATGCTTACCTTCAGTTTTGGGCTAATTTTTAAAGTATGCTATAAGCATATGCTCCTGTTA
TAACAGAATGGAGGGATTATGAGAGATGATGCAGGTGTGTCCTGGGCCTCCCCTGGCCCACTGGGCCCTAGAGATGCC
TTCCCAGGCATCGCTGTCAGGGCTTCCCTCAGAGGGAGTCCTGTATTGACCTCACCACCAAGGTCTGGAGCAGGGGAT
CCTTAGATATTGGTTGGGGTTATCTCACCTTAGGTCTGAATATGGGGTTGTCTTAGACTGTTTTGTGCTGTTAGAATA
GAATACCCAAGACTGGGAAATTTATACTGACAGGAAATTTATTTCTCACAGTTCTAGAGGCTGTGAAGTCCAAGAGCA
CAGGTGCCAGAGCAAGTCCAAGAGCAAGGGAAAGTCCAAAGCAAGTCCAGGAGCATCTGGCGAGGACCTTCTTGCTGT
GTCATCACATGGCGGAAGGCAAGAAAGAGAGCAAGAGGGGGCCGAACTCACCCTTTTATAACAGCACCAATCCCACCC
ATGAGGTGGGGACCTTATGACCTAATCACTCTTCATACTGTTACAATGGCAATGAAATTTCAACATGAGTTTTGGAGG
AGAGAAGCATTCAAACCACAGCAAGGGTGCTCCTACCTCCTCTCAGGGCATCTGCAGAAAGAGCTGCAACTGCACG
TCCTTCCTCCGTCCATCCTCCATCCCTTCCCAATGTCCGTGCATATCCTGTGACCCAGGAGGTCTGGCATAGGGGTG
CTCCTGCCTTAGGTCTGAGGCCCTGTCTGAAGAGGGGTAGGTGAGGAGGCCATCTGATGGTCTGGGCCAAGACAGTCA
CAGGACGCATCATTTATCATCAAGGAGGCTGAGGGTTGAGTCTCCAGGTCCAGGGAACTCCCCACAAAGTGGGAACCC
TGCCCAGCTCCACACAGCCTCTGCTGGGGACCCTGCTCTGGTGCAGAGCCTGGGACAGGTCTTGAGCTCAGCCAGA
GTCTGCCTCCCTGTCATTTAGGAACTAAACCAAGCGGCAGGATGCTGGAGCCCAGCCCCATCTGACCTTACAGGGCC
AAGGCTGGGGCCTGGGTTCCCCTCAAGGCACAGCAGGACTGGAGCCCCAGGCAGTGCAGGAGTGGCCAAAGCTGGGG
CTTCCTCCAGAGCCCCAAGCATCATGGCACCAAGAAGGGTAGGACCCTGGCCTGAGGAATTGGCACCAAAGCCCCAG
AAACTACCCTGGACACCATGGAGAGAGGCTTGGAGGGGAAGCACCAGGCACTGCCTCCCCTTCTGATCCCACCTGAGG
TGGCTGCCAAGCCCAGAGAGCCGCTCTGATGTCCCCCAGCCCTGCAGCCCAGGGATACCTGTACTGTGCCCCTGGGG
ACCCCTGGCCAGTCTGTGCAAAGAAGTCACCACCCTACACTCAGACAGTGGGGTCCTCGTCCCACATCCTCAGAG
CATGCCCGGCTGCTGCAGGGATGGTCTCCTTGTCCTCAGAGCATGGCCCGGCTGCTGCAGGGATGGTCTCCTTGTCC
TCAGAGCATGGCCCAGCTGCTGCAGGGATGGTCTCCTGGAGGCCCCCAGTGCTCTATTGTCAGGGCTCCCTCCACCC
CCCCGCACCAAGAGAGAGCCAGACCCCAGCCAAGGCTTCCAGTGGCTTCAGGTCACACCCCTAGGCTGACCCCAGCCCC
ATTAACACCTGCCTGAGAAAGCTCCACGCACCAGAACTGACCGTCTGCTCCAACTCTTGACCTCCCGTTCTCAGGGCG
TCTGCTGAAAAGGCTGCAACTGCACATCCTTCCTCCGTCCGTTCCCGATGTCCGTGTGTCTCCTGTGGCCAGGAAGGT
CTTTCTCGGGACCTGAGAGCCGCTCCCTGAAGTGTCCCCATTGGGAAGGATGGGGCCTGTGTCTCCAGGCTCTGGGAG
```

Fig. 4 (Cont.)

```
GACAGAATCCTGACCTCAACAGTGGCCGGCACGGACACAACTGGCCCCATCCCGGGGACGCTGACCAGCGCTGGGCAA
CTTTTCCCTTCCCCGACGACTGAGCCCCGAGCACCCTCCCTGCTCCCCTACCACCTCCCTTTACAAGGCTGTGGCCTC
TGCACAGATGATAATGGAGCTTGGCTCATTCCCCTAGAGTCGGTAGGGAGTTAAGGACAAAACTCAGTTTCCTCCACC
TGAACTCAAGTCTGCCTATGTTTACCTAATCACACCTGGTGGACAGTTTGGACAAACTTGCACACTCAGAGACACAGA
CACTTCTAGAAATCATTATCTCCCTGCCCCGGGGACCCCACTCCAGCAGAAGTCTGCTAGGCACTGGCCTGGGCCCTC
CTGCTGTCCTAGGAGGCTGCTGACCTCCTGCCTGGCTCCTGTCCCCAGGTCCAGAGTCAGAGCAGACTCCAGGGACGC
TGCAGGCTAGGAAGCCGCCCCCTCCAGGCCAGGGTCTAGTGCAGGTGCCCAGGACAAGAAAGATTGTGAATGCAGGAA
TGACTGGGCCACACCCCTCCCGTGCACGCCCCCTCCTGCCCTGCACCCCACAGCCCAGCCCCCGTGCTGGATGCCCC
CCCACAGCAGAGGTGCTGTTCTGTGATCCCCTGGGAAAGACGCCCTCAACCTCCACCCTGTCCCACGGCCCAAGGAAG
ACAAGACACAGGCCCTCTCCTCACAGTCTCCCCACCTGGCTCCTGCTGGGACCCTCAAGGTGTGAACAGGGAGGATGG
TTGTCTGGGTGGCCCCTAGGAGCCCAGATCTTCACTCCACAGACCCCAACCCAAGCACCCCCTTCTGCAGGGCCCAGC
TCATCCCCCTCCTCCTCCCTCTGCTCTCCTCTCGTCGCCTCTACGGGAAATCCGGGACTCAGCAGTAACCCTCAGGAA
GCAGGGCCCAGGCGCCGTTTAATAGGAGGCTTCCTCACAATGAAACTTTTAGAAAGCCTTGACTACAATGATGACCTT
GGTGTGGCTGTGAACACTGTCAGCTCCCACAGCTGCTGCAGCAAAAAATGTCCATAGACAGGGTGGGGGCCCGGGGTC
GTCTGCTGTCCTGCTCAGCCCACAGCACGCATGGAGGATCTGAGGTGCCACACCTGACGCCCAGGCCAGAACATGCCT
CCCTCCAGGGTGACCTGCCATGTCCTGCATTGCTGGAGGGACAGGGGCAGCCTATGAGGATCTGGGGCAGGAGATGA
ATCCTATTAACCCAGAGGAAAACTAACAGGACCCAAGCACCCTCCCCGTTGAAGCTGACCTGCCCAGAGGGGCCTGGG
CCCACCCCACACACCGGGGCGGAATGTGTACAGGCCCCGGTCTCTGTGGGTGTTCCGCTAACTGGGGCTCCCAGTGCT
CACCCCACAACTAAAGCGAGCCCCAGCCTCCAGAGCCCCGAAGGAGATGCCGCCCACAAGCCCAGCCCCCATCCAGG
AGGCCCCAGAGCTCAGGGCGCCGGGGCAGATTCTGAACAGCCCCGAGTCACGGTG▓▓▓▓▓▓▓▓▓▓▓▓CACCGT
                                                         D1-1
GAGAAAAACTGTGTCCAAAACTGTCTCCTGGCCCCTGCTGGAGGCCGCGCCAGAGAGGGGAGCAGCCGCCCCGAACCT
AGGTCCTGCTCAGCTCACACGACCCCCAGCACCCAGAGCACAGTGGAGTCCCCACTGAATGGTGAGGATGGGGACCAG
GGCTCCAGGGGGTCATGGAAGGGGCTGGACCCCATCCTACTGCTATGGTCCCAGTGCTCCTGGCCAGAAACGACCCTA
CCACCGACAAGAGTCCCTCAGGGAAACGGGGGTCACTGGCACCTCCCAGCATCAACCCCAGGCAGCACAGGCATAAAC
CCCACATCCAGAGCCGACTCCAGGAGCAGAGACACCCCAGTACCCTGGGGGACACCGACCCTGATGACTCCCCACTGG
AATCCACCCCAGAGTCCACCAGGACCAAAGACCCCGCCCCTGTCTCTGTCCCTCACTCAGGACCTGCTGCGGGGCGGG
CCATGAGACCAGACTCGGGCTTAGGGAACACCACTGTGGCCCCAACCTCGACCAGGCCACAGGCCCTTCCTTCCTGCC
CTGCGGCAGCACAGACTTTGGGGTCTGTGCAGAGAGGAATCACAGAGGCCCCAGGCTGAGGTGGTGGGGGTGGAAGGC
CCCCAGGAGGTGGCCCACTTCCCTTCCTCCCAGCTGGAACCCACCATGACCTTCTTAAGATAGGGGTGTCATCCGAGG
CAGGTCCTCCATGGAGCTCCCTTCAGGCTCCTCCCTGGTCCTCACTAGGCCTCAGTCCCGGCTGTGGGAATGCAGCCA
CCACAGGCACACCAGGCAGCCCAGACCCAGCCAGCCTGCAGTGCCCAAGCCCACATTCTGGAGCAGAGCAGGCTGTGT
CTGGGAGAGTCTGGGCTCCCCACCGCCCCCCCGCACACCCCACCCACCCCTGTCCAGGCCCTATGCAGGAGGGTCAGA
GCCCCCCATGGGGTATGGACTTAGGGTCTCACTCACGCGGCTCCCCTCCTGGGTGAAGGGGTCTCATGCCCAGATCCC
CACAGCAGAGCTGGTCAAAGGTGGAGGCAGTGGCCCCAGGGCCACCCTGACCTGGACCCTCAGGCTCCTCTAGCCCTG
GCTGCCCTGCTGTCCCTGGGAGGCCTGGACTCCACCAGACCACAGGTCCAGGGCACCGCCCATAGGTGCTGCCCACAC
TCAGTTCACAGGAAGAAGATAAGCTCCAGACCCCCAAGACTGGGACCTGCCTTCCTGCCACCGCTTGTAGCTCCAGAC
CTCCGTGCCTCCCCCGACCACTTACACACGGGCCAGGGAGCTGTTCCACAAAGATCAACCCCAAACCGGGACCGCCTG
GCACTCGGGCCGCTGCCACTTCCCTCTCCATTTGCTCCCAGCACCTCTGTGCTCCCTCCCTCCTCCCTCCTTCAGGGG
AACAGCCTGTGCAGCCCCTCCCTGCACCCCACACCCTGGGGAGGCCCAACCCTGCCTCCAGCCCTTTCTCCCCCGCTG
CTCTTCCTGCCCATCCAGACAACCCTGGGGTCCCATCCCTGCAGCCTACACCCTGGTCTCCACCCAGACCCCTGTCTC
TCCCTCCAGATACCCCTCCCAGGCCAACCCTGCACATGCAGGCCCTCCCCTTTTCTGCTGCCAGAGCCTCAGTTTCTA
CCCTCTGTGCCTACCCCCTGCCTCCTCCTGCCCACAACTCGAGCTCTTCCTCTCCTGGGGCCCCTGAGCCATGGCACT
GACCGTGCACTCCCACCCCCACACTGCCCATGCCCTCACCTTCCTCCTGGACACTCTGACCCCGCTCCCCTCTTGGAC
CCAGCCCTGGTATTTCCAGGACAAAGGCTCACCCAAGTCTTCCCCATGCAGGCCCTTGCCCTCACTGCCCGGTTACAC
GGCAGCCTCCTGTGCACAGAAGCAGGGAGCTCAGCCCTTCCACAGGCAGAAGGCACTGAAAGAAATCGGCCTCCAGCA
CCCTGATGCACGTCCGCCTGTGTCTCTCACTGCCCGCACCTGCAGGGAGGCTCGGCACTCCCTGTAAAGACGAGGGAT
CCAGGCAGCAACATCATGGGAGAATGCAGGGCTCCCAGACAGCCCAGCCCTCTCGCAGGCCTCTCCTGGGAAGAGACC
TGCAGCCACCACTGAACAGCCACGGAGCCCGCTGGATAGTAACTGAGTCAGTGACCGACCTGGAGGGCAGGGGAGCAG
TGAACCGGAGCCCAGACCATAGGGACAGAGACCAGCCGCTGACATCCCGAGCCCCTCACTGGCGGCCCAGAACACCG
CGTGGAAACAGAACAGACCCACATTCCCACCTGGAACAGGGCAGACACTGCTGAGCCCCAGCACCAGCCCTGAGAAA
CACCAGGCAACGGCATCAGAGGGGGCTCCTGAGAAAGAAAGGAGGGGAGGTCTCCTTCACCAGCAAGTACTTCCCTTG
ACCAAAAACAGGGTCCACGCAACTCCCCCAGGACAAAGGAGGAGCCCCCTGTACAGCACTGGGCTCAGAGTCCTCTCC
AACACACCCTGAGTTTCAGACAAAAACCCCCTGGAAATCATAGTATCAGCAGGAGAACTAGCCAGAGACAGCAAGAGG
GGACTCAGTGACTCCCGCGGGGACAGGAGGATTTTGTGGGGGCTCGTGTCACTGTG▓▓▓▓▓▓▓▓▓▓▓▓
                                                          D2-2
```

Fig. 4 (Cont.)

```
░░░░░░CACAGTGACACAGCCCCATTCCCAAAGCCCTG░░░░░░░░░░░░░░░NN  D3-3 to D2-8
absent from this locus N░░░░░░░░░░░░GGGCAGAGCCTGAGCAGGGCCTTTTGCTGTTTCT
GCTTTCCTGTGCAGAGAGTTCCATAAACTGGTGTTCGAGATCAATGGCTGGGAGTGAGCCCAGGAGGACAGCGTGGGA
AGAGCACAGGGAAGGAGGACCAGCCGCTATCCTACACTGTCATCTTTCGAAAGTTTGCCTTGTGCCCACACTGCTGCA
TCATGGGATGCTTAACAGCTGATGTAGACACAGCTAAAGAGAGAATCAGTGAGATGGATTTGCAGCACAGATCTGAAT
AAATTCTCCAGAATGTGGAGCAGCACAGAAGCAAGCACACAGAAAGTGCCTGATGCAAGGACAAAGTTCAGTGGGCAC
CTTCAGGCATTGCTGCTGGGCACAGACACTCTGAAAAGCCCTGGCAGGAACTCCCTGTGACAAAGCAGAACCCTCAGG
CAATGCCAGCCCCAGAGCCCTCCCTGAGAGCCTCATGGGCAAAGATGTGCACAACAGGTGTTTCTCATAGCCCCAAAC
TGAGAGCAAAGCAAACGTCCATCTGAAGGAGAACAGGCAAATAAACGATGGCAGGTTCATGAAATGCAAACCCAGACA
GCCACAAGCACAAAAGTACAGGGTTATAAGCGACTCTGGTTGAGTTCATGACAATGCTGAGTAATTGGAGTAACAAAG
TAAACTCCAAAAAATACTTTCAATGTGATTTCTTCTAAATAAAATTTACACCCTGCAAAATGAACTGTCTTCTTAAGG
GATACATTTCCCAGTTAGAAAACCATAAAGAAAACCAAGAAAAGGATGATCACATAAACACAGTGGTGGTTACTTCTG
CTGGGGAAGGAAGAGGGTATGAACTGAGATACACAGGGTGGGCAAGTCTCCTAACAAGAACAGAACGAATACATTACA
GTACCTTGAAAACAGCAGTTAAACTTCTAAATTGCAAGAAGAGGAAAATGCACACAGTTGTGTTTAGAAAATTCTCAG
TCCAGCACTGTTCATAATAGCAAAGACATTAACCCAGGTCGGATAAATAAGCGATGACACAGGCAATTGCACAATGAT
ACAGACATATATTTAGTATATGAGACATCGATGATGTATCCCCAAATAAACGACTTTAAAGAGATAAAGGGCTGATGT
GTGGTGGCATTCACCTCCCTGGGATCCCCGGACAGGTTGCAGGCTCACTGTGCAGCAGGGCAGGCGGGTACCTGCTGG
CAGTTCCTGGGGCCTGATGTGGAGCAAGCGCAGGGCCATATATCCCGGAGGACGGCACAGTCAGTGAATTCCAGAGAG
AAGCAACTCAGCCACACTCCCCAGGCAGAGCCCGAGAGGGACGCCCACGCACAGGGAGGCAGAGCCCAGCACCTCCGC
AGCCAGCACCACCTGTGCACGGGCCACCACCTTGCAGGCACAGAGTGGGTGCTGAGAGGAGGGGCAGGGACACCAGGC
AGGGTGAGCACCCAGAGAAAACTGCAGACGCCTCACACATCCACCTCAGCCTCCCCTGACCTGGACCTCACTGGCCTG
GGCCTCACTTAACCTGGGCTTCACCTGACCTTGGCCTCACCTGACTTGGACCTCGCCTGTCCCAAGCTTTACCTGACC
TGGGCCTCAACTCACCTGAACGTCTCCTGACCTGGGTTTAACCTGTCCTGGAACTCACCTGGCCTTGGCTTCCCCTGA
CCTGGACCTCATCTGGCCTGGGCTTCACCTGGCCTGGGCCTCACCTGACCTGGACCTCATCTGGCCTGGACCTCACCT
GGCCTGGACTTCACCTGGCCTGGGCTTCACCTGACCTGGACCTCACCTGGCCTCAGGCCTCACCTGCACCTGCTCCAG
GTCTTGCTGGAGCCTGAGTAGCACTGAGGGTGCAGAAGCTCATCCAGGGTTGGGGAATGACTCTAGAAGTCTCCCACA
TCTGACCTTTCTGGGTGGAGGCAGCTGGTGGCCCTGGGAATATAAAAATCTCCAGAATGATGACTCTGTGATTTGTGG
GCAACTTATGAACCCGAAAGGACATGGCCATGGGGTGGGTAGGGACATAGGGACAGATGCCAGCCTGAGGTGGAGCCT
CAGGACACAGGTGGGCACGGACACTATCCACATAAGCGAGGGATAGACCCGAGTGTCCCCACAGCAGACCTGAGAGCG
CTGGGCCCACAGCCTCCCCTCAGAGCCCTGCTGCCTCCTCCGGTCAGCCCTGGACATCCCAGGTTTCCCCAGGCCTGG
CGGTAGGTTTAGAATGAGGTCTGTGTCACTGTG░░░░░░░░░░░░░░░░░░░░░░CACAGTGTCACAGA
                                                 D3-9
GTCCATCAAAAACCCATGCCTGGAAGCTTCCCGCCACAGCCCTCCCCATGGGGCCCTGCTGCCTCCTCAGGTCAGCCC
CGGACATCCTGGGTTTCCCCAGGCTGGGCGGTAGGTTTGGGGTGAGGTCTGTGTCACTGTG░░░░░░░░░░
                                                              D3-10
░░░░░░░░░░░░░CACAGTGTCACAGAGTCCATCAAAAACCCATCCCTGGGAGCCTCCCGCCACAGCCCTCCCTGCA
GGGGACCGGTACGTGCCATGTTAGGATTTTGATCGAGGAGACAGCACCATGGGTATGGTGGCTACCACAGCAGTGCAG
CCTGTGACCCAAACCCGCAGGGCAGCAGGCACGATGGACAGGCCCGTGACTGACCACGCTGGGCTCCAGCCTGCCAGC
CCTGGAGATCATGAAACAGATGGCCAAGGTCACCCTACAGGTCATCCAGATCTGGCTCCGAGGGGTCTGCATCGCTGC
TGCCCTCCCAACGCCAGTCCAAATGGGACAGGGACGGCCTCACAGCACCATCTGCTGCCATCAGGCCAGCGATCCCAG
AAGCCCCTCCCTCAAGGCTGGCCACATGTGTGGACACTGAGAGCCCTCATATCTGAGTAGGGGCACCAGGAGGGAGGG
GCTGGCCCTGTGCACTGTCCCTGCTCCTGTGGTCTCTGGCCTGCCTGGCCCTGACACCTGAGCCTCTCCTGGGTCATT
TCCAAGACAGAAGACATTCCTGGGGACAGCCGGAGCTGGGCGTCGCTCATCCTGCCCGGCCGTCCTGAGTCCTGCTCA
TTTCCAGACCTCACCGGGGAAGCCAACAGAGGACTCGCCTCCCACATTCAGAGACAAAGAACCTTCCAGAAATCCCTG
CCTCTCTCCCCAGTGGACACCCTCTTCCAGGACAGTCCTCAGTGGCATCACAGCGGCCTGAGATCCCCAGGACGCAGC
ACCGCTGTCAATAGGGGCCCCAAATGCCTGGACCAGGGCCTGCGTGGGAAAGGCCTCTGGCCACACTCGGGCTTTTG
TGAAGGGCCCTCCTGCTGTG░░░░░░░░░░░CATAGTGATGAACCCAGTGGCAAAAACTGGCTGGAAACCCAG
                    D4-11
GGGCTGTGTGCACGCCTCAGCTTGGAGCTCTCCAGGAGCACAAGAGCCGGGCCCAAGGATTTGTGCCCAGACCCTCAG
CCTCTAGGGACACCTGGGCCATCTCAGCCTGGGCTGGTGCCCTGCACACCATCTTCCTCCAAATAGGGGCTTCAGAGG
GCTCTGAGGTGACCTCACTCATGACCACAGGTGACCTGGCCCTTCCCTGCCAGCTATACCAGACCCTGTCTTGACAGA
TGCCCCGATTCCAACAGCCAATTCCTGGGACCCTGAATAGCTGTAGACACCAGCCTCATTCCAGTACCTCCTGCCAAT
TGCCTGGATTCCCATCCTGGCTGGAATCAAGAAGGCAGCATCCGCCAGGCTCCCAACAGGCAGGACTCCCGCACACCC
TCCTCTGAGAGGCCGCTGTGTTCCGCAGGGCCAGGCCCTGGACAGTTCCCCTCACCTGCCACTAGAGAAACACCTGCC
ATTGTCGTCCCCACCTGGAAAAGACCACTCGTGGAGCCCCAGCCCCAGGTACAGCTGTAGAGACAGTCCTCGAGGCC
CCTAAGAAGGAGCCATGCCCAGTTCTGCCGGGACCCTCGGCCAGGCCGACAGGAGTGGACGCTGGAGCTGGGCCCACA
```

Fig. 4 (Cont.)

```
CTGGGCCACATAGGAGCTCACCAGTGAGGGCAGGAGAGCACATGCCGGGGAGCACCCAGCCTCCTGCTGACCAGAGGC
CTGCCCCAGAGCCCAGGAGGCTGCAGAGGCCTCTCCAGGGAGACACTGTGCATGTCTGGTACCTAAGCAGCCCCCCAC
GTCCCCAGTCCTGGGGGCCCCTGGCTCAGCTGTCTGGGCCCTCCCTGCTCCCTGGGAAGCTCCTCCTGACAGCCCCGC
CTCCAGTTCCAGGTGTGGTTATTGTCAGGCGATGTCAGACTGTG▓▓▓▓▓▓▓▓▓▓▓▓▓▓▓▓▓▓▓▓▓▓CACAGTGGTGC
                                            D5-12
CGCCCATAGCAGCAACCAGGCCAAGTAGACAGGCCCCTGCTGCGCAGCCCCAGGCATCCACTTCACCTGCTTCTCCTG
GGGCTCTCAAGGCTGCTGTCTGTCCTCTGGCCCTCTGTGGGGAGGGTTCCCTCAGTGGGAGGTCTGTGCTCCAGGGCA
GGGATGATTGAGATAGAAATCAAAGGCTGGCAGGGAAAGGCAGCTTCCCGCCCTGAGAGGTGCAGGCAGCACCACGGA
GCCACGGAGTCACAGAGCCACGGAGCCCCCATTGTGGGCATTTGAGAGTGCTGTGCCCCCGGCAGGCCCAGCCCTGAT
GGGGAAGCCTGTCCCATCCCACAGCCCGGGTCCCACGGGCAGCGGGCACAGAAGCTGCCAGGTTGTCCTCTATGATCC
TCATCCCTCCAGCAGCATCCCCTCCACAGTGGGGAAACTGAGGCTTGGAGCACCACCCGGCCCCCTGGAAATGAGGCT
GTGAGCCCAGACAGTGGGCCCAGAGCACTGTGAGTACCCCGGCAGTACCTGGCTGCAGGGATCAGCCAGAGATGCCAA
ACCCTGAGTGACCAGCCTACAGGAGGATCCGGCCCCACCCAGGCCACTCGATTAATGCTCAACCCCCTGCCCTGGAGA
CCTCTTCCAGTACCACCAGCAGCTCAGCTTCTCAGGGCCTCATCCCTGCAAGGAAGGTCAAGGGCTGGGCCTGCCAGA
AACACAGCACCCTCCCTAGCCCTGGCTAAGACAGGGTGGGCAGACGGCTGTGGACGGGACATATTGCTGGGGCATTTC
TCACTGTCACTTCTGGGTGGTAGCTCTGACAAAAACGCAGACCCTGCCAAAATCCCCACTGCCTCCCGCTAGGGGCTG
GCCTGGAATCCTGCTGTCCTAGGAGGCTGCTGACCTCCAGGATGGCTCCGTCCCCAGTTCCAGGGCGAGAGCAGATCC
CAGGCAGGCTGTAGGCTGGGAGGCCACCCCTGCCCTTGCCGGGGTTGAATGCAGGTGCCCAAGGCAGGAAATGGCATG
AGCACAGGGATGACCGGGACATGCCCCACCAGAGTGCGCCCCTTCCTGCTCTGCACCCTGCACCCCCAGGCCAGCCC
ACGACGTCCAACAACTGGGCCTGGGTGGCAGCCCCACCCAGACAGGACAGACCCAGCACCCTGAGGAGGTCCTGCCAG
GGGGAGCTAAGAGCCATGAAGGAGCAAGATATGGGGCCCCGATACAGGCACAGATGTCAGCTCCATCCAGGACCACC
CAGCCCACACCCTGAGAGGAACGTCTGTCTCCAGCCTCTGCAGGTCGGGAGGCAGCTGACCCCTGACTTGGACCCCTA
TTCCAGACACCAGACAGAGGCGCAGGCCCCCAGAACCAGGGTTGAGGGACGCCCCGTCAAAGCCAGACAAAACCAAG
GGGTGTTGAGCCCAGCAAGGGAAGGCCCCCAAACAGACCAGGAGGTTTCTGAAGGTGTCTGTGTCACAGTG▓▓▓▓▓▓▓
                                                                     D6-13
▓▓▓▓▓▓▓▓▓▓▓CACAGTGACACTCACCCAGCCAGAAACCCCATTCCAAGTCAGCGGAAGCAGAGAGAGCAGGGAG
GACACGTTTAGGATCTGAGACTGCACCTGACACCCAGGCCAGCAGACGTCTCCCCTCCAGGGCACCCCACCCTGTCCT
GCATTTCTGCAAGATCAGGGGCGGCCTGAGGGGGGGTCTAGGGTGAGGAGATGGGTCCCCTGTACACCAAGGAGGAGT
TAGGCAGGTCCCGAGCACTCTCCCCATTGAGGCTGACCTGCCCAGAGAGTCCTGGGCCCACCCCACACACCGGGGCGG
AATGTGTGCAGGCCTCGGTCTCTGTGGGTGTTCCGCTAGCTGGGGCTCACAGTGCTCACCCCACACCTAAAATGAGCC
ACAGCCTCCGGAGCCCCGCAGGAGACCCCGCCCACAAGCCCAGCCCCCACCCAGGAGGCCCCAGAGCTCAGGGCGCC
CCGTCGGATTCCGAACAGCCCCGAGTCACAGCG▓▓▓▓▓▓▓▓▓▓▓▓▓▓CACTGTCAGAATAGCTACGTCAAAAACT
                                 D1-14
GTCCAGTGGCCACTGCCGGAGGCCCCGCCAGAGAGGGCAGCAGCCACTCTGATCCCATGTCCTGCCGGCTCCCATGAC
CCCCAGCACGCGGAGCCCCACAGTGTCCCCACTGGATGGGAGGACAAGAGCTGGGGATTCCGGCGGGTCGGGGCAGGG
GCTTGATCGCATCCTTCTGCCGTGGCTCCAGTGCCCCTGGCTGGAGTTGACCCTTCTGACAAGTGTCCTCAGAGAGAC
AGGCATCACCGGCGCCTCCCAACATCAACCCCAGGCAGCACAGGCACAAACCCCACATCCAGAGCCAACTCCAGGAGC
AGAGACACCCCAATACCCTGGGGGACCCCGACCCTGATGACTTCCCACTGGAATTCGCCGTAGAGTCCACCAGGACCA
AAGACCCTGCCTCTGCCTCTGTCCCTCACTCAGGACCTGCTGCCGGGCGAGGCCTTGGGAGCAGACTTGGGCTTAGGG
GACACCAGTGTGACCCCGACCTTGACCAGGACGCAGACCTTTCCTTCCTTTCCTGGGGCAGCACAGACTTTGGGGTCT
GGGCCAGGAGGAACTTCTGGCAGGTCGCCAAGCACAGAGGCCACAGGCTGAGGTGGCCCTGGAAAGACCTCCAGGAGG
TGGCCACTCCCCTTCCTCCCAGCTGGACCCCATGTCCTCCCAAGATAAGGGTGCCATCCAAGGCAGGTGCTCCTTGG
AGCCCCATTCAGACTCCTCCCTGGACCCCACTGGGCCTCAGTCCCAGCTCTGGGGATGAAGCCACCACAAGCACACCA
GGCAGCCCAGGCCCAGCCACCCTGCAGTGCCCAAGCACACACTCTGGAGCAGAGCAGGGTGCCTCTGGGAGGGGCTGA
GCTCCCCACCCCACCCCCACCTGCACACCCCACCCACCCCTGCCCAGCGGCTCTGCAGGAGGGTCAGAGCCCACATG
GGGTATGGACTTAGGGTCTCACTCACGTGGCTCCCATCATGAGTGAAGGGCCTCAAGCCCAGGTTCCCACAGCAGCG
CCTGTCGCAAGTGGAGGCAGAGGCCCGAGGGCCACCCTGACCTGGTCCCTGAGGTTCCTGCAGCCCAGGCTGCCCTGC
TGTCCCTGGGAGGCCTGGGCTCCACCAGACCACAGGTCCAGGGCACGGGTGCAGGAGCCACCCACACAGCTCACA
GGAAGAAGATAAGCTCCAGACCCCCAGGGCCAGAACCTGCCTTCCTGCTACTGCTTCCTGCCCCAGACCTGGGCGCCC
TCCCCCGTCCACTTACACACAGGCCAGGAAGCTGTTCCCACACAGAACAACCCCAAACCAGGACGCCTGGCACTCAG
GTGGCTGCCATTTCCTTCTCCATTTGCTCCCAGCGCCTCTGTCCTCCCTGGTTCCTCCTTCGGGGGAACAGCCTGTGC
AGCCAGTCCCTGCAGCCCACACCCTGGGGAGACCCAACCCTGCCTGGGGCCCTTCCAACCCTGCTGCTCTTACTGCCC
ACCCAGAAAACTCTGGGGTCCTGTCCCTGCAGTCCCTACCCTGGTCTCCACCCAGACCCCTGTGTATCACTCCAGACA
CCCCTCCCAGGCAAACCCTGCACCTGCAGGCCCTGTCCTCTTCTGTCGCTAGAGCCTCAGTTTCTCCCCCCTGTGCCC
ACACCCTACCTCCTCCTGCCCACAACTCTAACTCTTCTTCTCCTGGAGCCCCTGAGCCATGGCATTGACCCTGCCCTC
CCACCACCCACAGCCCATGCCCTCACCTTCCTCCTGGCCACTCCGACCCCGCCCCCTCTCAGGCCAAGCCCTGGTATT
```

Fig. 4 (Cont.)

```
TCCAGGACAAAGGCTCACCCAAGTCTTTCCCAGGCAGGCCTGGGCTCTTGCCCTCACTTCCCGGTTACACGGGAGCCT
CCTGTGCACAGAAGCAGGGAGCTCAGCCCTTCCACAGGCAGAAGGCACTGAAAGAAATCGGCCTCCAGCACCTTGACA
CACGTCCGCCCGTGTCTCTCACTGCCCGCACCTGCAGGGAGGCTCCGCACTCCCTCTAAAGACAAGGGATCCAGGCAG
CAGCATCACGGGAGAATGCAGGGCTCCCAGACATCCCAGTCCTCTCACAGGCCTCTCCTGGGAAGAGACCTGCAGCCA
CCACCAAACAGCCACAGAGGCTGCTGGATAGTAACTGAGTCAATGACCGACCTGGAGGGCAGGGGAGCAGTGAGCCGG
AGCCCATACCATAGGGACAGAGACCCAGCCGCTGACATCCCGAGCTCCTCAATGGTGGCCCCATAACACACCTAGGAAA
CATAACACACCCACAGCCCCACCTGGAACAGGGCAGAGACTGCTGAGCCCCCAGCACCAGCCCCAAGAAACACCAGGC
AACAGTATCAGAGGGGGCTCCCGAGAAAGAGAGGAGGGGAGATCTCCTTCACCATCAAATGCTTCCCTTGACCAAAAA
CAGGGTCCACGCAACTCCCCCAGGACAAAGGAGGAGCCCCCTATACAGCACTGGGCTCAGAGTCCTCTCTGAGACACC
CTGAGTTTCAGACAACAACCCGCTGGAATGCACAGTCTCAGCAGGAGAACAGACCAAAGCCAGCAAAAGGGACCTCGG
TGACACCAGTAGGGACAGGAGGATTTTGTGGGGCTCGTGTCACTGTG▓▓▓▓▓▓▓▓▓▓▓▓▓▓▓▓▓▓▓▓▓▓▓▓▓▓▓▓▓▓▓
                                              D2-15
▓CACAGTGACACAGACCCATTCCCAAAGCCCTACTGCAAACACACCCACTCCTGGGGCTGAGGGGCTGGGGGAGCATC
TGGGAAGTAGGGTCCAGGGGTGTCTATCAATGTCCAAAATGCACCAGACTCCCCGCCAAACACCACCCCACCAGCCAG
CGAGCAGGGTAAACAGAAAATGAGAGGCTCTGGGAAGCTTGCACAGGCCCCAAGGAAAGAGCTTTGGCAGGTGTGCAA
GAGGGGATGCAGGCAGAGCCTGAGCAGGGCCTTTTGCTGTTTCTGCTTTCCTGTGCAGAGAGTTCCATAAACTGGTGT
TCAAGATCAGTGGCTGGGAATGAGCCCAGGAGGGCAGTCTGTGGGAAGAGCACAGGGAAGGAGGACCAGCCGCTATCC
TACACTGTCATCTTTCAAAAGTTTGCCTTGTGACCACACTATTGCATCATGGGATGCTTAAGAGCTGATGTAGACACA
GCTAAAGAGAGAATCAGTGAGATGAATTTGCAGCATAGATCTGAATAAACTCTCCAGAATGTGGAGCAGTACAGAAGC
AAACACACAGAAAGTGCCTGATGCAAGGACAAAGTTCAGTGGGCACCTTCAGGCATTGCTGCTGGGCACAGACACTCT
GAAAAGCCCTGGCAGGATCTCCCTGCGACAAAGCAGAACCCTCAGGCAATGCCAGCCCCAGAGCCCTCCCTGAGAGCG
TCATGGGAAAGATGTGCAGAACAGCTGATTATCATAGACTCAAACTGAGAACAGAGCAAACGTCCATCTGAAGAACA
GTCAAATAAGCAATGGTAGGTTCATGCAATGCAAACCCAGACAGCCAGGGGACAACAGTAGAGGGCTACAGGCGGCTT
TGCGGTTGAGTTCATGACAATGCTGAGTAATTGGAGTAACAGAGGAAAGCCCAAAAAATACTTTTAATGTGATTTCTT
CTAAATAAAATTTACACCAGGCAAAATGAACTGTCTTCTTAAGGGATAAACTTTCCCTGGAAAAACTACAAGGAAAA
TTAAGAAAACGATGATCACATAAACACAGTTGTGGTTACTTCTACTGGGGAAGGAAGAGGGTATGAGCTGAGACACAC
AGAGTCGGCAAGTCTCCAAGCAAGCACAGAACGAATACATTACAGTACCTTGAATACAGCAGTTAAACTTCTAAATCG
CAAGAAGAGGAAAATGCACACAGCTGTGTTTAGAAAATTCTCAGTCCAGCACTATTCATAATAGCAAAGACATTAACC
CAGGTTGGATAAATAAATGATGACACAGGCAATTGCACAATGATACAGACATACATTTAGTACATGAGACATCGATGA
TGTATCCCCAAAGAAATGACTTTAAAGAGAAAAGGCCTGATGTGTGGTGGCACTCACCTCCCTGGGATCCCCGGACAG
GTTGCAGGCACACTGTGTGGCAGGGCAGGCTGGTACATGCTGGCAGCTCCTGGGGCCTGATGTGGAGCAAGCGCAGGG
CTGTATACCCCCAAGGATGGCACAGTCAGTGAATTCCAAAGAGAAGCAGCTCAGCCACACTGCCCAGGCAGAGCCCGA
GAGGGACGCCCACGCACAGGGAGGCAGAGCCCAGCTCCTCCACAGCCACCACCACCTGTGCACGGGCCACCACCTTGC
AGGCACAGAGTGGGTGCTGAGAGGAGGGGCAGGGACACCAGGGCTGAGCACCCAGAGAAAACTGCAGAAGCCTCA
CACATCCACCTCAGCCTCCCCTGACCTGGACCTCACCTGGTCTGGACCTCACCTGGCCTGGGCCTCACCTGACCTGGA
CCTCACCTGGCCTGGGCTTCACCTGACCTGGACCTCACCTGGCCTCCGGCCTCACCTGCACCTGCTCCAGGTCTTGCT
GGAACCTGAGTAGCACTGAGGCTGCAGAAGCTCATCCAGGGTTGGGGAATGACTCTGGAACTCTCCCACATCTGACCT
TTCTGGGTGGAGGCATCTGGTGGCCCTGGGAATATAAAAAGCCCCAGAATGGTGCCTGCGTGATTTGGGGGCAATTTA
TGAACCCGAAAGGACATGGCCATGGGTGGGTAGGGACATAGGGACAGATGCCAGCCTGAGGTGGAGCCTCAGGACAC
AGTTGGACGCGGACACTATCCACATAAGCGAGGGACAGACCCGAGTGTTCCTGCAGTAGACCTGAGAGCGCTGGGCCC
ACAGCCTCCCCTCGGTGCCCTGCTGCCTCCTCAGGTCAGCCCTGGACATCCCGGGTTTCCCCAGGCCAGATGGTAGG▓
▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓CACAGCATCACACGGT
D3-16
CCATCAGAAACCCATGCCACAGCCCTCCCCGCAGGGGACCGCCGCGTGCCATGTTACGATTTTGATCGAGGACACAGC
GCCATGGGTATGGTGGCTACCACAGCAGTGCAGCCCATGACCCAAACACACAGGGCAGCAGGCACAATGGACAGGCCT
GTGAGTGACCATGCTGGGCTCCAGCCCGCCAGCCCCGGAGACCATGAAACAGATGGCCAAGGTCACCCCACAGTTCAG
CCAGACATGGCTCCGTGGGGTCTGCATCGCTGCTGCCCTCTAACACCAGCCCAGATGGGGACAAGGCCAACCCCACAT
TACCATCTCCTGCTGTCCACCCAGTGGTCCCAGAAGCCCTCCCTCATGGCTGAGCCACATGTGTGAACCCTGAGAGC
ACCCCATGTCAGAGTAGGGGCAGCAGAAGGGCGGGGCTGGCCTGTGCACTGTCCCTGCACCCATGGTCCCTCGCCTG
CCTGGCCCTGACACCTGAGCCTCTTCTGAGTCATTTCTAAGATAGAAGACATTCCCGGGGACAGCCGGAGCTGGGCGT
CGCTCATCCTGCCCGGCCGTCCTGAGTCCTGCTTGTTTCCAGACCTCACCAGGGAAGCCAACAGAGGACTCACCTCAC
ACAGTCAGAGACAAAGAACCTTCCAGAAATCCCTGTCTCACTCCCCAGTGGGCACCTTCTTCCAGGACATTCCTCGGT
CGCATCACAGCAGGCACCCACATCTGGATCAGGACGGCCCCCAGAACACAAGATGGCCCATGGGACAGCCCCACAAC
CCAGGCCTTCCCAGACCCCTAAAAGGCGTCCCACCCCCTGCACCTGCCCCAGGGCTAAAAATCCAGGAGGCTTGACTC
CCGCATACCCTCCAGCCAGACATCACCTCAGCCCCTCCTGGAGGGGACAGGAGCCCGGGAGGGTGAGTCAGACCCCAC
CTGCCCTCGATGGCAGGCGGGGAAGATTCAGAAAGGCCTGAGATCCCCAGGACGCAGCACCACTGTCAATGGGGCCC
```

Fig. 4 (Cont.)

```
CAGACGCCTGGACCAGGGCCTGCGTGGGAAAGGCCGCTGGGCACACTCAGGGGCTTTTTGTGAAGGCCCCTCCTACTG
TG▓▓▓▓▓▓▓▓▓▓▓▓▓▓▓▓CACAGTGATGAAACTAGCAGCAAAAACTGGCCGGACACCCAGGGACCATGCACACTTCTC
D3-17
AGCTTGGAGCTCTCCAGGACCAGAAGAGTCAGGTCTGAGGGTTTGTAGCCAGACCCTCGGCCTCTAGGGACACCCTGG
CCATCACAGCGGATGGGCTGGTGCCCCACATGCCATCTGCTCCAAACAGGGGCTTCAGAGGGCTCTGAGGTGACTTCA
CTCATGACCACAGGTGCCCTGGCCCCTTCCCCGCCAGCTACACCGAACCCTGTCCCAACAGCTGCCCCAGTTCCAACA
GCCAATTCCTGGGGCCCAGAATTGCTGTAGACACCAGCCTCGTTCCAGCACCTCCTGCCAATTGCCTGGATTCACATC
CTGGCTGGAATCAAGAGGGCAGCATCCGCCAGGCTCCCAACAGGCAGGACTCCCGCACACCCTCCTCTGAGAGGCCGC
TGTGTTCCGCAGGGCCAGGCCCTGGACAGTTCCCCTCACCTGCCACTAGAGAAACACCTGCCATTGTCGTCCCCACCT
GGAAAAGACCACTCGTGGAGCCCCCAGCCCCAGGTACAGCTGTAGAGAGACTCCCCGAGGGATCTAAGAAGGAGCCAT
GCGCAGTTCTGCCGGGACCCTCGGCCAGGCCGACAGGAGTGGACACTGGAGCTGGGCCCACACTGGGCCACATAGGAG
CTCACCAGTGAGGGCAGGAGAGCACATGCCGGGGAGCACCCAGCCTCCTGCTGACCAGAGGCCTGCCCCAGAGCCCAG
GAGGCTGCAGAGGCCTCTCCAGGGGGACACTGTGCATGTCTGGTCCCTGAGCAGCCCCCACGTCCCCAGTCCTGGGG
GCCCCTAGCACAGCTGTCTGGACCCTCCCTGTTCCCTGGGAAGCTCCTCCTGACAGCCCCGCCTCCAGTTCCAGGTGT
GGTTATTGTCAGGGGTGTCAGACTGTG▓▓▓▓▓▓▓▓▓▓▓▓▓▓▓▓CACAGTGGTGCTGCCCATAGCAGCAACCAG
D5-18
GCCAAGTAGACAGGCCCCTGCTGTGCAGCCCCAGGCCTCCAGCTCACCTGCTTCTCCTGGGGCTCTCAAGGTCACTGT
TGTCTGTACTCTGCCCTCTGTGGGGAGGGTTCTCTCAGTGGGAGGTCTGTTCTCAACATCCCAGGGCCTCATGTCTGC
ACGGAAGGCCAATGGATGGGCAACCTCACATGCCGCGGCTAAGATAGGGTGGGCAGCCTGGCGGGGACAGTACATAC
TGCTGGGGTGTCTGTCACTGTGCCTAGTGGGGCACTGGCTCCCAAACAACGCAGTCCTCACCAAAATCCCCACAGCCT
CCCCTGCTAGGGGCTGGCCTGATCTCCTGCAGTCCTAGGAGGCTGCTGACCTCCAGAATGTCTCCGTCCCCAGTTCCA
GGGCGAGAGCAGATCCCAGGCCGGCTGCAGACTGGGAGGCCACCCCCTCCTTCCCAGGGTTCACTGGAGGTGACCAAG
GTAGGAAATGGCCTTAACACAGGGATGACTGCGCCATCCCCCAACAGAGTCAGCCCCCTCCTGCTCTGTACCCCGCAC
CCCCCAGGCCAGTCCACGAAAACCAGGGCCCCACATCAGAGTCACTGCCTGGCCCGGCCCTGGGGCGGACCCCTCAGC
CCCCACCCTGTCTAGAGGACTTGGGGGGACAGGACACAGGCCCTCTCCTTATGGTTCCCCCACCTGCCTCCGGCCGGG
ACCCTTGGGGTGTGGACAGAAAGGACACCTGCCTAATTGGCCCCCAGGAACACAGAACTTCTCTCCAGGGACCCCAGC
CCGAGCACCCCCTTACCCAGGACCCAGCCCTGCCCCTCCTCCCCTCTGCTCTCCTCTCATCACCCCATGGGAATCCGG
TATCCCCAGGAAGCCATCAGGAAGGGCTGAAGGAGGAAGCGGGGCCGTGCACCACGGGCAGGAGGCTCCGTCTTCGT
GAACCCAGGGAAGTGCCAGCCTCCTAGAGGGTATGGTCCACCCTGCCTGGGGCTCCCACCGTGGCAGGCTGCGGGGAA
GGACCAGGGACGGTGTGGGGGAGGGCTCAGGGCCCTGCGGGTGCTCCTCCATCTTCGGTGAGCCTCCCCCTTCACCCA
CCGTCCCGCCCACCTCCTCTCCACCCTGGCTGCACGTCTTCCACACCATCCTGAGTCCTACCTACACCAGAGCCAGCA
AAGCCAGTGCAGACAAAGGCTGGGGTGCAGGGGGCTGCCAGGGCAGCTTCGGGGAGGGAAGGATGGAGGGAGGGGAG
GTCAGTGAAGAGGCCCCCTTCCCCTGGGTCCAGGATCCTCCTCTGGGACCCCGGCTCCCATCCCCTCCTGGCTCTGG
GAGGAGAAGCAGGATGGGAGAATCTGTGCGGGACCCTCTCACAGTGGAATATCCCCACAGCGGCTCAGGCCAGACCCA
AAAGCCCCTCAGTGAGCCCTCCACTGCAGTCCTGGGCCTGGGTAGCAGCCCCTCCCACAGAGGACAGACCCAGCACCC
CGAAGAAGTCCTGCCAGGGGGAGCTCAGAGCCATGAAGAGCAGGATATGGGGTCCCCGATACAGGCACAGACCTCAG
CTCCATCCAGGCCCACCGGGACCCACCATGGGAGGAACACCTGTCTCCGGGTTGTGAGGTGGCTGGCCTCTGTCTCGG
ACCCCACTCCAGACACCAGACAGAGGGGCAGGCCCCCCAAAACCAGGGTTGAGGGATGATCCGTCAAGGCAGACAAGA
CCAAGGGGCACTGACCCCAGCAAGGGAAGGCTCCCAAACAGACGAGGAGGTTTCTGAAGCTGTCTGTATCACAGTG▓
▓▓▓▓▓▓▓▓▓▓▓▓▓▓▓▓CACAGTGACACTCGCCAGGCCAGAAACCCCGTCCCAAGTCAGCGGAAGCAGAGAGAGCA
D6-19
GGGAGGACACGTTTAGGATCTGAGGCCGCACCTGACACCCAGGGCAGCAGACGTCTCCCCTCCAGGGCACCCTCCACC
GTCCTGCGTTTCTTCAAGAATAGGGGCGGCCTGAGGGGTCCAGGGCCAGGCGATAGGTCCCCTCTACCCCAAGGAGG
AGCCAGGCAGGACCCGAGCACCGTCCCCATTGAGGCTGACCTGCCCAGACGGGCCTGGGCCCACCCCACACACCGGGG
CGGAATGTGTGCAGGCCCCAGTCTCTGTGGGTGTTCCGCTAGCTGGGGCCCCAGTGCTCACCCCACACCTAAAGCGA
GCCCCAGCCTCCAGAGCCCCTAAGCATTCCCCGCCCAGCAGCCCAGCCCCTGCCCCCACCCAGGAGGCCCCAGAGCT
CAGGGCGCCTGGTCGGATTCTGAACAGCCCCGAGTCACAGTG▓▓▓▓▓▓▓▓▓▓▓▓▓CACCGTGAGAAAACTGTG
                                         D1-20
TCCAAAACTGACTCCTGGCAGCAGTCGGAGGCCCCGCCAGAGAGGGAGCAGCCGCCCTGAACCCATGTCCTGCCGGT
TCCCATGACCCCCAGCACCCAGAGCCCCACGGTCCCCGTTGGATAATGAGGACAAGGGCTGGGGGCTCCGGTGGTT
TGCGGCAGGGACTTGATCACATCCTTCTGCTGTGGCCCCATTGCCTCTGGCTGGAGTTGACCCTTCTGACAAGTGTCC
TCAGAAAGACAGGGATCACCGGCACCTCCCAATATCAACCCCAGGCAGCACAGACACAAACCCCACATCCAGAGCCAA
CTCCAGGAGCAGAGACACCCCAACACTCTGGGGACCCCAACCGTGATAACTCCCCACTGGAATCCGCCCCAGAGTCT
ACCAGGACCAAAGGCCCTGCCCTGTCTCTGTCCCTCACTCAGGGCCTCCTGCAGGGCGAGCGCTTGGGAGCAGACTCG
GTCTTAGGGGACACCACTGTGGGCCCCAACTTTGATGAGGCCACTGACCCTTCCTTCCTTTCCTGGGGCAGCACAGAC
TTTGGGGTCTGGGCAGGGAAGAACTACTGGCTGGTGGCCAATCACAGAGCCCCCAGGCCGAGGTGGCCCCAAGAAGGC
```

Fig. 4 (Cont.)

```
CCTCAGGAGGTGGCCACTCCACTTCCTCCCAGCTGGACCCCAGGTCCTCCCCAAGATAGGGGTGCCATCCAAGGCAGG
TCCTCCATGGAGCCCCCTTCAGACTCCTCCCGGGACCCCACTGGACCTCAGTCCCTGCTCTGGGAATGCAGCCACCAC
AAGCACACCAGGAAGCCCAGGCCCAGCCACCCTGCAGTGGGCAAGCCCACACTCTGGAGCAGAGCAGGGTGCGTCTGG
GAGGGGCTAACCTCCCCACCCCCCACCCCCCATCTGCACACAGCCACCTACCACTGCCCAGACCCTCTGCAGGAGGGC
CAAGCCACCATGGGGTATGGACTTAGGGTCTCACTCACGTGCCTCCCCTCCTGGGAGAAGGGGCCTCATGCCGAGATC
CCTGCAGCACTAGACACAGCTGGAGGCAGTGGCCCCAGGGCCACCCTGACCTGGCATCTAAGGCTGCTCCAGCCCAGA
CAGCACTGCCGTTCCTGGGAAGCCTGGGCTCCACCAGACCACAGGTCCAGGGCACAGCCCACAGGAGCCACCCACACA
CAGCTCACAGGAAGAAGATAAGCTCCAGACCCCAGGGCGGGACCTGCCTTCCTGCCACCACTTACACACAGGCCAGGG
AGCTGTTCCCACACAGATCAACCCCAAACCGGGACTGCCTGGCACTAGGGTCACTGCCATTTCCCTCTCCATTCCCTC
CCAGTGCCTCTGTGCTCCCTCCTTCTGGGGAACACCCTGTGCAGCCCCTCCCTGCAGCCCACACGCTGGGGAGACCCC
ACCCTGCCTCGGGCCTTTTCTACCTGCTGCACTTGCCGCCCACCCAAACAACCCTGGGTACGTGACCCTGCAGTCCTC
ACCCTGATCTGCAACCAGACCCCTGTCCCTCCCTCTAAACACCCCTCCCAGGCCAACTCTGCACCTGCAGGCCCTCCG
CTCTTCTGCCACAAGAGCCTCAGGTTTTCCTACCTGTGCCCACCCCCTAACCCCTCCTGCCCACAACTTGAGTTCTTC
CTCTCCTGGAGCCCTTGAGCCATGGCACTGACCCTACACTCCCACCCACACACTGCCCATGCCATCACCTTCCTCCTG
GACACTCTGACCACGCTCCCCTCCCTCTCAGACCCGGCCCTGGTATTTCCAGGACAAAGGCTCACCCAAGTCTTCCCC
ATGCAGGCCCTTGCCCTCACTGCCTGGTTACACGGGAGCCTCCTGTGCGCAGAAGCAGGGAGCTCAGCTCTTCCACAG
GCAGAAGGCACTGAAAGAAATCGGCCTCCAGTGCCTTGACACACGTCCGCCTGTGTCTCTCACTGCCTGCACCTGCAG
GGAGGCTCCGCACTCCCTCTAAAGATGAGGGATCCAGGCAGCAACATCACGGGAGAATGCAGGGCTCCCAGACAGCCC
AGCCCTCTCGCAGGCCTCTCCTGGGAAGAGACCTGCAGCCACCACTGAACAGCCACGGAGGTCGCTGGATAGTAACCG
AGTCAGTGACCGACCTGGAGGGCAGGGGAGCAGTGAACCGGAGCCCATACCATAGGGACAGACACCAGCCGCTAACAT
CCCGAGCCCCTCACTGGCGGCCCCAGAACACCCCGTGGAAACAGAACAGACCCACAGTCCCACCTGGAACAGGGCAGA
CACTGCTGAGCCCCCAGCACCAGCCCCAAGAAACACTAGGCAACAGCATCAGAGGGGGCTCCTGAGAAAGAGAGGAGG
GGAGGTCTCCTTCACCATCAAATGCTTCCCTTGACCAAAAACAGGGTCCACGCAACTCCCCCAGGACAAAGGAGGAGC
CCCCTGTACAGCACTGGGCTCAGAGTCCTCTCTGAGACAGGCTCAGTTTCAGACAACAACCCGCTGGAATGCACAGTC
TCAGCAGGAGAGCCAGGCCAGAGCCAGCAAGAGGAGACTCGGTGACACCAGTCTCCTGTAGGGACAGGAGGATTTTGT
GGGGGTTCGTGTCACTGTG▓▓▓▓▓▓▓▓▓▓▓▓▓▓▓▓▓▓▓▓▓▓▓▓▓▓▓CACAGTGACACAACCCCATTCCTAAAGCCCT
D2-21
ACTGCAAACGCACCCACTCCTGGGGCTGAGGGGCTGGGGGAGCATCTGGGAAGTATGGCCTAGGGGTGTCCATCAATG
CCCAAAATGCACCAGACTCTCCCCAAGACATCACCCCACCAGCCAGTGAGCAGAGTAAACAGAAAATGAGAAGCAGCT
GGGAAGCTTGCACAGGCCCCAAGGAAAGAGCTTTGGCAGGTGTGCAAGAGGGGATGTGGGCAGAGCCTGAGCAGGGCC
TTTTGCTGTTTCTGCTTTCCTGTGCAGAGAGTTCCATAAACTGGTATTCAGGATCAATGGCTGGGAGTGAGCCCAGGA
GGACAGTGTGGGAAGAGCACAGGGAAGGAGGACCAGCCGCTATCCTACACTGTCATCTTTTGAAAGTTTGCCCTGTGC
CCACAATGCTGCATCATGGGATGCTTAACAGCTGATGTAGACACAGCTAAAGAGAGAATCAGTGAAATGCATTTGCAG
CACAGATCTGAATAAATCCTCCAGAATGTGGAGCAGCACAGGAGCAAGCACACAGAAAGTGCCTGATGCCAAGGCAAA
GTTCAGTGGGCACCTTCAGGCATTGCTGCTGGGCACAGACACTCTGAAAAGCACTGGCAGGAACTGCCTGTGACAAAG
CAGAACCCTCAGGCAATGCCAGCCCTAGAGCCCTTCCTGAGAACCTCATGGGCAAAGATGTGCAGAACAGCTGTTTGT
CATAGCCCCAAACTATGGGGCTGGACAAAGCAAACGTCCATCTGAAGGACAACAGACAAATAAACGATGGCAGGTTCA
TGAAATGCAAACTAGGACAGCCAGAGGACAACAGTAGAGAGCTACAGGCGGCTTTGCGGTTGAGTTCATGACAATGCT
GAGTAATTGGAGTAACAGAGGAAAGCCCAAAAAATACTTTTAATGTGATTTCTTCTAAATAAAATTTACACCCGGCAA
AATGAACTATCTTCTTAAGGGATAAACTTTCCCCTGGAAAAACTATAAGGAAAATCAAGAAAACGATGATCACATAAA
CACAGTGGTGGTTACTTCTACTGGGGAAGGAAGAGGGTATGAGCTGAGACACACAGAGTCGGCAAGTCTCCTAACAAG
AACAGAACAAATACATTACAGTACCTTGAAAACAGCAGTTAAACTTCTAAATCGCAAGAAGAGGAAAATGCACACACC
TGTGTTTAGAAAATTCTCAGTCCAGCACTGTTCATAATAGCAAAGACATTAACCCAGGTTGGATAAATAAGCGATGAC
ACAGGCAATTGCACAATGATACAGACATACATTCAGTATATGAGACATCGATGATGTATCCCCAAAGAAATGACTTTA
AAGAGAAAAGGCCTGATGTGTGGTGGCAATCACCTCCCTGGGCATCCCCGGACAGGCTGCAGGCTCACTGTGTGGCAG
GGCAGGCAGGCACCTGCTGGCAGCTCCTGGGGCCTGATGTGGAGCAGGCACAGAGCTGTATATCCCCAAGGAAGGTAC
AGTCAGTGCATTCCAGAGAGAAGCAACTCAGCCACACTCCTGGCCAGAACCCAAGATGCACACCCATGCACAGGGAG
GCAGAGCCCAGCACCTCCGCAGCCACCACCACCTGCGCACGGGCCACCACCTTGCAGGCACAGAGTGGGTGCTGAGAG
GAGGGGCAGGGACACCAGGCAGGGTGAGCACCCAGAGAAACTGCAGAAGCCTCACACATCCACCTCAGCCTCCCCTG
ACCTGGACCTCACCTGGCCTGGGCCTCACCTGACCTGGACCTCACCTGGCCTGGGCTTCACCTGGCCTGGGCTTCACC
TGACCTGGACCTCACCTGGCCTCGGGCCTCACCTGGCCTGGGCTTCACCTGGCCTGGGCTTCACCTGACCTGGACCTC
ACCTGGCCTGGGCCTCACCTGACCTGGACCTCACCTGGCCTGGGCTTCACCTGGCCTGGGCTTCACCTGGCCTGGGCT
TCACCTGACCTGGACCTCACCTGGCCTGGGCTTCACCTGACCTGGACCTCACCTGGCCTCAGGCCTCACCTGCACCTG
CTCCAGGTCTTGCTGGAGCCTGAGTAGCACTGAGGCTGTAGGGACTCATCCAGGGTTGGGGAATGACTCTGCAACTCT
CCCACATCTGACCTTTCTGGGTGGAGGCACCTGGTGGCCCAGGGAATATAAAAAGCCCCAGAATGATGCCTGTGTGAT
TTGGGGGCAATTTATGAACCCGAAAGGACATGGCCATGGGGTGGGTAGGGACAGTAGGGACAGATGTCAGCCTGAGGT
```

Fig. 4 (Cont.)

```
GAAGCCTCAGGACACAGGTGGGCATGGACAGTGTCCACCTAAGCGAGGGACAGACCCGAGTGTCCCTGCAGTAGACCT
GAGAGCGCTGGGCCCACAGCCTCCCCTCGGGGCCCTGCTGCCTCCTCAGGTCAGCCCTGGACATCCCGGGTTTCCCCA
GGCCTGGCGGTAGGTTTGAAGTGAGGTCTGTGTCACTGTG▓▓▓▓▓▓▓▓▓▓▓▓▓▓▓▓▓▓▓▓▓▓▓▓▓▓▓CACAGTG
                                       D3-22
TCACAGAGTCCATCAAAAACTCATGCCTGGGAGCCTCCCACCACAGCCCTCCCTGCGGGGACCGCTGCATGCCGTGT
TAGGATTTTGATCGAGGACACGGCGCCATGGGTATGGTGGCTACCACAGCAGTGCAGCCCATGACCCAAACACACGGG
GCAGCAGAAACAATGGACAGGCCCACAAGTGACCATGATGGGCTCCAGCCCACCAGCCCCAGAGACCATGAAACAGAT
GGCCAAGGTCACCCTACAGGTCATCCAGATCTGGCTCCAAGGGGTCTGCATCGCTGCTGCCCTCCCAACGCCAAACCA
GATGGAGACAGGGCCGGCCCCATAGCACCATCTGCTGCCGTCCACCCAGCAGTCCCGGAAGCCCCTCCCTGAACGCTG
GGCCACGTGTGTGAACCCTGCGAGCCCCCATGTCAGAGTAGGGGCAGCAGGAGGGCGGGGCTGGCCCTGTGCACTGT
CACTGCCCCTGTGGTCCCTGGCCTGCCTGGCCCTGACACCTGAGCCTCTCCTGGGTCATTTCCAAGACATTCCCAGGG
ACAGCCGGAGCTGGGAGTCGCTCATCCTGCCTGGCTGTCCTGAGTCCTGCTCATTTCCAGACCTCACCAGGGAAGCCA
ACAGAGGACTCACCTCACACAGTCAGAGACAACGAACCTTCCAGAAATCCCTGTTTCTCTCCCAGTGAGAGAAACCC
TCTTCCAGGGTTTCTCTTCTCTCCCACCCTCTTCCAGGACAGTCCTCAGCAGCATCACAGCGGGAACGCACATCTGGA
TCAGGACGGCCCCCAGAACACGCGATGGCCCATGGGGACAGCCCAGCCCTTCCCAGACCCCTAAAAGGTATCCCCACC
TTGCACCTGCCCCAGGGCTCAAACTCCAGGAGGCCTGACTCCTGCACACCCTCCTGCCAGATATCACCTCAGCCCCCT
CCTGGAGGGACAGGAGCCCGGGAGGGTGAGTCAGACCCACCTGCCCTCAATGGCAGGCGGGGAAGATTCAGAAAGGC
CTGAGATCCCCAGGACGCAGCACCACTGTCAATGGGGCCCCAGACGCCTGGACCAGGGCCTGTGTGGGAAAGGCCTC
TGGCCACACTCAGGGGCTTTTTGTGAAGGGCCCTCCTGCTGTG▓▓▓▓▓▓▓▓▓▓▓▓▓▓▓▓▓▓▓CACAGTGATGAAACCA
                                            D4-23
GCAGCAAAAACTGACTGGACTCGCAGGGTTTATGCACACTTCTCGGCTCGGAGCTCTCCAGGAGCACAAGAGCCAGGC
CCGAGGGTTTCTGCCCAGACCCTCGGCCTCTAGGGACACCCGGGCCATCTTAGCCGATGGGCTGGTGCCCTGCACACC
GTGTGCTGCCAAACAGGGGCTTCAGAGGGCTCTGAGGTGACTTCACTCATGACCACAGGTGCCCTGGTCCCTTCACTG
CCAGCTGCACCAGACCCTGTTCCGAGAGATGCCCCAGTTCCAAAAGCCAATTCCTGGGGCCGGGAATTACTGTAGACA
CCAGCCTCATTCCAGTACCTCCTGCCAATTGCCTGGATTCCCATCCTGGCTGGAATCAAGAGGGCAGCATCCGCCAGG
CTCCCAACAGGCAGGACTCCCACACACCCTCCTCTGAGAGGCCGCTGTGTTCCGCAGGGCCAGGCCGCAGACAGTTCC
CCTCACCTGCCCATGTAGAAACACCTGCCATTGTCGTCCCCACCTGGAAAAGACCACTTGTGGAGCCCCCAGCCCCAG
GTACAGCTGTAGAGAGAGTCCTCGAGGCCCCTAAGAAGGAGCCATGCCCAGTTCTGCCGGGACCCTCGGCCAGGCCGA
CAGGAGTGGACGCTGGAGCTGGGCCCACACTGGGCCACATAGGAGCTCACCAGTGAGGGCAGGAGAGCACATGCCGGG
GAGCACCCAGCCTCCTGCTGACCAGAGACCCGTCCCAGAGCCCAGGAGGCTGCAGAGGCCTCTCCAGGGGACACAGT
GCATGTCTGGTCCCTGAGCAGCCCCCAGGCTCTCTAGCACTGGGGGCCCCTAGCACAGCTGTCTGGACCCTCCCTGTT
CCCTGGGAAGCTCCTCCTGACAGCCCCGCCTCCAGTTCCAGGTGTGGTTATTGTCAGGGGGTGCCAGGCCGTG▓▓▓▓▓
▓▓▓▓▓▓▓▓▓▓▓▓▓CACAGTGGTGCCGCCCATAGCAGCAACCAGGCCAAGTAGACAGACCCCTGCCACGCAGCCCCA
D5-24
GGCCTCCAGCTCACCTGCTTCTCCTGGGGCTCTCAAGGCTGCTGTCTGCCCTCTGGCCCTCTGTGGGGAGGGTTCCCT
CAGTGGGAGGTCTGTGCTCCAGGGCAGGGATGACTGAGATAGAAATCAAAGGCTGGCAGGGAAAGGCAGCTTCCCGCC
CTGAGAGGTGCAGGCAGCACCACAGAGCCATGGAGTCACAGAGCCACGGAGCCCCAGTGTGGGCGTGTGAGGGTGCT
GGGCTCCCGGCAGGCCCAGCCCTGATGGGGAAGCCTGCCCCGTCCCACAGCCCAGGTCCCCAGGGGCAGCAGGCACAG
AAGCTGCCAAGCTGTGCTCTACGATCCTCATCCCTCCAGCAGCATCCACTCCACAGTGGGGAAACTGAGCCTTGGAGA
ACCACCCAGCCCCCTGGAAACAAGGCGGGGAGCCCAGACAGTGGGCCCAGAGCACTGTGTGTATCCTGGCACTAGGTG
CAGGGACCACCCGGAGATCCCCATCACTGAGTGGCCAGCCTGCAGAAGGACCCAACCCCAACCAGGCCGCTTGATTAA
GCTCCATCCCCCTGTCCTGGGAACCTCTTCCCAGCGCCACCAACAGCTCGGCTTCCCAGGCCCTCATCCCTCCAAGGA
AGGCCAAAGGCTGGGCCTGCCAGGGGCACAGTACCCTCCCTTGCCCTGGCTAAGACAGGGTGGGCAGACGGCTGCAGA
TAGGACATATTGCTGGGGCATCTTGCTCTGTGACTACTGGGTACTGGCTCTCAACGCAGACCCTACCAAAATCCCCAC
TGCCTCCCCTGCTAGGGGCTGGCCTGGTCTCCTCCTGCTGTCCTAGGAGGCTGCTGACCTCCAGGATGGCTTCTGTCC
CCAGTTCTAGGGCCAGAGCAGATCCCAGGCAGGCTGTAGGCTGGGAGGCCACCCCTGTCCTTGCCGAGGTTCAGTGCA
GGCACCCAGGACAGGAAATGGCCTGAACACAGGGATGACTGTGCCATGCCCTACCTAAGTCCGCCCCTTTCTACTCTG
CAACCCCCACTCCCCAGGTCAGCCCATGACGACCAACAACCCAACACCAGAGTCACTGCCTGGCCCTGCCCTGGGGAG
GACCCCTCAGCCCCCACCCTGTCTAGAGGACTTGGGGGACAGGACACAGGCCCTCTCCTTATGGTTCCCCCACCTGG
CTCCTGCCGGGACCCTTGGGGTGTGGACAGAAAGGACGCCTGCCTAATTGGCCCCAGGAACACAGAACTTCTCTCCA
GGGACCCCAGCCCGAGCACCCCCTTACCCAGGACCCAGCCCTGCCCCTCCTCCCCTCTGCTCTCCTCTCATCACTCCA
TGGGAATCCAGAATCCCCAGGAAGCCATCAGGAAGGGCTGAAGGAGGAAGCGGGGCCGCTGCACCACCGGGCAGGAGG
CTCCGTCTTCGTGAACCCAGGGAAGTGCCAGCCTCCTAGAGGGTATGGTCCACCCTGCCTGGGGCTCCACCGTGGCA
GGCTGCGGGAAGGACCAGGGACGGTGTGGGGAGGGCTCAGGGCCCTGCAGGTGCTCCATCTTGGATGAGCCCATCC
CTCTCACCCACCGACCCGCCCACCTCCTCTCCACCCTGGCCACACGTCGTCCACACCATCCTGAGTCCCACCTACACC
AGAGCCAGCAGAGCCAGTGCAGACAGAGGCTGGGGTGCAGGGGGGCCGCCAGGGCAGCTTTGGGGAGGGAGGAATGGA
```

Fig. 4 (Cont.)

```
GGAAGGGGAGGTCAGTGAAGAGGCCCCCCTCCCCTGGGTCTAGGATCCACCTTTGGGACCCCCGGATCCCATCCCCTC
CAGGCTCTGGGAGGAGAAGCAGGATGGGAGATTCTGTGCAGGACCCTCTCACAGTGGAATACCTCCACAGCGGCTCAG
GCCAGATACAAAAGCCCCTCAGTGAGCCCTCCACTGCAGTGCTGGGCCTGGGGGCAGCCCCTCCCACAGAGGACAGAC
CCAGCACCCCGAAGAAGTCCTGCCAGGGGGAGCTCAGAGCCATGAAGGAGCAAGATATGGGGACCCCAATACTGGCAC
AGACCTCAGCTCCATCCAGGCCCACCAGGACCCACCATGGGTGGAACACCTGTCTCCGGCCCCTGCTGGCTGTGAGGC
AGCTGGCCTCTGTCTCGGACCCCCATTCCAGACACCAGACAGAGGGACAGGCCCCCCAGAACCAGTGTTGAGGGACAC
CCCTGTCCAGGGCAGCCAAGTCCAAGAGGCGCGCTGAGCCCAGCAAGGGAAGGCCCCCAAACAAACCAGGAGGTTTCT
GAAGCTGTCTGTGTCACAGTC░░░░░░░░░░░░░░░░░░░░░░░░░░CACAATGACACTGGGCAGGACAGAAACCCCATCCCAAGT
                     D6-25
CAGCCGAAGGCAGAGAGAGCAGGCAGGACACATTTAGGATCTGAGGCCACACCTGACACTCAAGCCAACAGATGTCTC
CCCTCCAGGGCGCCCTGCCCTGTTCAGTGTTCCTGAGAAAACAGGGGCAGCCTGAGGGGATCCAGGGCCAGGAGATGG
GTCCCCTCTACCCCGAGGAGGAGCCAGGCGGGAATCCCAGCCCCCTCCCCATTGAGGCCATCCTGCCCAGAGGGGCCC
GGACCCACCCCACACACCCAGGCAGAATGTGTGCAGGCCTCAGGCTCTGTGGGTGCCGCTAGCTGGGGCTGCCAGTCC
TCACCCCACACCTAAGGTGAGCCACAGCCGCCAGAGCCTCCACAGGAGACCCCACCCAGCAGCCCAGCCCCTACCCAG
GAGGCCCCAGAGCTCAGGGCGCCTGGGTGGATTCTGAACAGCCCCGAGTCACGGTG░░░░░░░░░░░░░░░░░░░░░░░░CA
                                                          D1-26
CTGTGAGAAAAGCTATGTCCAAAACTGTCTCCCGGCCACTGCTGGAGGCCCAGCCAGAGAAGGGACCAGCCGCCCGAA
CATACGACCTTCCCAGCCCTCATGACCCCCAGCACTTGGAGCTCCACAGTGTCCCCATTGGATGGTGAGGATGGGGGC
CGGGGCCATCTGCACCTCCCAACATCACCCCCAGGCAGCACAGGCACAAACCCCAAATCCAGAGCCGACACCAGGAAC
ACAGACACCCCAATACCCTGGGGGACCCTGGCCCTGGTGACTTCCCACTGGGATCCACCCCCGTGTCCACCTGGATCA
AAGACCCCACCGCTGTCTCTGTCCCTCACTCAGGGCCTGCTGAGGGGCGGGTGCTTTGGAGCAGACTCAGGTTTAGGG
GCCACCATTGTGGGGCCCAACCTCGACCAGGACACAGATTTTTCTTTCCTGCCCTGGGGCAACACAGACTTTGGGGTC
TGGGCAGGGAGGACCTTCTGGAAAGTCACCAAGCACAGAGCCCTGACTGAGGTGGTCTCAGGAAGACCCCAGGAGGG
GGCTTGTGCCCCTTCCTCTCATGTGGACCCCATGCCCCCCAAGATAGGGGCATCATGCAGGGCAGGTCCTCCATGCAG
CCACCACTAGGCAACTCCCTGGCGCCGGTCCCCACTGCGCCTCCATCCCGGCTCTGGGGATGCAGCCACCATGGCCAC
ACCAGGCAGCCCGGGTCCAGCAACCCTGCAGTGCCCAGCCCTTGGCAGGATTCCCAGAGGCTGGAGCCCACCCCTCC
TCATCCCCCCACACCTGCACACACACACCTACCCCCTGCCCAGTCCCCCTCCAGGAGGGTTGGAGCCACCCATAGGGT
GGGCGCTCCAGGTCTCACTCACTCGCTTCCCTTCCTGGGCAAAGGAGCCTCGTGCCCCGGTCCCCCCTGACGGCGCTG
GGCACAGGTGTGGGTACTGGGCCCCAGGGCTCCTCCAGCCCCAGCTGCCCTGCTCTCCCTGGGAGGCCTGGGCACCAC
CAGACCACCAGTCCAGGGCACAGCCCCAGGGAGCCGCCCACTGCCAGCTCACAGGAAGAAGATAAGCTTCAGACCCTC
AGGGCCGGGAGCTGCCTTCCTGCCACCCCTTCCTGCCCCAGACCTCCATGCCCTCCCCCAACCACTTACACACAAGCC
AGGGAGCTGTTTCCACACAGTTCAACCCCAAACCAGGACGGCCTGGCACTCGGGTCACTGCCATTTCTGTCTGCATTC
GCTCCCAGCGCCCCTGTGTTCCCTCCCTCCTCCCTCCTTCCTTTCTTCCTGCATTGGGTTCATGCCGCAGAGTGCCAG
GTGCAGGTCAGCCCTGAGCTTGGGGTCACCTCCTCACTGAAGGCAGCCTCAGGGTGCCCAGGGGCAGGCAGGGTGGGG
GTGAGGCTTCCAGCTCCAACCGCTCCACTAGCCGAGACTAAGGAAGTGAGAGGCAGCCAGAAATCCAGACCATTCCAT
AGCAAATGGATTTCATTAAAGTTACCAGACTTCAGTGTAAGTAACATGAGCCCCATGCACAACAATCCCTTATGAAGG
GGAAGTCAGTGTCGCCTCGGATTTCTTGAAAAACACAAAAACTTATCAATGCCTGTAAAAGTCTGTTGGAAAGAAAAT
ATGATTCAAGAATGTTATGCCCAACAAAGCTGGCATATTTTCTACCCGGACACACTCAGGGAATGTGGTCCCTTGAGT
GCTTCTCTCACTGCGTAAATCCTACGTGGTGTTTAAGCATATTCATAAATGTGTATGTCTATTTTTATGTGTAAGATG
GTTCATTTTTATTTTATTTATTCAATATGTACAATAAAGAATATTGACAAATAGGCTGGACATGGTGGCTCCCACCTG
TAATCCCAGCCCTTTGGGAGGCCGAGGCGGGCAGATCACCTGAGGTCTGGAGTTCGAGACCAGCCTGGCCAACATGAT
GAAAACCCATCTCTACTAAAAATACAAAGATTAGCCAGGCATGGTGGTGCATGCCTGTAATCCCAGCCACTCAGGAGG
CTGAGACAGGAGAAATGCGTGAACCCGGAAGGCGGAGGTTGCAGTGAGCCGAGATCACACCACTGCACTCCAGCCTGG
CGACAGAGCAAGATTCCATCTCAAAAAAAAAAAAAAGACAAAGAAATTTGTTTTTTTGAATAAAGACAAATTTCATCAC
ACGAAGATAAAGATGCAAAGCTCCAGACAGGAAGGCACGGACAGCACAGTGAAGCCCGGAGCGGGCGCTGGGGGGCCA
GGGGCATGGCGGGGGTGCCAGCGTCTCTCGGTGCCTACCATGGCCACTCCAGCCTGTGTTCTCACGAGGATGGCTGTG
CAATGCTAGGAGCGTGTTCGAAGCTCTAGGGCAACCACTGGAAGTGAGGCTGAGGAGCAGAGCCCAGAGGCCCGTGGA
GCTGATGAAAAGAAAGCTGGAGAAAGTGTTTGCTGCCTCCAACATGGTAAGAAAAGATAGAAAGAGAGAGCACACGG
CAAAGGGAGCTTGCTGAGGGACTCTTTACAATGGCTTGCACAGAGCTCAGGGGGTCTGGGAGGCTAGGGCCCTGCGCA
GGGCAGTCACCCCAGCCTGCTGACCAAGGTTTGCTGCAGGCAGCTCTGGGGGTGGTTGAGGCGCGGTCCCTGGAGCCA
CCCCTCAAGGGAACGAGGCAGCAGAGTGGGCCAAGGCCCAGGTCGGCTGCAAGGCTGCCCAGGACTTGGGGTCCTTAC
ATCAGCAGCCACTGATGCAGCTGGCCCAGAGAGAGGCGCCGAGCAGGTTGCCTCCAGGGGACAAACCAGGTCGGAGAG
GGTGAGGCAGTGGATGGAGCCACAACAACCCCGGGCACGGGTGACACGCACGTTCATGCACATCTGACCCTTCCTCCC
TCACCAAACAGGTCCCCCTGCCTTCCCCATGGTTGCGAAAAAGCAAATGTAGACGTTTTTTCTTTTTTAATTCATGT
TTTAATTGACAAATGAAGCCGTATATATTTATTGTGTACAACATGATGCTTTAAAATATGTATACATCGTGGAACAGC
AACGTTGAGCTAATTTAACACGCATTACTTCACATACTTGTCATCTTTTGTGGCGAGAATGCTTAAAATCCACTCTCT
```

Fig. 4 (Cont.)

```
TAGTATTTTTTAAGAATGCAATACATTGTTGTCAACTGTGGTCACCGTCATGCATAGCCAAGCTCCCGACCTCACCCT
CCTGCCAGCTCAGGCTGTGCATCCTTTCACCAGCATCCCCCACCCCGGCCCCTGGCCCTGGTAACTACCACTCTATAC
TCTACGTATGAGTTCAGCTTTTTAAGATTCCACAGATGAATGAGATCATACAGTATTTGCTTTCTATGCCTGGCTTAT
TTTAGTTAACACACTGTCCTCCAGATCCATCCGTTGTTGCAAATGACAGGGTTTCATTCTTTTTAAAGTCTAAAGAGT
ATTCCATTGTGTCAATGGACCTCATTTGCTTTATCCATGCATCAACTATGGACATTTAGGTTGATTCCATTTCTTAGC
TGTTGTGGATGGTGCTGCAGTAAACATGGGGCTGCAGATGTCTCTTCAACATACTGACATCATGTCCTTTGGATAAAT
ACCCAGTAGTGGGATCGCTGGATCACAATGTACAGTTTGTTTTTAATGGAAACTTTCATTTTTTGGTGAAATTAGGA
AAACAGATAAAACCCACAGAATCCAAAATATATGTGAAGATGCCAAAAACAGTTGACATTGGGCAGGGTCACATGGA
AGGAAGTGAATACATGACGGGGTGTGAGGGCCCAGAGGCAGCTGAAATACGCTTTCTAAACACAAGGACCTCTTCTGA
GAGGGCAGAAGTTTTATCCTGCACATGCAATGACCAGCACAGCTAAAATACACTTTCTAAACATGAGGACCTCTTCTG
AGAGGGCAGCTTTATCCTGCAAATGCAATGACCAGCACAGGACCCAGAATAAAGAGAGTTGCCAGCGGACGCCTGGTG
TCCATGTGTCCAGGTGAGTTCGAGATGCGGACGGCGCTGGCCAGCCAGTCACACCCTAAGTCAATCTGCTGCATGCAT
TTGTCCTTGCCACAGCAGAAAACGAGAAAGCCTTTGGGCTGCAAAGCTTCACAGGCTCCTCTTCTCCCGACTCCATGG
AAACAGCTACAAAGAGCAGGCCCAGTAGAGCTTAATTCATGAAAATGAGTAATAAACTTGAACTGGAACAGTATCGAC
TTTTTAGAAACGGCAGCAAAGTGTATAAAAAATATTCACCAGAACAATATTTCCAAACGATGAGATGAGAATTTCAGC
CAAGTAATCCTCCATGGATAGAAAATAATGAAGGGATTGGATTTATGAAGGAAAATCATGGAGCTCAAATACAAGAGA
AGAGAATCAAAAATGAACAGGAGGAGATAAAATATGGTTTGGCCAAAGTTACAAAATAAATTTTTTAAAAACCCTTCA
TCATGGCAAGTAGAAAGAGCGAGAGGAAAAACAGATCCCGTGGAAGACACAAATAGGACATGGGGAGAAAAATGAATG
AGATGAAACAGAGCAGAAATAAAATTTTACGGAACTAAAGACAAGTGATCTGAACCTGCCTGGGGCCTGGGGGACCTC
GCCACCCTGAAGGGAAAGAACATGCCTGGCTGGCTTTGCCACCTGCTCATTGCAGAGCCCCACAGCTTGCAACAAACA
TAGGCGGTAGCCAGGGAGTGGTTACAGCAGGCCTTGAGCAAGACCCAGTGTTGTGCTGACTTCAGGTCTGACCCAGCA
CTGTCATAGTGGTGGTGTCCATAGTGGTAGTGGGGGTGCTTGTGTCACTCCACCCCCATCTCCAGGAGGCTCAGAACA
GACAGAGAGAGACTCCATTTGTTTGGGAGAAAGTAAGGGATGAGAACAAGAGTCTCTGCCTGGTAATCCAGAGAATTA
TTCTAGATCTTGGCCAAGATTATCAAAGCAGTACCTCTATGAGTCTTTTGGGCTTGGAGTCCCCTAAAGCAGATATA
GCTAAGATCACAACACCCAAGTCCTTTTGAATATGTGGGAAGACTTCCCAAGGACAGGAGCAAACAAACAAGCCCAGA
CTGCAAAAAAACAAGCCCAGACTGCAATAAACACCTCACTCTTCAATGCCCAGGCACTGAAGAACATCTCCTAGCAGC
AACACCATCCAGGAAAACATGGCCTCAACCAGTGAACTAAATAAGGCACCAGGGACCAGTCTCGGAGAAATAGAGGTA
TGTTATCTTTCAGAGAATTCAAAGTAGCTTTGTTGAGGAAACTCAAAGAAATTCAAGATAACACAGTGAAGGAATTCA
GAATCCTATCCGATAAATTTAACAGAGATTGAAGCAATTAAAAAGAATTAAGCAGAAATTATGGAGCTGAAAAATGCA
ATTGGCATACTGAAAAATGCATCAGAGTATTTTCATAGCCTCTTATATCAAGTAGAAGAAAGAATTAGTGAGCTTGAA
AACAGGCTATTTGGAAAAGCACGATAAAAGGAGACAAAAGAGAAAAGAATAAATAACAATGAAGCATATCTACAGGAT
CTAGAAAATAGCCTCAAAAGGCCAAATCTAAGAATTATTAGCCTTAAAGAGGAGGTAGAGAAAGAGGGATGGAGAGTT
TATTCAAAGGGATAATAACAGAAAACTTCCCAAACCTAGAGAAAGATATCAATATCCAAATGCAAGAAGGATGTAGTA
CACCAAGGAGATTTAATGCAAAGAAGACTACCTCAAGGCATTCAATACTCAAACTCCCATATGACAAGGACTTTAAAA
AGATCCTAAAAGCAGCAAAAGAAAAGAAATGAATAAAATACTATGGAGCTCCAATATGTCTGGCAGCAGACTTTTCAG
TGAAGACTTTATATGCCAGGAGAGAGTGTCATAATGGATTTAAAGTGCTGAAGGAAAAAACTTTTACCCTCGAACAGT
ATAGCTGGTGAAATTATCCTTCAAACATGAAGGAGAAATAATTTGTTTCCAGACAAATGTTGAGGGATTTCATGAACA
CCAGACCTGTCTTTTAAGAAATGCTAAAGGGAGTACTTCAATCAGAAAGAAACACGTTAGTGAACAATAAGAAATCAT
CTGAAGGCACAAAACTCACCGGTAATAGTAAGTACACAGAAAAACACAGAATATTATAACACTGTAACTGTGGTGTGT
AAACTCCTTTTGTTTGTTTGTTTGTTTGTTTGTTTTTGTTTTTAGACGGAGTTTTGCTCCAGCCCAGGCTGGAG
TGCAATGGCACAATCTCAGCTCACTGCAACTTCCACCTCCCGGGTTCAAGCAATTCTCCTGCCTCAGCCTCCCAAGTA
GCTGGGATTACAGGCATGTGCTACCATGTCCAGCTAATTTTGTATTTTAGTAGAGACGGTGTTTCACCATGTTGGTCA
GGCTAGCCTTATCTTGAGTAGAAAAACTAAATGATGAAGCAATGAAAAATAATAACTACAACTTTTCAAGACATAGTA
CAATAAGATATAAATCATAACAAAAAGTTAAAAGGTGGAGGGATGAAGTTAAGGCAAAGAGTCTTTATTAGTTTTCTT
TTTACTTGTCTGTTTATGCAAACAGTGTTAAGTTGTCATCAGTTTAAAATAATGGGTCATAAGATACTATTTGCAAGC
CTCATGGTAACGTCAAACCAAAAGCAATACAACAGATACACAAAAAACAAAAAGCAAGAAGCTAAATTACGTCATCAG
AGAAAATCACCTTCACTAAAAGGAAGACGGAGAAAAGAATGAAGAGAGAGAAGACCAAAAGCAAATAGCAATATGGCA
GGAGTAAGTCCTTACTTATCAATAATACCATTGAATGTAAATGGACTAAACTCTCCAATCAAAAGACATAGAGTGGCT
GAATCAATTAAAGAAAAACAAGACCCATTGATCTGTTGTCCACAAGAAACACACTTTATCTATAAAGACACACATAG
ACTGAAAACAAAGGGATGGAAAAAGATACTCCACGCCAATGAAAACCAAAGAAAGAGCAGGAGTAGCTACACTTATAT
CAGGCAAAATAGATTTCAAGACAAAAACTATAAGAAGAGACAAGGTCACTAATGATAAACAGGTCAATTCAGCAAGAG
GATATAACAATTGTAAATATATATGCACCCAATGCTGGAGCACCCAGATATATAAAGCAAGTATTTACTAGAGCTAAA
GAGAGAAATAGACTCCAATGCAATAATAGCTGGAGATTTCAACATCCCACTTTCAACATTGAACAGATCCTCCAGATA
GAAAATCAACAAAGAAATATTGGACTTAATCTGCACTATCGACCAAATGGATCTAACAGATATTTACAGAACATTTCA
TCCAACAGCTGCAGAACACACATTCTTTTCCTCAGCACATAGATCATTCTCAAGGATAGACCATATGTTGGGTCACAA
AACAAGTTTTAAAATATTCAAATACATTGAAATAATATCAAGCATCTTCTGTGACCACAATGGACTAAAACTAGAAAT
```

Fig. 4 (Cont.)

```
CAATAACAAGAGGAATTTTGGAAACTATATAAATATATGGAAATTAATGAATGCTGAGTGGGTCAATGAAGCAATTAA
GAAGGAAACTGAAATTTTTCTTGGAACGAATGATCATGGAAACAGAAAATACCAAAACCTATGGGATACAGCAAAAGC
AGTACTAAGAGGGAAGTTTACAGCTACAAATGCTTACATTAAAAAAGAAGAAAAACTTCAATAAAAAAACCTAACAAT
GCATCTTAAAGAACTAGAAAAGCAAGAGGAAATCAAATCCAAAATTAGTAGAAGAAAACAGTAAAGGTCAGAGCAGAA
ATAAGTAAAATTGAAATGAAGAAAACAATACAAAAGATCAATAAAACAACAGGTTGTTTTCTTGAAAAGTTAAACAAA
ATTGACAAACCTTTAGCCAGACTAAGAAAAAAAGACAGAAGATCCAAATAAATAAAATCAGAGATGAAAAAGGTGACA
TTACAACTTACACCACAGAAATTCAAAGGATCATTAGTGGCTACTATAAGCAACTATATGCCAATAAATTGGAAAATC
TAGAAGAAATGCAGAAATTCCTAGACACATACAACCTCCCAAGATTAAACCAAGAAGAAATTCAAAACCTGAACAGAC
TGATAACAAGTAATGAGATCAAAGCCGTAATAAAAAGCCTCCCAGTAAAGAGAAGCCCAGGACCCGACGGCTTCACTG
CTGAATTCTACCAAACATTTAAAGTAGAACTAATACCAATCCTACTCAAACTATTCCAAAAAATAGAGGTGGAAGGAA
TACTTCAAAACTCATTATACGAGGCCAGTATTAACCTGACACCAAAACTAGACAAAGACACATGAAAAAAAGAAAACT
ACAGGCCAATATGTCTGATGAATATTGACACAAAAATCCTCAACAAAATACTAGCAAACCAAATTCAACTACACATTA
GAAAGTTCACTCATCATGACCAAGTGGAATTTATCTAACTTGGGATGCAAAGATGGTTCAACATATGCAAATCAATCA
ATGTGATACATCATATCAACAGAATGAACAACAAAAACCATTTGATCATTTAATTGATACTGAAAAAGCATTTGATAA
AATTCAACATTCCTTCATAATAAAAATTCTCTTCTATACTAGGTACAAAAGAAACTTACCTCAACATAATAAAGCCAT
ATATGACAGTCCCACAGTATGATACTAAATGAGGAAAAACTGAGAGCCTTTCCTCTACGATCTGGAACATGACAAAGA
TGCCCACTTTCATCACTGTTATTCAACATAGTACTGGAAGTCCTAGCTGGAGCGATCAGACAAGAGAAAGATATAAAA
GACATCCAAATTGGAAAGGAATAAGTCAAATTATCCTCATTTGCATATGGTATGATCTTCTATTTAGAGCTAACTAAA
GACTCCACCAAAAAAAGTTATTAGAACTGACGAACAAATTCAGTAAAGCTGCAGGATACAAAATCAACATACAAAAAT
CAGTAGCATTTCTATATGCCAACAATGACCAATGTGAAAAAGAAATTAAAAAGTAACCCTATTTACAATAACCACAAA
TAAACACCTAGGAATTAACCAAAGAGGTAAAAGATTTCTGTAATGAAACTATAAAAAACTGATGAAAGAAATTGAAG
AGTACACCAAAAAATGGAAAGCAATTGCATGTTCATGGATTAGAAGAATCAGTGTTGTTATAATGTCCATACTATCCA
AAGCAATCTACAGATTCAATGCAATCCTTATCAAAATACCAATGACATCATTCACAGAAATAGAAAAAAAAATCCTA
AAATTTACGTGGAACCACAAAGACCCAGAATAGCCAAAGCTCTCCTAAGCAAAAAGAACGAAACTGTAGGAATGACAT
TGCCTGTCTTCAAATTCTACTACAGAGCTATAGATAGTAACCAAAACAGCGTGGTACTAGCATAAAAACAGACACAGA
GACAAACAGAACAAAATTTAAAAACCCAGAAATAAATCCACACACCTACAGCAAATTCATTTTTGACAAAGTTGCCAA
GAACATACTCTGGGGAATAGATAATGATATCTCTTCAATAAATAATGTGGGGAAAACTGGATATCCATATACATAACA
GTGAAACTAGACCCCTCTCTCTCACTATATACAAAAATCAAATCAAATTGTTTAAGGACTTAAATCTAAGACCTC
ATACTATGAAACCACTGCAAGACAACCTTGGCGGAAACTCTCCAAGACATCAGTCCAGGCAAAGATTTCTTGAGTAAT
ATCCCACAAGCACAGACAACCAAAGCAAAAATGGACAAATGGGATCACATCAAGTTAAAAAGCTTCTGCACAGTAAGG
GAAACAACCAACAAAATGAAGAGACAACCCACAGAATGGGAGAAAATATTTGAAAAATACCCATCTGGCAAGGGATTA
AAAACCAGAATATATGCAGAATATATAAGGAGCTCAAACAGTGCTATAGAAAAAAAAATCTAATAATCTGATTTAAAA
ATGGGAAAAATGTTAGAATAGACATTTCTTAAAATAAGACATACAGATGGCAAACCGACATGGAACGGTGCTCAACAT
CATGGATTATCACAGAAACACAATCAATCAAAACTAAAACTAAAATGTGCTATCATCTCACCCCAGTTAAAATGGCTG
ATATCCAGAAGACAGGCAATAACAAATGCTGGCAAGGATGTGGGGAAAAGGGAGCCCCATACACTGTTGCTGGGATT
GTAAATTAGTACAACCACTGTGGAGAGCAGCATGAAAGTTCCTCAAAAAACTGAAAGAAAGCTACCATAGGATCCAGC
AATCCCACTGCTGTGTATATACTACAAAAGAAAGGAAGTCAGTATATGAAGAGGTATCTGCACTCCCATGTTTGTTGC
AGCCCTGTTCACAACAGCCAAGATTTGGAAGCAACCTAAGTGTCCATCAGCAGTTGAATGTATAAAGAAAATGTGGTG
CATATACACAATGGAGTATTATTCAATAATAAAAAGGAATGAGATTGAGTCATTTGCAACAACATGGATGGAACTGGA
GATCATTATGTGAAGTGAAATAAGCCAGGCACAGAAAGACAAACATTACAATGTTCTTACTTATTAATGAGATCTAAA
AATCAAAACAATTGCACCCATGTTCATAAAGAGTAAAAGGATGGTTACCAGATGCTGAGAACGGTGGTGGGGGATAG
GGAAAGGTGGCAGTGGTTAACGGGTACAAAAAAATAGAAAGAATGAATAAGACTTACTACTTGATAGCACAGCAAGGT
GGCTATAGTCAGTAATTTAGTTGTATATTTTTAATAATGAAAGGTGTATAATTGGATTGTTTCTAACACAAAGGATAA
TGCTTAAGAGGATGGATACCCCATTTTCCATGATGTGATTATTTCACATTGCACGCCTAGATCAAAACATCCAATGTA
CCCCATAAATATATACATCTTCTATGTACCCATAAAATTCTGTAAAATAAAATATATAAAAGAGGTGACAGATATG
GAAGACAGGCAAAGAAGAGACGACATCCACATAATCCGAGTACCTAAGAAAGAATGGAGTCCAGTGCATCTCAGGAGC
CACCATTCTAAGCCAATTTTCTCTGGTTCTCTCAGTCACCCTACCAATACGTGGGCAATCTTGTTTTATTTCAGGATA
GAGTTTTTGAAATTATAGATTTAAGTATGCTTTCTGTTCTATTACTTTTGGTAATTAATTTTAGAAAGAACTAATTTG
GGCACAAATTTGAAAAAATTCTAAATCCAAAAAAAAAAGAAAAAAACACACACAATCATCTATAAGGGGATGAT
GACCAGTCCTAGATTTCTCACCAGCCACATTCAAGATCAGTAAATGGTAGGACAAAACCTGTAGGGTCCTTAAGGGGG
AAAGAAGTAGTGGATAGTCCAGAGTCTATATACAGCCAACTGTTCTTGAAGAAAAAGGCTGCTGAAAAGGAGTTCCA
AACATTCTATAATCCATAATCTCATGATGAAACTACTAGAGGAAGACCACCAGCCATCAAAAGGTGCTTGGAGAACCC
AGGGCCAAGAACCAAAAGTAAATATTAAGTGTCCTTAACTGCGAGACTAAGATAGAAATGACTGTGGGGACCATGTG
GCCTCAACAGAGGTGAAATGGTGTCTGCCTGACAAAGTGGACATTTTACAATGATCAAAACACAGAATATGAGATAGA
GAGCACTTCTGAATTACTGCCTCACTCCAAATAACTCTCAGCCAAAGGACTTCAGTAAAACCAAATTGGGCATATTAG
ACAGTACAAACAAATTCTAAGAAAATAATATTACTGATTACAATCACATGATGCTAGAGATGGAGGGGAAAAGGAAGA
```

Fig. 4 (Cont.)

GGAAACCAGGTAATTTCATACTCGTATATAGTAAAGAACTAAAGTACATTGTCCAAAGAAGAACAAAGAATATTTTGG
AAAGTTATAAAGGTAGCCACTACACATAGAAGATAGCAAAGAACAAGAAAACTTAAGATGGAAAACTTTTTGGAAGCA
TAAAAATAGAAAATATAAACTACTAAGATAAGATTGAAGCCAAACAGATCTATGAAAACAACAAACATCAATGGCCTT
AACTTGCCTATTAAAAGGAAGAGACTTTCAAATTGGACCACAAGATAAAACCCAACTCTATATAGCATATGAGTATTA
CACACAAAATGGGAAAAGCTGAAAAAACTTGGGCAAAATTCACCCCAAGCAAATTCCACTGTTTCCTTTGGGACAAAA
TGCCAAGCTCCATGCCAGGGAAGATGATTCTCCTCAGACCTTCTCCTCACTCTCCCAGTCCTCTTAGGGAAGGAATTG
GGTGTTAGAGGAGGGAGACTCTGTCGATTATCAGCTGAAGCAGTGGTGTGCTCCTGCGTTGCTTCTGACCTGGGAAAT
GAAGCAGCAAGACTCTTTCTGCTGTGTCTTTGCCCAGAAGGGCCATCCCCCCAGAGCAGAGTACCCAGGCCGGCAGGA
GCAGTGGTGGAAGCGTGGAAACCACGTCTCCTACAGCAGAGACCATCAGAAGCGGAGCCTCGGGTATAAGGGAAACAA
CGCGTTCTCCCTAACCTGGGAGTGACAGACAGCGTCATTCCTCACAGTGATACCCTGTGTTCTAGCCATCTGGCCCAT
GACAGAGCCAGCCCAGAGCCAGCCCAGAGCCAGCCCCTGACCATCCTGGAGCCTGGCCAGCTCGCCAAGCTGCACCAT
AGGCCTGGAAGGCGTGGAGACCTGCGGCAGTGCCCTGTCCTCCCGTGAGGCCTGCCATCCCTGCCAGGGGTCGCCTCT
GGCTTCTCCTTCTCCAGGACCGCACGGTCCAGAGGCTCAGTGCCTGGAGTAGGTGTTGCCTCCCTGCTTCTAGGCCCA
GACCCTCCCTTGTTCCTGACCCCGGGCCTTTCCCTCTGGCTTGGACATCCAGGGCCCTGTCTCAGCTGGGGAGCTGCT
CCTGCTCAAGGACTGTCTTCCGCGGGATCGAAAGGCCGCGTCCTGAACAATGCGTGGGCCACGTGAGCGGAGCAGGCT
CTAAAGGCCGCGTCCTAAACAGTGCGTGGGCCACGTGAGCGGAGCAGGCTCTAAAGGCCGCGTCCTAAACAGTGCGTG
GGCCACGTGAGCGGAGCAGGCTCTAAAGGCCGCGTCCTAAACAGTGCGTGGGCCACGTGAGCGGAGCAGGCTCTAAAG
GCCGCGTCCTAAACAGTGCGTGGGCCACGTGAGCGGAGCAGGCTCTAAAGGCCGCGTCCTAAACAGTGCGTGGGCCAC
GTGAGCGGAGCAGGCTCTAAAGGCCGCGTCCTAAACAGTGCGTGGGCCACGTGAGCGGAGCAGGCTCTAAAGGCCGCG
TCCTAAACAGTGCGTGGGCCACGTGAGCGGAGCAGGCTCTAAAGGCCGCGTCCTAAACAGTGCGTGGGCCACGTGAGC
GGAGCAGGCTCTAAAGGCCGCGTCCTAAACAGTGCGTGGGCCACGGGAGCGGAGCAGACTCTAAAGGCCGCGTCCTAA
ACAGTGTGTGGGCCACGTGAGCGAAGCGCCCTCTCCACTGCCCTCGGGGCCGCAGCTCCCAGCTCAGCTCCCAGCCCT
GCTCAGGGCCAGCCAGGCCAGGAGGTACCATCCAGGCTAAGTGACCCTCAGGGGGGACAGGTGCCCCAGGAGATGCCAG
CTGTTGGGAGAGGCTGGGGGACCAACTCGACCTGGCCTGTGGGCCCTGCCCTGGCCACCCATTGTAGGATCCAGCCGC
CACGCCTGTGACACTCGTGTGCTTTCCCTGGTGTGTGCTTGTGGCAGGTGGGGGCAGAGGGTCCTCAGGCCAGAGAGC
CACTCCCCAGCGCCAGACCACCCTCTTCCTCACTCCCCCACCTCACCCCCTCACAGGTGCCTCCCAGGCCATCAGGG
CCCAACCACCCCTAAACAAATGGGTTCTCGGCCCCTCGTGGCTGGAGGTGGGTTCTCTCACCATTCCCAGCCTAAGAC
TCCATCCCCATGCTGGCAGCTGTTCAACCATGTCTAGAGAGATCCACTGTCCCAGACAGCACCTCAGGGTCCCCGTC
CTGCCTGGAACCCTGTAGGAAACTCCACAAACCGCCGCCATTCTGTCCACACCCCTACAGGAGCCCCAACCCTCTCCC
CACATCCAGGCTTCCCTCCCAGACCCCTCATCCCTGCCCGCACGGTGCCTGAGGGGCCTTCTTGGGCAGCGCCTAAG
CAAGCCCCCAGCACCCTTCGGCCCCTTCAAGGCACACAGGCCCCCTTTCCACCCAGCCTCAGGAAACCACCTGTGTCC
TCCAACGACAGGTCCCAGCCTCCCAGCCTTTGCCTTGCCTGTTCCTCTCCCTGGAACTCTGCCCCGACACAGACCCTC
CCCAGCAAGCCCGCAGGGGCACCTCCCCTGCCCCCAGACACCCTGTGCCCGTCAGTTCATCCCCAGCAGAGGCCCTCA
CCAGGCACACCCCCATGCTCACACCTGGCCCCAGGCCTCAGCCTCCCTGAGGGCCCCACCCAGCCCGCGTCTGGCCAG
TGGTGCGTGCAAAGCCCCTCACCCAGACTCGGCGGAAGGCAGCCAGTGCAGGCCTGGGGAGGGGCTCTCCTTAGACCA
CCTTGCACCTTCCCTGGCACCCACCATGGGAAGAGCTGAGACTCACTGAGGACCAGCTGAGGCTCAGAGAAGGGACCC
AGCACTGGTGGACACGCAGGGAGCCCACGCCAGGGCGCCGTGGTGAGTGAGGCCCCAGTGCCACCCACTGAGGCCTCCC
GTTCAGTGGGACGACGGTGAACAGGTGGAACCAACCAGGCAACCCCGCCGGGCCCCACAGACGGGATCAGAGCAGGA
AAGGCTTCCTGCCCCTGCAGGCCAGCGAGGAGCCCTGGCGGGGCCGTGGCCCTCCAGGCGAGGAGGCTCCCCTGGCC
ACCGCCACCCGGGCCTCTCTGCTGCTGGGAAAACAAGTCAGAAAGCAAGTGGATGAGAGGTGGCGTGACAGACCCAGC
TTCAGATCTGCTCTAATTTACAAAAGAAAAGGAAAAACACACTTGGCAGCCTTCAGCACTCTAATGATTCTTAACAGC
AGCAAATTATTGGCACAAGACTCCAGAGTGACTGGCAGGGTTGAGGGCTGGGGTCTCCCACGTGTTTTGGGGCTAACA
GCGGAAGGGAGAGCACTGGCAAAGGTGCTGGGGGCCCCTGGACCCGACCCGCCCTGGAGACCGCAGCCACATCAGCCC
CCAGCCCCACAGGCCCCCTACCAGCCGCAGGGTTTTGGCTGAGCTGAGAACCACTGTG▓▓▓▓▓▓▓▓▓CACAGTGAT
                                                          D7-27
TGGCAGCTCTACAAAAACCATGCTCCCCGGGACCCCGGGCTGTGGGTTTCTGTAGCCCCTGGCTCAGGGCTGACTCA
CCGTG▓▓▓▓▓▓▓▓▓▓▓▓▓▓▓▓▓▓▓▓▓▓▓▓▓▓▓▓▓▓▓▓▓▓GTGAGTCTGCTGTCTJ1GGGG
     JH1
ATAGCGGGGAGCCAGGTGTACTGGGCCAGGCAAGGGCTTTGGCTTCAGACTTGGGGACAGGTGCTCAGCAAAGGAGGT
CGGCAGGAGGGCGGAGGGTGTGTTTTTGTATGGGAGAAGCAGGAGGGCAGAGGCTGTG▓▓▓▓▓▓▓▓▓▓▓▓▓▓▓▓▓
                                                          JH2
▓▓▓▓▓▓▓▓▓▓▓▓▓▓▓▓▓▓▓▓▓▓▓▓GTGAGTCCCACTGCAGCCCCCTCCCAGTCTTCTCTGTCCAGGCAC
CAJ2GGCCAGGTATCTGGGGTCTGCAGCCGGCCTGGGTCTGGCCTGAGGCCACACCAGCTGCCATCCCTGGGGTCTCC
GCCATGGGCTGCATGCCAGAGCCCTGCTGTCACTTAGCCCTGGGGCCAGCTGGAGCCCCAAGGACAGGCAGGGACCC
CGCTGGGCTTCAGCCCCGTCAGGGACCCTCCACAGGTAGCAAGCAGGCCGAGGGCAGGGACGGGAAGGAGAAGTTGTG
GGCAGAGCCTGGGCTGGGGCTGGGCGCTGGCTGTTCATGTGCCGGGGACCAGGCCTGCGCTTTAGTGTGGCTACAAGT

Fig. 4 (Cont.)

```
GCTTGGAGCACTGGGGCCAGGGCAGCCCGGCCACCGTCTCCCTGGGAACGTCACCCCTCCCTGCCTGGGTCTCAGCCC
GGGGGTCTGTGTGGCTGGGGACAGGGACGCCGGCTGCCTCTGCTCTGTGCTTGGGCCATGTGACCCATTCGAGTGTCC
TGCACGGGCACAGGTTTGTGTCTGGGCAGGAACAGGGACTGTGTCCCTGTG▓▓▓▓▓▓▓▓▓▓▓▓▓▓▓▓▓▓▓▓▓▓▓▓▓▓
                                                   JH3
▓▓▓▓▓▓▓▓▓▓▓▓▓▓▓▓▓▓▓▓▓GTAAGATGGCTTTCCTTCTGCCTCCTTTCTCTGGGCCCAGCGTCCTCTGTCCTGG
AGCTGGGAGATAATGTCCGGGGGCTCCTTGGTCTGCGCTGGGCCATGTGGGGCCCTCCGGGGCTCCTTCTCCGGCTGT
TTGGGACCACGTTCAGCAGAAGGCCTTTCTTTGGGAACTGGGACTCTGCTGCTGGGGCAAAGGGTGGGCAGAGTCATG
CTTGTGCTGGGGACAAAATGACCTTGGGACACGGGGCTGGCTGCCACGGCCGGCCCGGGACAGTCGGAGAGTCAGGTT
TTTGTGCACCCCTTAATGGGGCCTCCCACAATGTG▓▓▓▓▓▓▓▓▓▓▓▓▓▓▓▓▓▓▓▓▓▓▓▓▓▓▓▓▓▓▓▓▓▓▓▓▓▓▓▓
                                   JH4
▓▓▓▓GTGAGTCCTCACAACCTCTCTCCTGCTTTAACTCTGAAGGGTTTTGCTGCATTTTTGGGGGGAAATAAGGGTG
CTGGGTCTCCTGCCAAGAGAGCCCCGGAGCAGCCTGGGGGGCTCAGGAGGATGCCCTGAGGCAACAGCGGCCACACAG
ACGAGGGGCAAGGGCTCCAGATGCTCCTTCCTCCTGAGCCCAGCAGCACGGGTCTCTCTGTGGCCAGGGCCACCCTAG
GCCTCTGGGGTCCAATGCCCAACAACCCCGGGCCCTCCCCGGGCTCAGTCTGAGAGGGTCCCAGGGACGTAGCGGGG
CGCCAGTTCTTGCCTGGGGTCCTGGCATTGTTGTCACAATGTG▓▓▓▓▓▓▓▓▓▓▓▓▓▓▓▓▓▓▓▓▓▓▓▓▓▓▓▓▓▓▓▓▓
                                           JH5
▓▓▓▓▓▓▓▓▓▓▓▓▓▓▓▓▓▓▓▓GTGAGTCCTCACCACCCCTCTCTGAGTCCACTTAGGGAGACTCAGCTTGCCAGGGTCTCAG
GGTCAGAGTCTTGGAGGCATTTTGGAGGTCAGGAAAGAAAGCCGGGGAGAGGGACCCTTCGAATGGGAACCCAGCCTG
TCCTCCCCAAGTCCGGCCACAGATGTCGGCAGCTGGGGGGCTCCTTCGGCTGGTCTGGGGTGACCTCTCTCCGCTTCA
CCTGGAGCATTCTCAGGGGCTGTCGTGATGATTGCGTGGTGGGACTCTGTCCCGCTCCAAGGCACCCGCTCTCTGGGA
CGGGTGCCCCCCGGGGTTTTTGGACTCCTGGGGGTGACTTAGCAGCCGTCTGCTTGCAGTTGGACTTCCCAGGCCGAC
AGTGGTCTGGCTTCTGAGGGGTCAGGCCAGAATGTGGGGTACGTGGGAGGCCAGCAGAGGGTTCCATGAGAAGGGCAG
GACAGGGCCACGGACAGTCAGCTTCCATGTGACGCCCGGAGACAGAAGGTCTCTGGGTGGCTGGGTTTTGTGGGGTG
AGGATGGACATTCTGCCATTGTG▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
                       JH6
▓▓▓▓▓▓▓▓GTAAGAATGGCCACTCTAGGGCCTTTGTTTTCTGCTACTGCCTGTGGGGTTTCCTGAGCATTGCAGGTTG
GTCCTCGGGGCATGTTCCGAGGGGACCTGGGCGGACTGGCCAGGAGGGGACGGGCACTGGGGTGCCTTGAGGATCTGG
GAGCCTCTGTGGATTTTCCGATGCCTTTGGAAAATGGGACTCAGGTTGGGTGCGTCTGATGGAGTAACTGAGCCTGGG
GGCTTGGGGAGCCACATTTGGACGAGATGCCTGAACAAACCAGGGGTCTTAGTGATGGCTGAGGAATGTGTCTCAGGA
GCGGTGTCTGTAGGACTGCAAGATCGCTGCACAGCAGCGAATCGTGAAATATTTTCTTTAGAATTATGAGGTGCGCTG
TGTGTCAACCTGCATCTTAAATTCTTTATTGGCTGGAAAGAGAACTGTCGGAGTGGGTGAATCCAGCCAGGAGGGACG
CGTAGCCCCGGTCTTGATGAGAGCAGGGTTGGGGGCAGGGGTAGCCCAGAAACAGTGGCTGCCGTCCTGACAGGGGCT
TAGGGAGGCTCCAGGACCTCAGTGCCTTGAAGCTGGTTTCCATGAGAAAGGATTGTTTATCTTAGGAGGCATGCTTA
CTGTTAAAAGACAGGATATGTTTGAAGTGGCTTCTGAGAAAAATGGTTAAGAAAATTATGACTTAAAAATGTGAGAGA
TTTTCAAGTATATTAATTTTTTTAACTGTCCAAGTATTTGAAATTCTTATCATTTGATTAACACCCATGAGTGATATG
TGTCTGGAATTGAGGCCAAAGCAAAGCTCAGCTAAGAAATACTAGCACAGTGCTGTCGGCCCCGATGCGGGACTGCGTT
TTGACCATCATAAATCAAGTTTATTTTTTTAATTAATTGA▓▓▓▓▓▓▓▓TCTTATCATGGTTGTCGCAATGTGACAATTGG
TTTGCTTACTGGGGCCAAGGCACTCTGGTCACTGTCTCTTCAGGTGAGTCCTAACTTCTCTCATTCTAAATGCATTTG
GGGGAACTTTGAGCATTCCGGACCAAGACTCCCTGCAAATGGGAGCCAAGATTCGACCCCTTTGTCCCATATTGAGAC
ACGGGTCTGGGTCAGGTATCTCTACCTGCTGGTCTGTGGTTATACCAGAACTGGAGTGTGATGAAGGGTCTGCCAGAA
CTGAGGCTTGAAGTCTGGGCAGACTCCTGTCCAGAGTCTATTGGACTCTTATGAGAATTAGGGGCTGACAGTTTATA
ATAATAATTCGAGAGTCAGTGACTGTCTTTTTTTCTCAGAGGTGAGGCTGGAATATGGGTCACATTAAAGGCTAAAAA
GGGGTCCAGGGACCTTTCTGCCCAGGCAGGGAACAGAGTATGGGACAGTGATTTAAATGGTTGATTATGTATGACAC
TAGGAGACAGCACGGTGTCTTGAGTTGCCCAGGGGTTATTCTAGTCATTCTCTGGGGTTTTTGTGGGGTATGAAGGGA
AAATCCACTATTGTGATTACTATGTTATGGATGCCTGGGGTCAAGGAGCTTCAGTCACTGTCTCCTCAGGTAAGAATG
GCCTCTCCAGGTCTTTATTTTTAATCTTTGCCTATGGAGTTTTCAGAGTATTGCATACTAACCCCGGAGATGTGTCAA
GCTGGCCGGGAGAAGCTAGGGACTAAACTGCCTAGGGGATCTCAGAGCCTTGGGGATAAACTAAGAATCTCTTTGATG
GTGTTGGTAGAGTCCCTAAATGATGGAGCAGGGATTTTGGAGCCTCATTTGAGGGAGATGCTAAAAAGATTCCATGGC
TAAAGGGATAGTTTGGGCTGTGGTTGGAGATTTTCAGTATTTAGAGTAATAGTGTTAGCTGAGAAATATAATTCAGGA
CCCTCTGAGACAGCATCTGTACAGTATCTGATGCACAGGGACAAAGAGTGGAGTGGGACACTTTCTTCAGATTTGTGA
GGAATGTTCTGAGTGAGATTGTTTAAAACATCATTTGTTGAAAAGAGAACTTTTAGTGAATCAATCAAGGAAGGAAGGA
AGGCTCAGTCTCAAAAGGGTAGCTGATATCCAGAGGAATCTGGATAAGCCTGCAAAAGTCTAGCTTTCAAAGGAATGC
AGAAGTATGCATGTGGAAAATTAGAAGATTTTTTTTACCCTTAAAGTGGTTCCTATGATAGTTAGAATACTGTGACT
TTACTATGTGAGAGAGTTTTCAAGTATTCACTTTTTTTTTAAATGTCCAAGTACGAAAAAATTTTGTCAGTTTGAAG
TCAGGTTTGTACAGAATTGATATTGTTGAAAGTTTAACCAAAGAATGGGAATGAGGCTCTTTCACACCCTATTCAGAA
CTGACTTTTGACAATAATAAATTAAGTTTAAAATGTTTTAAACAAATTGAGCAATGTTGAGTTGCAGTCAAGATGGC
```

Fig. 4 (Cont.)

```
CGATCAGGACCAGGACACCTGCAGCAGCTGGCAGGAAGCAGGTCATGTGGCAAGGCTATTTTGGGAAGGGAAAATAAA
ACCACTAGGTAAACTTCTAGTTGTGGTTTGAAGAAGTGGTTTTGAAATGCTCTGTCCAGCCACGCAGAACTGAAAGTC
CAGGCTGAGAAAAACAACACCTGGATAATTTGCATTTCTAAAATAAGTTGAGGATTCAGTCGAAACTGGAAAGGTCCT
CTTTTAACTTAGTGAGTTCAATCTTTTAATTTTAGCTTGAGAAGTTCTAGTTTCCCTCAAACTTAAGTTTATCGACTT
CTAAAATATATTCATTTTCAAAATTAAGTTATGTAAAAAAATTGAAGGACTTCAGTGTCTTTAATTTCTAATGTATTT
AGAAAACTTTTTAAAGTTACTTTATTATTCTTCCCTCTGATTATTGGTCTCTGTTCAATTCTTTTCCCAGTACCCAAA
GCATTTACAGTGACTTTGTTCATAATTTTTTTTAAGTTAGTTGTTTTCTGCCTTACTATTAAGACTTTAGCATTCTGG
TCGAAGTGGCTTCATAAATCTTTTTCAAGGCCACTTTTTAGGAGAAAGACATCTTTTTTTTAATGAATGCAATTATCT
AGAATTATTTCAGTTAAACATGTTAGTTGGTGGTTGAGAGGACACTCAGTCAGTGCAGAAGGTCTGTAAGCCAGTCCA
CAGAGACATTCCTGGGTGAACTCCCTCTGGCCCTGCTTCTTGTTGGAGAACTGGCCAGAGGTCTGAGACCAGGCTGCT
GCTGGGAAGGCCTGGACTTTGGTCTCCCAGTACCGCCCAGACCTGGGGATGTATGGTTGTGGCTTCTGCCACCCATCC
ACCTGGCTGCTCATGAACCAGCCAGTCTTGATGGCTTTGAAGGAATGATTCCACACAAAGACTCTGGACCTCCCTGAA
ACCAGGCACTGCAAACGGTAAGCCAGCGCCAGCCACAGCTGTGGCCGCTGTCCTTAAACCTTGTAATTGTTTCTGCTT
GATTGAGTCTTAAGTCATTGCTTTAGGAGGAGAAAGAGACATTTGTGTCTTTTGAGTACCATTGTCTGGGTCACTCGC
ATTTAACTTTCCTTGAAAAACTTATAAGAGAAAAACGTTGCCTGTTAACCATTAACTACAGGGCTCGTGATACTTTGA
GAAAATCTTAGAAAAAAATGTATACAGTTGTCTGGAATTATTTCAATGAAGTGTATTAGTTGGGGTACTGGCGCTGTC
TCTACTTCAGTTATACATGTGGTTTTGAATTTTGAATCTATTTTGTCTCTTCTTAAGCACCAAGTATAGATACAGTGG
ATACACTCACTGGTTTTTAACGGTGGTTTTAATCTAGAAGGAATTTAAACTGGAGGCTAATTTAGAATCAGTAAGGAG
GGACCCAGGCTAAGAAGGCAATCCTAGGATTCTGAAAGAAAAGATGGTTTTAGTTTTTATAGAAAACACTACTACCAT
TCTTGATCTACAACTCAAGACGGTCTAATGAATTTTGAAGTTACTGGTAAATATACTTCCTGGTTGTTAAGGAATGAT
TATCAAATGGATCAGTGCTTGGATCTGAGGTCAGTGTGAGAGGACAGGGCCTGGGCTGTGGATATACAGAAGGAAGGC
CACAGCTGGATAGAATTGAAAAAGAATGGAGACCTGCTGCTGAAGCAGATCAGCCGGACTCTTTCCAGCCATAG
CAAAGAACCAGATTAATAAAGAGAAGGCCAGATTAATAAAGCTTGCTGAGCAAAATTTAGTGAACAAGGTTGACAGCC
TGGCTAGGAAGCTAGGCTCTAGTTAAGCACAGTTGGACTGAGATGTGTAGGCTTCCCTGAGCCCTTCAAAAATGTGCT
AAGCTGAGATGATTACTCTGAGGTAGCCAAAGCTGGACTTGAGCAGGAACGAGGTAGACTGCAATGAGCTGAATTGAG
CTAGGCCGGCTAAGCTAAACTAGGCTGACTTAACCAAGATAGCCAAATTGGAATGAATTGTCTTGATCTGGGCTGATT
GGAGCTAAACTCTACTGGACTGCTCTGAACTGAGCTGTGTTGGGCTGTGTTGTGCTGGGGTGAGCTGAGCTAGCATGA
GCTACTCTGTGGTAGCTGGGGTGAGCTGGGATGAGCTGAGCTGGGTGAGCTGAGCTGGGTGAGCTGAGCTGGGTTAGC
TGAGCTGGGGTGAGCTGGGGTAAGCTGGGGTGAGCTGAGCTGGGTGAGCTGAGCTGGGTGAGCTGAGCTGAGCTGGGT
GAGCTGGGGTAAGCTGGGGTGAGCTGGGCTGACCTGAGGTGGTTGAGCTGAGCTGGGTGAGCAGAGCTGAGGTGAGCT
GAGCTGAGCTGGGTGAGCAGAGCTGGGGTGAGCTGAGCTGAGCTGGGCTGGGGTGAGCTGAGCTGAGCTGGGTGAGCT
GAGCTGGGTGAGTTGAGCTGAGCTGGGTAAGCTGAGCTGAGCTGGGTGAGCAGAGCTGGGGGTGAGCTGAGCTGGATG
AGCTGGGCTGAACTGGGGTGAGCTGGGGTGGGGTGAGCTGGGTGAGCTGAGCTGGGCTGAGCTGGGCTGAGCTGGGGT
GAGCTGAGCTGGGATGAACTGGGCTGAGCTGGGCTGAGCTGAGCTGGGCTGGGCTGAGCTGAGCTGGGATGAGCTGGG
CTGGGCTGGGCTGGGCTGGGCTGAGCTGGGCTGAGCTGGGCTGAACTGGGGTGAGCTGGGGTGGGGTGGGGTGAGCTG
GGTGAGCTGAGCTGGGCTGAGCTGGGCTGAGCTGGGGTGAGCTGGGTGAGCTGAGCTGGGCTGAGCTGGGCTGAGCTG
GGCTGAGCTGAGCTGGGCTGGGCTAAGCTGAGCTGGACTGAGCTGGGCTGAGCTGGGCTGAGCTGAGCTAGGCTGGGC
TGGGCTGGGCTGAGCTGGGCTGAGCTGGGCTGAGCTGAGCTGGGATGAGCTGGGATGAGCTGAACTGGGTGAGATGAG
CTGGGGTGAGATGAGCTGAACAGGGCTGAACTGGGGTGAGCTGAGCTGGGATGAGCTGGGGTGAGCTGAGCTGGGTGA
GATGAGCTGGGTGAGCTGAGCTGAGCTGGGCTGAGCTGGGTGAGCTGAGCTGGGTGAGATGAGCTGGGGTGAGCTGAG
CTGGGGTGAGCTGAGCTGGGTGAGCTGGGCTGAGCTGGGCTGGGTGAGCTGAGCTGGGTTGAGCTGAGCTGGGCTGAG
CTGGGCTGAGCTGGGCTGAGCTGGGCTGAGCTGGGCTGAGCTGAGCTGAGCTGGGATGAGCAGGGCTGGGATGAGCTG
GGCTGAGCTGAGCTGGGATGAGCTGGGTGAGCTGAGCTGGGGTGAGATGAGCTGGGGTGAGATGAGCTGGGATGAGCT
GAGCTGGGATGAGCTAGGTGAGCTGAGTTGGGGTGAGCTGAGCTGGGGTGAGCTGGGCTGGGTGAACTAAACTAGGGT
GAGCTGGGCTGAGCTGATCTGGTTGAGCTGGGCTGGGTGAGCTGAGCTGGGTGAACTGAGCTGGGGTGAGCTGAACTG
AGCTGGGTGAGCTGGGGTGAGCTGAGCTGAGCTGGGTGAACTGAGCTGAGTTGAGTTGGGTGAGCTGAGCTGGGTGAG
CTGAACTGAGCTGGACTGAGCTGGGGTGAGCTGGGGTGAGCTGGGCTGGATGAGCTGAGCTGGGTGAGATGAGCTGAA
CAGGGCTGAACTGGGGTGAGCTGAGCTGGGATGAGCTGGGGTGAGCTGAGCTGGGTGAGATGAGTTGGGGTGAGCTGA
ACTGAGCTGACTGAGCTGGGGTGAGTTGGGCTAGGTGAGCTGAACTGGGGTGAGCTGAGCTGGGGGTGAGATGAGCTG
AACAGGTCTGAACTGGGATGAGCTGGGATGAGCTGGGGTGAGCTGGGGTGAGCTGAGTTGGGTGAGCTGAGCTGGGTG
AGCTGAGCTGGGGTGAGCTGAGCTGGGATTAGCTGGCTGAGCTGGGATGAGCTAGGTGAGCTGAGTTGGGGTGAGCTG
AGCTGGGGTGAGCTGGGCTGGGTGAACTAAACTAGGGTGAGCTGGGCTGAGCTGATCTGGTTGAGCTGAGCTGGGGTG
AGCTGGGCTGAGCTGGGCTGGGTGAGCTGAGCTGGGTGAACTGAGCTGGGGTGAGCTGAACTGAGCTGGGTGAGCTGG
GGTGAGCTGGGGTGAGCTGAGCTGAGCTGGGTGAACTGAGCTGAGTTGAGTTGGGTGAGCTGAGCTGGGTGAGCTGAA
CTGAGCTGGACTGAGCTGGGGTGAGCTGGGGTGAGCTGGGCTGGGTGAGCTGAGCTGGGTGAGCTGAGCTGGGCTGAG
CTGGGGTGAGCTGAGCTGAGCTGGGCTGGGTGAGCTGAGCTGGGTGAGCTGAGCTGGGGTGAGCTGAGCTGAGCTGGG
```

Fig. 4 (Cont.)

```
TGAGCTGGGCTGAGCTGAGCTGAGCTGGGGTGAGCTGGGGTGAGCTGGGCTGGGTGAGATGAGCTGTGCTGGGCTGGG
TGAGCTGAGCTGGGTGAACTGAGCTGAGCTGAGTTGGGTGAGCTGAGCTGGGTGAGCTGAGCTGGGCTGAGCTGGGGT
GAGCTGAGCTGAGCTGGGGTGAGCTGGGGTGAGCTGGGCTGGGTGAGCTGAGCTGGGTGAGATGAGCTGTGCTGGGCT
GGGTGAGCTGAGCTGGGTGAACTGAGCTGAGCTGAGTTGGGTGAGCTGAGTTGGGTGAGCTGAGTTGGGTGAGCTGAG
CTGGGGTGAGCTGAACTGAGCTGGACTGAGCTGGGGTGAGCTGAGCTGGCTGAGCTGAGCTGGGTGAGCTGAGCTGAG
CTGAGCTGAACTGAGCTGAGCTGGGCTGAGCTGGGCTGGGTGAGCTGGGCTGAGCTGGGCTGGGTGAGCTGGGCTGAG
CTGGGCTGGGTGAGCTAAGCTGGGTGAGCTGGGATGGGTGAGCTGGCCTGAGCTGGGTGAGCTGAGCTGAAAGGATCT
GGGTTGGAGTCAGCTTTGCTTGGGTGAGCTGAGCAGGGTTTAGCTGAGCTAGGATGAGTTGAGTTGGCTGGGCTGAGC
TGGGATGAAGTAGGCTAAATAAGCTAGCTTGAGCTAAATAGAGCTGGGGTGAGCTGTACTTAAATGAGCTGTGATTGA
AGTGGGCTGGGATGAGCTCAGCTGAACTGGGCTAGCTGATGTGGATGATGGTGAGGCTGAGTTAGGATGAGCATGACT
GAGCTGGTTTGGACATGAATGAGCTGGACCCGGCTGACTTGGGCTGGTTGAGCTTTGCAAGATGATGTGGACTAAACT
GGGCTAGCTGGCAGGATGAGAGAGGTTGAACTAGGCTCAGATGAGCTAGGCTGAGCAGGGCTTAGGTGAGGTGGTTTG
GGATGAGCTGGGATAAGTTGGGCTCAGATGAGCTACCATGAACTGGGCTGAGGTGGCCTGGGAGAACATGAATCGAGT
TGCACTGAGTACAGCCAGGATGAACTGGGATAAACTGGGCTAAACTGGGTTGGGCTAAGAATGGACTGCCTGAGTTAT
GCTAAGCTGAGCTGGGATGAATTGGGGATTGTCAAGACTTAAATGAGCCAGACTGAACTGGTTGGACTTGGGTGAGCT
GAGGGGACCTGCTGCAGGGCCGGCATAGCTGAGTTGAATTTAGATGAGGAAGGGTGAGCTAGACTGAGCAAGGCTAGA
CTGCTTATGCTGAGCTACACTAACCTGGCCTGAGTTGGGCCAGGCTTTGTTGGCCATGTCTAAACTGAGTTAAGATCA
ACAGGGAGTCTAGAGGGGTAGGGGATGAACTAAGATGAATTACACTAGCTGAGCTGAATTGAGATAAGGTATGGTAAC
CTGAGCTGAACTGGAAAGAGATGTACTGGATAACCTTAACTGGGCTGAGATGAGCTAGGTCTACCCAGGCCTGGATCA
GCTTAATTAGGGTAGGCTAGACCAAACTGTAGCAGTATGTATTAGCCTGTGCCAAGCTGGGCTACATTAAACTAAACT
GGACTTAGCTAGGCTCAGATTAGTTTCGCTACTCTAGAATGGGTAAGTTGGGCCAAACTGGGATGAACTAATTTAACT
AGCCTGAGATGGGCAGATCTGAAGTGTAGCAAACACAGCCAGGGTGAACTGAATGAGTTTGACCAGGCCTGGACCAGT
TAGGCTAAGGACCTTGTCCTGGGCAGACCGTGTGCTATGGTGGAGTTTCATGATGATGCCATAAGAGTTCCCCCACCA
TAACCCACGTTTCTCCTACCCCATATACCTGTCTGGTGTGTAAACCTAATCTTTGTGTGCTGATACAGAAGCCTGAGC
CCATCCCCCTTCCACCACCACCTACCTATTGCTTTGGAATGAGCAAGGTTATCTCAGCGAATGTCTCAAAGGGAAGCC
GGGACCTAGGCCTGTCCCTGAGAGCAGATGTTCATGCCCCTGGAGTGGCTGCCGGTGGCTGAAGGGCCAGAACCACCT
ACTCTAGAGGCATCTCTCGCTGTCTGTGAAGGCTTCCAAAGACATTCCTGTGGTTAGAAGGCAGCCCTGCTGTGGCTC
TGTCCCATAGACCAAACTTACCTACTATCTAGTCCTGTCAACCTTAAGAGCAGCAACATGGAGACAGCAGAGTGTAGA
GAGATCTCCTGACTGGCAGGAGGCAAGAAGATGGATTCTTACTCGTCCATTTCTCTTTTATCCCTCTCTGGTCCTCAG
AGAGTCAGTCCTCCCCAACTGTCTTCCCCCTCGTCTCCTGCGAGAGCCCCTGTCTGATGAGAATTTGGTGGCCATGGG
CTGCCTGGCCCGGGACTTCCTGCCCAGCTCCATTTCCTTCTCCTGGAACTACCAGAACAACACTGAAGTCATGCAGGG
TGTCAGAACCTTCCCAACACTGAGGACAGGGGACAAATACACAGCTACCTCGCAGGTGTTACTGTCCGCCAAAAATGT
CCTTGAAGGTTCAGATGAATACTTGGTATGCAAAATCCACCATGGCAACAAAAACAAAGATCTGCATGTGCCGATTCC
AGGTAAGAACCAACCCTTCCCGAGGGGATGGGGAGAGGGGGCAGGCCCAGGCATGGCCCAGAGGGAGCAGTGGAGTGG
GTCCTAAGCCAGCCTGAGCTCACACCTCAACCTTTCATTCCAGCTGTCGTTGAGATGAACCCCAATGTGAGTGTGTTC
ATTCCACCACGTGATGCCTTCTCTGGCCCTGCACCCCGCAAGTCCAGACTCATCTGCGAGGCCACCAACTTCAGTCCC
AAACAGATCACAGTATCCTGGCTACAGGATGGGAAGCCTGTGAAATCTGGCTTCACCACAGAGCCAGTGACTGTCGAG
GCCAAAGGATCCAGACCCCAAACCTACAAGGTCATAAGCACACTGACCATCACTGAAAGCGACTGGCTGAACCTGAAT
GTGTTCACCTGCCGCGTGGATCACAGGGGTCTCACCTTCTGGAAGAACGTGTCCTCCACATGCGCTGCCAGTGAGTAG
CCTGTGCTAAGCCCAATGCCTAGCCCTCCCACATTAGAGCAGTCCTCCTACGGTTGTGGCCAATGCCACCCAGACATG
GTCATTTGCTTCTTGAGCCTTGGCTTCAACAGTGGCCAAGGCCAAGGATGAGCAGTAGGCAGCAGGGGATGAGAGT
CAGATGGAGGGAATCAGCATCTTCCCTTAAGCAGATTTGGAAGATGGAGACTGAGCTTTTATCCAACTTCACAACTAG
ACACATCACAACCTAACACAGTGTTCTCTTGACTGCAGGTCCATCTACAGACATCCTAGCCTTCCCCATCCCCCCCTC
CTTTGCTGACATCTTCCTCACCAAGTCTGCTAAGCTGTCCTGTCTGGTCACAAACCTGGCAACCTATGACACCCTGAA
TATCTCCTGGTCTTCCAAAAGTGGTGAACCACTGGAGACCAACACTAAAATCATGGAAAGTCACCCCAATGGCACCTT
CAGTGCTGTGGGTGTGGCTAGTGTTTGTATGGAAGACTGGGATAACAGGAAGGAATTTGTATGCACTGTGACTCACAG
GGACCTGCCTTCACCACAGAAAAAATTCATCTCAAAACCCAATGGTAGGTATCCCCCTTTCCTTCCCCTCCAATTCCA
GAGCATACCCTGTACCTCACAGGGAGGGCAGGTCCCCTTCTACCCTATCCTCACTATTATCTTTGCTTACAGAGGTGG
CCAAACATCCACCTGCTGTGTACCTGCTGCCGCCAGCCCGTGAACAACTGATCCTGAGGGAGTCGGCCACAGTCACCT
GCCTGGTGAAGGGTTTCTCTCCTGCAGACATCTTTGTACAGTGGCTTCAGAGAGGGCAACCCTTGTCCTCAGACAAGT
ATGTGACCAGTGCCCCAATGCCAGAGCCTGGGCTCCAGGCCTGTACTTCACCCACAGCATCCTGACTGTGACAGAGG
AGGAATGGAACTCCGGAGAGACCTACACCTGTGTTGTAGGCCACGAGGCCCTGCCACACATGGTGACCGAGAGGACCG
TGGACAAGTCCACTGGTAAACCCACACTGTACAATGTATCGCTGATCATGTCTGACACAGGTGGCACCTGCTATTGAC
Cμ
CATGCTAGCGCTCAACCAGGCAGGCCCTGGGGGTCGAGTTGCTCTGTGTATGCAAACTAACCATGTCAGAGTGAGATG
TTGCATTTTATAAAAATTAGAAATAAAAAAAAATCCATTCAAATGTCACTGGTTTTGATTGTCCGATGCTCATGCCTG
```

Fig. 4 (Cont.)

```
CTGGGGCAACTGTTGTGTTATGCTTGTCCTGCACACACCCTGTATACTTGCCTCCACCTTGGCCCTTCCTCTACCTTG
CCAGTTACATCCTTGTGTGTGAACTCAGAAAGGCTTACAACAGAGTGTGAGCATGCCATTCCTCCAGCTACTTCTAGA
TATGGCTTAAAGCTTGCCTACCCTGGTGCAGGCAGCATTCAGGCACATCCACAGACACACAGAGACAGACATGCATTT
ATACATAGATCTAGAGATGAACATGTATAGATACATGCACGAATATGTATTCATAGACACACAGATAGAGGTTCCGCA
TGCGTGCATGGACAAATACAAATACCTTCAGAGACAAATATGCACAGACACACAACCCACACATGGAAACAGGCACAAA
CACACATGATCATGTGTGCACCAAAACAGAATATAGGCAAATATAGACAAGTGAACTACATAGACATGAAGACATGCA
TACACAGACATGTAAAGAAACATCTTGAAATGTGTACACTAACATGTGGACAGACATGGCACACAGTTACACCTGGTC
TCTGACCAGGACCATAATCTCCAGGGTTCAGGGCTCAGAGAGTCCATACTAGGCTGGGTGGCACTGATACTCCTCAGG
GTCCCACTCTATGATTAGGGGAAATAGCCCGAGGAGCAAAATGTGCATTTTTGGCTCAACACCATGGGGCAGAAGATA
CCCCACTAACCACCCATGACAGAAAATTAGCCTTGGTTGTGTCTCCATTAATAGAATACCTCAGGAGATCAATGAGAG
AGCGCTTGACCCACTCACTTCCCAGTCCAGATGCAGAAGACACAATGCAATTGTCCAAAAGAATTGTACACACACACA
CACACACACACACACACACACACACACCAACAAAGGAACCTCTATAAGGAGTCACCACCCAATAACATTGCCTCTT
TGGATTCACATCCTGGACATTCTTCATATTCATATCCATTTGGGACCTGGGCTTTAGAAATCCCCAAGGGCTCATCTT
TACAGAGGTCAGAGATCCCAATAAATGCCCTGGTCCCACAGCCTCTCTATCTCTTGGTACCAAGACCCAACACTGCTG
GCAGGGGTAGAACAATCAACACACAGGAACTCTGATCAAAGAGAGGCATGAGATGCCTGGGTCCTTCAGGAAGTAAGG
AGGGATAACCTCTGATATGCCTACTCTTATTCCCAAAGCCCAGGAGAAGGGAAACCTGCTCTGAATTCTCAGTCTAAC
AGCCCGATGGTGCCACCTGCTCAGAGAAAGTCCAAAGAACACAAAAATCATTATGCCACATTTCCTGAGTCTGCCTT
TACCCATGTCCGTATGTTGCATCTGCCTTGCTTGCTCTGCTGCCCCAGAGTTCCTGGGACAAGGCCCCAAGTTAGTGC
CTCCTCCAGTTTGACCTGTGCTTTGTCTCTGTCTAGCTTGAGCTATTAGGGGGGCCAGTCAATACTCCAGAACCAGCA
GAACACCCCAACCCTGAGGCAAATGTTCAATCACCCCAAGGCTTGGCTTGACCCTCCCTCTGTGTGTCCCTTCACAG
AGGGGGAGGTGAATGCTGAGGAGGAAGGCTTTGAGAACCTATGGACCACCGCCTCTACCTTCATCGTCCTCTTCCTCT
TGAGCCTCTTCTACAGCACCACTGTCACCCTGTTCAAGGTAGTGTGTGTGGTGGGGCTGAGGACACAGGGCAGAGACA
GGGAGTCACCACTCCTCACTGCCCCTACCTCTACTCTGTAAAAGGGAACAGCAATTCACACTGTCTCTGTCACCTGCA
GGTGAAATGACTCTCAGCATGGAAGGACATCAGAGACCAAGAGACCCTCCCACAGGGACACTACCTCTGGGCCTGGGG
TTCCTGCCTGTATGACTAGTAAACTTATTCCCACATCTTTCCTGTGTTGCCCTCCAGCTTTGATCTCTGAGACGGGCT
TCTTTCTAGACTGGCCAAAGACTTTGTCCACTTGTGCAACCTGGAACAATGTCTGGAACCACAGACAGCTGTGCTGTA
TACAAATGTCACTTTGAAATAAATACTTCACCTTGCGAACCCACTCTATTGTGAAGGAATTTGTTCTTGTTTTCAAAC
TTTTCCTGTGGTGTTGACATCCCAAATACTCTCTAAATAGAGCCTGGGAACTTGAAGTGAACAGTCTGATGGGCTTA
AGAGTGAAAGAGGGAAAGGAGGTGTGGAAGAAGAGAGAGAGAGAGAGAGAGAGAGAGAGAGAGAGAGAGAGAGAGAGA
GAGAAACCACCCTGACAGCAAAGTATAGCACAGGCAGCCAATGGGTAGCAGTCTGGTTTATCCACCCTGATAGAAGAA
AGTAGGGCAGAGAAAACTCCAGGCCTGATCTCACAAAAGCAACCGAATCTGAAAAGTAGCCTCTAGCCTGGGGTGTCT
GCTCCATCCCTCAGCCCACCCACTTGGGCTGGCGTTGCTTCCAGCTAGTGCAATACTTTGGTGTTAGCCAAACCTTTG
TGGTATGTGGGGTGTGCCTTGGGAGAGTTGGCTGAGATCTCTAGGATGTTTGTATCCCTTCTGCAACATGACAAGCCC
TAGGGGTTAGCCCATAACTTGAGGACTCAAACCCTCTGTCTATAACAACTGCTGTGGTCACTGGAGAAGGACAGCTAA
AGGCCTGCTCACACAGCAGGAAAGGAAAGGGAGGTAGGTCATGTACTTCAGCTCAGAGGAGGAAGCACAGCAGATACA
AGGTGAGGGCAGTGCTAGGGGTTCTGCTGTTCACCGTGTGGATGGCTGGAGGAACCTCACAGAGGTGGGACTAGCTGG
TTACATTGAGAGCAGGACCTGGGAGCAGGGCATAAGAAAGAATATCAGACAGTGGGAGGGAACTGTGTAGATGCCAGG
GTCCGG▓▓▓▓▓▓▓GAGTCAAGCTCTATACCAAGTGGACAGCTAAACTTTGCATTATTAATTATATGGCTATGGCTTTAG
AGTCATGAAGGATACATGAGTAAAGGGACTGTAGGATCTTCCTCTGTGCTGAAGAGTTCATGAGGCCAAGTGTGTGAC
GGGCTCCCTGTGTGGAGTCACTGGTAGGCCATTGGATAAAGTTATAAAAGGCTACAGGATTTGGAGTTTTCTCCGCTT
GGCTTCACTCTTGTTTTGGTTGAGTATTTCCTCAATATGTCCCCATTCCTCACTTTTGGAATGGTAATATATTTTTCA
GTATCACTGTATGATAAAAGTATGTAATTTTCTTTAGTACTTTATGGGGCTTACGATAAAGACATTGCCTTGAGTCTC
AGAAGAGACTTTGGATTTTGGACTTTTAAATTGTGCTGAGAATTTAAAAGTCTACAGGGACTTCTATCACAGGGCTGA
ATGTATAGTGCACTCTGATATGGCCAGGAACACACGAGGGCCAGGAGCCTATCTGGTGGTTTAAATAAGAATGATCCT
TTTAGACTCATATGTTTGAATACTTGGTCCACAGTTGGAAAGGATTAGGAGCTGTGGCCTTGTTGGAGGGACTGTGTT
ACCGGCAATAAGTTTTGATGTTTCAAAAATCCATACCATTCCCAGTTAGTTCTCTGTGCCTCAGGCTTGTGGATCAAG
ATGTAAGTTCTCAGCTACTATTTGAGTTTCCTGCCTCCCTACCTGCTGTCATGCACTGTGCCATAACAGTCATGAACT
CTAACCCTCTGAAACAATCAACCCCCAATGAATGCTTTCTTTTATACGTTACTTTAGACGTGATGTCTTATCCCAACA
ACCACAAAGCAACTTAGCCGGTGTGTGGCCCGATGAGTGGTGCCTGCTCTCAGTTCCCATGTGCTCTTCACAAACTCA
GGTCCATGACCTTGGTCATGCAGGCTAAGCCTTCAGAGTTGGGTTTGAGCTAAAGAGAGTGAACAAATCCCACTCCTA
GGCTCCTGACTCTGAGTCTGCACTGGCTGCACGATGCCCATGGGACACTTCCTCAGCCTGCGGGCTACTTCAATTCCT
AAATCTGGGCTCTGGGCTCTGCTTGACCTTGGTACTCTTTGAATCTTCTTCCTTGACTTCTGAGGTTCAGCAAGCCTG
TCATGAAGCTTCCCAGCATGGGCATCCCTGGTCTGCCCTGTCCTGATTTCTCTGGATGTCTCTGTGCTTCTTGTCCTC
TGCAGCGTGTTTTTCTAATGGAAATCTAATGAGCTCAGCTCTAGTTCCCCTACTGCCTCTTCTCTTATCCTGAACCCC
ACACTTACCCCTGCCTTCTCCTGTGTCACTGGTGCTGCTGTCTCTACTCCCAAGGAACCCTCTCTTTCCAGGAACCCT
CAGCCTTCAAATTTAGAGTCTACCACCATTCTTGAAGAAGATGGCCATATTCCTATCCCTTGTGATCCTGGTGCATCC
```

Fig. 4 (Cont.)

```
CCTTCAGTCCCAGAACCCTGCAGACCTTGCCCCCCTCTTCTAACCTGCACTTCACCCTCTGACACATGCCTGTCTGGT
TCTATGACATCATCCCTCCCTTCTCCCCATGCAATCCACTGCCCTGTGCACACCACATTGCTGTACCAGTTTTTCTCT
TTCCTTTCCCTGTCTCAGTGTATTCCCTGTCCTCTGGACAGGCCATATTAGCCAGCCCCAGGGACCTTCCCTGCCTAG
GTCTTCTCAAAGTATAACCAAAGGCCCCTCCTGGCCACTAGCACAGGTTCCTTCTGTAGCTATGCTATTCCTGAATGT
GAGCTGAAGTCTTTAACACGTTCTGGTCACCATCAGGCTCATACTCTGTGTTCTATCCACCTGCTGTCAGCCCCATT
CTCTTTCCTAAACCACAGATTGGTTGGGATTCCCCTAAGGAAGCACTGTCTGGAGAGAACTGGGAGACACTGCCACCA
TATTTGGACTTTAACCTGAATAAAAAGCCTCCCTATGCAGAGAGATGATAAAGGCAGAGAACAGACTCAGCCAGCCCA
GGAACCTAAGGAGGCTATGAACACAGAGAAGCAGGTAAGGGCCAGGCTTCCTGATTTCTCCCCTGGGTCTCAATGGTA
CTACCTCATCCACCCCCACCCATCCACGTGATGCAGCTTCGACCTGATCTAGGCTCCCCTTATCCCCTGACACAGAAA
CCCCTAAAAAAGGGGAACTTTAGATAGTACCTTCTGACACCTAGTTTCAATCCTGTTCTTAGCCTTGCAGAGATGGGT
ATGGGGTGGCATTCAGACCTTTGTGACAATTTGGTTGCAGCTCCTGAGAGGAAGGATCCCAGAGCTAAGCTCCTGGCG
GACATGGGCCAAAGCAAGAAAAGAGGCAGTCACTTTTATATTGCCCACGCAAGAGTTGTATCAGCCGAGAAAGGAGAG
TACAGTGGGAGGTCTGGGTCAGTGGTGAATATCAGCAGAACGGAACAACCAACAACCCATGGAAGAGTGGGAAGGAGT
TGAGATACAAGACTGTGGAGGGGTTCCATCTGCTGTATAGGTAAGACAGTCTGAAGAACATTGACCAGACAGGGGTCT
AGGAATGCCACAGGGTGGAACATGGGCCAGTGGATCTGAACACACACACACAACAATAACTACTACTAATACTCCCAC
CACCACCAGAGTCAGCCTCAAGGAGATGATGGGCTACATCAGGAGGCCTGTGAGATGAACTTGGTCTGTCTGGAAGCT
TATAGGACCACATCAGCTAAATCAGCAGAGAGGAGGTGTCCAGAGGAGCCAGAGCTCTGCAGCAGAAATCTTTAGGGC
TGACAAAGGTGAGTTGATAGTTCATCCAAGAGGGACACTAAGGCGTGCTGGCAAAGCCAAGAGTGGTATCCCTAAGGT
TTGGGAATCAAGCTCAGTGTGGAAGAGATGAGAAGCAGAGGCAAACTTGAGCTGAAATAGGCCAAGATTGGCAGGAAG
AAGTCTAAGAAACTCCTAGGATCAGGTGAGTCAGCTACAGGTGAGCTGTGAAAGCTGGACATTTGGGAGGACAAAGAC
AGACTCAGAAGCTCTGGGAATTATGAAACAGCAGAGAGGAATTGAGGTACCTAAGATTTTAAGGTACCAGATTGAGCA
GCCACAGGAGAGCTGGGGCAGGTGGGAGCTTAGGGGACCTGAATAAACCATTATGTAGGAGCCGAGGTAGCTGGAAAT
ATGGGAAAATAGACTGACCAGCTACGGGAGAACTAGAGGAGAATGAACTTAAGGAAACTGAGTGAGCAGCCATAGTGG
GGCTGAGGAAGCTGGGTGGGTGGGAGACCAAGCTGAGAGGCTAAAAGATAACAGGGATAGGTGAGAGTGTGTGGTACC
AGGATGAGAGCTAAAGGAGATTTGGGCAGGTACCAATATGGGGAACCAAGCTGAGAATCTACAGGGAGCCAGGTGGCA
GTTCCACAGCTTCAGGACAGTCCTAGGAGTTTAGGAAAACAGGATGAGATGTTACCTGGACACTGAAGTAAGTGGGAA
CTCGGACAACCAGACTGAACACCTCCAGGGATCCCAGAGGTATTCGGTGAGGGGGAGTTGGGAGGGAGGGTGGTCATG
GAGCTCAGGAAAACCTGAGCACCAACAGCAGTGCTGAGGCAGCACTGGGGAGCTGGGGTAGGTGTGGCTGTGGGGACC
AGGCTGGGCAGCTCTGGGGAGTTGGGGTAGGTGTGACTATGGAGACCAGGCTGGGCAGCTCTGGGGAGCTGGGGTAGG
TGGGTGTGTGAGGACCAGGCTGGGCAGCTCTGGGGAGCTGGGGTAGGTGGGTGTGTGGGGACCAGGCTGGGCAGCTCT
GGGGAGCTGGGGTAGCTGGGTGTGTGGGGACCAGGCTGGGCAGTTCTGGGGAGCTGGGGTAGCTGGGTGTGTGGGGAC
CAGGCTGGGCAGCTCTGGGGTGCTGGGGTAGGTGGGTGTGTGGGGACCAGGTTGGGCAGCTCTGGGGAGCTGGGGTAG
GTGTGGCTGTGGGAACTAGGCTGGGCAGCTCTGGGGAGCTGGGGTAGGTGTGGCTGTGGGGAGCAGGCTGGGCATCTC
TGGGGAGCTGGGGTAGGTGAGGCTATGGGGACCAGGCTGGGCAGCTCTGGGGAGCTGGGGTAGGTGTGGCTGTGGGGA
CCAGGCTGGGCAGCTCTGGGGAGCTGGGGTAGGTGGGTGTGTGGGGACCAGGTTGGGCAGCTCTGGGGAGCTGGGTA
GGTGTGGCTGTGGGGACCAGGCTGGGTAGTTCTGGGGAGCTGGGGTAGGTGAGGCTGTGGGGACCAAGCTGGGCAGCT
CTGGGGAGCTGGGGTAGGTGTGGCTGTGGGGACCAGGCTGGGCAGCTCTGGGGAGCTGGGGTAGGTGGGTGTGTGGGG
ACCAGGCTGGGCAGCTCTGGGGAGGTAGGGTAGGTGGGGGTATGGGGACCAGGCTGGGCAGCTCTTTGGAAGCTGGGG
TTGGTGAGATATGGGGACCAGGCCAAGTAGTCCTGGGAGTGCTGTGATATGTGGGGGTGTGGGGACCAGGCTGGGTAG
TTCTGGAGGAGCTGGGATAGGTGTGACTGTGGGGACCAGGCTGGGCAGCTCTGGGGAGCTGGGTTAGGTGTGGCTGTG
GGGACCAAGCTGGGCAGCTCTGGGGAGCTGGGTAGGTGGGAGTGTGGGGACCAGGCTGGGCAGCTCTGGGGAGCTGGG
GTAGGTGGGTGTGTGGGGACCAGGCTGGGCAGCTCTGGGGAGATGGGTTAGGTGTGGCTATGGGGACCAAGCTGGGAA
GCTGTGAGAAGCTGGGTTAAGCAAGGCTGTGGGGACCAGGCTGGGCAGCTCTGGGGAGCTGGGGTAGGTGTGACTATG
GAGACCAGGCTGGGCAGCTCTGGGGAGCTGGGGTAGGTGGGAGTGTGGGAACCAGGCTGGGCAACTCTGGGGGGCTGG
GGTAGGTGGGAATGTGGGGACCAGGCCGGGAAGCTCTAGGGAGCTGGGGTAGGTGGGTGTGTGGGGACCAGGCTGGGC
AGCTCTGGGGAGCTGGGGTAGGTGGGAATGTGGGGACCAGGCTGGGGAGTTCTGGGGAGCTGGGGTAGGTGGGTGTGT
AGGAACCAGGCTGGGCAGCTCTGGGGAGCTGGGGTAGGTGGGAATGTGGGGACCAGGTAGGGCAGCTCTGGGGAGCTG
GGGTAGGTGGGCTGTGCGGACCAGGCTGGGCAGCTCTGGGGAGCTGGGGTAGGTGGGTGTGTGGGGACCAGGCTGGG
CAGCTCTGGGGAGCTGGGGTAGGTGGGTGTGTGGGGACCAGGCTGGGCAGTTCTGGGGAGCTGGGGTAAGTGGGTGTG
TAGGAAGCAGGCTGGGCAGCTCTGGGGAGCTGGGGTAGGTGGGTGTGTGGGGACCAGGTTGGGCAGCTCTGGGGAGCT
GGGGTAGGTGTGACTATGGGGACCAGGCTGGGCAGCTCTGGGGAGCTGGGGTAGGTGTGGCTGTGGGGACCAGGCTGG
GCAGCTCTGGGGAGGTAGGGTAGGTGGGGGTGTGGGGTCCAGGCTGGGCAGCTCTGGGAGTGCTGTGATATGTGGGGG
TGTGGGGACCAGGCTGGGTAGTTCTGGAGCAGCTGGGGTAAGTGGAAGTATATGATATCAAGCTGAGAGTAGCTGCAG
CTGAGCTGGGGTAGGTGGAGTGTAGGGACCAGGCTGGGCACCTCTGGGGAACTGAGGTGGGTAGAAATGTGAATAACC
TTTCTGATGAGCCACAGGGGAGCTAGGGCTGTCAGATCACAGGTCCCAGGTTATACAGCTTCTGAGTCAGGGTAGGGG
GTAATTCTTGAGCAGAGGAACCAAGCAGGTAGGATAGATTGAGCAGCCACAGGGGAATGGGTTGGTAGGAATTGGAGG
```

Fig. 4 (Cont.)

```
GACCAGGCTGAGTATGTACAAGGTGATTGGGAAACGTCGAAGTTTGGGGTGGGGACGGGGCGCAGATCAAGCACTTGC
TAAGGTTCTGGGGCAGATGGGAGTGTGGGAAAGTGGACTGTGTTGTTACAGGGAACCAGGACATGTGGTTGTGTGGGA
AGCCAGTGTGAATGACCACAGTGTACTGAGGCAGGTTTTAGTGCTAGGATACCAGATCAAGCACAGGAACACAGTAGT
TCTAGCCAGGGCGACTAGGAGTGCTGTGGCAGGAGAGTAAACATGAACCAGCCCAGGGCCTTTGAAGACCTGAGATGA
GTCAGGAGGTGACAGTTGAGGGCTTGGGAATCCAGTGAGGCGAGAGGACAGGAGACAGCTTAGGGAAACTGGTCATCT
CACCTCCCTGCTGTGTCAGCGCTCCTATAGCCGCTCTGCACCTCGTATCTGTATATACCTATTAGCAAGAAAATAGTA
AGAGCTGGGTTTGGATATAGGACTGTGAGCAAGGACTAGATGGAGGGGGAAATGATGGAGAAAGAGAAAGGGAAAGTG
CCCGGGGCCTGTCTAACTCACAGGCAAGAGAGAATCGATAATGAGGGACAAGAAGGGCCTTGGCTAAGCAGGGCAGGG
AAAGTCCCTGCAGCTAACAATTTCCGAGGAACAATATAGATAGCAGTTCTCAACTGGGGGCCCATTTTAGCTTCTGGA
GATGAAGAGGAACATACCGTAGGAAGGTCAAACTCTTACAGAAGTTAGGTATAGAGTTGGATGCACAGGGCGGGGGCG
GGGGGCATATCAGGGTATGAGCAGTAGGAGCCAGCAGCTATGGTTAAAAGAAGGATGATCCTGAAGCTAAGAGAAGGA
GACCTGGCTGGAGAGAATGTAGCCTGACAACCAGTTTCCTCGTGAATGGCAGCATATCCTAAACTCAGGGGCTCAAA
GCTTCTAGAAAGAAAAGGGGGACTCGTTGGGATCTGGAGACACTGGCGCCAGTGACACAGGAGAAGGCAGGGATGAGT
GTGGGGTTCAGGATAAGAGAAGAGGCAGTAGGGGAACTAGAGCTGAGCTCATTAGATATCCATTAGAAAAACACGCTG
CAGAGGACAAGAAGCACAGAGACATCCAGAGAAATCAGGACAGGGCAGACCAGGGATGCCCATGATGGGAAGCTTCAT
GACAGGCTTGCTGAACCTCAGAAGTCAAGGAAGAAGATTCAAAGAGTACCAAGGTCAAGCAGAGCCCAGAGCCCAGAT
TTAGGAATTGAAGTAACCCAGAGGCTGAGGAAGTGTCCCATACATCGTGCAGTCAGTGTAGACTCAAGAGTCAGGAGC
CTAGGAGTGGGATTTGTTCACTCTCTTTAGCTCAAACCCAACTCTGAAGGCTTAGCCTGCATGACCAAGGTCATGGAC
CTGAATGTGTGAAAGACCTGAGACCAGGGCCACAAATTAAAAACAAGGCCTATTAAAAACAGATGCCAGACACATAAG
CTGGCACCAGTGACACAGGAGAGGGAGCAAAGGAACACCAGGACAGCAAGAGGCAGCATAGCAGGACAGGCAGAGCCA
GGGAAGGCAATGAAGACCCACTGAAGGGAAACACGAATGACGTGCACAGCCTCAAGACACAGATGCAAGAGGCTCTAG
AGCGGGACATAGGAAACACATGGAGAACTCATCCACCAGCTTTCTGAAAATGCATTTGGAATAGAGCTGTGCTCAGAA
GTTCAACTGGCCAAGCCTAGCTGGTGATCCTGGGGTGGAGAGGGTCTAAGGTAAGGCAGTTGGAACCGTCAAGGTGAT
GCCTTGGTCTAGGTGATATGCATGCTCTTTGCAGAAGCCTGGCATCCTTGTAGGACCAAGGACAGAACTCCTCCAGGT
GCCTGGATCCAGCCCTGTCTGATAAGCTCACACATCTTCCTATCTTGCAGCCAGAACAACAGCCCCATCTGTCTATCC
CTTGGTCCCTGGATGCAGTGGCACATCTGGATCCTTGGTAACACTAGGATGCCTTGTCAAAGGCTATTTCCCTGAGCC
GGTAACCGTAAAATGGAACTCTGGAGCCCTGTCCAGCGGTGTGCACACCTTCCCAGCTGTCCTGCAGTCTGGGCTCTA
CACCCTCAGCAGCTCGGTGACTGTTCCCTCCAGCACCTGGTCCAGCCAGACCGTCACCTGCAGCGTAGCCCACCCAGC
CACCAAAAGCAACTTGATCAAGAGAATTGGTAAGAGGGTGACCAAGGGAGATAATATTTAATCAGGAGGTCAGGCTGG
GGTCAACCCCTTGTATAGAACAACCAAACTGAACAGACCTTGGCAGAGAGACAACACCAATCAGGGCAGTGGGCTTCC
TTTGTGTCTACCTCCTAGAAACTTCTTTTTGTGTTCCTCACACTCAGAAAGTGGTCCTCTGGAATGACTACCAGTAGC
TCACATCAGGGACACACAGAAGTGGACATGGGTCTCAACTTGTAAATGGTCATATCCAGGAACACCTTGGCCTGAGAC
AACACTAGGGCCATCGTTCTCCTCCCCAGACTATTGCCTTCTCCCTTCCAGGCCCCATTAATGCCCAGTCTTTTCTCT
GCAGAGCCCAGAAGACCCAAGCCCAGACCCCCCACAGATATCTGTTCATGTAAGTCATTTAAGTATCCTTTAGTTCCA
AGACATGATCGTCCCAAACAGCCAAATGATGGAGGACAGTTGCTGACCCACCCTATCTCTCTCCACCAGGTGATGACA
ACTTGGGTAGACCATCTGTCTTCATCTTCCCCCAAAGCCCAAGGATATACTCATGATCACCCTGACCCCCAAGGTCA
CCTGTGTGGTGGTGGATGTGAGCGAGGAGGAGCCAGACGTCCAGTTCAGCTGGTTTGTGGACAACGTACGAGTATTCA
CAGCTCAGACACAACCCCATGAGGAGCAGCTCAACGGTACCTTCCGAGTGGTCAGTACCCTCCATATCCAGCACCAGG
ACTGGATGAGCGGCAAGGAGTTCAAATGCAAGGTCAACAACAAAGACCTCCCAAGCCCCATCGAGAAAACCATCTCAA
AACCCAGAGGTGGGAACTTCAGGCTGACTTCATGGGGGCTGGGATGGGCGTAAGAATAAATGCCTGCGTGGACGGCCA
TGACCTCTGTGTCTGCTTCTAACCCCACAGGAAAAGCCCGGACACCTCAAGTATACACCATTCCTCCACCTCGTGAAC
AAATGTCCAAGAATAAGGTTAGCCTCACCTGCATGGTCACCAGCTTCTACCCCGCATCCATCAGTGTGGAGTGGGAAA
GGAATGGGGAGCTGGAGCAGGACTACAAGAACACCCTACCCGTGCTGGACTCAGATGAGTCCTACTTCCTCTACAGCA
AGCTCAGTGTGGACACGGACAGTTGGATGCGAGGAGACATTTATACCTGCTCTGTGGTGCACGAGGCTCTTCATAACC
ACCACACACAGAAGAACCTGTCCCGCTCTCCTGGTAAATGAGCACAGTGCTTAGCCACACCCCAGGTCTTACAAGACA
```
Igγ2c
```
CTGACACCAGCCCTAACCCCTGATCCTATAAATAAAGCACCCAGAGATGGGACCCTGTGAGATTAGCCTGGTTCTTTA
TATGGTATATAGTTCACGATATGCCTCAGCCACAGGCTGTGGGGTCTGGCCAGGGTTCAAGGTGTAAGTTACCCTCCA
AGAAAGAACAAGGTCTTACACTGCCTCCAGACCCAGAGCATGCAAGTGTACCTGGCCTTGCCAGAGATCCTCCCTCTCTGG
ATACTAAGTTTGGCCCAAGGGGCCCTCTCCATACTCTTCCCCACAACCAGCAACTGTTCTGTGATGGGACTGGAAATA
ACTATAGAAAATATCCCAAAAAAATCAGCATAGGGAATGCCTCCCACCTCAACACAAACCCCACCTTCGTCTGTCTGT
CCTTCCCTCTACCACAACTCACCTATCTTGACCAAGGAGGTCTTGTGTGCATTACATAGGCAAGCTGTGACACTGACA
GAGTCTTAGTCATACATGAAGTCCATTCATCTCGGCCAGACCTCCAGAGATAGGGATAGGGATGACTTCTCTGAAGGA
CACTACCTCCCATATGACATCCGTTCAGACCTAAGCTCCAAGACACTGAGACCTGTGACTCTAGCTGCTCCCAAGGAA
GTGGCTACTCAGATACCCACATAGAACTATTAGAACCAGCCTGCTAAGCATCACTCAAACCTCATGGTACCTCCAAGC
ATACATTCACCCATTGATACCTCACCTAGGCAACCTGTATAGCCACCAAGTCCATCTTAGTGTCCGGATATACTTAAA
```

Fig. 4 (Cont.)

```
CACTATCTAAATGTCCACATTTGGACCAGTGCAGATGAAAGATCTCTCATGGACACCTAACCATTTACCCCTAACACA
CACAAGTACCCCTAAACCCAGTTTGACCCTCTATCCCTATTTCCCTATTTTCATCCCTTAAAGTTAACACTCTCCCAT
AGCTGTATAACCAGGCTCACTTCCCAATGTGGACCTTCTAGGAAGCCCAGGCATCACCAAACACGGGCTCTACCCTCA
CTCTGGCCCTCTGAATTCAGTCACCAGGAGACAGGCAGTAGATCAGGCAGGATGCAGAGCTTCTACCTACAGGGGTCT
CAAGACTTGACTCAGCCTAGCCAGGCTCAGAACTGAAGGTGGGGACACACAGAATGACCTACTGTACAGGCCAGACCA
CCATCATGTCCAGGGTGTCTGGTGAGCTCAGGGACAAAACTGCAGCACTTTGGGGAGCTGGAGTTTCTGATCTAGAGA
GAACAGAAAAGAAAGATGGCCCCAGGGAGGGTCTGCTGGACCAGTCAGGCTGCAGCTTTCTCCTGGGTCTACACACAG
CCTCCTGTCACACAGGGAATGGCCCTAGCCCCACTTTGTTGGGGCAAGGACTGACTGCCCTCTCTGTGCAGAGCTGGA
ACTGAATGAAACCTGTGCTGAGGCCCAAGACGGGGAGCTGGACGGGCTCTGGACAACCATCACCATCTTCATCAGCCT
CTTCCTGCTCAGTGTGTGCTACAGCGCCTCTGTCACACTCTTCAAGGTCAGCCCCATTTCCCCCACCATCCCCACAAT
ATCTACACTATACCCAAGCCATCCCCATAGTGACCCATGATGTCCCTACCTGTCCCATACCGTCTCAAGCTCTCTCTC
ATCATCATATGATATCTTCCACAAAGTCATATGCTGTACTCATGCCACTCCCTCCTTGTCCCTCTGTTCTATATTGTA
ACCACATTGTCCATGTTGTCTCTAATTTGTCTTGATGCTCCCCCAAGTTGTCACCCACCCTATCCTTACACTGTCTCC
AATACTCGCTGCACACTGTTCCTGTGGCTGATCCCCACTCTACACCTGGTCCTCACCAGATCCCTATGCTGTCCCTAC
AATGTCCCCCTTGCTATAGCTATAAGCCATCCCAAAACTCCACTCACAGCACGCCCTGTGATCTCACTGTTTTATCCT
CACTCTAGATGTATGACACCCTAAGATTGGGGACTGCCCTGTCTTGGTGTACAAGACGGAGGAGAGTGAGGTCAGGCA
CATAACATCTCACTTTTGCACCTCGCAGGTGAAGTGGATCTTCTCCTCGGTGGTGCAGGTGAAGCAGACGATGGTCCC
TGACTACAGAAACATGATTGGGCAAGGTGCCTAGCTTGTCTCTACAGAAGGCGCCAGAGCTTGCTAGCCCTCTAGGAC
CAAGCCCATGCTGCTGAACAACCAGACACACAGGTTATACTGCCTTCTCATCTCAGCATTCTTTGATCTTATGGCTCT
CACTCTGCTATCAACATCCCTTCCACATTGGAAGGAGCATGTGGAGAGCAGGCTTTACCACAGACGGTAGCCAACAGG
ACCCAAGTACTACTACCACAGCCAGAACAATGGATAGGCCAAAATTGCTGTGTTTCTTCTACATGGTGTCTAGCTCTC
AGCCAGGCACTCTCCCAGGAGGGGTTGCATCACCTGCATGCATTTAGAAGCAGATGAGCCTTAGAGCCAATCCTGTCT
ACACAGTCCTCTGAAAAAACATGCTTCTCTGGGAGAGGAGGACTTTCCATATATCTCTGAGACTGAGAAGGCCCCAAA
GGGACCTCTCTGGGAAAGACTACCAAAGGTGATTCTAACGGCCTTCACCCGACCAGTGCCTTGCCATGTTTTTCTCTG
ACACCTAAGTGAACTCTCACTTCTTGGACTGTAAGATGGGGCTCCTTGTGAAGATGCCTCTTCCTGCCATCCATGCGA
TGTGATGAATTCCCAGATATAAAATCCCATCGGAGACACTGCTGACTCCACAGCTTGAAGACCCTGTTACCTCACCAG
ATGATCTAGAGAGATACTCAGCTTCATAGTCTCTGTTGGGCCCTAGCAGGTGCAGGAGCCCCTGAGCAGTGGCTGAGC
AACACAGAAAAGTCTGTAGGAGAAGAGCATGATGAACACACCCTGATCAGTCCAGAAGGTGGTCCAGGAGCAACATGG
GGGAAAAGAGAGGATGCTTTGAAAGCCAGGCAGGAGTGGGCTTTTCCTGCAGCCCGGCATCCAGATTGGGCCACTGAC
AGCAGAGAACACCAATTAGAGTAAACATCCAAGGAGAGAGCCCAGGCCTGGGGCACTGAGGCTGACTGACCGCTGGCA
TTGGAGAGGCGCCGTGACTGTTTCTCCATTTCATATCAAGGCAAATGCCAGGCCAGAGTTCCCCAACAAAGTCAAAGG
AGAAACTCTGGAAGGAAAGCGGGGGGTGGGGGCTTGGGGGGAGTTCTTGGCGCTTAGGGGACTCCAAGAGATATTCA
CTGACCTGAAGCTTAGCTTTGCCAGCTTTTTCTTTAAATTTTCTGGAGTCCAGTCATGTCTTTAAGGTCCCTGTTCAT
CTTTTTAAAATAATAATAAAACATCCTTCAACATTGTACAACTCGCTCTGTTCTTCCTGTGTGGACCAGCCCCCACTC
TCCTTATACAAAAATCACACACACACACACACACACACACACACACACACACACACACAAATATATACATGCACATGTACAC
AAACACACTCACACATGCATACATACACATGTACACACACACTCACATCACATACACACACACACACACACACACACAC
ACACACACACCACACACAAAACATGCTAACATTCCCAAAGCACAAACCACTCAGCTCAAGTCCCCTCCAACTATCCCA
TAATCAAGTGGGGATGATCTATGGTTGGGAGTCATTCTGAATTTGCAGGCCATGGTGGCCATGAGGGAGGGATAGTCA
GGAAGCAAAAGATAGGAACCACCCATATGAGAGGAACAGATGCTGTAGCTTGAGTGAGGGTTATAGCCTGATAACTTG
CAGTAGAGAAGACAGTCTGGTGGAAATGGCCTCCACTTGCGCTGGTACAGGGTAACAGACTTTCTGAGGCAGATCGGG
GGGCTGGGGAAAGAAAGATGGAGCTCAGTAGTGTCAGGGTGGTCTGTTCTCACTGCATTCCAAGGCGTAGTTTTGTA
GCTGGAACATCCTAAGATGCAGGTCTACATAGGCCCTGGCAGAGGAGTGTGGTGGAGACTCAGGGACTGGACTAGCCA
CAAAATCTGGTGCAGTTGCAGCAGCAGTGTGGACCTGGCTAGCAATGCAACTGCAGCTTCTGCTGTTGTGGGAGAAGC
GTTCTACCTGGGACTGAGAAGCATCTGATTCCTGTAAGTGGCATTTCTGCTTTGGGAGCCACACAATGACAGGCAATA
AAGTGTGCCATTTGACTCATAACCAGTACCTACG▓▓▓▓▓▓GACTTAGATCACACATGAACAAGAGGCCCAGAGGCTA
TGAACCCTCTCCAATGAGCTGGTCAGGAAAGAGTGGGCATAATCACTCAGCCTCAGCCAGCTCAGGGACCCAGAAGGC
CCAGGTGCACAGAGTAGGAGCACATCCAGGCTTCCTACCTTGTCCCCTGAGTCTCAAGAGTACCACATCAACTACTCC
CACACATCCACATGAACTAATCTCAGTCAGCTTTGGACTCCCCCTCATGTCCAGATACAGAAACCTCCCCAGAATAAA
GGGGAACCTCAGGAAATACCTTATGCCACCCACTGTCAATCATGTTCTTACTCAATCATAGGGTGGAAATAGGGTGGC
ATTCGCATCTCTGGAACAAAGGCTGTGACTCTGGGAAAGACAAGAGAAAGCCAGGAACAAATACATCTGCTTTCACAG
CTTCCACATGTCAAAGGGGTCAGCACTAAATGAAGCTGCAGAAGAGGACCTCACAGACAGCCAGCATCTGTAGCC
CTTCCAGATCTTTGAGTCATCCTATCACAGGAGATTGAGAAGGAGTTGACGGACCAGCCCAAGCAGAGGAAGCCTGTG
TGTTCAACAGTAAATGTGTTTGCCAGCAGCCTGATGTCAACTGAGAAGACTGTGGCGAGTGCTTGGGAGACAATCACG
GGCAGCTAGAGCTGCACAACCCCATAGACAACAAGCCTGAAACACAAGGAGATGATGAAATATATCCAGAAGACTGCG
GAATCAGTTTGGCCTGGACCACAGGTTGATAGAACCAAGGCAGCTGAGCCCTGTGGTAAGTGACCAGGAGGGCAGAGG
GAGGGAGCTTCCAGGAGCATGCCTGGGAATGCCTTCAGGCCTTCTGAGAAGCAGAAAGTAGGCACTCTGGGGTTCCAG
```

Fig. 4 (Cont.)

```
GAACCATCCCAGCACTCAAGAGTTACTAAGGGAATAGAAGCAAACCTGAGCTGAAGGAGAGAAAGAAAAGTGGAGGGA
AGCCCAAGCCACTCAAAGTAACAGGCAGGACAACTTCCAGTGAGCTGAGAGAATAGGAGTGCTGGAGAAGGCAGAGCA
AGCCCAGCAGATCAGGAGAACCTGCATAGGAGTCTGGATGACTAGAGAAACCCAGAAGGTGAGAGAACAGGCTTAACA
GCTGTCATGGACTTAGGGATATGCAAGCCTGGGGCACCAAGCTGATCTGCATAGAGGGCAAGGGTAAGTGGGAATCCA
AGAGATCTAAGAATGACCAGCGCTGGGCAGAGAGGTGGCCTGGGAGAAGATGGCTGGTCTTCCCCATGAGTCCAATAG
CAAGATTGTCGGAATAGGTTATCCTATGACAGATGGCAGTATCAGTGACCAAATGAAGACGCTATGGAAGAATTGGAC
CATGTGGGAGTTGAGAGTTGAGGACACAAGGCTGACCTGCCCATGGGAACTACAGCTGATAAAAGTGCTGTGATTCAG
GGCATTTCTGGAAGCTCTGTGATCCAGGTTGCAGTACACAAGTAAACTGGGACAGACGGGAGTTCTGGGGGTTCAGTT
CAGATACTAGGAACTTAGGAAACTGGGAAAAGGGAAGTTGGGGCTGATGGCAGAACTATGAGAAGGCACTGGAATTCT
GAAGACCAGACCTTCTAATCAACTATAGAGGAAATGGAGTGGGTAGGAGTGGTGGATACAGCTGAGCATCACAGGGGA
CCTGGGGATTGGGGACAGCTATACTGGGGCTAGCAGTGCAAACACAGAAATTGGGGGACCAAAGGGGGAATTGAGGAT
GACCTTGGGTAGATAGAAATGCTGGATGCCTAAGGTACCTCCAGGAGCTTAGGGAACCTCGCAGAGCAGCTACAAAGC
TGGTGGTGTTAGTGACACTTTCAGAACCAGATCGGGCAGGTTGGCATGTAGAAATGGGGTTAATGGAGACCCAGGACA
GTGGCAGATTCAGAATAAAATACAAACAACCGAAAGAGTTATGTGCCCTGTAAGAAGTTGATCTGACACCCACAGCAG
AGACATCTAAGGTCTCACAGCCCACATCAAACAGGCTTCTGATCTAAGGACAGCACAAAAGGAAGGAGGCATCAAACC
ATCCTGGGGAAGACAGTGCAGTAGTAGCCAGAAGTGTAAGCCCAACAGCAGTGGGACTGGTGTAGCAGCCAGGGACAG
GGTCCCTGCCAAGATGAGCCTCAGGGGAGCTGAGCAGCTGAGAAACTCACCAGCTGAGAAGCTCAGGGGAATCAGGGT
AAGTGGAGGTTCCAGAGAATCAGGGGAAGTCAGGAGCTCAGAACCCAAGAAGGGGCACCTGCAAAAGAGCTAAGGCCT
ATGAGAGTGTGGGGAACACTTTAAGCAGCTTTAGGGGAGCCAAGACAGGTAGAAGTGTGGGGACCCAAACAGGGAAGC
TCCAGGGGAGCTAGGAAAGGTGGAACTGTGGGAATCCAGGCAGAGCAGCACCTGGGGACAAGGAAAGAAGTGTGGGG
ATCCAGGCAGAGCAGGTCCAGGGGAGCCAAAAAGTGGAGGTGTGGAGACACAAGCAGGGCAGCATCTGGGGAACCAGG
ACAGGTGGAAGGGTAGGGACCCAGGCAGAGCAGCACCAGGGGAGCCAGGACAGGTGGAACTGTGGGGATCCAGGCAGA
GTAGCACCAGGGGACTAAGGAAAGAATAAGTGTGGGGATCTAGGCAGAACAGGTCCAGAGGAGTCAAAAAGTAGAAGT
GTGGAGAGCCAAGCAGGGCAGCATCTGGGGAGCCAGGACAGGTGGAAGTGTGGGGATCCAACCAGAGCAGCACCAGGG
GAGCCAGGAAAGGTGGTAGTGTAGGGTCACAGGCAGAGTCGAACCAGGGAACCAAAGAAAGAAGAAGTGGGGGGACCA
GGGGAGCCAGGACAGGTAGAAGGGTGGGGACCCAGACAGAGCAGCTCCAGGGGAGCCAGGACAGGTGGAAGGGTAGGG
ATCCAGGCAGAGCAGCACCAGGGAAGCCAGGACAGGTGGAAGGGTAGGGACCCAGACAGAGCAGCTCCAGGGAGCCA
GGACAGGTGGAAGGGTAGGGCCCAGGCAGAGCAGCACCAGGGAACGCGGGACAGGTAGAAGGGTGGAAACCCAAACA
GGGCAGCACCAGGGGAGCAAGGAAAGGTTGTACTGTGGAGATCTAGGCAGAGTAATACCAGGGAAGCCAAGACAGGTA
GAAGTGTGGGGACCCAGACAGAGCAGCTCCAGGGGAGCCAGGACAGGTGGAAGTGTGGGGACAAAAATGGGGCGGCTT
CAGTGTGTCTGGGGAGCAAGGAAAGGTAGAAGTGGAGAGACCCAGGCAGAGCAATACCAGGGGCTAACAAGGTAGAAG
TGTGGGGACCAGAACAGAGCAGCACCAGGGGAGCCAGGACAGGTGGGGATGTGGGGACCCAGGCAGGGCAGCTCAAGG
GGAGCCAGGACAGGTGGAAGGGTAGGGAGCCAGACAGAGCAGCTCCAGGGGAGCCAGGACAGGTGGAAGGGTGGGGAC
CAAGGCAGAGCAGCTCCAGGGGAGCCAGGACAGGTGGAAGTGTAGGGACCCAGGCAGAGCAGCACCAGGGAAAGCCAGG
ACAGGTGGAAGGGTAGGGATCCAGGCAGAGCAGCACCAGGGGAGCCAGGACAGGTGGAAGGGTAGGGACCCAGACAGA
GCAGCTCCAGGGGAGCCAGGACAGGTGGAAGGGTAGGGCCCAGGCAGAGCAGCACCAGGGAACGCGGGACAGGTAGA
AGGGTGGAAACCCAAACAGGGCAGCACCAGGGGAGCAAGGAAAGGTTGTACTGTGGAGATCTAGGCAGAGTAATGCCA
GGGAAGCCAAGACAGGTAGAAGTGTGGGGACCCAGACAGAGCAGCTCCAGGGGAGCTAGGACAGGTGGAAGTGTGGGG
ACAAAAATGGGGCGGCTTCAGTGTGTCTGGGGAGCAAGGAAAGGTAGAAGTGGAGAGACCCAGGCAGAGCAATACCAG
GGGCTAACAAGGTAGAAGTGTGGGGACCAGAACAGAGCAGCACCAGGGGAGCCAGGACAGGTGGGGATGTGGGGACCC
AGGCAGGGCAGCTCAAGGGGAGCCAGGACAGGTGGAAGGGTAGGGAGCCAGACAGAGCAGCTCCAGGGGAGCCAGGAC
AGGTGGAGGTGTGGGGACCCAGGCAGGGCACCACCAATGGCCAACAAGGTAGAAGTGTGGGGACCCAGGCAGAGCAGC
TCCATGGGAGCCAGGACAGGTGGAGGTGTGGGGACCAAGGCAGAGCAGCTCCAGGGGAGGCAGGACAGGTGGAAGGGT
GGGGACCCAGGCAGAGCAGCTCCAGGGGAGCCAGGACAGGTGGAAGTGTGGGGACCCAGGCAGAGCAGCTCCAGGGGA
GCCAGGACAGGTGGAAGGGTGGGGACCCAGACAGAGCAGCACCAGGAGTGTCAGGAGAGGTGGAAGTTAAGTAGTTAT
AGGGGAACAGGGGCAGAATAGAATGAGGGATGCAGGCTGAGAGGATACAGGGAAATGTGGCAAGTGGAAGGGCAGGA
AGAGAGGCAGAGTGGCTACAGGGAAGTTGAGGCAGGTAAGACTGTCTGTTCCAGGTCAAAAAACACTGAAGGCCAGTA
GAAAGGAAACTGGTGCATGTGGTAGTGGGGATTCTTAGCTTAGCAGTCACAGGGAAAGTGAGCCAAGTAGGAATGCA
GGCATGGGGGCAGGCACAGCTGAGCAAACACTAAAGAGCTGTAGCTGAAGGGTTATAAGGTACCAAGCTGAGAAGCT
GCTGGGAATCTGGAGCTAATGGGGTGTGGGGGAGCAGGCTGAGCAACTACACAGGATCAGGGATAGGTAACTGTGTAA
GGAGGCAGGCTGAGCATCTCCATGACAGCTGGAGCTACTATGAATGTTAAGCTCCAGACTGAGCACCTGCAGGGAAAC
AGAGGCAAGAGGGAGTGTGGGGATCCAGGCTGAGTAGGTCCAGGGAAGCTGTAGTAGGTGGAGGTGGAGGCCCAGGCT
GAGGAGCTACAGGAGAGATGGGACACTAGGGAGGGCAGGGATCATGGCCAAGCGGATACTCAGTAGCTGAGATAGATG
TGGGGAATCAGCTTAAGCAGCAGACACAGGGGAGCAGGATCTAGTCAGCTTCTAGGGATCCAGGCTGTGTAGACATGG
AGGGACTGGGGAGCTATAAGTAAATACACTAGGCATAAAATTACAGGGAAACGGAGGCCAGTGGGAACGTGGGCCTC
CTACCGAACAAGTAACAGAGAGCCAGAACTGACGGGTTGAAGAGGAACCAGGCTGATGAGCTCCAGGAAATCTGTGGG
```

Fig. 4 (Cont.)

```
GACTCGGTCAATGGGAGAACAGGGTGAGCAGCTATAGAGGATCAGGGATAGGCAAAGACGTATGGAGTCAGGCTGAGC
AGTTACATGAGAGCTGGAGCCCTAGTTATGTGGAGGTCCAGGCAGAGGGGCTGGAGGGTAGCTGAGGGAAATGGTGCT
AGAGAATCAGGCTAGGCAGACACAGGGGAGCAGGTTCTAGTCTACATATGAGTGGGGATCCAGGATGTGTAGAGAAAG
GATAGCAAAGGTCATGGAGGATTCCAGGCTTAGGGGTCACTGGGAAACTAAGACTGGTGGAAGTGGGATTGTCCTAAG
TGAACAAATTCCATGAAGCTAGAGCCAGTGGGTGTAAAGGTAGCAGACTGAAGGACTATAGAGTATCTGGGGGTGGAT
GGGAATGTGGGGAATCGTGCTGAGCCACTACAAGGACAGTGTGGCTAGCAGGCTGTAGGAGACCAAGCTGAGTATCTG
AAGGGAAACCAAGGGAAGTGGAAGTGTAGGATTCCAGAAATGAGCAAATGCAGGGCACTTGAGGCAGGTATCAGTGTA
GGGAACGAGACTGAGCAGTTCACAGGTCACCCAGGGTAGGTAAGAGTTCTGGATCATCAGAGAAGCCTCTGGAAGCCC
TAAGCACCTACAGTAGACCTAAGGCAGGTGGGGTGCAGGGAATAAGTTGTGCAGCTCCTGAGGAGGAGGACAGGTTGG
AGTAGAGGGGGTTCTGACTAAAGAGTTGAATGGGAGCAGGGCAGGTGGGAATGTAGAGGAACTAGCTAGACAGAAGTC
CAGATGAGATTGAGGGCCACATGATGCCCTGAGCCGATGAGCTGGCCTTAGAAATCACTTTGCTGGGACCAGGGCCAG
GGGTTTGAGGAACAAGGCTGAGGTGAAATGGTAGCATGACAGGGAGGCAATGGCAGAGAGGAAGGAGAAGGCATGCTT
AATTCATGGTGGAGTGCAGGGAGGGAAAGAGCCAGGAGGTCTAGGCTGGAGCTGATCCAGCTTTCTGCACTGATGAGA
GGGGCGGGACTGAGTTCTTTTGGCTCCAGGAGCCAGGGCAACAAGACAAAGGCGCCTAGCATAGCAAGGACACATCTG
GATCTAAGACCAGGAGAAGAGGGCAAGACCGAAAGTTCAGGAGGTCATGGGAGGGAGCGGGAAATCTACAAGGGACTG
TCTTTAGAAAAGAGTAAGTGCCCAGTGGAGGGAGTGCCCAAGCAACAAGTCCAGTGTTGGGAGAGATCGGGGTGGGCA
AAGGCTGTATGTGCAGTAGGCAGGCCCAAGTCCCCAGGAAGGAAAGAAGAAGTGCATAGGAAAACGGGTCAGGTCTAG
CAGGAGCCAACCGAGGTGCTCAGGACTGAGAGGCAGAGCCCAAGACACAGGAATCGCTGAGCTCATGCAGGTACCAAG
AATAACTGAGAGCTAAGAGAAAAATTATCTAGGGAATAGGGGACATGAGGAAGGACTGTTGGCTGAGAAGGGAAAGG
GACAGGGAGAATCCTAAGGGTTGGCATAGACAAAGGAAACACACAGGCTTTGGGTTGTTAGTCCGGGGCTCTGCATAT
GATCCACCGAGATTGTGGAAACAGAAGAGCAGGAAGATCAAATCTGTCCCAACTATACAGGGACACACGGTCGACCTA
CAAAAGGAAGGAGATGTGAGGATCAGGGGCCGAGCAGTGAGGAGGTGTGTGGAGGTGTTAGAGCTCAGGTGCAGCAGA
GACTAGCATGGCCCTGGGGATAGAGGGAAGGACCCAAGGGACAGTAGGGACAGGAGGGCGAGGTGAGGTGATGACCAG
CATTATACAAATGGTGGCGCTGTCCAACTTCTAGGGCCCTGTGCTACTGAGAAAGGAAAGGGACTTCCGAGGTTTGGC
AATACAAGCCCCGTGCAAAGGCAGAACCCAGGGCACTGTGAAGACAACACTGCAAGACAGGAGAAGCCAAGGCTGAGT
TCACCGAGGTCACATTAGTGAGAATACACTGCGAGGAGAGGGGAGGCGCTGAGCACCCAGCCACACCAGACAGGCCCA
TGCTGAGTCCCTGGACAGTGGGGAGGGGAGCACCTGGTGACCTGTAAGAACTGTGAGACTGGAGGAGAACCAAGGTA
AAAGGTGTGTCAAAGGACACATGTTTAGCAGGCTGGGCCGACTTAATGCAGGACACACGTGGTGGCAAAGCCAAGAGG
GCTGCGTATGAGCCACAAGTGAATCCTGACCCAAGAATAGAGAGTGCTAAACCTACTTACATCAAAGCCAACTGAAAG
GACAAGGCCAGCAAAACGAAGCTAAGGCCAGAGATCTTGGACTATGAAGAGTTCAGAGAACCTAGGATCAGGAACCAT
TAGTGAACAGACAAAGGCAGGTAAAGCAGCCTAGGAGTGGACAAAGACAGGAGAATACAGAAGACGGCAGGGATGACC
CGACTTCAGTTTGGGCTTCACTGTTGTCCAAACTGTGTGCAGATTATGGCCCATGGGTAAGAGGTTTAGCATTAGAAC
ACAGATACCCACATTGGACAATGGTGGGGGAACACAGATACCCATACTGCAAGGCTCTTCGAGCCCTTTCCTAAAAGT
GTACTAGGAGTGGGACTGGGCTCAAAGGGATTAGGTGTGATCTGGCCTGGTGAGGCTGACACTGACAAGCCCAATGGT
TGGGTGTTGCATCCTCCATTTATACAGCCAGGGACTTGGGGAGGGTACAAAATGGAGGACTTGTAGGAGCTTGGGTCC
AGACCTGTCAGACAAAATGATCACGCATACTTTTTCTTGTAGCTGAAACAACAGCCCCATCTGTCTATCCACTGGCTC
CTGGAACTGCTCTCAAAAGTAACTCCATGGTGACCCTGGGATGCCTGGTCAAGGGCTATTTCCCTGAGCCAGTCACCG
TGACCTGGAACTCTGGAGCCCTGTCCAGCGGTGTGCACACCTTCCCAGCTGTCCTGCAGTCTGGGCTCTACACTCTCA
CCAGCTCAGTGACTGTACCCTCCAGCACCTGGCCCAGCCAGACCGTCACCTGCAACGTAGCCCACCCGGCCAGCAGCA
CCAAGGTGGACAAGAAAATTGGTGAGAGAACAACCAGGGACGAGGGGCTCACTAGAGGTGAGGATAAGGCCTTAGAC
TGCCTACACCAACCAGGGTGGGCAGACATCACCAGGGAGGGGGCCTCAGCCCGGGAGACCAAACATTCTCCTTTGTCT
CCCTTCTGGAGATTTCTATGTCCTTTACACCCATTTATTAATATTCTGGGTAAGATGCCCTTGCATCATGACATACAG
AGGCAGACTAGAGTATCAACCTGCAAAAGGTCATACCCAGGAACAACCTGCCATGATCCCACACCAGAACCAACCTGG
TGCCTTCTAACCTATAGACACCAATAACACACAGCCTTCTCTCTGCAGTGCCCAGAAACTGTGGAGGTGATTGCAAGC
CTTGTATATGTACAGGTAAGTTACTAGGCCTTAAATTCCAGCCCCAGGTCCAACAAATGTCCTCTGAGGCCCATGTTG
GAGGATATTGGCATATTTCCACCTTTCTTCTTCATCTACAGGCTCAGAAGTATCATCTGTCTTCATCTTCCCCCCAAA
GCCCAAAGATGTGCTCACCATCACTCTGACTCCTAAGGTCACGTGTGTTGTGGTAGACATTAGCCAGGACGATCCCGA
GGTCCATTTCAGCTGGTTTGTAGATGACGTGGAAGTCCACACAGCTCAGACTCGACCACCAGAGGAGCAGTTCAACAG
CACTTTCCGCTCAGTCAGTGAACTCCCCATCCTGCACCAGGACTGGCTCAATGGCAAGGACGTTCAGATGCAAGGTCAC
CAGTGCAGCTTTCCCATCCCCATCGAGAAAACCATCTCCAAACCCGAAGGTGGGAGCTGGCAGGGTGTGGTGTAGA
AGCTGCAGTAGGCCATAGACAGAGCTTGACTTAACTAGACTTCTGCCCTCTTACTGACCTCCATGCTGACCACTCTCT
GTATCCACAGGCAGAACACAAGTTCCGCATGTATACACCATGTCACCTACCAAGGAAGAGATGACCCAGAATGAAGTC
AGTATCACCTGCATGGTAAAAGGCTTCTATCCCCCAGACATTTATGTGGAGTGGCAGATGAACGGGCAGCCACAGGAA
AACTACAAGAACACTCCACCTACGATGGACACAGATGGGAGTTACTTCCTCTACAGCAAGCTCAATGTGAAGAAGGAA
AAATGGCAGCAGGGAAACACGTTCACGTGTTCTGTGCTGCATGAAGGCCTGCACAACCACCATACTGAGAAGAGTCTC
IgG1
```

Fig. 4 (Cont.)

TCCCACTCTCCGGGTAAATGACCCCAGAGTCAGTGGCCCCTCTTGGCCTAAAGGATGCCAAAACCTACCTCTACCACC
TTTCTCTGTGTAAATAAAGCACCCAGCTCTGCCTTGGGACCCTGCAAAAATGTCCTGGTTCTTTCTGAGATACAGAGT
CCAGCGAGGTCATGGGCTGAGGGGCGTCCAGGGTTTGAGGCCTGAGGTTTGACTAAGGAAAAAGGGTGATCTACACTG
CCAGACACAGCACTTTTGATTTGCTGGCATGAACAGAATTTACCTCTCACTGAAAAGTGGAGGCTTTATCCCGAGGCA
ATCCCTCTTGCTTTCTCTTCCTCTACCTAATACATCTATAGTGGGCACAGAATATATCATGAAAGTAAGGACGACCCA
AACTCCACCTCCCTAGTCCACCTTTACCCCTCTTCCTAGCCAAGGATCCCACTGAAGGCACTCAATGGACACATATGG
TCACAGACAGACCCTTGCTATTCCACCACTCAATGCAAGAAGCGTTCCAGAGACTAAGTCTAATGTAACGATGCACAT
AGCTGTCACTGCTCTCTCACTGCCCATGAGAATCAACATGGACCCATTAGACACAACCTGATGAGCAACACTGAGGGC
AAAAGGCCCATATGTATGCATGCACACACATCTTCAAATGCACAGCACAGTGACACACACACACACACACACACACAC
ACACACACACACACACACTGGAACCTCACATGGGCATCCTGTGCAGTACTCCCAGATGAAAAGAAACCAGGTCTACAC
ACAGGATCATCCCAACATTCACAAGTGGGCCAGCTGAGACAGATACAACTTTTCTCTGCCTTGGATGCCCACAGACAT
CTTCATGCACACATGAGTTTCCTGGGGTCAATCTGTCCCTGACCCTGGGATGGTGCCCCAACCTCACACAGTTGGCAC
CCATCCGAAACTGTATAACTTACTCACTTCCCACTGTGGATCTTAACTGCAGTCCTAGCATCATGGGGAATCAGCTCT
GCAATCCCTCTGGCCCTCAGTTCTCGGTCATCAGCAGATACAGGATCAGGCAGACCACACAGACACTACCCATGAGAG
GCACAGGCCCTGACTCAGCCTAGCCAGGTTCAGAACTCAAGGCTGGAGCACACACAGAATGACCTAGTGTATAGGCCA
GGCCACCATCAGGTCCAGGGTGTCTGGTGAGCTCAGGGACAAAACTACAGCACTTTGGGGAACTGAAGTTTCTGGTCC
AGAGAGAGATCAGAAAGGAGAGATGGCCTCAGGGAGGGTCTGCTGGCCCAGTCAGGCTGTAACTTTCTCCTGGAACTC
CACACAACCCCATCTGACACAGGGAATGGCCCTAGTCACGCCGTGTTGGGATAAACAAACGCTGACTTCCCTCTCTGT
CCAGGGATGGAAGTGGACGATGCCTGTGCTGAGGCCCAGGACGGGGAGCTGGACGGGCTCTGGACAACCATCACCATC
TTCATCAGCCTCTTCCTGCTCAGCGTGTGCTACAGTGCAGCTGTCACACTCTTCAAGGTCAGCCACGCCATCTCCACA
GTGTCCACACCATCCTCACACTGTTCCTCATACTGTCTCTGTGATCAGCTATGCCCCACACTGTCCCATGCTATTGAC
CTGTCTTACATGCTGGGCAATGCCACCTAACCTTCTCTATGATACAGTCTCACAGTGTCCCATGCAGTCTCCCTAATT
CCCCAAGATGTCCGCACTCTATTGCTGTGTTGCCTCATGCTGCCCCCACACTGTCCATCCCTCCCTGGTATGCTATCC
CAGGCTGTTGTCTCTATTTTTCATGCTCTCCTCACACTGTCCCTAGTGTCTCATACTGCCAATGTTGGCTCCCACATTG
TCCCCACACTCTGCACACAACCGGACAATAAACCCTGCTGTCCCATAATGTTCCCTGTGGTCCCCAACTCTATCCCTG
CACATTTGTCTATGTTCCCTGAATTCTCATGTTGTTTGCACACTGTTAGTGTCTAACGAACTCTCTCCCAGGTGTACC
TTCTTCCATGCTGTCTCACCTCATCTCCCATTCTGTCCTTGTACTAACCCCACTCTATCACGACACTGTCCCTATTCA
CTGTCCCTATGAAGTGCCCATGCTGTCTGCATTCTGTCCCATGTTGTATCCTCATCCCGGTCTCATGCAGTTCAGATC
TATCTGACACTATTCCCACTCTATGCACACATTTCCCCCTATACCATCCCTGTCTGATCAACATGCAATCCTCTAGAC
ACCCATGTAGCAGGTTAGAGACTCTAGGGATGGGTACCTGCCTGACTGAGCTACCTCTCTTGGTGGGAGAGGAAACAC
AGGTGAGAGTGCAGTCCTGATCTTATCTTATTCACCCAGTCCCACAGGTAAAGTGGATCTTCTCCTCAGTGGTAGGGT
TGAAGCAGACGCTGGTTCCTGAATACAAGAACATGATTGGACAAGGGCCCTAAGCCACCTCCTATAATGGCAAAGGAT
TCCCCACGCCCTAGAGGACCCTGTCCAATGTGCCAAGCAGTCTGACTCAGATCACACTGTCTGCTCACTTCACTATCT
TCTGTCTATGAGACCCAACCTCCCTCAATTCTTCTCTCTGGAGGACTATGTGGACATTAGATTTCCAAAAGCCACA
GCCTCCAGGACCTAAAATACCATCACAGCAGCAGCCAGGACACTAGATAGGGTCAGAAGGACCATAGTTTCCTGACTA
GTTTATCCAATCTGTTGGGACAGAAGAATCACTGAAAAAGTGACAAGTGCCCAAGTTGCCTGTGTTCAGCTTGGAAGG
GACCAACCTTGGAACCAGTCCTGTCAGCATCATCTTCTAAAACACAAGAATTGAGTATGTAAATGGCAGATTTTGGAT
CCCCAGGGTAAGACAGACTTCAACCAGGCCACGACCTGGACAATCATGGCCCAGCTGAAGTTGACTGAATTATTCCAG
TGGCCTTCACATCGTCTTGCCAGGTTCCTTCTTACCACTTCCATGAACCCTGGGATACAGAAAAGAACTGTGCTTCTC
GGGATCTTGGGACAGAACTGTCTAATTGGTGGGATCCTTAGGTAGATCTTTCTTCCAGTCACGGGTATAATACAATAC
ACTAGATTCTCACATAAAGGAAAAAATTCACACACAACTCCGGCCAGTCCTGAGGCCTAGACACCACCACCTCTCTGG
AATTCTGAGCTCTATGCTGGAGGCACAAGAGAGGAAGGCCTGGACTTCATGGCCTCTGTGTAGCCCTAGTAGGTGCAG
AGGCCCCTAAGCCGGGGTTGGGTGACCAGCAAGGACCTCCTGGAGAGGGATCTGATGAGTAGATTCCACCTGGGACAG
AAGGAAAAAGATGAAAAGCAACAGAGGTGGAAGGGCACTGGAGAGAGCCATGGTATAGCAGGTTTATCTTGCAGACCT
GACATCTGTCCATGACTCTGAGACTTAGCTAATGACAGCTGGGCAGCAGTCCAAGGAATTACCATGCCCCTAACAC
CAGGCTCCTGGAGTGTGGAGTGGGTCTACTCCAGAGCTCCAATACCTGTTTCTCCATCACTTCTCAGCCAATGAGAAA
TCGGTTTCCAGACAGGAAGAAAAAATGAAGGCAGGAAGGAAAAGTGGGCACCTGTTCTTCTGTGAGTGGCAGGAAGTTC
TCAAAAGACTCAGGACTTTGGCTTCTAACTTCCTGTGGATCATTGATGTCTCTAAGGTCTCTGTCTGCTTTGTTGGTT
TTGTTTGTTTTTGGTTTGGTTTTTTTTTTTTTTTTTGGTCAATAAAACGTTTTTTCAAACATTCCACAATCTCT
GTGTTCTTCCTATGTGAACCAGCCCTGGTACTTAGAAACAGCACTGTTAAAGC▓▓▓▓▓▓AGGACCACTTCACCTACCC
CTACAGGAGGTAACCCAGACCATGTCTGGACTCCCCCTGGTCTCCCCCTACCCCAAACACTGAAACCAACAGAAGAAA
GAGGAACCTCAGGAAGTGTCCCGTGTCACCCAGTTTCGATCCTGTTCTTAGTCTGTACTGGGTTGGGAGAAGTGTGAT
GTTCACACCTCTGGGCAAGGACTGTGAATCCTGGAAGGATGAGACAGATCTCAGAGCTGGGCTGTTAGCAGCCCAGC
ACCAATGCAAAAGAGCAGCAGTCACAAGGTTCCACACGTGAATGTAGTCAGCAGAGAAGCTGGAGAAAGCCACAGCC
TAGGGAGAGCAGTGAGCTTTTCCAGACCTAATAGACGGCAGAACACAGGAGGATGAGGAGTTGACAGATCAGCCCCAA
CAGAGGGGCCTGTCTGTTGCAAAGAAAAGGTGCCTACCTGCAACCTGGTGCCAACCAGGCAGACACCAGACTTTCCAC

Fig. 4 (Cont.)

```
GGACAGAAGCCAAGACCACTAAAGCCGTGCCCACCTACAGACAACCAGAGTAAGCCTCAAGGAGTTAATGGGATAGAC
CCGGAAACCTGAGGGTCTAGCCAGGCCTAGAGGCCGGTGGACCCAGGACAGCTGAACCAACAGAGAAAAGAAAACCCA
GTGGAGCAAGGGCAGAGGCATACAGAATTGAGAGAGTTGGTAAAGAGGGGATGGGGAACGTTCACCTGGGAGGACTGA
TACACCTATTAGAAAGAGCTAGAGTCAGAGTGGATGCCCTTGTGACTCCCGGCATTGGATAGCAGATCCCAAGAACAA
AGCTGAAAGAAGGTAAATTTCTCAAGAGAAAGTCTTCCAGAGGAACTATGGGTACCAGGCAATAAGTAGTACATCCGT
AGGAGGGAACCAGACAGTAGTACATCTGTAGGAGGGGACCAGGCAGTACAGCTGCAGGTAGGGACCAGGCAGTATATC
TGTAGGAGAGGACCAGGCAGTATATCTGTAGGAGGGGACCAGGCAGTAGTATACCTGTAGGAGGGGACCAGGCAGTAT
ATCTGTAGGAGAGGACCAGGCAGTAGTATATCTGTAGGAGAGGACCAGGCAGTATATCTGTAGGAGAGGACCAGGCAG
TAGTATATCTGTAGGAGGGGACAAGGCAGTACAGCTGCAGGTAAGCTAAGGACAGTAAGAGTAGTAGAGAGCCATGGT
GACTCCAAAAGCTCAGAAGACCTGGCAGAGCAGCTACAGGGAATCCGGGGCTGGTGGAGTTGGGAGGACCAAGCCAAA
GAGCTATAGGTAAGCCGAGGCTGGTGAAGGCACAAAAACAAGCTAAGGAGCTACAGAGGGGCAAGGGCTGTGGCAGG
TGTGGCTAAGAGAGGTCCAGGGCACCCCCAGGAACCAGAAAGAGCTTTACAGGAGTTCTAGAGGAGGAAGGAGTTGGG
GAGACAGGCTGGGTATCTGTAAAGATAAGGTAGCAGTTGTCACAGTTTGGGTCTCAGAGCTGCCCAGGGGATTAGGGG
AAAATTCTGAGAAGCTGTGGGAGAGTAGGGGATGGTAGGAATGTGGAGGACCAGTCCTAGCAGCTGTGGGGAAGCTGG
GGATGGTAGGAATGTGGGGGATCAGTCCTAGCAGTTTTGGGGGGAGCTGGGGATGGTAGGAATGTGGGGGACCAGACC
TAGCAATTTTGGGGGGAGCTGGGGATGGTAGGAATGTTGGGGACCAGTCCTAGCAGCTATGGGAAAGCTGGGGATGGT
AGGAATGTGGGGGACCAGTCCTAGCAGCTATGGGGGGAGCTGGGATGGTAGGAATGTGGGGGACCAGACCTAGCAGTT
TTTGAGAGCTGGGAATGGTAGCAATGTGGGGTCCAGTCCTAGCAGCTATGGGAGAGCTGTAGATGGTAGGAATGTGGG
GGACCAGTCCTAGCAGCTGTGGGGAAGCTGGGGATGGTAGGAATGTGGGGGACAAGACCTAGCAGCTATGGGAGAGCT
TGGAATGGTAGAAATGTGGGGGACCAGTCCTAGCAGCTGTGGGGAAGCTGGGGATGGGNNNNNNNNNGGAGGACCAGT
CCTAGCAGCTATGGGGGAGCTGGGGATGGTAGGAATGTGGAGGACCAGTCCCAGCAGCTATGGGAAGAGCTGTGAATG
GTAGGAGTATGGGGGACCAGTCCTAGCAGCTATGGGAGAGCTGGGGATGGTAGGAATGTGGGGGACCAGTCCTAGCAG
CTATGGGAGAGCTGGGGATGGTAGGAATGTGGGGGACCAGTCCTAGCAGCTATGGGAGAGCTGGGGATGGTAGGAATG
TGGGGGACCAGTCCTAGCAGCTATGGGAGAGCTGGGGATGGTAGGAATGTGGGGGACCAGTCCTAGCAGCTATGGGAG
AGCTGGGGATGGTAGGAATGTGGAGGACCAGTCCTCACAGCTGTGGGGAAGCTGGGGATGGTAGGAATGTGGAGGATC
AGTCCTAGCAGCTATGGGTGAGCTGGGGATGGTAGGAATGTGGGGGACCAGTCCTAGCAGCTATGGGAGAGCTAGGGA
TGGTAGGAATGTGGAGGACCAGTCCTAGCAGCTATGGGAGAGCTGGGGATGGTAGGAATGTGAGGGACCAGTCCTAGC
AGCTATGGGAGAGCTGGGAATGGTAGGAATGTGGGGGACCAGTCCTAGCAGCTATGGGAGAGCTGGGGATGGTAGGAA
TGTGGGAGGCCTGTCCTAGCAGCTATGGGAGAGTTGAGGATAGTAGGAATGTGGGGACCAGACCTAGCAGCTATGGG
AGAGCTGGGGATGGTAGTAGTATGGGGACCAGTCCTAGCAGCTATGGGAGAGCTGGGAATGGTAGGAGTGTGGAGGA
CCAGTCCTCTCAGCTGTGGGGAAGCTGGGGATGGTAGGAATGTGGGGGCCTGTTCTAGCAGCTATGGGAGAGCTGGG
AATGGTAGGAATGTGGGGGACCAGTCCTAGCAGCTATGGGAGAGCTGGGGATGGTAGGAATGTGGAGGACCAGTCCTC
TCAGCTGTGGGGAAGCTGGGGATGGTAGGAATGTGGAGGCCTGTCCTAGCAGCTATGGGAGAGTTGAGGATAGTAGG
AATGTGGGGGACCAGACCTAGCAGCTGTGGGGGAGCTGGGAATGGTAGGAATGTGGGGGACCAGTCCTAGCAGCTATG
GGAGAGCTGGGAATGGTAGGAATGTGGGGGACCAGTCCTAGCAGCTATGGGAGAGCTGGGGATGGTAGGAATGTGGGG
GACCAGTCCTCCCAGCTGTGGGGAAGCTGGGGATGGTAGGAATGTGGAGGACCAGTCCTCTCAGCTGTGGGGAAGCTG
GGGATGGTAGGAATGTGGGAGGCCTGTCCTAGCAGCTATGGGAGAGTTGAGGATAGTAGGAATGTGGGGGACCAGACC
TAGCAGCTGTGGGGGAGCTGGGAATGGTAGGAATGTGGGGGACCAGTCCTAGCAGCTATGGGAGAGCTGGGAATGGTA
GGAATGTGGGGGACCAGTCCTAGCAGCTATGGGAGAGCTGGGGATGGTAGGAATGTGGGGACCAGTCCTCACAGCTG
TGGGGAAGCTGGGGATGGTAGGAATGTGGAGGACCAGTCCTAGCAGCTATGGGTGAGCTGGGGATGGTAGGAATGTGG
GGGACCAGTCCTAGCAGCTATGGGAGAGCTAGGGATGGTAGGAGTGTGGGGGACCAGTCCTAGGAGCTATGGGAGAGC
TGGGGATGGTAGGAATGTGGGGGACCAGTCCTAGCAGCTATGGGAGAGCTGGTAATGGTAGGAATGTGGGGGACCAGT
CCTAGCAGCTATGGGAGAGCTGGGGATGATAGGAATGTGGGGACCTGTCCTAGCAGCTATGGGAGAGCTGGGGATGG
TAGGAATGTGGGGGACCAGTCCTAGCAGCTATGGGAGAGCTGGGGATGGTGGAATGTGGGGGACCAGTCCTAGCAGC
TGTGGGGAGCTGGGGATGATAGGAATATGGGGGACCTGTCCTAGCAGCTATGGGAGAGCTGGGGATGGTAGGAATGT
GGAAGACCAGTCCTCACAGCTGTGGGGAAGCTGGGGATGGTAGGAATGTGGAGGATCAGTCCTAGCAGCTATGGGTGA
GCTGGGGATGGTAGGAATGTGGGGGACCAGTCCTAGCAGCTATGGGAGAGCTAGGGATGGTAGGAATGTGGAGGACCA
GTCCTAGCAGCTATGGGAGAGCTGGGGATGGTGGAATGTGGGGGACCAGTCCTAGCAGCTGTGGGGGAGCTGGGGAT
GATAGGAATATGGGGGACCTGTCCTAGCAGCTATGGGAGAGCTGGGGATGGTAGGAATGTGGAGGACCAGTCCTCACA
GCTGTGGGGAAGCTGGGGATGGTAGGAATGTGGAGGATCAGTCCTAGCAGCTATGGGTGAGCTGGGGATGGTAGGAAT
GTGGGGGACCAGTCCTAGCAGCTATGGGAGAGCTAGGGATGGTAGGAATGTGGAGGACCAGTCCTAGCAGCTATGGGA
GAGCTGGGGATGGTAGGAATGTGAGGGACCAGTCCTAGCAGCTATGGGAGAGCTGGGAATGGTAGGAATGTGGGGGAC
CAGTCCTAGCAGCTATGGGAGAGCTGGGGATGGTAGGAATGTGGAGGCCTGTCCTAGCAGCTATGGGAGAGTTGAGG
ATAGTAGGAATGTGGGGGACCAGACCTAGCAGCTATGGGAGAGCTGGGGATGGTAGTAGTATGGGGACCAGTCCTAG
CAGCTATGGGAGAGCTGGGAATGGTAGGAATGTGGAGGACCAGTCCTAGGAGCTATGGGAGAGCTGGGGATGGTAGGA
ATGTGGGGGACCAGTCCTAGCAGCTATGGGAGAGCTGGTAATGGTAGGAATGTGGGGGACCAGTCCTAGCAGCTATGG
```

Fig. 4 (Cont.)

```
GAGAGCTGGGGATGGTGGGAATGTGGGGGACCAGTCCTAGCAGCTGTGGGGGAGCTGGGGATGATAGGAATGTGGGGG
ACCAGTCCTAGCAGCTAAGGGAGAGCTGGGGATGGTGGGAATGTGGGGGACCAGTCCTCGCAGCTGTGGGGAGCTGGG
GCAGGTGGGAATGTGAGAAAACAATCCTTGAGCTATGGAGGAGCTGGGGATGGCAAGGATGAAAAGGGGCAAATCCTA
GCAGCTAGAGGGAAGCTGGGGCAGGTGAGGGCGGGTGTAAGGAACCAGACCTAGAAACTATGGGGGAAGTGGAGCAGG
TAAAAATGTGATAAACCAGTTATGCAGTCCAGAGGCTGGTAGGAGTGTAAGGGAGCAGACATAGTGGCTATGGGGAAC
TGGGATATATGGGAGTGTAAGGGACCAGATTCAGTAGCTATGGTGGAACTTGGGAGTGTAGATGAGCACGCTGAAAAG
CTATGGTGCAACTGCAACAGGTTGTCAGGGTGTAAAGAACCAGACCCAGCAGCCATGGGAAACCTGGGGAAAGTAGCG
ATGTGGGGGACCAGATTTGGCACCTATAAGGGAGCTGGGGCATGTGGACATATGAGGGGCCAGAAGCAGCAGTTATAG
GGAAACTTTGAAATATAGGCAAGTGTACCAAGAAGCCGTAGTGGAGCTGAAACAGATCCTAGGTCCTATGGAGGAGCT
GAAGAAGGTGGGAGTGTGAGGGACCAGGCCGAGCATCTGTGGAAGGGCTGAGGCAGGGCTCTGGGTCGGATGGGAGTG
GCACCCCAGAGAAGCCCTAGAAGCTCTGGCGATGGAGCTGAGCAGTTACAGTGGACTTGGGGCTGGTGGGATCGTAGG
AGACCATGTAGCTGCAGAAGAGCTGGAGAAAACAGGAGTATGAAAGACCCAGCCAAGTAGCCACTGAAGAGCTGGGGT
GTTATTGGGGTGTGTGGGGACACAGTCCCAGCAGGTTTATAGAGGTTGGAGCCTTGGCAGTATGTGCAGTACCAAACC
CAGCAGCTTGGTTCAGGGGCTTGAGTAGAGGCAGGCTAATGGGGTCCACGGTAACCCTAGGCACTTAGGGGACTGGAT
TGCGAATCTTCAGGGGAGCTGGAACAGGCAAAGTTAAAAGGAATCAAGCACCTGGAAGAAAGCAAGGAAAGATAGGAT
TGATGGGGATCCAAGAAACTCCCAGGAAGTAACCCCAGCAGGGACATCTGGGAGCTCAGTTCAGACACTGAATCAAAA
GCACAGAGGAAGGAGAGGTGGTAGGTTTCCAAGCTATCCTGTCCAGGCCAATGGAGCAGCCAGGAAGGAGGGAAGGAG
ACCAACAGGAATGGGGCAGCTGTAGCCAGCAGGGTGTGAGAGACAGGGATGAGGCTAGGTGGCTAGCAAGAAGGGCAA
CTTAGTGGGAGAGGGGTGAATTAACCACCCTGACCTCATGCTGACAGGGGCTGAGCAACAGACAAAAGAATAAGAAAG
CCAAGAGCTCATGGCTGGAACTATTCTGGCTGTCTGCTCTGACTGTGTTGAAGGGGCTAAGCACCTGTTAGCTAATGA
GGCTAAAACAGTTAAATGAGCAAAGTAGAGCAAAAAGCTCTCACAGCGGAGAGCATGGGAGAACGGGAGACTGTGAGA
TCCTCGGGGGGTCTAGGAGTTTATCTCAGAGTGAAGAACAGTGAAAAGCTCTGCTTGGGAGTTCTTTGGGGAATGGCG
ATCATCCTGGGAACTCCCTTATAGACCTCATGGCATGGAGGAGAGCAGGAGCTCAGGCAGACAGAGTAGCTGTGTGTG
AGCTGGATAAGAAAGAAAAGAGACAACAGGGAGAGAAGAGAAAAGGGATGGGAAAGGACTCAGGGCTCTACTGAATTC
AGGCAGAAGAGCTTGGCTTCAGGATGCTGGGGGCCAAGGAAGGTGTCTGATTGAGTAGGAACATAGTCAGGAAAAGAC
CCTGGTGCTCACATTCCCAGACAAATCTTACAGGTTAAAGTTCTAGTATCAGAACCCCTCGCTCAGATCCTAGGGGCT
TATGGGAACATAAGACAGGAAGTGAAACCTCTTAGGACAGCACGAAGTAGCCTGTGTTGGCCCACAGAAGAAGAGCAA
GGTAACTCTCAGAGTTTGAGCAGGGGATTGAGGAAGGTAGTGTACAGGAGAGGCAGAAAGACCAGAAAGGTCCCCAGA
GTAAGAATGAATCAAGAATTTATGTGTGGTTTGGTTCGATGAAGGCAAAGGCAGGGAAGATAGATGAGAAACTGATCC
TCTTTCACAACCAAGAACTCATTGTTCAGTGTGAGTTTTGATATATAGAAGGGGGGGAATGTGCTATTAAAAGTAAA
AAAGAATGAACCAGATTCAAAAGGGAAAGGGGACTAAATGTCTTCCTGAATAATGCAGCATACATTCCTATTTCAAGA
GCTACCGGCAAGAGAAAGGGACACTTCTGGGATGTGCCCAGTAACATTAGCACTGTCAGAGAGAACCCAGGGCAGTGC
GAAGGGTGAGGTGGGGAGGAAGGTGTCTGCACTCATCAGCGTCTCATCAGGGGGCACTGAGCTGTGTAGAACAAGAG
TGGCCAGCTAGGTCAAGACAGAAAGGATGCCCACACACAGAAGGTGTAGGGTAGAGGGTTGGTAGTAATCCCCAGGAA
GCAGGGAGCAAGGTCCAAGGAGAGCTAAAGTCACGGATAGAGACCTAGGGCACAGATTTAGGAGCCAGAGTTTGCGTA
ATGTTAGTAGATTCAGTAGGGGCTTCTGAAGGGCCTCATCACTGAAAGATCAAGGCTCCTAGGGCTGGAGAGTTGGCT
CAGTGGTTGCTGCTCTTCCAGAGGACCCAAGTCCAGTTCCCAACAACCACATGGCATCTTACAACTATCTGTAAGAAA
CTCCAGTTTCTCGAGATTCAATACCCTCTTCTAACAGCACAGGCATCAGGCACACACATAGTACACATAGTCATACAT
CTAAAATAAAATACCTAAAAAAAAATTAAGGTCAGAGTGCAGGGTCTAGAAGTGGAAGCTGCTGACACCACTTACCCC
AGAGCAACTTGAGAAGACACAGTCTTTTTAGAGCAAAGCTAAGGCCAGAGCCTCTCCAAATATCTGAGGCCACGCATG
TTGGAAAAGCTCACACTCCCTCCTCTCTTGCAGCCCAAACAACAGCCCCATCTGTCTATCCACTGGCTCCTGGATGTG
GTGATACAACCAGCTCCACGGTGACTCTGGGATGCCTGGTCAAGGGCTATTTCCCTGAGCCAGTCACCGTGACCTGGA
ACTCTGGAGCCCTGTCCAGCGATGTGCACACCTTTCCAGCTGTCCTGCAGTCTGGGCTCTACACTCTCACCAGCTCAG
TGACCTCCAGCACCTGGCCCAGCCAGACCGTCACCTGCAACGTAGCCCACCCGGCCAGCAGCACCAAGGTGGACAAGA
AAGTTGGTGAGAGGACAACCAGGGGACGAGGGGCTCACTAGACGTGAGGATAAGGCATTAGATTGCCTACACCAACCA
GGGTGGGCAGACATCACCAGGGAGGGGGCCTCAGCCCGGGAGACACTGTCTCTGCCTCCCTCCTGGAGGCCTCCTGGA
GGCCTCTGCCTATGCCCACCCACCCCCTAAGACATGATCCTCTGGTATAGATGTCTGTGTCATGCATAGGATCATACC
AGGGACAAACTTTCCTCTCTGGTTTGGTGCCTTCTCTCCTTGAAAACCCAGTAACATCCAGTCTTCTCTCTACAGAGC
GCAGAAATGGCGGCATTGGACACAAATGCCCTACATGCCCTACATGTCACAAATGCCCAGGTAAGTCACTAGACCTGG
ACCCCAGCTCCACAATGATGGCAAGAGCTGTAAGCATCCCAGCACTGCAGGATAAGCCACGTACTGACCCATTTCTAT
CTCTCCTCATCAGTTCCTGAACTCTTGGGTGGACCATCTGTCTTCATCTTCCCGCCAAAGCCCAAGGACATCCTCTTG
ATCTCCCAGAACGCCAAGGTCACGTGTGTGGTGGTGGATGTGAGCGAGGAGGAGCCGGACGTCCAGTTCAGCTGGTTT
GTGAACAACGTAGAAGTACACACAGCTCAGACACAACCCCGTGAGGAGCAGTACAACAGCACCTTCAGAGTGGTCAGT
GCCCTCCCCATCCAGCACCAGGACTGGATGAGCGGCAAGGAGTTCAAATGCAAGGTCAACAACAAAGCCCTCCCAAGC
CCCATCGAGAAAACCATCTCAAAACCCAAAGGTGAGAGCTGCAGGCCGACTGCCTGGGGACTGGGATAGGTATAAGAA
TGAATGCCCGTGTGGACGGCCATGACCTCTGTGTCTGTTTCTATCCCCACAGGGCTAGTCAGAAAACCACAGGTATAC
```

Fig. 4 (Cont.)

```
GTCATGGGTCCACCGACAGAGCAGTTGACTGAGCAAACGGTCAGTTTGACCTGCTTGACCTCAGGCTTCCTCCCTAAC
GACATCGGTGTGGAGTGGACCAGCAACGGGCATATAGAAAAGAACTACAAGAACACCGAGCCAGTGATGGACTCTGAC
GGTTCTTTCTTCATGTACAGCAAGCTCAATGTGGAAAGGAGCAGGTGGGATAGCAGAGCGCCCTTCGTCTGCTCCGTG
GTCCACGAGGGTCTGCACAATCACCACGTGGAGAAGAGCATCTCCCGGCCTCCGGGTAAATGAGCACGGCACCCAGAA
```
IgG2b
```
AGCTCTCAGGTCCTAAGGGACACTGACACCCATCTCCACCCTTCCCTTGTGTAAATAAAGCACCCAGCACTGCCCTGG
GACCCTGCAAAACTGTCCTGGTTCTTTCCGGGGTATAGAGCCTAGGTCACGGGCTTTAAGGTCTGGCTGGGGTTTAAG
GCCAGAGTTGTCTTCAGGAAGAGAGTGAGGTTTCCACACTGCCAGACTCAGAGCTCATGAGTCATCAGGGCCTGGAGT
GTTGGGGCTTAGCTTTAGGAAGTGCCTATTCCTTGACTTCAAACTAACCAGCAGCTGCCAGACGGAGAGATACACCTA
GGAAACCTCCAAGGGAAGAAACACACAAACTCCACCACCCTCTGCCTGTTCCTATCCCCATGTCCCACTCCTCTGCCT
ATGGGTTTCTCTGAGTCTATTGCACACATGGCCATGGGCGTGCCAGAGACCCTTGCTATCCCTACACTCAACTAAACC
CAGGCAGCTTTTCATGGGCTAGGTCTGCACACCCATACAGACTGCCCACTCATGCCTGTGCCACGTGAGACTGAGGCA
GATGGCTCTTGCCGCCCAAAGGGAGGGTCTGTTAGCCACATGCATACTGAATCCTGACCCATTCAAATCAGCCTGCCG
AACATCATCCAGTCCGTATAGCACATGTATCCACGTGCACATGTGCACACACATTTAACACACCAGGACTCCGCCTGT
GTGCCCTGCACAGCACCTACACCCAGCAGTGTATCAGGATACCCACAACCACCACTTGAGTGCCCACGTTTCTGCCAT
CACAACCAGACACACCTTTCCCCTTCTAAGGTCACTGCATTCTAGGCTCAGCACAAGTCCTCTGAAGCCAGATCCGTC
TCTGGTACCTCAGGGTCACGCTTCAACCCCACATGAATTATACAACCCAGAGCCATAATGGTCTGAGTCACTTCACAC
TCTGGAATTTTCTCAAGTTCAGGCAAGACCAGGCACAGGCTCCGCTGGTGATTGAGGGACAGGTAAAGGGTCAGACCA
GCTGTATAGCCACTGTCCACTGGGGTCACAGGCCCTGCTGACCCTTCACCTTCTCCTGTACTGCAAACAGAGAGGGCC
CTTGCACAATCCAGGCCGCCATGAGGTCCACTGTGTCTGGCAAACCCCAAGGCCTTATCCAACTCAGCCGGAGGGAAC
TTAGACTGATGTCCCAGAGGGAAAAGAAAGGAAAGTAGGGAGTAGAAAGTCTCCCAGGGAGACTCTGCTGGCCCAGCC
CAAATGGAGCTTTCTCCTCTGCCACATGGGGAATTGCTCCCAGCCCCCACTTTATTGGGACAAATTCTGACTGCCCT
CTCTGTCCAGGGCTAGAAGTGGATGATGATTGTGCTGAGGCTCAGGACGGGGAGCTGGACGGGCTCTGGACGACCATC
ACCATCTTCATCAGCCTCTTCCTGCTCAGTGTGTGCTACAGTGCCTCCATCACACTCTTCAAGGTCAGCCACACCATC
CCCCACCATCTGCTGTGATGCCTGTGTCAACCCTGCGATGTCCTCACACTCCTCTCCTGACGTAGTAGGATGTTCCCT
TGCTGTCCCCACTCTGCCCCACACACCATTCCCACCGTTCCTGAGCCGTCCCACATTGCTCTGTGTGGCTACCCATG
GCGTCCATACTGTCTGACATTCTATCTCTCTTGCTGTCCTATGTGATCTCCATACTGTCTTACGAAACCTCCTTGCAT
GCCACACTACCCTTCATGACGTCCCTGCTATCTACCATGCTACCCCTCTGGGTGTCCCCATCAGCCTCACCATGTATT
CTTTGAGCTATCCTCATACCATCTCAACCTCAACTCCCACGATGTCTCCACACCGGCTCCTAGTCTATGTCACCCTGA
CCCCTTGCCATCCCCAGTCTCCTGCCTGTATGAAAGGAACTGCAGGAGGGACGGGCCTCTGTCTTGCCCACAGGGCTG
AAGGGCCTAAGCATGGGTGTGTTCTCTGACTTACTCCCACCTCCCCACAGGTAAAGTGGATCTTCTCCTCAGTGGTGG
AGCTGAAGCAGACAATCTCCCCTGACTACAGAAACATGATTGGTCAAGGAGCCTAGGCCACTTCCTCTGGGATGAGCT
TCCTGGGCCCCGCACAACCCCATCCATCCTACTGTGCACCCTAATGTGGAGGCCACACTGCCGTCTGACAGTGCCACC
CTCTAGCCCTGTGACTCTGATCCAGAACTCTAGACTGTCTTCCTTTTGGAGGATCATGTGGACAATGAGCTATACCCC
AGACCCAAACAGCACCTCCACAGCAGTTGCCAGGAAACTAACTGGTTGGGACCAGAAGAACCATCTCTAGGATGTTTG
CCTCAGAGGAGCTGGGAGTCCACGGTGCCTGAGTCGAGCTCCATGGGAATCAGCCGTGTCTGAAATGGGTCTTCCCAG
AAAGAGCAATGTTTTCAGATCCTTGAAAGGAAACATCTGCTAGGAAGACCATGGTCGCCACAGCCCCAAAGAGTCACT
TCACTCTGGTAGCCTTTGAACCAGTTATATCTGGACACCTTCTTTCCCGGTACTTCTGTGAACCCTGGGCTGAGTAAG
GGGTTTATGTTTCTCAAACTGTTGGGATGAGCCTCCCCGAGATGAAGCTCCTTGTGCAGTCTTCTCTTCCCGAAACCC
ACTCAACATGCTGGACTCTTGGGTTCAGGATCCGATCCGAAGACACCATTGACGACGCAACCTCAAGACAAGGCCACT
GTCACCTCCATAGAGACTCCATCCACACTCTGCAGGGACAGGAGGACTGCTTTGTGTAACCTCCGCAAAGCCCTAGCA
GGGACAAGTGCACAGACCACTGAGTATTGGTGAGGTGACCAGGCAGGAAAACCTCCAGGAGAGGGCCCTGATGAGAAG
ATTCATATTGGGCTCAAAAAATGGGATGGGGGAGGGGGCGGGTGGGAAAGAACAGTGGGCAGGGTGTGAACAGATG
ATTAGAAGACAGTCACAGTGCCGCAGATCTGCCCTGCAGGCCTGCTTTCCAGACTGGACCACTTACAGCAGAAAACAA
CAGTTACAGTAAGCATCTAGGAGAGTGGACCTGGAATACCAGGGCTGCTGTGGCCAGTGGAGAGTAGCCCTGCATCTA
CTTCTCCATTACCTCTCATGGCCAATAAGAAGCCAGAGCATCCAGGCAGAAAGAAAGTGTGCGTTTCTGTGACTGG
TAGGAAATGCTTAGAGAACTTGGATCTTTAAAACAGCTTTTTCTAGACTGTGAATGTCTTTAAGCACTCTCTTTCCT
CTCCATTCCCTCCCTCTCTCTTTCTCTCTCTCTCTCTCTCTCTCTCTCTCTCTCTCTCTCTCTCTCTGTGTG
TGTGTGTGTGTGTGTGTGTGTGTGTGTGTGTGTGTGCACTCACACACACTGTTGTTTTGGCATTTTAAACAATAAA
ACATTCTTTTAACATTTTGTATCTCATGGTGTCCCTTCTTAATGGATTAG        GCACCAGAGTTGGTGAGATGT
CAACATGTAGAAGGTGCGGCTTGGGCAGCAATGTGGGCTGTCCGCATGGATACTTTGAGACAGGACTTTGAAGAGC
CTCAATTTGACCTATCAAATGCTGGTCACCCAGGTCTTTCAGCATCAGGGTCACTCCATATTGACTGAATAACCACAA
AAGCACAAGAACCCAGAGCCTAGAGTCCCCACTAGGCCCCACCTAGAGCACAGAGTCAAAGCTGGGACACTCAGAATC
AACCCAAAGTCCAGACCCTTGCTCCTCAGAAGGAATCCTGCCCCACTGCTTCCAGACAGACCTCTGGCCTAGGCAGAT
CGTCCTACTGCCAGATAAGGAGCCTCCCACAGGGCAGCAGCAGACTCAAGCTCTGAGGCCCCATCAACCCCAGCCCCA
GCCTGGCAGTCCTACTTTGTCTCTGGTCTCTTTAGTAAAGTTCTTTTCCATAACTCCTGAGAGTGCTTTGAGAAGGTA
```

Fig. 4 (Cont.)

```
TTTAAGGCTACCATTATGGTGATGACAGGTCCCAAGAACATGGACAAGGACCAGATGATAAGAGCCTGGGGATTAAAC
ATCCACCTCTATGCCATCCTCCTCAAACCACAGAGTTCTGCCCCAGTCTCCATCCGGTCCATCATTCCTGCTGACCAG
ACTCACCTCCCAGGGGAATTGAGGTGGAATCAGGGCTGGGCCCCGGGAACCTGGCTGCAGGTCACTCTTCAAGACCA
CAATCTGCCCACCCAGTAAGTGCAGACTGACAGGCCAGTCCCCTGACCCAAGCTGGGACACTAGAGGGACTAGGTAAC
AGCACGCAAGTGTACAAGAACCATCCAGAATGGGTTGTGCCATCCTCAAGACATGATCTCACATGACAAAAGACAGGC
TTCTCTCATATATAATGATTGCTCAGGGACTAAGAAGAAAGGCCTCTTCATGGGACGGAAAAACCAGCAGTCACTGTT
TTTTTCCTGAAGAAAATGCTTCAATGGTGAGAACACTTCTAGAAAGAAGGATGTTAGGGTGAGTGTGGCCCTGCTGGG
CCCTGGGTAAAGAAAGGCATGAGAACTACTTAGACCATTTTGAGGGTCAGTTGGCCAAACACTCTTGTCATCACAAGT
GACAGTCCCACAAAGAGGTCCACACTGGGGTGTCAAGCTCAGCACCAGGGGACTTTGGGGGAACTAAGATAGGGATAA
ACCAGCCGGGATCAGGCCATAGTCCACAGGCATCTGAGCCCTCTGCTGCTGAGTCCGGCTTCTACGGGCCTTGGAGTA
GGGCCCAGATGGCAAAGACACAGAAAGCTACCCCTCCTGGGTGCAGAAGACCCAGGACTGGGAGAATGACTGTTCTGA
TGAGAAAAGAGGCTCTGTTTAGGATGTGTCCCAAGCCATTAGTGTGGCCAGCTTACTAATGTGCATTCATGCTGCAAA
CCATTGCTCACAATCAAATGTATACCACGCACACAGTCACGTAGTTTGCGCAGACCCACTCATGTGGCACATGCCTGT
GGGCACATGGGACCACACATACACGTGATGCTTTAAAACACAGATCTGCACGGTCTTGTACTTAGACACACATTGTCT
CAGGAAGCCCAGGTGTGGACCACCCTGTCCTCCTGCCACATTCTCCTAAGCCATATCCCCTGCCAAGCTGAGGCCTAG
GTGCCTCTTCCTCAACCAGCTCCTAGACCAACATCCCTGAGGCATAGCTCAGTGTCTTCTTCTAATCACTATCCCTCC
AAGCCACGAGACCCCATAGACACTGGACACGGGCAGCAAGGGTTCAGCTCAAAGAACACGGTGTGGCAGGAACTCCTA
CCAAATCCCAACTAGAAGGAAGGAAAGTCCCACAGAGAGCTAGACTCACTCTAGACAACCCAGACAGTGACCCTGGCT
TCTACATACCATGAATGAATGACCTTCTGAGACTAAGAGGTCGCTTTCTTCTCTATTCCTACATTATCAGTCCACCAT
GGAGGGCTACATGGAAAACCCCAAAAGACATAACCACATTTTGGAACCCATAAATGTAGCCTCTTGGGAATAGTTCTT
CATCAATGTGACCAAGGTAACTATCTCAAGACGAGGTCATCAAGGACTAGCTAGTGGACTTTAACCTGGTGACAAGAG
TCATAAGAGACAGAAGCAGGACCTGGGGGGTAAACAGGGCCTGCATTCTCCAAAATCAACGTGTCAAAACAGAAATAT
GGCAGCAAAACAGAAGTACCGTGCCCAACACTGGTCAAGACCAATGGGGGAGGCTCATGAGGGGTTGCCTAACAAGAG
CAGGCACAAGTGCTTAGATAAAACCACAACCTACACTCGGCCACCGTAACCCTACATAGAAAATGTACCTATGGGACG
TCAGCTCAACGTCAGTCCCACCTCGTTGCTGTGCGCAGACAGCTGCAGCCTGAATAACCTGTCCAAGTGTGCATGTCA
CATCCTTGATGACACACTGTAACCAGTGATGCCATGTTAGCACGATGTCCTGTGAGGGTGTCTGCTGACTCGGGATGG
CAAACCCTAAGACCAAAAGGAGGTGCTTGGTTCACGAGAGCGGCCTCGTGGCTGGACACATGGCGTTAAATGAGCCTC
TGTGGACTAGGAAGCAGCTTTAACCAGAAAGACTATACCAGCACCCTGCTTCACGTTTCCACCTTTGAGCCTCTACTG
ACTAAGCCACTGGCAGCCACTCAGTCTGTGGTATTCTCTAACGGCAACAGAAATGACTAAGACAGGCAACCACAATGT
CCCCCACTGCTGATGGCTCCAGGGCATTCTTGGCCTGATGACAGGACCTCCAGAGCCTCCTTGAGACAGGCAGATCTC
TGGAGGGCAGGACCAAGCTTTCTCCTCTCTACCTCCCCAACATCTTTGACTAGCTTCACAGATAAAAGGCTAGGGGGA
CATCAGTTTATTCCACACTTTCTAAGTCTGATGCAGGAGCCCTTCCTCTGCGAAGTATCTATCCAAGAACCCAGAAAA
GGCTAACTTCCCCAACTCAACACTTAGCACCACTGACACACCTGACCATACCCACTGATTTACAACCTTTCTCCCAGA
CAGGGCCATTCCTGGGCAAAGACTGTGGTGTGAGGGCCCAGAGTCCTATTGTTGTATAAATGAGGCACAGTGGCAGAG
GCAAGCTACAAAGAGTGACATTGTGGAGAGAGGACACTGGGGACAGTCGGATGTGTAGAGGATCATATGAAGGGTGGA
GCCCTACCCTGACAATCTACAAAGAGTGACATTGTGGAGAGAGGACACTGGGGACAGTCGGATGTGTAGAGGATCATA
TGAAGGGTGGAGCCCTACCCTGACAATCTTCAAGAGGCTCCATAGGTCAAAGGCCCATCCTGAGAAAGCTGTGATAGG
AAATTGACTCAGGGCAGATGGGATCCAAATGAGGGTAGCACCTAACTGTGACCTACAGACCTCCATGTTGGTCCTCAA
GTTGGGGCACCCACTTTCTCATGGACGTAGCCATGGAGGTAGCCACAGCTCGTGAAAGCCATTCCAGACACTTGCCT
CACCCCGTTGTCAACCCTGTGACCTCAAAGCTCTTCTCTGAGGCCCCCCTCAGCTTAGGGACCCCTCTGGAGTAGCCC
TGTTACTTTGGCTCCTTGACAACAAGCTCTCAGGTCTCCCTTCTACCCCTAATTGTCCTCTCCCTCTCCATCTCTGCC
TTGGAGTCTCTGAGAAACTAGATGTTCATTTCATTCCCTCCTGCATCTCCTGCCCAACCTACCCCTGTGGCCATGCAT
GTGGAGTCCTGGCCCCATCCAGGCCCGTGTGGTCAGACACACCTGTCTCCACCACAGCCAGACCACAGGCCAGACATG
ACGTGGAGGTAAGCGGCCACAATGTGGAGGTGGAACAGGAAGTGGGTGAGGGACCCCATCCAGGGGCCAGACACACAG
TCGTGCAGCCCCTCACCGCTCAGTCTGACCCATCCACAGGCAACCACACACAGAGAAAACCAGTTTCCAGCCAAGGC
TTCACCCAGTCCTAAGCTCTCTCCGGTAGGGCAGACGGCCTTTAGCCATGAGAATGGACCTTCAGGGTGGGACCACCT
GGCCATGGGAGGCCTGGCTGTTCCCCTATGAATGACACTCAACAACCTTGGACAGGTGGGTCCCGGTACCATCTGGAC
TGCTCTGCTCCTTGGTGCACTGGGGAATCTCAACCAGGCCAGACCTGAGAACATAAGGCAGAGAAGCATTAGCAAGGA
GAAGGTGATTCGGAGAGCAAGAACCAGAGGAATACAGGACATGAACACAGGCACGAGGCGGGTCATGGTCTGAGCTG
CAGAGAAGAGAGAAAATGGATGAAACTCAGCTTCCTGGAAAGCAGCAACAAGAGACTCCCAGGCTAGACTGAGGCAA
GGATAAGGAGGCATCAACAAAGAATGGGGTGACTCGGGCTGCCATGGCTCAGCCGAGCTGGATTTAGCCAGGCTGAG
CTGAACTAAGCTTAGCTGAGGTGAATGGGACTGAGCTGAGCTGAGCTGGGACAAGGTAGGCCAAGTTGGGCTGACTGA
GCTAGTCTAGACTGGTCTGGGCTAGTCTGATCTGGACTGGTCTGAGCTGAACTGAGCTAAGTTGAGCTGGGATAAACT
GGGCTGAGGTGGGATAAGATGGCCTGACTTGGGTAACTAAGCCAGTCTAGAATTGGATAAACTGAACTAGACTGGTCC
AAACTGGACTAGACTGAGCCGGACTGAGTTAGAATGAGGTGGACTGGGCTAAACTGGGCTGAGCTGGGTTAAGCTAGG
GTGGACTAGAATGCTGATTTAAGATGGCCTGGGGTGGGAACGCTAGCTAAGCCAGACCAAGCTGGGCTAGGCTGGGTT
```

Fig. 4 (Cont.)

```
AAGTTGAGTTGAGCTACAGTAAACTAGCCTGGGCTGTGCTGACCTTACTACACCAGGCTGGGTTTGGTTGGCATGAAT
GGAGCTGATTTGAGCTGGGCTAGACCAGGTTAGTATGAGCTATGCTGTCCTGGTCTAAGTAGACTGGGTGAGGCTGAG
AAAATTCGAGATGGAAACTGGACTGAGATGGAAAAAGATAGGCTTAGTGTTGGCTTACTGAACCAGTCTAGAATGAGC
TGAACTGGACTTGGAATGGCCTGAACTGGGCTTAGCTTATCTAGCCTGGGCTTGGCTAGGCTGGCCTAACCTAGGCTG
AGTTGATCTGAACTGGTGTAGGCTGGGATAGGCTTGCTGAAATGGACTAGGTCAAGCTGGGCTGGAGTGGGGTTAGCT
AAAATAGGTGGACTAGGCTGAGATGAGTTAGGATGACCTGAGCTATATTTAGGGGATGGATGGGATGGGATGGGCTAT
CCCAAGCTAAGCTGGGCTAGAATGGGCTAGTGTAAGCTAAACTGGCTGGGTTGGAATGTGCTGGGCTGTGCTAAGCTA
GAATAAACTAGAGTGGACTGGCCAAAATCGGCTGGGACGGTCTGTACTGAACCAGGCTGGGCTGGGCTAACTGAGCTA
GACCGGTCTGAGGTGAGCTAATCTGGGATGGGGCGGACAGAGCTGGGATAGGCTAGATTAAGCTGGGATGAGCTAGGC
TAGGCTCACTGAGCTAGGCTGGAATAGACCGGTCTAAGATAGGCTGCCTGAGCTAAACATAGACTGAGATGAACTGTAA
TGAGCTGGGATGAGCTAAGCTAATCTGGGATGATCTGGGCTAGGCTGGAATGGACTGAGCCGAGCTGGTCTCAGCTGG
GCTGGGTTGTGCTGAATGGGGGTAAACCAGACTAGGCTACCCAGACTAAGCTGGGCTGTGCTGGGCCAAGCTGGGCTG
AGCTAGGGTGGGTTGGGCTCGATGGCTGGGCTAATCCAAGCTAGGCTGAGCTGAGCTGGACTGAGCTGGGCTGGACGG
AGCTAGGATGGGATTGACTGAGCTGAGCTGGACTGAAATGGGCTGGGCTGAGCTAGGCTGAGATTCGCTGAGCTGGGC
TGAGCTAGACTAGGCTGGACTGAGCTGAACTGAGCTGGACTGAGCTGGGCTGGGCTGAGCTAGGCTGAGATTCGCTGA
GCTGGGCTGAGCTGGGCTGAGCTGGGCTGAGCTGAGCTGAGCTGAACTGAGCTGAGCTGGGCTGAGNNNNNNNNNNNN
NNNNNNNNNNNNNNNNNNNNNNNNNNNNNNNNNNNNNNNNTGAGCTGGGCTGGTCTCAGCTGGGCTGGGTTGTGCT
GAATGGAGGTAAACCAGACTAGGCTACCCAAACTAAACTGGGCTACGCTAGGCTGGGCTGGACTGAGCTGAGCTAAGC
TGGACAGAGCTGGGCTGGGCTGGGCTGAGTTGAGCCAGGCTAACTTGAGCTGAGCTGAACTGAGCTGAGCTGGACTGA
GCTAGACTGAGCTGGGCTGAGCTGAGCTAGGCTGGGCTGAGCTGGGCTGAGCGGGCTGAGCTGAGCTAGGCTGGGCT
TGGCTGAGCTGAGCTGAGCTGGACTGAGCTGGGTTAGCTGAACNNNNNNNNNNNNNNNNNNNNNNNNNNNNNNNNNN
NNNNNNNNNNTGAGCTGGGCTGAGCTGGGCTGAGCTGAGCTAGGTTGAGCTTGGCTGAGCTGAGCTGGACTGAGCTGG
GCTGAGCTGGACTGAGCCGAGCTNNNNNNNNNNNNNNNNNNNNNNNNNNNNNNNNNNNNNNNNNNNNNNNNNNNNNN
NNTGAGCTGTGATGAGCTGAGCTGGGCTGGGCTAAGCTNNNNNNNNNNNNNNNNNNNNNNNNNNNNNNNNNNNNNNNN
NNNNNNNNNNNNNNNNNGAGCTGGGCTGAGCTAGACTAGGCCAGGCTGAGCTGGAATGAGCCGAGTTGAGCTGAGCT
GAGCTGAGATAAACTTAGTAAGGCTAGAATGAATTGAGCTGAGCTAGGCTGGGCCGACCTAAAGTTGCTCTGAGGTAG
GTTAGACATGGTTGTCTGAGCTGGGCTGAGTTAGGCTAGCTATACCGTCTGGGCTGACCTAATATGCCCATATTAGTT
GTAATGACGTGACCTAGGTTGACACGGGCTTGCTGATCTGGGCTGGACTGGGCCAAACTGGAGTTAGTCTAGCCTGGG
CTGACTTAGTGTAGCCTGGGCAGAGTTAGACTGGAATGGGCTACACTGAGCTGAACTAGGATGGGATGGGAAGGGATA
GGCTGAACTGACTGAGCTGGGTTCAGTTGGCCTTGCTGGGCTGAGCTGGGCTGGATAGTCTAGCTGGGCTGGCCAGAA
TGAGGCAGAGCTAGGCTGGAATTAGGCTAAACTTGGTTTGGCTGGTTAAGATGAGCTAACATAAATTAGGCTGGCTGA
ACTACACTGGACTGTAAGCTAGCCTGGGTGAGTTCGCATGGCTGGACGCCTTCACAGCTCTAGTCTGAGTTTTACTGG
TTTGTTCTCCTCAGTGCTGAGGTAATAGAAAGACTTTGGAGTAAATGTGAACCAACTCTTGTTTCATGGGTCCAGACT
GTGGCCTCAGTTTGTCTTATATGAACGGAGCCACGCCACTCCAGTGTCCAATTCTCATGCCCTCTTCTCCTTCCCTGAT
TACCTGGTGGAAACTCACATGTACCTGTAGATAGTGCCTACATGGACAGAACCACTGCTCAGATTTAGTCCTCTGGCC
TTTTGGTCCACTGCTTGCTGGGTGGATGGGCAGGTGGCTGGAGTGGTGGGTCTGAAGCCAGGACAAGGCAAGTATAAA
GTAAAAACACAACAAAATGGCCCCCACCCCCCAGTGTAACCTCCAAGCCAGCTGTTCCCCAACCATTCCTGCCCTGTG
CTGGCTGAGGTTGGCCGTCCCTGCTCAGGCCCACCAGTTCTGGACCTCCTAACCTGGGACTGAGAACACGGCTCTACC
CACTGCCCAAGCAGGAGTGGGGCTCAGAAATCTGGGGCGCTAGACTGCTCAGGAGCATAGCCATGTTTACAAAGACAC
TCACAGTGCGTACAAGCCCTGCTGGAGGCATCTAGCCAGATCCTTGAAAAAGACAACCTGCAGGTCACGTTCAAAATC
TATGCAGCCAGTCGGTCAGCTCCAACTGCGGGTACATGATGCAACCCCTATGTGATACTGGGCCTAGGTTCTCCGGTA
TAAAGAAGAAAAAGGCATGGTCCTTTCTCCAGAGATTGTCTCAAGATGGGCAGTGTGAGGACTACTATCTCACTCATG
TTTTATGTTCCAGAGTCCGCGAAAGATCCCACCATCTACCCACTGAGACCCCACCATCTCCGTCAAGCGACCCAGTG
ACAATCGGCTGCCTAATTCAGAATTACTTCCCATCCGGAACTATGAATGTGACCTGGGCAAGAGTGGAAAGGATATA
AGCGTCATAAACTTCCCACCTGCCCCAGCCTCTGGGCCATACACCATGTGCAGCCAGTTGACATTGCCAGCTGCAGAG
TGCCCAAAAGGAACATCTGTGAAATACTATGTTCAATATAACACAAGCCCCGTCAGAGAATTGAGTGTGGAATGCCCT
GGTAAAGAAGGTTGGGGGGTCTGGGGTGGGCTAAGTCCTACCTTAACCTGGTATCTGGACCCATATACCCTCTGAA
GCACACATCCCACTCAGAAACCTCCCATGGGGATGGGGGAGGGGGTGTGAACAGGCAGAGGACGAGGGGCCTCAG
AACATCCAGAAAAGGGGACAGCAAAGGAGAAAAGGAGACTATTCTGATTTGCTAAAACTTCTATGTTACAGGTCCAAA
ACCCTCCTTAGTCTGCCGCCCTCGCCTGTCACTGCAACGGCCAGCCCTTGAGGACCTGCTCCTGGGTTCAGAGGCCAG
CCTCACATGTACTCTGAGAGGCCTGAAAGAGCCTACGGGAGCCGTCTTCACCTGGCAGCCCACCACTGGGAAGGATGC
AGTGCAGAAGGAAGCTGTGCAGGACTCCTGTGGCTGCTACACTGTGTCCAGCGTCCTGCCTGGCTGTGCCGAGCGCTG
GAACAATGGAGAGACCTTCACATGCACAGCTACCCACCCTGAATTTGAGACCCCCTTAACCGGCGAAATTGCCAAAGT
CACAGGTGGGCCCAGATGCATACCTGGGACATTGTATGATGTTCCCTGCTTGCGTACCTGCTTTCTTCCTCTAATACA
GATGCTCAGCTGCTCAGGCCCTTGTGTCACAGAGGGAAACTGGAGCTATCCAAAGAACTGCCCAGAAGGGAAGGGCAG
AGAGGTCTCTGCTCTCCTTGTCTGAGCCATAACTCTTCTTTCTACCTTCCAGAAAACACCTTCCCGCCCCAGGTCCAC
```

Fig. 4 (Cont.)

```
CTGCTACCGCCGCCGTCGGAGGAGCTGGCCCTGAATGAGCTCGTGTCCCTGACATGCCTGGTGCGAGGATTCAACCCT
AAAGATGTGCTGGTGCGTTGGCTACAAGGGAATGAGGAGCTGCCCTCTGAAAGCTACCTAGTGTTTGAGCCCCTGAGG
GAGCCAGGCGAAGGAGCCATCACCTACCTGGTGACAAGCGTGCTGCGTGTGTCAGCTGAAACCTGGAAGCAGGGTGCC
CAGTACTCCTGCATGGTGGGCCACGAGGCCTTGCCCATGAGCTTCACCCAGAAGACCATCGACCGTCTGTCGGGTAAA
CCCACCAACGTCAACGTGTCTGTGATCATGTCAGAGGGAGATGGCATTTGCTACTGAGCCACCTTGCCTGCCCCTACT
```
IgA
```
CCTTAAATAAACTCTGTGCTCATCCAAAGTATCCCTGCACTTCCATCCAGTGCCTGTCCATCATCCTTAGGGTCTACA
AAACACTGGGAGGGGTCAGGGCCCAGGGAAGGAGGAACCCCCACCACCTGAGCTTGTAAGGCCTCAGAGACTCTGAAG
GACCTACATGCCTAGAGTATATGTGTATGCATGTATACGTATTAGTGAGTGCCTTTGCGTGTGTACCTGTGTGTAACA
AGAGAGGAGTGAGTTTGTGCGTGCCTACGGGTTTATATAGGTATGTATATGGGCATAAGTGCATACGCCTTTAAGTGT
GAGCATATCTGTGTCCCCGTGAGCACATGTGTGTCTGTGTATGCCTATGAGTGTGCACGTATCTGTGTATGCTCATGT
TGGTGGAAACATGTGTGCCTATAGTGTGTGTACCTGCCAGGTGGATGTGCAATGAAAGGGAGGTGAGAATGGGGGTGA
AGTCCGAGATGAGCAGATTCAGCCAAGACAGGCAAACCTCAGGGGAGAGTCCCAAGAGCAGTGGGTTGCTGCAGAGGT
ACTCTGAATGGTACTTCTGGATGGTGGTGTGGCTGTCTGAGTATAAGATTACAGCTTTTGTCCCAAACAAGAAAGGGA
TAGATGGAGCAAGAGAGTAGCAAGACCAAGGCTGGTACTGCCTGGGAGTCCCAATAGGAACGGTAGAGGAGTGAGGAG
ATGAATCCAAGGGGCACTGGGAAGAAGATGCCACCCACCCTCAGTGGGCCAGCCCTGAATGGAGGCGTGCATAGCCAC
TCAGGGTGACCACTGACTCATGAGAAAGAGACATAACATGGCACAGACAGCCCTCAGCAGCACCCTGCTCTGCATATA
TGCACATGGGCATACACCCTGGTCTGCATACAGATACATGGGCATACACGCACATACATTTGCACACTCACACAGACC
CGAACCCTGGAGGAGGACGAAGTTCACAGCCCACACGCAGCTTCTGGAAAGCAATGGGAGTCCCCTCCCAAGCCCAAC
CATGACAACTCATGGACAAGTCTATAAGCTCCTCCAGGTGGCCCCTTTCTAACCTAAGTCTCCCTTCCCATCCTGAGC
CCAAGTATAACAAACCAGAAACAGGGTATGTGGCAAGCTGGGAAAAGACAGGAGCAGGCCATAGAGACCACTCTCACA
CAGGCCTTGGCCTCCTCCATGGGCACCCCTAGAACACAAAGTTCTACAACCAGGTACACTTGGCACCCAGATGCCCAC
AAGAGGGCAGTGGGGCCCCTGCTCCTGTCTCACGGGCCTTCAGAACCTCTCCAGGGGCCTGGTTTCTAGCAACTTCCC
TCTGCTGTCAGAGCAAGGCCCATGCACACCCTGGATACCCTCCAGCTTGAAAGTCCACTTCCCGAGGATAGCAAAAG
CGACAGGCCAGCTTTGGAAACCTGACCCAGAAAAGCGCGATAGCCACCCATGGAACCCAAGGCCTGGTCCAAAACAGA
ATTCTAGTAAGGAGGAGCCAATAGGTGAAAGACTGAACACACACAGGGAGAGAAGACAGAGGAGCACGATAGTCGAGA
GAGGGGGGCTGGTGGGTGAGGCGATGAGTGAGTGACTGGAACAAGGTTGGGTGGATATGCAGATGAATGATGGGAATG
GTGGATGGACTGATGGATGGCTGCAGTGACAGAAATATGAGTGACTGAGTATCGGCACACAGTCCCTACCTCCACTTA
AAATCAAAGTTCTATGCGCGGAGACTCTGAGGGCAGTGGGGTTGTCTCTACCGGGAGACTTTAGTGTTGGTTAACCCC
CCCCCAAGTTCTTTATAATGCAACAGAATCCTCTGACCACATGTCCACCCCTTGGTATTCCAACCTCGGCCCAGAAAT
CACCTTGGCCTGTATCTGTTTGAGAGTGTCCGATCTTACCGAACCCTAGTACCCAGGCCAAGTTCAACCTAAGAACTG
GGGCTTTTGTGAGGTGTTGCTAAATGTCTAGAGAGGTCTGAGACAAGTGGCCTTGGGCTCAAACTCTTCTCAGAGCCT
CAAAGACAGAAACAACTCTCTTACCATGATAGTTCTCTAATTAAGATCCCCTGAGGGAAAGAGAGAGAGTCAGGTCTT
GGGGGGCATCTCAAGAACTTCAAGGATTCCAGCCCCTTACCTGGGACCCTGCCTTCTCATTATCCCAGAACAAGTCCC
TTCTCAGAGATAAGGAACCCCTGCCACCACCGTCCCCAAAGCCCAAGGGGGCATAGAAACAGAGGCCTTAAGCCTGAG
CCCCCATCCCCATGGGTTTGGATCTAGAAGGTCATCTATGTCTTACAGAATGCCAAGAGCCACCTTCCTACGTGATAC
TGGACCAGTCACAAGACATCCTGGAGGAAGAGACCCCGGGTGCCAGTCTGTGGCCCACCGCTGTGACCTTCCTCACCC
TCTTCCTACTGAGCTTGTTCTACAGCACAGCACTCACCGTCACAACTGTACGAGGCCCATTTGGCAGCAAAGAGGTCC
CCCAGTACTGACCAGGAGCCAGCCACAGGTGGCTGTCATGGAGACGGTGGGTACAGGGTGGGGCAGGGGCCTTGAG
GATTTACTCAGCCCCTCCACATGTGGCCTTGCAACCCTTCACAGACATCAAGGAAGTGGAAGGAAGTAGAAGGAAATT
ATGGCAGCACTTCCTGGGTTTAACCCAGTCTTCCAGAAGCCAGGCTGAGACCTCAGCAAAAGCAAAGACATAACCCAA
CTCCAGGATCCTCCCCTCTGGCTGACCACTTGTGTCTTTGCACGGATGAAGCTTGGAGAAAGTCC░░░░░CAAATCT
TCCAGAAGCCAGGCTGGGACCTCAGCAAAAGGGAAGACATAACCCAACTCCAGGATGCCCTGTGGCTGATCACTCTTG
TCTTGGCGGGATGAAGGTTGGAGAAAGGCCTCCACGTCTCAGAGCTAAGACCGACGTGACAACTTCCCAGCCCACTC
ACAGACTTTCCTGAGCAATAAATTGATACAAAACCACAAATTCCTACTCTCAAAAACAAACATTAACAAAGGATTGGG
GGAGGGGGTCAGGGGTAGTATGGTGGCGTTGGGCAGGGTAAACTCAGGGTACCCATTGTCTAATGTCTGAGACATAAC
TTGAACATATGTGTAGCTGCAGCCAAAGATGAACAAGTGATGGTATTTGTGTCCTCTTCAGACCCGATACCAGGTCAT
TAAGCTTGAGATCTGGACCTGATTTCTAAACATTTGGCCTCTGTGAGCACCCTTGGCAAATACTGAACAGCAAACCCT
GGTCCTGGCTGTGAACCTTGGTCCTGATCACTGAGCCCTATATTGGTAACTGAACCGTGATCCTGATCTCTGACCTCA
GTCATGGTCATGAGGCCCTGGTCCTGGCCACTCATTCTAATAACTGGTCCCTAGTCCTGAGCCCTGAACCTTGGTCCA
GGTCACTGAATCCTAGTCATGATCACTGGGTTTGATCCTCATTACTGAGCCTAGTCTTGATCACCGATGACTGGTTTT
GATCATAGCAATTAACCTGATCACTAGTCCCCGTTCCTCATCACTGGGCCATGATACTGGTCACTGGGTCCTGATCCT
GATCACTAAATCCTGTTTCTAAACAATGTGTAGTGGAATGTATAGTGAAGCCTTTGTGTCTGGCTCTGGGTGAAATGT
CTCAGCAGAGCCTTTGCTAGGTTTGGGTTAATCAGTTGGGGCTGAGAAATGTTTTTGAGGCTGTTTGAACTTCAAAAG
AAGAAATGTCTCCCTGGACAATCTGCACATTTGCAGCTGCGCAAACCTTCATCCTAAAACTTAACTCCTGGCAAACTT
AGAATTCTTACTTTTAATAATGGCTAACCATGGTTGAAAGGGACTGAGATGTCTGTGGGTGGATGGAACCTTTCCCAG
```

Fig. 4 (Cont.)

```
CTCCAAGTAACTCTGTATACTGTTTGAATAAAGTAACTGAAGTGAGCTAGCTGGGGTCAATCTTCTTTCCAAGGAGAA
TAAAGCCCTCCGCTCCTCCAGAAAATGAAGGCTTAGCTCCTTGGTTAGCTTCTCTCTCTACTGCGGCACCTACAACCA
ACTCAGCAGTCCTAGGTTCCTGTCACCAGATCCAGTCCTGATAGCTAAGTGTCAATCCTCGTCATTAAGGCCTGACCC
TTAGCAATATGCCTGGGGTCTGATAATCAGACTGACATTCTGATAACTGGACCCAGATTCTTATCACTGGGTCTTTGT
CCTGGTCATGGGCATTTGACCCTAGTCTACAGCACTGAGTTCTGGGCATGGACCCTGGGTCCCAGTTCTAGATACTGA
GTTCTGGTTCTAATAACTGGCTCCTGTACTGATCGATGGGTCCTGACCTAGTCATTGGGCCCTGATCCTCAACATTGA
CTTCAAAACCTGAACTCTAGCCCCATGCCTCATTCACATTAGGAGGATCCCTACAGGGGATTCCTGCAGAAGATTCCA
GAATCCCCACAACACTGTTCACACACTGGGCTGCAACTGGGACAGTGACCCCTTTGCTCATAGGACTTGCCCAGGCTC
AGATGCACTGAATGGAGACAAAGCAAGCCCAGGCCCTGGGAGATGGAGCCTCTGGCCTGGGGTCTACAGATGTGGGGT
CAGCATCATAGGGAGGTTTGCAGGGCAGGTGTGGGGCAGGGCAGAAGTGGTCATGCTTGTAGATACTATTTTTCTCTC
CTCTGGAGCCTCCTTTGTCTATCACCTGCTGTCCTGGGATCTCTATCTGGGGTCAACAATGTTTGCAGTACAGGTGTG
GGGGTAGGGCAGGGATGTTCACATTAGCAACTTGTTTTTCTCTCTTCTGAAGTCTCTGTTGTCTATCACCTGCTGAAA
CATTCAAAGCAGCTCTGAGCTGAGGGCAGCTGAGTCATCCTGAGCCTGTCTCAGCACAGGTGCCCCAAACCAGAGCTA
CTGTTCTGAGAATCACACCACACTGGACCAGGCCAGGTGGGCCTGGGGCCTGGATGAGGGTGGGAGCCAGGGGAGCC
CTGCCAGGGGCTGAGGAGGCCCCAACCCCCATCACCCAAGGCCATCCACACTCGTGCCTTAATGAGGCCATGTTCTGT
CCCAATGAGAACAAGTCCAATTAAGATTAAGTATGGTCTTCCCAGGGTCATCCAGAGTCAAGGGGTGTCAGCCAGGGA
CAACCCAGACCAGCCTGAGGTCAGCCAGCATCACCCAAGGCCACACAGCTATTTTGGCAGAGGACTAGAATAGTCAGC
TCATCGAGGCCCTGGAGATGCAGAATGGAGAGTTTATCCCTGCCAGACAGGGTTCCTCGGATAGGCAGGTCCCTCACC
ACACATGACCTCCCTGAATATTTCCCAGAGTCCAGTTGGTTCTAGACTATCACAATAGTCTTCTGTATTCCTGATAAG
CATGCAGAAAGCTAACAGGATGACAAGAAATTTTATGCAGAAAACAGAAGCATCTACAGGATAGAACAGAGGAGAATA
GATACTGGAAGTCTGCTGGAGACCCCAGTGGAGTCTCTTTGTAGAGTCAAGCCGTAAGATCAAACCTGCACTGAGCCT
CAAGATTGAGTCAAGTACAGAGGCAACCTTCAGGACCCTAAAGACCTTACAGGCAATGGACAGGATGGAGTCCAGGCA
GACAAGTAAACGGGCAGTCATATGTAACATAATGAACCATGTCAACAGAGGGTACTGAGCCAAGGAAGGCTCTGGGAC
ACTTGTGGATAATCTGCCACTGGATCTCTTGATGTATATACCAGGTGATCAGATGACAGTTCAGTGGCGCCATCGCCG
TTACAGTGTTAGGTGTTGTCCTCGTCATGGGTTCACGTGAGAATGTGACACCTTTTAGTTGGATGTGTACAGTAAGC
TCTCAGGCCTGGTGTTCCTGGTATGATTTTAATGATCCATGTGTTCCTATATCTTTAATAAGTTTATAGGGTGACATT
AAGCTTGGGGATAAGTTGTTTATCAGGCTGTGCCTTTAGAAGTTGATGTGCAGGGATTGTTGTTTACACCAAGATGCC
CAGTCTTCCTCCAGCTTCCAAACGGAGTCAAAGGCCATTTGAAAATGTGAAACCTCTCAGGGCAAGGTACAATCTTTT
TTTTTTTTAAAGCCACTACCTCACACAACATGGAGTAATTTAAAGCAGGGCACAGCTTGATCGAAACACACACACACA
CACACGCATACACACAATGTAAGATACCGAGAAGGGGATCAAGGGACACAGAAGTAGAGAGAGAATGAGACAGTTCAG
GGATGTAGAGATGAGAGGTAACTAGAGGAAAGGAAAAACAAGGACTGGAGGGTAAAGAGCCAGGGACAGAAAGATC
CATGCAAGCAAGACAGACAGACACAAGGAAGGGAAAGGTGGGAAGAGACAGACAGACAAGGTGCAGCAATGTAGCCCA
CCTGAGACTCCCATGAAAGTCTGGCACCCACTCTCAGATGAAAGCCAAGTACCTACAGACACGTACCCACAGCACCCA
CACAGAGCACCTGCCTGCCTAACTCAAGCCCACCTACCCATCGCCTCTCCTCCAGGCCTCTGTCCTCAGGAAGCACAC
TGAGGGTAACTCAGTCTGGACACTTCTAACTATGGCTTAGTGAACAGCCTGAGAGGCTCTGGATCCACAGGTCACTAC
CACTTGCTGGCCCTGTGCTCCATGCCATGCTTCAGGGGGGATTCACTGAATGCATGAACCATAGTCTGGGGTCAACA
TGTACTAAGGGATAGGATCCTATCAGGATTTGTCCAAATAAGGTCCAAACAAAGTGAAGAAGGTGATAGGCGAGAACA
GCTGGCAGCTGAGAGAACGCTGGCCAGTTCTTAGGCCAGAGCTTAGGGACAATTTCCAGACCTAGCCTTTCATCTCAA
CTCTAGGTCATGGGTAACTTCCCAGATCTCTATTTTGTTCCTGGTAACTATGCATGCTGGTACAAGTCTAAGAACCTC
GGTGAGACACAGAACCAGTAAGATGAAAGCATCCGTGGATAAGGAAGAAAGGAGGAGAGTAGAAGGGACAGGACCCTG
GACACATGAGATTCCCACACCCAGGAACTGCTCATCCAGCCCGAGAAACGGTATACCCCTAGCACACAGAAAGAAAAC
AGTACCACAGGTCTAAAAGAGTAGAGTCAGTGGGAAGGGGTACTACTAGGGCGCCTCCTGCCTGGTCCAGGAGCAGAG
GCTGGGAAGGGGCACTAAACAGGGGGGAGCATGGAGACAGGGAGATGAAGGAGCCTTTGGGACTGCATGGTGGGAACT
AGACTGTTCTCTGAATGAGCCTGTGTGTGTGGCAGCTGCCTGAGAGGGAAGACACCCAGAGGCCAGGCAGAGGAAAAG
AGTAATCAGGGCTGAGGGGACTGGGGTGGGGGTCTGAGGAAGTCAAGGTAGCTATCGCCCATTTATCAGGGCCATGAC
ATGCACTTCATGGGCACATATCTAAAACCAGACCTGGCCCTCACCTACACTCAGACAATGTCCCTTTTGTGGATTTAG
GGATTTCAGTACTTCATCCCATGGCCTCTCAAACTGGAAGATCCATCTAAAAGGCTGATGTTGTGGTATCAGGGCCCA
GGACTAGAGAATGGGACACTGAGTGGCAGAGGTGCAGAGGACACATACACTCACTCAGATGAAAGCAATGCACAAGAA
GACAGAGCCATGTATGAACACTCCTCAGACTCAGACCCACAGCACTCACACCCAGCTCCCACAGACACACAGCCC
CTGCCTGCCTGTTCCAAAAATCAAACCCATCTACCCACTCCCTCTCCTGCAGGCCTTTGTCCTCAGAGTGGCACACTG
AAGGTAGCTCAGCCTGAACACTTCCCATGGGACCTGGTGAACAGCAGGAGCCTCTGGTCCACACTCCCCACCTCTTGT
TAGCCTTGTAGTCTATGTGATGCTGTTGAGAACAGGGTACATGGCCTCTGCCTGGTACAGTCTGGGGTGCAGGCTTCA
GGTGAGGCCCAAGTGTGAAGAGTGCAGAAGACAGTGGGCAGAGCTGAGAGACTGCTAGCCAGTTTTGTTCAAAGGACT
GTGATGGCTGCTCCAGGCTACTGAACATTCCAGGACTGCTTCCTACCCTCCTCAAAGATGCTGGAACACAACCAATCC
TCAACACAATCCAATGTAGTTGCCTGTAGCAGGGCATGCCTCTGTACAGCAGGGAGTCACACAGAGCCACATGAGACT
CTAGACCTGGGGACTGCAGAGGGGAAGGCATGTCCAAGACGGCCTCCTCCTTGTTACCCTAGGTTTTCAGGCCTCAGG
```

Fig. 4 (Cont.)

```
ATAACCACTGAACAACATATGCTGAGTCCTGTTCCCCAGGATGCTGATGGACACCAGGTCACAGGGCTAGAGGCCAGG
AGGGCTAGAGCCTGTGGGCAGGGGGGCTATATTCATTCTTCCTGTGCTTGCCCAGGAGCAGGTGCTGGGCAGGGGCAC
AGGACAGGGTGAGGCAGGGAGACAGGGGCATGAAGGGGCCTCTGGGACCACAAGGTGGGAACTAGGCTGTGCCTGACT
GAGCCTGTGTGTGTGACAGCTGATTCATGGGGAAGACACCCAGAGACCAGGCAGAGGAAAAGAGTAATCAGGGCTGAG
GTGACTGGGGGTTGGGAGGTCTGAGGAGGTAGAGGCAGCTATGTCCCATTTGTCAGGGTATGGGGACATGTACTTCAT
AGACACAGATCTAAGAACCAGGCGTGGTTCCCACCTACCCCCAGACAGTGTCCCTCATATGGGCTTAGGGATTTCAGT
ACTTCATCCCACGGCCTCACACCTTGGAAGATCCACCTCAAAGGCTGATGTTGTGGTGTGGGGGTCCAGGACTGGGGC
CAGGGACACTGGTTGGCAGAGGTGCCCAGGACATAGAGTGCTCAGAGTGTAGTTGGGGACATGCTGAGCACTGTTCCT
CTGTGAGGGGACAGGCTGAGACAGGGACTGAAGTCCATCCATAGGCTCAGCACATACCAGGCTCTGGATGGGAACACT
GAGCTCTGCCACCCTCCAACATCTGGCACAGCAGCCTCCTGTGCCAGGGAAGCTAGTCAGCAGGGACAGAGTTCCTGT
CCGGGCTGGATGGAGTCTTCTCTGCTAGCATCCAAAATAAGTGCATCTTCAGCAATAAGGTCCAGTCATGGTGGACGG
CCAGGAACAAAGGCAGTAAACAGCCTGGTTTGTGTTTGGTTATCTACAGTCTCTCTCACTAAAGCATCAAGACTTCTT
TTAATAAATTTAGAAGTTGTTTTCTTTTGAAACACGGTCTCTCTATGTAGTCCTGGGGGTCCTGGAACTCCCTGTGTA
GAAGACCAGACTGTCTTCAAACTTAAGGAGATCCTCCTGTCTCTGCTTCCTGAATGCTGGGATTAAAAGCATGTGCCA
CCACACCCAACCTAACCCTTTCCTCTGAGAGCAACATGCATACAATTTCCCCTCTTATTTCCCCAGATTTTCAATCCT
TTTATCCACACTTAAATCTTTAATGCTAAAATCTCCCTCCCTCCATTTCCAAGCTGCATGTGTTCTACTATTCCCTCA
AATTATTTTTCCTTGTGTGCAGGTTTTAGATTTGAATGCAGGAAGCCTTCACTCTGGCAAAGCCTCCCCCAACCCAGC
CTTTCCCATTTCCACACCTCCTAACACGTGATTTAGCCCACATCCCCTCATGTGTATGGTGTTTCCCTTCAGTCTGAG
GTATTACCCCCAGTGTCCCCTTACAGCTGCCTATGGTCACAAATACCTTTCATCTGTTTTTGCTGTGGAAAGCGTTTA
TTTCCCCTTGAATTTTAATAGCTTTCTGGGTATACTACCCTGGGTTGAGAGTTTAGATTTTTCAGATCTTGGAATATG
TCTTTCTAGACATCTAGCCTTAAATGTTTCTACTGGGGGCTACAGAAATGGCTTGGTGGTTGACAACACATGATGTTC
TTGCAGAGGAGTGGGTTTTGATTCCTAGTACCCCATATCAGCTAAGAGCTATGGAAGACACAAATGGAAGAGGGGACT
CTGAGATTCTGAGAAAAGCCTCATGGTTAAGGGTACACTGAGATACTGAGAGAGAAAGACAGAGACACTGAGAAAGAC
AGAAGCACAGACCACTAAAAGAGACAGGGAAACAGAGAGAGACAGTGATGAGATGCAGGGACAGAGCAACCCAGAGAG
ACAGACAGAGACATAGACACTGATAGAGACACAAAGAAGAGAGGGGTCGTGGAAGTTTTGAGAGAAACTGGTAGGAGG
TGAGAGAGACACAGAGCCAATACAGACACAGAAAGACAGAGACTCCAGAGAGACAGAGACTGAGAGAGACAGAGACTG
GGAGAGACAAAGATACTGAGACAGTCAGAGACACCAATGGGTGCTTTTCCAGGGGATCCAGATTCAATTCCCAGCACC
CACATGGCAGCTCTCTACTGTAATCCCAGTTCCAGGGTGCCCTGAAAAATCCTTCATGCATGTGAAGCTTAGAAGCTC
ACACACAAACACACAGACAGACAGACAGACAGACAGACAGACAGACACACACACACACACACTCAAATGAAGAGTG
TGGTTCTCTTTCTCTCTCTCCGATGAAAGCCATGCACCAGAAGACAGAGCCATGTGTGAACACTCCTCAGACTCAGAC
CCACAGCACTCACACCCAGCTCCCCACAGACACACACAGCCCTGCCTGCCTGCCTGTTCCAAAACTCAAACCCATCTA
CCCACTCCCTCTCCTGCAGGCCTTTGTCCTCAGAGTGGCACACTGAAGGTAGCTCAGCCTGGACACTTCCCATGGGAC
CTGGTGAACAGCAGGAGCCTCTGGTCCACACTCCCCACCTCTTGTTAGCCTTGTAGTCTATGTGATGCTGTTGAGAAC
AGGGTACATGGCCTCTGCCTGGTACAGTCTGGGGTGCAGGCTTCAGGGGAGGCCCAAGTGTGAAGAGTTCAGAAGACA
GTAGGCAGATCTGAGAGACTGCTAACCAATTTTGTTCAAAGGACAGTGATGGCTGCTCCAGGCTACTGAACATCCCAG
GTCTGCTTCCTACCCTCCTCCAAGCTGTTGGAGCACAACCAACCATCTTTGTAATTGCCCAGTTGTTTGTTATTGCCT
ATAGCAGGGCATGCCTCTGCACACCAGGGAGTCACACAGAGCCACATGAGACTCTAGACCTGGGGACTGCAGAGGGAA
AGGCATGTCCAAGAGGGCCTCCTCCTTGGGACACTGGGATTCCAGGTCTCAGGATAACCACTGAACAACATCTGCTGA
GTCCTGTTCCCCAGGATCCTGATGGACCCCAGGAGGTCACAGAGCTAGAGGCCAGGAGGGCTAGAGCCTTTGGGAAGG
GGGAATGTTAGGGTTTCTCCCATCCTGGTCCAGGAGCTGCTCACCTGACAGTGATACAGGACAGGGTAAGGCAGAGAC
AGGGGGATGAAGGAAACTTTGGGAGCACATGGTGGGAGTGTAGGTTGTGCTTTTGCTTAGCCTGTGTATATAGCAGCT
GCATCATTGGGAAGACACTCAGAGGCCCGACAGAGGAAGAGTAATCAAGGCTGAGGGGACAGCAGTGTCTAAGGAAGT
GGAGGCAGCTATGGTCCATTTGTCATAGTATTGGGACATGTACTTCATGAACACTGATCTATGGACCAAGCCTGGTTG
TCATCTGCCCTCAGTCAGTGTCCCTCATGTGGGTTTAGGAATTTCAGTACTTCATCCCAAAAGCCAGTCACATTGGAA
CATAAATGAAATGCTGATGCTGTGGTGCTGGGGCCCAGGAGTGCGGGGTTAGTATACTGGGTGACAGAGGGTGTCCAG
TAAATAGATTGCTTAGAGTGTAGGTGGGGACAAGCTGTGGCGTTTCCTCCATGAGGGGAAAGACTGGTACAGGTTTT
GACATCTCTTTCGTATCCATAGGCCCTGCCATACTGCCCTTGTCCATGGTCCCTGTGGGGTCACATACTTAGTGTCAA
GTAAACCATACCACAAACTGGAAGGGTCTACACTATCCTTGTAGGTTCTACACTCTCCATGACTTCTCCCAACTCACA
CAGACTGTTCCAATACACTACTCTCTTCAGTGGGCAATCATGCCATGAACAGAGAGTGGAGGGTTATGGTTGCCCTAT
ATTCTGACACATCCAACAGTCTTGTGCATTTGACTCTCATGTGTACAAGCGTGCTCAGGCCTGCTGTAGTCCCCTCGA
GACAGTGATGCCTTCCTTGAGAGCCGATTCTCACTGTCAGCATCTCCTCAGACCAAAGCCCTATAGATCCAGCCCCTT
TGAGGAGCTAATGTAGTCAGTCACAGGGCTTGATGTTGGTGGCTATAGCTGCTGTCCCATGGCTGCCAGAGATGCTT
GACCACCATAATCCCAGACTTGAGCATAGGAATAACCTGGAATCAACAGCATCCAGACACTGTAGGGACTGGCCAGAG
ATGTGCATAGACCCTATGTCATGTGACCAAGACCTCTTTTTCTAGTATCTTATTTCATGAAAGTCTACAAAATACGAT
CTTCTATTCCTTTTATTCCTCTTTGCCTGCTAACATGGAGCCTTCTAGGAAGAGGGTCCCCTCTCTGTCTACTGACTG
TGAAGATAGATCCTGTAGGTGTGATCACAGAGTAATGTTTCATTTCTTGGCCAGCCTCAAGCCAGGGGACTCAGGGAG
```

Fig. 4 (Cont.)

```
AGAGACAGGAGAAGGAGAGATGGGGAGAGAGACAGAAAGACAGAAAAACAAAGCAAGGGAGAGACAGAAGCAGGCAGA
CCTGGAGACTGGGTGCTTAGGAAAGAGATAAATGTGGATACAGGGAGTGAAAGATAGGGAATTGAAGACAGAGGTGGA
GATAAAGACCAGAATATGGGAGTCAGAGACAGACAAGAGACATAGAGATCAATATAGGCAAACAGAGACTGAGAAAGA
CAGTGATGAGACAGAGAGACATGGAGACAGACAAGGAGACAGACATGGAGACAGACAAGGAGACAGAGATAGAAATAG
GGAGAGAAAATAATACATAATTAGTGGTTGATTAAGGAAGAGATAATGAATGGCAAGAAGGGACAGAGGCAGGGAGAG
ACATATACAGGTAGAGAAAAAGATGAAGACAGACAGAGAGACTGAAAGAGGGAGAAAGATACAGAGAGAAGAGAGA
CTATGAAACAGGCAGAGATATAAAGACAGTGAGAGAAAAACAGAGAGACAGAGATGGAAGAGAGACAGAGAGACAGGG
AGATAGAGAAATGGGAAGACAGGAGGACCAAGAGAAGAGACACACGGCGAGGCAAGATGTAGTAGAGAGACCTCTGAT
GGAATCGGCATAGGTGGAGGCAAACATAGATAGACCCTCTCCAACTGCAGTTGACAGACTGAGCAGAGAGAATACCAT
TCAGAGAGAAACAGAGGCTAAGGCTAGGAAAGGCAAGAGTAGCCAGAGGAGACAGAGTTGAGCCTGTGGGACAGGACC
AGACGCCATCTTGGAAGAGGCAGTGACAAGCCAGGGAGGTGACAGGCTGGCACAGTTTCTATCCCACAGTCCACAGGC
TGGTGTCACAGGCCTGTCTCCTCGTGGCCACAGTCTATCCCTGCCTGCCAAGCCTGTCTGTGAGGGATGGGGGGGGG
GGGGGCTGGGCTGAGGCAGGCCAGGACTTTTCCAGTGGAGTGGCCAGGCACTGGGCTGAGGGCATGATCCCTGCCCAC
CATCCCAGTGGGTCTGGGTAATGGATGGCCTTGATTATTTTCCTTCGTGTTTAGGGTGGAACCTGCTTAGAGGCAGCT
AGGGCTCTCCATGATGGCCTAGCCTGTGGTGAGTTAATGAACCCCTAAGGGTAGTTCTTCCACATGGGCTAGGGTTAC
AATCTGGGGGTTGGGGGCTCAGATATCAGTACCAGAAACAAGGCTTACTCCCAACATGTCACACTCGCACACACACAG
CTGCCGAGTTACTCATTCTGTGCAGAGTTGGCTCACAAGGGCACATGCAAAAGGATGTTTGTTTCATACAGAAAAACA
TGTTTCTCACTTTCTGAGGTTGTTTCCAGAAATAGCATCAGTGACTCCCCACCTGCAGCTGCAGGTTCACCCCAACC
TGGCCAGGCTGACCAGCCTTGGGGATGGGGGACTCCCAGCATAGGCCACTGGGACTGGGGGTCCATGACCCCTATTGA
TGACGTTGAATTCAGTGTTTCCCAGTTATCACCACTGCTGGAATCTGACCCACCAAGAGGACATGACAGGAGATGGGC
AAGGATGGGTGGCTCAACACCCCAGGGAAGTGAGAGAGGCAGGAAGGCTGTAGGTGTGCTCCAGATCCTGGGTCTACC
CAGAACCATGGGAATGGTGGGCAGTGATCATGCCCTCAGCCCAGTCCCTGGCCACTCCACTGGAAAAGTCTTGGCCTG
CCTCAGCCCAGACCCCCTCCCCCACCCCTTCTCAGACAGACTTGGCAGACAGGGAGCTAGCCTGTGGCCACATGGAGA
CAGGCCTGTGACTCCAACCTGTGGACTGTGGGATAGAAACTGTACCAGCCTGTCACCTCCCTGCTTGTCACTGGCTCT
TTCAAGATGGTGTCTGACCCTGGCTCCATCTCTGGCCAACCCTGCCTTTCCCAGCCTTAGCCTCTGCCTCTCTCTC
TCTCTCAGTGTGATTCTTGCTCAGTCTGTCCCTCAGTTACTGTCTCCGTCTCTAACAAAACATAAGAGTTGTCTCT
ATTAACACCTTGTCTCTCCTCTTTCTTCTTCTCCTTCTCCTTCTCCTTCTCCTTCCTCTCTCTCTCTCTCTCTCTC
TCTCTCTCTCTCTCTCTCTCTCTCTCTCTCTCTCTCTCTCTCATCTCTGCTTGTGCCCCCTTTCTCTAGGTGCACA
TCTCCTACCTCTGTCTGTCTATCTGTGTCTCTTCCTTCTGTCATCTCCTCTCTATCATTCTTTCAGTCTTTCTCTATG
TCTCTTTTCTGTTGACGTCTGTCTTTGTGTGTCTCTCTCCATCCCATTCCTTTTATGACTCTGGCTCCCCTTATCT
CTCTGTCTGTATTTCTGCCCCACTTCTCTGTCTTCCTATCTTTTTGTCTTTTCTCTGTTTCTGATTTTTCTCTCCATG
TCTTTCTCTCCACTTTTCTCTCTCCCTTTCTGAGTCTTCCTGCATCTGTCTCATTGCTTCTCCATCTCGCTCTCTCTT
TCTCTGTTTTCTGTCTCTGTTCTTGTATCTCTGTGTGCCTCTCCATGTCTCTCTGCTGTCTCTTTTTCTCCATACAGC
AATTTACTAAAAGAACAAACATCAAGGCAGGAAAGTATATATATTTCAAATAAAAGTTCTTCAAATTGCTATGTCCTA
TACTCCAAGAAGCATTTCCAAAGTATAGATTAATTTAACCCTTTTAAATGAAAAGATACATTTTTAACTTCTAAAGTG
TCTCCACAAAGAAATGAATGTTTTTAATTAAGAAATGTTGTAATTTAGTGTTGGGCTCCTGTCTTATAATGTACACTT
CCTTATAAATCTAGCCATGTGGCTTATATCCATTTGGTATGCTCGGAGCTTTATGTAATAAACGTCTTCCCGATAGGT
GCAAGGATTGGTGTTTTGTACTGCTTACTACATACATGCTTTTAATCATTCCAGGACATACCGTCCCTCTGCTGCTGC
TTCTCACCGTCTTTGCCTTTCTCTCACCCTGTCCATCTTTCTCTCTCCCCATCTCTCTGTTTCTGTCCCTTCCTGTTC
CAGTCTCTCTCCAATCTCCCTGTGTTTCTCTCTCTCTCTCTCCTGATGTCTCTTTCTCTGTGGGCTTGTCTCCCCA
TCTGTCCTCTTCATTTCTGTATTTCTCCTTATCTTTCTATCTCTGTCCATGACTCTGTCTCTTTCTGCCTCGTTCATC
CCCTGCCCCCTGAAGGCACAATGACACTTTTATCAGGGTTTAATAGGAAAGTTTCAGGGCAGGAAAGTTGTAAGACT
CAAGCAGCTGCCCCGAGGAGGCCAGTGGGGGAGATTGGTAAAAAGCCATGACATCTAATCTGACATGGAGGTCAGGCA
CATGTCCCACAAGCAGCCACATGGCGAGAAGGGGGCAGTTAGAGAACAAGTAAGAAAGCCCAGCATGTTGGGGAGGAA
GCCAAGGTGTTAAGGAAAACTTGCTCAGAGGGAGACAGAAAGAAGGAAGCTACAATTCTGTGAATTCAGAAAGGAAGC
TGACTTACAGCCCCACATGGCTATAGCCCCTAAGCTTCTGGCCCTTCCCCTTCTGTCTCTTCCTGTTCTCTGTCACCC
CTGTTTCTCCCTATTCTCTGTCACACCTGTCTCTGTGCTCCCATTAATCTCTCTCTGTCTCTACACATCTCCACCTCT
GCCTCCTTCATCTCTGTCTTTTCCGGAACCCTGTCTGTCTCTGTCAGGCTTCTCCTTGTCTCCCCCTGCAGACTTGCA
GTTTCTCCCTTTGTCTTCCTCTGTCTTACCTTTATTATGTCTCCCCGTCTTTCCTACCTTCCTGACTTTCTGTCTCTT
ACCCTGAGTCCCCTGGCCTGAAACTGGCCAAGAAGGAAAACATCAGTCTGTGATCACTCCTACAGGGTCTGTCTCCAT
AGCCAGCAGAGAGGGGACCCTCTTTCTAGAAGGTTCCCTGTTCGCAGGCAATGAAGAATAAAAGGAATAGAAGATCCC
GTTGCATTAAGGTTTCATGAGATAACATACTAGGAAAAGAGACCTAGGTCTACGTAGAAGTCTGGTCAGTCCCTGAAG
TGTCTAGACGCACTTGATCCCTAGGCCATCACTATGTCTGAGGTCATGGTGGTCAAGCATCTCTGGCAGTCACAGTGA
AAGCAGCTGTGGTCACCAACATCAAGCCCTGTGACTACAATAGCTCCTCAAAGAGGCTGGGTCTGTGGGTTTTGTTT
TGAGGGTCAGCTAGAAATGGGAGTGAGTCCAAGGAAGACCCACTGCCCCCGCCCCGAGAGATAGGGGAATGAGCATG
CTTGCACACGTGGACATGAAAGGCACAAGAGTGTTTGTATGTGACAGTTTGAGGTGACCACATTCTGCCCTCTCTGTGC
```

Fig. 4 (Cont.)

```
CTGTCATGGTTACAACTGAGGACAGTGGTGGATTTGGGCAGAGTCTGTGTGAGCTGGGAGAAGCTGTGGAGAGTTGCA
AGCATGGCATGTAGATATCAGAAGCCCTGGTCTTCCAGCAGTCCTCATGGTGATGGTTCAGTAGGACACTGGATGTGT
GGCCCATGCTAGGGTCATGGGCAAGGCTGGTATGGGTTGACTCTATGGCTGGACAAAGAGCTTTAACCTCGTCAGCTT
CCGCAATATGGAGGAACACTGCACAGCTTGCCCCCACCTGCACTCTGAGCACTCTGTACACTGGACATGCTCTACTAC
CCAGTGTCTCAGACTCCAGTCCTGGGCCCCAGCCCCATAGCACAACCATGTTTATAATCCCTCCAGTGTGAGAGGCCA
TGAAATGTTGTGGAGCTCAGTCTGAAGGCAGGTGGGAGACAGGCATGCTTTTGGATCCATGTCCATGAAGTATATGTC
CACATTCCATGACAAAGGAGCCGAAGCCACCTCTATTTTCTCAAGGACCCCCTCAGTCCTCATTACTCTTCCTCTGCC
TGGCCTCTGGATGTCTTCCCCATGAATCAGCTGTCACAAACACAGGCTCAGTCAGAGCACAGTCTAGTTCCCACCTTG
TGGTCCCAAAGGCTCTTTCACGCCAGTGTCTCCCTGCCTTACCCTGTCATGCACCTCTGGCCAGCCAGCTGCTCCTGG
GCAAGGACGAGAAGAAGCCAAGTAGTTCCTCTTCTCACAGACTCTAGTCCTGCTGGCCTCTAACTCTGTAACCTTCTG
GTGTCCATCAGGATCCTGGGGCCACATCACTCTGAGTGTGTTTATCACCGGCAATCCTGAGGGCTAAGATTTCAGATT
CTAAAGGAGGAGGCCCCCGTGGACATGCCTTCCCCTCTGCAGTCCCCAGGTCTAGAGTCTCATGTGGCTCTGTGTGAC
TCCCTGATGTACAGAGGCATGCCCTGCTACAGGCAATTACAATGGATTGGGTAGAGGGTTGGTTGTGCTCCAACATCT
TTGAGGAGGGTAGGAAGCAGACCTGGGATGTTCAGTAGCCTGGAGCAGCCATCACTGTCCTTTGAACAAAACTGGCCA
GCACTCTCTCAGCTCTGCCCACTGTCTTCTGTACTCTTCACACTTGGGCCTCACCTGAAGCCTGCACCCCAGACTGTA
CCAGGCAGAGGCCATGTACCCTGCTCTCAGATGATGTTTCATACAGATTACAGAGCTAACAAGAGGTGTGGTGTGTGG
ACCAGAGGCTCATGCTGTGTAGTCACCCATGGTCCTGCTGAAAAGCAGGCTGGGGCTAAAAAGAGAATAGAGTATGAG
ACACACCAAGACAAATGCTGATCAAAGCCCAATGTTTACTAAAAATCTGTGCTTATATAAAAGGAAAGCCCTTCTCCT
GCAGATCCACTTTTGATGTCTGTTGCCAGCCTGTAAGCAATTTGTCTGACAGCACTAGTTTGACAAGAAGGTGTCAAT
CACTGCTGTCTTTGGAATCTCTCAGCCTCTCAGCAGGTATCAGTGTCTTGGAGAAGAAGAGCAATGGTGACAGAACAA
TAGAATCATCTAGGTGGGAAGGCTCTACCCCAGGTGGTCTCATTCTCAGTGGCAGCAAGGTCTGAGCCAGCCTGCTCA
AGGCTGGGGAGGCTACAATGTTATTCAACAGGTCCCATGGGAAGTGTCCAGGCTGAGCTACTCAGTGTGCCACTCTG
AGGACAAAGCCTGCAGGAGAGGGAATGGGTAGATGGGTTTGAGGTTTGGAACAGGCAGGCAGGGCTGTGTGTGTCT
GTGGGAGCTGGGTGTGAGTGCTGTGGGTCTGAGTCTGAGGGGTGTTCACACATGGCTCTGTCTTCTGGTGCATGGCT
TTCATCTGAGAGAGAGAAAGAGAACCACACTCTTCATTAGAGTGTGTGTGTGTGTGTGTGTGTGTGTGTGTGTGTGTG
TGTGTGTGTGTTTGTATGTGAGTCTGTCTGCTGTCTGTGTAAATGTGAGCTTCTATGCTTCACATGCATGAAGG
ATCCTTCAGGGCACCCTGGAACTGGGATTACAGTAGAGAGCTGCCATGTGGGTGCTGGGAATTGAATCTGGATCCCCT
GGAAAAGCAGCCAGTGCTCTTAATCCTTTTGGTGTCTCTGCCTGTCTCAGTATCTCTGTCTCTCAGTCTCTGTCTC
TCTGGAGTCTCTGTCTTTCTGTGTCTGTACTGCCTCTGTGTCTCCCACACCTCCTACCAGTTGCTCTCAAAACTTCCA
CGTCCCCCCTCTTCTTCATGTCTCTATCAGTGTCTGTGTCTCTGTCTGTCTCTGTGTCTCTCTGTCCCTGCAGCTC
ATGACTGTTTCTCTCTAAGTGTTTCCCTGTCTCTTTCAGTGGTCTGTGCTTCTGTCTTTCTCAGTGTCTCTGTCTTTC
TACTTCAGAATCTCAGAGTCCCCTCTTCCATTTGTGTCCCTTCTTGGGCTCATTCACTCTGCCTCCAGTGTCATCACT
TGTGAGACCAGAACCTACTATGAGTCCAGAGGACTGTCCTTCATGGTCTGTGACCAGCTGTGATCTGGGGAACACTGG
GGAAGGCATGAACAGGGAGGGACCTGCCTGTCTGTGGAGCCCTGCCTGTCAGCATGAACTCCCCATTCTGCACCACCA
GAGCCCTGCTGAGCTGACTATTCCACACCACCTCCAGAAAAGGGCATTGAATCCTGCTGGAACCGATGGCTCTTAGCTG
ATACGGGTACTAGGAATCAAAACCCACTCCTCTGCAAGAACATCATGTGTTGTCAACCACCAAGCCATTTCTGTAGC
CCCACAGTAGAAACATTTAAGGCTAGATGTCTAGAAAGACATATTCCAAGATCTGAAAAATCTAAACTCTCAACCCAG
GGTAGTATACCCAGAAAGCTATTAAATTTCAGGAGAAAATAAAAAAGCTTTCCACAGCAAAAACAGATGAAAGGTATT
TGTGACCATAGACAGCTGTAAGGGGACACTGGGGGTAATACCTCAGACTGAAGGGAAACACCATACACATGAGGGGAC
GTGGGCTAAATCACGTGTTAGGAGGTGTGGAGATGGGAAAGGCTGGGTGGGGGGAGGCTTTGCCAGAGTGAAGGCTTC
CTGCACTCAAATCTAAAACCTGCACACAAGGAAAAATAATTTGAGGGAATAGTAGAACACATGCAGCTTGGAAATGGA
GGGAGGGAGATTTTAGCATTAAAGTTTTAAGTGTGGATAAAAGGATTGGAAATCTGGGGAAATAAGAGGGGAAATTGT
ATGCATGTTGTTCTCAGAAGAAAGGGTTAGGTTGGGTGTGGTGGCACATGCTTTTAATCCCAGCATTCAGGAAGCAGA
GACAGGAGGATCTCCTTAAGTTTGAAGACAGCCTGGTCTTCTACACAGGGAGTTCCAGGACACCCAGGACTACATAGA
GAGACCGTGTTTCAAAAGAAAACAGTTTCTAAATTTATTAAAAGAAGTCTTGATGCTTTAGTGAGGGAGACTGTAGAT
AACCAAACACAAACCAGGCTGTTTACTGCCTTTGATCCTGGCCCTCCACCATGACTGGACCTTATTGCTGAAGATGCA
CTTATTTTGGATGCAGAGCAAAGAAGACTCCATCCAGCCTGGACAGGAACTCTGTCCCTGCTGACTAGCTTCCCTGGC
ACGGGAGGCTGCTGTGCCAGCTGTTGGAGGGTGGCAGAGCTTAGTGTTCCCATCCAGAGCCTGGTATGTGCTGAGCCT
ATGAATGGACTTCAGTCCCTGTCTCAGCCTGTCCCCTCACAGAGGAACAGTGCTCAGCATGTCCCCAACTACACTCTG
AGCACTCTATGTCCTGGGTACCTCTGCCAACCAGTGTCCCTGACCCCAGTCCTGGACCCCACACCACAACATCAGCC
TTTGAGGTGGATCTTCCAAAGTGTGAGGCCGTGGGATGAAGTACTGAAATCCCTAAGCCCATATGAGGGACACTGTTT
GGGGGTAGGTGGGAACCACGCCTGGTTCTTAGATCTGTGTCTATGAAGTACATGTCCCAATACCCTAACAAATGGGAC
ATAGCCGCCTCTACCTCCTCAGACCCCCCAAACCGCAGTCCCCTCAGCCCTGATTACTCTTTTCCTCTGCCTGGTCTC
TGGGTGTCTTCCCCATGAATCAGCTGTCACACACACAGGCTCAGTCAGGCACAGCCTAGTCCCCACCTTGTGGTCC
CAAAGGCCCCTTCATGCCCCTGTCTCCCTGCCTCACCCTGTCCTGTGCCCCTGCCCAGCACCTGCTCCTGGGCAAGCA
CAGGAAGAATGAATATAGTCCCCCTGCCCACAGGCTCTAGCCTTCCTGGCCTCTAGCCCTGTGACCTGGTGTCCATCA
```

Fig. 4 (Cont.)

```
GCATCCTGCACAACAGGACTCAGCATATGTTGTTCAGTGGTTATCCTGAGGCCTGAAAACCTAGGGTAACAAGGAGGA
GGCCCTCTTGGACATGCCTTCCCCTCTGCAGTCCCCAGGTCTAGAGTCTCATGTGGCTCTGTGTGACTCCCTGCTGTA
CAGAGGCATGCCCTGCTATAGGCAACTACAATGGATTGTGTTGAGGGTTGGTTGTGTTTCAGCAGCTTGGAGGAGGGT
AGGAAGCAGACCTGGGATGTTCAGTAGCCTGGAGCAGCCATCACTGTCCTTTGAACAAAACTGGCCAGCACTCTCTCA
GCTCTGCCCACTGTCTTCTGCACTCTTCACACTTGGGCATCCCCTGAAGCCTGCACCCCAGACTGTACCAGGCAGAGG
CCATGTACCCTGCTCTCAACAGCATCACATAGACTACAAGGCTAACAAGAGGTGGGGAGTGTGGACCAGAGGCTCCTG
CTGTTCACCAGGTCCCATGGGAAGTGTCCAGGCTGAGCTACCTTCAGTGTGCCACTCTGAGGACAAAGGCCTGCAGGA
GAGGGAGTGGGCAGATGGGTTTGAGGTTTGGAACAGGCAGGCAGGCAGGCAGGGGCTGTGTGTGTCTGTGGGGAGCTG
GGTGTGAGTACTGTGGGTCTGAGTCTGAGGAGTGTTCACACATGGCTCTGTCTTCTGGTGCATGGCTTCCATCTGAGG
GGGTGTGTGTGTGTGTGTGTGTGTGTGTGTGTGTGTGTGTGTGAGCTTCTAAGCTTCGCATGCATGAATGATCC
TTCAGAGCACCCTGGAACTGGGATTACAGAGGTGAGCTGCCATGTGGGTGCTGGGAATTGAATCTGGATCCCCTGGAA
ATCAGCCAGTGCTCTTAATCCTTTTTGTGTCTCTGCCTGTCTCAGTATCTCTGTCTCTCTCAGTCTCTGTCTCTCTGG
AGTCTCTGTCTTTCTATGTCTGTACTGCCTCTGTGTCTCCCTCACCTCCTACCAGTTGCTCTCAAAACTTCCATGTCC
CCCCCTTCTCTGAGTTTCTATCAGTGTCTGTGTCTCCGTCTGTCTCTCTGTGTCTCTCTGTCCCTGCAGCCCATGACT
GTTTCTCTCTAAGTGTTTCCCTGTCTCTTTCAGTGGTCTGTGCTTCTGTCTTTCTCAGTGTCTCTGTCTTTCTCTCTC
AGAATCTCAGTGTCCCCTCTTCCATTTGTGTCCCTTCTTGGGCTCATTCACTCTGCCTTCAGTGTCATCACTTGTGAG
ACCAGAACCTACTATGAGTCCAGAGGACTGTCCTTCATGGTCTGTGACCAGCTGTGATCTGGGGAACACTGGGGAAGG
CATGAGCAGGGAGGGACCTGCCTGTCTGTGGAGCCCTGCCTGTCCGCATGAACTCCCCATTCTGCACCACCAGAGCCC
TGCTGAGCTGACTATTCCACACCACCTCCAGAAAGGGGCATTGAATCACGTGGAACCTAAGAACACCGTGTTGTCAAC
CACCAAGCCATTTCTGTAGCCCCACAGTAGAAACATTTAAGGCTAGATGTCTAGAAAGACATATTCCAAGATCTGAAA
AAAATCTAAACTCTCAACCCAGGGTAGTATACCCAGAAAGCTATTAAATTTCAGGAGAAAATAAAAAAGCTTTCCACA
GCAAAAACAGATGAAAGGTATTTGTGACCATAGACAGCTGTAAGGGGACACTGGGGGTAATACCTCAGACTGAAGGGA
AACACCATACACATGAGGGGACGTGGGCTAAATCACGTGTTAGGAGGTGTGGAGATGGGAAAGGCTGGGTGGGGGGAG
GCTTTGCCAGAGTGAAGGCTTCCTGCACTCAAATCTAAAACCTGCACACAAGGAAAAATAATTTGAGGGAATAGTAGA
ACACATGCAGCTTGGAAATGGAGGGAGGGAGATTTTAGCATTAAAGTTTTAAGTGTGGATAAAAGGATTGGAAATCTG
GGGAAATAAGAGGGGAAATTGTATGCATGTTGTTCTCAGAAGAAAGGGTTAGGTTGGGTGTGGTGGCACATGCTTTTA
ATCCCAGCATTCAGGAAGCAGAGACAGGAGGATCTCCTTAAGTTTGAAGACAGCTTGGTCTTCTACACAGGGAGTTCC
AGGACACCCAGGACTACATAGAGAGACCGTGTTTTAAAAGAAAACAGTTTCTAAATTTATTAAAAGAAGTCTTGATGC
TTTAGTGAGGGAGACTGTAGATAACCAAACACAAACCAGGCTGTTTACTGCCTTTGATCCTGGCCCTCCACCATGACT
GGACCTTATTGCTGAAGATGCACTTATTTTGGATGCAGAGCAGAGGAGACTCCATCCAGCCTGGACAGGAACTCTGTC
CCTGCTGACTAGCTTCCCTGGCACGGGAGGCTGCTGTGCCAGCTGTTGGAGGGTGGCAGAGCTCAGTGTTCCCATCCA
GAGCCTGGTATGTGCTGAGCCTATGGATGGACTTCAGTCCCTGTCTCAGCCTGTCCCCTCACAGAGGAACAGTGCTCA
GCATGTCCCCAACTGCACTCTGAGCACTCTATGTCCTGGGTACCTCTGCCAACCAGTGTCCCTGACCCCAGTCCTAGA
CCCCCACACCACAACATCAGCCTTTGAGGTGGATCTTCCAAAGTGTGAGGCCGTGGGATGAAGTACTGAAATCCCTAA
GCCCATATGAGGGACACTGTCTGGGGGTAGGTGGGAACCACGCCTGGTTCTTAGATCTGTGTCTATGAAGTACATGTC
CCCATACCCTGACAAATGGGACATAGCTGCCTCTACCTCCTCAGACCTCCCCAACCCCAGTCCCTGCCCTCAGCCCTGATT
ACTCTTTTCCTCTGCCTGGTCTCTGGGTGTCTTCCCCATGAATCAGCTGTCACACACACACAGGCTCAGTCAGGCACA
GCCTAGTTCCCACCTTGTGGTCCCAGAGGCCCCTTCATGCCCCTGTCTCCCTGCCTCACCCTGTCCTGTGCCCCTGCC
CAGCACCTGCTCCTGGGCAAGCACAGGAAGAATGAATATAGTCCCCCTGCCCACAGGCTCTAGCCCTCCTGGCCTCTA
GCCCTGTGACCTGGTGTCCATCAGCATCCTGGGGAACAGGACTCAGCATATGTTGTTCAGTGGTTATCCTGAGGCCTG
AAAACCTAGGGTAACAAGGAGGAGGCCCTCTTGGACATGCCTTCCCCTCTGCAGTCCCCAGGTCTAGAGTCTCATGTG
GCTCTGTGTGACTCCCTGATGTACAGAGGCATGCCCTGCTATAGGCAACTACAATGGATTATGTTGAGGGTTGGTTGT
GTTTCAGCAGCTTTGAGGAGGGTAGGAAGCAGTCCTGGAATGTTCAGTAGCCTGGAGCAGCCATCACTGTCCTTTGAA
CAAAACTGGCCAGCACTCTCTCAGCTCTGCCCACTGTCTTCTGCACTCTTCACACTTGGGCATCCCCTGAAGCCTGCA
CCCCAGACTGTACCAGGCAGAGGCCATGTACCCTGCTCTCAACAGCATCACATAGACTACAGGGCTAGCAAAGAGGTG
GGGAGTGTGGACCAGAGGCTCCTACTGTTCACCAGGTCCCATGGGAAGTGTCCAGGCTGAGCTACCTTCAGTGTGCCA
CTCTGAGGACAAAGGCCTGCAGGAGAGGGAATGGGTAGATGGGTTTGATGCTTGGAACAGGCAGGCAGGGGCTGTGTG
TGTCTGTGGGGAGCTGGGTGTGAGTGCTATGGGTCTGAGTCTGAGGGGTGTTCACACATGGCTCTGGTGCATGGCTCT
CATCTGTGTGTGTGTGTGCCACAGGCTCCATTTGAGTGCTCGGTTGGCTCCATTGCTGTACCTCTGTCCCCCTTGTTT
TCTATCTGTCTGTCCTCCCTGTCTGTCTGTCTCTCCTTTCCTATGCCTCCTCCTCATATCCACGTCTGCATCTCTTTC
TATCAGTCTCTATCCCTGTGACCCCTGGTTTCCATTTCTGTCTTTCTGCATATCTTTCCATCTTTCTCTCTGTGTGTC
TGTCCTCATCTCTTCCAGTGTCCGTGTTTCTGTTTCCCTCTGTTCCCATGCGGAGGTATGTTCTCACAATCCTTAAGT
TCCCTGGTCCCCTGTCCCCATTTCTTGTCATATTATCCCATCAGTGTCTCTGTGCCTCTCTGTCTGTGTCTCTGTGT
TGTCTCTGTGTGTGTCTCTCAGTATCTCTCTCTCTCTCTCTCTCTCTCAGTATCTGTATTTCTTTTAGTA
ACTTTGCTATCTTTTTAAGTATCTCTGTCTTTCTTCATCTCTGTCTCTCTTGAGGTCTCTGTCTTTCCGCATGTCTAA
TGTTTCTGTATCTCTCTCACCTCATCTCTGCCTCTCTCAATATTCAGTAGATCCATGCCCCTTTATTCTTTGTGCCTC
```

Fig. 4 (Cont.)

```
TGTCTCTGTTTGTCTCTTTCTCTGTCTCTCTGTCTTTCTCTCTCTCAGAATCTGTGTCCCTCATGTTATTTCTCAAAA
TGCCTCCCTAACTCTTTCAATAACAGTTTCTGCCTCTTCTTTCTGGGCCTGGCTCAATCTTCCTTCTTGGACCTCAGT
TTCATTGGTTGTGAGACCATACCCTGCTATGAGTCCAGAGGACTGTCCTCCATAGTCTAGAACCACATGCTATCTAAG
GGATATTGGGGCAATACATGTGTAGTGAGATACCTGCCTTTCTGATGAGCCCTGTCTGGCAGGGATAAATTCTCCATT
CTGCATCTCCAGGGCCTTGCTGAGCTGACTATTCTAGTCCTCTGCCAAAATAGCTGTGTGGCCTTGGGTGATGCTGGC
TGACCTCAGGCTGGTCTGGGTTGTCTCTGGCTGACACCCCTTGACTCTGGATGACCCTGGGAAGACCATACTTAATCT
TAATTGGACTTGTTCTCATTGGGACAGAACATGGCCTCACTAAGGCACGAGTGTGGATGGCCTTGGGTGATGGGGGTT
GGGGCCTCCTCAGCCCCTGGCAGGGCTCCCCTGGCTCCCACCCCTCATCCAGGTCCCAGGCCCACCTGGCCTGGTCCA
GTGTGGTGTGATTCTCAGAACAGTAGCTCTGGTTTGGGGCACCTGTGCTGAGAAAGGCTCAGGATGACTCAGCTGCCC
TCAGCTCAGAGCTGCTTTGAATGTTTCAGCAGGTGATAGACAACAGAGACTTCAGAAGAGAGAAAAACAAGTTGCTAA
TGTGAACATCCCTGCCCTACCCCCACACCTGTACTGCAAACATTGTTGACCCCAGATAGAGATCCCAGGACAGCAAGT
GATAGACAAAGGAGGCTCCAGAGGAGAGAAAAATAGTATCTACAAGCATGACCACTTCTGCCCTGCCCCACACCTGCC
CTGCAAAGCTCCCCAGGATGCTGACCCCACATCTGTAGACCCCAGGCCAGAGGCTCCATCTCCCAGGGCCTGGGCTTG
CTTTGTCTCCATTCTGTGCCTCTGAGCCTGGGCAAGGCCAATGAGCAAAGGGGTCACTGTCCCAGTTGCAGCCCAGTG
TGTGAACAGTGTTGTGGGGATTCTGGAATCTTCTGCAGGAATCCCCTGTAGGGATCCTCCTAATGTGAATGAGGCTTG
GAATAGCAAAGGGACGTCTTGTAAAATACCACTGATTCCTTGGGCCTCAGACAATGGATTTGAGATGAGGACCAAGGT
CCAGGGCCAGTGTTGGTAAGCAGAATTTGGGGCTAGAGTTCAGGCTTAGAAGTCAATGATGAGGGCCAGGGCCCAGTG
ACTAGGTCAGGGCCCATTGATCAGTACAGGACCCAGTTGTTAGAGCCGGAGCTCAATGATCTGGACCAAGTCACAAGG
CCAAATGATCAGGATCAGTAGCCAGTTACCAGGACCGAGATCCAGGTTTCACAGCCAAAGCCAGGTTACCCCAACCAG
AGACCATTCATCGGAATCTGGGTCTGTTGATCGGAGCCCAAGCACGCTGCTGTAAACCAGAGCTGCTCTAAAGCAGAA
CTCAGTGCTGAGCACCAGAGATAAGTGATGAGACCAGGATTCAGTGATTAAGGAAACAAAACCAAAGGTCAATAGGAT
ATTATGTGGAGAGAGGGGAGAGAGAGAGAGAGAGAGACAGAGAGAGAAAGAGCGGTAGGTTCAGGACTAAGTCTCAG
TGAGGAGGGTCAGGAGTCAGTGGTTTGAACCCAGACACACTGCCCAGGTCCACAGTTCAACGGTGAGAGCCAGGGGTC
AGCTATCAGAACCAGGTCCAGTAACTACAACCAAAAACCAGTGGCCCCAACCAAAAACCAGTTACTAAAACCCGAATA
GAATAGAAACTAGCCAGGCAGTGATAGCTTTAATCCCAATACTCAGGAGTCAGAGGCAGGTGGATCTCTGAGTTCAAG
GTCAGCCTGGTCTACACAATGAGTTCTAAGACAGCCAGGGCTACACAGAGAAACCCTGTCTGGAAAACAAGCAAAAGC
CTAGAAACCGTGGACTCAGTGGTCAGTGGCAGTTCTTGGTGACTAAGACCATGGTCAAGAGGTCAAGCAGGACTCAGC
GGTTAGAATCAGGGCATGGGTGATGACAGCCTGTTCCAGGGATCAGAACCAGGTCTAAGGGCAAAGGCCATGACTGAG
TCATCAAACAGTGTCTCTTCATAAGTCCTAGCCAGGCCCAACCAGGCCTAGGGTGTCAGATCAGGCAAGACTGATGCG
GTATGTGTGAGGTGGTATGACAATACATCTCAGTATCTCTGGGACCCCACCACCATCTTCCCTGCCTCGGTCCACTCA
CAAATCTCTGGCTCTCTCACTGTCTTTGTCTCATTCTTGTCTAGCTTTCTACCGTGTCCCCTCTCCCCACATTTGTCT
CTCCCAGTATCTGTCTCTCTGAAAGTCTCTGTGTCCCCTCTGACTTTCTCAGTGCTTATGTTCCCTGCCCCTTGATCA
TTTGAGAGGGGATGGTGAGTAGAGAATTATGGAACAGTGAGTGTGTGTCTCTATATGTGTGTGTGTCTGTGGGGC
TGGCAGTGGGTATGTGTGAGTATGTGTGTGTCTGTGTGAGTGTGTCTGTGGGGTGACAGTATGTATGAGTGTCAGT
GTGTGTGTGTGTGTGTGTGTGTGTGTGTGTGTGTGTGTGTGTCTGTGTCTGTGTGTCTGTGTCTGTGTGT
CTGTGTGTCTGTGGGGTGGCAGTGTACATGTGTGAGTGTGTGAATCAAAATGTGTGAGCATGTGTGTGGAGGTGGT
AATGTATGTATGTATGTCTGTGTGTATGAGTGTGTGTCTACGGGAGTGGCAGTGTATATGTGTGAGTATATTGTGTAT
TGTGGGTACGGGTGTGTGTCTGTGTGAGTGTGTGTTTCTATGTGTCTGTGGAGGTAACAGTGTGTATGTGTGAGTGTG
TGTCTATATGAGTGTCTGTATGTGTGTGTATGAGAGAGAGAGAGAGAAAGAGAGAGTGTGTGCAGGGTGATAGT
GTATATATGTGAGTTTGTGTGTATGTGAGTGTGTGTTTGTGTATGAATGTGTGTTTATGGGGTGACAGTATGTA
TGTATGAGTGCATGTGTCTGTGGGGTAGCAGTGTGTATGTGTGAGTGTGTGTGTGTGTGTGTGTGTGGTATG
TGTGTGTGAGAGAGAGAGTGCAGGGTGATAGTGTATATATGTGAGTGTGTGTCTGTTTGTGAGTGTGTGTTT
GTGTGTATGAGTGTGTGTGTCTATGGAGTGACACTATGTATGCATGAGTGCATGTGTCTGTGGGATAGCAGTGTATAT
GTGGGAGTGTGTGTGTGTGTATGTGCAGGGTGGTAGTGTATATATGTGAGAGTGTGTGTTTGTGTATGAGTGTG
TATGTCTATGGGGTGACAGTATGGATGGATGTATGAGTGCCTGTGGGGCAGCAGTGTGTATATGTGAGTGTGTGTGTG
TGTGTGTGTGTGTGTGTGTGTGTGCAGGGTGGTAGTGTATATATGTGAGTGTGTCTGTCTGTGTGTGAGTGT
GTGTGTTTGTGTATGAGTGTGTGTCTATGGGGTGACAGTATGTATGTATGAGTGCATGTCTGTGGGGCAGCA
GTGTGTATGGTGAGTGTGTGTGTGAGTGTGTGTGTCTGTGTGTGTGTGTGTGTGTGTGTGTGTGTGTGTGTG
TGTGCCACTTCCCTAATATGTTCTCTTCCAGCTATGGCTTCTGCTTCATCCTTCACTCAAGGCCAGACCTCACTGGCC
AGTCCACAGCATAATACCAGCCATGCCTCTACCCAATAATTGTATGTGTCAGGGAGCCAAGAGGATGGACAGGGATCT
TGTTCTTGGGGTGAGAATGTGAGAACTTTTGGGGAGCCCTTCCACACACCCATGCAGTAGTAGACACCTCTGCAAAGC
TATGCACATCCTCACACTAGCACACTGCACAACCATGCACTCTCTGCAGACTCACTGTTCACCATGAACCCAGCTAGT
CAGATTCATATGTGAAACTCATATCAGCCTCTGCACACACATACACACATATTACACCCATGCACACACATGTACACA
TACATACACATGTACACATACATGTGTACACACACATATAGAGAAGGCATTGGTGGGAAAACATTAGGCCATGGCTA
CAGTACAGGGCACAAGGATGGTGGTACAGAATGAGGTCAGGCTGGGTCAGCATAACAAGAACACTTGGACAAAGTGAG
GGTAGTGTGTGTGTGTGTGTGTGTGTGTGTGTGTGTGTGTGTATATGTGTGTGTGTGTACACGTTGAAAGTCTTCAGT
```

Fig. 4 (Cont.)

```
AGACTGGTATCACTAGCCCTGATATGGGCAACACAGCAAGCCTGGGTCACACTCAAGCTGAGTATCAGGGTAACCAGG
GCCTTCTAACCAAGGGTAGATGCAGCCTGTGTTCCGTTTACTGACCAGTGAGAAGCCATGAGCTGAACCAGACCAGAA
GACCCTTACTGTTCCCACCCAACCCCCACCCAGTTTAGTCTCAGCAAGACCCTGTACTGTGGGCCACAGCTCTCCCCC
ACACCCCACCTGTAGCACAAACACTATTTGCAAACATTTCTAAAAATGATGAGAACAGGAACCACAGAGCAGAGGGGG
GGACTGGCGTGGAAAGCCCCATTCACCCATGGGACTGAAACTCGGGGAACCAGAACCGTAAGGAGATCTGCATGGTGC
TGGGGGAGGTTGGCCCTGGATCAGTGAGCCCAGAGAGTTACTGGTTTCTCACTTCCATCAGGTCAACCTCCTCAACCC
CCAAAAATGGCCAGGCCTAGGCTATGGATGAGTTTCAATGACCAGGCCCTAAGGACGAGTCACAGAGGACTTCCTGGT
GGGCTCAGGCAGCAGACCTGCCCAGATGGATTGCAGAACCAGGGGGAGCCATGGCCAGGAAGGCCAGACGCCTTAGGG
GTGTGCTGTCTCTGCATCCTTTGCCCTCTCTGCTCCTCACAGTCCATCTGCCATCTCACAATCCCTCCTGTCGCTCTG
GGGCCCAGACCTGGCCAGTCTGGGTACCTGTGGAATACACCCAAAGAAGCAATCCCCAGCCTCAGGACCCACAACTAC
TTCCCCTACAGACATGAGTGATCTCAGCCCACATGTCTGGGGGCCACAGAAGCCCCTAAGACCCTACTCTGCTAATAG
GCCCTCCTCCCACCAGCCAAGACAATACACAGGCAAGGTGATGTGGATGAGTCACCCCATGGGTACCTGTGTCTGAGA
TACACCCTGTGGGTATCCTGGCCAGAATCGGTGACCAACCCAACCTGTGTCCCTAGAGGAGAACTCCGTGCCTGCAC
TCACCTACCCACCTAACTCCAAGCTTGGTATGATGCAGAGCCCTGTGTAGACCTAAAAGTCAGCCATAGGACAGGGT
CAAGAATGACTCTTCCTACACATAAAGTCTTCTACTAAGACAGTAAGGTAGACACACAAACATACCGGATGCAGAGA
CACACAGGCATGCAGAGAAGGCATGTAGACACAAACGCATGCATAAACGCACAAACATACAGATATATGCTGACAAAT
ATACACAGCAACTTACAAGTACACAGACACACAAACAGACAAACATGCACAGACAGAAACACACAGAGCTCAAAATCA
AGTATACACAGACAAATTTACACAGAGACTTACAGATACACAGATATATGAGACACACCCAAACAGACACACACATGG
GGGCACAGAAAAACATACAAGCAGACACATGCAGACTTAAAGACCCACAAGACATGGAGAGATACAAAAACACACAAC
ACAGACACAGAGATATAGAGACACACAGACCCACAAATATGAACAGACGCAGAGACACCCAGAAACAAAAACACACTC
AGGCATTCCACTCCCAATGGGCGTACACATGGGCATACACAGCCCAGTCACACAGACAAACATAACACATACAGAAGT
GCAGGCATACATATCACACAATACACGCTGGTATTCACACACAGGTGTGCTCACAAACCCCACACACTCACACATAAA
AGTTGACACTGGCACTCCCACTCCGAGGCACATGCTTAGCCACAGCCGGCTGACACTGCACACCCCACACACGTTCCA
GAGACTCCCACAGAACTGGAAGCTCACCCAGGCCCACCCAGGCTCTCAGGCCACACACATGGGACATCTCAGAGGCAT
GTGGGATACAGTTGCTCACAGGTTTCATGAGGACTCACAGGCCTGTCCTTGAACATTCCCCTGAGCAGGGGCTCCCTT
CTTAAAGCACAGGGATCCCATTCTTTACAGATAAGCACCCAGACAGAGGCACTACCAGGCCCAGACCACACTAGACAC
ACACAGCTCTGCATTGTCCCACACTCAAACACAGCTCTGTCGCCTGAGCTCATGCCAGTCACACAGAACACAGACATG
GGCTCGTGTGCTAGAGAGACATAAGCAATGGTAGCCAAGGTGCTCACATCATGCCCATACACACACACACACACACAC
ACACACACACACACACACACACACACACACCCTGTGAACAGGCCTGCAGTCCTGACTGAAGCCCTGCTCTACCCAA
TTTAGTGAGTCCTGCACCTGAACCCTCTTACCCTCACAGCCCCTGACCTCTCCCTGTGTGCTGCTCAGCTATGGCCCC
TTCCCATTCCTAACGTGCCACCCTAAGATGTCGGTTCCGTGCATCACCGCACACATGCTCTTGGGATAAGGCCTTAGA
AGGCTCTGTACCATCTGCAGCTCATGCCACTGCCTTCCCTGGTAACCCTCTCCTGCATACAAGGGCTGCAAGGGTCAA
TGATATGAATCCATCCATGCTCTGACCCCAGCTTGGCCCAGGGCAGCCATGATGGGAGGACAACCCCTGACCCCAGCC
TAAGATAGTTGTTGCACAGAGCAGTCCCTTAACGCAGGATAACTGTTGGAGGTAGGCAGCACTTGACCCCTGCCCAAG
CTAGATGATGGGAGAGGATAGGTCCAGCCATTGACAGCTGCTGTAGCAAGGCAGGCCCTGGTCCCAGGTTAACTCAAG
GCTGCTGCTTAGGCAACCCCTGACTCCAGCTCCAGAAGTCTGCTGGGGGTGTATCCTCTGGCTACAGGAGCTGAACAA
ATGGCGCGCCGCGGCCGCTCGACCAATTCTCATGTTTGACAGCTTATCATCGAATTTCTGCCATTCATCCGCTTATTA
TCACTTATTCAGGCGTAGCAACCAGGCGTTTAAGGGCACCAATAACTGCCTTAAAAAAATTACGCCCCGCCCTGCCAC
TCATCGCAGTACTGTTGTAATTCATTAAGCATTCTGCCGACATGGAAGCCATCACAAACGGCATGATGAACCTGAATC
GCCAGCGGCATCAGCACCTTGTCGCCTTGCGTATAATATTTGCCCATGGTGAAAACGGGGCGAAGAAGTTGTCCATA
TTGGCCACGTTTAAATCAAAACTGGTGAAACTCACCCAGGGATTGGCTGAGACGAAAAACATATTCTCAATAAACCCT
TTAGGGAAATAGGCCAGGTTTTCACCGTAACACGCCACATCTTGCGAATATATGTGTAGAAACTGCCGGAAATCGTCG
TGGTATTCACTCCAGAGCGATGAAAACGTTTCAGTTTGCTCATGGAAAACGGTGTAACAAGGGTGAACACTATCCCAT
ATCACCAGCTCACCGTCTTTCATTGCCATACGGAACTCCGGATGAGCATTCATCAGGCGGGCAAGAATGTGAATAAAG
GCCGGATAAAACTTGTGCTTATTTTTCTTTACGGTCTTTAAAAAGGCCGTAATATCCAGCTGAACGGTCTGGTTATAG
GTACATTGAGCAACTGACTGAAATGCCTCAAAATGTTCTTTACGATGCCATTGGGATATATCAACGGTGGTATATCCA
GTGATTTTTTCTCCATTTTAGCTTCCTTAGCTCCTGAAAATCTCGATAACTCAAAAAATACGCCCGGTAGTGATCTT
ATTTCATTATGGTGAAAGTTGGAACCTCTTACGTGCCGATCAACGTCTCATTTTCGCCAAAAGTTGGCCCAGGGCTTC
CCGGTATCAACAGGGACACCAGGATTTATTTATTCTGCGAAGTGATCTTCCGTCACAGGTATTTATTCGCGATAAGCT
CATGGAGCGGCGTAACCGTCGCACAGGAAGGACAGAGAAAGCGCGGATCTGGGAAGTGACGGACAGAACGGTCAGGAC
CTGGATTGGGAGGCGGTTGCCGCCGCTGCTGCTGACGGTGTGACGTTCTCTGTTCCGGTCACACCACATACGTTCCG
CCATTCCTATGCGATGCACATGCTGTATGCCGGTATACCGCTGAAAGTTCTGCAAAGCCTGATGGGACATAAGTCCAT
CAGTTCAACGGAAGTCTACACGAAGGTTTTTGCGCTGGATGTGGCTGCCCGGCACCGGGTGCAGTTTGCGATGCCGGA
GTCTGATGCGGTTGCGATGCTGAAACAATTATCCTGAGAATAAATGCCTTGGCCTTTATATGGAAATGTGGAACTGAG
TGGATATGCTGTTTTTGTCTGTTAAACAGAGAAGCTGGCTGTTATCCACTGAGAAGCGAACGAAACAGTCGGGAAAAT
CTCCCATTATCGTAGAGATCCGCATTATTAATCTCAGGAGCCTGTGTAGCGTTTATAGGAAGTAGTGTTCTGTCATGA
```

Fig. 4 (Cont.)

```
TGCCTGCAAGCGGTAACGAAAACGATTTGAATATGCCTTCAGGAACAATAGAAATCTTCGTGCGGTGTTACGTTGAAG
TGGAGCGGATTATGTCAGCAATGGACAGAACAACCTAATGAACACAGAACCATGATGTGGTCTGTCCTTTTACAGCCA
GTAGTGCTCGCCGCAGTTGAGCGACAGGGCGAAGCCCTCGAGTGAGCGAGGAAGCACCAGGGAACAGCACTTATATAT
TCTGCTTACACACGATGCCTGAAAAAACTTCCCTTGGGGTTATCCACTTATCCACGGGGATATTTTTATAATTATTTT
TTTTATAGTTTTTAGATCTTCTTTTTTAGAGCGCCTTGTAGGCCTTTATCCATGCTGGTTCTAGAGAAGGTGTTGTGA
CAAATTGCCCTTTCAGTGTGACAAATCACCCTCAAATGACAGTCCTGTCTGTGACAAATTGCCCTTAACCCTGTGACA
AATTGCCCTCAGAAGAAGCTGTTTTTTTCACAAAGTTATCCCTGCTTATTGACTCTTTTTTATTTAGTGTGACAATCTA
AAAACTTGTCACACTTCACATGGATCTGTCATGGCGGAAACAGCGGTTATCAATCACAAGAAACGTAAAAATAGCCCG
CGAATCGTCCAGTCAAACGACCTCACTGAGGCGGCATATAGTCTCTCCCGGGATCAAAAACGTATGCTGTATCTGTTC
GTTGACCAGATCAGAAAATCTGATGGCACCCTACAGGAACATGACGGTATCTGCGAGATCCATGTTGCTAAATATGCT
GAAATATTCGGATTGACCTCTGCGGAAGCCAGTAAGGATATACGGCAGGCATTGAAGAGTTTCGCGGGGAAGGAAGTG
GTTTTTTATCGCCCTGAAGAGGATGCCGGCGATGAAAAAGGCTATGAATCTTTTCCTTGGTTTATCAAACGTGCGCAC
AGTCCATCCAGAGGGCTTTACAGTGTACATATCAACCCATATCTCATTCCCTTCTTTATCGGGTTACAGAACCGGTTT
ACGCAGTTTCGGCTTAGTGAAACAAAAGAAATCACCAATCCGTATGCCATGCGTTTATACGAATCCCTGTGTCAGTAT
CGTAAGCCGGATGGCTCAGGCATCGTCTCTCTGAAAATCGACTGGATCATAGAGCGTTACCAGCTGCCTCAAAGTTAC
CAGCGTATGCCTGACTTCCGCCGCCGCTTCCTGCAGGTCTGTGTTAATGAGATCAACAGCAGAACTCCAATGCGCCTC
TCATACATTGAGAAAAAGAAAGGCCGCCAGACGACTCATATCGTATTTTCCTTCCGCGATATCACTTCCATGACGACA
GGATAGTCTGAGGGTTATCTGTCACAGATTTGAGGGTGGTTCGTCACATTTGTTCTGACCTACTGAGGGTAATTTGTC
ACAGTTTTGCTGTTTCCTTCAGCCTGCATGGATTTTCTCATACTTTTTGAACTGTAATTTTTAAGGAAGCCAAATTTG
AGGGCAGTTTGTCACAGTTGATTTCCTTCTCTTTCCCTTCGTCATGTGACCTGATATCGGGGGTTAGTTCGTCATCAT
TGATGAGGGTTGATTATCACAGTTTATTACTCTGAATTGGCTATCCGCGTGTGTACCTCTACCTGGAGTTTTTCCCAC
GGTGGATATTTCTTCTTGCGCTGAGCGTAAGAGCTATCTGACAGAACAGTTCTTCTTTGCTTCCTCGCCAGTTCGCTC
GCTATGCTCGGTTACACGGCTGCGGCGAGCGCTAGTGATAATAAGTGACTGAGGTATGTGCTCTTCTTATCTCCTTTT
GTAGTGTTGCTCTTATTTTAAACAACTTTGCGGTTTTTTGATGACTTTGCGATTTTGTTGTTGCTTTGCAGTAAATTG
CAAGATTTAATAAAAAAACGCAAAGCAATGATTAAAGGATGTTCAGAATGAAACTCATGGAAACACTTAACCAGTGCA
TAAACGCTGGTCATGAAATGACGAAGGCTATCGCCATTGCACAGTTTAATGATGACAGCCCGGAAGCGAGGAAAATAA
CCCGGCGCTGGAGAATAGGTGAAGCAGCGGATTTAGTTGGGGTTTCTTCTCAGGCTATCAGAGATGCCGAGAAAGCAG
GGCGACTACCGCACCCGGATATGGAAATTCGAGGACGGGTTGAGCAACGTGTTGGTTATACAATTGAACAAATTAATC
ATATGCGTGATGTGTTTGGTACGCGATTGCGACGTGCTGAAGACGTATTTCCACCGGTGATCGGGGTTGCTGCCCATA
AAGGTGGCGTTTACAAAACCTCAGTTTCTGTTCATCTTGCTCAGGATCTGGCTCTGAAGGGGCTACGTGTTTTGCTCG
TGGAAGGTAACGACCCCAGGGAACAGCCTCAATGTATCACGGATGGGTACCAGATCTTCATATTCATGCAGAAGACA
CTCTCCTGCCTTTCTATCTTGGGGAAAAGGACGATGTCACTTATGCAATAAAGCCCACTTGCTGGCCGGGGCTTGACA
TTATTCCTTCCTGTCTGGCTCTGCACCGTATTGAAACTGAGTTAATGGGCAAATTTGATGAAGGTAAACTGCCCACCG
ATCCACACCTGATGCTCCGACTGGCCATTGAAACTGTTGCTCATGACTATGATGTCATAGTTATTGACAGCGCGCCTA
ACCTGGGTATCGGCACGATTAATGTCGTATGTGCTGCTGATGTGCTGATTGTTCCCACGCCTGCTGAGTTGTTTGACT
ACACCTCCGCACTGCAGTTTTTCGATATGCTTCGTGATCTGCTCAAGAACGTTGATCTTAAAGGGTTCGAGCCTGATG
TACGTATTTTGCTTACCAAATACAGCAATAGTAATGGCTCTCAGTCCCCGTGGATGGAGGAGCAAATTCGGGATGCCT
GGGGAAGCATGGTTCTAAAAAATGTTGTACGTGAAACGGATGAAGTTGGTAAAGGTCAGATCCGGATGAGAACTGTTT
TTGAACAGGCCATTGATCAACGCTCTTCAACTGGTGCCTGGAGAAATGCTCTTTCTATTTGGGAACCTGTCTGCAATG
AAATTTTCGATCGTCTGATTAAACCACGCTGGGAGATTAGATAATGAAGCGTGCGCCTGTTATTCCAAAACATACGCT
CAATACTCAACCGGTTGAAGATACTTCGTTATCGACACCAGCTGCCCCGATGGTGGATTCGTTAATTGCGCGCGTAGG
AGTAATGGCTCGCGGTAATGCCATTACTTTGCCTGTATGTGGTCGGGATGTGAAGTTTACTCTTGAAGTGCTCCGGGG
TGATAGTGTTGAGAAGACCTCTCGGGTATGGTCAGGTAATGAACGTGACCAGGAGCTGCTTACTGAGGACGCACTGGA
TGATCTCATCCCTTCTTTTCTACTGACTGGTCAACAGACACCGGCGTTCGGTCGAAGAGTATCTGGTGTCATAGAAAT
TGCCGATGGGAGTCGCCGTCGTAAAGCTGCTGCACTTACCGAAAGTGATTATCGTGTTCTGGTTGGCGAGCTGGATGA
TGAGCAGATGGCTGCATTATCCAGATTGGGTAACGATTATCGCCCAACAAGTGCTTATGAACGTGGTCAGCGTTATGC
AAGCCGATTGCAGAATGAATTTGCTGGAAATATTTCTGCGCTGGCTGATGCGGAAAATATTTCACGTAAGATTATTAC
CCGCTGTATCAACACCGCCAAATTGCCTAAATCAGTTGTTGCTCTTTTTTCTCACCCCGGTGAACTATCTGCCCGGTC
AGGTGATGCACTTCAAAAAGCCTTTACAGATAAAGAGGAATTACTTAAGCAGCAGGCATCTAACCTTCATGAGCAGAA
AAAAGCTGGGGTGATATTTGAAGCTGAAGAAGTTATCACTCTTTTAACTTCTGTGCTTAAAACGTCATCTGCATCAAG
AACTAGTTTAAGCTCACGACATCAGTTTGCTCCTGGAGCGACAGTATTGTATAAGGGCGATAAAATGGTGCTTAACCT
GGACAGGTCTCGTGTTCCAACTGAGTGTATAGAAAATTGAGGCCATTCTTAAGGAACTTGAAAAGCCAGCACCCTG
ATGCGACCACGTTTTAGTCTACGTTTATCTGTCTTTACTTAATGTCCTTTGTTACAGGCCAGAAAGCATAACTGGCCT
GAATATTCTCTCTGGGCCCACTGTTCCACTTGTATCGTCGGTCTGATAATCAGACTGGGACCACGGTCCCACTCGTAT
CGTCGGTCTGATTATTAGTCTGGGACCACGGTCCCACTCGTATCGTCGGTCTGATTATTAGTCTGGGACCACGGTCCC
ACTCGTATCGTCGGTCTGATAATCAGACTGGGACCACGGTCCCACTCGTATCGTCGGTCTGATTATTAGTCTGGGACC
```

Fig. 4 (Cont.)

```
ATGGTCCCACTCGTATCGTCGGTCTGATTATTAGTCTGGGACCACGGTCCCACTCGTATCGTCGGTCTGATTATTAGT
CTGGAACCACGGTCCCACTCGTATCGTCGGTCTGATTATTAGTCTGGGACCACGGTCCCACTCGTATCGTCGGTCTGA
TTATTAGTCTGGGACCACGATCCCACTCGTGTTGTCGGTCTGATTATCGGTCTGGGACCACGGTCCCACTTGTATTGT
CGATCAGACTATCAGCGTGAGACTACGATTCCATCAATGCCTGTCAAGGGCAAGTATTGACATGTCGTCGTAACCTGT
AGAACGGAGTAACCTCGGTGTGCGGTTGTATGCCTGCTGTGGATTGCTGCTGTGTCCTGCTTATCCACAACATTTTGC
GCACGGTTATGTGGACAAAATACCTGGTTACCCAGGCCGTGCCGGCACGTTAACCGGGCTGCATCCGATGCAAGTGTG
TCGCTGTCGAGCGGCCGC
```

Fig. 5

```
GTCGACAGCGACACACTTGCATCGGATGCAGCCCGGTTAACGTGCCGGCACGGCCTGGGTAACCAGGTATTTTGTCCA
CATAACCGTGCGCAAAATGTTGTGGATAAGCAGGACACAGCAGCAATCCACAGCAGGCATACAACCGCACACCGAGGT
TACTCCGTTCTACAGGTTACGACGACATGTCAATACTTGCCCTTGACAGGCATTGATGGAATCGTAGTCTCACGCTGA
TAGTCTGATCGACAATACAAGTGGGACCGTGGTCCCAGACCGATAATCAGACCGACAACACGAGTGGGATCGTGGTCC
CAGACTAATAATCAGACCGACGATACGAGTGGGACCGTGGTCCCAGACTAATAATCAGACCGACGATACGAGTGGGAC
CGTGGTTCCAGACTAATAATCAGACCGACGATACGAGTGGGACCGTGGTCCCAGACTAATAATCAGACCGACGATACG
AGTGGGACCATGGTCCCAGACTAATAATCAGACCGACGATACGAGTGGGACCGTGGTCCCAGTCTGATTATCAGACCG
ACGATACGAGTGGGACCGTGGTCCCAGACTAATAATCAGACCGACGATACGAGTGGGACCGTGGTCCCAGACTAATAA
TCAGACCGACGATACGAGTGGGACCGTGGTCCCAGTCTGATTATCAGACCGACGATACAAGTGGAACAGTGGGCCCAG
AGAGAATATTCAGGCCAGTTATGCTTTCTGGCCTGTAACAAAGGACATTAAGTAAAGACAGATAAACGTAGACTAAAA
CGTGGTCGCATCAGGGTGCTGGCTTTTCAAGTTCCTTAAGAATGGCCTCAATTTTCTCTATACACTCAGTTGGAACAC
GAGACCTGTCCAGGTTAAGCACCATTTTATCGCCCTTATACAATACTGTCGCTCCAGGAGCAAACTGATGTCGTGAGC
TTAAACTAGTTCTTGATGCAGATGACGTTTTAAGCACAGAAGTTAAAAGAGTGATAACTTCTTCAGCTTCAAATATCA
CCCCAGCTTTTTTCTGCTCATGAAGGTTAGATGCCTGCTGCTTAAGTAATTCCTCTTTATCTGTAAAGGCTTTTTGAA
GTGCATCACCTGACCGGGCAGATAGTTCACCGGGGTGAGAAAAAAGAGCAACAACTGATTTAGGCAATTTGGCGGTGT
TGATACAGCGGGTAATAATCTTACGTGAAATATTTTCCGCATCAGCCAGCGCAGAAATATTTCCAGCAAATTCATTCT
GCAATCGGCTTGCATAACGCTGACCACGTTCATAAGCACTTGTTGGGCGATAATCGTTACCCAATCTGGATAATGCAG
CCATCTGCTCATCATCCAGCTCGCCAACCAGAACACGATAATCACTTTCGGTAAGTGCAGCAGCTTTACGACGGCGAC
TCCCATCGGCAATTTCTATGACACCAGATACTCTTCGACCGAACGCCGGTGTCTGTTGACCAGTCAGTAGAAAAGAAG
GGATGAGATCATCCAGTGCGTCCTCAGTAAGCAGCTCCTGGTCACGTTCATTACCTGACCATACCCGAGAGGTCTTCT
CAACACTATCACCCCGGAGCACTTCAAGAGTAAACTTCACATCCCGACCACATACAGGCAAAGTAATGGCATTACCGC
GAGCCATTACTCCTACGCGCGCAATTAACGAATCCACCATCGGGGCAGCTGGTGTCGATAACGAAGTATCTTCAACCG
GTTGAGTATTGAGCGTATGTTTTGGAATAACAGGCGCACGCTTCATTATCTAATCTCCCAGCGTGGTTTAATCAGACG
ATCGAAAATTTCATTGCAGACAGGTTCCCAAATAGAAAGAGCATTTCTCCAGGCACCAGTTGAAGAGCGTTGATCAAT
GGCCTGTTCAAAAACAGTTCTCATCCGGATCTGACCTTTACCAACTTCATCCGTTTCACGTACAACATTTTTTAGAAC
CATGCTTCCCCAGGCATCCCGAATTTGCTCCTCCATCCACGGGGACTGAGAGCCATTACTATTGCTGTATTTGGTAAG
CAAAATACGTACATCAGGCTCGAACCCTTTAAGATCAACGTTCTTGAGCAGATCACGAAGCATATCGAAAAACTGCAG
TGCGGAGGTGTAGTCAAACAACTCAGCAGGCGTGGGAACAATCAGCACATCAGCAGCACATACGACATTAATCGTGCC
GATACCCAGGTTAGGCGCGCTGTCAATAACTATGACATCATAGTCATGAGCAACAGTTTCAATGGCCAGTCGGAGCAT
CAGGTGTGGATCGGTGGGCAGTTTACCTTCATCAAATTTGCCCATTAACTCAGTTTCAATACGGTGCAGAGCCAGACA
GGAAGGAATAATGTCAAGCCCCGGCCAGCAAGTGGGCTTTATTGCATAAGTGACATCGTCCTTTTCCCCAAGATAGAA
AGGCAGGAGAGTGTCTTCTGCATGAATATGAAGATCTGGTACCCATCCGTGATACATTGAGGCTGTTCCCTGGGGGTC
GTTACCTTCCACGAGCAAAACACGTAGCCCCTTCAGAGCCAGATCCTGAGCAAGATGAACAGAAACTGAGGTTTTGTA
AACGCCACCTTTATGGGCAGCAACCCCGATCACCGGTGGAAATACGTCTTCAGCACGTCGCAATCGCGTACCAAACAC
ATCACGCATATGATTAATTTGTTCAATTGTATAACCAACACGTTGCTCAACCCGTCCTCGAATTTCCATATCCGGGTG
CGGTAGTCGCCCTGCTTTCTCGGCATCTCTGATAGCCTGAGAAGAAACCCCAACTAAATCCGCTGCTTCACCTATTCT
CCAGCGCCGGGTTATTTTCCTCGCTTCCGGGCTGTCATCATTAAACTGTGCAATGGCGATAGCCTTCGTCATTTCATG
ACCAGCGTTTATGCACTGGTTAAGTGTTTCCATGAGTTTCATTCTGAACATCCTTTAATCATTGCTTTGCGTTTTTTT
ATTAAATCTTGCAATTTACTGCAAAGCAACAACAAAATCGCAAAGTCATCAAAAAACCGCAAAGTTGTTTAAAATAAG
AGCAACACTACAAAAGGAGATAAGAAGAGCACATACCTCAGTCACTTATTATCACTAGCGCTCGCCGCAGCCGTGTAA
CCGAGCATAGCGAGCGAACTGGCGAGGAAGCAAAGAAGAACTGTTCTGTCAGATAGCTCTTACGCTCAGCGCAAGAAG
AAATATCCACCGTGGGAAAAACTCCAGGTAGAGGTACACACGCGGATAGCCAATTCAGAGTAATAAACTGTGATAATC
AACCCTCATCAATGATGACGAACTAACCCCCGATATCAGGTCACATGACGAAGGGAAAGAAGGAAATCAACTGTGA
CAAACTGCCCTCAAATTTGGCTTCCTTAAAAATTACAGTTCAAAAAGTATGAGAAAATCCATGCAGGCTGAAGGAAAC
AGCAAAACTGTGACAAATTACCCTCAGTAGGTCAGAACAAATGTGACGAACCACCCTCAAATCTGTGACAGATAACCC
TCAGACTATCCTGTCGTCATGGAAGTGATATCGCGGAAGGAAAATACGATATGAGTCGTCTGGCGGCCTTTCTTTTTC
TCAATGTATGAGAGGCGCATTGGAGTTCTGCTGTTGATCTCATTAACACAGACCTGCAGGAAGCGGCGGCGGAAGTCA
GGCATACGCTGGTAACTTTGAGGCAGCTGGTAACGCTCTATGATCCAGTCGATTTTCAGAGAGACGATGCCTGAGCCA
TCCGGCTTACGATACTGACACAGGGATTCGTATAAACGCATGGCATACGGATTGGTGATTTCTTTTGTTTCACTAAGC
CGAAACTGCGTAAACCGGTTCTGTAACCCGATAAAGAAGGGAATGAGATATGGGTTGATATGTACACTGTAAAGCCCT
CTGGATGGACTGTGCGCACGTTTGATAAACCAAGGAAAAGATTCATAGCCTTTTTCATCGCCGGCATCCTCTTCAGGG
CGATAAAAAACCACTTCCTTCCCCGCGAAACTCTTCAATGCCTGCCGTATATCCTTACTGGCTTCCGCAGAGGTCAAT
CCGAATATTTCAGCATATTTAGCAACATGGATCTCGCAGATACCGTCATGTTCCTGTAGGGTGCCATCAGATTTTCTG
ATCTGGTCAACGAACAGATACAGCATACGTTTTTGATCCCGGGAGAGACTATATGCCGCCTCAGTGAGGTCGTTTGAC
TGGACGATTCGCGGGCTATTTTTACGTTTCTTGTGATTGATAACCGCTGTTTCCGCCATGACAGATCCATGTGAAGTG
```

Fig. 5 (Cont.)

```
TGACAAGTTTTTAGATTGTCACACTAAATAAAAAAGAGTCAATAAGCAGGGATAACTTTGTGAAAAAACAGCTTCTTC
TGAGGGCAATTTGTCACAGGGTTAAGGGCAATTTGTCACAGACAGGACTGTCATTTGAGGGTGATTTGTCACACTGAA
AGGGCAATTTGTCACAACACCTTCTCTAGAACCAGCATGGATAAAGGCCTACAAGGCGCTCTAAAAAAGAAGATCTAA
AAACTATAAAAAAAATAATTATAAAAATATCCCCGTGGATAAGTGGATAACCCCAAGGGAAGTTTTTTCAGGCATCGT
GTGTAAGCAGAATATATAAGTGCTGTTCCCTGGTGCTTCCTCGCTCACTCGAGGGCTTCGCCCTGTCGCTCAACTGCG
GCGAGCACTACTGGCTGTAAAAGGACAGACCACATCATGGTTCTGTGTTCATTAGGTTGTTCTGTCCATTGCTGACAT
AATCCGCTCCACTTCAACGTAACACCGCACGAAGATTTCTATTGTTCCTGAAGGCATATTCAAATCGTTTTCGTTACC
GCTTGCAGGCATCATGACAGAACACTACTTCCTATAAACGCTACACAGGCTCCTGAGATTAATAATGCGGATCTCTAC
GATAATGGGAGATTTTCCCGACTGTTTCGTTCGCTTCTCAGTGGATAACAGCCAGCTTCTCTGTTTAACAGACAAAAA
CAGCATATCCACTCAGTTCCACATTTCCATATAAAGGCCAAGGCATTTATTCTCAGGATAATTGTTTCAGCATCGCAA
CCGCATCAGACTCCGGCATCGCAAACTGCACCCGGTGCCGGGCAGCCACATCCAGCGCAAAAACCTTCGTGTAGACTT
CCGTTGAACTGATGGACTTATGTCCCATCAGGCTTTGCAGAACTTTCAGCGGTATACCGGCATACAGCATGTGCATCG
CATAGGAATGGCGGAACGTATGTGGTGTGACCGGAACAGAGAACGTCACACCGTCAGCAGCAGCGGCGGCAACCGCCT
CCCCAATCCAGGTCCTGACCGTTCTGTCCGTCACTTCCCAGATCCGCGCTTTCTCTGTCCTTCCTGTGCGACGGTTAC
GCCGCTCCATGAGCTTATCGCGAATAAATACCTGTGACGAAGATCACTTCGCAGAATAAATAAATCCTGGTGTCCCT
GTTGATACCGGGAAGCCCTGGGCCAACTTTTGGCGAAAATGAGACGTTGATCGGCACGTAAGAGGTTCCAACTTTCAC
CATAATGAAATAAGATCACTACCGGGCGTATTTTTTGAGTTATCGAGATTTTCAGGAGCTAAGGAAGCTAAAATGGAG
AAAAAAATCACTGGATATACCACCGTTGATATATCCCAATGGCATCGTAAAGAACATTTTGAGGCATTTCAGTCAGTT
GCTCAATGTACCTATAACCAGACCGTTCAGCTGGATATTACGGCCTTTTTAAAGACCGTAAAGAAAAATAAGCACAAG
TTTTATCCGGCCTTTATTCACATTCTTGCCCGCCTGATGAATGCTCATCCGGAGTTCCGTATGGCAATGAAAGACGGT
GAGCTGGTGATATGGGATAGTGTTCACCCTTGTTACACCGTTTTCCATGAGCAAACTGAAACGTTTTCATCGCTCTGG
AGTGAATACCACGACGATTTCCGGCAGTTTCTACACATATATTCGCAAGATGTGGCGTGTTACGGTGAAAACCTGGCC
TATTTCCCTAAAGGGTTTATTGAGAATATGTTTTTCGTCTCAGCCAATCCCTGGGTGAGTTTCACCAGTTTTGATTTA
AACGTGGCCAATATGGACAACTTCTTCGCCCCCGTTTTCACCATGGGCAAATATTATACGCAAGGCGACAAGGTGCTG
ATGCCGCTGGCGATTCAGGTTCATCATGCCGTTTGTGATGGCTTCCATGTCGGCAGAATGCTTAATGAATTACAACAG
TACTGCGATGAGTGGCAGGGCGGGGCGTAATTTTTTTAAGGCAGTTATTGGTGCCCTTAAACGCCTGGTTGCTACGCC
TGAATAAGTGATAATAAGCGGATGAATGGCAGAAATTCGATGATAAGCTGTCAAACATGAGAATTGGTCGGCGGCCCG
CGCACCCCAATGTCGAGCAGTGTGGTTTTTGCAAGAGGAAGCAAAAAGCCTCTCCACCCAGGCCTGGAATGTTTCCAC
CCAATGTCGAGCAGTGTGGTTTTGCAAGAGGAAGCAAAAAGCCTCTCCACCCAGGCCTGGAATGTTTCCACCCAATGT
CGAGCAAACCCCGCCCAGCGTCTTGTCATTGGCGAATTCGAACACGCAGATGCAGTCGGGGCGGCGCGGTCCCAGGTC
CACTTCGCATATTAAGGTGACGCGTGTGGCCTCGAACACCGAGCGACCCTGCAGCCAATATGGGATCGGCCATTGAAC
AAGATGGATTGCACGCAGGTTCTCCGGCCGCTTGGGTGGAGAGGCTATTCGGCTATGACTGGGCACAACAGACAATCG
GCTGCTCTGATGCCGCCGTGTTCCGGCTGTCAGCGCAGGGGCGCCCGGTTCTTTTTGTCAAGACCGACCTGTCCGGTG
CCCTGAATGAACTGCAGGACGAGGCAGCGCGGCTATCGTGGCTGGCCACGACGGGCGTTCCTTGCGCAGCTGTGCTCG
ACGTTGTCACTGAAGCGGGAAGGGACTGGCTGCTATTGGGCGAAGTGCCGGGGCAGGATCTCCTGTCATCTCACCTTG
CTCCTGCCGAGAAAGTATCCATCATGGCTGATGCAATGCGGCGGCTGCATACGCTTGATCCGGCTACCTGCCCATTCG
ACCACCAAGCGAAACATCGCATCGAGCGAGCACGTACTCGGATGGAAGCCGGTCTTGTCGATCAGGATGATCTGGACG
AAGAGCATCAGGGGCTCGCGCCAGCCGAACTGTTCGCCAGGCTCAAGGCGCGCATGCCCGACGGCGAGGATCTCGTCG
TGACCCATGGCGATGCCTGCTTGCCGAATATCATGGTGGAAAATGGCCGCTTTTCTGGATTCATCGACTGTGGCCGGC
TGGGTGTGGCGGACCGCTATCAGGACATAGCGTTGGCTACCCGTGATATTGCTGAAGAGCTTGGCGGCGAATGGGCTG
ACCGCTTCCTCGTGCTTTACGGTATCGCCGCTCCCGATTCGCAGCGCATCGCCTTCTATCGCCTTCTTGACGAGTTCT
TCTGAGGGGATCGGCAATAAAAAGACAGAATAAAACGCACGGGTGTTGGGTCGTTTGTTCGGATCCTCTAGAGTCGAG
ACAGTTCCTATTCCGAAGTTCCTATTCTCTAGAAAGTATAGGAACTTACG▨▨▨▨▨▨GCAATGAGTCAGAAAGGAGAAGA
CAGAGAAAGTGGCCAAAAAAATTTTGGAGGGATGACAAAAGCTTTCAAGAAGCAATGAAACTCATTCGTCTATAGATA
AAAGAAATTGAAAGAACTTATTCAGGACAAACACAATGATACACATAACTATACATATTATAATTAAAATGCTGAACC
AGCGACAAGGAGGAAATCGCAAATGCACAAAAATAAAATGACTCTCTATATACAGAAATACAGTGATAAAGCCATCAG
CTAACTTTTCATCGTGCCCAAAGGAGGCTAGAAAACAGCGGAATGACATATGTAAATGCAGGGAAACAAAACAAAACA
AAACCTAGGATTCAATATCCAGTGAAAGTATGCATTCAAAATAAAAGTAAAGTAAAAACATTTCTTGATAAACAAAAA
TGAAGAGAAATAATTACTTAAAGACATGCTGTATAACAATTTATCTAGGAAATTCTTCAGATTCACAAAAAATGACAG
CAGACAGTAACTTGAATCTGTAAGGAGGAAGGAAGGCCTCAAAAGTACTAAGGGAACAAAAAAAGAGCTAGACCAAAC
CAACATGTTTACTTCCGTTTATATGAGGTTTCGTATAGGGAAAGCCAATCTATTTGGACAGATGTCAGAATGCCAGTT
TCCTTGATTGGGATGGGGAAACAGCTGTTTCCTGAAAGGTAGGTACATGAGGGAAGAATCTGGAGATTCTGCAGTATT
CTACAGTTTAATCTCGGTGGAGAATATATGTAAAACTTTATTCGGTTGCACTTTTTAACATTTCTGTCTTTTACTTTG
TGTGTGTTTTATTTAAATTTTTAAAAAATTGAAAGGGCCAAATCTGAACTCTTTTAAACAAAAATGAACAAAAACATA
AGAATTAGTAAATATTTGTGGAAACATGGCCTTATTAACAAGAAGCATAAAATGTGCCTGGGAGAGTACTATGAAACA
```

Fig. 5 (Cont.)

```
AGAAATCTGTTAGGGAAGACAGAAGGAAATACTTAAATTTCTCCAACATAGACAGCATAGATTTTATGCCTATTCGTT
TCCCTCCAAACAGAGAAGATATTTAAGTCATTTTGCTCACAAGAGAGGCTCCTACCCTCCCCTTGGCTCTTTCCACCC
CACTGCACCCACCAGGTGATTTGCATATTATCCCTTAGTGAAGACTTTCCTTGTGAGTCTGAGATAAAAGCTCAGCTC
TACCCTTGCCTTGACTGATCAGGACTCCTCAGTTCACCTTCTCACAATGAGGCTCCCTGCTCAGCTCCTGGGGCTGCT
AATGCTCTGGGTCCCAGGTAAGGGTAGAAGGGAGATGAGGGAGGAGAATGGCATGGAACGGTGAGTTCTGGGGCCCCA
CTGCCTCTAACAACAGTGATCTCTGGGGGTCTCACTACACTCCTATGTGTGTTCCTTTCCTGTATTGGACATGCACAT
GTTGTCCTCCAGAGTGGGGCATGTGATGATCAGATCTGTGAGAGTGAGGAAGATTCAGGCAGAAACAAGGATCTGTGC
TCTGGGGAAGACTGACACAGAAAGGGGATGGTGTGGGGTCTTCTGGAGACCCCTTTGAGCCTTGGATCCCTTGAGTTC
CATTTTGAAACTGTGTATTTTTGAAATATGAACAAATACATATATAGCCTGAAATAAACAACAAATCAAAATTTATGA
AAATTACACATAAACTTTATACATAACCTTTGCTCTTCTTTCTATTTATTTCAGGATCCAGTGGGGATGTTGTGATGAC
TCAGTCTCCACTCTCCCTGCCCGTCACCCTTGGACAGCCGGCCTCCATCTCCTGCAGGTCTAGTCAAAGCCTCGTATA
CAGTGATGGAAACACCTACTTGAATTGGTTTCAGCAGAGGCCAGGCCAATCTCCAAGGCGCCTAATTTATAAGGTTTC
TAACCGGGACTCTGGGGTCCCAGACAGATTCAGCGGCAGTGGGTCAGGCACTGATTTCACACTGAAAATCAGCAGGGT
GGAGGCTGAGGATGTTGGGGTTTATTACTGCATGCAAGGTACACACTGGCCTCCCACAGTGGTACAGCCCTGAACAAA
                                         VK2-30
AACCTCCCTGTGGAGTGGCCCAGCTGCCCACATGTGGTGCTTGTCTGGGGAGCAGCTCAGCAGGGTCTCAGAATCTGT
GTAAGAGGAAGATGCTGGAGAACCAGGGAACAATTCACATCTGAGGACTCTGGACTTTGAGAGCCCAGCCACACCTCA
GGCACCACTCCTTTATGCCCTGCCAGTTGCCACCACCTTGACTGTCATAAGCAGCAGGAGAATGAGGGGTCCAAGTGC
CCTGTGAGTAAACAAGCAAGATGGAAGGGGGAGGAGAATGAAAGCTCACCCTAACTCTCCCTACCTTGTGTCCATTTG
TTAATTAAATGTAATTAGCAGAGCAGCCAGGCCATTGACACAGATTGTGACTATCCATGTTGGATACATCTTTGGGTT
TAGCAGTTTTTGGCATATCGTTCAGAGGACATTTGATAATATTTAATGTTGGTATTTTGCCAGTTTTCTAACTTCCTG
CTTCCCCTTTTCTCCCACTCCCAAAATAGAGTAGAGACAGCATTCTATACCAGTTATCCTAAGCGGAAGCTGGCTGAG
GACAGTCAGTAAAAATCTTGATTTTGGAGTATCAAATAGATTTTTGTAAATTCATAGAAGATACAAGATCCTAATGCT
AAAACTGTTTAGTTAGCCTTAGTTACCTCTTAATGATAGAAAAAAGGAGTACCTGAAATTCCAGAAGTTGTTTTCAAA
AATAAAAAGCATATACTGGAAAATGTAGAGTATATAATTTTTCCCATAGAAAACTGGAAAAGTACAGAATGATGTGAA
CGTTTTTATTTCCAAATGTTAAGAATTTAAGATTGGGCAGCATTAGGGATGAAAGCATGAAGGAAACCCAGGAGAGG
TCAGCTTCAATTAAACTACCCTTGGCCTTTGGTAGGTAGGGATGTGGATGGTGGTGGAGTTGGCAGTTCATGATGTGG
ACCCAGGAGGCCTGATGTGTTTCTTGTGAAGAATCACAGAGTTGAAGGCACCACTACCTGGCTTCCTGGGTGGAGCCT
GCATCACTGCGAATTTTCTGGGAAAATAATGCTTTGGGAAGGGTTTTAGATCTGTAATCACCAAAGGCTTAGTGAAAT
CCCTGTGCAAGGAGACCTGAGGTCATGTCACTCATATCTTGTCAACCCCACACAGCCAAACAGAGCATCTGAAACTCA
TTCTGTCCCTAGAGACTGCTGGTTGGGTCTGGAGATGTCACAAGCACTGACATGCTGAGCAGAAGGCCCAGCAGGGTC
TACACCAGCAGGGGGCGCAGTGGGGATGGAGACCAGTGTCCATGATTCAGACATGTATTCGGGATACATGTATCTGTG
TAGCCTTGGGGATTGGGGGAGCATGCTGAATCTGTGGAAGTTTTATGTCCTTGTAGCCCAGCACCTCCATCCCTGCCT
GCTGACTCAGACCTCAACATGTGTCCCATGGAAAGCACGGGCCACTTATAGAGGCTGCCCTGTGCAACCCCCAAGGCT
CAGCTGGATTCCCCTTTCCAGGAGAGCTCCTCTGCCTGTACCAAGTCAGAGCTTGTTTCCACAGGCGAACTTGGCGG
CTATGGCAGAAGGACAAAAAGTCAGGTGAGCATCAGCTCAACAATGAAAGGTTCTTTTTACTATGGAATTTTAGATCA
TGCATTCCTTATTCCTTCCACTACTTTCTAAAGTCATTTAATTCTAACTTTGGTATTCTATTGTTTAAATGGTTTGT
ACCTTTTGCAGTGGTTGTTTTGGCCTTTCCACTTCTATCTACATTGCTGTACCTGGGAATGAAGATTCCCTTCATTTT
TTTTTAAACACAAATAAAGTTTTAGAAGTGACTATGTTGGTACTATTTAGTCAAAAAAAGTAAAACATTTTTAAACAA
TAAATTAATGTATTATTTTCACTGTACCTTGTCAGTACTTGGACATAAACCTGATTCCCACATTCTAACAATAGTGAT
ATAAAAAATGTATGCTTTCCATAGAGTCAATTTAAAATAGTTCTCTATGAATATTTGTGAATTAGTAATGAGCCTGTG
ATTTACGTCCTATAGTGTGGTATGACTAAAGTAAAACAATGTTGCAATCAACAGGATAAAGTAATCCAGATTTAGATT
AAAGAAATATGTTACATTCGAGATAATTTTCTATTAAAGATAATGTATTCCATGACAAGCATAATTAAATCTGTAGTT
TTAACCAGACAGACAACATATACAGTAAAAATTTGGTTTATAGCAAGTGGTGTATAAGACAAAATTAATAACAAGTCT
CCAGAGTATATTTTTACACATACCAAAAAGTAAGGACACACATACAATCAAAATTTTATTCATTTCTTCATCACAGGC
ACCAGTTTGGAGCCTGGAGATG         GTTCTCCTGTGAGCAGAAAACTCACCAGGTCGAGCTCTGAACCAAGTGGA
CCTAATAGACATCTACAGAACTCTCCATCCCAAATCAACAAAATATACATTCTTCTCAGCAGCACATCGCACTTATTC
TAAAATTGACCACAAATGCCTTATGTAAATGACGAGTTGATGGGTACAGCAAACCCATATGGCACATGTACACCTATG
TAACCTGCAAGTTGTGCACATGTACCCCAGAACTTAAAGTGTAATAATACAAAAAAATGACATGTGACTAGTAGTATC
TTATCTAGAATCTTCATTCTAAGATACTCAAGGACGCATAAAAGGGACCCTAAGTAGTCTTTTCATACATATATATGC
ACATATATATGTATGAAAAGCAGTCTTTTCATCAACTAGAGAAACCCTCAGGACAGCCCTTAATACCCTTGGTGATAC
ATTTCAGATGAGTAAACTGTTATCAGAGCCCGTAGTTGAAACTATTCAACAGAGATGGTTTGCCCAAAGATATGTGGT
CAGCAATTGTCAGGGCTGAGCTTGGAACCCAGGTCTGCATAACCTTAAATATGTTGCTTCCACATGGCCACGTTTGGT
TCATATACGATTGAATGGCCTTTAAATTCAAAGAAGAGACAAAGCCAGAAGAGTGGTGTGAAATTCTCAACACAAGCT
CCCTGCTACCTCTACACCTTACCGTGATTACTCCAATTATAAACTCAGGCCCTCATGCAGTTTTGTCTACAAAGCAAA
```

Fig. 5 (Cont.)

ACTTCCTCAAAGTCTTTACAAATACTAAATGTCTTTCTTTCAGATTCGAGGGCAAGAGCACATCTTGCATTGCCCTGA
ACACTTTGCATCTTTTCTACCATTCTCATCTTTCTGTCCCAGTCCTTCCTTCTCAAATGATGTCCTGTAAATCTGATT
TCTCCCCCAATATGAAAACAAATGAACAAATATTCCCCTACTTTTCTCATATCCAGAGGATACAAGAGTTAATCACAT
ATCCAGAGAGTACGAGAGTTAATCAAGGGATTTATGCAAGAGTGTTTACACATAACAAGGATTCTGGTGCTAGCCATC
TTCACAGTGAAATTTTCTGTGTGTCTTGCTAAAATTGACACTAAAAAATGACAAGATAAAAATATTTGGAAGAACAGA
GGGCAACCATGCCCTTAAGGAGGCAAAAGACACCCCTGCCCCTTGTGTTAGTTTCCTACTCCTGCTGTAACAAGTTAT
CAGAATCTTACTAGTTTCATACAACACAAATTTATTATCATACAGTTCTGGCAGTGAGAAGTCTCACTGATTTATAAT
CAAGGTATCCGTAGTTCTATATTCCTTCTGGAAGTTCCAGGGGAGAGAATCTGATTCTCAGCTTTTCATCTTCAAAGA
TAGCCCCATGTTCCGGGCTGCCTGGCCCCTTTCTCCATCACTGAAGCATCCCTGTCCATTGTCCCTATTCCTCTCTGA
CTGTTACCCCCACTCCTCCCTATTATAAAGACCCTTCTGATGACGCTGTCTTTCCTAGATAATTCAGCTGTTTCCTAA
ATTTTCTGAATATCCCTATGCATGAAAAAAAAAGAATTGGCAAGTATTCAGACTATACTTTCCAAGAATGAGGATTTG
TCCACTGTTTTAGGTTGGATCTTTCAGGGACAATGATGCCCATGCAGGCAGCATATTTATAATGCACAGTAAACACTA
GGAGGAAACAAGGCAGTGAGAGAGGAAAGAGAGCAGCGATACCGAAAATGTCCTCAGCGAGAAGCTACCACAGAGGAT
GAATGGAGATCAAGCCCACGTGGAAACATGGGAAAATGTCTCAGTATTTTTCCACCTAAGAAGGGAGGGAGATGGGGT
ATGTATACACCTCCCTGTCCTCACTGATTGAGGGCTTTCCGAGAGGATGCTCATTCCAGGTGCTGTGATAGGCCATGT
GTACAGGCAGGGCTGCCTTCTCCAGCTTCAGATAGAGCAGTGAGGAAAAGATATGGCCATGGGGGGTCAGCAGAAGTA
CAGCAAAGGGAAAAGGGAAAGGGTAGCAAGAGTGACAACTATATTCACCCCCCCCACACACACACACACACACACGAA
ATTGTGTATTGCAATCCAGAACTGCTTCTCTCTGAACCTAAATCTTAGCAAGCAGTTTACCAGTAACTGCCCTTGAAA
TTCAGGCCCCTGGAAAGGAGCAGGGGGTTGTGTACAGGCTATACCACAGCAGTCTGCCCACCCTTAGTGATGCATGAG
TAATGCTCCCTGGACTCCCCAGGTTCTAGTCTTCTCATGTCGATGTAGTTGATTCCACTTCCCTTGCTGCACAACCAG
GCTGGGATGCCTGGGCAGAGGCAGACATGTGAGGTATAGGGGTTCAAATCTGTTTCCAAGTTTTATCCAGCTTCAAAG
CATTTCTCCGTGTACATGAGCGGTGGCTTGACAGGAGATGGAGACTCTCTTTCCTGGATGTGAGGCAAGGAGGCAGGC
GTCTGAGTCAGGATGATGTCCCTACTCACTGCTAAAGAGAAAAGTGGCTTTGATGGTGCAGGGCAGGGAAATGCACTG
AGTGGTCGCCACCCTCACAGAAGAGAAAGTGTTCACTGACCTGGCCTTTCCCCAGGGCCTCTCCCTCCCATTGCTTTC
CAGAAAGCCATGATTTTTGAGAGCCACACCTGAACACTCACAAACATTATGGTGGGAAAAGCAGATCAGAGCATTAGG
CAAGTTGCATTACCTTGGCCTTCTTCCTTTGGAGACAATTGATGTGGGGTTCTAGATTGACCCAGAGTTTCAAGTTTA
TCCTGATTCAGGCTTCAACAGCTGGAGGAAGAAACAGAGATGTTTTTTGAAGTAAACAGATCTAGCATTACTAATCAA
CCCTTCATACTGATGACCTATGGGAAATAATACCCAAGGGCAGAAAATGGGCAGAATAAGGGGAGCCCCAAACCAAG
ACGAAGCTGCTGCCCATTGAGACCCTGGGTATTACAGAGACCTATAGCTCTGGATAATGGAAGATCTATGAGTGGCAC
AGGCGCTGAGGAATCACAGCATCATTATCGTGCATCTGCAGGGAATTGCTTGTAAATATACTGGTAATTACAAATGTT
TAAGGTCACTACAAATACTTTGGAGTGTATTAAATATGCTTCTGATAAAGACTGTTTTTCTCACATGAAACAATGGGA
ACCATGTGACAATCACAGAGGTGTTGTTACTATAGCAAAAGGGATTGTTACTCTCCACATCCCTTTAAGTAACTTGAA
GGCCTGATAGACCCACCCTCTAAGACTTCATTAGACATTCCCTACGAATGGTTATACTCTCCTGTATACTCCCAATAC
AACTCTAAAATATATTATTCCATATAGTCCTTAGGTTTGTATTAAAGTTTGACTTTTTTCCTTCAAAATATCTCTTGT
CACAACAGCGGCTCTAGAGAGAAATACATTCCTTCCAGGCAAATCTATGCTGCGCTGGTCTGACCTGGGACCCTGGGG
ACATTGCCCCTGTGCTGAGTTACTAAGATGAGCCAGCCCTGCAGCTGTGCTCAGCCTGCCCCATGCCCTGCTGATTGA
TTTGCATGTTCCAGAGCACAGCCCCCTGCCCTGAAGACTTTTTTATGGGCTGGTCGCACCCTGTGCAGGAGTCAGTCT
CAGTCAGGACACAGCATGGACATGAGGGTCCCCGCTCAGCTCCTGGGGCTCCTGCTACTCTGGCTCCGAGGTAAGGAT
GGAGAACACTAGGAATTTACTCAGCCAGTGTGCTCAGTACTGACTGGAACTTCAGGGAAGTTCTCTGATAACATGATT
AATAGTAAGAATATTTGTTTTTATGTTTCCAATCTCAGGTGCCAGATGTGACATCCAGATGACCCAGTCTCCATCCTC
CCTGTCTGCATCTGTAGGAGACAGAGTCACCATCACTTGCCGGGCAAGTCAGAGCATTAGCAGCTATTTAAATTGGTA
TCAGCAGAAACCAGGGAAAGCCCCTAAGCTCCTGATCTATGCTGCATCCAGTTTGCAAAGTGGGGTCCCATCAAGGTT
CAGTGGCAGTGGATCTGGGACAGATTTCACTCTCACCATCAGCAGTCTGCAACCTGAAGATTTTGCAACTTACTACTG
TCAACAGAGTTACAGTACCCCTCCCACAGTGTTACAAGTCATAACATAAACCTCCAAGGAAGCAGATGTGTGAGGACG
VK1-39
AGCCACCCCAGATGCTCCTCCTGGTGCCTCCATCTGCTGAGAGCATTTCTCAAACTCAGTCAGGTTTTGAAAGTCATT
GGGAGACTTTTGTAGAGGGGACCAGGGAGGCTCCTCTGAACTCTAAGCCTCTTTTGCCCCTATCCCCAGGAGAAAAGA
TGTGACAATGCCTGTCCTGATTGAATAAGGAAGAGATACAAGTCCACCTGAGGAGTCTGTGTTATGGGATAATTGGAA
TTTACACAGCAAAAGAGAAGCTATTCTCGGTATTTCAAGGAGAAATTGTTCAAGTTGAATAAATTAGAGTCTAAACTA
GTCTTTTTGAAGCCTACGGTATGTTATTCGTGAAGCAGCCACTAGAGACAGGGGATTCTCAGATGCTCCTGCAGAAGT
CAGAGTGCACCTGCCCCTGGTGGTATGTGCTGAGTACCGTGTGATGATCCTCAGACCTGTCTGGGAAGCCGAGGGCTG
GGGTGCTGATGCTCTCAGCTGCCTGCAGCACGTCTCCAGGTGATTCTCCAGTCCACAAACAATTCCACATGTTTTACT
TCAGATGTCAGAGTACATGAATCCACCACTCTGACTTCCCAATCTCATGGGAGTGCCTCTCATTAAGCAACTCTAAAG
AAACCATAGAGAGAAAAGGAGTTTTGGAAAATGTGCGTCCAGAAGTGATAGTAGCGATGGGAATTGACAGCTGACAG
GTCAGTAAGGTTGCTCTTTCCACAAGGCTCAAAACTTTGCCAGTTACAGATTGTCCCAGAATATACTCGAATGTGCTA

Fig. 5 (Cont.)

TCACGTCTTACGAGCAACTCTGGGTTCATAGCAAGAAAACTTCATTAAGTCATAGATGAAACAGAAAAATCAGGAAAC
TGTATGAAATACATTATAAGGCTGTGTGTGGTAGCTCATGCCTGTAATTCCCAGCACTTTGAGAGGCTAAGGCAGGAG
AATTGCTTCATCCTAGGAGTTTGAGATTGGACTGGGCAACATAGGAAGACTCTGTCTCTACAAAAAACAAAACAAAAC
AAAAAGATAAATAGATAGTTATAACAATCGTTTGACAACCTTTTTCCTTGACAAAAAGGAAAACAAGAGAAAATCCTA
AACATGGATGTAGCATTTTTCCTCTTAATATGAAAGTCCTCTGCTACTCAAAACTATCCAGAATCCAGTAGCACCTTA
GCAATACTGAGAGGGTGCCTTGCAAGATACATAGCAGGCCCACCTCAAATTACCTGAAAGAGAATCTTCATTTTAACA
CGGTAACAAGTGATCTACATAAAGCTTAACAAGGTATGTTTTAGGTGATATTTTAGCTAAAGAGATTTATTTTTTCT
CAATGAGGATATTTAAGAAAATTTCAATGGAGAGTCACATGTTGAAAGCACACCCAGCTTTACTTTCAAATTGATGCA
ACATTGCATTTGAAAACATTTTGAAGATTACAAAGGTTGAAAATCATAATTATATATGTCCATAGAATTATCAAATAA
CTTCATGTTTAAATGGAGTAAACATTTTAGAAACTTTAATAATTACCAAGTGAAAGAATCAATTAAAGTTGTGTGTA
CCTATGTTAGAGATTCTCGGGCTTAATTGTATCAGGTCAGCTTGGTTTGGGATTTGTCTACTCCTGCGACCCTGCCAT
GAGAATCTTCTGCCCTGAGTAGTCAGTGCCCTTCAGGCTTGGCCTCAGATAAATGCAATCCATAGGCTGGAGACAAGC
TCGATTCCCTGCAGCCGAACCAACCAGCTGAGCCCTGCCTTGGGATCAGCCAACTGATTATTAAAATGAACATTCAGG
AATATGAAAATAAATACTTAGTGTTAATAAGACACTAAGAGTTTAAGTGGTTGATTGTCAATAATTATTGTGCAAAAA
CTGACCAATACAGTATTTATACATCTACCTATTTAGATAGATGCATTTTATTAAAATTGATGGCATAAATATGAATAT
TTATTAATCCATATATAGAGATACTAAGACAACATTTAAAACATTAAAACTTAATACCAATAAAAACCATGAAATTGA
TGTCATTTGGGGAAAATACATATTTGAGTGTATATAACATACATATTGGTGCATTTATATTTTGAAAAATTATTGGC
TGCATATACGTATATGTACACATATTTATCTTTAAATAAGTCTATTTAAGTATATTTATATATCCATATAGAAGTAAC
ACATGCATATTTACAAAACAATTATGTAAAAATGAAATCTGTGAAGGTGATTTCAGTTTCCCCCCATAAGAACACTGG
TGCCCGAGACCTGGTGTAGTATCTGCTGTGGCTACAGAAAGTTCCTTTATAACCTTTAGTTATAAAATACTCACCTAA
TGGGTATTTACACCTTAAAATATTTTTCTAACTCAAGTGGAGGGGTAAAGGGTATGAATGGGGATAACTGCCTACTGT
TAAAAATTAATCATTTCATCCTATGGAAGTCCAATCATGCATATGCTGCCAATGATGCCATGCTGGATGGAGTTCTCA
TAACTGGGTGCTGTATTGATGTTATACCACTGCCATGGTAAAGGATACCCTGGGAGACTAGCAGTCACAAGAGTGGGC
AAACCCGAAGGGTGAAGTCACCGTACACTTTGCAAAGAGGGATTAGCAATTCCATAACATTGGCTATTGGTTTGGAGA
GATCACCAGGTCGAGCATTCACCAGGT▨▨▨▨GAGCATAGTACTGCAATCTATTACGTTGGCTCTCCCCAGATGTT
TTCTCTCCAGGACAGTGCGTGTCCTTGTGAAGGGATCTGATGTAGGCACAATCTTTCAAGAGCTGTTCAACTCAATCT
TGAGCATATCATTGACAAACAAATAGTTGGATTGTTTCCCTGTTTTCATGATCAGCTGTGTGGTAGATTGACATCTCT
GAGCTGTGATCGTCTTTACATGAAAGCTCAGGAAAATGCCAGTCATGGGTAATGGTGACCATGAGACAGTAAAGCTGT
GGATCCAGTTCGTGCTCTTCTTACATAGAGAATTTCCACTCGAATTGTGAACTCATGGCTGTGGCTGCACCACTTACA
GGCCCAGGGGACACTCAGATCTCACTTGGTAGTTGACGAAAAACTGGAAGTCCTGATAGGACCTCATTCCACATGATG
AGGAAGACTGTGGGAAGAGCTTTTGTTAACACCATTCAGAAAAACATAGTGCAAAGTTAGTTTTTGTTCTTTCTATAT
AATTATCCTAGAAAAGTCTTCCCTTAATAAATCCTTCTGGTTAATCTGGCATATGTGAGATGATTATGATGGGATATA
TACCAGATTGAACAATTGGTCACCAGGAATTTTATATTCACTGCCTGAGGAATAAATTGTTTCCCACTTTCCTCTTAC
CTGCACTGGGCTCTTGAATCTAAATATAGAGACCCACATTATTTTCCCTATGAGGCCCTTGACAGAGCGCTCTTATG
GGGCTCACTCACCAGGTGCCAGGGGAGGGTAGATTCCAACACTTGCTATGAACATTCTTGAACAGTTATCCTGGAAAC
CGCAGATACCAGACCACTCTTGAACTGGCTCAAGACTATGTTTTATTTGTAGGCTGTCTGCTCATCAGTGCTTGTAGG
AAAGGGTAACGTTTCCTTTTTTAGATTAGCTGGGAGGGAGCCAAGAAGAATGGCATTCATCCATATTCATTCTAGACA
TATCTCTACATTGTTAGGGTTGTTATGCTTTCCTAGAGTTGCATATCCTATACAATGGGACCTACCCAAGATCCAAAC
TGTCACAGTCAGATCCTTCCTCCCATTTTATATCACATTGCTCACAGGAGAGACATATCCCCTGCCCGCCTGCCCCAT
TGACTCTTTCCACACCACTGCATGCACCAGGGGATTTGCATATTGTCCCACAGGGAGGACCTTCCCTTGTGAGTCTGA
GATAAAAGCTCAGCTGTAACTGTGCCTTGACTGATCAGGACTCCTCAGTTCACCTTCTCACAATGAGGCTCCCTGCTC
AGCTCCTGGGGCTGCTAATGCTCTGGGTCTCTGGTAAGAAAAGAAGGAGATGAGGAAGGAGAATAGGGTGGGAGGGTG
AGCTCTAGGGCTCCACAGCATCCCATGATCCCATGTTTAGTCTTACCCTGTGTTAGAGGAGTATAATCTGTGCTGTAG
AAAAGGGAACTTGATATTTTGCTCTGTGAATAATTAGAAGCCTCATAAGAAATATGACGTCTGGTGCTCTGATTAAGA
TCTTCAAAATATAAAGGTCTCTTATACTTTACAAAAATTGAATTCATTTTAGAATGTGTATTTTTATGGCATAAATCA
CTATTTTTAAAATTAAGTTTAAATAAATGACATAAGATAAATTATGAAAATTGCTCATTAGGTTTGTACATAACTTT
GCAATTCATTATTTCAGGATCCAGTGGGGATATTGTGATGACTCAGTCTCCACTCTCCCTGCCCGTCACCCCTGGAGA
GCCGGCCTCCATCTCCTGCAGGTCTAGTCAGAGCCTCCTGCATAGTAATGGATACAACTATTTGGATTGGTACCTGCA
GAAGCCAGGGCAGTCTCCACAGCTCCTGATCTATTTGGGTTCTAATCGGGCCTCCGGGGTCCCTGACAGGTTCAGTGG
CAGTGGATCAGGCACAGATTTTACACTGAAAATCAGCAGAGTGGAGGCTGAGGATGTTGGGGTTTATTACTGCATGCA
AGCTCTACAAACTCCTCCCACAGTGGTACAACCCCTAACAGAAACCTCCTCCTGGGGTTGCCTAGTTGCTCACATGTG
VK2-28
CTGCTTGTCTGGAGAGCAGCTCAGCAGGGTCTCTGAGTCTGCAGAAGAGGAGGCTGTTGGAGACCTCAGGGCAGAGGT
TGCTGCTGAGGACTCTGGCTCATGATAGCCTCAGCTGTACTTCAGTCCCACATGTTAAGGCCCCATTAGGTGAAAAAT
AAATGATTCCAAAAACTGAGATGAAATACCAAGGAGAATCAGAGTACAATTAAGGCTGTTACAAAGAAGCCTCAAAAT

Fig. 5 (Cont.)

```
ATGGTGGACTAAATGTGACATGGTTTCTGTGTCTGTTGCCTGACAGTGCAGAGGCAGGTGGTCGAGCGATCTCTGCAT
AGCTGCCCTTTCCCCCCGGGCTCTGACATTAGCAACAGTGTCCTCCACCCTTGTGACTGTCCTGCTCATCCTCATCC
AGCTGTGATGTCCTGCATAAGTGGGAGGAGGGGTCTTGCATC░░░░░ACCCAGGTAGGGATACTTGTCTCTGCTAAC
TATAGCTTCAACGCCCAGGTGGGCTTTCCTCTACACCCCACAACACGGGTGCACTTTCTATACTGTGTAGGCTCAGTA
TCTCATACAATTCCCTGGCTTTTTGTTGCATAGTTTTCTTTCTGAACCTGCTCGGATCAAGTGCCCTAAACCCAGTCA
CTAAGAACTGTTTTCTCTTAGGAGCTGGAAGAGATTGGTGATTTGGAAATATGCAGGTATAAGAAACAGAGTAGTCAC
AGGGATAGAGGGTGACAACTTGGTTTAGAGGACACCTCAGCTTCTGAAGGGGAATGGCTTGGATAAGAGAAATAAAAG
GCATAAATAAAATTCAGGGAGCACAGGGAAATATCTAGCATGAGACTGTAGGATGGCATACAGAGCTAGAATATAGCT
GAGAACTTTCAGAAGTAAAGGGAGAAAATTTATCATGTTGGCTGGCCCAGCTGAAAGAGGTAGGAAAGAACATTCAGA
TATGGAGGATAACAATTATGTGTCTGGAGATGGGAGATTAGCTATGCCAGATAGCCAGTGGCAGGACCCTTCCTTGCT
GTGGCACTATTTTCAAGTATTAGGTTTTTTTTAAGTTTTTTATTTCTTTTTTAATGAGCAAATCTATCTATCTATCTA
TCTATCTATCTATCTATCTATCTATCATTCATGATTATACCTTAATGCATCCATTGTTGGTAGCACTGACAATT
TACAGCACTGGTGGTTCCAGGGAATTGGACCAAAAAGGAAGTCTCTCTGACCTTAATAGTACTCATCTGTATCAAATG
CAGGAAACTTCTAAAATGTCTTGAGTTTCTAGAGATGTTTTTCCCTAGCAGACCTTGTCATAAATAGAAAGCTAGCAA
GAGAAGCATGTCATGAAACATGAAGAGAGCAAAAGAACACTCCACATATAGGACAGTAGGCTGATTCTGTCCTGTAGC
CTGCAGGGAGAAACACATGCTCTGCAGACTTTGGACACCTGGGAGGCACTGGGCCTGTGCAGTGTTATTGAGATAAGA
CATCTTTGCAGCTGTGCAGATTTGCATGTCCCACAGAGCAACGCCTACTGCCCTGAACATTTATCAATAGGCTGGTGA
CATCCTGTGCAGAAGTCTCTCTCAGTCAGGACACAGCATGGACATGAGGGTCCCTGCTCAGCTCCTGGGACTCCTGCT
GCTCTGGCTCCCAGGTAAGGAGGGAAACAACAAAAATTTTATTCAGCCAGTGTAGCCACTAATGCCTGGCACTTCAGG
AAATTCTTCTTAGAACATTACTAATCATGTGGATATGTGTTTTATGTTCCTAATATCAGATACCAGATGTGACATCC
AGATGACCCAGTCTCCATCCTCCCTGTCTGCATCTGTAGGAGACAGAGTCACCATCACTTGCCGGGCGAGTCAGGGCA
TTAGCAATTATTTAGCCTGGTATCAGCAGAAACCAGGGAAAGTTCCTAAGCTCCTGATCTATGCTGCATCCACTTTGC
AATCAGGGGTCCCATCTCGGTTCAGTGGCAGTGGATCTGGGACAGATTTCACTCTCACCATCAGCAGCCTGCAGCCTG
AAGATGTTGCAACTTATTACTGTCAAAAGTATAACAGTGCCCCTCCCACTGTGATACAAGCCCGAACATAAACCATGG
VK1-27
AGGGAAGTAGATGTGTGAGTCTGGGCTGCCCCAGCTGCTCCTCCTGGTGCCGCCCTCTGCTGACAGCAGTTCTCAGAT
GCAGCCAAGGTTTGAAGCTCCCTGGGAAGTTTTGGTAGAAGGGGTCAGGGAGGCACATTTACATTCTATCTCTCTTTA
TCCTCAGCTCCATCAGCTGATATGCAAGTATCTCTCCTGATTATTATTAATAAAGGACAAAGAAAATTAAACCTAGGA
GGTCTAGATTGCAGCAAAAGTCAGACTTATACAGAAAAGGAGAAGGTACTCTACATATTTTAAAGAATTTTTTTTGA
TACAGGGGATTAGAGTCTAAATTATGACCTTTCAAAGATCAGACATAAGTACATACACATATAAGTATGTTCAGCCAA
CAACATATCAGATAAACATATTGCACCTATATGTATACTGTAAACATTTATGCTCCGATCCCACCTTCTTCCG░░░░
CAGTACTGTGTACTAAGTGAAGAATAAGACATTACCTGTTTTTTTCAAGACTTGCTACAAATAGATTAAAATGTTACA
TAGTCCCCTGTCACCATGGAGCAACTCAGTTTGGCGGGGCAAAAAGACTTTAGGGGAACAGAGACTAACGATGGACTA
TTTCACGTTGAATGCTAAGGCCACTTGGACAGGAAACCAAGGAAGGATAGCAGATATAGTTAAACATTGTTGGTACTA
GCAGCAACCATTAATAAAGGACAACAGCTGGTAGGCTTCTTTGAGTATTGGTAACAGCATAAACCTCTCTGGGGTGGG
CTTTCAGTCCCCTTAGTCAAAATCAAAATCACAAACAAAACCACCAACCTTGAACAGAGCCCTTTGCAACAGCAGCCT
TGGAAGAAGTTCAACAGGACATGGTCCAAACACTTCTTTTAGACCTTTAGAGCCTGTTAGCCTGATGGAAGTTCAGGT
GTCCACAGTCTCTATGTATGCTGACTGTAGTATGTGGCAACAGAAAATTGTCACTGAGTGAGCCAGCCTCTCAGATAC
TGAACACAAACCAGCTGAAGCAGCCACCAGATGTCCCTCTTTGGCATAGCAACTCCTTGCTTGCTATGGGAAACTGAC
AGGGACTGGACATCTTGGGGCTGAGCACCAAGTGTGGCGCTGCTGGGTGAACTGCTCCTTTTCACTTGGGTGCCTAAA
ATCCAACCAGTGAAACTGGACAGGCTCAATAGAGCTGCGTTATCAAATGGAAATGGTGTATTCAGAATCAGGCCCAGC
CAGCAACCCGTGGGATCCAAAGGCTCCATAAACAAATGGCGAGCTTGCTAGAAGGGACTAAATGACCCATGGGGATG
GTTTGGCTCTGCTTTTGGCTACCCGAAGTCCAAGATTCAGAGACATGCCGACATCGGTATGGCATGGTTCACTTAGGG
CTCTGCAAAACATGTAGACTGGGGGTGGCTACCATCTAGCCAGTGGATGACTATTTCTTTCCTGAGACTGATAATGG
TCATTCCACCCAATGGTCCAAACTACATGCAGTGGTAATGGTCATGCAGGCCTTTCTGCCACCTCTTGCTATATTTTT
ACCAACTCATGGGCCACTGCCAACAGTCTAGCTATCTGATCAGGAAAATAGCAACCGAGTGACTGGACTATTAAAGCA
TCCCCTCTGTGGAGAAAAGGACTATGGCAACAGCTTGCCACCTATAAGAGACAAATATGTCACTCAGCTGGATGCTGG
GTCTACCATGACCACCCTTGAGATGAACTTATGCCATGTTTTGGATGCCCACTGAGACTTTGCTTTGACCAAGGAAA
GTTCTTTACTGCCCAAATGACGTCAATGGACACACTCTCATGGGACATGATGGATTTTCCATACACCTTGTTATCCAA
AGGCCAATGGATCTATTTAATGCTAGAACAGCTGACTCACACGGCAACTGAAGAGTGTACATCAGGGCAACCTGCTAG
TAGGGTGGTACCCCATCTGACTACAGCAATTGGACATTAAACCTGCACTGCAGAGCAAGGGAAAGACGGCACGGAGG
TGCAGGTTGAAAAACACTGAGTTGAGTGAGGAAGAAGTTGGGCAAGGCCCAGTTTCCTGATAGACGTGCCACTGTGAA
ATCCCAAACTCAGTGTTTCCAATCATTTTTTCCTTTTATAGTGATGTTCTTGGGGGTGTTGCAGTTTAGGCCACCAT
GATAACCCAGACAGGCCTCCTAACTCTAATTGGATGGAATGATTCCCCTGGGTGCCTTCTATGGGTTCCACAGGATCA
AGAAATATCAGGGTGTTAATTTCCTTCTGCTGGTAGGAGGGTCATCTGATTCCTCCATTAGGGTGGATGACGTTATTA
```

Fig. 5 (Cont.)

```
GACATGTCAATTTTCTACAGTACTTGACCTGCCTTCTAGAACTGGACAACCGAGGGTGAAAGGACTGGATCAAGCAAC
AATGGCAATGGGTGCCCAAAGAGGTAGTAGTCTCAGAACAGGGAGAGACAGACTGAGTCCCTCCACTAACTCAGCCCA
ACACCTGTGGATGAGTAGGGGATGCCTGAGATCCTGGGGTGGATGGGAGGTGGGGCACTGATCTGTCAATCTGCTTTT
TCTTCAAGGATCAGGCAGCAGAGACCCAGAAGCTTCATGTCTTTGTAAGGCTCTTCCAAGCCAACACAGATAATTTGA
CAAAACACTGTATCTGCATCCCAGACCTCACCCTGTCACAGACTGAAGTGGTTGTTTCATCCTACTAAGGGTAAACTA
TACCAGCTATACAGAATAAAAGGACTGGATAGTTTAGAGGATCACCCAAGAAATAGTTCTTTGCCTGCATGGACAAAA
CCATCTTCTGTCTTTAGGGAAATGGTATCACTACCCTGAGGATTTGGAGCCCAGGTCTCACTTATCTGTGCAGTTGTG
AAAGTCCTCACACCCACAGTGCTGAGGTTAATTGAATGTTACTCTTTTAATTTCTGCAAAGAATGAGACAGCTTCTGG
ACCCTCAGGAAAGATCACTAACAAGTAAATACAAGTATATCCGGAAGATAAAGTTGTAATAGACTCTTCCTTTCAACC
TGATCCATCATGCATTTAGGGAGCTGACTGGGCACAAGTTGGAGCAGAAAGAGAAAAATGAAACCACAGCCTTCTATT
TTGTTTCTAACAGACTTGTACCAAACATTCTGTGGCTCAATCTAGGTGATGGTGAGACAAGAGGACACAGGGGTTAAA
TTCTGTGGCCGCAGGGGAGAAGTTCTACCCTCAGACTGAGCCAACGGCCTTTTCTGGCCTGATCACCCGGGCATGGGC
TGCTGAGAGCAGAAAGGGGAGGCAGATTGTCTCTGCAGCTGCAAGCCCAGCACCCGCCCCAGCTGCTTTGCATGTCCC
TCCCAGCCGCCCTGCAGTCCAGAGCCCATATCAATGCCTGGGTCAGAGCTCTGGAGAAGAGCTGCTCAGTTAGGACCC
AGAGGGAACCATGGAAACCCCAGCGCAGCTTCTTCTTCCTCCTGCTACTCTGGCTCCCAGGTGAGGGGAACATGGGAT
GGTTTTGCATGTCAGTGAAAACCCTCTCAAGTCCTATTACCTGGCAACTCTGCTCAGTCAATACAATAATTAAAGCTC
AATATAAAGCAATAATTCTGGCTCTTCTGGGAAGCAATGGGTTTGATTTAGATTACATGGGTGACTTTTCTGTTTTA
TTTCCAATCTCAGATACCACCGGAGAAATTGTGTTGACGCAGTCTCCAGGCACCCTGTCTTTGTCTCCAGGGGAAAGA
GCCACCCTCTCCTGCAGGGCCAGTCAGAGTGTTAGCAGCAGCTACTTAGCCTGGTACCAGCAGAAACCTGGCCAGGCT
CCCAGGCTCCTCATCTATGGTGCATCCAGCAGGGCCACTGGCATCCCAGACAGGTTCAGTGGCAGTGGGTCTGGGACA
GACTTCACTCTCACCATCAGCAGACTGGAGCCTGAAGATTTTGCAGTGTATTACTGTCAGCAGTATGGTAGCTCACCT
CCCACAGTGATTCAGCTTGAAACAAAGACCTCTGCAAGACCTTCATTGTTTACTAGATTATACCAGCTGCTTCCTTTA
VK3-20
CAGATAGCTGCTGCAATGACAACTCAATTTTAGCATCTCTTCTCTGCTTGGGCATTTTGGGGATCTTAAAAAAGTAAT
CCCTTGATATATTTTTGACTCTGATTCCTGCATTTTTCCTCAGACCAAGATGGACAGCCAGGTTTAAGCACAGTTTCA
CAGTAATGGCCACTGGATCAGATTTACATCAGTGGATGTCAGTAAAGGTCCCAACCAGAGCCATAAGGCAACAACAAT
AGCAACAAATAATCAAAATTGGAAAAGAAGAATTAAAGCTGTCATAATTCACTGATGAAGGATTGTGTGCAGATAAAA
TTCAAATTTGTCTACAGAGAAACTACTAAAATTGACATGAGAAATAGAAAATCATTAGATTCAAGATCAATTTATTAA
TTCATAGATTCAAAAATCAATTTCATTTCTGCATAATAAAAAATGCTAAAAATTAACATTATAAACAAACACACCAT
TTACAAAAACATCAAAGTATCAATTATTTAAAAAAAATAGACTAAATACACTGACGTCTCCAGAATATTATTTTGAAA
AATAAAAGAAAACCTAAGTAAATAGAAATTCAGTTCAAAGACTGAATGTCTCAGTACTATAAAAATGTCAATTCTTCA
AAGATTAAAATATTGATTACATATAAGAAAAATCAAAATCCTAAAGTATACTCCAATTTAAATTAAGAAGCTAATCTA
AATATTATATGGGAATGTCAAGGATGTAGAATAGCCACAGTGAACCTGAAGAAACACCAAAATGAGAACTTCCAGTGC
CTGAATACCTGGAATATAGTGTGGGTGCCAGTATGGTGATGGTGAGATCAGAAGTTTAAAAATTTGCAAACGTGCTTA
TTTTTGGAAATAATCACTACGCAGATGTAGCCAAACCCTCTTCAACTGTGCCACCAGAATCTCAGATTTCCAGAATTA
GTTTCTCACAGTGTGATTCTTAACATGACATCAATAATTCTCAGTCTCCCCAGTAAACGCAGCTCAGTGCATGGTGCA
GCTATCCATTTGACTTCTACAAATATTTTAAAAGGTAGAAAATTATATTTATCCAACTAATTGACTCAGTAACAGCTG
TTCATTTGCAGAGAGGTACTCTGTTTTAATAAATAACAAAACTAAGAAAGTTAGTGAATGACCAAGTAGGAAGAGTGA
TAGGAACAGCTGTCTTAGCTTTGTCAAAGGCTTCCTTCCAAAAGGAATTTCACTGGTCACTTTCATTTATCACCACCA
ATAATTTATTATAACTTATTGTAATGTGGTTTATTGAATATTATATGAAAGTGAAAAACAGAGTAGTTGTACCAGTAC
TGGAAGCACTGTTTCTACTGAATACAAATAATTTTCACACTATTGTAAAGTCAAAACATCTTAAGTGCAACCACCATG
AACTAGGGACTTACTGTAAGTTCAGGGAAGTAACTATAAAGAAACTCACAAATTTCAAGAAAAATAGAATATATTCCT
GATAGTGGTACAGGAATATATTATCTAAAATATACAGTTTTCCATTAAAAAATCCTGCAAAGAAACAGAAAGTATGA
TCAATATTGAGGGAACAAAACAAAACAACTGCAGCAAGAAAGCACAGTCAATGAAAGCTGATTCTGACTTGTCCTGAA
TATCAGCTTTAGCAAAGACTACAAAGCGATTATTATATAGATGTTTAAATAATTATTCTTAAAACTACGATCATATAG
TTTTAAAGATATAAAGAGGAAAATATAAAGACAATGACTCAGCAAATGGAAACTCTTAAAAAATAGAAACTATGGAAA
AGAATCAAGTGAGAATTCTAGAAACAAAAAGTACAATAACTCAACTGAAAAATATATTACATAAGTCCAACATCAGTT
TAAGATGGCAAAAGATTCAGTGAACTTAAAAATAGATGTACAGAAATTATTGAATCTAAATAAAGAAAGGAGTTTAAG
AAAAAATGCGCAAGACTTGACAGAATTACAGCTCAGGTTGAAAGATACCAACAAGTGTGTAAAACGAGTCACAAAAAA
AGCAGAGAGAGAGAGAAAGTGATCAAAAAATACTTGGAAAAGTAATGACAACAGCTTTTCAAAAATAATGAACCACAA
AGGTAATTTAATCTATAGATGAAAGAAACTCAATGAAACGCTTTCAGGATATAATACAAGATTAATAACAAAATACAT
TATACTTTAAAATGTTGAAAGACAAAGAGAAATTCGTGAATGTGTCAGGACTAAAAGCTGACTCTACATATGGAGACA
CAATAATAATGCCATTGGCTAAGTTTTCATTAGGACCGAGGGAGGCTGGAAGAGATTGGAATGAGATCTTTAAATACT
AAAAGGAAATGAAAGAGGACAACCAGCAATTTTGTTTCTGGTGAAAATATTCTTCAGAACTAAAAATATTCCTTGATA
AACAGAATAAATTCATTAATAGCAGCTCTGCCTTATAAGAAATTCAAGATGAAATCTTTCAGAATCACAGAAGATTAC
```

Fig. 5 (Cont.)

```
AGCAGGCGGGATTTTGAGCCCACAGCCTATAATGAAGGACTCAAAAGTAGTAAACAATAAGAATAAAGCTAGAAAAAA
GCACACAATTCAATTTATATGACATTAAAGACATAAAAACCCAAATTACTGTGTTCGATGTCAGAATGACAATTACCT
TGGTTGAGATGGGGAAGCAGCTACTGAAGAGGAAGGTGCATGGAGGAGGCATCAGCAGAAGGTAAATATTCTGTAGTT
CCATCTGGCCAATGAATACACAAAAACTATTCAGTTACAATTTGAAGATGTGTGCCCTTTGTGCCCTCTGGGTGTTTT
ATCACTTAAAATAATACGTAAAAATACCATATAGAATAGAAAATATTTATGAAAACTCAGCCTATTAAAGACCAATGT
AAAATATGCCTGGGAAAGGGAAAAATAATTAGAAACCTCTTAGAGAAAACAGAAGGATATTAAAAAATATGTCCCCTC
GGCCGGGCGCGGTGGCTCACGCCTGTAATCCCAGCACTTTGGGAAGCCGAGGCGGGGGGATCATGAGGCTTAAGATC
CAGGTCTGGAAGGTCGAGCGACAGCAGCTAGAAGGTTTGATACTCATACAAATAGTACTGTAGCTTTCTGTTCATAAT
TGGAAAAATAGACAAGACCCAATGTAATACAGGCTTTCCTTCAGCCAGTTAGCGTTCAGTTTTTGGATCACCA▓▓▓▓
▓ACATATACCCAGCATATGTCTAATATATATGTAGAAATCCGTGAAGCAAGAGTTATAATAGCTTGTGTTTTCTATTG
TATTGTATTTTCCTCTTATATCATCTTCTTCTTCGTTCATTATAAAAAAAACCCGTTCAAGTAGGTCTAAATTAATTA
TTGGATCATAAGTAGATAAAATATTTTATTTCATAACACATTGACCCGATGAATATGTTTCTTTGCCAGACATAGTCC
TCATTTCCAAGGTAACAAGCCTGAAAAAATTATACTGGAGCAAGTCAACAGGTAATGATGGTAGCTTTTCCTTATTGT
CCTGGGGCAAGAATAAGACAAAAGATAACAGGGTAGAATAAAGATTGTGTAAGAAAGAAGGACAGCAACAGGACATGG
GAACCTTTTATAGAGTAACATTTTGATAATGGATGATGAGAATTAATGAGTTAGACAGGGATGGGTGGGAATGATTGA
AGGTGTGAGTACTTTAGCACAGATTAAGACCAAATCATTAGGATTTAAAGAGTTGTGTAGAGTTAGTGAAGGAAAAGC
CTTAGAATTAAATTTGGCTGTGGATAAAACATTCTTGGATTAGACTGAAGACTCTTTTCTGTGCTAAGTAAGTATATT
TATGATAATGATGATGACTGTAGTGCTGAATATTTAATAAATAAAAACAAAATTAATTGCCGCATACATAATGTCCTG
AATACTATTGTAAATGTTTTATCTTATTTTCTTTAAACTGTCTACAGCACTATAAGGTAGGTACCAGTATTGTCACAG
TTACACAGATATGGAAACCGAGACACAGGGAAGTTAAGTTACTTGATCAATTTCAAGCAATCGGCAAGCCATGGAGCA
TCTATGTCAGGGCTGCCAGGACATGTGACTGTAAACAGAAGTTTTTCACTTTTTAACTCAAAGAGGGTATGTGGCTGG
GTTAATGGAAAGCTTCAGGACCCTCAGAAAACATTACTAACAAGCAAATGAAAGGTGTATCTGGAAGATTAAGTTTTA
ACAGACTCTTCATTTCCATCGATCCAATAATGCACTTAGGGAGATGACTGGGCATATTGAGGATAGGAAGAGAGAAGT
GAAAACACAGCTTTTTATATTGTTCTTAACAGGCTTGTGCCAAACATCTTCTGGGTGGATTTAGGTGATTGAGGAGAA
GAAAGACACAGGAGCGAAATTCTCTGAGCACAAGGGAGGAGTTCTACACTCAGACTGAGCCAACAGACTTTTCTGGCC
TGACAACCAGGGCGGCGCAGGATGCTCAGTGCAGAGAGGAAGAAGCAGGTGGTCTTTGCAGCTGAAAGCTCAGCTCCC
ACCCCAGCTGCTTTGCATGTCCCTCCCAGCTGCCCTACCTTCCAGAGCCCATATCAATGCCTGGGTCAGAGCTCTGGG
GAGGAACTGCTCAGTTAGGACCCAGACGGAACCATGGAAGCCCCCAGCGCAGCTTCTTCTTCCTCCTGCTACTCTGGCT
CCCAGGTGAGGGGAATATGAGGTGGTTTTGCACATCAGTGAAAACTCCTGCCACCTCTGCTCAGCAAGAAATATAATT
AAAATTCAATGTAGATCAACAATTTTGGCTCTACTTAAAGACAGTGGGTTTGATTTTGATTACATGAGTGCATTTCTG
TTTTATTTCCAATTTCAGATACCACTGGAGAAATAGTGATGACGCAGTCTCCAGCCACCCTGTCTGTGTCTCCAGGGG
AAAGAGCCACCCTCTCCTGCAGGGCCAGTCAGAGTGTTAGCAGCAACTTAGCCTGGTACCAGCAGAAACCTGGCCAGG
CTCCCAGGCTCCTCATCTATGGTGCATCCACCAGGGCCACTGGTATCCCAGCCAGGTTCAGTGGCAGTGGGTCTGGGA
CAGAGTTCACTCTCACCATCAGCAGCCTGCAGTCTGAAGATTTTGCAGTTTATTACTGTCAGCAGTATAATAACTGGC
CTCCCACAGTGATTCAACATGAAACAAAAACCTCAAGAAGACCATCAGTGTTTACTAGATTATACCAGCTGCTTCCTT
VK3-15
TACAGACAGCTAGTGTGGTGGCCACTCAGTTTTAGCATCTCTGCTCTATTTGGCCATTTTGGAGCTCAAGTTCTCAAG
TCCAAAATTACTTATGTTAGTCCATTACATCATACCATTTCAGTGTGGCTATTACATTCATTTAAACGCATTTCAGAA
GGCATCTCTGTTTATGGCATCACAAAGAGTTTAATAAATCTGTGCAAGAATAAACAACAAACACACCTATAAATATAA
AGCTGAAATATCAAAACTATTTCAGCACTCTGAAAATTGGCAAAGCATAAAATAATTAAGGATGCATATTTTTTATAG
AAAAAAAAAGTACTAGTGCTTTGAGTAAGGACAGAAAATGTCTGTAGCCTTTTGCCTGTGACAGCACCCTTCTATTCC
CAGCTCAGTCAATATGAATTGCAGAACTGGAGTTTTACCCATGTAAGGATAGCAAATAAAACTGGCAGCTTGCTGCCA
AAGTGGGTGGACTTGAGTAAAGCCAAGGAGTGGGAAATAATTCTTCAGTGTTTCCAGCTAAACAGGGAGAACACCATA
GGAAATGAAC▓▓▓▓▓GAAGCAAGAGTCATAATAGCTAGCATTTGATATTGTATTGTATTTTCCTCTTATATCATCTTC
TCCTTTTCGTCCTTAAAAAAAATCTGTTCAAGTCAGTCTAAATTAATTATTGGATGATAAGTAGATAAAATCTTTTAT
TTGATAACACATTGACCCAATGAATATGTTTCTTTGCAAGACATAGTCCTCACTTCCAAGATAACAAGCCTGACAAAA
TTATACTGGAGCAAGTCCACAAGTAATGATGGTAGCTTTTCCTTATTGTCAGTCCTGGGGCAAAAATAAGACAAAAGA
TAACAAGGTAGACTAAAGATTATGTAAGAAAGAAGGAAAGCAGCAGGACATGGGAAACTTTCATAGGATAACATTTTG
ATAATGGATGATGAGAATTAATGCGTTAGACAGAGATGGGCGGGAATGATTGAAGGTCTGAGCATTTTAGCACAGATT
AAGACCAAATCATTAGGATTTTAAGAGTTGTGTACAGTTAGTGAAGAAAAAGCCCTAGAATTTAATTTGACTGTTGAT
AAAACATTCTTGGATTAGATTGAAGACTCTTTTCTGTGCCAAGTAAGTATATTTATGATAATGATGATGACTGTAGTG
CTAAATATTTAATCAATAAAAACAAAAATAATTGCCGCATACATAATGTCCTGAGTACTACTGTAAATGTTTTATCTT
ATTTTCTTTAAACTGTCTACAGCACTGTAAGGTAGGCACCAGTATTGTCACAGTTACACAGATATGGAAACTGAGACA
CAGGGAAGTTAAGTTAGTTGGTCAATTTCAAGCAATCGGCAAGCCATGGAGCATCTATGTCAGGGCTGCCAGGACATG
TGACTGTAAACAGAAGTTTTAACTTTTTAACTCAAAGAGGGTATGTGTCTGGGTTAATGGAAAGTTTCAGGACCCTCA
```

Fig. 5 (Cont.)

```
GAAAACATTACTAACAAGCAAATGAAAGGTGTATCTGGAAGATTAAGTTCTAACAGACTCCTCATTTCCATCGATCCA
ATAATGCACTTAGGGAGATGACTGGGCATATTGAGGATAGGAAGAGAGAAATGAAAACACAGCCTTTTATATTGTTCT
TAACAGGCTTGTGCCAAACATCATCTGGGTGAATTTAGGTGATTGAGGAGAAGAAAGACATAGGAATGAAATTCTCTG
AGCACAAGGGAGAAGTTCTACACTCAGACTGAGCCAACAGACTTTTCTGGCCTGACAACCAGGGTGGCGCAGGATGCT
CAGTGCAGAGAGGAAGAAGCAGGTGGTCTCTGCAGCTGGAAGCTCAGCTCCCACCCAGCTGCTTTGCATGTCCCTCCC
AGCTGCCCTACCTTCCAGAGCCCATATCAATGCCTGTGTCAGAGCCCTGGGGAGGAACTGCTCAGTTAGGACCCAGAG
GGAACCATGGAAGCCCCAGCTCAGCTTCTCTTCCTCCTGCTACTCTGGCTCCCAGGTGAGGGGAACATGAGGTGGTTT
TGCACATTAGTGAAAACTCTTGCCACCTCTGCTCAGCAAGAAATATAATTAAAATTCAAAGTATATCAACAATTTTGG
CTCTACTCAAAGACAGTTGGTTTGATCTTGATTACATGAGTGCATTTCTGTTTTATTTCCAATTTCAGATACCACCGG
AGAAATTGTGTTGACACAGTCTCCAGCCACCCTGTCTTTGTCTCCAGGGGAAAGAGCCACCCTCTCCTGCAGGGCCAG
TCAGAGTGTTAGCAGCTACTTAGCCTGGTACCAACAGAAACCTGGCCAGGCTCCCAGGCTCCTCATCTATGATGCATC
CAACAGGGCCACTGGCATCCCAGCCAGGTTCAGTGGCAGTGGGTCTGGGACAGACTTCACTCTCACCATCAGCAGCCT
AGAGCCTGAAGATTTTGCAGTTTATTACTGTCAGCAGCGTAGCAACTGGCCTCCCACAGTGATTCCACATGAAACAAA
VK3-11
AACCCCAACAAGACCATCAGTGTTTACTAGATTATTATACCAGCTGCTTCCTTTACAGACAGCTAGTGGGGTGGCCAC
TCAGTGTTAGCATCTCAGCTCTATTTGGCCATTTTGGAGTTCAAGTTGTCAAGTCCAAAATTACTTATGTTAGTCCAT
TGCATCGTACCATTTCACCGTGGCTATTATGTTCAACTAAATGCATTTTAGAAGGCATCTCTGTTTATGGCATCACAA
AGAGTTTAATAAATCTTCGGTGCAAAAATAAACAACAAACACACATTTAAATATAAAGCTGAAGTATCAAAACTATTT
CAGCACTCTGAAAATTGGTGAAGTATAAAATAATTAAGGATGCATATTCTTTATAGAAAAAAAAAGTACCAGTGCTTT
GAGTAAGGACAGAAAATGTCTGTAGCCTTTTGCCTGTGACAGCAGCCTTCTACCCCCAGCTCAATCAGCATGAATTAC
AGAACTGAAGTTTTACCAATATGAGCGTAGCAAAAAAAACTAGCAGCTTGCTGCCAAAGTGGGTGGACTTGAGTAAAG
CCAAGGAGTGGAAAAAAAATTATTCAGTGTTTCCAGCTAAACATGCAGAACTCCATAGGAAATAAGGAAGAA
GGAAAGTGTAGCAGGAAATAGAAGATGGGTGGCAAAAGTCTCCCCTAAAAGCCACTTAACTCTTAGGATGACTGAAGC
TTCATCCCATGTGGAAATATCGGGACAATGCCTCTGGGCTATTCCATCTGAGGGGAGAGAGCTGGGGTATGTTATCAT
ACTCCTGTTATCATCTACTGATAGTGTCTCTCTTAGTCTGCTGTGTCTTGGTATAACAGAATGCCTGAAATTGTAACT
GATAAAGAGCAGACAATTATTCTCTCACACTTCTGGAGGATGGGAAGTCTAAGATCAAGGAACTGTCAGATTAGGAAT
CAGTTTATCTACTTTCAAGATGGCACTATGACTCCCGAGTCCTCCAGAAGGAAGGAAGTCCATGTCCTAGCATGACTG
AAGAGCAGAAAAGAGAGAGAGAAACCCTACTCCCACAAATGGGAAAGAGCAAGGACTCACTCTCAGGAGCCTGCAA
CCCCCACACCCCAAGCATGGAAAGAATAGAAAATCTTGACTCTCTTCAAAGGAAATTCCAAGCACCTACCTAGCCTTA
AGACGTAAGTAAGTAACGTGATAAGCAAGGAAGTAAAAACAGCCTAAAATGGCCAAATAAGCTAGACTCAGAAGATGG
TGGGTTCCCCTATAGAAACCGAAGGTGACATTTTAGTATATGTCTCTGAGGTGTTTTTGAGGAAACAAGACCCCCTCC
AAATGAATCTGCCAGCACATAGATCTCACAAAAGGGAGAACTGGGGACTGAGCTCTGACCATGGTACTTTGTTCTAAA
TATCTTACAGAGGGGTCTGGTAAAAGTCATATCCATAAACCTGAGCTAATTCGTCTCTTCTGCTGAACCCAAATGTTT
AAACAAAGCTTTTCTTCCTCAGCCAATTGTAAATTAGAAATCTTGTAATCCACCCTTGATCTGTAAGCCCCTGTTTCA
AGATATCCTGCCCTTTTAGGCCAAAACCAATATGTGACCTCCATGTATTAATTTTCAATTTGACCTGTAACTTCTGCT
TTCCTGAAATTTACTCCTGCCTTAAAAAACCCTTACCTGCAAGCCATCAGTGAGGCCAGGATTTGAATCTTAGCTGCC
TGATTCTCTTTACCTGATGCCCTACAAAAAAACAAACAAACAAACAAACCTTTACTTTCTCCTGCTGCAAACTC
AGTGTGAATATCTGATCTGACTGAGCTGAGTGAGTGGACTCCAGTTCGGTTCCACAGCACAAGCTCTGTTTATAGTGG
CATTTATCCACTCATGAGGGCAGAGCTCTCATGACTTCAACACTTCCCATTAGGCCCCACCTCCCAATTCTGTTGCTT
TGAGATAAATTTAAAAACAGATGGGTTTTGAAGGACACAGTGAAACCATAACACTGCCCAAAGAGAGGGCCATTCGAG
CCCCTGTGGTCTGCTATGCATGCAGGCAGAGCTGCCTTCTCCAGGTTCAGAAAGAGCAATGAGGGGCATAGATGGCCA
TTGGAAGTCAGCAGCAGTACAGCGAAAGGGAAAGGCATAGCCTGTAGACAGGGATTGCAATCTTGATATATTTTCTAT
TTAGTTTCCTTTCTAAAAACAGAATAATTTCATGCTAACAGAAGTGTTGTAAGTACAGCACAAAGTGCTTTTTTCCAA
TTAAGTGCATATTGTATTTTTAAAAAATAATCTCCATCTCCATACACGAATAAAATACATTACTCCATCTAGTCCTC
AGGAATATTTCAAATTTTGACAATTAACTCAAAAAAGTTCTTTGTAACCAAACAGCCTCCAGGAAGAAACACTTATTT
ACGGACAAATCTGTGATGCCCTGGTCCGACCTGGGACACTGGGGACATTGCTCCTATGCTGAGTTACTGAGAAGAGCC
AGCCCTGCAGCTGTGCCCAGCCTGCCCTATCCCCTGCTGATTTGCATGTTCGCAGAGCACAGCCCCTGCCCTGAAGA
CTTATTAATAGGCTGGTCGCACCCTGTGCAGGAGTCAGTCCCAACCAGGACACAGCATGGACATGAGGGTCCCTGCTC
AGCTCCTGGGGCTCCTGCTGCTCTGGCTCTCAGGTAAGGAAGGATAACACTATGAATTTTCTCAGCCAGTGGGCTCAG
TACAGCCTGGCTCTTGACGGAAGCCTTCCTATAATATGACTAATAGTATGAATATTTGTGTTTATGTTTCTAATCGCA
GGTGCCAGATGTGACATCCAGATGACCCAGTCTCCATCCTCCCTGTCTGCATCTGTAGGAGACAGAGTCACCATCACT
TGCCAGGCGAGTCAGGACATTAGCAACTATTTAAATTGGTATCAGCAGAAACCAGGGAAAGCCCCTAAGCTCCTGATC
TACGATGCATCCAATTTGGAAACAGGGGTCCCATCAAGGTTCAGTGGAAGTGGATCTGGGACAGATTTTACTTTCACC
ATCAGCAGCCTGCAGCCTGAAGATATTGCAACATATTACTGTCAACAGTATGATAATCTCCCTCCCACAGTGTAACAA
VK1-33
```

Fig. 5 (Cont.)

```
GTCATAACATAAATCACCCAGGGGAGCAGATGCGTGAGGCTCAGCTGTCCCAGATGCCCCTTCTGGTGCCTTCGCCTG
CTGAGAATGTTTCTCAAATTGCAGTCACACTTTGAAGTTCACTGGAGAGTTTTTGTAAAAGGGCCATGAAGGCCCACT
TCATCGTAGCTGTCTTTCCTTGTCCTAATCCCCAGTATCATAGACAGGGCAATGCCTCTCCTGATTTCATTGAGAAGA
AATGGTTACACCTGAGGGGTCTGAGTTGTAGCATCAGTTGGAATTCATGTAGCAATAGTGAGCCACTCTAGGTATTCC
AAGTAGGATTTTTTTAAATACAAGATGTGAGAATCTAAACTACAGCCTTTTAAAGGTTTGCAAGTATAGTAGTCAAA
GACGCAAATACTAGAGAAGAGGAATTCTCTTCTGGAATCCAGAATGCATCTGATAGAGAAGGTACAACTGCCAATCAT
GTGGTCCTCAGACCTTTCTGAGAAGCCCATGGGTGGGGTGCAGATGCTCTCAGCTGCCTAGAGGACTTCATCAGGTG
CTTCTGCAGTCCTCACCTCGGTCCATATGTCTTGCTGCAGGTGTTGATGGATAGTATTGAATCCTCCTCTTCTTACTT
CTCAATCTCAGGGCAGGCCCCACACTGGGCAACTCCACCAAAAACCAGAGAAGGCATAGGGTTTCTGGCAAATGTGCT
TCCAGAATAATAGTGATGATGGGGAAGTGACAGCTGACATCGTAGTGTGGTCATGTATCTCGACTCTCAGGATTTTTT
CAGTGAAGTGATGGCCTCAGAATACACTTGGATGTACTTCCATACACTATGAGTAAGTTTGAAATCATAGCATGAAAA
TGATATTTAGTCATATGATAAATAGAACTACATGGCTACATTAATCAAAATAGCATAGTGCTGGTACAAAAAGATACA
CAGACAAATGGAACAGAATAGGGAACTCAGAAATAATGCTGGAGACCTACAACCATCTGATCTTCAACAACCCTGACA
AAAACAAGCAATGGGGAAAGTACTCCCTATTTAATAGATAATGCTGGGAGAACTGGCTAGTCATATGCCAAAAATTGA
AACTGGACCCCTTCCTTACACCTTACACAAAAATGAACTCAAGATGGATTGAAGACTTAAGTGTAAAACCCCAAACTA
TAAAAACCCTAGAAGAAAATCTAGGCAATACCATTTAGGACATAGACACGGGCAGAGATTTCATGACAAGAATGCCCA
AAGCATTGCAACAAAAGCAAAAATTGACAAATGTGATCTAATTAAACTAAAAAGCCTCTGCACAGCTGAAGAAACTAT
CATCAGAGCGAACAGACAACATTAAGAATGGGAGAAAATTTTTGCAATTTATTCATCTGACAAAGGTCTAATATCCGG
AGTCTATAAGGAACTTAAACAAATTTACAAGAAAAAAAAACAACCCCATTAAAAGGTTGGCAAAGGACATGAACAGAC
ACTTAAAAGAGGACATACATGAGGCCAATAATCATATGAAAAAAAGATCAACATTACTAATCATTGAAGAAATGCAAA
TCAGAAACACAATGAGATACTATCTCACACCAGTGAGAATGGCGATTATTAAAAAGTCAAAAAACAATAAGTTAGGCA
ACGTGACTCACACCTGTAATCCTAGCCCTTTGGGAAGCCGGGTAAGTGGATCACTTGAGGTCAGGAGTTCAAGACTA
GCCTGGCCAATATGGCGAAATCTCATCTCTACTAAAAATGCAAAAATTAGCTGGAGGTGGTGGTGGATGCCTGAAATC
CCTGTTCCTTGAGGGGCTGAGGCACAAGAATCGCTTGAACCTGGAAGACAGAGGTTGCAGTGAGCTGAGATCATGCCA
CTGCACTCAAGCCTGGGTGACAGAATGATATTCCTTCTCAGATATAAAAAAAAATCAAAAAACGACAGATGCTGCGG
AGGTTGTGGAGAAATAGGAG░░░░GCATTAAAGAGACTTATAGCTCTGGACAATGCAGGAACTGTGGATGTCATATGC
TTTAAGGAATCCCAATATCATCTTCTTTGTCAATCTGCAGTAAACCTCTTCAGCTTAGACTGGTAATAACATTGGTTT
AGGGCCATTACAAAATGCTTTTGAGAACATTTTACTTGCTCATGACTAAGTGTTCTTTTTTACTTAAAAAAAGATCAA
TTTCATGCTTACAAAAATGTAGTATGTATGTCACAAAGTATCGCTCCCAACTGGAACAATTTCACAGTGTGTTGAAGA
CCTGATAGCCCCACTCTCTAAGACTTTATTAAGAATTCTCTACAAACAAGGATATTCTCCTACTTATGCCCAATACGG
CATTGAAATATATTATTCCATCTAGTTCTCACAACCACTTCGAGATTTGCCAATAAATGCTCAAAAATGTACTTGGTA
ACAAAATATCCTTTAGGAAGAAACATTCTCTGCAGGCAAATCTAGGTGCCCTGGTCTGACCTGGGACACTGGGGACAC
TGCCCCTGTGCTGAGTTACTGAGATAAGCCAGCCACGCAGCTGTATCCAGCCTGCCCCACCCCCTGCCGATTTGCTTG
TTCCCAGAGCACCACCCCCTGCCCTAAAGACTTCTTAATAGGCTGGTCACACCTGTGCAGGAGTCAGTCCCAGTCAGG
ACACAGCATGGACATGAGGGTCCCCGCTCAGCTCCTGGGGCTCCTGCTGCTCTGGCTCCCAGGTAAGGAAGGAGAACA
CTAGGAATTTACTCAGCCCAGTGTGTTCCGTACAGCCTGGCTCTTGAGGGAAGTTCTCTTACAACATGATTAATTCTA
TGGACATTTGTGTTTATATTTCCAATCTCAGGTGCCAGATGTGACATCCAGTTGACCCAGTCTCCATCCTTCCTGTCT
GCATCTGTAGGAGACAGAGTCACCATCACTTGCCGGGCCAGTCAGGGCATTAGCAGTTATTTAGCCTGGTATCAGCAA
AAACCAGGGAAAGCCCCTAAGCTCCTGATCTATGCTGCATCCACTTTGCAAAGTGGGGTCCCATCAAGGTTCAGCGGC
AGTGGATCTGGGACAGAATTCACTCTCACAATCAGCAGCCTGCAGCCTGAAGATTTTGCAACTTATTACTGTCAACAG
CTTAATAGTTACCCTCCCACAGTGTTACAAACCTGAACATAAACCCCAGGGAAGCAGACATGTGAGGCCGGGCTGCC
VK1-9
CCAGCTGCTCCTCCTGATTCCTCCATCAGCTGAGAGTGTTCCTCAGATGCAGGCACACTCTGATGGTGTTGGTAGAGG
GGGATGTGAAGTCACCTCTGCATCCCAATTTCTTTTTCTTTCTCAGCACCAGGTGCACAGACATAACAGTTCCTCTCC
TGATTTAAAAAAGGCAGGGATCATGACACCTGAGGAGTCTAGTTTATGGCTTCAGTTGGAATTCAAGTAACAGAGAAA
GAAGCCACTATAGATATTCTAAGCAGGAATTGTCTTGATACAGAGAAATAGAGTATAAACTATGGAAGTCTAAATAAA
AATATAGAGATGAATCTCAAATTTCATGTTTTATTTGCTAAGAAATATTTGCTAAATGGGGCATACAGAAAAACTCAA
TGGTCTTCAATATGTTGG░░░░GCAGGCTGCTTACAAAGCAGCAGAAATGTTTGTGCATGGGCTGCAGCACTGTGATT
TTGCTCCCTAGTCAGGCATCAGTAAAATTTTGTGGAGCCCGAGGCTGCAGCCCACTGATGCTGATGTGGTTACATCC
ACTTCCCCTGCTACTGAGTCAGGCTGGGACGTTCAGGGTACATTAGAGATATGAGATATAATGAATGCAAATCCATGT
CCAGTTTCATCTGGATCCAACTGATTTCTCCATGTACATAGACAATTGCTTGATAAGAGATTGAGTATGTTTTTCCTA
AAGGTGTTAACAGGGAGGCTGGTGTCTGGGTCAGGATGATGTCCCCATGCACTGATAAAAAGTATAAGAAGAAAGTGT
CATTGATGGTGCATGGCAGGGACATGCTCCGTGCAGTGGCCACCCTCACTAAGACAGATGAACTTTGGGAAATAATAC
CCAATGGCAGAAAAGAAGGTAGACTATGAAGGTACCCAAAACAAGAATAAGGTGCACCTCATTTAGTCTCTGGGTATT
AAAGAGACCTGCAGTTCTTGATAGTGGTGGATCTGTGAGTGCTGCATGCATGGAGACAACACGGTATCATCTTTGTAT
```

Fig. 5 (Cont.)

```
ATCTGTAATAAATTGCTTGATCTAATACTAGTAAGAACAAAGGCATAACACCATTACCTAATACTTACAAATATATAG
CATCATGCCGATACATTTTATTTTTAATTTTTTTTAGAAAGGAACAATGTTAAACTCACAGAAATGTTGCAGGTATAG
CACAATTACCCCCTTCCCTACCCGGAATCTTATGAGAGTCTTTTGAAGACTTGAGAATCCTACCATCTAACATTTTAC
TATGTGTTTCCTACAAACAAGAATATTCTCCTAAATAATCCTGATACACCAATGAAATACATTACTCTATCGGCTCCT
GAGGAATATTTAAAATTCTCAAAAAAATACCTAAAAATTGTTTCTCATAATAAAATAGTCCCCAGTAGAAACACATTC
TCTGCAGACAAATTTGTGCTACCCTGGTCTTACCTGGGACACCTGGGGACACTGAGCTGGTGCTGAGTTACTGAGATG
AGCCAGCTCTGCAGCTGTGCCCAGCCTGCCCCATCCCCTGCTCATTTGCATGTTCCCAGAGCACAACCTCCTGCCCTG
AAGCCTTATTAATAGGCTGGTCACACTTTGTGCAGGAGTCAGACCCAGTCAGGACACAGCATGGACATGAGGGTCCCC
GCTCAGCTCCTGGGGCTCCTGCTGCTCTGGCTCCCAGGTAAGGAAGGAGAACACTAGGAATTTACTCAGCCCAGTGTG
CTCAGTACTGCCTGGTTATTCAGGGAAGTCTTCCTATAATATGATCAATAGTATGAATATTTGTGTTTCTATTTCCAA
TCTCAGGTGCCAAATGTGACATCCAGATGACCCAGTCTCCTTCCACCCTGTCTGCATCTGTAGGAGACAGAGTCACCA
TCACTTGCCGGGCCAGTCAGAGTATTAGTAGCTGGTTGGCCTGGTATCAGCAGAAACCAGGGAAAGCCCCTAAGCTCC
TGATCTATAAGGCGTCTAGTTTAGAAAGTGGGGTCCCATCAAGGTTCAGCGGCAGTGGATCTGGGACAGAATTCACTC
TCACCATCAGCAGCCTGCAGCCTGATGATTTTGCAACTTATTACTGCCAACAGTATAATAGTTATTCTCCCACAGTGT
VK1-5
TACACACCCGAACATAAACCCCCAGGGAAGCAGATGTGTGAGGCAGGGCTGCCCCAGCTGCTCCTCCTGATGCCTCTA
TCAGCTGAGAGTGGTCCTCAGATGCAGCCACACTCTGATGGTGTTGGTAGAGGGGGACATGGAGTCACCTCTGCACCC
TAATTCTTTTCTCTTTCTCAGCCCCAACTGCACAGATCTAGCAATGCCTCTCCTGATTTAATAAAGACAGAGATCATG
ACACCTGAAGAGTCTAGTTTATGGCTTCAGCTGGACTTTATATAACAGAGAAGAGGCCACTATAGATATTCAAAGCAG
GAATTGTCTTAATACAGACAATTAGAGTCTAAACTACTGAAGTCTAAATAAAATGTAGAGATGAATCTCTAAATTTAA
TGTTTTACGTGCAAAGAAATATTTGCCAAATGGGGCATACAGGAAAACTCAGTGGTCTTCAATATGTTGGAAGAACAA
AGAGAAGGTTAGAGTTTTACGAAAAAGGGAACATGTTACCTATGGCTCTTTGAGAAAGTTCATGGGCACTAGGAAGGG
TTGGGAGCTGGCAAGCTCAGACTGGGAAGCAGTGGTGGACAAAGTGAATCCTACAGTTATATCAAGTTATCTCAGAAG
TTGTGGATAAATTTGATTTCAGGTTACAATAAGCCAAAGGCAGTG▓▓▓▓CATCAGGAGCATCAATGGCTATTCAATA
TCCTATTTATGTACCATAGTTTATAAATGTATTGACATTTTAAGTGATAATTTATTATGTTTTTTGCTATTATAACTT
ATTGAATTGATGAAATGACATACTTTTATTAACTGATTTTTCTAATATTAATTTCTAGTTCCATGAGGCTTTCCACTT
TGGATGGTAAAAAGGGAGATAGCATTTCTACTTATATGCATAAATTAATTCTAGGTAGTGAATTTTATTTATCTGGGA
ATAATTTTTAGATATGGCAACTCTCATTCATTTTGACAAGAAAAATCTAAAGCTCATAAACCCTGAATCCTATATGCT
TACTCTCACAAAAATCTCTAATGTCCTGCTGGGATTTATCCACAGTTTAGATTAGACCTGGAATACATATGGTCATGC
AACAATGATCTTAGAACAGGACTTTAACTTGGCTTTAGGAACTGAGGCTGAGAGTAATAGAATTGATTTTTTGTGTG
TGTGTGAAGCTCCTATTATAATAATGAGAATACTTTGATTCACTCAGTTAAAGTTTTCCCCTGATTTATTGTGTACAT
ACAATGAAGGATCAAGAAAGAGAAATTTTTAAATGGAAGCATTAGCCAGACAAGTTTGACCTCACAGTTTTACTAGGG
GATATATCACCTAGTTTTGGATCTATTTCTAACATCTTAACATTGTGAAAAGAGTCTTGGGAAACTGGTTAAATCCCA
AAGAATGCTGCAATAGGAGGTTGGCCCTTATGAGTTATTTAATATCTTGAGCTGCCTTCGGAAAATGTTGCTGAGCAG
GCATTGAAGAGTATCGATAAAATTTATTGAGAATTTGTTTATTATGATTAACAGAGGTAAAAGCCAGTATATTACTGA
TTAATATAGGTAAAAGGCAGTTAAGAAATTGGGAATGCTTTCTCTTCTGCTTTCTTCTACGATGCACAAGGCGTTTCA
CATTTATGCCCCTATGAAAATTACTAGGCTGTCCTAGTCATTAGATCTTTCAGCAGTTTGTAGTTTTAGAGCTTCTAA
GTTGACTTCTGTCTTTTCTATTCATACAATTACACATTCTGTGATGATATTTTTGGCTCTTGATTTACATTGGGTACT
TTCACAACCCACTGCTCATGAAATTTGCTTTTGTACTCACTGGTTGTTTTTGCATAGGCCCCTCCAGGCCACGACCAG
CTGTTTGGATTTTATAAACGGGCCGTTTGCATTGTGAACTGAGCTACAACAGGCAGGCAGGGGCAGCAAGATGGTGTT
GCAGACCCAGGTCTTCATTTCTCTGTTGCTCTGGATCTCTGGTGAGGAATTAAAAAGTGCCACAGTCTTTTCAGAGTA
ATATCTGTGTAGAAATAAAAAAATTAAGATATAGTTGGAAATAATGACTATCTCCAATATGGATCCAATTATCTGCT
GACTTATAATACTACTAGAAAGCAAATTTAAATGACATATTTCAATTATATCTGAGACAGCGTGTATAAGTTTATGTA
TAATCATTGTCCATTACTGACTACAGGTGCCTACGGGGACATCGTGATGACCCAGTCTCCAGACTCCCTGGCTGTGTC
TCTGGGCGAGAGGGCCACCATCAACTGCAAGTCCAGCCAGAGTGTTTTATACAGCTCCAACAATAAGAACTACTTAGC
TTGGTACCAGCAGAAACCAGGACAGCCTCCTAAGCTGCTCATTTACTGGGCATCTACCCGGGAATCCGGGGTCCCTGA
CCGATTCAGTGGCAGCGGGCCTGGGACAGATTTCACTCTCACCATCAGCAGCCTGCAGGCTGAAGATGTGGCAGTTTA
TTACTGTCAGCAATATTATAGTACTCCTCCCACAGTGCTTCAGCCTCGAACACAAACCTCCTCCCATACGCTGGGCC
VK4-1
GGTAGGTCTTTGCTGCAGCAGCTGCTTCCTCTGCACACAGCCCCCAACATGCACGCTTCCTCTGTGTGTTGGGGAGGT
CACTCTCTTGATTTATTCGTTGGAGGGTTTGCAGGGCCCAGGATTAAATTAAGAGACTTGACTTTTGCTGGATCTCTT
TTTGTAGAAGATTATTAAAGCAAAATGTTGTAAAGATCCCTTAGAGACATTGTCAGGAGTTTTTGTGTTGCAGGAACC
TGCATGTTTCACATGGACACATCACATGACCGAGCCAAATAGATTTATCTTTACTCTCTAGAACAGGGTCCACTCAGT
TTTACGCACAGATGGGTCAATTCTTTCCTCTATGTGCCTCCTTGACTCTGGAAAGTTTCTACTTGGATTCCTAATTCT
CTTTTTTCTTTCTTCATCTGCAATCCTTCCCAATATTAAACCTTGATCCTTCCTATTCATAGCCTCCCACATAGAAGG
```

Fig. 5 (Cont.)

```
TAGTGTCCCTCTGTAGCTTTTTCCTTCCAGAGACCCTGTTTCTTTCCATCATATTAATACTTTCATAGGCAATTTTCT
AATTCTTTATTACTCTAGAAATATGTGACAGCATTTCGTCGAGAAATATTTGGCGCGCATCCTCCTTTGACTTTCCAG
TCACTAAGGATTTACCATCTCTTATTTACAATATCAAATATATAGAAAGAACTCAAGAAGTTGAACTCCAAAAAACCA
AATAACCCTATTAAAAAATTGGGTGTAGAGCCAAACAAAGAATTCTCAACTGAGGAATACTGAATAGATGAGAAGCAC
CTAAAGAAATGTTCAACATCCTTACTCATCAGGGTAATGCAAATCAAAACAACCCTGAAATTCCTCACGCCAGTCAGA
ACTGGTACCAACAGAAACCACTAAGATCAAAAACTCAGGTGACAGCAGATGCTGGTGAGGATGTGGAGAAAGAGGAAC
ACTCCTCCATTGCTGGTGGGATTGCAAGCTGATACAACCACTCTGGAAATCAGTTTGGCGGTTCCTCAGAAAATTGGA
CATAGTATTACCTGAGGATCCAGCTATACCACTTCTGAGCATATATCCAAAAGATGTTCCAACATATAACAAGGACAC
ATGCTCCCCTATGTTCACAGCAGCATTTTTTATAGTCCAAAGCTGGAAACAAACCAGATGTCCTTCAACAGAGGAATG
GATACAGAAAATGTGGTACATTTACACAATGAAGTACTACTCTGTTATTAAAAACAATGAATTTATGAAATTTTTAGG
CAAATGGATGGATCTGGAGGGTATCATCCTGAGTGAAGTAACCCAATCACAAAAGAACTCACATGATATGTACTCACT
GATAAGTAGATATTAGCCCAGAAACTCAGAATACCGAAGATACAATTCACAAGCCACATGAAACTCCAGTCCTTCTTA
GAATGGGGAACAAAATGCCCATAGAAGGAGTTACAGAGACAAAGTGTGGAGCAGAGCCTAAAGGAAAGACCATCCAGA
AACTGCCCCACCTGGGGATCCATCCCATATATAACCACCAAACCATTGTGGATGCCACCAAGTGCTTGCTGACAGGAG
CCTGACATAGCTGTCTCCTGAGAGGCTCTGCCAGAGCCTGACAAATACAGAAGTGGTTGTTCACAGCCATCCATTGGA
CGGAGCACAGGGTCCCCAATGAAAAAGCTAGAGAAAGTACCCAAGGAGCTGAAAGGATTTGCAGCCCCATAGGAGGAA
CAATATGAACTAACCAGTACCCCCTGAGCTCCCTGGGATTAAGCCACCAACCAAAGAAAACACATTGTGGAACTAATG
GCTCCAGCTGCATATGTAGAAGAGGATGGCCTAGTTGGTCATCAATGGGAGGAGAGGCCCTTGGTCCTGTGAAGGCTC
TATGCCCCAGTGTAGGGGAATGCCAGGAAGGAAAAATGGGTGGATTGGTGAGCAGGGGAAGGGGGGAGAGGATAGGGG
GTTTTCGGAGGGGAAACCAAGAAAGACAATAACATTTGAAATGTAAATAAAGAAAATATCTAACTAAAAAAGAAAAGA
ATCTTCACAAAAGCAAAAAAAAAAGAAATGCAAATAAAGAAAATATCTAATAAAAATTAAGCTTTGATACGCAAAAA
CTGAAAGAATTAAGTATAAATAAAACCTTCTCAAAGGGAATAAAAATTACCTGAATGGGGTGAACATGTCAAGTCACT
CTTGGGGTGAGAATGGGCAGGAAGAATAGTCAAGAATATGATGTCTACTCTCTAAAGTGTGAATAGAAAACAAAGGCT
CTGAGTCTATAGACAAGCCACTCAAACAGCACCAGACAAGATAAAATCTGCTGTAATTCTAGGAGAAATCCAGAAATA
TGGAGGTGAGTGAGTTCCTTCAACACCGTCAATGACTGAAAAATGCCATCATAGCATAGAATGTATATTTAAAAGTGG
AATTAACAGTGTTGGTTAAGTATGAATATATATGACTATATATGACTAAATATGAATATATGACCAGGAAACAGGAAA
AGTATCTTTGCCTGGCAGATTAGAAGTATGTTTTGAGAATGAGTACTATATTAGCTACAAATAAGAGAAATAAACTTA
TGAATGAAAACAATAACTAGGGCCTAGAGAGATAGCTTATCAGTTAAGAGTTCTTGCTGCTTTTCTGGAAGACCCAA
ATTTTATTCACAGCACCCTTGCTGGGCACCTCACAAGTACCTGTAACTCCAGCTTCATGAAATCTGATGCCCTCTTCT
GACCTCTGTGGGCATCTGTATGTATGTGTAGCATTCATGCATACACATACACATAAATAAAGATAATCTTGACATAAG
AGAAAATAAGTGGATAAGCTTTGACTATAATTTCATAAAATTGCATTTACTTTAAAAAAACCAAGTGATAAAGATGTA
AGATGTTTATACGATAATTTTCTAACTAAAACCGGGTGAAAAGAAGAAATTATATTAGAATTATTTATATTATATATG
TGTATATATGAAGTGACCACATTTAAAATGTGTGGTAGTATTCAAATGTAAATATCAGTATTCCAGTGATTATGTGTT
ATTTATTCATGCATTCAGAAAACAAGCGTGCACATAGATAGAGCAACTGTTCAATTAAGGACATAGAAATGGAAAGAC
AAACCTATGAAAAGCAAATAAAACATCATAAAGAATAAAAGCAGAACCACCAACAGATTGGAAAAGGATCTTTACCTA
TCCCGAATCAGATAGGGGACTTATATCCAATATATATAAAGAACTCAAGAAGGTGGACTCCATAAAATCAAATAACCC
CATTAAAAAGAGGCTCAGAACTGAAGAAAGAATTCTCGCCCGAGGAATACCGAATGGCAGAGAAGCACCTGAAAAAAT
GTTCAACATCCTTAATCATCAGGGAAATGCAAATCAAAACAACCCTGAGATTCCATCTCACACCAGTCAGAATGGCTA
AGATGAAAAGTTCAGGTAACAGCAGATGCTGGCGAGGATGTGGAGAAAGAGAAACACTCCTCCATTGTTGGTGGGATT
GCAAGCTTGTACAACCACTCTGGAAATCAGTCTGGCGGTTCCTCAGAAAATTGGACATAGTACTACTGGAGGATCCAG
CAATACCTCTCCTGGGCATATATCCAGAAGATGTCCCAACCGGTAAGAAGGTCACATGCTCCACTATGTTCATAGCAG
CTTTATTTATAATAGCCAGAAGCTGGAAAGAACCCAGATGCCCCTCAACAGAGGCATGGATACAGAAATGTGGTACA
TTTACACAATGGAGTACTACTCAGCTATTAAAAGGATGAATTTATGAAATTCCTAGGCAAATGGATGGACCTGGAGG
GCACCATCCTGAGTGAGGTAACCCAATCACAAAGGAACTCTCACAATATGTACTCACTGATAAGTGGATATTAGCCCA
GAAACTTAGGATACCCAAGATATAAGATACAATTTGCTAAACACATTAAACTCAAGAGAACAAAGGCCAAAGGGTGGA
CACTTTGCCCCTTCTTAGAATAGAAAACAAAACACCCATGGAAGGAGTTACAGAGACAAAATTTGGAAGTGTGATGGA
AGGATGGACCATCTAGTGATTGCCATATCCAGAGATCCATCCCATGATCAGCTTCCAAACGCTGACACCATTGCATAC
ACTAGCAAGATTTTGCTGAAAGGACCCAGATATAGCTGTCTCTTGTGAGACTATGCCAGGGCCTAGCAAACACAGAAG
TGGATGCTCACAGTCAGCTATTGAATGGATCACAGGGCCCCAATGGAGGAGCTAGAGAAAGCACCCAAGGAACTAAA
GGGAACTGCAACCCTACAGGTGGAACAACAATATGAACTAACCAGTACCCCGGAGCTCTTGTCTCTAGCTGCATATGT
ATCAAAAGATGGCCTAATAGGCCATCACTTGAAAGAGAGGCCCATTGGACTTGCAAACTTTATATGCCCCAGTACAGG
GGAATGCCAGGGCCAAAAGGGGGAGTGGGTGGGTAGGGGAGTGGGGGGGTGGGTGGGTATGGGGACTTTTGGTAT
AGCATTGGAAATGTAAATGAGCTAAATACCTAATAAAAAAATGGGGAAAAAAGAATAAAAGCAGAAACTAATGAAAAA
TGTGGTTATAAAGTGAATAAAACTGTGATTGAAATATCTTTCTCTTGAAAAGGATCATTAAAACAGATGAATATTGAG
CTATTTAAAGGTAAAACATGCCAAAAATCATGTTATGAAGGAGCAAAGAGAAAACAACTGTATCTATAGCTCCTGAAG
```

Fig. 5 (Cont.)

```
AGCTTAAGTTTGGAGGAGTGTGTCCTGCTTTTAAAGAGGCAGAACCATGCTGTAGATGAAGCCCATGATGTTCTGTGG
AAAGAGAAGTAACCCTGACTCCAGAAGATGTGTTCAACTGGAAAAGATCAATAATCAAAGATCGTAAAACAATTGGGA
GAGACCCACCATCCCCTCCTCTGTGGGAAAGTTCAAGGTCATTTTCTTGAAAAGTTCTAGCATATGTTTTTGGAGTAG
TAGTAGTTGTTGCTGTTGTTGTTGTTGATGATGATGATGATGATGTTGTTGTTGTTGTTGTTATATAAACCTTCT
TTGGAGCATAGAAAACTACAAAAACAGAAACAAAAAAACACAAAAAAAATATCTATTTCAGATAACCTATATTCAATA
CAGCTGCATTAATGAGGCAATTTATCATCAATGAAGCATCACCTATTGTTGATTTGTTAAAGATTATTTATCTTCAAT
ATAAGTAAAAGCCTGATAACTGGCCCTGTTGACTGTGGCTTTTACTGCTGTTTCTCTGTGCTGAAACTATCCATACAA
AATAGAAATAAAGTCTGAAAAGTCAAAAAAAACACAATGTTCTGATAGTTGGAAACCGTGTGTATATGTGGGGTGGGG
GAGGGGGTAATGCTCATAAATGTGTGACAGAGAGATAGGGGAAGAGGAGAAAGACAGATCTTCTAAAAACAACAGTCT
GGTCCCATTATGGGGTGGAGACCTGGCCAAATTGAGATCTCTGCTTTTGTTTGCAGGACAGTTCTGTGACCCATGAC
TGGGCCTCTGTAGACTTGCCGCTTATACAACACTGCCATCTGCTGATACAGCATTAGCACCCTGACTTGCTCTGGTGA
TAAACTGGAGGCACTGTGAGATCATTTCCTTGTCACTGTTTCCTGTGCCACACCCATTCATATGTACTAGAAATAGTC
TGAGAAGAAAAAGACGTTCAGATAGGAAGGGAGCATGTAATGTACCTATATATCTACATAGATACTTACTCAAGGGGA
GGGAGGGTTTGGTGTGTGTGTGTGTATCTCCCGTGCACACACACACACGCGAAAAAGTTGGAGAGGAAAGATTTTT
TTTTTAAACAACAGTCTGATCCCATTATAGAGGTGGAGACCTGACAAGATTCAGATCACTGGCTTTGTTTGCAGGCCA
GCTCAGTGACCCATGATCGGGCCTCCGTAGGCTCACTGCTTATACAGCACTGCCATCTGCTGACACAGCTTCTCTGTT
GACACAGCTTCTGCCCCCTGCCATGCTCAGATAATGAGCTGTTCATTGGCTCTGTGAGATCGATTCCTTTTCATTGCT
TTCATTTTTGATATCTAAACAATGTTTCTACAATTCAGAGACACAAACAAATTGTATAAATAACTTCAATTTTACAAG
TTAACATTTTCCACCTTTTACTGGTATCAAACGGCTTGCCGTGGTTCTGACCTGCCAAGATAGGGAGTAAAGCTCTCT
TTGGTCTCTAGTCCCAGGCCTTGGAGTTCCAAAAGCCTGGGTTTGGAGGGAGTCCCAGAAGTTTACAGCTCCAAGCCC
TGAGAGCTAGAGGCCTACTGTTCCAGGTTTTGAAATCAACAGGATGACTAGGGAGAGGTGGCTCAGTGGTTAAGATG
TGCCCTGCTTTTTCAGAGGATGTAAGTTCAGTTCCTAGCACCCATATCAGGCAGCTCACATGCAGTTACATATAACCA
GCCTGTAATTTCATCTCCAAGGATCTGAACATCTCTTCTGGCCTCCTCAAGCACTGTGTTCACATGCATGCACAGTGT
GTGTGTGTGTGTGTGTGTGTGTGTGTGTGTGTGTGTGTGTGTACTATATATACACACATATATAGTAGAGTGAGTT
GAGCTGGTAGCCTGGGGTGTCTGACACCTTGGCCCTTTGACAGTTCCTTAGAAATCTCCCAGTACCAGGGCCAGAAGT
TTCTTGTCTTCAGCAGCTGTCTCTATTGCCTCTGCTCCTCCTCATCTCTACCACAGCCTTTTGATGTCACTGCCGATG
TCACCAAGGACACTTCCTTCACCACTGACATTGCCTTCATTGTCCCTGCTTCCTTCCTTTCCTCATGTTACCAGCTCA
ACTCACTCTACTAATGATAAAACGCAAAAATAGGCAAGACCGGGCCTTTTATTGCAACTTAATGCTTCAGCTTCAACA
CCAGAGAGCAACATCTAGCTGGTATCTCCAGGTTAACTTGCAGAGTGAACCAAGCAGAGCACTTATATAGCCAGAGTG
GGAGTGTGTCCAGTGTGTGTGCACGTGGCAGTACATCACACCAATGAAGAACAGTATTCTCACCAAGCATGAAGGGCT
GCACCTGTCCCAATCACAGCAGTCCCTCAGACACTCAGAATGAAGTCACACACCTTCAGACTGCCTTCTTGACTGATA
TTCCTTCATTCAAGGCCATACATAGCTCCATAGGATGAAGCAGTCTTAATTTACCATTCAAATCATCCAAGCTATCAG
GAAAATTGACATTAAGAAACACATCTACAATAAAGTTGTCATTCACAGTGATTTAACAATAGGTTAAGAATGCATAGC
TCCTGCCTCAGTGATCCCATGAGTAATGGGCCTCCTAATATGACTGTTTTACTTATCCCACCATCCAACCACCCTTGG
CAACCACCACACACATCTCTTTGACATGTGTGCATGAGATATTTAATCATATTCAAGGCTGATTACCTTCTCTTATC
TCCCTCACATTCTAACTACATCCCTGCTAACTTTGTGTCCGTTTTTAAGGTTTATTTTTATTTATGTGTATGTGTGTG
TGTCTGTTATGGACCATGAGAATGTGTCCAATCGCCTGGACCTGGAGTTACAAACAGTTGTGAATTGCCTGCTGTGGG
TGCTGGGAATCAAATTCAGGCCCTCTGCAGGAGCGTCAAGTGTTCTTGGCCGCTAAGCCACCTTCCCACAACCCCACA
CACTTTTTGATAACCCGTTAGCTGAGGTAACTTACATAAACTCGGGTTAGGGGTTATTTAACAAAGCATGATCAACTT
AGCAGTGGGTATATCACTGAAGAAACTTTTGTTCCCTCCCCTAGCAACTATTAACAGCCAAAAGCTGTTTAGAAAAGG
GTAGGGGCCTTAAAAGCCCCAATTAACCTAATTAGAAGTCCTTAACTGACTATAAATCTTAAAGGAAAAGAAGAGCCT
CATAAGCCCCTGCCCTGCCCGTGATGGAATATTGGCAGGCCAGATCTTCTGGTTGTGAGAAAGTAATCAAGCTGCTCT
GAGTCCGTGAGTGCAACCAGCCATGTCTGATTCCCAAGGATGGTGCACAAAGCCCCTTTCCCTCCACCAACTCTGTGT
TCTTTCTACCCCTTCTCCTGCAGTGTACTCTGAACCTTGTATGGTGATGACATAAACGAACCATTGATGACTGAGCAC
TCAATCATCCCTTATTTTCAGCGCTTTGACCCGTTATAAGTCTCTGCATAAAACACACACACACACACACACAAGGGA
GGAGGGTCTGAGCAACACTAATCTATAGGTTTTCAACCTAGCAATATTTACAAGGCCATTCAAAAAACAAACCATGTC
CATTTAGTGAAACAACAGCAGTAAGTTTCCCACTAGGGCCTTTAACCACACCCCATAAGCCTTTAACCAGGTTTACA
GTAGCAGGAATGAATACTGTGGAGTGGACCTCAAACCCAATCAGAAATGGTTGGTTACCCCCATTCTAGCCATACCA
CTATTGCTCCAGTGGGCATATCTTACCCTGCCGTGGGGTCGATCCAATAGGGCACAGGGTCTATAGCTAAATGCAACT
GCTGACTAGCTCCTTCACCCAGAAGACTGTGCACCATCGTCTGGCACTGTGAAATCCACCCAGCTGAAAGGAAGCCTC
CAATCGGCTCCATCTGGCTTTTCCATGGTCTACAACCAGGAGCATGGTGTATCCAGCAATAGGGTCTTAGCATCTAG
AAATTAGCTATGGTAATTGCCTATATTGTTTGAAGGACCTTAAGGACCTCAATGACCAACATATAGCATGGAATCTCA
CCCCTGGCACCAGGATTTTTATTTAATAACCTATGCTTCCGGGAGCAGCTTTATCCTCCCATGCAGGGTACCTCACA
CCAACTCCTTTTTATTAATTGTACGTTAAATCACTTGCAAAGTAGTATTCTTCCTTACGGCTTTTTCATGCACCCTCA
CGCAGCTTTGAATGGCCATCTCTCCCCCCTCTCCTCTTTCCCATTTTTCTGCACTACATTCCTACTTCCTACAAAATT
```

Fig. 5 (Cont.)

```
TGTCCTAAACAGTTTTTCCTTTCTCTCCACCATTGTCCCTTCCAAGATTCCTAGATTTTGGTTACCTTAAATGCCAAC
AAGGTACAATTTTCAGAGGCTTTACAGTAACAGAAAAAAAGAGGTTACAAGGTACTTTTCAAATTTATTGATGGGCA
CAGGAGTGCAGGTTAAAGCAAAGTGGGGAACCTCTGCTACAGACCTCGGATGCTATCTGACGGTCCCAGTGTTTGCCG
TGAGGATGCTGCTCGGCCAACAACTCAAGTCAGGATGAGTTGGGATCTGTTCTTGTATTCCAAAGGATTTACCTAACA
GTCACAAAGATGATAGGTCACAGACGGCAGTAAATGGCCTCAAGTAGCAGTTAATGGCCACTTGAGGGAGCTAAAGAT
AACTTGTCTCTGGGCCTGCACAGATTCCACCCCTCCACAGTCACTGAAGTTCTTTATTATCATTATTGTTGTTGCTGC
TGTTGTTGTTGTTGTTTATATCCATAAATGTTGCCGCCCCCGCCCCCAGCCTCCCTTTGCAGATTTCTTCCCCAACA
CCCCCTTAGCTTCTAAGAGGGTACCCCCACCCCAGTCATCCCGCTTCCCTCAGGCATCAAGTCTTTACAGGATTAGCT
CATGCTCTCCCACTGAAGCCAAACAAATATGTCTGCTACATATGTGCGGGGGAGGACGGGGGGGGGGGGGGGACTCG
GACCAGCCCATATATGCTCTTTGGTTGCTGGATTTCTCTCTGGGAGCTCTCAGGGGTCTGGGTTAGATGACACTCTTC
ATCTTCCTATAGAGTTGCCATCCCTTCCTTTCCTTCAGTCCTTCCCCTAAGTCCTTCCCCTAACTCTCCCATAGGGGT
CCCCGACTTCAGTTCAATGGTTGGCAGTAAATATCTGTCTCAGTCAAGGGCTGGTAGAGCCTCTCAGAGGACAGTCAT
CCAGGCTCCTGTCTGCAAGCACAACGTAGCATCAATAATGGCGTCAGGGTCCTAATCGGTGATTCAGCCTTTGTAAAG
TGGTCAACGTAAGGTGCAGGTTCTTGGGGAGGGACTTGAAGGGGACACGAGGACTTTAATTCACATGGATAAAATAGA
AGACTGCCTCTATGAGAAAGGTGAGTCTGTGGACTAAATGGATTCTTTCCCGCAGAGAGAAATAGAGGAAGAATTTCA
GATGCTCATTTTAAAGATAAAAGAATACTTGAAAAGAAGGGGGGTGGGAGGAAAGTATGACAGAGAAATCAGCTAAA
TGCTGCCCCCAGCTTACACTTCCTTAGAAGGGAAAGGGAAGGGAAAGCTACTCCTGAAAGAAAAGCTAACCGAAGCAG
AGCAGTCCCACCCTCAAGACAGGCACAGAGCTAGCTCTCACATGCTAAAGTACAGATGCAGAAACCTCTTGCATTGGG
ATCAGCCTTGGATAAAAATAAGTCGGTGAAAGACAGACTGCAAAGCTCAATGTGGCCAGCAGAGGCCCCTAGTCAGCA
ACAAGGAAAACTCTCACGCTAACCAGACAAACAATACAGACTCAGCAAAAACATAAACGGAAGGATGTGCCCACAAGT
TCACCTGACCCTCTTCCTCCGTGAGTGTGCTTTTCTGAAGAGGCAGCTCCAACACTGCCTCACATCTTCCTCTCTATT
GTTTTCTTTGTGTATTCCCCCACAATACTCGCTTAGCAGGATTTTTACTGTATGTATTTGGGGTGGATATATGTGTGT
GTGTGTGTGTGTGTGTGTGTGTGTGTGTGTGTGCATGTGTGTGTGTGTGTGTGTGTGTATTGTTAT
CTCTTTTCATACAATCATTTAATTTTGTTCGTGCGTTTTTTCAGTTTAGAGCAGGTTTTTTTCCTTAGTTTCTTTCTT
TTTTCCTTGTTTACTCCTGTGTCCCTTACACATACACACACGCACACACACACACACACACGTATTCATACTTCTA
ATTGTTTTATACTTTTCTTAAGTTTTACCTTTTTCTCTTCTAGTTTTTGGTTGTCAACGCTTTCATTATTGTTAAGTC
TTTTTTTTCCCTACTTTTCCTTTTTCCCAAGTCTAGAAAAAGAAACAGACAGTGAAATAAAAAAGGAATTGAGAACTC
TAAACAGACTTCACAAGAGAAAATCCTCTTCACTCCATTTTATAATCAGAAAATTAAAAAAAAAAAAATGTTAAGCAAA
GAACAAATGTTAGGAACCGTAGGGGGACACCAGCTCATGCACGGGACACAAATTCCAGAGCACACAAATCCTCCCCTC
TGCGGTCCTAAAAGCCAGGAAAGTACGAAATGATGCCCTTCAATTCGGAAAGTAAATACCATCTAACCACGCTTTAAA
TTGATAGCAAAGCTACTCGTGTAACAAGCAATCTATAAGTGAGTTCGTGACTGCCAAGACTACACTACAAGATAGTTT
TTAAAATTCTTTACAGAAAAGGAAGAATGACACCGGCCATCACAGAGGCACAGGAAAGACTGGGTTTCATGAGAGGAA
TCTATGTCCTGGATTGGGAGAAATAACGTGTGAAATGTTGTACTAAAAAACACAATCTTCAGATTTAATGCTATCACC
ATCATGGTTCTAGTGACATTCTTTACAGAACTAGAAAGATAATACTAAGCTTGTATGGAAACACAAAAGACCATGAGT
AGGCTAAGCAGGACAAACCCTACATCACATCACATCACATCACTGAAACTCACATTATCCCACATAAGTGTAA
TGACAAAGAGAGTAAGGTGCATCCACAAAAGCAGACAGAGAACAATGAACTGGAAGAGGGCCCATAACCTGCACTTCT
GTGGACAGATAATTTCTGACAAACGTGTTAAAAACATAAATGAAAAAAAAAAAAACAAGTTGCAAATTGGACATCCACA
AGGACTACATTGGATCCATATCTATCATCCTGCACAAAAATCAATTCAAAGTTGGGTCAAAGGCTTTGATTCAAAACA
TGAAAAGTTGAAACTGCACAGGAAAAAAAAAACTTTGAAGTGTAAGAACTGGCAAGAACTTTCTGAACAGAACCTCCA
TATCACTGGAAATATTCTCAAGAATTGATAAGGAGGATTATATAAAACTAAATGTCTTCTGCACAGTAAAAGAAACCA
TCAACATAACAATAGTCCAGCTACAGAGTGAAAAAGAATTGCTTTACTTTAACGAGGGATTGGCTCCTAGAATATACA
AAGAACTGCAAAAATTAAACACCAAAAGTATAAAATGTCCAATCAATAAATGAGATAATGGACTGAATAAAGAAATAT
AGATAGACAAAATATGATATAATCAGGAAGTTGCAGATAAAAACTAAAATAATAGTATGTATATCACTCTAGTCAGTA
TGGCTATTATTAAGAAAACAGCTGATAACCCCTGGCAATGGATAAAGGGACACCTTGGTGGTGGTGGTGTTCTTCTAT
CAGTCAGGGGCAGAGCAGATGGCATGGCAGTCCTTTGTTCACCCTAGCTTGATGGCTGGCTCAGTGGCCTAAGCTGTT
TTATGCCTGGGAGACATAAAAATCAAATCAAATCCAGGCAGTGCAGTGCAAGAGGAGGAAGACAGAGTTCTGCAACAC
TATGTGGGGCAGGTCCTCCACCCTACAGCATGGGAGGGCCGAAGATGCACAGGGGCCTGCCTACCACCTACCCAACAC
AGTCCGGAAGAAGGAAGGCCGAGACCTGAAGACCGCAATGCCACCCACAAACCCTCAGGTGCGTGGCATAGACAGCCA
AAAACACCACTTGCTGCCACACCACGCAGTGCCGAGAATGTCACCTAGGGGCCCGTCTATATCAGGAGCCTCCACAAT
GCACGAGTGAGTGGTGGGCAGATGAGAGAGAAAGAAATGCAGCAGCTGGACAGCAGCCTGTTGTGAGGCCATGGTG
AGATCCCAGCCTCAGCTTCTGCTGAGAGTCGGGTCTGAGGCTGAGGCTACACAGAGTAGCGGCAGGGTGTGGGGTTGA
TATCCGAGGCTCACATTGCCACCTGAGAACATGGGACATCCCTGATCTGAGCAGCCACTTTTGTCGACATGAATGTC
CAGGGGCTGTGCAGAACTGTCCCTGCCCCTCACTGGCTGCAGCTCTCTTAAAGAGATAGTCCCGCCTCTCACCATGGC
AGCACTTAGGAGAGCAGGCCCTGCACCTCGCCCAGCTAGCACCGTGGAGCGGGCCCTGGTGGCAAGTGAGCAAGCCCC
ATGAGTGTGGGAGAGTTGACCCCTCCTTCTTCTGCAGTGGGCTGGCACAGGTGCAGGGGTGATGCCCCCTCCCACCCC
```

Fig. 5 (Cont.)

```
TCACTACCTCAGCAGTCAGAAAAGTAACCACAGGGTCAGGAGAGTTGGAGGACACAACAGAGTTGACCTTGGTGGTGG
GGACACAGATGAGCCACCACCAAGATCTGAGTCCACCACAAGTCTGCTACAAGGTGGTATATGTACATGGTTGATGTC
CCCTCCACACCTCCCCCTCAACGCCTTCAGTAGTCAGGAAAGAAAATGAAGATGTGTGGACAGAGGGACATACTTTGG
AACACACTGTGACACACTACAGCTTCCATGATGAGATTTCTATGCTTCTGTTCTCTCTCTCTCTCTCTCTCTCTCTCT
CTCTCTCTCTCTCTCTCTCTCTCTCTGTGTGTGTGTGTGTGTGTGTGTGTGTGTGTGTGTGTGTGTGTGTGTGTGTGT
GTGTGTAGGAGGGGGGAGGTTGCAAGGGCAAAGGGCAGATATGAGGGTAAAGGGACATTAGTGGGACTGGGGTGTATG
ATGGGAAACTCAAAAAATTAATTAAAAGGTTTTTTTTAATTAAAAGAAAAGAAGTGACAACAAATGCTGATGAAGATG
AAGGAAAAGAGGGAGTCGTTATTCACAGGTGGTGTGAGTGTAAGCTGGTGTGGCCACCATGGAAATAAGTATAACTTTC
CTCAAAAGATTAAACACAAAACTACCATAAAACCTATTTATATCATTCCTGGACTTGTGTACAAAGGGCTATATTTTA
CTAGAGAACCTTATACATTCATGTTTATTGATGTTCTAGACACAAAACTTAAGAAGTAATATCAACCTGATGTCCACA
AACTGATGAATAAATCATGAAAATATTGTATGTAAACACTATAGATTTTATCCAGTCGTATAATAAGATAGGAAAATA
AGTGGAATGGGGGCGGGGGACATTCTCTGTCATGAGTAGATCCCAGCTTCCAAATTTTGTGTATGAGTATTTATGTG
GGAGTTTAGACAGGGGTCAGGAGCCTAGAGACCGTGAACTATAGAAGTAAATAAAAGTACTTTAAAAGAAGAGGTGAG
GAGGTAGGGGAGGTGATATGCAGTATGAAAGGGGAAAGTGGAATACTAAAAGTACAAGCAGAGGTGGAAGGCAGGGAG
ATGAGGTTGTAGCCTGGTGGGTCCATAGACCTCAGCCAATCTCTACATTCTTCTTCAATTTCTTCAGTCCCCAGGCTT
CACTGGCAGTAGTTATACAACCAACCTTTGCCCAGAGCATGCGTGTGGACAGAAGTGTTTCTCTGGTGGTTTCCACAG
CCCTCGCTGGAATACCTTGATGCAGTTAGGCTCCATGCCTTGTTATTCCTGCGTGGAAAAAATATTTTTTAGCTTAAT
AAGCTTATGTACAGATCGTGTCTCTTATGCTAGGGTGCATGCAGTTGTATTTTTGTACAATCCAGTGACTACTGCTAG
AGCTCCCTGTAGATTGATCTTCATATTTAATTCCTCTACTTAGCACAATAACCTTACAAGTCTATGGACAAGACAAAA
CATCTTCAAACTAGCTAGCTTACCACCTTCTTCCTCAATGATCTATCCAAAGAAGGCCATTCAATTCTAGCACACATA
TGCCAAATTACATCACCTGGGGAACAAAACTGGAATGGTAAAAACAACCAAGCACAATATGTCAGTGGTAGACACATG
GGGGAAGGCAGAGAGCTCAGAATTCAGTTTATCACACGTATAGAGTAAGCTGGAACCCACAACAGCCAATATGTAAAT
TTCAGAGGCTTAGCCCCTCTGAGGTTAGTAAACCCTGATCCACTTACTGTTTCTCTTTCATGTGGAGTGAAATGGCT
GTAGCCTAATGTCCTTCTGAAATCAAGAGACACATCTTCACTTTCCAGACTGGGACCAGACTTTTGTGCCACGTTGTG
ACATGCACACATGCACACACAGGAAAGGACTTGGCTTGTGCCACATGCCTTTCTTCAGGGACAAGTGGGAATGGACA
TAAGGAGCGTCTCATCCTTACGTGGCCTCCTTTGTCTTCCTCCTTCCTGGCCAAGACGGTGATTTACTGCCCAAAGAC
AAGTCCATCTGAAGCAAGAACTGACTATCGAGGACTCTGTAGTGACTGATAAACTGGGAAGAGAAAATTGGACCAGAG
ACTTCAAGGCAGCTCTCAGACAAGAATATTCCAGTGCCAGGTAGGGAAGCCAACAACCTTCAAACTTTGCAGAGAACA
AAATTGTTTCTGACATGCAGGATAATCCTCTCTGTTACTAATATGGGAAAAAAAAAACTCCCTTAAAAGACTGTTTAA
TGATGGAAAAATTACTTAGCAACAGCAACAAAAAAAAAAAAAAAAGTTTCTGGAATTGTTATATCTAAAGATGTCACT
AATGTAGTTTGTGAAGTATGTTTGGAATAATTTAAAGATGTGTTTTTATGCTTACTGGCTCCCTTTCCCTCTCCCTCC
TTTTCCCCATCTCCCTTTCTCTCCACAAACAGGTTAGAAATTACTCTGAGGATTGCCTTTGGTGAGGGTGAAGTGGGA
AGCAACATTAAGAATGAATTTATTGAGGTGCTTCCCCCAGAATTCTATTCTCATCACTCTAGTGAGTTAAGTCCAGGA
ACCACAGGGATTGTCTTATAGATACTTAGCCTTTCCTCAATAGACCAATCAATACCCAACATGGACACTCTACAGGGT
CATAGATCCCAGAAGAGCCTCATCAATGCTCCTGACACATTCTTTGTCTGCAAATAATGAATCCCAAATTAAAGGTTT
CAACCACTTCTAGAGTAGAGATCTTAGCCCATATCCATCAACCACTACTGTATGACCAAACACGGCTTCATAATGATC
TAGTTCAAACCAGATCTTGTTTCCTCCAAAATGTTTCTCTTATGCTGCCAACTCATGCAGTCCACTCCCATGTTATAG
TCCCTCATTCTCTGTTTGGAAAAAAATTATCTCCTGTGCAGAACCAGAGAGGCTTTTACCGTTTTTTAACTCTGTTTA
AAGATATTTTAAAAAATTAATTGAGGAAAAAGAAAAGGGTAATTTCAGAATTCACATTTTTGATGGTGTAGTCTCTAC
ACACCAAACAACTGAAAATGGTTTCTGAAAACTATAAAATGAATGTATAAAATGAACTATTATAAAAGAAACAAATAT
AACAATCAGCCAATATGCCATGTAAACACACATATATAATAGATAGGAGGACAGTATGTGTCCTTACTGCCCTTGAGC
TGCCCCAGGGGAAACCTCTAAGCACAGCTTGTGCAGCCTCCTAGAAGAAGCCTGTACTACAGCATCCGTTTTACAGTC
AGACCATACACCGTATCCAGTGCCCCATATTTTAACAAAAACATCTAGAAACATATTTCCTTTTATTAACTGATTTGT
GTTCGTTGTGGTCTACATAAACTAGTTTATCCAAACTCCTATCGATGGATATTTGGTATTCCTATTCTTTTTACCTTT
TAAAAAATAGTGTAGTCTCTACAGACATCTGAGCACACTTAGCTCTCATTTCCCACCCCAGGATGGCCTAAGGGGTTC
CTCTTCCTCCTACTCCAGTATTCTCTCTCTTACATGCATGCTGCTCCTATTCGGTAATTTTGTCCCTCGTGTCTACTC
TAATAACTGTGCACTAAGTGCATAAACAGCAGATTTAAGTCTAAGCTTTGTTCTTTAATGTCACAGACAAACAATATT
AATTTCTAGTTCATAGAGTTTTATGGATAGCTAAATATAATGAGCCATATATGATGTCTGGCATTTTATAAGTTCTCA
ACAAACATCAATTTTTATGGTTGATATCGCTTCCATAACTACAGAGAAAAATCACTTTTCATTCTCTTTATGATCCAT
GTTAATTGAGATCATCAGCTACTTTACATAGTTAAGTTTTATTGACAATTTCTCTTTTCTTTCTATTTCCTACTTGAT
TCTTTTTCTTTCTCCATCTTCTGGTGAAACACATGTAGAATCTGCCATTCCAGATTAGCAAAACCCTAATAACATAAAC
AAGTAGACCTCTCTAATCTTGGTTAGAGTTGCAATTTTTCTAAGAAAGTTGATTCTTGTAGAGGTCAGTACTAACCTT
TTGTCTGTTGTAGATTACTATCACTGATCTATACTATTGGCTTTTTTTATTGCTTTTTTTTCATTTATTCTGCAAAT
GTCTGATGAGTGCTTGTCAATTAAAATAAATGGACCAGAATTCCCAAAATCCTAGCTAATAAAATAACAAACATCTT
ACTATCTCAGAGCAAATGGGTTCTACAGGCCTAACAACCTATCTATAAAGCCAACTTGGTGGTAGAAAGAATCTCTTG
```

Fig. 5 (Cont.)

```
AGCTGAATCTTGAATGACAGCTCAAGGGATAGGGAGGACAGGGTGTTCAGAAGCAGAGAAGATGCCTTGTAAATGTGG
AAGGCTGTGGCAGGAGTTGGAAGGACTTTGGGGTGGTAGGAAGGGGATGGGAATGGGTGGTTACAAGAGAAACAAGAC
TGTAGTAAATAAAGCTGAAACTCAAAGCAAGCTTTCAGCATCTTTAATTGGAGACACAAACTTCAAAGGTATCATGAA
TGTGGTTGATCTTGGTGAAAGTTGAGCTTCACCTGTCCTAACAACAGACCAATCCATGAGTGAAAGCTTATCTTTCTC
CTTTATTAATGGTTGCTGTTGTATCCATAACTCAATTCCAAAGGATATGAACCTTAACATATAGATATAATTTTGTGT
ACCTTCTATGAAACAGCATTAAAGCAAAGAAGTTCAAATAGAAAGACTGGCTTAGTTATTATTAACTAAGAGATGCTA
GTGAGTTCTAAATTAATACCATTTAAAATTTATAATTTGCAGAATTACCACCACCGCCACCACTCAGCCCAGGAAAAG
TTACAAAGAACTGGCTATCCAATTTGTTTGTTTTCCTCCTTTTTAGAGTTCTTTTATTTATGTGTGAGTGAATGCCAT
GTACTTATGGATGCAGAGGCTGTCAGATTCCTTGCAGCTGGAGTAATAGACAGTTGTGAGCTACTTATAGTACTAGAA
CTAAGATCCTATGGAAGAGCAGCGAGTGCCACTAACTGCTGAGGCGCGCAGTCCAGATGTGGCAAGTTGCTAAAGAAA
GGAACCATCAGGCCATAGACGTAAATATATTCTCTTCTTGGATTTTAGGTCTTACCTAAGAAAATAAACACATGCTAT
GTCAGAGAAGCCTCAGGGTTTCCACACCTGCTCGAAAAGGGAGTTGAGCTTCAGCAGCTGACCCAGGACTCTGTTCCC
CTTTGGTGAGAAGGGTTTTTGTTCAGCAAGACAATGGAGAGCTCTCACTGTG▓▓▓▓▓▓▓▓▓▓▓▓▓▓▓▓▓▓▓▓▓▓▓▓
▓▓▓▓▓▓▓▓▓▓▓GTGAGTAGAATTTAAACTTTGCTTCCTCAGTTGTCTGTGTCTTCTGTTCCCTGTGTCTATGAAGTG
IgK-J1
ATCTATAAGGTGACTCTGCAATCAGCCTCTGATATCCTTCAGGGAAAGGATAAAGATAAGTCTGTAGTCAAACTCGAG
AATTGATTGCACATTTTCTTTGAAGAGCAAGCAAGATTCAGTCATTGGGTGAGAATAACTTGTCTAAGTAATAGCTTC
AGAAATGTCCTGGGGAACATAACATGTTCTGGACAGAGCCTTGGTCAATTGTCAGAAAGGGAGTTTTTGTATAGGAGG
GAAGTTAAGAGGAACCATTGTG▓▓▓▓▓▓▓▓▓▓▓▓▓▓▓▓▓▓▓▓▓▓▓▓▓▓▓▓▓▓GTAAGTACTTTTTTCCA
IgK-J2
CTGATTCTTCACTGTTGCTAATTAGTTTACTTTGTGTTCCTTTGTGTGGATTTTCATTAGTCGGATGCCAGGGATCTA
ACAAACTTCATTCCCGGGTTAGGTACAGAGGAGGGGAAATTGTTCCACAGGACGCTAGCTTGTGGCTAATTTTTAAGA
TTTCTAAATCAAAATAACTTCATTGGGGGAAAGAGGCTTGCTGAGCTTTCAGGGAGGTTTTTGTAAAGGGAAAAGTTA
AGACGAATCACTGTG▓▓▓▓▓▓▓▓▓▓▓▓▓▓▓▓▓▓▓▓▓▓▓▓▓▓▓▓GTAAGTACGTCTGTCTCAATTATTC
IgK-J3
GTGAGATTTTAGTGCCATTGTATCATTTGTGCAAGTTTTGTGATATTTTGGTTGAATAAACCTGGTGACCCAGAAGTA
AATAGCAGGACACCAGAAAATGAACTTAAAAAGCTGAGCAAATAGACGAATCATTGGGTTTGAGAGGAGAATAGGATT
CATGGGGGAAATGGGGAAGAAATAGCTAGATTTTTCTCTGAACAAGCAGCCTATCTCATATGATTGGCTTCAAGAGAG
GTTTTTGTTGAGGGGAAAGGGTGAGATCCCTCACTGTG▓▓▓▓▓▓▓▓▓▓▓▓▓▓▓▓▓▓▓▓▓▓▓▓▓▓▓▓▓▓▓▓▓GT
IgK-J4
AAGTGCACTTTCCTAATGCTTTTTCTTATAAGGTTTTAAATTTGGAGCGTTTTTGTGTTTGAGATATTAGCTCAGGTC
AATTCCAAAGAGTACCAGATTCTTTCAAAAAGTCAGATGAGTAAGGGATAGAAAATTAGTTCATCTTAAGGAACAGCC
AAGCGCTAGCCAGTTAAGTGAGGCATCTCAATTGCAAGATTTTCTCTGCATCGGTCAGGTTAGTGATATTAACAGCGA
AAAGAGATTTTTGTTAAGGGGAAAGTAATTAAGTTAACACTGTG▓▓▓▓▓▓▓▓▓▓▓▓▓▓▓▓▓▓▓▓▓▓▓▓▓▓▓▓
▓▓▓GTAAGTAATTTTTCACTATTGTCTTCTGAAATTTGGGTCTGATGGCCAGTATTGACTTTTAGAGGCTTAAATAG
IgK-J5
GAGTTTGGTAAAGATTGGTAAATGAGGGCATTTAAGATTTGCCATGGGTTGCAAAAGTTAAACTCAGCTTCAAAAATG
GATTTGGAGAAAAAAAGATTAAATTGCTCTAAACTGAATGACACAAAGGCGCGCTGCAGATAGCGTTGTCTTCTAGAA
GTTTAACTGGGAGATTTGGGGGGGGATGAGGAATGAGGACACTTCAAGATAAAAGAGGGCTAAAGTCAAGATCAGCTG
CATAAATGGATGTGGAAGCAAAGTTTTTGAGATAAACTGAATGACTCAGAGGAAGAAAATGTGCAGATGAAAATAGGG
GCTTGGAGCTCTGAGAACAGAAGTAAGTTGAGTTTCCACAAATATTGTGTTGAGCTTTGTATTAAATGTGGGATAGCA
TTGTTGATTGAGGAGAGCCTTAGACTGTTTTCTCTCTTCTGTCTCCTAATTATTTGACGACTACAAAACTCAGTATTA
TTCCCTGAAATAAAAATCAGTAAAATGTTTGAAAGTATGACTGTTTGCCACGTAGAAATGGTGGCTTACTAAATAATC
AGAAGAGGCGCGATTCTTAGAGTCTAAAATCTGTCACAAATGTCAAAATGAGAGACTCTGTAGGAACAAGTTCTGTAC
AGACAGCTCAGGGTCTTTTTTGGCTCATTTCTACATGAATGTAAATTTGAAATGATCTCTTTTATTACGACACTAGAA
ATACAATTTTGGGTGTATAAATTATGTGTTTTAATGGCCACGATTTTATAAGACATCGGCCCTTCACTTTCCCAGTTA
TTAATCGCTTGTGTTTTTACGCCGCCAGCAAGGGGCTGAAATGGTCCGCAACCTCTTCTTTACAAATGGGTGACTTCG
CGGCCACGCCAGCCATTTAGAGTTCACCCTTCCCTGCCGCTAACGGCCATGTGAACCCCGCTGTAGGGCCTTTTGCTC
CACGTGGACCACTTTCCTGAGGCACAGTGATAGGAACAGAGCCACTAATCTGAAGAGAATAGAGATGTGACAGACACT
ACACTAATGTAGGAAAAACAAGGGTAACTTATTGGAGATTTCAGAAATAAAATGCATCTATCATTATATTCCCATATC
TTAATTTTTCATTAGGGAATTAGAAAAGGCTTAAAACTGTTTTAGCCAGTGTTATATTAAAAGTTTTATGCATGTAGT
CTTTTGGAGGTAAAATCTACAACCAGCAAAAGTCACGGTAAACCTACTTTGACTGAACCCTCATTAAACTCTGTTTAA
AAATTATATTTCATATTAACTGGTTAAAATAAGATAAATTTGTGACATGGTCTTAACTGGTTAGGTAGGATATTTTTC
TTCATACAAAAAATATGACTAATAAAAATTTAATATAAATTCCTAATACTTTAATTCTGTGATAGAAAATGTTTAAC
TTGGCTACTATAATCCCATAATTTTGAAAACTGTTTATTAATTTGTTTCTGTGGTTGACCCTTCCCTAGCTAAAGGCA
```

Fig. 5 (Cont.)

```
ACTGTTTAAGGACCCTTTAAAACCCTTAAAACTACTTTAGAGTCTTTTAAGTTATTTAACCACTTTTAACTACTTTAA
AACAATGTCAACTCTGTTTCAAACTATTAATTTCTTTAAAGGGGAAAAACAGCTGGTCATAATTCTGTTGTTTTCTT
GGTAAAGGACTCTCAGTTTTCATTTTTACTACCACTCTGTCACTCAAGGGTTGGCATCTCAACAGAGGGGGCTTTCCG
AGAAGCCATCTGGCAGCTGCTTAAGGTCAGAAGTGAAGCCAGCCAGTTCCTCCCAGGCAGGTGGCCCAGATTACAGTT
GACCTGTTCTAGTGTGGCTAAAAATTGTCCCATGTGGTATCAAACCATTAGACCAGGGTCTAGTTAGCGCTCAGAATG
TTTCTGGACATCCACCCAAACACATACCCTGACTTAAGGCCCCATCCATAGAGTAAGTTTAGCTTGGCCACACCAAAG
GAAGCCATAGAGAGGCTGATATCAGAGTATTCTTGGAATAGGCAGGAGAAAATGAAAGCCAACCTCTGCTCCTACCTT
ACATGTTTGTGTTAGGGGTGTCAGATAAACTGGTCTGGTATCTCTGTCTGATGCATGGAACTATTGTAGCTGAAGAAG
AACATAGTTTCAGGGAAGAAAGGCAATAGAAGGAAGGCTCTGAATAGCTTCAAAGGGTCAGACCCAATTTACTTTCTA
AAGTAGCTAGGGACTAGGGAATAACTCAAAACCCACAAGACTGTGTACATGTGTCCTGGCTTCATTGTTCCTAATCTG
TAGGGATAAGTGTGCTTTTCTGTGTGTCTGTGTGTCTGTCTATAACATGTCTATAACATGCATAATGCACTGATTTTC
CTTGTTACTTCATACCATCCTCTGTGCTTCCTTCCTCAGGGGCTGATGCTGCACCAACTGTATCTATCTTCCCACCAT
CCACGGAACAGTTAGCAACTGGAGGTGCCTCAGTCGTGTGCCTCATGAACAACTTCTATCCCAGAGACATCAGTGTCA
AGTGGAAGATTGATGGCACTGAACGACGAGATGGTGTCCTGGACAGTGTTACTGATCAGGACAGCAAAGACAGCACGT
ACAGCATGAGCAGCACCCTCTCGTTGACCAAGGCTGACTATGAAAGTCATAACCTCTATACCTGTGAGGTTGTTCATA
AGACATCATCCTCACCCGTCGTCAAGAGCTTCAACAGGAATGAGTGTTAGACCCAAAGGTCCTGAGGTGCCACCTGCT
IgK-C
CCCCAGCTCCTTCCAATCTTCCCTCCTAAGGTCTTGGAGACTTCCCCACAAGCGACCTACCACTGTTGCGGTGCTCCA
AACCTCCTCCCCACCTCATCCTCCTTCCTTTCCTTGGCTTTGATCATGCTAATATTTGGGAATATTAAATAAAGTGA
ATCTTTGCACTTGAGATATTTGTCTTTCTTACTAAATAGTGGTTAACAGTTATTTATCCTGTAACCTGGTTTCTCTTC
TAAAGAAGTTAAATGTTTAGTTGCCCTGAAATCCACCACACTTAAACAACAAATAAAACTCTCCCCCTTGCCCTACTT
GGTTGCCCACTACATGGCAGTCCTCTCTAAAGTTCACAAGTACTATTCATGGCTTATTTCTCTGGGCCATGGTAGGTT
AGAGGAGGCATACTTCCTAGTTTTCTTCTCCTACGTCACCAAAGTCCTGAAGGAGGACAGTGTTTACAAGCACATATT
CTGTAATCTGTTTCAACCTTTCCAGAAACCTTGACAAAGCAATGGGGAGTCATTATCACAGGAAGGGGAGACAACTTA
AATGACCAAGCAACCGAAAAACACGTTGAAGCCCATAATAGTACCTGGGCTTCATCAGCTCTTAGGCTAGCATGAGCT
GGCTCCTATCTGCCATTGGCAAGGCTGGGCACTACCCACAACCTACTTCAAGGACCTCTATACCGTGAGATTACACAC
ATACATCAAAATTTGGGAAAAGTTCTACCAAGCTGAGAGCTGATCACCCCACTCTTAGGTGCTTATCTCTGTACACCA
GAAACCTTAAGAAGCAACCAGTATTGAGAGACTCATTTATGAAAGTCTAAAACTGGATACAACCAAAATGTCCACCAA
CAGTTAAATTATGACATGTTCACAATTGAGCTATTACTTAATAAGGAGAATTAATAAAATAAAACTTAAGAGCATAGT
TTAATCTCATAAACAAGATAATAAGCAAAACAAAACATTTTTTCATCCATGTAAGTTTAAAAGCAGGTAAAATTTAAA
ATTAAGAGAGACATAAGTTTTGAGGTAGCAAGATGGAAACTCTGGGGCTTGGGGAATGTTCTGTCTCTCTGTATGGGA
TGTGAAAGTTACTATTGTGGAATTGGGATCTATGTTCTTCCTGTATATATTGTATACTTCATAATAACTTCACCTAAA
GAAATATCTAATACCCAGTGCATACATAAAAGAGGATACAAGGAATGAATCATACGTCAAGGCCAGAAAGACAATAAA
GTAGGGGATCCAGGATCAAATCTCCCACAACCTTGAGCCTTCTACTATTCTGCCTTCCAGAGCTCAAAGTACAAAACA
CATAATTCAAACACATGATCCCTCCTTGGGGTCTCTTCCTTCATGCATCGAATTAGAAATAGCCATGTATAAAATGAG
ATAGAAGAGACCTTCATCAACAGGTCAAAGAATATAGGTAATTTTGTCTGGGTATGAAGAGCCCACGTATCAAAGGTT
ACATTAGGGAAGGAAGAGGACACTAACAGTGACTTTCATTCTCCCCCTCTTCCTGGAGGCCCCTGCATTTAGTCCCTC
GTGGGCTCATCCACTCAGCACACATTTACTAAGCATCTTCTCAGCCTACACTCTGAAGGCAGTGCAGAATAATGTTAG
TGTCCCTTCCCCCAGTTAATATGCAGTCCAGTTTCCCTGCTCCTTCCCTTTCTCAGTCCACATAAGGATGATGGGAAA
GGACAGTCACCAAATAGGAGAGGGCAACCCTTTGCCTTCCTACCTCTTGAGAATGTACATTATTATCCACTTTTTGAA
ACTTCTTTTAATTGCTTTTTTTTAATTTGTCTTTTCAAATAGCATAACCTTGTTCATCCATTTCTGGGAACCAAATTT
ATCAATCAACAGTGCCTCTAATCTGGCTATTAATACAAAAATGCCTCCTCAAAATATATATGTTCGAGTCTTATCTAA
AACAGAACCCACAATAAAAAGAAGAAAGAATACATATAAGCATTTATATAATTCTGAGCAACCTTGTGCTTTGTGAA
AAAAATATAATCTAATGTCACATGCTGTATTCTTTTTATTTAACACTGGTGAAATTATACCATTAGAGAGAAAGAGGA
CAGATCACTGATCCTAGGATCTAGGGATGTTACAGATAAGAAAACAAATGTGACAAAGAGCTGTCACAAGGAGGATCT
TCAAGGTCACAGAATCACTGTCTTGATTTCAGTGGTGGTTACATACATTTAAATATGTGATAAAATGTTGTTGAACTA
TATTCATATATTGTACCAACGTCAAATGCTTAATTTTGGCTCTATAGTATAATTATGCACTAAATAACTATTTGGACA
AAGAAAATGATGTTTACATCAAAGGTGAGGCCATATTTGTTAGGAACATAACTTAAAAACCATTTTGGATAACTAATG
AAAAGCCATTTTGTGTGCCTTGGCATATCATGCCTAAGCTGTCACCAGATAGATCTAATAAGACCTAAGCCTCAGAAG
CAAGCCCCTGCCCAGCAAGCAGGCAGCACAGATAAGAGCTAAACCCAGGACAGGCCATGATATGCCAATGAACTACCT
TCAAGGTGGTGTTGCTGACCTAGTGAACCAGCCCCAAGCTGTGAGCCCCAATAGCACAAAGCTACTGCCCAAAGAAAT
TATACAAAAATTGGAACTTTGGGAATGGTGTGCAGGATCGCTCTGCTGTATGCCTGGAACACAGCTTCTCTATGTTTT
GTATTGATACCAGTCTAGAAGCTTCCAAAACTTTCTCACTGAAGAAGATTCCCCATGTGGGACCCCTACAGACTCTTT
TGCCCAAACAACTGCTTCCCTCCTGGTGTGATATCTGTTTTGCTTTTATGTTAGCATAATATTATAAGGAATGTTTGT
GTGAATAAACCAAACATATTTTAAAAGCAAATATTTGTATGCACATCCTAATTGCTAAAAAGTTTACAGCTAATAGTCC
```

Fig. 5 (Cont.)

```
CATGCTCTCCACAATACTGGATCCAAATAAGTCCTAATTTCAATGTTGGGCATCCTTACAGAGAGAAAGACATTAAAA
ATGAAGAGACATGCAGAGAGTGCACCATGCCATCGTGGAGACAGACTGAAGTGACACAACTGTTAGTCAAAGAGGATT
AAGGACTTCCAGAAGCCACCAAAGGAAGGAGGTATGAAGTGGTTTCTCCCTCAGAGTATCCAGAGGAGACTAAACCAA
CCAACACCTTTTTGCTTAAGACTTCTTGCCTTCAGGACTGTGAGAAGGTAGCTTCCTATTGTTCTAAGCCCCAGTATG
TGGCATTTTGTTAAGGTAGAGTCAAGAAACCAATAAAATGCAGACAGACAAAAGGATAGCTGAGTTTTCCAGGCCCTT
CCTTCTTATTTTTGGTTTTGTTGGTGGTGGTGGTGGTGGTGATGGTGGTGGTTTTGTTTATGTTTTGTTTGGGGA
GTTTTTTGGGGTTTTTTTGGGTTTTGTTTTTGTTGTTGTTTTGGGGGTTTTTGTTGTTGTTGTTTGCTTTTTTGT
TTTTTGTTTTTTGTTTTTTTGAGACAGTGTTTCTCTGTATAGCCCTGGCTGTCCTGGAGTTCCTTCTATCTCTAATGT
CTACATCTCAGAGGGGATCCTCTAATTTCAAATGAGCAGTAGCTCTCCATTTTTAGCTCTTATTTATTCATTTATTTA
CTTACTTACTTATTGTCTGTAGATGAAAGAATTTTGGAGTGGGAAAGGGTTCATGAGCCCCCAGCAACTAATGAGGAG
CTACAGACAATTGATGTTTCTGGGGAAAGGAGACTCAGTTTCTTTGAGAGTATAGCTTCTGACGGGTCAACCATGTTC
CTGTGGCTGATGTCACACCCAGGAGTATGCAGACAACAGAAACTGGAGTTAATGAGTTGTTTTAAAAATAAAAAAGGG
CATGAAGCTTGGGATAGAAATTAAGGATAAATACAATTAAATACAGGAAATTCTGAAAGAATTAATAAAAACATTTCT
TTTTTTAAAAAAAAATCCAGAATTAGCTATGCTTCTTCAAAATTGCTTCTGGAGAACTTTACAAGTTAAATAAGTTAT
ATTGTAGAAAAGGTAGAGAGGAGAATAGTGGAAGAGAGAGATGAGGAGACTTCAAAAGGAGTGGAGGGAGATAGAGGA
GGAGAAAGCAGAAGCAATGGCTGATAGACACAGGATAAGAGGGAACAGAAAGGAGAAAGAGGAAGCCAGGATGGGTAT
TTCTTTGCCTATCTGTGACTTGCACATGGTCTTGGCAATTATTGATGAGTTCAAGGCTTAATTCTTCACTTGTGCCAA
CTCAACAGAGTCTTTCTTTCTTATAACCAGGCCCCCAGTATGCTCATGTATGTATCAGGTCCTCTTATCTCCTTATAG
CAATCCTGTTTATAACTGGGTAACTTTGTGAAGGGAAGGAAGTGCACACTGAGATGTGCTACAACTTTTTAATACAAA
ATTTTGAAGAGTTTGTACAATGTATGTATAATTAATAATTAATATTATGCACTTTAGATTTTGATTTCAACTCAAGAT
ACTAATTCTATATATATGGGTTAAATCAATATATTAATAAGTTTAATTTCACATGCTTATTTTTATCGTGGTTTTCGA
GACAGGGTTTCTCTGTATAGCCCTGGCTGTCCTGGAACCCACTTTGTAGACCAGGCTGGCCTCAAACTCAGAAACCCT
ACCCTGCCTCTGCCTCTGCCTCTGCCTCTGCCTCTGCCTCTGCCTCTGCCTCTGCCTCTGCCTCTGCCTCTGCCTCTG
CCTCTGCCTCTGCCTCTGCCTCTGCCTCTGCCTCTGCCTCTGCCTCTGCCTCTGCCTCTGCCTCTGCCTCTGCCTCTG
CCTCTGCCTCTGCCTCTGCCTCTGCCTAGTGCTGGAATTAAAGGTTTGCGCCACCACGCCGGTGAAATTTTTAAACT
TTATATATGTCTCATTCTATTTCTATCAGATAGGACTGTGTAAACTGTGCTAAACTAATAAATGTGCCCTCAAAAGTA
ATCGCAAGTTGTATTGTTGTTGTTTTGCTTTGCTTTGCTTTGCTTTGCTTTGCTTTGCTTTGCTTTGCTTTGCTTTGC
TTTGCTTTGCTTTGCTTTGCTTTGCTTTGCTTTGCTTTGCTTTTTTGTTTTGGGTTTTTTTCCGGGGG
AGGGAGGGTGGAGAAAGAATCTTACTATGAAGCTCTGACTGTCCTGGGAACTCACTATATAGATCAGGCTTGATTCAA
CTCATAGAGATCTGCCTTCTTCTGCCTCCCAAGTGCTGGGAATAAAGGCATACACCTCCATGCCCAGATAGTGATCCC
AAGTTTTAGCAAAAGTTTCTAGACTTGACATTAATCGATGGAGATAGACATGAATTACACAAAGAACTAATGTGGAGT
TTACCTGAATCATACTCTATACTTTATCAGAGATTAAATTAACATTTAATAATCCAGTGCCAGGCTAGAGGCACCATT
CAATGGCAGTGTTTGCCATCATGCATAGGCTTAGTCTTCAGTGCTGAAAGGCATTGGGGGCAATATTACTCATTATAC
AGATGAGAAACTGGGAAAGACTTGCCTCAGATTCTCTACTGAAAGGCTGAGTTTGTGGCTTCTAGAAAATCCTTTACT
TTCAATATTTTTAATGTATAATTTTTTTATTTCCACTGATTTTATTTTTATTTTTAACATTTATAAGAAATAAATGC
AATAAACCAAATACATGGACAAAAAAATACAAGAATCATATGATCACCTCAATGGAAGGAAAAAAAAAGAAAGAAAAA
GTCTTTGATAAGATTCAACATTCATTCTTTTTTATTAGATATTTTCTTCATTTACATTTCAAATGCTATCCCCAAAG
CCCCCTATACCTTCCCCTGCCCTGCTCCCCAACCCACCCACTCCTGCTTTCTGGCCCTGGCATTCCTCTGTACTGAGG
CATATGATCTTCAAAAAACCAAGGGCCTCTCCTCTCATTGGTGGCCGACTATTAGGCCATCTTTTGCTACATATGCAA
CTGGAGACACAGCTCTGGGGGTTACTGGTTAGTTCATATTGTTAGTCCTCCTATAGAGTTGCAGACCCCTTTAGCTCC
TTGGATACTTTCTCTAGTTCCTTCATTAGGGGCCCTGTGTCCCATCCAACAGATGACTGTGAGCATCCACTTCTGTAT
TTGCCAGGCACTGGCATAGCCTCACGAGAAAGAGAGAGCTATGTCAGGATCCTGTCAGTAAAATCTTTCTGGCATATG
CAATAGTATCTGGGTCTGGTGGTTGTATATGGGACGGATCCCCAAGTGGAGCAGTCTCTGAATGGTCCTTCCTTCCAT
CTCAGCTCCAAACTTTGTCTCTATAACTCCTTCCATGGGTATTTTGTTCCCATTCTAAGAAGGAGTGAAGAATCCAC
ACTTTGGTCTTCCTTCTTCTTGAGTTTCATATGTTGCATCTTGGATATTCTAAGTTTCTGGGTTAATATCCACGTATC
AGTGAGTGCATATCATGCGTGTTATTTTGTGATTAGTTTACCTCACTCAGGATGATATCCTCCAGATGCATCCATTTG
CCTAAGAATTTCATTAATTCACTGTTTTTAATTGCTGAATAGTACTCCGTTGTGTAAATGTACCACATTTTCTGTATC
CATTCCTCTGTTGAGGGCATCTGGGTTCTTTCCAGCTTCTGGCTATTATAAATAAGGCTGCTATGAGCATAGCGGAG
CATGTGTCCTTATCAAGTTGGAACATCTTCTAGGTATATGCCCAGGAGAGGAATTGCTGGATCTTCCGGTAGTACCAT
CAACATGCATTCTTAATAAAAGCCCTAGAACAAGGAGGACTGTAGGAAACATATTCCAACATAATAAAGGTTATGTAT
GACAAACTCATGACCAATATCATCCTAAATGAATGAAACCATTAATAAGCTCCATTAAAATCAGAGGACTGCCCACTA
TCCCTACTTCTCATCCATAATGAGATTGAAGCATTAGCTGGAGCAATAAGGCAAGAGAAGGGATACAAATGGGAAAAT
ATTAAGTCAAATTGTTTTCAATTGAAGATTATATTATCTTATACCCAATGACCTCAAATTTTTGACTAGAAAAATTGTA
GAAATTATCAATAATTTCAGCAAAGTGTTATGATGCACCACATCCTTATTCTTCTCCCCAGCTTCTGCTTGCTTCTCT
CTTCTTGCTCTTCATCCTTTCTGTCCTTCCATCTGCCTGCACTCTTGTCTCAAGACTGAGTGCAGCGTGTAACTCTCC
```

Fig. 5 (Cont.)

```
TGTGACTGAGTATCTCACAAAACGTTCTACCTGCCAAACCTGGATGAGCCCTTTGTCTTTCTGAAGCTATGAGGCTCT
CTACATAGACTCAAGAAGGAAATGACAGGGAGGAGGTAATAATGAAGTGGGGAAGGCTGACATTAGCATTGCTCCTGT
GTGGCTCCTTAATTTCTCATACTTCACACTGAGATGTTATTAACTGTGACTCATAGGTGAAGAAGCCAGAGCTAAGGT
TCTCATATTTGAGTGTTATAGAATGAGTAGAGCAGTAGTTCTCAAACTAAGGGTCATGACTCCTTTATGGGTCAAACT
ACCCTTTCACACAGGTTGCATATCAGATATCCTAATTTTATATACATATATATATGCATATGTATATATATATATTTC
ACAACAGTAGGAAAATTATTTAGTAATCATTTTATAGTTGTGGGTCATGGCAACATGAGGAACTGTATTAAAGGGTTG
CAGCATTAGGAATGTTGAGACCCACTGTAATAGAGAATGAGGCTTAAGGCAGGGCTATAAAGCCCAATGGACCATGTG
CCTTTTCCAACATTTGCCACATGGTAAGCTCTGTATAGACTTTTTAAAGAACATTGGTTTGTAATTTTAAATGGATAA
GGGTCTTCACTGTCTATCACCCATCTATATAATAAATACATAAGTTTTGATTCCACCATGGATTCAAATGCAAAATC
CTCAACCTAAGACATAGCAGTGAAACATTGATGACCAAATAGGAAATCCATGTAGAGACCTTCTATCTTCTGATGGCT
CCACAGGCACCATCTTGCAACAGAGTTCTACTTTGCTACCAGTAATGAATACAGTGTCTCAACTCCTGCCATTGAATC
TTCAGGAAGCCCCTGAAATGACTTGTACTACACCATTTCTTAAAGACAGAAAAGCTAAGACTTAGAGGGAATAAATGT
CATGCCTGAGATCATGCAACCAATTAAGTCCAACTTGGCCTGATCAAGAGGCACAATTCAAAAGCAATGTTGTTCCTT
CACTAGCTCTTGTGTATGGTTGCTGATTCCGGAAGCAAAGTATCAGTGAATATCCCTAGTGGGAAAAGACTTGGAAAT
CAAATGTCTCATTTAACAGATTAGGAGATGAAACGGTAGACTCTGTGTAGTTGTACACCCCTGTGATCCCATCGCTAG
GAAGACTGAGGCAGGAAGTCCTCGAGCTCAAACCAGCTTAGGCTACACAGAGAAACTATCTAAAAAATAATTACTAAC
TACTTAATAGGAGATTGGATGTTAAGATCTGGTCACTAAGAGGCAGAATTGAGATTCGAAGCCAGTATTTTCTACCTG
GTATGTTTTAAATTGCAGTAAGGATCTAAGTGTAGATATATAATAATAAGATTCTATTGATCTCTGCAACAACAGAGA
GTGTTAGATTTGTTTGGAAAAAAATATTATCAGCCAACATCTTCTACCATTTCAGTATAGCACAGAGTACCCACCCAT
ATCTCCCCACCCATCCCCATGCCAGACTGGTTATTGATTTTCATGGTGACTGGCCTGAGAAGATTAAAAAAAGTAAT
GCTACCTTATTGGGAGTGTCCCATGGACCAAGATAGCAACTGTCATAGCTACCGTCACACTGCTTTGATCAAGAAGAC
CCTTTGAGGAACTGAAAACAGAACCTTAGGCACATCTGTTGCTTTCGCTCCCATCCTCCTCCAACAGCCTGGGTGGTG
CACTCCACACCCTTTCAAGTTTCCAAAGCCTCATACACCTGCTCCCTACCCCAGCACCTGGCCAAGGCTGTATCCAGC
ACTGGGATGAAAATGATACCCCACCTCCATCTTGTTTGATATTACTCTATCTCAAGCCCCAGGTTAGTCCCCAGTCCC
AATGCTTTTGCACAGTCAAAACTCAACTTGGAATAATCAGTATCCTTGAAGAGTTCTGATATGGTCACTGGGCCCATA
TACCATGTAAGACATGTGGAAAAGATGTTTCATGGGGCCCAGACACGTTCTAGAAGTACCTGAGAGTGGCAAAAAATA
GTTGTGCTAAATAGTTTGGCCATCTTTAGGCTGAGAGACTAGGAAATACAGCGATGGACTATATCAGCATTGCAGGAT
AGTTGTCAGTAAACACCCCACAACCCATAACAGAAGTATTCTCTTCTTTCTATATCCCTTTTCCATCCATGTAGATGG
CTGTCTTCATATTTGTTCTAGACATTGGTTCTACTCAAGTCAAGGCAAGTCATCTGACCTTCACCAAGAAAGTCCAGC
ATCCAGGAAAGGAAATTGTATGTTTGGATATGTGAGTAGTCACTTTTATTCATCTTGTGGGTGGTTTTTGGGGCAGAA
TCTCACTATGAAGCCTAGGTTTGTCTCAAACCCTTAATCCTCCCATTTAAGATGGTTATAACTATATACAACCATGCT
GGACTTCATTCCAATCATTGGTATCTCCATGCACCTACTTCTGAATTCTGTTCTACAAATAATATAGTCCATGATAAG
AAGTTCCAGTGTCAAGGTGCTTCCAGTCTAAGGTAGACACAATCAACCAGAAGTTGCAACATGGAATAGGTGGGTATG
TGTGACTTATATTGACAGTTCTAAAGAACCAAGCTACAAAAAGGGCACACATCATGTATTGAAGGTCAAAGAAGGTGT
ATACCCGCATCCACCTGTCAAATGTTAGTCAAACTAGGAACTAACTGGCGCCAAGGACAATCCTCACAGACCATTCCA
ATGCTTCAGCCCTCTGACTAGGAATGGGTCATGTGAGAGTTCATCAATTACAAACTTATTTGCTCTTCCTTTGTCTTT
AGTTCTCTGTCTATATTAAAGCAATACCTACAAGATCTCTACTTCATTGTCACTCTGAACAATAAATGAAATACTACA
TATAGTCTACTTATTATAAGACATGGTATGTCTTGTATATGCTCACACCTTTTATAGTGTCTTTTTTATTTAACTGT
TTGGTTGACAATTTGATTTTTGTGGCTGTTGCTGTTGCTGTGCTTATTTGGTTTTTGAGACAAAGCCTTCTTCTAGAT
AGCCCTGGCTGACCTGGAACTCACTGTGTAGAACAAAGTAGCCTCAAATTTGCAGTGATCCTTCTGCCTCCACCTCCC
AAGTCCTTACCACATACTACCATGTATTGCTCATATTTTTAATTATTAACACAGTTTCTTGGACACCATCCTGAGCCC
AGTAGATATTCTTCCAGCAGTAACCCCACAAGGAATCCTGCAGTTTAGACTGAAATATTTTTTCTTCCAATATGCAAA
AACACATTTAGCAATGTAACAGGTAAAAAAAAAAATCTCACAATTGGGAAGATAGAGAAAATGAGGCACACAGTGAAGA
TATTGTTTGCCAATCCTGTATCTCACCCTAGGCCTAGGGAGCTAGGTCAGATCCACATAGTTTCCCCCATCCACACCA
TCCAGTTCCATAAAGAAATTTAGGAAATGTTACAAGGTACATGTGTATCTCAAAAGACTAATATTTTATACTGAAGAA
TAAAAGAAATGTACTTTCTAATCGTGAGCAAAGAGTTTCACGAGATCCAACAATCCAGCTGCCTCCTCTCACCAGGAC
ACTGAGTTGACGGTGTGCTCTTTACCCTTGTTAGAGAGAGAGAGAGAGAGAGAGAGAGAGAGAGAGAGAGAGAGAGAG
AGAGAGAGACCCTGGATACTGAAATATATCACAGTCATTGGCCTACAAACCAAGTTAGACCTGCCTTCAGTTCACAGT
CAGGGAGTGATGATGAATTTTATATTTTGGCCTTTCGTGATACAGAGATTTTTTTTATAAGGGGAAAGAACTAACA
TTGTAAATAGAGGAGAATTAAAAACAAACAAAAACATAACAAACAAAACTAACAACCAAAAATATATATGACCTTG
GGGAATTAAGACATAGTTGACACCGAAATTATAAGAGATTGTAACTTTATGCCCCCACAGGTAACCTGAATTGTTCAG
TCCTATAGATGTGACTTGCCCATTAAAATCAGAGGAAGACTGGGTAAGGTACTCCAGGACCAGCAGGATATGGCAAGC
CCTGCCCATCTGGTGCAGGAGCATGACCCACATGTGATCAGGACTCACCTTCCTTCCAGTCAGAGCCTCAGGCTCTGC
ACAAAGACTCAAATGTGCTGCCTGGGAAGGAGGAAGGGGAGGAGGAGGGCTTCTGACCTATTACTACTTGGTCCACAA
TGGTCTCTCAGAGCCCTAAGGATCTGCACGTGGGCTCCACTGCACAGCTTCCTTTGTTATCAACCAAAAACAGTAATG
```

Fig. 5 (Cont.)

```
TAGACATGAGGAAATTCTGGAATAAGGTTCACCGTCCTGACACTAAATGGAACACCCTCTACAGCTGCCCAACCCCTC
CCCCTCTCCATCTCCCTCTCCCTCTCTCTCTCTCTCTCCCTTCCCCTTTCCCTCTCCTCCTTCCCCATCCATGGCT
GGGGTGGGGGGCTTCTGGTTTAGTTTTTGTTTATTTGGATTTACTGAGACATGATTTCACAATCTACCCAAGTTGGCC
TCAATCTCACAATCCTCCTGCCTCAACCTCCTGAGTGCTAGAATTGTAGGTATGTGTCCCACTGTCTCCAATCTTTCT
CTCATCCTTCCTTTCTTTCTTTCTCTCTTTCTTTCTTTCTTTCTTTCTCTCTTTCTTTCTTTCTTTCCTTCTGAAGCA
ATTGAGAATACTTCATGGGTATAGATAAGAGTATTTATGAAGTATTTTATTTAACAAATTAAAATGTTTGTGCTTTAG
TTCCATAATATGCCCAATTAAAAATTTAAATAACTCTGTGGAAAAGATTTTTTAAGCTGGGGAAAAAGTAGAGAAAA
AACTATGAATTAAAAAAAGGAAAACACTGGGAGGTTGCAATGGCTGGAGGAACTTGACTGTGTGTCTAGGAATGAG
GTTGTGTGTTGCAATGCTTGTCACCTAGTCTGCCACTCCATATTCCAGGATCCATTGTTAAATGACATGCTTTTGGAG
ACTCCAATGGTGATGTTAACCAAAGCAGCTCACACCAATAATGAAAGAGTCCCCTGGATTATGGCAATAGAAATATAA
CCCACTGCAGCCAAAAGACTAGAAGGTCCCGTGCTTCCCAGCCCTGCAATGCCTTGCTTTTTATTTACATCTACCCTC
CATTCCAGGCATCCTTTAGGACTATAAATGTTAAAGATACAGACAGGAACTTCTAAGAATAACTACCAATAAAAGGAG
CAAAGTCCTAGAAGCAAAGCAGGCATATGTGACAAATGGCAGCACACAGTCCCCACTGCTGCCACCCTAGCATAAGTG
CATACAAGCATAAACATATTCTTTGTCCAGACTGCTCATCAGTCTCCTACTGACTCTCTCCACTCTCAACCTCACTGT
GGCTTTTTAACACATTGATGTTCAGAAATACAGTGAAATACAGCATTTCTTCTTTCCAGTCCTATACATTGTTGCAAT
AGATGTTAAGTGACATTAAACAAATTCCAAGCATTTGTTTCACTGACCTGCTTGATACAACCATGGCAAAGAACATTA
TCACCCTTGTTGTCAGATATCAGATACATGTAATGGGCCTGGAGAAATGACTCAGCATTTAAGGCATGGACTGTTTGC
TCTTCTAGAAGAAGTGAGTTTGCTTCCCAGATTCGTGTAATGTCCCAAAATACTGAGACATAAATGTCTTAACTGTGA
CACTATCAAATCTGTTAACCTGAAAACTCCTATGACCTGTTTCCCTTCAAGCATGTCTGAACAATGAAAACTTGGCTC
TACTTCCATCTGACCTGAAGAAATTTCATCTTTCCTGAAATGGGTATCTCCTACTCTCCACCCCACACTAACCCTCTT
CGATTTTCTACGTCACAAGATTTACTAAATGCCACCTATCATATGTGTATTTGACTTGTGCAAGTTTCTGGGTCTAGT
AGCACAACCTCAAAATCTCAGCAACTTGGGAAGCTGAGGCAGGAGGATCTCATGTTTAAGACTTGCCAGGGCTGTGGT
GCAAACTTGAAGCTAGTCTGGTTAAGTTAGTGAAACCCTGCCTCAAAATATCTATATAGCTTGGGATGTAATTCCATG
GCAGAGTGCTTGCCTAACATGTATAAGGCCCCAAATTTAATCCCCAGTACCACAAGACAATAATGTACATAACTATAA
TAAATTTTACATAGTAAACTTTTATAAGTATATTTCACAAATATTTTCACAATAGACAGAATCTATTGTCCAATAAGC
AAAACCTGATAGTTTCCTTGAAAACTGTGCGCTAAAAGCATTTAATGATTGTAATCATAGAAAACTTAGAGGAAGTCA
TCCTTGATTTCCATGCCTCAGTGTATAATTTACTACCACTCATTGGAAACAGGATTTTTCAAACCTTGAACCTTAGTT
AATTGTATTGTTGTTCTGTTATTGTTGTTGTTGTGGAGTTTGTTACAAAGCATAGCACCTTGGTCTGACCAGCATCTG
TTGAATAAATGACTAGATGAGCAAATGTGTTGTTGATGGCAGATGAGTATGTTTGTCCATGTTTAAAGGGTAGTTTTT
TTCTGTAAGCATGGGTGTGTTTGTTTTCTGGATACACTGACTGACAGAGTGTGACATTATTACCTTCTGTTTACAGGT
GAAGAAGCAGAACTGTCTAGAGACTTGCTCAAGTGGAAGTCACCTCTCACACCTGCCCTATGCAGTCAGGCCTTCTGT
GCACACAATCAATTGCCTGGATTAATGTCACAGGAAATCCACTCTGTGTGTATTTTCTTTGTGTCATATTTCTGCAT
TGTAACCTGAAGCTCCAGAAATGTTTCCTGTAAGGACAGCAGACTCCACCTTCTGGGGCCAGACAGCTAGCACAAATT
TTTTCTCATTCTTGACTCTGGATAATCCAGTCCTATTCCACCAGCACTACCCTCCACCCAGTACCGTGGCCACATTGTG
AATATACATGGTCATTTACTGTTAGTGTCAAGAGAGCGAGTCTACACTGGGGTCGAGTAATTTGGTCCCGTGTAAGAG
TTCATTAAGTTGGCAGGGAAAGAATGGCTTAGTCACTCTGATTGCTTTAGAATTACTGGAGTTTCACAAGTGGAAGAG
GGGTGTGTGTGTGTGTGTGTGTGTGTGTGTGTGTGTCCAGACAAATTTCTCAAACAACCTCATTTAATAAGAAGAATA
AATCTTTTAAAAGACTTTTCAACATTTACTGCAATATATACATACATAAAAATGATCTATAAACATTCAATTTATTTT
TAAAAACTGACCACTTTTCACTTGAGTTAAAACCATTTTGCAGACATGAGAAAGACTCTAAAGGTTAGAGGCCAGGTG
TGTGTGCCTTACGGCAGTAGCCTGACTCACTCTACCTTGTTAGTAGCTAACATTAAAACAAGATTAGAAGTCAGGTCT
CAGGACTTTCCATTCTGCTCTTCCTCTACACTCGTAACCTAACTTAGACCAGGAGACCCTAAGAGGCTGTCCAGTAGC
ATGAGGGATGAGTGTACCCTCAGTGAGAGAAAGGCCAGAGCATGTCAGCCACCCTGTTTAACTCTAACTCAGACAGGA
ATTTGGTCACTACACTCACTGGCACTAACACTCATGAACTTAGAGAATGCTTGCATTGGGCAAGCTCTCCTGGACTGG
CTTAGGTAAAACTTCCACCTATTAGTGTGACTTGAATCACAAATGTGATTCAATCACAGTTGTTGTGTGGTCTCAG
GTTCCTCTCCTCGGGCAAGAACCCAGTTCAAGTCCCAGAATAGGAAGCATTGCTAGCTACAGTATAAAGTGCTACATG
GAATCTGCACATAGCTGAAGAACCAAAGCTTTTATTGGATAAGGTGTTCTTTCCAGAATAAAGCCTCCATCAGCCAAG
AAAGATGTAGAGATGGGGAAATGCCCCAGCAGTTAAAGCACTCACATGAACCCAAGCAGGAGGACCTGAGTTCAGATC
CCCACAAAGAACCGGACACAGGAGGACACATCTCTAATTGCAGCACGCCTACAGGGACAAGAGAGGTGGAAACTAAAC
AATCGCTGGAAGGAAGTATGCAGGCCAAGCACCCTGGAATGTTTAATGGCAAACAAGAGACCCTCTCTCAAACGAAGT
GAAGTGAGGATCAGTGCCTCTGACTTCCACACAAAGCAGCATGTGACTGAACTCACATCCAAATACATAAATTATACA
CATAAAACATGCACACATGTGCACACACACACAACTTCGAAAAGACAATGTAAACCCCCTGCCCTGCTGTCTAC
TTGGCAAGCTGACAATTACTTACCATACTCCTTTCACTTTTTTACTTTTTTTTAAGGGATTTGTACTTCTATCGGTTT
TTAGAAGAACTGGGTAGTTTTCCCAACGAACAGTAGGACAAATCCCTGAAGCCTGACATCAGAGCTACCAGAGCCTCC
CCTTCCTTTGGACTCAATACTAGGTTATAAGTATGTGGGAAGACAGAGCCACAGCAAGACAAACAGGAGAGTCCCATT
GCCCGCTGTGTGTTATATCTCACACTCTTTAAGAAAACCATCCACTCAAAGCTAAGACACAAACCAGAAAGGAAGT
```

Fig. 5 (Cont.)

```
TCTGGCCCAGAGATGGATGGAATCCCTCAGGTGGGGACCACTTGATCATTCAACGCAGTCATTATTCAATATTTTTAA
AAGGTATCTATGTCAATTATTAAATAGAAAGTCTTTTAAATCCACCTGTAAATCTCTAACCCTAGCATCCATCTCTTT
CAGTTGTCACATTGTGTTCTTTTCTGAAATGTATCGGCATACTCCATGCATAGCCCCTGGATCAGCCACAAAATCGCA
ACTTGATGTGCAGCTCTGTGCACTCAGAGCACTTGTTTCTCCCTTGGACTTGGAACACTGTACATTATTCTCATTCCT
GGCTGACTTGGTCTCTCTGTCATTACAGCTCATATCTGTGGTCTTAACTTTTTCCTAGACTGATCAGCTGTGCTGGCT
CTCCACAGTCTCCATCGTTGTGAGGATCCATCTGCTCTCCCTGGGGTAGGTTTGATCCAAATCCATCAATTGTTCATT
TCCTAACAATCTGTGCTGTGATTGTTTCACCTGTATTCATTGGGTCTCATGAAAACAAATCTAGCGTGGGTTGAAGTA
GTGAAGATCTCACCGGCACACCCAAGGCCTTGAACTTGATCACCCCAATAACAACAACAAACAAATAATAAAATTGCT
TAGTTGAGATGCGAGGGCTCATCTTAAACATTTTCTAGACCCATAGTTAATCCATGAGCTGGTGCTCACAGCAGAGGA
AACAGAGCCAAGGGTTTGACCCAGAGTGATCATTTTCTTGATGCTCAGCCAGACACTTGAGTAGTACTATGACTTCGC
TCATTTAATTTCCACCTGGTATTGTTAGTAGAGCCTGGCCCTCAATGTATTCTTATTAAATGAATAATGATACCCTTT
TCTTGGAGTAGTAGTAGAAATTAGTAAATTTTAATAAATACCAATGCTTGACAGTATAATCTCTCAAGATGTTGAGCT
CCGAAGAAGAAGAACATTTACTGTTTAAGCAAAAAAGTATGAACAGTTGTCATGGAAAGGCCTGTCCCAAATTTTAAA
TTGAATCATCTCCAATTTTCTGTGATTCAAAATGTACACAAGAGTCCTTGATCAAGCTTCTGGGTGTATCTGATCGTT
TTAGAATGACTGTGAACAGGCTAAACATCATATCAAAATGGTGAGACAAGACATTTTAAATATCAAAAGCCATCGTTA
GCCCCAGCTGTCCTTGCCAGAACAGCATGACTGGGAGAATCAAACAAGATGAAGAGAATTCTAAAACAGTCCTAATCA
GAAGCACAGGCACAGGGAATCAAAGGCAGAAGGAAGCTTGACACCACCAAGATCAAGTCCTGTTACAAACGGAGAAAC
TAGAGAAGCCAAATGAGAAACGAAAGGTCTCATAGAAGCCAGGGAAATGCCACAGAGAAGGGACAGATCACCATTTCG
TTAATCTGAACATGAGGTAATGAAGTCAGGGGGGTTTCCACTGTGCCACATCACACAGAACAAAGTTTCTATTTTAAG
AGTCCAGCCCTGCACCTGTGCAGTGCAGATGGACTTGGCAAAAGAAGAAATGAAACAGATTTTTCTCACTGCCCAGCT
GGCCTGAAGGTGCAGGGCACAGGCTAGATGAGCAACCGTGAAGGGGCCAAGTGTCGCAGCATGGAGACCATCCAGATG
TGGAGACATTTGCCCTAAGATTCCCAGTTTTTCTCTACCCTAGCTTGAGCCCCAACACCAAGGGAGAAAACACGGCAG
AGTCAGAGGAAAGAATCGTTGCTATCCTGGCTTGTATGTAGTCCCACTGTCTGCTGCTTAAGCAAAAAGAATGGGAAA
TTAAATTAAAGAGGGAACAGCACTGCCATTGGCCATAAGTAAGGGCCTAGGGTTCCATGCTGTCTGCTCCACAGCCCA
GGGAAAGGAAACAGGCCTCGGAATGATTTGTCAATAAAGGCAGGAAATATCTCATCATGTCTTCAGTATACTAACAAA
ACTGCAGTGGGAAAATGACAAGCTGTAAAGCTAGCGAACCTGATTATGACCCTAGCTCCTTCTCAACCTGGTTGGTTG
GCCTTGACTAAACTGCTAACATTACCTAGACTTCATCTCCCCACTTGTAACTTTTTAATATCTAACAAACCACACTTC
TGGGTGTGATTATCACTGTACTGACAACAGCTCCTAGGGAAGGATCAAAGGAAGGTAAATTGTTTTGCTATTTTTTAT
ATTGTTCACTTGTCTGCATACACATGCATTCATGTGTACACACACATATGCACAAACACACACACACGCACACACACA
TGCACCGAGAGAGACATACACACATCCCTGAGTGTACATAGCATACATATGAAGGTAAAAGGGCTTTGGGGAGGAAT
TAGTTCTCTTCTTCTACCATGTAAGTTCTAGGGCTTGGATTCAGGTTGTCAGACTTGGTAGCAAGTGCCTTCACCCAC
TAAGCCATTTTCCAGGCCTGTATTCTTAGTGTTATCAATACATGTGAACACTGCTGAGCAAACTCCAAAGCTCAGACT
AGAGGCTCCACTCTTCTGTGTCTCTACACCAGAACATGAGCCATAATTCCATCTGTAGCATCTTACTAGTTATGCAAA
AGGCCAGGTTGTACTACCTTCCTTCTTCTGAGGATCTGCCATTCAAATTGAAAGACTTATCAAAGTTTAGCTTAAACC
ATGCCATTAGATCATCTTTCTCTAGTAAAACCTGATAATTTAAGACTTACTGTGTACAGTTTTTAAATATCTTCAAAG
TCAATTTCTTTAGCAAAGAAAGAAAAAAGGAAAGAAAGAAAGAAGAGAGAGAGAGAGAGAGAGAGAGAGAGAGAGAGA
GAGAGAGAGAAGAACAGAGAGAGAGAGGGAGGGAGGGAGGGAGGGAGGGAGGGAGGGAGGAAGGAAGGAAGGAAGG
AAGGAAGGAAGGAAGGAAGGAAGGAAGGAAGGAAGGAAATCAAGAGGCTGGGGAGAGGGCTCAGTGAGTAAAACACTT
GCTGGGCAAGCATGAGGGACTGAGTTCAAATCCCCAGGACCCCACATAAAAAATATGAAATTTAAAAATTCCAATCCC
AGGGCCAGAGGGTGGCTCTGAGCCTGAAAGCACTGCTGCTCCTGCAGAGGAGCCAGAACCCACATCTGGTGGATCACA
ATTACCTGTAACTTTCTACAGGATCTGACTCCCTCTTGGGCCTCTACAGGAATTCACACACGTGGCATAAACATACA
AACAGATACACACATATACACATAACTGTTTTTCATCTCAATCCAGAGCTTGGATTATAGCTCAGTAAGAAGAGTGCT
TGCCTTGTATGTTCATCCCCAGATCCTGTGTAAAAATAACCAGAAACAGTGACACACACTTGTAATCCCAGGATTGGA
AAGGCGCGCCTGTACAGCGGCCGCAATTGTCGAC
```

Fig. 6

```
ICGCGCCGCGGCCGCTCGACCAATTCTCATGTTTGACAGCTTATCATCGAATTTCTGCCATTCATCCGCTTATTATCA
CTTATTCAGGCGTAGCAACCAGGCGTTTAAGGGCACCAATAACTGCCTTAAAAAAATTACGCCCCGCCCTGCCACTCA
TCGCAGTACTGTTGTAATTCATTAAGCATTCTGCCGACATGGAAGCCATCACAAACGGCATGATGAACCTGAATCGCC
AGCGGCATCAGCACCTTGTCGCCTTGCGTATAATATTTGCCCATGGTGAAAACGGGGGCGAAGAAGTTGTCCATATTG
GCCACGTTTAAATCAAAACTGGTGAAACTCACCCAGGGATTGGCTGAGACGAAAAACATATTCTCAATAAACCCTTTA
GGGAAATAGGCCAGGTTTTCACCGTAACACGCCACATCTTGCGAATATATGTGTAGAAACTGCCGGAAATCGTCGTGG
TATTCACTCCAGAGCGATGAAAACGTTTCAGTTTGCTCATGGAAAACGGTGTAACAAGGGTGAACACTATCCCATATC
ACCAGCTCACCGTCTTTCATTGCCATACGGAACTCCGGATGAGCATTCATCAGGCGGGCAAGAATGTGAATAAAGGCC
GGATAAAACTTGTGCTTATTTTTCTTTACGGTCTTTAAAAAGGCCGTAATATCCAGCTGAACGGTCTGGTTATAGGTA
CATTGAGCAACTGACTGAAATGCCTCAAAATGTTCTTTACGATGCCATTGGGATATATCAACGGTGGTATATCCAGTG
ATTTTTTTCTCCATTTTAGCTTCCTTAGCTCCTGAAAATCTCGATAACTCAAAAAATACGCCCGGTAGTGATCTTATT
TCATTATGGTGAAAGTTGGAACCTCTTACGTGCCGATCAACGTCTCATTTTCGCCAAAAGTTGGCCCAGGGCTTCCCG
GTATCAACAGGGACACCAGGATTTATTTATTCTGCGAAGTGATCTTCCGTCACAGGTATTTATTCGCGATAAGCTCAT
GGAGCGGCGTAACCGTCGCACAGGAAGGACAGAGAAAGCGCGGATCTGGGAAGTGACGGACAGAACGGTCAGGACCTG
GATTGGGGAGGCGGTTGCCGCCGCTGCTGCTGACGGTGTGACGTTCTCTGTTCCGGTCACACCACATACGTTCCGCCA
TTCCTATGCGATGCACATGCTGTATGCCGGTATACCGCTGAAAGTTCTGCAAAGCCTGATGGGACATAAGTCCATCAG
TTCAACGGAAGTCTACACGAAGGTTTTTGCGCTGGATGTGGCTGCCCGGCACCGGGTGCAGTTTGCGATGCCGGAGTC
TGATGCGGTTGCGATGCTGAAACAATTATCCTGAGAATAAATGCCTTGGCCTTTATATGGAAATGTGGAACTGAGTGG
ATATGCTGTTTTTGTCTGTTAAACAGAGAAGCTGGCTGTTATCCACTGAGAAGCGAACGAAACAGTCGGGAAAATCTC
CCATTATCGTAGAGATCCGCATTATTAATCTCAGGAGCCTGTGTAGCGTTTATAGGAAGTAGTGTTCTGTCATGATGC
CTGCAAGCGGTAACGAAAACGATTTGAATATGCCTTCAGGAACAATAGAAATCTTCGTGCGGTGTTACGTTGAAGTGG
AGCGGATTATGTCAGCAATGGACAGAACAACCTAATGAACACAGAACCATGATGTGGTCTGTCCTTTTACAGCCAGTA
GTGCTCGCCGCAGTTGAGCGACAGGGCGAAGCCCTCGAGTGAGCGAGGAAGCACCAGGGAACAGCACTTATATATTCT
GCTTACACACGATGCCTGAAAAAACTTCCCTTGGGGTTATCCACTTATCCACGGGGATATTTTATAATTATTTTTTT
TATAGTTTTTAGATCTTCTTTTTTAGAGCGCCTTGTAGGCCTTTATCCATGCTGGTTCTAGAGAAGGTGTTGTGACAA
ATTGCCCTTTCAGTGTGACAAATCACCCTCAAATGACAGTCCTGTCTGTGACAAATTGCCCTTAACCCTGTGACAAAT
TGCCCTCAGAAGAAGCTGTTTTTTCACAAAGTTATCCCTGCTTATTGACTCTTTTTTATTTAGTGTTACAATCTAAAA
ACTTGTCACACTTCACATGGATCTGTCATGGCGGAAACAGCGTTTATCAATCACAAGAAACGTAAAAATAGCCCGCGA
ATCGTCCAGTCAAACGACCTCACTGAGGCGGCATATAGTCTCTCCCGGGATCAAAAACGTATGCTGTATCTGTTCGTT
GACCAGATCAGAAAATCTGATGGCACCCTACAGGAACATGACGGTATCTGCGAGATCCATGTTGCTAAATATGCTGAA
ATATTCGGATTGACCTCTGCGGAAGCCAGTAAGGATATACGGCAGGCATTGAAGAGTTTCGCGGGGAAGGAAGTGGTT
TTTTATCGCCCTGAAGAGGATGCCGGCGATGAAAAAGGCTATGAATCTTTTCCTTGGTTTATCAAACGTGCGCACAGT
CCATCCAGAGGGCTTTACAGTGTACATATCAACCCATATCTCATTCCCTTCTTTATCGGGTTACAGAACCGGTTTACG
CAGTTTCGGCTTAGTGAAACAAAAGAAATCACCAATCCGTATGCCATGCGTTTATACGAATCCCTGTGTCAGTATCGT
AAGCCGGATGGCTCAGGCATCGTCTCTCTGAAAATCGACTGGATCATAGAGCGTTACCAGCTGCCTCAAAGTTACCAG
CGTATGCCTGACTTCCGCCGCCGCTTCCTGCAGGTCTGTGTTAATGAGATCAACAGCAGAACTCCAATGCGCCTCTCA
TACATTGAGAAAAGAAAGGCCGCCAGACGACTCATATCGTATTTTCCTTCCGCGATATCACTTCCATGACGACAGGA
TAGTCTGAGGGTTATCTGTCACAGATTTGAGGGTGGTTCGTCACATTTGTTCTGACCTACTGAGGGTAATTTGTCACA
GTTTTGCTGTTTCCTTCAGCCTGCATGGATTTTCTCATACTTTTTGAACTGTAATTTTTAAGGAAGCCAAATTTGAGG
GCAGTTTGTCACAGTTGATTTCCTTCTCTTTCCCTTCGTCATGTGACCTGATATCGGGGGTTAGTTCGTCATCATTGA
TGAGGGTTGATTATCACAGTTTATTACTCTGAATTGGCTATCCGCGTGTGTACCTCTACCTGGAGTTTTTCCCACGGT
GGATATTTCTTCTTGCGCTGAGCGTAAGAGCTATCTGACAGAACAGTTCTTCTTTGCTTCCTCGCCAGTTCGCTCGCT
ATGCTCGGTTACACGGCTGCGGCGAGCGCTAGTGATAATAAGTGACTGAGGTATGTGCTCTTCTTATCTCCTTTTGTA
GTGTTGCTCTTATTTTAAACAACTTTGCGGTTTTTTGATGACTTTGCGATTTTGTTGCTTTGCAGTAAATTGCAA
GATTTAATAAAAAACGCAAAGCAATGATTAAAGGATGTTCAGAATGAAACTCATGGAAACACTTAACCAGTGCATAA
ACGCTGGTCATGAAATGACGAAGGCTATCGCCATTGCACAGTTTAATGATGACAGCCCGGAAGCGAGGAAAATAACCC
GGCGCTGGAGAATAGGTGAAGCAGCGGATTTAGTTGGGGTTTCTTCTCAGGCTATCAGAGATGCCGAGAAAGCAGGGC
GACTACCGCACCCGGATATGGAAATTCGAGGACGGGTTGAGCAACGTGTTGGTTATACAATTGAACAAATTAATCATA
TGCGTGATGTGTTTGGTACGCGATTGCGACGTGCTGAAGACGTATTTCCACCGGTGATCGGGGTTGCTGCCCATAAAG
GTGGCGTTTACAAAACCTCAGTTTCTGTTCATCTTGCTCAGGATCTGGCTCTGAAGGGCTACGTGTTTTGCTCGTGG
AAGGTAACGACCCCAGGGAACAGCCTCAATGTATCACGGATGGGTACCAGATCTTCATATTCATGCAGAAGACACTC
TCCTGCCTTTCTATCTTGGGGAAAAGGACGATGTCACTTATGCAATAAAGCCCACTTGCTGGCCGGGGCTTGACATTA
TTCCTTCCTGTCTGGCTCTGCACCGTATTGAAACTGAGTTAATGGGCAAATTTGATGAAGGTAAACTGCCCACCGATC
CACACCTGATGCTCCGACTGGCCATTGAAACTGTTGCTCATGACTATGATGTCATAGTTATTGACAGCGCGCCTAACC
TGGGTATCGGCACGATTAATGTCGTATGTGCTGCTGATGTGCTGATTGTTCCCACGCCTGCTGAGTTGTTTGACTACA
```

Fig. 6 (Cont.)

```
CCTCCGCACTGCAGTTTTTCGATATGCTTCGTGATCTGCTCAAGAACGTTGATCTTAAAGGGTTCGAGCCTGATGTAC
GTATTTTGCTTACCAAATACAGCAATAGTAATGGCTCTCAGTCCCCGTGGATGGAGGAGCAAATTCGGGATGCCTGGG
GAAGCATGGTTCTAAAAAATGTTGTACGTGAAACGGATGAAGTTGGTAAAGGTCAGATCCGGATGAGAACTGTTTTTG
AACAGGCCATTGATCAACGCTCTTCAACTGGTGCCTGGAGAAATGCTCTTTCTATTTGGGAACCTGTCTGCAATGAAA
TTTTCGATCGTCTGATTAAACCACGCTGGGAGATTAGATAATGAAGCGTGCGCCTGTTATTCCAAAACATACGCTCAA
TACTCAACCGGTTGAAGATACTTCGTTATCGACACCAGCTGCCCCGATGGTGGATTCGTTAATTGCGCGCGTAGGAGT
AATGGCTCGCGGTAATGCCATTACTTTGCCTGTATGTGGTCGGGATGTGAAGTTTACTCTTGAAGTGCTCCGGGGTGA
TAGTGTTGAGAAGACCTCTCGGGTATGGTCAGGTAATGAACGTGACCAGGAGCTGCTTACTGAGGACGCACTGGATGA
TCTCATCCCTTCTTTTCTACTGACTGGTCAACAGACACCGGCGTTCGGTCGAAGAGTATCTGGTGTCATAGAAATTGC
CGATGGGAGTCGCCGTCGTAAAGCTGCTGCACTTACCGAAAGTGATTATCGTGTTCTGGTTGGCGAGCTGGATGATGA
GCAGATGGCTGCATTATCCAGATTGGGTAACGATTATCGCCCAACAAGTGCTTATGAACGTGGTCAGCGTTATGCAAG
CCGATTGCAGAATGAATTTGCTGGAAATATTTCTGCGCTGGCTGATGCGGAAAATATTTCACGTAAGATTATTACCCG
CTGTATCAACACCGCCAAATTGCCTAAATCAGTTGTTGCTCTTTTTTCTCACCCCGGTGAACTATCTGCCCGGTCAGG
TGATGCACTTCAAAAAGCCTTTACAGATAAAGAGGAATTACTTAAGCAGCAGGCATCTAACCTTCATGAGCAGAAAAA
AGCTGGGGTGATATTTGAAGCTGAAGAAGTTATCACTCTTTTAACTTCTGTGCTTAAAACGTCATCTGCATCAAGAAC
TAGTTTAAGCTCACGACATCAGTTTGCTCCTGGAGCGACAGTATTGTATAAGGGCGATAAAATGGTGCTTAACCTGGA
CAGGTCTCGTGTTCCAACTGAGTGTATAGAGAAAATTGAGGCCATTCTTAAGGAACTTGAAAAGCCAGCACCCTGATG
CGACCACGTTTTAGTCTACGTTTATCTGTCTTTACTTAATGTCCTTTGTTACAGGCCAGAAAGCATAACTGGCCTGAA
TATTCTCTCTGGGCCCACTGTTCCACTTGTATCGTCGGTCTGATAATCAGACTGGGACCACGGTCCCACTCGTATCGT
CGGTCTGATTATTAGTCTGGGACCACGGTCCCACTCGTATCGTCGGTCTGATTATTAGTCTGGGACCACGGTCCCACT
CGTATCGTCGGTCTGATAATCAGACTGGGACCACGGTCCCACTCGTATCGTCGGTCTGATTATTAGTCTGGGACCATG
GTCCCACTCGTATCGTCGGTCTGATTATTAGTCTGGGACCACGGTCCCACTCGTATCGTCGGTCTGATTATTAGTCTG
GAACCACGGTCCCACTCGTATCGTCGGTCTGATTATTAGTCTGGGACCACGGTCCCACTCGTATCGTCGGTCTGATTA
TTAGTCTGGGACCACGATCCCACTCGTGTTGTCGGTCTGATTATCGGTCTGGGACCACGGTCCCACTTGTATTGTCGA
TCAGACTATCAGCGTGAGACTACGATTCCATCAATGCCTGTCAAGGGCAAGTATTGACATGTCGTCGTAACCTGTAGA
ACGGAGTAACCTCGGTGTGCGGTTGTATGCCTGCTGTGGATTGCTGCTGTGTCCTGCTTATCCACAACATTTTGCGCA
CGGTTATGTGGACAAAATACCTGGTTACCCAGGCCGTGCCGGCACGTTAACCGGGCTGCATCCGATGCAAGTGTGTCG
CTGTCGAGCGGCCGCTAGGGATAACAGGGTAATACGCGTTATTAATTAAGGGCGCGCGAGTATATCAGGAATAGAGAT
TCCTCCGAGGTGAAAAATTAGAGGCAGAGGGAGGGGCAAATGGGCAAGGAAGCTTGCACCAAGTCGGGAGTGATCCAG
TGTAGGCTGAGAGAAAAAAGGTCTTAAAATCAGCCTTGTAGCTGAAACCAAAAACACACAAGATGGTTGGTGTTCTGA
GCATCATTAACAAATGATAAATGAAGTTGAACTTTTAAATGTATTGCAAATTTTTATAAAGCAAGTAGATCGTTAAAC
TCAGAATGCAACAATGGAATAAAGAAGAGAGTTTGAGATGTTTTAAAATTTATTTATTTATTTTTGAGATGGA
GTCTCACTCTGTTGCCAGGCTGGAGTGCAGTGGCACAATCGCGGCTCACTGCAACATCCACCTCCCGGGTTCAAGAAA
TTCTCCTGCCTCAGCCTCCCAAGTAGCTGGGATTACAAGCTCTCGCCATCATGCCAGGCTAATTTTTGTATTTTTTGT
AGAGACATGGTTTCACAATGTTGACCAGGATGGTGTCAATCTCCTGACCTCATGATCCACCCGTCTCGGCCTCCCAAA
GTGCTGGGATTACAGGCATGAACTACCGTGCCTGGCTGAGTTTGAGATTTTAACTGTAAGTCCTCCAACTAAGTTGCC
ATGACAAGAACAGGGATGATGAGAGTGGAAATATGTTATCCTGCAAATTATCGTTTATGTAAAAGAATATTTTCCCT
CTTTTAGGTAAAGGAAGCATCTTCTGGAGCACCTTCTCTCTGACTATCAAAGCACCATTAAGCCACAAATAAACTGTA
ACATGAAGTAGGAAACAACTGCCCTTTTATATAACCATTGAGAGGTGGCTTTATATGCATACCAAAATGTTGATGCTC
AATGCTAAAATTGGATTTAGTAATTTAATATGCCTACAAGAAATTAATTTTCTTTGGATTATATTATTTCTGTGTACG
ATTTATCTTAGTTAACTTGGAAATATTCTGCTCTAAAAACAACTCTTGTTTTTTGGGTTATATTTTCTGTATCAACTA
TAGCTCTTTTCCAAATGCTGTCAGAGATAGCCCATGGCTACTGATCACAAAATTCAATTTTATGGCATTTAAATTATT
CTATACTCTAAATTATTTTAAAAGTGCACAGATGTGAATTTTTCACATCTGACTCAAAAATGTTGCTGATGTTGACTC
ACTTTTTTATTTCAATCTTATTGAAGTAGGAGTTTACTTTTCTGGAACCTGGATGATAACAGGAGACTGGAGAGGAAA
CCCCCCAAATTGTTTTCCTTTAAACCCTCAGGATGAATCATCCTGGATAATCACCCACACTTGATTTGGGTGATATCT
AAATGAGAGTTGGGTCTTAGAGTAGGTGCTGAGTTAGTTTAGGACTTGCGCTGTTGGAATGAGTTGAATGTTTTACA
AGTGAGAAAGACATGAGTTTTTTGGAGTCCAGAGGGTGGGGGGTTATTGGCTGAATTAAGTCCCCCAAAATGTATGCA
TTGAAGCTGTAACACACAATATGTGACTGAAATTGTGCATAGGGTCTTTAAAGAGGTGACTAAGTGAAAATGAAAAAA
TTAGGGTGGATTCTTCTCAAATTGGACTGATGTCCTCCTAGGAAGAAGAAATTTGCACACACAGAAATGAGGCACCAG
AGGTGAGCGTGCAGAGAAAAGACCAGGTGAGGATTCAGCAAGGAGGTAGCAACCTGCAAGCCAAGGAGAGAGTCCTCA
GGGGAAACCAAACCCACTACCACCTTTATCTTGGGTTTTCCAGCTTCAGAACTGTGAGAAAATATGTTTCTGCCATTT
CGGTCACTAATTCTTTCCTATCTTCTTGTGGGAGCTCTAGCAAAAACAAGAGGGACCCCAAAGACCTTGGATGAGGGA
GAAGGAGGAGATGGAGCAGGGTGCAGGAGGCGGTGCAGGAAGGGGCTGGAAGGTCGGGCTCTGAGGTGCATCTCCTGG
GTGGAATCTTGACTCCACTCCTATTGTCTGGAGGACTTGGGAAAACATTTAACCTCCTAATATTCACTCACTAATA
AAGATGGGCTTGAAGCACAAGGCTCCCCATCATCCTATTCTATATTACAAAAGTCTTCTTGAGGTAACACTTGTAAAA
```

Fig. 6 (Cont.)

```
CTCTCGCTAATGCATCTGGCATGTATTATGGACTCATAAGTAGCCCTTCTGAGTGATCTAGTGATGTGCAGAAAATGG
CATTCATGCTGTGTGCACCAGGGGGCACTGTGAGGTTTAGTCTGAGGCCCCTAATGAGTCCAAGCCCCTAGTAATGCT
CAAGGGCGAAGAGCCTGACTGTTGCTTCCTATGAGGCCCCTTCTAGTGGGTAAATCTGAAAATGCACTTGGCCCTTCT
TCTGATCTTGAGAAATTACTCAGAGAAGGCCATCAGGCTCAGGGCTCAGACAAGAACCAGGACAAATGTTTTAGGGAA
TGGAGAACAGATTTGCATCCACTGCTCACCAGAGCCACCTAACGACGACACAAGAATAAAGGAAGTAGATTTGCATGA
AGAGACTTCCCTTCCTATGATAAGAGAGGCCTGGAGGTTCCTCCTTAGCTGTGGGCTCAGAAGCAGAGTTCTGGGGTG
TCTCCACCATGGCCTGGACCCCTCTCTGGCTCACTCTCCTCACTCTTTGCATAGGTGCTGCCTCCCAGGGCTCAACCC
CATATTATCATGCTAGCTGTGCCAACCTGGCCCTGAGCTTCGGCTCAACACAGGCAGTAGTGTAGGGTGTGGGACTCT
AGGCGTGAAACCCTTATCCTCACCTCTTCTGTCCTCTTTGCAGGTTCTGTGGTTCTTCTGAGCTGACTCAGGACCC
TGCTGTGTCTGTGGCCTTGGGACAGACAGTCAGGATCACATGCCAAGGAGACAGCCTCAGAAGCTATTATGCAAGCTG
GTACCAGCAGAAGCCACGACAGGCCCCTGTACTTGTCATCTATGGTAAAAACAACCGGCCCTCAGGGATCCCACACCG
ATTCTCTGGCTCCAGCTCAGGAAACACAGCTTCCTTGACCATCACTGGGGCTCAGGCGGAAGATGAGGCTGACTATTA
CTGTAACTCCCGGGACAGCAGTGGTAACCATCTCACATTGACACAGACAGATGGGGAAGTGAGACAGAAACCCCTTCA
                                    IgLV3-19
CTATCTGTGTCATCCTCTCTCTCCAGCCCCAGCAGGACTGTGAACAAAGCCATAAACAGGGCTGGCCCAGTTCACCTG
CATCTGAGACCTCCAGGCTGCCTTTCCCTCCATTCCTCCAGGTAGGCTCTGCAGAAGGTGGGTCAGGATGATGTGAGG
CTTGAAGGACCAGGCTGTTCTGCTGTTGTTTAGACTGAGTGTGCCTTGCCTCAAGATGACCTGAATGGAAGGACCACA
AGAAGGAGATGGGCAGCTGTTGAGTGGTCATGATCCCTGGAGTTCCTCTTGTGTGGTGACTGGATCTAACACAATGCC
TGTACTTTGTGGCCCAAATGCCCTGGATTATTGGTCTGAACTCCCCATGTTTAACTGAGACCCTCAAGCCCCAGCTCC
ATGCATCCTGATGTTCTGAACAGGAAAGTCTTTTCTAGTGAGCACTGTGGCATCCCTTGGCATCCCAGCTTCACACAG
CAATTCCCCACCAAAAAATGCCTTTGAGTGCAAAGAACGGCTTCATGCAAAGATGTGCCTCCTTCAGAATGTAGTTCA
GGAGCAATAACTACCTGATGCCTTAATCCCAAAGCCATATTTTAATTTAGAATGACCTTGAAATGCCTTCTAGCTGAG
CAGTCAGTTGTAACACATTCCCAGTCACGCCTCCCACACTTCTTTCCTGACAGTATGTCATGAAACCCTACTGCATGG
AATCCTGCCTCTTAGAGTAGGATTCCAGGGATCTCAAAAATTGTTTAGAAATGAACAAAAACAGTCTAGTTGGAAGAG
TATCAAAGAGGAGGCAGTTGCACATGCAGAGAACTCTGAGGTCTGCAAATATACATGAACTGATGAGCACTTGTGTGT
AAAGAAACACCTCCGAAAGAGAAAAGAACCACGCAAAGACTCTTGAGGGAACACCTCACAGAGCTCACTCCCACACAC
ACCCACCCACGCACTCACAGACACACTCACACACACAGTCACAGAGGAAAGGCCTGACTTACAGGGCATGAGGTTGACT
CATCAGAAGAGCTTTGCCTCAGTACTGGGGAAAAAGTCACCCTAGACAAAATGCTGCTCAGGTCTCAACTATGAAAGT
GTAAAAGCAAACAGAAAACTCAAACTGTTTTTCTGAACAGTAAAGTAACTTTACTGAATTCAACAATAAAAGACAGAA
ATAGAGAATGAACTGCAAAAGAATTCTCAACCCAGCAGGAAAATGCACAATGCCTTCATCCTGTCAATATTTCCTGC
AAGGTAACCAGAAAATATATGCTATATCAAACAGAGAAGTGAATCAATCCCAAATGGCAATAAAATTGCACACATGAT
AGACCTTGTAGGCAAGGATATGAAAGAAATTCTTATAACTCTATTCTATTCTACTTGTTCTTGAGGATATAAGATTGA
AAAATCATATTAAGTGGATACATAAAACATATAAAGACAGACGCAAGTTATACTCTTATAAATGATCCATAATATGTC
TGCAATAAAAAATACACTGAATGAGACTGATTGCAGATTGGATTCTGTGAAAGAATAGATGAGTGAACTTGAAGATAT
GGCAATGGCAGCTATTCAAGACGAAGCACAAAAGCGTAAACAGAGTATCAGTGAGTTTTAGGACATCTTCAACTGCCT
AAATTGGTATAATGAAAGTCATTAAAGGAGGTAAGATTGGACAGGGAAGAGAAAAGGCAGAAAAACAATTTAAAGGAA
CAATGACCAAAATTTCCCAAATTTTGTGAAAACTAGAAACCTCCTATTCCAAAAAGTTTAACATGTCCCAAAGACACA
CACACACACACACACACACAGAGAGAGAGAGAGAGAGATAGAGAGAGAGAGAGAAAGAGAGAAAGGGAGAGAGAGA
GATACAGGTGAACAACAAAATGACAAGAACAAATTTGGTTTTTAAAAATTTTTTTAATTTTAGTGGCTTCATAGTAGG
CATATATTTTTATTGGGTACACGAGATGTTTCAAAACAGGCATGCGGCGCGCTCTGTCAGTCCTGACAGCAGTTCCAG
AGACACTTCCCCATTAAGATGTCCCCAGGCTCTTATAATACAACCTGTCTGTTATTTTCTGCCTAAATCTTTTTAATT
ATCCCCATAGCATTTACAACTGTAGGAATCTTTGCCTATTGTTAATTTTATTAATTGATTGGTGTTAAATATTTACTT
AATTGGTCATGGATGCTTTTTTACCACAGAATCACACATAAAAAACAGACACAAACAGCTAAGGGTGTATTTCTCGCT
GCAATAATACCCACCACTTTCACGAAGACACCAGGGTCTTTCTCACTTTTTGTCCCACCATCCCTATGATATTGGCTT
TATTTTCATCCCTGCTGATGTGTGACCTCAGGGTGGCTGCTGCAGCTCCAGCTATCACTCCCATATTCAAGGAGAAAA
GGGCCTCATGAATCTAGTGCTCTTTCACAAGAGCAAAGCTTTCCTAAGAAGAATTTCACCCACTGATCTCACACCCCA
CTGATCAGGCCTGAGTCACATGGTCAATCCCAGCTGAGCAGGACCTGGGAATCACAGGCACCAGTCTTTTCGGTGAAT
ATAGAAGACAGTGCTCAGGTGGAAGGTGACAGGGACTGTCTGCTGGGTCTGCAAACCCAGTTTTCCCGCACAGCCAAA
CCAGCACGATGAACAACTCACTTCAAGAAGGCTGTGTCTTGTTCCTGCTGAATTCACCGCATGGAACGTGTCCCAGAC
CACAGTGGGTCTGGATTAACATTTGATGGGTGGATGTTCTTCTGTCTCTGACTTTGGTGCAGGAGTCACCACTGTACG
CTGGTCCTGCATCCACAGCGGGGACCAGTAAGAGCCAGTCCCTGAGTCCTGTGATCCCGCCCTGCATGCCAAGCCCT
GGTATTACCCCCATGACCACCCACCGCCCAGACACATGTGCAGGCAGCCTCAGATGGACCTTCCTCCTCCTCTTCCAA
ATATTCATGTTCATATTGTCATGAGTAATCTGCACCCCTCGCACCTGGTATTGAGGCAGGCATGAGTCACAAAGAGAA
GAGAAAAATTTCCTCCATTGGCACCAGCAGTCTGCAGACCAGGGAATCAGGGACCTGAACAGAAGATTTTAATTATAC
ACCCGGACCCAGGAGGCCCTTGAGCCTCCAGCAGCCAGTATGGAGCAGCCACCAGGGGACAGAACAGAGTCACCTGGC
```

Fig. 6 (Cont.)

```
AAAGTCACTTGGAGATAGGGTAGACCTGGGTGACAAGGAGATGCTGACATGCAGGGAGGGTCAGTGACCACAACCTGA
GATCTAGAAAGGTGTCGTTTTTCTACAGCATCATCCTTAACATCGAGTACAAATTCTCCAGGCTTTGTGTTTCTCAGC
TTTGTCTCTGGCCAATGTTGCATATTTGACACAGGTGCAGACACTTTGCTTCCCCCTACACACTGGCCCACTCTTCTG
TGCTAAAACGCTGTCATTGCCACAAACGCCATCCTCCCCTGTGGGCACATGTGTTTCATCACCCTCCTGTTTGCTCTG
AGAGCCCCCTCATTCTGCTACACAGCAAAGTTTTCTTTCAGCATCTAAGCTGTACCTGACCATGACCACATACTGGGG
GTACATAGGCACAGCACCTGTGCCCTACCCTAGGAGCTCACAGCCAAGGCCAGGAACTTACAGCATCTCCTGAGTCTT
TCAACACTCCGTGTGCACATGACAAGGGTGAAGTTTGATTGTGGAAAGCACCACTCAGAAGCAATGGCAGGTCCCTGC
ATGTGTGCCAGCCTTACGGTGTCACCTGTAGAGTGGGGTCATGAGGGTCACTGCACTGGGTTGAAAAGTGCCCTCCAG
AGGGGGAGCTAGAACCACACCTAACTTCTGGATTTTGCCACAAAATATTTAGGGACAGGACACCCTGGAGTCCTCAA
TTACCCAAGTTATTCTGAGCCAGTATTCAACAGAGGAAGTACCTTAGATCTCAGAATAATCCCTCAGTCGCCATTGTA
AGTCAGTCCCTGGCCATCTCCACGCAGGACAAGGAATGGCCACATGGGCAGGACATCATACTACCTGGAAAACGCACA
AAGAATTCCTCTCAGAGTTCTGCATGGCCAGATCAGCTCAGGAGTGAGGCCATAACACAACCTACAGTGACGATGTCA
ACCCAGATGATGGGACCAGAAGGAGAATGAGAATTCTGTGTGCTGAGGGTGGGTCTTTAGGGGCCCCCTCTCTCTCTG
TCCCTTGGGGCTGAGCCCTTCTCTGGAAACCACACAGCTCCTCCTGCAGCAGCCCCTGACTGCTGATTTGCATCACGG
GCCGCTCTTTCCAGCAAGGGGATAAGAGAGGCCTGGAAGAACCTGCCCAGCCTGGGCCTCAGGAAGCAGCATCGGAGG
TGCCTCAGCCATGGCATGGATCCCTCTCTTCCTCGGCGTCCTTGCTTACTGCACAGGTGCTGCCCCTAGGGTCCTAGC
CACTGGTCCAGTCCCAGGGCTCTGGGTCCAGCCTGGCCCTGACTCTGAGCTCAGCAGGGCCCCCGCCTGTGGTGGGCA
GGATGCTCATGACCCTGCTGCAGGTGGATGGGCTCGGCGGGCTGAAATCCCCCCACACAGTGCTCATGTGCTCACAC
TGCCTTAGGGGCTCTTTCATCCCTGTTGATCTGTGTCCAGGCCAGGCACGTGGGAAGATTTACTTGGAGTTCAGCTCCT
CAGTTTCAAGCCTTTTCTCTCCCGTTTTCTCTCCTGTAGGATCCGTGGCCTCCTATGAGCTGACTCAGTTCCACCCTC
AGTGTCCGTGTCCCCAGGACAGACAGCCAGCATCACCTGCTCTGGACATAAATTGGGGGATAAATATGCTTGCTGGTA
TCAGCAGAAGCCAGGCCAGTCCCCTGTGCTGGTCATCTATCAAGATAGCAAGCGGCCCTCAGGGATCCCTGAGCGATT
CTCTGGCTCCAACTCTGGGAACACAGCCACTCTGACCATCAGCGGGACCCAGGCTATGGATGAGGCTGACTATTACTG
TCAGGCGTGGGACAGCAGCACTGCACACAGTGACACAGGCAGATGCGGAAGTGAGACAGAAACCAGCCACCTCGGCCT
IgLV3-1
GGCTCACAAGACCCTTCCCTCTCTCCTGCCCTGTCACACTGAGCAGGAGGGAGCCTTCCATGTGGAATGGAAGTTTCC
AGTCCTATCCCTGCCCTTATGTTCCTGAGAGACGGGAGCAAGTTCCTGCCCACCTCTAGGCTCAGCTTATCCCAGAAT
AAACTGAGCTAGTCATTTTGATGATCAAATGCCAGCTCCCAAAAGACCCCAGAAACCCTGATATCTAAGTAGCACCGA
CTCTATTAGTATCAAGGGAGACTAGCCCTAGGGTGGAATCATTTTAGTGTCTCAGAAGGCACAGGGCAATGGAAAGTG
TTTATGAGGTTTCAGGATATGCACGTGAGCAGTTAAAGGCAGGTCTTACAAGGAAGGAACCTACTAGAATTGGGGCCC
ATCTGTGACATCATAGCACAGCCTGGTGGACACAGAAGGGAAGGTCCTGAATCAAGTCTTGATCAGTAAATATTTA
TTGGATAAGTGAGCAATTTACATAGGTGAGAACTGTGTGCTCTCTTGAGCAGAACACTTACCTGGATAATTGGTTTTC
AGGAATTCCCTGAAGCAATGAGTGACATTCTTTATTGTTTTCACCCTCATCCACCTGGGAAAGAGTATCCTGGAACCA
GCAGTTAACATTGACACAGCTGGTCTCGGTCCTCAGCACAAACATTCATTGCAGGCTGAAAAGTGACAACGGAAGAGA
AAGGAGTTTATTAAATCCCTAGACACAAACAAATCCATAAGCAGAGATGAGAGATGCGGGCTCAGCTGGCCCAGTCCC
ACAGGGGTCATTCCTCTTGTGATGGAAATGACCACATGAGGGTCCCCAAGCGGTGTTGGGGGCAGTCATGGGGAAC
TGGCCTCCCAGGGCTACCTGCTGCTTGGGCTGGGCAGAGGTTAGAGGGATGGAAGTCTGGTCCAGTCCTTCCCAGCAG
CATCTCCAGGCTCCTCCTCCCTCTACTGGGGCTTCCCCTCCACTCCCCAGAACCATCATTGCTTCCTCATCTCCTGTC
TCCTCCCTGCCCCAAGGCCCTCCCTGTGCTCACCCTGGCTCCTCCCCCTGCTCCATGCCCAGCCTCTGCAGAGCAGCC
CAGGCCCAGAGACTTGGGCAGAAGCTTCCGTCCCACCAGCTGCAGAACCTTCCCTACAGAACCAGGCCAGTCCCTGTG
TCTCATATTTGTAGAGATCCCAATCACCCTCAGAGATGACGGGTGGGAAACCAGCCCACAGTGACCTAGGCTGTTGGG
CATATGGCCTTCAAGCTGGCCTTCAAGCCCACTTGGCTGCATCTCCTTGGCCAACTCCAACATCCAGGCTGGGAGTCT
GGAATCCTAGTTCCCCTGGCCCATTCACTCCCACTAGGGTTGCTTCTAAACTCCCTGGGCCTCAGCTTCCTAGTCTGC
CCACTGGAAGCAGCGACAGGCATTTTCCAGGGCTGCGGTAAGGGCCCTGGAACACCCTCTCTCACCCTCTCTCTCCCT
TTCTCTCTCTCTCTCTCTCTCTCTCTCCCCCTCCCCCTCCCCCTCCCTCTCCCTCTCTCTCTGCCTCTGTTT
CCTCCTCAGTAGTGGGAAGACCCCCTGTCAGGTGGGCCAGTCCATGACATCTACAGAGGGAGCAGGAACCTCTCCTAT
TTCCTGGAGGAGAGCTGGGGTGGAGGCTGCAACCCAGGATCATCAGAGGAGCTGGGGTCTTCAAGGTTCCTAGGGACC
CCTTAAGCGGGGTCAGAGTGGCTTCAGCGGTCTTATTGCTCGGTCCAGACAGAAGATGTTTCCAGTTGTGAAAAACG
ACTTCAGGGACAACAAAAACAGAGATTCGCCTCTCCAGACACCAGTGGTTGGTGTGCCTGGAGTACTCCTCGTACCAG
GCAGGGGAGAGAGTCCTAGACAGAGGAGGTTCTAAGTGTCACCTAGATTTCGGGCCTCGGGGCCTGTATTGGGTAGGT
GATGTCACAGTGAGTTGAGGCGCGCTGGTGCAGAAAACAGACTCCTCCAGGTCTATGCCCTTTCTCAGTGAGGTTAGA
TTTCATGACTGCCTGAGGCCGAGTTCTCGACTCTGCCTCAATATAGGAAGACCTGAAAATCCTCCCAGCTCCACAGCT
CTCTGTAGGAAAGACTTGAGACCTCAATGAGGGTCAGGGTCTCCTGCCCAGGGTTGCCTCCCTCACCTCCTTTCACAT
CCTCTGTGCATGCAATTCCTCATCTCAGAGTCTGCTTCCAGGGAACCCAATTAAGATCACCAGCCATCCCCAACATGG
GCCATGTGGGACTTCAGGAGGCCACTGTATGCTGGAAAGCACCTGTTTATTCCTAAATTAGCACTGTGAGTATCCACA
```

Fig. 6 (Cont.)

```
CGCCCAATGAGATCTGAGTGTTTCTTGCATTTGCATGGAATGAGAAGGGAGCCTGACTCGCCAGGTGCTCTGGGGTCT
AAGGGAGAGTTGGAGTCAGATCTCCCTGCAGGGAAACCTGGGGCAGGAGGAGCAGCCTTACCCCATGCAGGGACCACA
GATGCACCCACAGGGTGAGCTTAAGTATGGACACTGCCTACCTCCACCCTCCACATCCTGTGTAAAAAATCATTCTTT
CCACCCCTCCTCCAGCCTATCAAAGTTGACACTTAAAAAGCCACCACAACCCACCCTTGTCAACAGGAAACCCATTCA
CATCTCCATCAGCCACACAATCTCCACATAAAGATTCTTCAAAAAATAATAACAATAGCCATGCAAAGTATATGATAT
ATATCATAAATAATTGTACTTAGATTATATATGAAAATGATACTCTTTTTGATATGCTAGGTAAATAAAATACATTAT
TTAAACTCATTGACTTCTTCTCTTTGTATTTATAACATGATGACTAGACAGTGGGATTCCCATGAGGCTCACATCACA
TTGTGATTGAACAAGGCTGGTCTGCAGGGCTTCAGGTTACAGGGGCTGTGGAGTGACCTGGTGCAGGAAGCCCCGTCT
CCATCCATAGGACATCAGTGTGAACCCAGGGAGAGGCGCTGGTATAAGAGAGATGAGAACACAGGTGTGAACCACCTG
CTTGTGCAGGGGACTGAGCCTTCACTTTGAGCCAAATAAGTTTTCTTTCCCAAGTTCGATCCTGAACAAGAGGGCTTT
CTGGACTTCTTTTTGTTTTCAGGTTTGTGCCCCTTCAGGTTTGGGGCTGTCTGGAGTCCCAGCCAGGGGACAGTGAGG
AAATCCAGCAGTCTCACACTGACTCTGTTGTATTTCATCTGCTGGGCCATCCCAAACTGCTGCGTACCATTTCCTTT
CCTGGTGCTCAAATAGCTGCTCCATGCACTTGTCATGGTTTTATAGCTCAATCTAGATGGGAAGACAGGATAGTGTAT
GTTACAATATTTAAATAGAACCTGAATCCCTTAATAGTTATTTTAATATGGAACATTAAAAGAGTTGCATCATAGGCA
ATGGGGAAAGATGAAGAAAGATTAAACGCATTTGGAGGAAAAACTAAAAATGTCTTTATTGAATGTCTGTGTGTCTTC
AGTGTCGAAGGGTTGAGAGAGGTCAGCTTTAGGTTGTCCTGAGGATGTGCTCAGATGGGGAAAGTAAGAAAGCCGGA
AACGTGCATCTCTGTGACCTGACACATAAATCACAGTAAAATGGAAGTAAATCTTTCAATAAACCTTTCAAGATAACA
TCACTCTGGTGCACATAGAAAGGCCTGTTAGCAAACTTTCCCTTTTCCCTGCTGGCTCATATCCCCATGGATCACCTG
TATGCAGAACGGACTCTGTGGTCTCCATTTATCAGGCTGAGAACCAGAGGCTGGGAAGGACAAGTCACCTGCTCATGA
GTGGGAGGGGCAGGATTGGGAGCAGCGGACTCAGGCTCAGGACTGTGGCCCTGGTTGGTGCTCCTTGTTCCCTTCACA
GGGTCCCACCCACATGTGCCCGTGTGGATGTGGGTGCACTGCCTGGGGTGGCTGATGTGCTCCAGGGATTTGATGGTG
CAGATGCTTCAGGACAAAGCATGGGAGTGGGGATGGGACGAGCTGCCGCTGGGCAGACCAGGGACCAACGCCACCCAG
CAGAGGCTTCCAGTGGGGTTGGGCAGCCCCATTTCCTGAGAATAGAGAGAACCTGGCAATGAGTGCCAGAAAGAGGTT
ACTTCGAGGTGTGCCCAGGCCTGGAGGGTCACAGAGACACAGGCACCACACAGCAGAGACACTGAGGGCCAAGAGCTC
ACTCAGGTGAGGGGCTTCAGCAGATTTTTCTCTCCTGAGCAAATCACGTGCAAAGAAATCAACTTCCTGTCATCAGAA
TAGACAATCAGGACTTTAGTCTCCTTGGCTGAGCCCCGCTGTCAAGGGAAGCAGAAGTCTCTAAGCCCAGGCCCAAGT
GAGGGTGGGGTGAGAAGAGGAGCTCAGGATGCAGATTTGCATGGAGGTCCCGCCCTTCTCTGAGGCAGAGGGATAAGA
CAGGGCTGGGGGCAGGCCCAGTGCTGGGGTCTCAGGAGGCAGCGCTCTCAGGACGTCACCACCATGGCCTGGGCTCTG
CTCCTCCTCACCCTCCTCACTCAGGGCACAGGTGATGCCTCCAGGGAAGGGGCCACAGGGACCCTCTGGGCTGATCCTT
GGTCTCCTGCTCCTCAGGCTCACCTGGGCCCAGCACTGACTCACTAGACTGTGTTTCTCCCTTTCCAGGGTCCTGGGC
CCAGTCTGCCCTGACTCAGCCTCCCTCCGCGTCCGGGTCTCCTGGACAGTCAGTCACCATCTCCTGCACTGGAACCAG
CAGTGACGTTGGTGGTTATAACTATGTCTCCTGGTACCAACAGCACCCAGGCAAAGCCCCAAACTCATGATTTATGA
GGTCAGTAAGCGGCCCTCAGGGGTCCCTGATCGCTTCTCTGGCTCCAAGTCTGGCAACACGGCCTCCCTGACCGTCTC
TGGGCTCCAGGCTGAGGATGAGGCTGATTATTACTGCAGCTCATATGCAGGCAGCAACAATTTCCACAGTGTTTTAAG
IgLV2-8
TCAATGAGGAAGTAAGATCAAAACCTGC19681CCTGGGCTCTCAGGCCCCTTCTTGCTCTGCAGATGCTTCCTCACG
CTGTATAAGGGTTTCCTGCAGGATGGCCTTTGACAATTCTCCTCTCTCAGCTCCTCTCCTTTCCCACCATGAGGTCTAA
AAGGAAACCTGCTCGTGATTTCTCGTTCAGGACTGTGGCAACTTCCTTTTGCTTGTGTGCTCTGGTCCCTTAACGTGC
AACTATTCCTAGCTCTTCAATGCAGGGACGTAGGGACAAGGAGTTTACTGCTTGGTGCAGTCCCCTCCTGTTTTCAGGA
ACATCCTCATTCTAAATGCATCCCCCATCTGTCACACTATGCAGATCAATCTGGACAGAAGCCATCAGGGGGATGGCT
TCTAGTTTCCAGGAATTGCATCTTGTTCCACTCTGTGTCCACCACGCTCTAATGAAGATGGCCCTCCTAGCTTAAAGT
GACCACTTTAAGAAGACTTGAAGATGTTTTTGAGGGATTAAGAACAAAGAGGATGCTGCTGTTTTCTTTTTATTGCT
CCTGCTCTTTGCCGAAATTCCTCAGGTTGCTGAGCTGGGGAGATTTTGAGTGACAGGCTCAGTGCTCTCGCAGAATTC
TCCTCCCCTCACATCGCTGAGGCCCTGTCCTGGAAACTCCTCACAAGTGGACGGTCTTCCCATAGGATGGGGGATTCC
AAAATGGCTCCACAGGAAAGAGTTAACCTGAGTCCACCTCCCTTCCTCATGGACATCGAGCATTTCTAATTTTCATGG
CTGTCAATACTTTTGTACCTGGAATCCCTAATAATCTAATGGTGAGAATTGATTTAGAACACATTCGGACATTAGCTG
GGTCCAATATTTAAATTTTCTGAGCCAGTTGTTAAATACAGCTATTATCATATATAGTTTAGGCTCCTTAAACTTCGA
TTATACAGATTATATTTAAAACAAAGTAACTAGTTTACTATATATATTTACAAAGTAACTACTATATAACATCATGTT
GTGTACCTGAAATATAAACACTAAAATTTATTTCAAAAACCAAAGTGTATTGTCTATTGATGCATAAAAAAACACTCA
CAAAACTTAGCACACTAAGAGAACACATGTCTGTGACCTTGTGACTTGGATGCACCTAGAATTGGGAGTAGCTTAGTT
TGGTCATTCTCGCTCCTGGTTAATCACGAGGTTGCAGCCAAGCTGTCAGGCCAGGCTGCATTCAGGCTACATCTGCCA
AAGAGGTTAGGAACTGTGGAAGCCTCCCTCTGGCTGTGGAAGCCTCCCTCTGGCTGTGGAAGCCTCCCTCTGGCTGGG
AGACTTCCGCAGTTCCTAACCTCTTTGGCAGATGTAGATCATCTCAAGGATAAAGGAGAGAGTGGAGTGAAGGCCCCT
GTCCTTGTCCTCCATGTAAAAGACCATCCCATGCATGCACTATTTTTATTCTTTGCTGAGACATCCTAGGCATAGAG
CACTGCCCCATTCATTCAAAGGTTGTAGAGTATTCTATGGTAGAATTTTAGCCAACTCACTTTTAATGGTTATTATCA
```

Fig. 6 (Cont.)

```
CTATTTTGATCTTATAAATAACACTGCAGCGAACATCCTTATGTAGACTCCTTTGATTTTATATGTAGACATGACCAT
AGAATAAATTTCTAGAAGTCAAATTGCTGAGTCAAAAGGATGTGTGCTTGTAATTTTCACTCACTGTCCTCAGATTCT
CCTCTAGAGGGGTTATCTACAAATTCGCAATGTCAGCCATAAATATTCGAACAGAGTACACTGGGGAAAGTTTAAATG
TTTTTCAACCTAGCAGATTTAAAAATGTTATTTTTTTAGTTTTGCTTTCTCCTGTTCTGCTTGAAGTTGAGCATTTT
CTCTAATACTTCAGTGCTATTTATTTTTATAATTTGGTAAACATTTTCTTAAATGTCCAGATAAGAAGGATTTTGGTC
TGTGGGGCGCGTTATTAATTAAGGGCGCGCGTCATACAATGGTGGTGTACAATGTCGCACCATGGACACTAGGGGGCG
CCTGCGCACCATTCCTGAGAAGACTGGGTGTGATGAGAGCAGGACCAGCGCCACCTGTCCTGCTTGGTGCCCTATGCT
TAGGGCTCACAGATGTCAACTCTCCACCCCCTGGGACCACACAGCCCCACCCCTGGCACTCTCTGACATCCTCAGGCA
GAGGAGCTTGACCCAGGGCCCAGGGTGGGATCAGAAAGCTGGAGGGTCTGATTTGCATGGATGGACCCTCCTTCTCTC
AGAGTATAAGAGGGGCAGGGAGAGACTTGGGGAAGCTCTGCTTCAGCTGTGAGCGCAGAAGGCAGGACTCGGGACAA
TCTTCATCATGACCTGCTCCCCTCTCCTCCTCACCCTTCTCATTCACTGCACAGGTGCCCAGACACAGGGTCAGGGGA
GGGGTCCAGGAAGCCCATGAGGCCCTGCTTTCTCCTTCTCTCTAGACCAAGAATCACCGTGTCTGTGTCTCTCCTG
CTTCCAGGGTCCTGGGCCCAGTCTGTGTTGACGCAGCCGCCCTCAGTGTCTGCGGCCCCAGGACAGAAGGTCACCATC
TCCTGCTCTGGAAGCAGCTCCAACATTGGGAATAATTATGTATCCTGGTACCAGCAGCTCCCAGGAACAGCCCCCAAA
CTCCTCATTTATGACAATAATAAGCGACCCTCAGGGATTCCTGACCGATTCTCTGGCTCCAAGTCTGGCACGTCAGCC
ACCCTGGGCATCACCGGACTCCAGACTGGGGACGAGGCCGATTATTACTGCGGAACATGGGATAGCAGCCTGAGTGCT
GGCACAGTGCTCCAGCCCAATGGGGAACTGAGACAAGAACCCCCTGTCTTCCTCCCCCAGGAGGGTGAGTGCCGCCA
IGLV 1-51
GCTGCTGCTCACGCCTGACCTGTAGCTTCTGCTGCTGCAGGTTCTCCCATGGGCCACGGGGCAGCCAGGGCCCTGCCT
AGGAGTGGAGGCTCCACCACTTTTGTCCTCAGAGTCAGGAACAGGGACTCCAGGAATGAGAATATCCTGCTCCTGCAG
CTTGGGCGCGTTATTACGCGCCCAGCTATTCATTGTGGGCATCTTTATTCCCAATCAGAATTAATTTAGTGGCAGGG
TCACAGAGGCTATGTGAAGACTCTAGGTCTTGTAGGCCTACACTTAGCCTTGCAATATACAGTAAAAGACAAAGCAAT
TCAACAATTCCCCCAGTTAGTCCAATAAATGGCTCTTTTCTCTCAGATATAAATTAAACACAATTATAACAATTATGC
AAATTATAAGATGTGATATACACTTATAATATCCAGGCAATCATATTTCACACTTTAGAATAAGTATTCTATCATCTA
TCTATAATTTAATGAGTTATAATTCTGTACCTAAATCATGTTTGATTTCAACATGTATTACCATCTGAAACCATCCTT
TCAAATCTAGAGCATCTTCTTTAATGCTGAACAACTAAGGTTTAATTGTGAGCTATGAATATCTAATCTTCACCCCA
ATCAGAGATTTGAAAAGGAATTAAATATTACCTGAGTATGTAGAAAGCACAAAGGCACAGGTTCCAAAACTTAAACAA
TTGGAGGAGACAGCTGATTGCCTGGAAACTCCCCAATGGTCCATATAACATTGGAACATCTCATCTATCTTCTGCCTT
CTAGCCTAAAACATCAGACAGACCTTAACTGAAATAGCAATTATGAAGGACTAGCTAACTTGCTTTTGGCAGAGCTTA
GCAATTGACTGCCCTATGTCCATTTGTCCTTTTTATATAGCATTCTTTCTGCAGATAAAATTAGGACATATCTTCTGC
AGTGGATAGTTTGCCCCAATTGAAGCAACTCCATATGGAATTATTTATACTCAATATCTTCTTTGAAGTGGAATGGGC
ATAGTATTAGAAGCAGACATGTCTTGTAGTCAAAAGATCTTTTAATAATGAATTCGCATTGAATGCCATATTCGGTAG
ATCTCTGATGCTTTTTATCTATATAGAGCCTAATTGAATCAACAAACATCAATTGATTTTAGCTATTTACTTTATGAA
TAAGCTTGAAAACATTCGGTTGTAATTAACTGAATAAGAATCTAATATGAACATGAAAATGAATATCTGACCATTAAC
TGGTAATATTAACTTAATTATTCCAAATACTTTTTAATAACAGCCAATAAAAGAATTGGATCTAATCTTTGTATTCTT
ATATGAGTTGAATAGGTTCAATGCCTATCTAAGAGTAAAAAAATAATAATTTTAAATTTTATATTAATTTACAAAGAT
TTATACCAATGATAACCTTAAGTATGTATCACTATAATTCTTGTACTAATGTAAGAAAATATAGCTTCAATTCTGCAT
GAAAATATAGAGATTTCTATTGATGTAACATTATGGCTATAAATGATTTGTTTATAAATTATAAAAAAGTAAATTTAT
GAATTAATCCCCATTTATCTAATGTCTTGTAATATTATTATATCCCTTTTTTTTTCTTTTCAACCCCCTTCCCTTTAC
CTAAGAAATAAAGAGAGAGAAGAGGAAAGGAAATATATAAATCACTGAGTCTAAGCTCTCTGTTTAGTTTACTACCTG
TCCAAGACAATAATTATTTTAAATTATCCTTTAAAATGATAGCATATTTATAATTCATAAAATAATCAAAATTATTTA
CCCCAATTAAAGGACCAGAGCAATGATTTTCCATGATTTCTTCCTGCTGTTTTGAATAAAGAATTCCCTTTTAGGTGA
TGGCAAGAAAATTAGAAAAAATTTGTTAGTCTTAAGAATGGATGAATCTTCACCAGGTTGCCTTTTGCTGTTTCATTC
TGTACTATATGAACCTTATGACTAATATTTAGTTTTATATACATATTTGTATGGATTGTGCAAGGTCACAGGTCAGTT
AAGGATGAATTTTTGTTCCTTATTTCAGCAAGTAAAAGACCATGATGTGCTCCCAAGCAAGCCATTGCAGGCCTAACA
TTTGCTTTCCACTCTATACAGACACCCCACTGCTGTGGTTCTGCTCCTCTATTGTTATTTCTCTACAGGTTTAAATCC
ATAAAAGAAGAGCAGTGCCTGCTGCCAGAGTTCCAGCAGAGACAACACCATCTGCTGAGACCTGCAGACAACCAAGCT
GCCTTCCTGCAGACACCTCATCTGACTGAAGATTCCCAAGACAGATGCTGAGATCCAGAGACAGGTGCTGAACCTCAC
AGAGGACAGATTTGGTACCTTCCAGCTACAGTTGAACTCCTTTGCCAAAGTCAAATGGCTACTGAACTTGGGGAAGT
TACATGATAGTAAGGAAAACATGATTTATCTAGATTAATCAAGTGCTGTATAAAACTGACATTATTACCCTCAAACTG
TATTACCCATGGAGCAATTAATTGATTCAGTGGACCCCTGCCTTCCCAAACCCTATTCTTAACACTCCTTACCACATT
GCCTTAGTTGTGTTACCCATTTGGGCTGTACAGTGTTTTCTTTTGATACTGCCTCCCCACCCAGAATTTTTACCACAA
ATGACAAGGTCACTCCAGTGACCCCTCTCTTTGAAAAAAGTAAAAGGGGGAGTTGTGGGGTGGTGAATTGTGCCCAGA
CATCCTGGTTACCCAGTTGAGCACAGGCCTGGAACCCCAGAGACCTGGTGGGCTGTGACTTCCCCATTCATGGGATGA
GAGGAGTTTGACCAGGCCTCCTATGCCTCTGGCTCTTGTTGCAGCTACAGACTCCCACAGCCCCTTCACAGAGGTGT
```

Fig. 6 (Cont.)

```
GTGGCCATCAGTCACACAGGCAATGCCCTTAAGCTCCTGGTATTCTGCCTGGACTCCATACCCACAGTTACCTGGCAAC
AGCCAGGTATGCTCCTCCACACAGTTACCTAGCAAAAGCCAGGATGGCACAGACAACTAAAAAAGGAGCTGCTTGCCC
CCTCCTCTCTTTCTTGCTCTCTTACTCTCTTGCTTCTCTCTTGCCCTCTTGCTCCCCCTTTACCCATTCCCTTTCCTC
CTCTCTCCATGTGTCCATGGTCAGTCTCTCCTTCCCCACTCTCTCCCTCTCTCTGCCTTTCTAAAATAAACACCTTAA
AACCATGGGCCATCTCTGCTTATCAGGAACTGCCATGCTGGAACAGTGGAGTAGGTTTCCCTCTAAAGAGCTGTGTGT
CTAACCTACCGCCAGGAGGCCTCCCTTCTCTCCAACCATGGCTGCCAGCCAACCCAGCCCCAGAACCAGCTGCCTGAG
CTAGCCAGACTTCCTCCACCCTGCAGTAACCTGCCACAGCTCTCCTCCTACCTTTTCCCTTCAGTTCCCAGGCCAGAG
TCTGCCTGAGGGTCCGGTCTCAGCAATTCTGCAACAAACAGCAGGGTCTGGGATATCGGAGAGCGAGAACCTGTCATC
CCTGGCCTCTGTGCAAACCAGGGACCCCAGAACTGGCTCTTCCACAATGCCCAGTGGTCTATGGTGCCCAAGAGTTGG
AGCCCGACTCTGGCAGTTCTGAAGGGACTCCAGACTGTGCCCTTTCCTCACCCAAGGAGTGGGATCCCGCAGCTTCCC
ACAGTTCAATGGCTGCCCAGCAGTTCCGTAGGGTCTGAGCACAGTCAGACTTCCTGAGACAGACTCCCCATGTCCACC
TTGCCCAGCGGCCCTAGCCCAGAGCAGACGTTGGACCCCCCCCCCATTTTTTTTTGACCTGCAGGATTCCACTGATGG
ATTGTTTCCTATGTTGAACCATGCCTGAATCCCTGGATGAAGCTTACTTTATCAGGTGGATGATGATTTTGATGTTAT
TTGATTTGATTGGTGAGTATTTTGAAGAGAATATTTGCATCAATATTCACAAGGGAAATTAGTCTAAAAATTCTTTCT
TTGTTGAGTCTTTTGTGGGGTTTAGGTATCATCTCTGAGATTGTTGTCTCAGAGAATGAGTTTGGCAACATTCTTCCT
GTTTCTATTTTGTGGAATAGTTTTGTGGAATAGTTTGAGGAGGATTGATATTATTTCTTCTTTAAAAGTCTGGTTGAA
TTCAACTTTAATACCTTATGTCCCTGGACTTATTTTGGTGGTGAGACTTTTACTGTCTGCTCCTGGTTGCTTAGGAG
TATAGCTCTATTTAAGTTGTTTTCTTGGAGTTGATTTAACTTCGGTAAGTGTTGTATCCATTTTATTTAGATTTTTCA
ATTTTATGGAGTACAGGTTTTTAGAGAAAGACTTAATGATTCTTTGGATTTCCTCAGTGTCTGTTGTTATGCTCCTCA
TTTCAATTCTGATTTTCTAACTTGCATATTCTCTCTCTGGTTAAGAGTTTTTATCTGTGTTGTTGTTTTACCTCATAG
ATTCAACTCTAGAGTCTGTTGCTTTTCTGTATTATTCTCTTTGTTTTTAATTTATTGATTTCAGCATGAATTTGATTA
TTTCCTTTTGCCTACTCTTCTTTGGTATATTTGCCTCTTTTTATTAATTTAATTAATTAAATTTTACACTCCATATT
TTATTCCCCCCAGCCACGTCAACCCTCCTACTGCTCAATACCCTACATCTCCTCTCAATCCCCTGTCTCCATGTGGAT
GTACCCAACCCCCATGCCACCTGACCTCTAAACTGTCTGGGGTCTCCAGTATCTTGAGGTTTAGGTGCATCATCTTTG
AATGAACCCAGACCCATCAGTCCTCTGCTGTATGTGTGCTGGTGGCCTCCACATCAGCTGGTGTATGCTGCCTGTTTGG
TGTTCCAGTGTTTGAGAGATCTCAGGCCTCCAGATTAATTGAGACTGCTGGTCCTCCTGCAGGGTCACCCTCCTCCTC
AGCTTCTTTGAGTCTTTCTCTAAATCAACAACAGGGGTTTAGCTGCTTATGTCCATTGGGTGCAAGTATCTGCCTCTG
ACTCTTTCAGCTGCTTGTTGGGTCTTCCAGAGTGTGATCATGCTAGATCCCTTTTTGTGAGTGCTCCATAGCCTCAGT
GATAGTGTCAAGCCTTGGGACATCTATTTGAGCTGGATCAGTCTTTGGGCCAGTCACTGGACCTTCTTTTCCTAAGGC
TCTTCTCCATTTCCATCCCTGTGTTAGACATTATGAGATATCATCTATTTCTTTATGAAGGCACTTAGTAATATGAAC
TTTCCTCAGCAATTCTTTCAGTGTGTCTCATAAGTTTGGCCATATTGTGCCCTTATTTACACTGAGTTCTAGAAAGGC
TTTAATTTCTTTATTTCTTCCTTGACTCAGTGGTCTTTGAATACGAAATTATTTAGTTTACATAAGTCTCTAGGCTTT
CTGTTGTTTCTGTTGTTGAAGAACAGCTTTAATAGTTCTTGGTCTCGTAAAATACAGGAGGTTATTTTAACTTTCTTT
TATCTGTTGAGACTTGCTCTTTAACAAATTATATGGACAAATTTAGAGAAGATTTCCTAAGATGCTGAGAAGAAGGTA
TACTCTTGTATTTGAGTTAAATTTCTATGGTTATCTCTTAGGTATTTTGATTCATAACATCCACTACCTTCCTTATT
TTTCTGTTAGTTTCTGTCTAGACAACTTGTTCATTGGTGACAGTGGGGTGTTTAAGTTTCCCACTGTTAATGTGTGGG
GTTTGATGTGTAATTTGATCTTTAGTAGTATTTCTTTTACTACTAAATGAAGTGTGTATGCCCTTGCATTTGGGGCAT
ATATATTGAGGATTCAGACATCATCTTAGCATATTTTTCCTTTGATGAGTATGAAATGTCATTCTCCATCTTTTTTGA
TTATTTTTCATTTAAAGTCTATTTTATTAAATATTAGAATAGAATACAAATTTGATTCTTGGCTCTGTTTGCTTGAAA
ATCTGTTTTAGACCTTAACTCTGAGGTAATGCCTATCTTGGATGCTGAGGTGTGTTTATTGTATGCAGTAGAATGAGT
AATGTGATTATGTATCCATTCTGTTAGCCTGTGATATTTCATTAATCAATGTATTTATTCTGATCTTGATAGATGTCC
TCTAGTCACCTTTTAACAGACTCTCCCCCATCCTCTTATCCTCTGAGAGTGGGAGACACCCCTGAGAATCACTATACC
CTTAAAGCCATTGTCTTTGATTGAGGACTTGAGACCATTGATATTGTGAGATACTAAAGAAAGACCAACAATTGTTAT
TTCCTAATATTTTGATGTTGATGGTGGTGTGTGTGTGTGTGTGTGTGTGTGTGTGTGTGTGTGTCTAAGGGT
GATTATGTGGGTGTGTGCATGTTTCTATTCTTTTGGTTTCACTAGTGTGGAATTATTTATTTTCTGTGTTTTGGAGTG
TAGTTAACCTCCTTTTCTTGCAATGTTGGCGCGTAAGGGCGCGTTATTACGCGCTGCCCTGCACATATTTTTAACAT
GGTCTCCACATGACCTCAAAACTATTCAGCAGCCGCTGACTACTTGTCAAGCTGAAGGATGTCATTCTTCACATATAA
TTCAATTATTAGAATTCATAAGCATTGATTTAAACACAGTGGAGGATTATAAGCCACAGGCACAGGCATAAATCCTCA
ATAATGTTTTGATTTGGTAGGAAGATGATTATGAGTAATGTGAACTTTGGACTGAGAGAAATTGAAACTCAGGTGTAT
CATTGAATGTGGATATGTTACAAGGAGATGGAACATTCTCACTGCCTGTTGAATGGCTCCTGGGCCCACCCAGTACTT
TGACTGATCTTATCACTTGTGTGCCCTAAGATCTTAGAAAGCTTTTCCCTCTTCAAGGGACACACACGTTTCAAAGAC
TTGAGGCTGGGACCTACTAAGCCTTTTATTAAATGTCTGACTTTAGTACAAAGTTTCATTGAACGGAAAGTGAAGTGT
TCTGAGGCATCTCCCATGCTGGTGCTCCAGCAGAGATGCAAAGGGTGCTAGGTCTGTTAAAGAACTCCCCTCTGGATA
ACTGAATCCTAATGTGTCTAGAAATACAGGCTCAGACGAATATCACTGATGTCACTGCAGAAGTTCTAACAGCGGTCT
TAAAGACTTATTCCTCCTATTGTTTGTGTCAAACAAGGGAGAATTTTGAGAGTGCCTGATGCAGGGGGAAAAAAGGTG
```

Fig. 6 (Cont.)

```
AATCCAAAAAGCAATCTACTAAGTGTCCCAAATTTCACAAGGGCAATCAATTATAAATTGAAATGTGATGGGGATGGT
CTTATCCTGTTTCTTTTAAACTCCTAAGGGACAACCTTTGGCCCTGCCTACAAGAGGGTCTTTCTCCAAAGAAACCAT
TTCAAATTAAATGGTTGTGAAATAGGTCACAATCTAAAGTTTACTGGACTGTACTAACTGAGTCAGTAAAGCCTCAGA
TGAATAGATATTGGGAAGGAAAACCATATAAGGCAATTAAAGTTACAGGGGCAGATGTCTCCATTATTAGGGCAAAAG
AGGCACCCTCTGTGTGGGTTCTAACAGCAGATCTTACTGTGGAGGGTATTGGTAATCCAAGCTGTTCTAAAACACCTT
TGACCTTTCTTATATGGAAGGACTCTTACGGACACACTGGAAAAGTTAAGCCCTTAATTCTTGAAGGCTTATCTAATA
ATCTCTGGGGAAAAGATACATTAGAACTGGCTGAAAGCACTTTTAATACTAGTGATCAAGCCTTTCAAAATGGTCTAG
AGCTCATGAAAGAGAAATTACATCTTCACTTCCAATATTAGGGGCTATTGTTTCACTTCCTGAGCCTGTAAAATTTCA
ATAGAAAACAGATGAACCTATAATTGGTAAAGAGAAACTAAAACATTCTCAGGGATTAATAGAACAAAAACAAGTAGA
ACATGTTGAACCAAGCATCAGTGATTGGAACTCTCCTATCTTTGTCATTCAGAAAAAAGGTAAAAAAAATGGAGATTA
TAACATAATTTAAGAGTCATTAATTTGCAGATAAACAAGAGGCCTTTATAACCTGGTCTCCACAAGGCCCTGTAATTG
TTATTAAACACAAATTATATTCATGTATATTAAAGATTATTTTTATTCTATCCTATTATACCAAGAAGATGGGGAAAG
CTTTTCTTCTTTTATGCCTGTGCCAAACAATATATATTCTGCTCAAAGATAGCAATGGAAAGTGTTGTGTCAAGGTGT
GAAAAACAGTCCTACTATGTATTAATATTATGTATTTTAGGCCTTGAATCCTTTGTAAAATAATCTCTCTATAACATT
TATTTATTACATGAATATTTTCCTTGCTGATTAGGATTCTAGCAAATTAGAAGTTTTTCAACTGGCTTTGAAAAATTT
GAACAATATAGGGCTCAAAGTTGCCCCTGAAAAATACAAGTAATCTTTCCTTTTACTTTTCTGGAATCTGTTATAATC
CTCAAGGTCAAGCTGTATTGGAGATAGTGTACATATAACCTAAAGCACAAATTGATAAATACAGGGGAGGGAATATTG
GTCTGAATATGACTCATCCTCAACATCTTACTAATATTCATCATTTACTTTAAATTTCCTGAAAACGGATAAGAGAAA
TACTGCAGTTCATTAACACTGGGTACCTTTGTCAGGGACTATGAAGTCACCTCTGGTGGCCTGGAAAGTTGTAATAAA
AGATAAATGACAATGACAATCACCAGCCCTATTACTTAACATTGGAAAAGGTTTTGTTTGTGTCTTTCCAGGACATGG
ACCACAGCCTATCTGGATCCTAATGTGGCTCACCATACCCTGGACAGCTAATACCAGCAATGAAGCAAAAAGTTGAG
CAGATGACAGAGAAGATAGCAAGACCTTCTTCTGTTGGCTTAGAGCCTGACTCCAAATAATTCCTGTGCTGAAAAATA
TCAGGCACTGGTACATAACCCTCTCTTGATATTAGGGAAGAAGGACAGAGGACTTTGTCCTCAGCTGTTTACAAACTC
CAACCAATTTTCTGATATAGGTCCCATAAGAGAAGTTTCTAAAATTTGGAATAGCACCATTCCCATGACTAGATACCC
TCTTTGCTTTCATAACCATTACAATCTACTTTCCTATTCTACTATCTTTTCACTTATAATATATTGGTTGGCATAGTC
TACTTATTGATCAGAAGACTCTGCTCTCCAGAAAGAAAATTATATAGAGGCAAGATCTATATGAGAAAACGCTGGCTT
GACCTGGCATTCAGCCTACCTAGCACACGGAATATACAATTTTAAATTAGAAGCATGGCATACAATGCTCCTGAGTAT
TCACAGAAGTCAGAATACTGAATTCTGAGATAGCATGAGAAGCCTGGATCTAGCCTGCTGATATGTCTACAATCTCCA
CATCTCCTTTTATGTGCTTCTTCATAGAGACACATGTGGTATTAGTGCTCACTGTCCAATCTGAGATAATGTGCTAAC
TTATCACAATTGATAGGTTCCCTATAAATAAAATAGTTGCTTATAGAAGTAAAACAGACACAGTTATGTAAAACCCTC
TCGAGCAGTTTTTCTCCATATCCTTTTCTGACCCACAAGGTATTATGTTCTTCTCAGGGGATGCCCCAGTTATTACTG
CAATTACAAAAATAGGGCTGACACAGATACACACAGCCAATACACAACACAGGCACAGTAGATAAACAACTGGTAGAC
AACATAGGCACAACAGAAAAGAAACATACAACACGTAGGTACAAAATACAGGCACACAAACATACATGACAAATAGAA
AAGAGGTAAAGACCGATAGACAGGGAGAGGGGTGTAAAATTAAAATTTTAGTTCATTCTTAGAAAGATATTTTATCTA
TTCTTTTTTTTCATTTTCTAATGTGACATGATGAATTTTGCTACCCTCTCTGAGGTTTCTTTAATGTATAATCAGTGC
CCAATAGGATAGATAAACACACCATCAGGAGTGAAGATAAACAGACAAAATACTAAGTTTCCTTCTTCTAAGCTATTT
TGGGTTTTTAACCTTGAACAGATAAACATGGTCCATATTTGATGAAGTATGTTCTGTTTCAAAAAGTATGATCAAGG
AACTTCTTCATAAGTGTGGCAAGTAGTTTGTGTTTTAGTTGATTTTATATGCTGTCAATTTAATAACAAAGATTAGCT
ATGGAATATGCAGAGCCAACCGTTGGGTAAGTACCCTGAGAGATTCAATACCCTTTGATCTTTATCCAAGATTTCTAA
AAGAGGAAATAAAAAGAGGTGAAAATATTTGGTGATTTGTGCAGGCAAGCTGACTCAGTGAGTCAAGGTATTTGTGGA
AATCCTGATAATCTGAGTTTCATCCCAGGAACTTGCATAGTAGGAGATAACCAACTGCTGCCAGATATCCTCTGACAT
CCACATGGGCATCACACACACACACACACACACACACACACACACACACAAACACACAAACACAAACACACAAACA
TACACACCACTAACCAAAACATAGGTTGAATAATTAAATGTAACATTTAAAATTAATTGTATTTATTTTGGGGAATGT
GAGAAGTGGAAAGAGAAACAGTGAACCTACAAAGAGAAGTATACTCTAGCTGCAGAAAAAGACTCTAACAGTTGTGAT
GGAGAGTGGTTAGGAGCTATTTAGGAGGAACCCAGAGAAGCCTGTCTCACACTAGAGTTGATAAAAAGATTCTGGGTA
GGAGACTTCCCTAACCTGGAAGAAAAAGTCTAGGTGACAAAGGTCTTGAACACAGAGTCAGCTCAATTGCACCTATCT
TCACAAGTTTGACTTGATTCAGCACTCAACCCATTTTAGTCCAGAGGAGCACAGTCTGGGCAGACAAACCTTAAACTA
TATGATGTGGAAATCCCTAGTATCCTTCCAGATATGAACATACATACCTACACTCTGAGGATTTGTTTTGTGGTCTGT
GATGAAATGCATACCCAGAAAACATGACAAATGCAGAGCCTTGGAGGAGAGCAACTAATGTTGCTAAATTTAGGAACA
GTCCCCTTTTTCATAAGACAATCGACTGTCCCTGAGGAGACTTCATATTCTGGGCTCTGAACCATGAAACACACATGT
TCATACGATGATGCTAGGGAACCTTCAGTCACCACAGGACCAAAGGAGTCCAATGTCAGAGGCAAGACAGTGCCCAAGA
CACAATGGAGAGAAACTTGAATAGATCAGAGGCTTCATAGGTCACCCTCACACTAATAATGGTGCCCACACCCTACT
TGATTAGAAGCATGCGAATTTAGAAAATTGGGGTATATGGAGTGATTTTTTTAACCTAACCTTTAGCACCAGACCTGG
TCATCAGAAGTTGCCTAAGCAGTTTTGTACAGTGACAATATATAGCCTGAAGAGCCAGGTAAGCTGATCTTGGAGAAA
TAAAAACCGATTAATCCTTGATCACTATCCTTAAATTCATATTTTCTTATTCCAATTGTCTTAGTCAGGGTTTCTATT
```

Fig. 6 (Cont.)

```
CCTGGACAAAACATCATGACTAAGAAGCAAGTTGGGAAGGAAAGGGTTTATTCAGCTTACACTTTCTAAATTGCTGTT
GATCACCAAAGGATGTCAGGACAGGAACTCAAGCAGGTCAGGAAGCAGGAGCTGATGCAGAGGCCATGGAGGGATGTT
TCTTACTGGCTTGCTTTCCCTGGCTTGCCTAGCCTGCTCTCTTGTAGAACCCAAGACTACTAGTCCAGAGATGGTGCC
CCCCCCACACACACACAAGGGGCTCTTCCCCCTTGATCACTAATTGAGAAAATGCCCCACAGCTGGATCTCATGAA
GGCACTTCCCCAACTGAAGCTCCTTTCTCTGTGATAACTCCAGCCTGTGTCAAGTTGACACACAAAACCAACCAGTAC
ACCAATATTACCATCATTATTGGGAGCTGAAAAAGGTGTAGGACTGTTCTCTACTGTTCTAGCAAGCTATGTCAGTTC
TGGAGTTACAGGTAAAAGATATGGAATTTTGGATCAGAGAACAAGAACAGCTTATCAGTTGCAGAAATACATGTACCA
GCATTTTAGTACAAATTCCACAAGACAATGCGAAGAGAACATTGTCTCTGCACAGCCAACATTGGAAATGTCATCTTT
TTGACATAGTTTTATGGTGTCTATACATTCCAAGTGCGGTCACATTTCAAACAACCTCAGTAGGGTAAATACAGAACA
AAAGCAATCATGCCTTTGCTAAAGACACTTGAGCAGATTCTTCCTAGAAGTCACAATAGTTATAAGTGAAATGAAATG
CTGGACAATTTTTCAGTCCCTGAACTCCATGAAAATATATACACTGGTTTGCAGCAAACATATTAAAAAGTAAAATAA
GTAAGCATGTATCTGATCTAAAAGAGGGCCAAAATACTCAAGTGGCCAGGAATTTCATTTTGCTATGTCCTGAGTGGT
GCTTGCTATAACTGTTGAAATGAAATATCAAAACCAGAAGCATATCAAAGATCACAAAGAACTGCAACTCTGAACTTA
AGCAGATTAGTTTAATGTGGGCGCGTTATTATTACGCGCTGTGTATGAGAGCTTGAGCTTATGTGTGTTCACTATGTT
ATTGCAGTTGCTTGTGAGGCCTTATGGTGTCCGATGCCCTGGACTGGAGTTACTGGTGGTTTTGAGCCACCTCCTGTA
AGAAACCTAGGACTTTTCCAATAGCAGTATACATTTTAAACTGCTGTGCCATCTGACTATCACATTTTTTTCTTTCT
TCAGAGATAGAGTGGCCCTCTGGTGCCAAGCTCAGTTGGTTTTGCAATCCTGGGATTAGGTGATGCTCTTCCATCAGT
CTCCAGTAGTCTACTGCTAATTCACACACCATGTTTTTTTGCTTTATACAGAGTATTTTGAGTCTTCCCAAGACAGAA
AAAAATAGTAAATGTTGGTGAATTTGTCAAAAACCTTGGTCAAATTGTAAATTGTAGACAAGCACTGACATATCACAT
ACACTCCATTAATAGGTATACTTGACGTTAATGTCATAAAAGTCTATGTGAAAGCTTTTGAGATAACTCAGTAGTCTT
GCACTTATGCCTCAAGATACCCAACAGTAGGGTGAGGGAAAATATAGTGCCCACCTACAGCAGGAAGACAGGACATCA
AGTGAGGGATGGGGTTGCTATTTCAAAGTCACATCTCTGACCCATAATTGTTCCTGTCTGAAATAATTACAAGAATGA
AAATGGAGAGGAGCCTGAGGAAAAGAAGGTCCAGCAACAGGCCCAAAGTGGGATCCTGTTGTGCCCACCTTGGCCGGC
AAGGAAGTCACAACACAGTCGGATTCTTCTTAACAGCCTTTAAGGCAGGAATGCCTGGATGCACCCAGGGAGCAGGA
CACCGAGGGAGCACTGCTTATATGCACCCCAGCACAGGAGAAGGCTCCGTGGCCCCCTGGGATTGGTCAGTTTGCCAG
CACCTAATTTGTATGCACCCGCTTGGGAGGGGTTGGCGCCAGATTCAAGCTAGCACCTGTGCAGTGGTGTTGTTTACC
ACAAAGGCACACCGGAAACCGGCGCCATCATAGAGTTGGCTTCCTACATCTCCCTCTTTTTTGTTTAATAAAATGAGG
CTGGTCTAGGCCTGAGCAAATCTGTCTATTGGCCACAGCTCCTGTCTTAGGTCGATCCTCTAGCATCACAGCCTTTCC
CATCATAAGGTTACCCTATCGCCTCCAGGCCCCTTGTCTTAGGTTGGTCTGTGCACGAGGAAAGTTGCCCGCCTCTGA
ATACCATGGATCTGTGTGACTACAAGTGCCAAATGACCTAGGGCAAACTCTTAATTTTTAAAAGAGGCCAGCCAAATA
TTAGGAGATGTGCCATCTTCAATTGCCAACAAAGCTTGGTAGACCACTGCTTTATGCTGAGCATGCTCTCTTTTTAGT
GGACACAATAGCCAGATGCAGAAGACACACCCCAGGAGGACCACTGCTCCCAGGCCAACATTTCTTCCCACTGCTTA
AAAAAGGAGAAGGCATTGGTGATCCAGGAGGTGAAGTCTCCCAGGGTGACAGGGTAGAGTTGAGTGCCATTGAGTTTG
GCAATCTGGAGGAGCAACTTTCTGGACAGCTGCTCTACCTTAGCTGACCAATTTCCTTTAAGATAAGCAATTTTCATG
TCAGCCTTTCTGGTACCCAAATCGGATGTTCTTTATCCTGTGGAAAAACACAAACAGCTCCCCTAGATCTCGAAATAA
CGGGATCTGGGCCATACCATTTACCAGTTAAGACATCGTTCCATTTTACATCATGTTGAATTACAGGTGAGGTCATGG
CAAGCCTGTCTGCAGCCGAGCGACCATGATCACCCAAAATTTAAAAATTTAAGGTTAAATAAAGCTAAAGATAATTGT
TCTTTGGGTGCTCGTCCGTAGGCAATACCTTTTTTTGTTTTTGTTTTTGTAACAGTTCTTTCAAGGTGTGATGTGCTC
TTTCCGCAATACCTTGGCCTTGTGGGTTATAGGGAAGGCCAGGGTATGACTAACTTGCATAGTTTCGCAGAAGACTTG
GAAGGATGTTGATGTATATGCAGGTCCATTATCAGTTTTTAAATTAGCTGGTTTTCCCCAAGCTGCCCATGTGTCTAA
GCAATGGCTAATAACATTGTGGGTTTTTTCACCAGACATAGGTGAGGCACACATGATACCTGAACAGGTGTCAATAGA
AACATGGACATATTTTAGTTTTCCAAAAGCTGGAAATTGTGTAACATCCATTTGCCATATTTTTAGAGGGATCAATCC
ATGAGGGTTAATCCCAACATGGGGATGGTGATGAAACTGCACGCATTGTGGGCATTGCAATACAACAGTTCGGGCTGA
AGCACGGAAAATATTAAATTTTTGCTGTAATGTGGCAGCAGGGACATGATACAATTGATGAAAACCTTTTGCAAGCTC
TAATGGAGTAACATGAAAAATGAATTCCATATGGGTACTTGCATCTACCAGGGCATTCCTTTCAGTCATAGGGCCTGG
CAGAGTAGAATGAGCCCGAATATGCTGAATAAAAAATTTACTTTTCCTATTCCAAATCAAGTTTTGTAATTCTAAGAA
AATGGCACATACAGGGCTGGTAGATTTGATGGGTCCTGCAACTTCCAATGCTTTTACTACATTCACTACATATGCTGA
ATCAGACACTAAATTAAAGGAAATTTCAAGCCTCTTAAATACTTCTAATACGATTTTACATTCAACTAGTTGTGGGGT
ACCAGGATCATATTGAAATAAAACAGGGTTTTGAGAATTAATCACATAAGCACCAACATCTGTTTTAGAACCATCTGT
ATAAATATCCAATGCACCTGGTATGGGTTTAGATGCTGTAACCTTTGGAAAAGTCACTGGATGTTCAGTAAAAAATTG
TAATAAGGGATCTTTATGATAATGATTATCTAATTCCCCATCATAACTACAAAGTAACAGAGCCCATTCATCAACTAA
AGAGCTCAGGGTTTGTATTTGGTTAGCATCATATGGTGTAATAATTTTTTTGGGGGGGGCTCCAAAATGTTGAATGCA
TGACTTAATGCCCAAGATTGCTAAATGGGCTACAGCGGTGGGATAATATTCAAGAGTTTTATTAGGAGACACATGAGG
ATAAATCCACAATAGTTGACCTGATTTCCACACTACTCCGGTTGGTTGGCGAAACATCTTCAGGACACACAAATGTAT
GTCCTCTCCTTCTTTCCATCTACATAATTTAGCTTTTTCTAAGCACCTCTCTACCTTTCCTAAGGCAACTCGGGCCTC
```

Fig. 6 (Cont.)

```
AGGAGTGAGGGCACGGGGGGAATGACAATTAAGGGTCACCTTTCAGCATATCAAAGAGTGGAGTTAATTCAGAATTGG
GTAGCCTCACATATGGGCGTATCCAATTTATATCACCTAACAATTTCTGGAAATCATTTAATGTTTTTAAATGATCTT
TGCGCAATTCAATCTTTTGAGGTGCTACATAATGCGAAGTAACTTGGGTACCTAAAAACTCTCCTAAATTTCCCATCT
GAACTTTGTCAGGTGCTACAAATAATCATTTCTTTTCTAATTCTTTTACTAATTCTATATAAGCTTTATCTAAACTTT
CTTTATTATTAGAAGCAAGGAGGATATCATCCATATAACGCACTATCCTCACTTTTGGAAATGCATCATGGGCAGGCT
GTAAGGCTTCTCCTACAAAAAGTTGACACATAATAGAACTATTGGCCATGCCTTGAGGTAAAATGACCCCTTGATACC
GTTTATCAGGCTCTTCATTATTTACAGAGGGGAGAATAAAAGCAAAGCACTCGCTATCACACAATGCAAGGGGAATAG
AAAAAAATCCTTAATATCAATTATTATTATAGGCCAATCAGCAGGCAGGCTAGAGAGCAGGGCAGGCCTCTTTGTAT
TGGGCCCATAATTTGCATTTGACTATTAATAGCTCTAAGATCATGTAAAAGCCTCCATTTACCTGATTTTTTTCTTGA
TTACAAATATAGGGGTATTCCATAGTGACTGGGAGGGTTTAATATGTCCTAATTCCAATTGTTCCCTTACTAATTCCC
TGGCTGCTGCCAATTTTTCAGAGGAAAGAGGCCATTGAGGAACCCATACAGGTTCCTCTGTTTTCCAAGTAATGGGTA
TACTGCCCTAAACGGCCCCTAGGAAAAACCCAGTTTTTTTTTATCTAGTTTAAACTTGGTTGGTACTGGCATAGTACT
GCCTTGTAATGACTTTCCCAATCCTTTACCTAGACATAATTTCTCGAGCTTGTGGGGAATACTCATTAGTTAATCTAA
GATCCATCTTGGTTAAGACATCCCTGCCCCATAGGGTCACAGGTATGTCCACAATGTAGGGGAGGAATTTTCCTGACT
TAGCTTCCTCATTTTTCCATGTCAATTCCTTAGTACTAATAAGAGGGGCAGTCTCATAACCCAGACCACGCAGGCTTT
GAGATGATGTCTGCAAGGGACACTTTGACGGCCAATCATGAGTGGAGATAATACTGCGATCTGCACCAGTGTCTAATA
ATCCTAAAAGGATCATCCTTCAATCTCTAAAGCTAACATGAGGCGATCTCCTAATTCCATTGATAAGAAAGTGAACCG
AGAACCTGTAGAACCTAGTCTGCTCTCTCCTCTTATTTTATTATTTGCTGGGAAATATTTATGTAAACTGGGTAATAG
CAACAATTGAGCAATTCTATCTCCTGGGGAGATAGCTGAGATGCCAGCAGGGGAGGCTACCAAAACCTTTACAATTCC
AGTATAGTCCAGGGGTTATCTGTAATCCTTTTAAAGCAGAAGATGAGCGGCCAAGCAATAGTCCTACAGTATCTTTGA
AAAGGGGGCCTTTAAAATCTGTATCTATGGGCTGTACCCCATCTGTGGGGTTAATACGAGTCTGGTGGTGGAGTGGA
GGTCCAATCCTGCAGAGCAAGTAGTGGCTCTCGGTGGTCTCTCGGATGATGGAGAGGTGGCCAAGGTTTCTTCTAGTC
ATTCTGAAGAGCCCCATATATTTAAGGGCCCTGGGGACGTGGGCCCTGCTGTCCATTTTTGGCCTGGTGCCACCATA
TCCTGCTTATAATGGTCGGCCTTCTATATCCTTTGTAGATCTGCATTCATTAGCCCAATGTTTTCCCTTCCTACATTT
GTGGCATAAGCCCGACTGTCTAGGTTTATCTAATGCAGCCCGTTTTCATTTCAGGGCAGTTTCTTCTAAAATGTCC
TCTTTGGCCACACTTATAACAAGTATCATTATTAGATCTAACCAATTGCACTACAGCTGCCGCTAGGCCTGCATTGGT
TAACGGGCCCCCTAGTTCTCTGCAAACCTTCATCCATACTTCTAAACCTTTATGTTTATAGGGTGTAATGGCTGCTCT
GCATTCCTTAGTGCATTGCTTATATACTAGCTGTTTGACTAAAGGCATAGCTGTATCAGGGTCAACAAAGATTCTAGT
AGCTGCCTCAACTAGGCATGCTACAAAGTCTGAAAATGGTTCTGTGGGACCCTGCAAGATTTTTGTAAGATTGCCTGA
GACTGTGCCTTTGTTTGGCAATGCCTTCCAGGCTTTGGTAGTTACCTCATTTATTTGGGCATAGACTGCTTTAGGATA
ATTTGTTTGATCTAAAGCAAAACGTCCTAAACCCAGCAGCATGTCTGCATCCCAATGTCTCTGAGGATCTTGTCCTGT
AGCTAAATTGGCCGCTGCCTGACTATTTGCATATTCATAAGTCAAGGACTTCCAGTCTAAATATTGCCCGGACGACAA
GCAAGCCCGAGCCACATGGCGCGTAAGGGCGCGTTATTAAGGGCGCGCGTCATGCCCAGCAGGCTCCTGCTCCA
GCCCAGCCCCAGAGAGCAGACCCCAGGTGCTGGCCCCGGGGGTTTTGGTCTGAGCCTCAGTCACTGTG▓▓▓▓▓▓▓▓▓
▓▓▓▓▓▓▓▓▓▓▓▓▓▓▓▓▓▓▓▓▓▓▓▓▓▓▓▓▓▓▓▓▓▓▓▓▓CAACCTTTCCCAGCCTGTCTCACCCTCTGCTGTCCCT
IgL-J1
GGCGCGCGATCTGCTCTCCTCAGACATAAGGACTGATTCCTGAAATTTCTCCAGGGTAGAGGAGGTAGACCATTTTGA
AGGAAGAACCAGAAGAGTGGAATCAGCTGGCCATAGGTTCTCATAGATACATTCTGATCTCAGGGGCGTCAGTTAGGG
TCTAGCCAGAGTTAAGAGCTCCACTCTTCGTACTCAAGAAGATTAATAATTTGGGACCCTGGGCCAAGTCTAAAAAGGG
GGCACTAGGATTTTCATGGCGCATACAATGTCTTTCTGGGTTGTCAAAAGTTACATCTAGAGGTGTTAGTCCAACTTC
CAGAGACTGACATTATCTAAATTGGAATCCACAGAATCATAGTGACAGAGTAGTCTTGTAATGTGTTCAGATATCTGT
TCTTATACTGGGCTGCTGAAGTCCTATGAGCATATAGATAGCTCTGACTAGTAGATCTGGTGGTCCTGGTCATCTCAG
GATTATCTCTAGAGTTAATCAGGGATTCTGTCTACAAAGCTCCATAACCGTGGGTTTCGCTGTTTCATGTTTCCATTG
CCAGCTTCTCGTTTTCCTTAAATGGCCTGTTATATGCAGGAGGTCAGGAATGAGAGACAAACTTGGGGTTTCAGAATA
CTAATTGACTGTCAGTCAATACTAATGCTGCTGCAGTGAGCAAGTGGCTGCGATGCTCTACCTCCTAGGGGAAGAAAC
CTCTAGAATATACTGAAGGGTATTGTGATCAGATCAAAATGTACTGTGGGCACCAGTCCCAGAGTAGCCTCAGATCTT
TTCTGGATGGAAACCACTACAAATTAGAAAAACTGAGTGGATTGATATAGAGAATTTGCTGCATATAATAAGCTCAGT
GTCCCCGGGGTGCTGGAGACAAAGAAGGAACTTCCTCAATCAAAATGCAGTCTGCAAAGCAAGGTGGAATGTACCCTG
TTTACCAGAGAGCTCTGATCACCACAGGGACAAAGGGGAAATAACTGCCCTGGGGAAGGTGATCAGATGCAGTTCAAA
TCCAAGTTAGATTATAAACAATAGGGTGGATAAAGCACAGTTATACCTGCTGACAGTGGAATTGAGGCAGAAAGGAAG
CGTCAAGGATATGTAAGTTGGGAGACTATTTTGAAAAAGGATAATGAGAAGGCTATCTGTACTCAACCAGGCTCAATG
GAGCAGTTGAGAAAAAACAAAATGCCAGGTAAAAGCATGACCAAACTTGAGAAGTTACTGAAATTTTGATATTTTATA
TAGTCTCCTGAATCAGTCCCCTTCTTTTATTGACACAGGTCAGCCCAAGTCCACTCCCACACTCACAGTATTTCCACC
TTCAACTGAGGAGCTCCAGGGAAACAAAGCCACACTGGTGTGTCTGATTTCTGATTTCTACCCGAGTGATGTGGAAGT
GGCCTGGAAGGCAAATGGTGCACCTATCTCCCAGGGTGTGGACACTGCAAATCCCACCAAACAGGGCAACAAATACAT
```

Fig. 6 (Cont.)

CGCCAGCAGCTTCTTACGTTTGACAGCAGAACAGTGGAGATCTCGCAACAGTTTTACCTGCCAAGTTACACATGAAGG
GAACACTGTGGAAAAGAGTCTGTCTCCTGCAGAGTGTGTCTAGGAGCCCAGGTTTCTCCTTAGCCTGGGAACCCTGCA
IgL-C3
GCTGTAGACCCAGAGCAGGGTCTCTTCTCTCTACTAGCTACCTTATCCCTTCTCCCTTGCCCACTGAATATTAAATAA
AATGTCATTAGCTGATCAAAAGTACTGTTTTGCTTCATTTGTTCTCATTATATATTTAATTTTCAACCTTTGAAACTA
CAATGTGGGTAGGTTGGATCATGGTCCCCAGTGAGAAATTAGTTCACATTTAAAACACGCTGACGGTACCACCCCAAC
AGTGACCTTTCCCCTGTTCTGTGCTGTTCTCTGGGCCTTGCCATGCAGGGACACCCATTTAGAATGCATCTCAGGTAA
GATATTGTGTTTCAGAGTTAAACAATTATATAGAAAGTCCCCAAATGTGTGAGTTCTTGCAATAAATTTAGAGAATTT
CATTGTATGCTTCAGAACATTGGTGTTCATGGTCATCTATACTGAGACATGAGACAGGATAAACACTCAAGCATAATA
ACTGTGTCTAGTGAGAAATACACCCAACTTGAGACTAGAAAGGGATATCAAATAATTGTGCATAAGAAGTGGTTTCAA
AGTGAACAGCTCTCACTTGAGCNTCTTGTGGGTGATGGGTGACTCCTGAAAGCAGAACTTGCATCCACATTGTTAGAG
CTAAATTCAAGCNNNNNNNNNNTGGGGAAACTTACATGTAATAAACACCTATTTTACTGACCCAAGTCCTCTCATGTAT
GGCACCCCAGTGTGCATTTTACAGTGATGCCAACCACAGTCTTTGAAATTGACATTCAAGCTCCTGTGGTCCTGCTTC
TATCCAGGTCAATATGTACTTAGTATTCAGGGTTTGAGGACATCATCTTCTATACCTCACAACATGGACACTGAGTAC
ATTCATAACTCTTTGCTGGATCATACAGTTCCATAGCATTGTCTTCAAAATCGAAATATTCTTCAAAAATGAGGCAT
AACAACAGTTGACAACATAGACTGGGATCTTAGACACCTATATTCCTAGGAGGAATATTTGGGATCTGTGCCCTGCAT
TCCATTTCTGATGATAGGCCATGATATAATCTGTCCCTAATAAATGGAAGTAAAAATTCTGGGTACCCTCACAGCAAT
GTTCCATGCTGGGGACACAGCCAACACTCATCTATACCCATTTATTTTTCAGAGACTCATAGGCTTGTTTCAAGTTTT
CACTGACAAGTTTGATCAGAAAAATTAGGAAACACAGAAATAGTAATACCCCATATCCCCACCAAGCAGACTCTTAA
CAACATTTTACCCAGATTTTGATTCACAACTACAACTATAATTAACTATATCTATAACTTTATAATTATAACTAGAGT
ATACCTATAACTTTAACTATAACAGAAAATTCTTCCCTATATATGTTAAGAAAGCTGATTCCAGAACTCACATCTTGT
TAGCTAAAATTATTCTTCAGAGTTTAAAAAAAAGAATGCCTAGGTATTATTTCAAACCTCAAAAGAAGTTATTACTTC
TATTTCTTCATAACATAGTCAACAAACATGTCATCATCTTACAGTGTTTATTGGTAATGAATGATTCTAAAGTGTAGG
AAGATGAGATGTACATTGATACTGATGGTTATGTGTGTTCTCTATCTGCTCTCTCCTGAAGGGCCTCAGGCATTTCTC
TTTGCCTTTTTCCAGGCATGAGCTGCAAAGATTGAGTTAGTGGTCTCTCAACACTTTGCATAGACTCTATACAGCTGG
TGGTTTCCTCAAGCCCTCACTGGGGACTCTTCTCTGTTCCTTCTTATTCTGTGAAGAGCTTCTTATATACAGAGTATG
GAAAATCCATGGATGAATTTCTGGCAAGGCTGGCTAAGGGGACATATAGATCCTGGGAAGAAGAATCTTTCCGTGATG
TGGCGCGTTATTAATTAAGGGCGCGCGAAATTCACTCCTTAGCGACACTAATGCCCTCTAATAAATTCAATCCTGGGC
CTGAGTGATGGTTGGTGCAAAAAACAAATTCAAGATCCCAGTGTCCTCCAGAAGCCTGGATTTCCAGGGATCCTGCTG
TGGGTCACAGGATGTCACCGGTCCCCTCTCTCTGTGGGTTGAGTGTGGGGCCATGTGGACTCCCTCATGAGCAGATG
CCACCAGGACCACTGGTCCCAGCTTCCTCCTTCACAGCTGCAGTGGGGCTGGGCTAGGGGCATCCCAGGGAGGGTT
TTTGTATGAGCCTGTGTCACAGTG░░░░░░░░░░░░░░░░░░░░░░░░░░░░░░░░░░░░GTGAGTCTCTTCTCCC
IgL-J3
CTCTCCTTCCCCGCTCTTGGGACAATTTCTGCTGTTTTTGTTTGTTTCTGTATCTTGTCTCAACTTGTGGTCAGCCTT
TCTCCCTGCATCCCAGGCCTGAGCAAGGACCTCTGCCCTCCCGGCGCGCGAATTCTGTATTCTAGTTCATGTCTAACC
CTAACTCTAGGTAAATAATCTCCTTCTTCTCTAGATTCTGTGTCTCATTTCAGACTACTCCCTGTAGCCTTTCATGTC
TAATCTCAAAGACATGGGGCTGAAACAGATAAACATCAATGTCTGTCTATAATTATGTTAGGATATGTAGCACTTTG
ATAAGTACTCCATTGTGCTATCACCTTTTAATGTCTATTTTTCTGATAAACTTTGTGAGGAATAAAATTTAATTGCCAT
CTCATGGAGAAGGAAAACCAGGGGCATAGAGGGAGACACAGCTGTTGAATTTAGAGAGCACAGTCATTCAGCACGGAG
GCTTGGGAAGGCTAATAACCTGGGCAATGGAACTCAAGATTAAGTTCCTAGGACAGCTGGGAGATAGAATGAACCCCA
GAGCCTTCATGGAAAGACACGAACAGAGCACCATCCAAGCTATGACTCAGGAAATTTAATTAGGAGTCAAAAGGGGAG
GGAGCTCTGGCCACAGAAATTCAAGAGAAGAGAGATATCTGTTGGGAATCTGGGCTCCTAGGATTCTCTAAAAGACTG
CTTAGAAGACACAGCAACTAAGTTCACATACATCTGGTCCTGATGCATGAAAATCATGTAACTCATCCAGAGATGTGA
ATATTCCGTCATTCTGTAGGATGAGACAAAGGTCAAGCAAGTACATGCTCTGCCTGTACTCAGGAGGAATAAACTCAG
GTGAGAACAAACTCAGGAGTTAGAGTTTAAGCTCAGAATAATGTTCCTACATCAGAACTGTCCTCAGGGTGGGTCAGG
AAGACTGTAGATACTCATAGAGTGAAGGGAGGATACAGAAGGGGTCAGGTGTCTGTGGTGAAGGTCAATGGTACAGG
TGTGTCAGGTGAAGCAGTGCACAAATGTGTAGATTTATAATTCCTAGGCACATAGGGAGCAGATAGAAGAAATTCATA
CACCCTCTTCTGTCTAAGCTCAAGGACCCTTTACACACTACTGCCAGGACTGCTACTGAAAGATCAAGATTCTGATCT
TCCTTTTTCTCTATCCTGCAGACCAACCCAAGGCTACGCCCTCAGTCACCCTGTTCCCACCTTCCTCTGAAGAGCTCA
AGACTGACAAGGCTACACTGGTGTGTATGGTGACAGATTTCTACCCTGGTGTTATGACAGTGGTCTGGAAGGCAGATG
GTACCCCTATCACTCAGGGTGTGGAGACTACCCAGCCCTTTCAAACAGAACAACAAGTACATGGCTACCAGCTACCTGC
TTTTGACAGCAAAAGCCTGGGAGACTCATAGCAATTACAGCTGCCAGGTCACTCACGAAGAGAACACTGTGGAGAAGA
GTTTGTCCCGTGCTGAGTGTTCCTAGGTCATCTGACTTTCATCTTACCCACAGAGACTTGGATCAGAAACATGTCCAA
IgL-C2

Fig. 6 (Cont.)

```
GTGTACCTATACTGCTTTTGCCTACCATAGCCCTTCTCCCTATTCTCGGCGCGTTATTAATTAAGGGCGCGCGACAAC
CGCCTGATTCACAGTTTCTAGTCCCACACATATTTCGCTGTCAAATCCTAAATGGAAAAAGCGCCGGGTTAGCACTGT
TCCAAACTTAACCCATATCCTTCCGCATCTCCAGCAACACTTTTAAAAAATGAAGTTTAAAGCCAACGCTCGCATAAA
TACCTGTTGCTCACCGAGCCCAATAAGATTCTCTGATTCTTTCATTCCCTTGGAGCTCCATACAAGATGCGATTCCCT
CCGGGTTTTCCCACCGTTCCCAAGATCCCTGTCTCGGACAGCAATCTGTTGTATGTCAGCCCGCGGCCTACTTGAACT
GGGTACACCTGGGAGGCAGGTTGGGGCTGAAAAAGACTTAGATGGCGAGAGAGATAATGAAGCCAAAATGATTCTCTG
TTCAAGGCTCAAGAATTTACTAAGAGAGTGTGCTTATAAGGGGAAGGCCCATCTCCCACCAGTCCATTCTTGGTGTC
TGGAGCCAGTCTGCAGGCGACGTGCAGGATAGGATGTTCCTCTGGAATATCTCAGGGGCCTCTCAGCAGGTAGCAGTG
TCTTGGAGGAGAGCAGTGGCAGGTGACAGAACAATAGAGCCATCTAGGTTGGAAGGCTCCACCCGAGGTAATCTCCTT
AGTGGCAGCAAGGTCAAGTCTGAATCAGCCTCCTCAAGGCTGGGGGAGGCTACATTATTGCAGATGCCAAAAAGTTTT
TGCTGACAGGAGCCTGATATAGCTGTCTCCTGTGAGGCTCTGCCAGTGCCTGGCAAAAACAAAAGTGGATGCTCACAG
TCATCTATTGGATGGAACACAGGGTCCCCAATGAAGGAGCTAGAGAAAGTACCCAAGGAGCTAAAGAGATCTGTAGCC
CTATAGGAGGAACAACAATATGAACTAACAAGTACCCCAGAGCTCCCTTGGACTAAATCAAACCACAAATCAAAGAA
AATGCATGGTGGCACTCATGTCTCTAGCTGCATATGTAGCAAAGGTGGGAGGAGAGGCTTCTGGTCCTGTGAAGGTTC
TATGCTCCAGTATATGGGAATGCATGGCCAGGAAGCAGGAGTTGTTGGGTTGGGAAACAGGGGCAGGGGTGAGGGAAT
AGAGGAATTTCTGAGAGGAAACTAGCAAAGGGGATAACATCTGAAATGTAAATTTAAAAAAATATCTAGTAAAAAAATT
TTAAAAAGAAAGAAAATGGCAAAAAAAAGAAAAGAAATCATATTGTACTATGTCAAGTGATTTTTTAGCATCAATCAA
GATGATTATGTGGTTTCTGTCCTTAACTTTGTTTATATGATATATTACATTTATTGATTTACATATGTTGAATCAATC
TTGTCTTTCTGAGAAAGAACACTCCTGATTATAATGTATAATTTTAACATATTTTTCTTAATTGTGTTTTCAAATGCT
TTGTTGAGAATTTTTGAATCTCTCTTCACCAAAGAAATTGATCTATTTATTTGTTGTTGTATCTTTATCTAATTTGGC
AATCAAAATAATATTAACCACATGTAGAGAATTTGTTACTTTGTATTTTAAAGAATAAGTTAAAAAGAATTGGTATTA
TATCATTTTATAGCCTGTTATATTTTAACAATGAATCCACATTAACCTCTGTTTCTGGGGGGGGGGGGTCTTTTGAT
TACAGATTTGATTCCATTTAAGGAATCATTAAGGTCCATTTAAGTTATTCATAGTTTCTGAATTTAACAAATTGTGCT
GTCAAGACTGTATCTACTTGCAGAAGAATGAAAGTAGATTCATATCTTTCACCTCATACCAAAATCAATTTTAAAATG
TATCAATAAACTTAATTTGAAACCTAATGTGGTAAAGTTTGTAAAAGAAAACATAGAGGGTACCCCTCAAATTTGGAG
TAGGCAAGTACTTTGGAACAGAATAATAATTGGGCAGACATTAATCTCAAGACTGCTCAGATGGGACTACAAGAAAAT
AAAACATTTCTACAAGCAAGAGAAGCTATCGTTAGAGCAAACAATCTACATAAAGGGAGCAAAAATCTTTGAAACAAAA
AACTAATATCCAGAATTTTAATAGAATTTCAGAAATTCGTATATCAAGTAAATAGATCAGCCAGCCAGCAAATGAGCTC
ATGAATTTGATGTTTTTTGAAGAGAGAAACACAACCACCAATAACTATTTTTCAGAGTGTTCAATACCCTTAGACACT
GGGGGAAAAAAACAAATAAAAAACTATTTTGAGACAGCACTTCACCAAGTGTGAGGAAAGAAAGGAGTAAGATGATGT
AACTCTATTTCAATTAAAGTATGTTATAAAAATCTTTAAAAATTAAGAATAGAAGTGGCATAATGTGTAATCATTTCA
CTCCTGAAAATATCCTACTGTAAGGAAATTTATACCCTCATACATATTGATGCTTTATTCACTATAGTGAAAAGACAA
AACCAAAATAGTTGGGTATCAACAGATGAATAGATGATTAAAACCTGGCACATATGTAAAATAGAATACAGTTCAGCT
CTGAAAAGGAATGTAATAAGAACTTTTCAGGTAAATTTATAGACATAAAATGGACAATTTTCTAAGTGAGGTTATACA
ATCTCAGAAAGAAAGAATTCGCATTCTCTCTTACATATGAATCCCAGATTATGCCAAATTATTTTAGTGCTTTATAAT
ATTAAAACTTATGTATTATATATGTAAACAAGTATATATGTGGGAACATTATAATATCTAGAAAGGAGAACAGGAAAG
GTTAAATAGTAGGCAGTGAGGAAGAACTCAATATAGGTTATGAACATGATCAGGAAACGATATAAAGCTACTTTTTTC
ATGGTTTTAGCTCGGTAACTGATTTTTAGATTTTTTGGAGATTGGCAAGCGTGTAAAATGTATTTGATAGTGTAGGT
GTAAAATCCAGTGTGTGGATCAGCACCTTTGGTCTATCTACTCTTGCTGCAGGATGTGTTTTTAATTTGTAAGCTCTT
TATAATGAAGTTTTTATTAAAATGCTGTTGATAATTTAGAAAGAAAACAGTCTTATAAACAATACTATGAAATATGTT
TATAATGAAATCATGTCATGATTGCTTAGTGACTAAGCACAACAAATGTTACTGTGACACTTTTCTTCTGCTTTTTA
CTCTGTGTGAAGCTGGACAGTGCATCACATAAACCAACTCATAATCTGCTTTATAAAACAAAAACCCTTTGGATGAAA
ATAAAGATATGAAAAGATTTTAACGTAATTGTATAAGTGTAGGAATAGACTTTTCACTTTAAACATTTCAAAAGCTAT
AAAAATCACATTTGTAGATACCAGTAAGACATTAAACAAACTCCCTCTCATTATTTGGGGTTGGACCCTGAGACTTTA
ATATGGTAAGCCAGAGTTTATCTCTGACTTTCATCTCAAGACCTATGCTTTACTTTTATTGTGAGACAGTATGCTTGA
TACATTGCTTAAGCTGGCCATGAACTCCCTCTGCTTCAGCTTTGGCTTCCAAAGTACCTGGGGGTGTATACAAGCACT
GACATGCCCAGCTGTAAGTCTGTCTTGAGAGTTCCACGCTCACACTATGGGTATATGCTACTGTTCATTTCTTACTAA
ATGACAATCTGGCTTTATATTGCCTCATCCTTAATTTCTCTTCTGCTTGATGAATCAAGAGCCCAGTTATTTCTGACC
AGGGGGTCTCTGGAAATAACCCATTGTGTACAACCAGAAATACAAAGCTGCATCTTTGATGTCCAGTGTCATCCCAACT
GTTGTCCATGTACTTAACATTTCACCCAAACCTTAGGCTCTATGCTCTACAGTAGGGTTCCTTTTAAACTTAAATAGA
TTGTCAAGTTTCTGTTTGTGCCTGTTCTTAAATTTTTAAGTAATACAACTAAGGACCCTAAGAGGGGAACCTCAATT
TCCCAGCGTCATACTTGGATTCCTCAATATTTCTAGTAACAAAGTTTCTGGTAACTAATTCTTTAATTAGCAGAGAAA
AAGGACCCATATCTGCACCTCTGGGTAGCATCTGTATCATTCCCAACAACATTTCTACAAAATCCCTAAGAATCAGAT
ATTTCAAAGGTTGCACATGAGGTCCTCAGTGAGATGATATACGGAAACCAAACTCCTGTGAAGATATCTTGAGGAATT
TCAGACAAGGCTTGGAAACACAAGTACAGAAACACGGTGTACAGTAGCCTGATCAAGGTCATACTTGTTTGAGTTCTC
```

Fig. 6 (Cont.)

```
TGAAAAGTCACAAGGTCAATGAGGACTACAAACCTATTGATTTTTCTAGGAAGTCCACATAATCCCTCTAAAGAACAA
CCTCGGCTAGTGTCCTTTAAACATTATGACCCCCAAAAAAAACTCTTTATTTTTGGGACATTCTCAGTTTTATGCCTG
CCATATTGGCTCCATCTCCTTCTTCCTGTTCTTGGAACTCATGTATCTGTGACATGTCTCAAATTGACAATCCTCCTA
TTTTCAACTATTTAGTGCTGGCCTTAAAAGACTGAAGAAAATATAAAGGTCAGGAAGACTGATCAGTGACTGAGGGAA
GGCTATTGTCCACAACCCCCAAAGTTATGCCCTGATATGATCTGTGCAGCAAACAAAAACAAAAAAATTGTAGGACAA
TCCCCAACAATCTCAGAAATCCTGTGTGCCCTGAGACATCCAAGAGCAGTTATTATGTGGAAGGGCTCAGCCAGGTGA
AACTAATCGCATGTGGACAACATATTCACATGAGGCAATCCCATAATAGAATCAGATATTAAGAGCACCTGTTAAGTT
ACAAGCGTATAGCAAGTGTGGGACAATCTAGTGTTATCAGGCTTAGAATACAGAAACCTAAAAGATAAATATGTCTAA
GAGATAAGTGCACAATATCACCTAAGACAGAGGGGATTATTTTGTGGAGAAATAAAGTATGTATAGTATGAAGGGGCT
GTAATAACGCCAACTAGGGTTTCCCAAAGATAATGTTCTAATAGCCAAAAGTAAATAGAAACTTACTTTTGACTATGT
TTAGCCTCAGTTTTCTCTCTGTGCAGCAGGATGATAATAATAGACACTTTGTTCTATGCATAGAAAGGAAAGGAGATC
AGATGAACAATGAGATTCTCATCATTATCCAAAACACAAAGCTCCAAGGTTTTACATTGTTCTCATCTTCCCTGAAGT
TGGTCCAACCACCAGACAGTGTTTCATTTGATCCAGCAAGCCCTTCATCTAGTTTCTGCCAACCTCACCACTCAGGTA
CTTTATGAGTTTTATGTATCTTGGTGATACCAATGTTGGCTTTGTGTCTGTGCTACCCAGTATTCACAACAGGATCCT
TAAATAAGGAGCAAGACCTGCAAAAACAGGAGACTCTGCTTCTTAAAATCAATCAACCATTATCTAAATATTCTGACT
ACCTTCAAAATGAGAAATGGTGCTGAGGGCAGATAGCAACATAGTGAAGGGCGCGTTATTAATTAAGGGCGCGCGTGC
TGAGGGCAGATAGCAACATAGTGAAGGGTCTTGAAACCATTTCCAAGCTAAGACTGCAAGCTGGATTTGCCCTAAATC
TACCCACAGAGGTAAAAGCACCTGATGCCAGGCCTGGGTCTGGCTGAAGTTTCTCAACTAATTTTGACCTCTGAGATT
CTTAAGCTCCACCAGTCCAACTGCACGAGATGAGAAATCAGGCCTTCAGGGACTCAAGCTAGGACAGAAGGATTGATC
CATATGCAGCAGAGGTTGTGGCAGCCTGAGATTAACAACTAACATGTAAACAGCAAAGTCTCCATGTTTCAATATCCA
CCCTTCCTTTCCTCCAAGAAATGAAAGTCCATTGACATCACTTTAGTTTTATGAGAAGTGCTTCCACTTTACCTTCCA
CCAGACATGGCCACCCATGAGTCTGCGAAAGTTTGGCTCTCTACTTAACTATGAACATCACCTAATACTTCCAATGTG
TGCTCAAAAGTGTTTCCTCCAATTTGCATTCTGGAAGCTAGCTGATCCTATGATGCAAGAGCTTACACTACAGAACAA
ATCTGCTATGGCATTGGTATATTGTAGGTCATGTGTGGTCATAACAAGATCCTAGAGCAGAGCCCAGGAGTTATACCC
CAAGACTACAAGGCAAATGTATGAAGGGCAACTTGGGTGACTGGCCTGGCCACGGAAATAGAGGGTGAGTACTATGGA
CTTTCTCTCTGCAGCCTGAGCAGTGAATTCAACATCATTTTACCTCTATCCCACAATCTTATGTCCCACTGTTCCTGA
CCTACCACCCTACTCTCCACACAGAAAGTCCCTAAACTCTGAGTACTATGGCTGGGTGGTGCTAAGAACTAGGCCACA
TGTGGGAAAGGAAAGAGAGGAGAGCAGAGATGTGAGCCCTATTGCAAGGAGAAAGAGTAATTCAACACAGTTAAAGTC
TGCACAGGGAGACTGAGCAAAAGCTCTTCATTTGAGGCAGCTCCAGGGAAGAGGTTTGGCTACTGATGAGGAACTAAA
TCTTGAATGTAATTTCTAGTTTGGGACAGGAACCAGAGATTTACAAATCTCACAGCCCAGGATATTTGTGACACCAGG
GCCTAGATCAAAAGGCCTGAAATAGAGGCAATAAAAGTTTCATTCTGGCCATATCTACCAATTTGAAAGGTGTCAATG
TCTTGAGCTTTACTGTCTTCTATACCATTTACAAAACTTGGAACATTCAAAATCAGAACAGGCATTTAGTAATCCTAT
GAAGCCAATACCTAGGACCTTCATTCCACTGCAGTGAAATCTCCAGAATCAGGCAGAATGGGCTCCTATCCATCTTTT
TTTAAGACACATTCCATATTTTATTTAAATTTTAAGACTAACTTTCATATTAAAATCACATATCCATACACTGATTTC
CTTTTTGTTAACTCCACTTAAAACATCTAAGCATGTTTTACTAAACAAAGACTGTAAAAAAATTATCATGTCTGTTAC
AAATGTTACAAATAGGAACAGCTTTTAACAGAAATTCAAAACCCCAAACATCTTTTATTATAAATACAGGTATCAAAA
CAATCCTGAACATATGTTTAAGACTAATAGTAGTCAGCACCCACACCACTTCAAGAATTAACACAATTGTTGACTAAT
CATTGTATCTTCTATTTTAAACAATTTCAACTGCAGCTCTAAATATGATAAAGCATGCCATTTCTGTTCTTCTTGAGA
CTTTACTTTCCAGAAAAACAGATGTTTCCATGGCCATCTGACACTCTTTTGTCATGCTTTTGTATTGAAAGCCTGAAT
TCCATTTTGAGTACTTCAGGTTCATGTTTAATTGACAGTGATTTAAGAAGAGAAAGGAAAGGGACTGGTGAGATGGCT
CAATGGGTAAGAGCACCCGACCGCTTCTTCTGAAGGTCCTGAGTTCAAATCCCAGCAACCATATGGTAGCTCACAACC
ATCTATAGGGGATCTGACTACCTCTTCTGGAGTGTCTGGAGAAAGCTACAGTGTACTTATATATAATAAATAAATAAA
TAAATCTAAAAAAAGAAGAGAAAGAAAAATTGTGCTGCACGTCTCTTGTTACCTGAAAACATAATAGGTGTGCATAT
ATTAAATATATTCTTGCAACTGTCCAGGTCATGTTTACCAGCTGCAATCTTTTACTTATTGTGTGACTATTGTGCATG
GTGATATTTAATCAAGACATTAACATGAGTATAAGGTTGCAGATTTAAGACAAGTTTGAGATCCACTAAAATTAGTTG
TTGTACATCTGTCCTTCTGGTGGCTTCATATTTTCTTTGGACCTCATAAGACATCTTAGCTCTTGAGGTATGACTTTA
ATTCTATAGAAATTTTGCCATTTTGCTAATACTGGTATGCTCTGTGCATCCACCATTCCACTGGAATTATTGATCCCA
TTCATATTAATTTTTGTTATAAATCTAACTGATGGAGGAACTTCTGGGTATTAGATCCACATTCTACTTTCAGGCTA
TATATTCTGTTTTCATAGTTTGTCCTTGGTGGCCCAATAATCATGCCTGTCCACCATGTAGGTGTCATGTCTCCATCA
TCTTCAAGGCCCCAGCTAACAGTACTATCACCTACTCCTTTTGTCCTTCTTCAAGTTCTTCCAACAAGCGAAAATTA
TGAGGAACTCCTGTGGAGACCGTCATCTTCTCCTGCTACCAGATGCACCACCCAACTCCTATCTATCTTCAATTCTAT
TCCAGAACCTTTCATTATGAACCAAGGAAACATATTCATTGGAGTAAGACACCTGCCTGTGCTCACACAGTATGGAGT
GCTGCCTCCTTCCAGGCAATGGACACTCTCACATAGAGAGATTTTTATTCATCATGCTAAAGTGAGCAGAGCAAAAAT
CAACCAGCAATGACAGCTGACATTGAGGAGAAGCTGACATACAGGTACTATGATCAACCATCTACAAGAAGCTAAGGG
TGTGGCTAGACAGCAACAAAGAATCAAGCAGAGCCTAGATACGTGTTTTATAGAAGACTCAAGGTGATATACAGGGGT
```

Fig. 6 (Cont.)

```
AGCTGCTACTTGCTCATTCTTTATCAGAACTTCACCCTGAGAAATTAACTTCCCCTCTGTGAACTTCAGTTTCCCTGT
CTTCACTAGGGAGTGGTTATCAATCTGTTCAGGAAAGTGTGGGGTCATAGATTAATTGAGGAGATGCTTAGAGTGTCT
CTGGTCAGTGGAGATCCTCGCTAATCTCTAGTTTCCACTATCATCTCCTGAGATGTTACATAGGCCTGCCATAGAAGG
GTAACTTCCCTTCCCTGGAGCTTCAGATTCCTATGACCAATGAGCAGTTACACGATAAATGTACACTATTGGGAAGCA
ATAGATTTACTATATGATGGAATTGGCCAGGAAAATCGGTTCTACACTTGGTAAAGCAGCAATGCTTGAAGTGTGATA
TATAGTAATAGTAAGAAGACATTACAAGCTCTGTGGAGGAGGTTGGGAAAGAGAGATGAACCTAGTTGCTTTACTGAG
CTCGCTATGACTGCAGCTGCCACCCTTGAGAGTCCACAAGCTAAAATTAAATCTGTGATAACTGAAACAAAAACTCAT
GGTCACAGAAAAAGAGAAATAATAGGAACTGAAACCAAGTCCATTAGCAGCAAGGCATGGCAAGTAGGGGTAGGTGTG
TCATTGGAGGGTCAGGGGCCAGTTTTGAAAGTGTAGGTTGTGCATCTAAATGTTAGGGACAACAGAGCCCCCTTTATA
CCTCATCTGTACTTTCATTCACATTCTTTGTGATGCTAACCCTTGGCTGCCTCCATATACCAAGCTCAATATTAAACA
CTTGAATCCTGGAAGGTCATGTCCCAAAGATCTGTGTGACCAGACAGTAGTGGTCATGTGGGTTATCAGAGCACAAAG
GAGTAAGCAACTTAGGTAGAGCACAAGGTTCTCACCTGAACAGAAACAGGTGATTGAATAAGCAAGCACCAGTCTCAC
TTCTTCAGAATCTGTGGTTCAGAGGTATATTATCTAGCCCTTCAGGCACACTGACTTTGTTCCTTATGTCTAGAAGGT
TGTAAACACCCTTCCTATTATCCAAAAATATTTATTTTGGCAATCAATCATGAAGCAATCACAGAACCAGCATGTGGA
AACATAGACGAGAGTTCATTGTTTTGGTGGGACATGTTATGGATGACTAGGGTACATGTGGTTTCAGTGGCTTGCAGA
ATGACCTGGACGGGTATCAACAGAAGGGAACACTGTCCTACAGACCCAGGAAAAGATCTCACTTTTGTTTAAAGACAC
GATTTCCTCTGGATAATAGTCTAAATAGATCCATAAAATGTACTCTCAAAGTTCTTCCCAGTAGAAATGAGCCTTTGA
GCTTTCCCGTGTTTTCTGATTTGTCAGTGAATGACTACAGGCTTTCTACCTAAGGAAGAAATGAATGGGCTGATGTAA
GAAACAAGATTCTCTACAAATACTCTCTGAGAAGAAATTAAAATACATTTGTAAAATGGTATACAGAATATTTCTTCA
AAGAGGTCCAAAGATTTGAGCAGGGCAGG
```

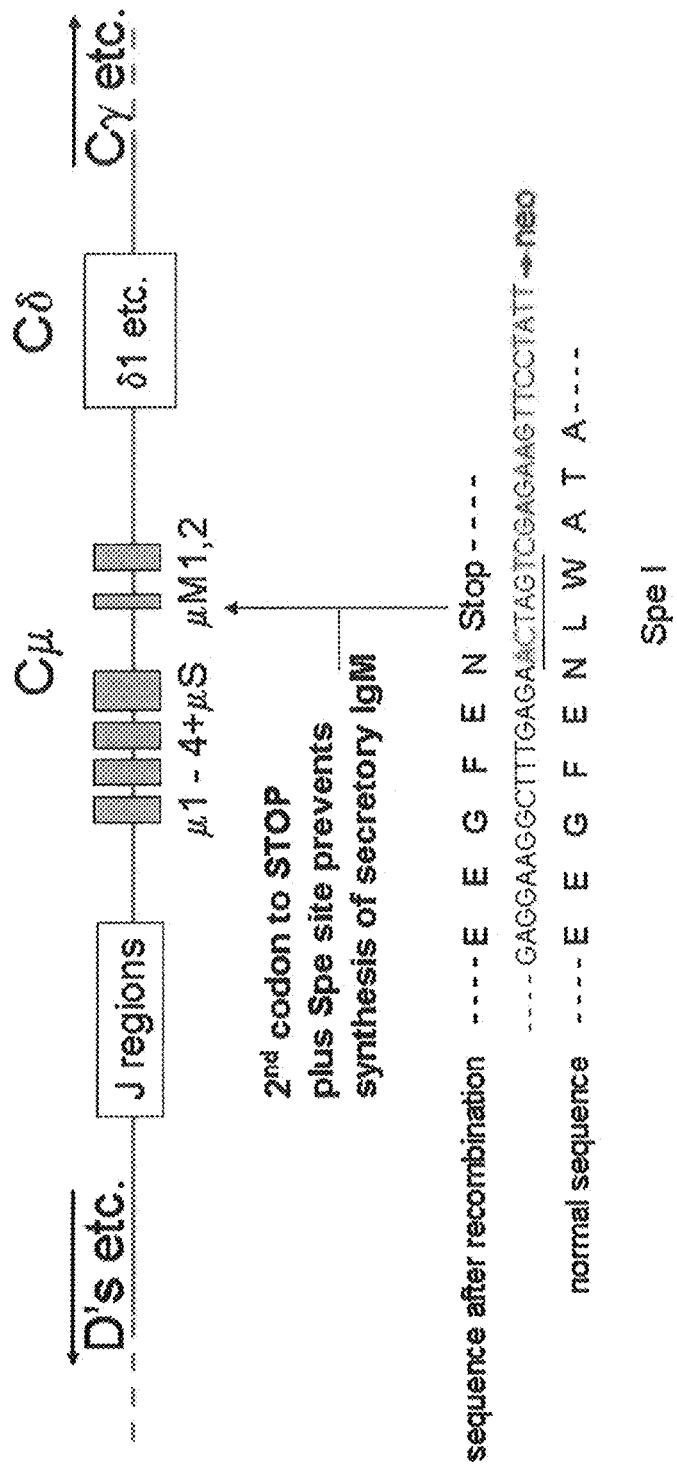

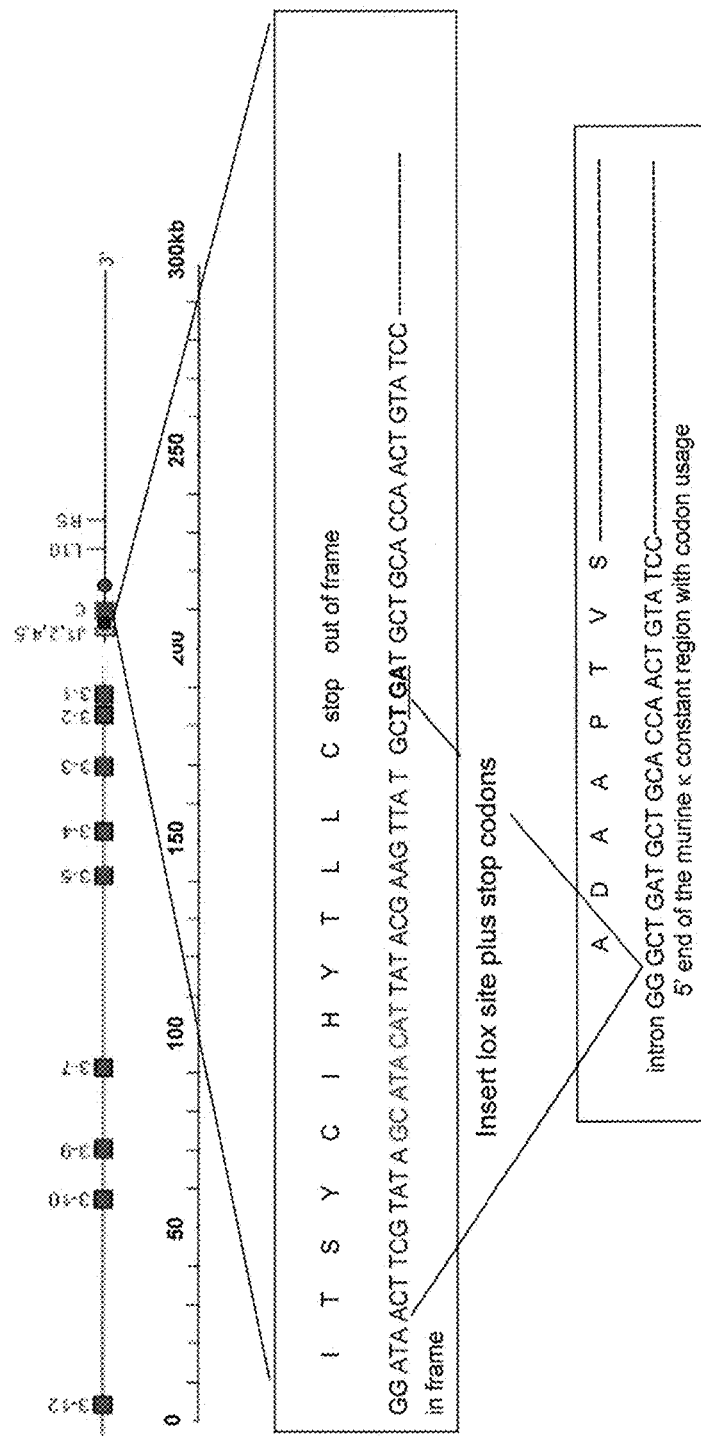
FIG. B

ANTIBODY PRODUCTION

FIELD OF THE INVENTION

The present invention relates to improved methods for the derivation and selection using transgenic non-human mammals of a diverse repertoire of functional, affinity-matured tetrameric immunoglobulins comprising heavy and light chains in response to antigen challenge and uses thereof.

In the following description, all amino acid residue position numbers are given according to the numbering system devised by Kabat et al. (1991) US Public Health Services publication No 91-3242.

BACKGROUND OF THE INVENTION

Antibodies

The structure of antibodies is well known in the art. Most natural antibodies are tetrameric, comprising two heavy chains and two light chains. The heavy chains are joined to each other via disulphide bonds between hinge domains located approximately half way along each heavy chain. A light chain is associated with each heavy chain on the N-terminal side of the hinge domain. Each light chain is normally bound to its respective heavy chain by a disulphide bond close to the hinge domain.

When an antibody molecule is correctly folded, each chain folds into a number of distinct globular domains joined by more linear polypeptide sequences. For example, the light chain folds into a variable ($V_L$) and a constant ($C_\kappa$ or $C_\lambda$) domain. Heavy chains have a single variable domain $V_H$, a first constant domain ($C_H1$), a hinge domain and two or three further constant domains. The heavy chain constant domains and the hinge domain together form what is generally known as the constant region of an antibody heavy chain. Interaction of the heavy ($V_H$) and light ($V_L$) chain variable domains results in the formation of an antigen binding region (Fv). Interaction of the heavy and light chains is facilitated by the $C_H1$ domain of the heavy chain and the $C_\kappa$ or $C\lambda$ domain of the light chain. Generally, both $V_H$ and $V_L$ are required for antigen binding, although heavy chain dimers and amino-terminal fragments have been shown to retain activity in the absence of light chain (Jaton et al. (1968) Biochemistry, 7, 4185-4195). Generally the proportion of circulating λ light chain is low, representing perhaps 2-5% of the total light chain complexed as a tetrameric immunoglobulin in plasma (Goldsby et al. (2003) Immunology, 5th edition, W.H. Freeman & Co NY).

The in vitro manipulation of heavy chain immunoglobulin genes to construct novel antibodies was first described in the 1980s. Much of the early antibody engineering work used a rearranged mouse immunoglobulin μ gene (IgM) raised against a well-characterised antigen. A feature of this antibody was that antigen binding specificity was known to reside in the $V_H$ domains, since assembly and secretion with an irrelevant light chain showed retention of antigen binding (Neuberger and Williams (1986) Phil. Trans. R. Soc. Lond., A317, 425-432). Using this system, it was shown that a mouse antigen-specific $V_H$ binding domain could be used to derive a novel antibody comprising a human ε constant effector region fused to a mouse antigen-specific $V_H$ domain. The resulting hybrid IgE retained antigen specificity and showed effector activity expected of an IgE (Neuberger et al. (1985) Nature, 314, 268-270). Other literature examples of heavy chain engineering include: hybrid mouse-human antibody genes encoding mouse $V_H$ human/IgA or IgG antibody fusions which retain anti-phosphocholine activity (Morrison et al. (1984) PNAS, 81, 6851-6855); an anti-carcinoma-associated antigen 17-1A antibody comprising mouse $V_H$ and human IgG (γ3) constant region (Sun et al. (1987) PNAS, 84, 214-218); and an anti-human T-cell antibody (anti CD7) comprising human IgG (γ1) constant region and mouse $V_H$ domains (see Heinrich et al. (1989) J. Immunol., 143, 3589-97).

Normal human B cells contain a single immunoglobulin heavy chain locus on chromosome 14 from which the gene encoding a heavy chain is produced by rearrangement. In the mouse, the heavy chain locus is located on chromosome 12. A normal heavy chain locus comprises a plurality of V gene segments, a number of D gene segments and a number of J gene segments. Most of a $V_H$ domain is encoded by a V gene segment, but the C terminal end of each $V_H$ domain is encoded by a D gene segment and a J gene segment. VDJ rearrangement in B-cells, followed by affinity maturation, provides each $V_H$ domain with its antigen-binding specificity. Sequence analysis of normal $H_2L_2$ tetramers derived from a heavy chain immunoglobulin comprising a single V segment demonstrates that diversity in response to antigen challenge results primarily from a combination of VDJ rearrangement and somatic hypermutation (Xu and Davies (2000) Immunity, 13, 37-45). There are over 50 human V gene segments present in the human genome of which only 39 are functional. In normal diploid antibody-producing B-cells, each cell produces an antibody tetramer ($H_2L_2$) from a single set of heavy and light chain antibody loci. The other set of loci are not used productively as the result of a process called allelic exclusion (Singh et al. (2003) J. Exp. Med., 197, 743-750 and references therein).

Fully human antibodies ($H_2L_2$) can now be derived from transgenic mice in response to antigen challenge. Such transgenic mice generally comprise a single human heavy chain immunoglobulin locus and a separate human light chain immunoglobulin locus. The corresponding endogenous mouse heavy chain, kappa light chain and, optionally, lambda light chain loci coding sequences are deleted or partially deleted. Thus, only human antibodies comprising a kappa light chain are produced in a low background of mouse/human antibodies comprising a human heavy chain and a mouse lambda light chain (WO90/04036; WO93/12227; WO98/24893; U.S. Pat. No. 5,877,397, U.S. Pat. No. 5,814,318 and U.S. Pat. No. 6,162,963). The deletion of segments of all endogenous murine heavy and light chain immunoglobulin genes to eliminate endogenous heavy and light chain gene expression completely has been achieved but remains technically demanding, particularly if the elimination of all lambda light chain coding sequence is deemed necessary. Elimination of the murine lambda light chain coding sequence has been achieved through the complete deletion of all functional V and J gene segments and the C1, C2 and C3 constant regions of the lambda locus, resulting in a mouse with a silenced lambda light chain locus (see EP1399559).

A different approach is to limit mouse B-cell development and immunoglobulin secretion by disruption of membrane exons of the gene encoding the murine heavy chain gene. Thus, whilst the endogenous murine heavy chain gene is functional, in that it is transcribed and undergoes VDJ rearrangement in response to antigen challenge, since the IgM is never expressed on the cell surface of pre-B cells, further development is arrested, resulting in a non-productive response to antigen challenge (Kitamura et al. (1991) Nature, 350, 423-426), even though both endogenous mouse kappa and lambda light chain genes remain structurally intact and functional (Tuaillon (2000) Molecular Immunology, 37, 221-231).

Where endogenous mouse heavy chain and light chain gene loci remain functional, any additional introduced immunoglobulin heavy chain transgene is also regulated by allelic exclusion, so that some B-cells functionally express mouse heavy and light chain loci only and others human heavy chain loci only and mouse light chain loci (Nussenzweig et al. (1987) Science, 236, 816-819). In any single non-human transgenic animal, there is a highly diverse population of B-cells expressing antibodies derived from potentially all immunoglobulin loci in response to disparate antigen challenge. The subsequent selection of antigen-specific antibodies using established hybridoma technology using HAT selection (Davis et al. (1982) J. Immunol. Methods, 50, 161-171) does not distinguish between hybridomas expressing one as opposed to another heavy chain immunoglobulin locus.

Regulatory elements present in immunoglobulin heavy chain transgenes comprise essential tissue-specific enhancer elements to ensure B-cell specific expression in a copy number dependent manner. The presence of a 5' intronic enhancer and the 3' Locus Control Region ("LCR") ensures that transgenes are active at all stages of B-cell maturation (Guglielmi et al. (2003) Biochim Biophys. Acta, 1642, 181-190). The inclusion of heavy and light chain specific LCRs in the transgene loci ensures not only that expression is B-cell specific, but that expression occurs irrespective of the site of integration into the genome (WO90/10077, Mills et al. (1997) J. Exp. Med., 186, 845-858 and Pettersson et al. (1997) Immunobiol., 198, 236-248)). Thus, provided an LCR is present, every transgene is functional irrespective of its position in the genome. In the event that the LCR present on the transgene is partially deleted, the chromatin surrounding the transgene is only partially open to transcription at any point in time, leading to positional effect mosaic expression, and so limited levels of expression of the transgene across the target tissue (Festenstein et al. (1996) Science, 23, 271 (5252):1123-5; Milot et al. (1996) Cell, 87(1), 105-14)

An alternative approach for the production of human immunoglobulins in a mouse background is to replace murine immunoglobulin gene segments with the homologous gene segments from humans. Thus, if only the mouse V, D and J gene segments are replaced by human homologues, a functional mouse/human hybrid antibody comprising human $V_H$ and $V_L$ domains and mouse constant (effector) regions will result following antigen challenge (WO94/04667). If all murine gene segments are replaced by human homologues, then an entirely human immunoglobulin will result following antigen challenge (U.S. Pat. No. 6,596,541). One perceived advantage of this approach is that, provided only coding regions are exchanged, then the resultant transgene retains all mouse regulatory elements, so ensuring maximal response to antigen challenge. This approach provides high serum titres of high affinity human antibodies or mouse/human hybrid antibodies depending on the final configuration of the transgenes. In reality, however, the replacement of all the individual V, D and J segments in the mouse genome by homologous recombination is a long and arduous task. Similarly, the construction of a heavy chain transgene comprising all 39 functional human V, D and J segments with constant (effector) regions is technically very demanding.

Therefore, there remains a need in the art for methods not dependent on the deletion of large segments of genomic DNA, or multiple deletions, which allow for (i) simplified and reproducible methods for the construction and B-cell-specific expression, of transgenic immunoglobulin loci, and whose functional expression is antigen dependent and ultimately determined by allelic exclusion; and (ii) the ability to select for hybridomas or B-cells and their derivatives (Babcook J S et al PNAS, 1996 Jul. 23; 93(15):7843-8.) expressing and secreting assembled immunoglobulin tetramers comprising the full V segment repertoire present on the heavy chain transgenic loci, or alternatively to select for cells which express a subset of V gene segments present on one as opposed to another heavy chain transgene locus.

SUMMARY OF THE INVENTION

According to a first aspect of the present invention, a non-human mammal comprises a transgene comprising one or more heterologous kappa light chain gene loci, with or without associated B-cell specific regulatory elements.

In particular, the invention provides a transgenic non-human mammal comprising a heterologous immunoglobulin kappa light chain locus comprising human Vκ gene segments, human Jκ gene segments, and a rat constant region gene segment, wherein the human Vκ gene segments comprise, in the following order 5' to 3', Vκ2-30, Vκ2-28, Vκ1-5, Vκ1-9, Vκ1-27, Vκ1-33, Vκ1-39, Vκ3-20, Vκ3-15, Vκ3-11, and Vκ4-1, the human Jκ gene segments comprise all five human Jκ gene segments, and the constant region gene segment comprises Cκ.

The non-human mammal may alternatively or further comprises a transgene comprising one or more heterologous immunoglobulin lambda light chain gene loci, with or without associated B-cell specific regulatory elements.

The invention thus provides a transgenic non-human mammal comprising a heterologous immunoglobulin lambda light chain locus comprising four human Vλ gene segments, two human J gene segments, and two rat constant region gene segments, wherein the human Vλ gene segments comprise, in the following order 5' to 3', Vλ3-19, Vλ3-1, Vλ2-8, and Vλ1-51, the human J gene segments comprise Jλ1 and Jλ3, and the constant region gene segments comprise Cλ2 and Cλ3.

In the non-human mammal as defined above, the transgene may comprise a heterologous light chain gene locus that further comprises a dominant selective marker gene.

The non-human mammals as defined above may alternatively or further comprise a transgene comprising one or more heterologous heavy chain gene loci with or without associated B-cell specific regulatory elements.

In particular, the invention provides a transgenic non-human mammal comprising a heterologous immunoglobulin heavy chain locus comprising human VH gene segments, human D gene segments, human J gene segments, and rat constant region gene segments, wherein the human VH gene segments comprise, in the following order 5' to 3', VH1-69, VH4-59, VH3-53, VH3-49, VH4-34, VH3-48, VH3-30, VH3-33, VH3-23, VH1-18, VH3-15, VH4-b, VH1-8, VH3-07, VH2-5, VH4-4, VH1-2, and VH6-1, the human J gene segments comprise all six human J gene segments, the human D gene segments comprise 21 human D gene segments and the rat constant region gene segments comprise Cµ, Cγ2c, Cγ1, Cγ2b, and Cα.

If desired, the non-human mammal may comprise two or more transgenes comprising two or more different heterologous heavy chain gene loci and associated B-cell specific regulatory elements.

In the non-human mammal the or each transgene may comprise a heterologous heavy chain gene locus which comprises a dominant selective marker gene.

Preferably, the non-human mammal comprises a transgene comprising a heterologous kappa light chain gene locus and a transgene comprising one or more heterologous heavy chain loci.

Alternatively, the non-human mammal may comprise a transgene comprising a heterologous lambda light chain gene locus and a transgene comprising one or more heterologous heavy chain loci.

In a further alternative, the non-human mammal may comprise a transgene comprising a heterologous kappa light chain gene locus, a transgene comprising a lambda light chain gene locus and a transgene comprising one or more heterologous heavy chain gene loci.

The invention thus provides a transgenic non-human mammal comprising:
  i) a heterologous immunoglobulin heavy chain locus comprising human VH gene segments, human D gene segments, human J gene segments, and rat constant region gene segments, wherein the human VH gene segments comprise, in the following order 5' to 3', VH1-69, VH4-59, VH3-53, VH3-49, VH4-34, VH3-48, VH3-30, VH3-33, VH3-23, VH1-18, VH3-15, VH4-b, VH1-8, VH3-07, VH2-5, VH4-4, VH1-2, and VH6-1, the human J gene segments comprise all six human J gene segments, the human D gene segments comprise 21 human D gene segments and the rat constant region gene segments comprise Cμ, Cγ2c, Cγ1, Cγ2b, and Cα; and
  ii) a heterologous immunoglobulin kappa light chain locus comprising human Vκ gene segments, human Jκ gene segments, and a rat constant region gene segment, wherein the human Vκ gene segments comprise, in the following order 5' to 3', Vκ2-30, Vκ2-28, Vκ1-5, Vκ1-9, Vκ1-27, Vκ1-33, Vκ1-39, Vκ3-20, Vκ3-15, Vκ3-11, and Vκ4-1, the human Jκ gene segments comprise all five human Jκ gene segments, and the constant region gene segment comprises Cκ; and/or a heterologous immunoglobulin lambda light chain locus comprising four human Vλ gene segments, two human J gene segments, and two rat constant region gene segments, wherein the human Vλ gene segments comprise, in the following order 5' to 3', Vλ3-1, Vλ3-19, Vλ2-8, and Vλ1-51, the human J gene segments comprise Jλ1 and Jλ3, and the constant region gene segments comprise Cλ2 and Cλ3.

Preferably, each heterologous locus incorporates a cognate LCR.

Each heterologous locus is preferably a human locus.

However, each heterologous locus may be a hybrid locus comprising variable regions and constant regions derived from more than one species, such as a hybrid locus comprising human variable regions and rat or murine constant regions.

The non-human mammal may comprise groups of transgenes comprising different groups of different heterologous heavy chain gene loci, wherein each group of transgenes comprises a different dominant selective marker gene.

Alternatively, the non-human mammal may comprise transgenes comprising heterologous light chain loci and transgenes comprising heterologous heavy chain loci, wherein transgenes comprising heterologous light chain loci and transgenes comprising heterologous heavy chain loci each comprise a different dominant selective marker gene.

In particular, the invention provides a transgenic non-human mammal comprising an immunoglobulin heavy chain locus comprising the sequence of SEQ ID NO:1. The invention also provides a transgenic non-human mammal comprising an immunoglobulin kappa light chain locus comprising the sequence of SEQ ID NO:2, and a transgenic non-human mammal comprising an immunoglobulin lambda light chain locus comprising the sequence of SEQ ID NO:3.

The invention also provides a transgenic non-human mammal comprising:
  i) an immunoglobulin heavy chain locus comprising the sequence of SEQ ID NO:1. and
  ii) an immunoglobulin kappa light chain locus comprising the sequence of SEQ ID NO:2, and/or an immunoglobulin lambda light chain locus comprising the sequence of SEQ ID NO:3.

The non-human mammal is preferably a rodent, such as a mouse.

In one aspect of the invention, the endogenous mouse heavy chain locus and/or the endogenous mouse kappa light chain locus may be disabled.

According to a second aspect, the present invention provides a method of producing an antigen-specific heterologous monoclonal antibody comprising:
  (a) immunising a non-human transgenic mammal of any of the preceding claims with the antigen;
  (b) preparing hybridomas or B cells, plasmablasts, memory B-cells or plasma cells each of which produces a monoclonal antibody from the B-cells of the immunised transgenic mammal;
  (c) optionally selecting at least one hybridoma or B cell, plasmablast, memory B-cell or plasma cell expressing the heterologous antibody by use of the dominant selective marker genes present in the transgenes comprising the heterologous immunoglobulin light chain and heavy chain loci; and
  (d) selecting at least one hybridoma or B cell, plasmablast, memory B-cell or plasma cell which produces an antibody which binds specifically to the antigen.

According to a further aspect of the present invention, there is provided a method of deriving a mammalian, preferably human, antibody from a hybrid antibody comprising:
  (a) carrying out the method as described above;
  (b) selecting at least one hybridoma or B cell, plasmablast, memory B-cell or plasma cell which produces an antibody which binds specifically to the antigen and comprises $V_H$ and $V_L$ binding domains of the species of choice;
  (c) cloning and sequencing the $V_H$ and $V_L$ domains;
  (d) recloning selected sequences comprising the $V_H$ and $V_L$ binding domain coding sequences with constant effectors domains of choice from the same species; and
  (e) co-expressing the recloned sequences encoding heavy and light chain polypeptides of the desired species using an expression vector in a cell type of choice.

Other methods for obtaining monoclonal antibodies can be employed. See, for example, Cheung et al., Nat Biotechnol., 2012 Mar. 25; 30(5):447-52, doi: 10.1038/nbt.2167; Pasqualini, R. & Arap, W. Hybridoma-free generation of monoclonal antibodies. Proc. Natl. Acad. Sci. USA 101, 257-259 (2004); Reddy, S. T. et al. Monoclonal antibodies isolated without screening by analyzing the variable-gene repertoire of plasma cells. Nat. Biotechnol. 28, 965-969

(2010); and Steenbakkers P G, van Meel F C, Olijve W. J Immunol Methods. 1992 Jul. 31; 152(1):69-77.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

The 3' end of the locus was obtained from the mouse (purple) containing the mouse κ 3' enhancer (purple). The mouse constant coding sequences were replaced with those of the rat, including its 5' enhancer obtained by long range polymerase chain reaction ("PCR") from rat genomic DNA (blue). The human $J_\kappa$ segments were obtained from a plasmid artificial chromosome ("PAC") covering this part of the human locus (light blue). The green boxes are $V_\kappa$ segments added individually or as a block. The resulting locus contains all of the frequently and moderately frequently used human $V_\kappa$ segments (green boxes).

Figure 2:
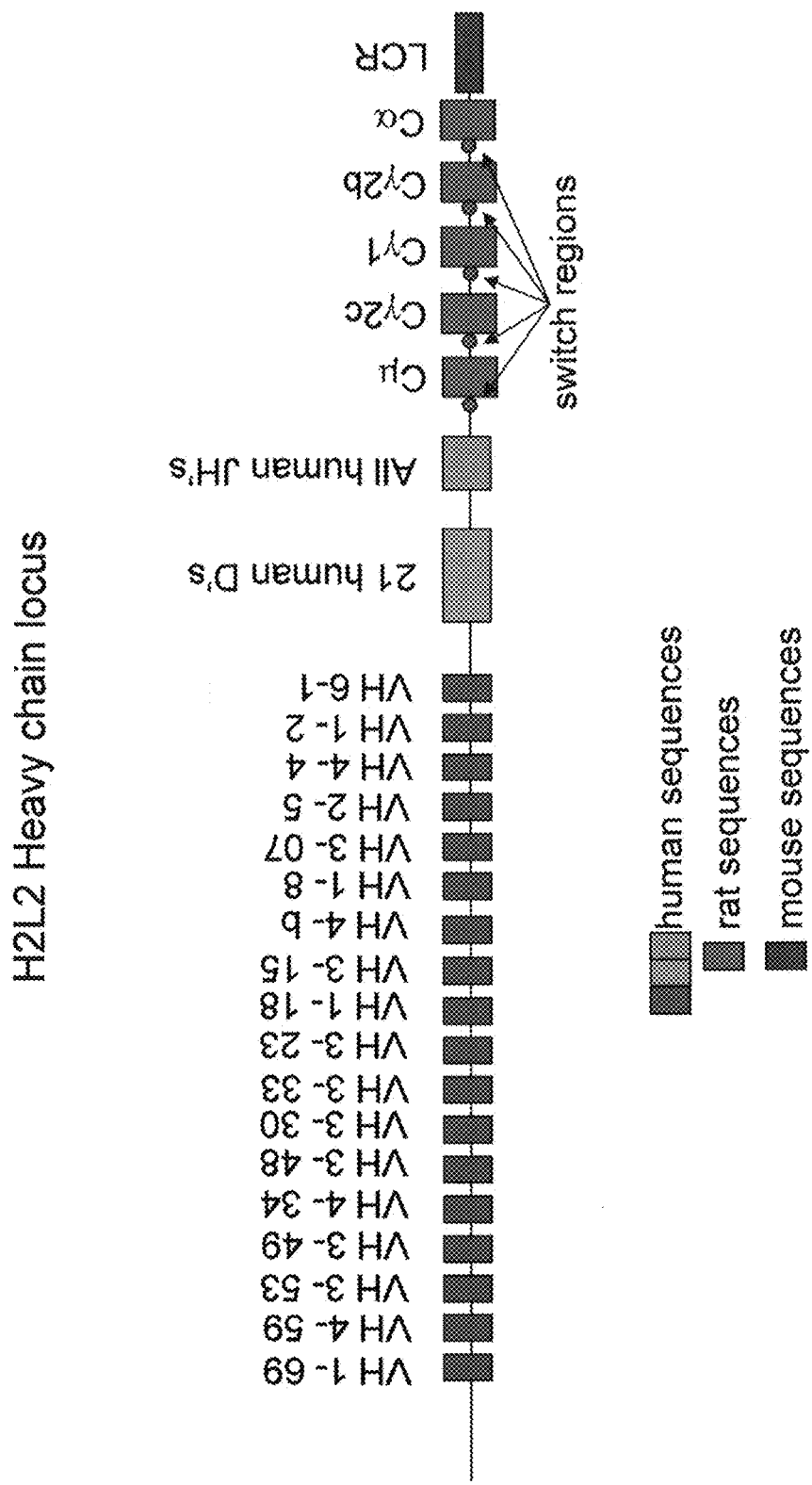

FIG. 2 depicts the composition of a hybrid human/rat IgH locus.

The locus was generated by ligating $V_H$ regions together to a concatemer of 17 consecutive human $V_H$ regions (green boxes) cloned between SceI sites. A mouse spacer region was added to a human 40 kb fragment containing 21 human $D_H$ (light green boxes) and all six $J_H$ segments (light blue boxes) to keep the appropriate distance between the $D_H$ and $V_H$ segments. This was followed by the addition of a $V_H$6-1 segment containing an SceI site. The concatemer was then added onto the $V_H$6-1. Finally, the various rat constant regions (blue boxes), including switch regions, and the murine LCR (purple box) were added at the 3' side. The resulting locus contains all of the frequently and moderately frequently used human $V_H$ segments.

Figure 3:
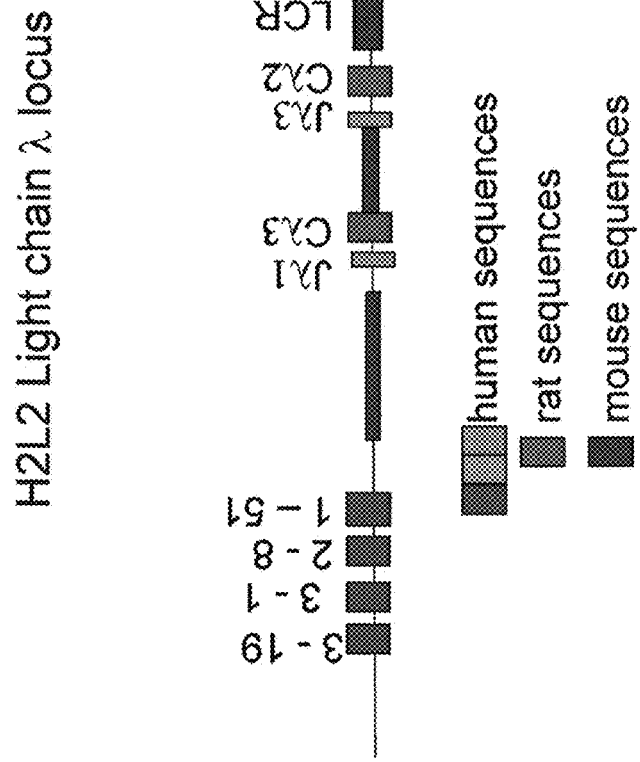

FIG. 3 depicts the composition of a hybrid human/rat Igλ locus.

The 3' end of the locus was obtained from the mouse (purple) containing the mouse λ 3' LCR (purple). The mouse constant coding sequences were replaced with those of the rat by long range PCR from rat genomic DNA (blue). The segment downstream from Vλ1-51 through to the human Jλ sequences were obtained from the mouse (purple) to maintain the proper spacing between the V and J regions. The human $J_\lambda$ segments were obtained by long range PCR of a human PAC covering this part of the human locus (light blue boxes). The green boxes are Vλ segments added individually or as a block.

FIG. 4 depicts a Heavy chain locus sequence (SEQ ID NO:1).

The green highlighted sequences are the amino acid coding and intron sequences of the VH segments. In red between these are the junction sequences. Each of these is flanked by a yellow sequence that signals the beginning and end of each VH segment (coding plus flanking sequences). D segments and J segments are marked in red and constant regions are marked in blue FIG. 5 depicts a Kappa light chain locus sequence (SEQ ID NO:2).

The green highlighted sequences are the amino acid coding and intron sequences of the VL segments. In red between these are the junction sequences. Each of these is flanked by a yellow sequence that signals the beginning and end of each VL segment (coding plus flanking sequences). The J segments are shown in pink; the constant regions are shown in blue.

FIG. 6 depicts a Lambda light chain locus sequence (SEQ ID NO:3).

The green highlighted sequences are the amino acid coding and intron sequences of the VL segments. The J segments are shown in pink; the constant regions are shown in yellow.

FIG. 7 depicts a strategy to disable mouse IgH.

The top line shows the Cμ region of the mouse with the different exons including the two exons coding for the membrane form of IgM. To the left are the J, D and $V_H$ region of the locus, to the right the other constant regions starting with Cδ. The bottom lines show part of the amino acid sequence of the normal M1 exon before (SEQ ID NO: 6) and after (SEQ ID NO: 4) recombination. The DNA sequence (SEQ ID NO: 5) shows the integration sequence. The stop codon is in red, the Spe I site in red and blue.

FIG. 8: depicts a mouse $C_\kappa$ insertion to disable the κ locus.

The locus is shown on the top line. The bottom shows the DNA sequence at the 5' end of the $C_\kappa$ exon (SEQ ID NO: 10, blue in top line) with the amino acid coding (SEQ ID NO: 9) written above the bases. The GG base pair at the start is immediately flanking the splice acceptor site coding for the amino acid R after splicing. The middle line shows the insertion of a 34 basepair lox site insertion (blue and red inverted repeat sequence) (amino acid sequence—SEQ ID NO:7; DNA sequence—SEQ ID NO:8), which puts the codon usage of the constant region out of frame and creating downstream stop codons (e.g. TGA bold print underlined). Black circle κ-enhancer and red circle κ-LCR sequences.

DETAILED DESCRIPTION OF THE INVENTION

In the context of the present invention, the term 'heterologous' means a nucleotide sequence or a locus as herein described which is not endogenous to the mammal in which it is located.

The non-human mammal may thus comprise a transgene comprising a heterologous immunoglobulin kappa light chain locus and associated B-cell specific regulatory elements, preferably comprising an LCR and/or a transgene comprising a heterologous lambda light chain locus and associated B-cell specific regulatory elements, preferably comprising an 89LCR.

The presence of cognate LCRs is not essential for B-cell specific expression. Their inclusion within loci ensures that high level transgene expression occurs at every site of integration and is not dependent on random integration events, only some of which fortuitously occur within chromatin regions actively transcribed in B-cells. The use of cognate LCRs significantly reduces the number of transgenic animals required to be screened for antibody expression and allows the insertion of more than one gene locus, with the certainty that all loci inserted will be expressed at essentially normal levels in a B-cell specific manner Thus, the use of LCR technology, combined with the surprising observation that allelic exclusion mechanisms will discriminate between endogenous immunoglobulin genes and multiple competing transgenes, opens the way for the assembly of transgenic non-human mammals comprising one or more immunoglobulin heavy or light chain gene loci, each locus being of reduced V gene complexity relative to the endogenous genes and comprising a relatively manageable piece of DNA (<300 Kb) to assemble in vitro relative to the endogenous loci (1-2 Mb). For example, the 39 functional human immunoglobulin heavy chain V gene segments may be cloned into two or more immunoglobulin heavy chain loci. Each will comprise different V gene segments, but have in common D and J gene segments, and constant (effector) regions. The inclusion of the LCR ensures that each is expressed in an identical manner, irrespective of the site of integration within the genome. Thus, the inclusion of two or more small loci in this manner provides the same V gene complexity of a single, more complex gene present in a single, large gene fragment which is technically difficult to manipulate.

Each heterologous light chain locus may comprise $V_L$ gene segments, J gene segments and a light chain constant region segment. Preferably, the $V_L$ and J gene segments and light chain constant region segment are derived from the same mammalian source, for example rodent, pig, cow, goat or sheep. Preferably, they are of human origin.

Alternatively, the heterologous light chain loci may be hybrid loci comprising variable domains of mammalian origin, preferably of human origin, and constant (effector) regions from a different mammal, such as, but not limited to, mouse, rat, hamster, rabbit, pig, goat and cow. Where the host mammal is a mouse, preferably the constant regions are of rodent origin, more preferably mouse or rat. Such heterologous light chain loci comprise $V_L$ and J segments preferably from one species only and a light chain constant region from another species.

Where hybrid kappa light chain transgenes are contemplated, the $V_L$ and J gene segments are preferably from the same species, contributing the heavy chain V, D and J gene segments, and are preferably of human origin. The kappa light chain constant and heavy chain constant regions are also preferably derived from the same species but a species different from that contributing variable domains and are preferably of rodent origin, and preferably derived from rat or mouse.

A feature of all light chain transgenes contemplated is that, following antigen challenge, the light chain rearranges in a B-cell specific manner and that, following transcription and translation, the resulting light chain is capable of complexing with transgene-derived heavy chain immunoglobulin produced in the same B-cell. The productive expression of immunoglobulin tetramers gives rise to B-cell expansion and transgene-encoded, antigen-specific tetravalent immunoglobulin complexes can accumulate in serum in the absence of significant levels of endogenous immunoglobulin tetramers.

Where endogenous lambda light chain expression has not been functionally suppressed, then low levels of host or hybrid antibody comprising endogenous lambda light chains may be detectable. These may be discarded following screening of hybridoma supernatants.

In humans, there are 36 functional kappa $V_L$ gene segments, five $J_L$ gene segments and a single kappa light chain constant region (http://imgt.cines.fr). Preferably, a heterologous kappa light chain locus present in a transgene in the non-human mammal of the invention comprises one or more human $V_L$ gene segments, all human $J_L$ gene segments and a single human kappa light chain constant region. The human $V_L$ gene segments may comprise 1, 2, 3, 4, 5, 6, 7, 8, 9, 10 or 11 human $V_L$ gene segments selected from Vκ2-30, Vκ2-28, Vκ1-5, Vκ1-9, Vκ1-27, Vκ1-33, Vκ1-39, Vκ3-20, Vκ3-15, Vκ3-11, and Vκ4-1. Optionally, the human kappa light chain constant region may be replaced by an alternate mammalian kappa light chain constant region, preferably of rat or mouse origin.

The transgenic non-human mammal may also comprise a heterologous immunoglobulin lambda light chain locus. A heterologous lambda light chain locus present in a transgene in the non-human mammal of the invention preferably comprises a murine lambda LCR, and human lambda light chain V1 and V2 gene segments, human lambda J1, J2, J3 and J4 gene segments, and human lambda light chain C1, C2, C3 and C4 constant region segments (WO90/10077 and WO2003/000737). The human lambda light chain V1 and V2 gene segments may comprise 1, 2, 3, or 4 human $V_L$ gene segments selected from Vλ3-19, Vλ3-1, Vλ2-8, and Vλ1-51. The human human J gene segments may comprise Jλ1 and Jλ3. The constant region gene segments comprise Cλ2 and Cλ3. Optionally, the human lambda light chain C1, C2, C3 and C4 constant region segments may be replaced by alternative lambda light chain constant regions, preferably of rat or mouse origin.

The non-human mammal may also comprise a heterologous immunoglobulin heavy chain locus. A heterologous heavy chain locus present in a transgene in the non-human mammal of the invention preferably comprises a heavy chain immunoglobulin LCR, preferably of murine origin, one or more human V gene segments, one or more J gene segments and one or more D gene segments. Preferably, 10 or more human different V gene segments and all human J and D gene segments are present. Preferably, 10, 11, 12, 13, 14, 15, 16, 17, or 18 or more human different V gene segments are present selected from VH1-69, VH4-59, VH3-53, VH3-49, VH4-34, VH3-48, VH3-30, VH3-33, VH3-23, VH1-18, VH3-15, VH4-b, VH1-8, VH3-07, VH2-5, VH4-4, VH1-2, and VH6-1. The human J gene segments may comprise all six human J gene segments. The human D gene segments may comprise 21 human D gene segments selected from D1-1, D2-2, D3-9, D3-10, D 4-11, D 5-12, D 6-13, D, 1-14, D 2-15, D 3-16, D 3-17, D 5-18, D 6-19, D 1-20, D 2-21, D 3-22, D 4-23, D 5-24, D 6-25, D 1-26, and D-7-27.

The locus also may comprise one or more human constant (effector) regions, preferably the μ and γ constant regions. Optionally, the human constant effector regions may be replaced by effector regions from other non-human mammals. Where the non-human mammalian host is a mouse or a rat, then preferably constant (effector) regions are derived from rat or mouse. The rat constant region gene segments may comprise Cμ, Cγ2c, Cγ1, Cγ2b, and Cα. In contrast with human, the transmembrane domains of the mouse and rat B-cell receptor complex (BCR) are 100% conserved. Thus, mice transgenic for antibody loci comprising rat constant (effector) region genes should function as well as those comprising mouse constant (effector) region genes following antigen challenge, and may be superior to those comprising human constant (effector) region genes (De Franco et al. (1995) Ann. NY Acad. Sci., 766, 195-201). The transgenes may comprise heavy chain, kappa and lambda light chain LCRs, preferably of mouse or human origin. LCRs which function across all mammalian species are known and may be substituted for human or mouse LCRs in the transgenes (Li et al. (1999) Trends Genet., 10, 403-8).

Where the generation of fully human antibodies is contemplated, cloned human antigen-specific $V_H$ and $V_L$ binding domains derived from hybrid antibodies expressed by hybridomas can be fused to human constant heavy and light chain constant regions, so deriving fully human tetrameric antibodies of any class.

As a further refinement, each immunoglobulin kappa and/or lambda light chain locus may also comprise a dominant selective marker gene.

The dominant selective marker genes incorporated in the loci may have the same or different mechanisms of action. For the purposes of the invention, any dominant selective marker gene can be used, provided that expression of the gene confers a selective benefit to hybridomas or transformed B-cells derived from the non-human transgenic mammal in the presence of a selective or toxic challenge. Typically, the dominant selective marker genes will be of prokaryotic origin and will be selected from a group which either confer resistance to toxic drugs, such as puromycin (Vara et al. (1986) NAR, 14, 4617-4624), hygromycin (Santerre et al. (1984) Gene, 30, 147-156) and G418 (Colbere-Garapin et al. (1981) 150, 1-14), or comprise genes which obviate certain nutritional requirements such that their expression converts a toxic substance into an essential amino acid, for example the conversion of indole to tryptophan or the conversion of histidinol to histidine (Hartmann and Mulligan, (1988) PNAS, 85, 8047-8051).

A necessary requirement of this aspect of the invention is that the dominant selective marker is incorporated within the immunoglobulin light chain transgenic locus and is co-expressed with the desired immunoglobulin light chain allele, so ensuring B-cell specific expression. Alternatively, the drug resistance gene maybe inserted into an endogenous or exogenous (transgenic) immunoglobulin locus using homologous recombination in combination with ES cells or nuclear transfer approaches (te Riele et al. (1992), PNAS, 89, 11, 5128-5132).

The non-human mammal may also comprise a transgene or transgenes comprising a heterologous heavy chain locus and associated B-cell specific LCR and regulatory elements. More than one different transgenic heavy chain gene locus may be present, each comprising an LCR and regulatory elements.

The heavy chain gene loci, each comprising one or more V gene segments, one or more D gene segments, one or more J gene segments, and one or more constant (effector) regions are introduced as transgenes, each locus comprising a cognate LCR.

Each locus comprises the 5' and 3' regulatory elements necessary to drive B-cell specific expression. Each heavy or light chain locus is expressed in an essentially identical manner to the endogenous loci in response to antigen challenge, leading to the circulation in mouse serum of transgene-encoded, antigen-specific affinity-matured, tetrameric immunoglobulins.

Preferably, each heavy chain gene locus comprises 18 V gene segments are present on any single heavy chain locus.

In one embodiment, each locus may comprise only one V gene segment. In one alternative of this embodiment, a number of V gene segments are present and each V gene segment is different from all other V gene segments. In this embodiment, the V gene segments in any one locus may all be derived from an organism of the same species, e.g. all V gene segments may be of human origin. Alternatively, the V gene segments in any one locus may be derived from organisms of different species, e.g. some V gene segments from human and others from sheep, cattle, rabbits, camelids or even shark. In a second alternative, each V gene segment is identical to all the other V gene segments. Irrespective of the number and nature of the V gene segments present, the remaining D and J gene segments in each locus may be the same as or may be different from those in all the other loci.

It is thus envisaged that the non-human mammal may contain multiple copies of a heavy chain gene locus. This has the advantage of optimising the chances that a productive re-arrangement in a B-cell will take place, thus allowing the optimal production of an immunoglobulin heavy chain for antigen recognition.

In another embodiment, each locus comprises multiple V gene segments.

Preferably, the V gene segments are of human origin.

The term 'V gene segment' encompasses any naturally occurring V gene segment derived from a vertebrate, including, but not limited to, sharks, rodents, camelids and human. The V gene segment must be capable of recombining with a D gene segment, a J gene segment and a gene segment encoding a heavy chain constant (effector) region to generate an immunoglobulin heavy chain antibody capable of complexing with either a kappa or lambda immunoglobulin light chain when the re-arranged nucleic acid is expressed in B-cells.

A V gene segment also includes within its scope any gene sequence encoding a natural or engineered homologue, derivative or protein fragment which is capable of recombining with a D gene segment, a J gene segment and a gene segment encoding a heavy chain constant region to generate an immunoglobulin heavy chain antibody capable of complexing with either a kappa or lambda immunoglobulin light chain when the re-arranged nucleic acid is expressed in B-cells. A V gene segment may, for example, be derived from a T-cell receptor locus.

Preferably, the multiple heavy chain loci of the invention comprise any number or combination of the 39 functional human V gene segments and engineered variants thereof. These may be on any number of loci, e.g. four loci comprising eight V gene segments plus one locus comprising seven V gene segments; seven loci comprising four V gene segments plus one locus comprising three V gene segments; or thirty-nine loci comprising one V gene segment each.

Human V genes are classified into seven families, $V_H1$ to $V_H7$, and the individual genes within each family numbered. The frequency at which each gene is used is dependent on the varying requirements of the particular immune response. For example, the genes of family $V_H3$ may be preferentially used in comparison to those of family $V_H5$ when responding to bacterial antigens. Therefore, in a further preferred embodiment of the invention, groups of V gene segments which have been shown to be useful for generating an antibody response against specific antigens are grouped into separate loci, each comprising a different dominant selective marker gene. The V gene segments may be grouped according to family or they may be grouped according to individual function. For example, if the V genes of family $V_H3$ are shown to be useful for generating an immune response against bacterial antigens, then these may be used to generate a locus which is particularly useful for generating heavy chain-only antibodies against bacterial antigens. Alternatively, if it is shown that several individual genes from families $V_H3$ and $V_H5$ are useful for generating an immune response against bacterial antigens, then these may be grouped together and used to generate a locus which is particularly useful for generating antibodies against bacterial antigens.

An "immunoglobulin heavy chain locus" in the context of the present invention relates to a minimal micro-locus encoding a $V_H$ domain comprising one or more V gene segments, one or more D gene segments and one or more J gene segments, operationally linked to one or more gene segments encoding heavy chain constant (effector) regions.

Preferably, the primary source of antibody repertoire variability is the CDR3 region formed by the selection of V, D and J gene segments and by the V-D and D-J junctions.

The advantage of the present invention is that antibody repertoire and diversity obtained in the rearranged V, D and J gene segments can be maximised through the use of multiple immunoglobulin heavy chain gene loci in the same transgenic non-human mammal by exploiting allelic exclusion. The process of allelic exclusion, which randomly chooses one of the loci to start recombination, followed by the next locus if the first recombination was non-productive, etc., until a productive recombination has been produced from one of the loci, would ensure that actually all the V gene segments present in the combined loci would be part of the overall recombination process.

The immunoglobulin locus in its normal configuration appears to have a three dimensional folded structure based on distance measurements made in B cells and measuring in the direction of and through the VH region (Jhunjhunwala et al. (2008) Cell, 133, 265-279). Such a folded or looped structure explains why different $V_H$ region can be used equally efficiently even when they are arranged at very different distances from the D, J and constant region of the immunoglobulin heavy chain locus.

It has also recently become clear that a folded structure formed by looping in a number of loci is mediated through a particular chromatin binding protein called CTCF. CTCF appears to be directly involved in the formation of chromatin looping as demonstrated by mutagenesis experiments (Splinter et al. (2006) Genes Dev., 20, 2349-2354). More recently it has been shown that cohesin, the protein complex that holds sister chromatids together, is present at CTCF binding sites (Wendt et al. (2008) Nature, 451, 796-801). The inclusion of a number of CTCF sites from the immunoglobulin $V_H$ region (Kim et al. (2007) Cell, 128, 1231-1245; Denger, Wong, Jankevicius and Feeney (2009) J. Immunol., 182, 44-48) increases the probability that the $V_H$ region of a transgenic immunoglobulin heavy chain locus can be folded properly and allow efficient usage of all the different V gene segments present in that locus. CTCF binding sites are present 3' to a number of the human VH gene segments used in the examples below. Thus, including the 3' sequence immediately flanking these segments in the locus also includes CTCF binding sites.

Each transgene comprising a heterologous heavy chain locus may further comprise a dominant selective marker. Preferably, the dominant selective marker is different from the dominant selective marker introduced within the kappa or lambda light chain loci.

For the purpose of the invention, any dominant selective marker gene can be used, provided that expression of the gene confers a selective benefit to hybridomas or B-cells derived from the non-human transgenic mammal in the presence of a selective or toxic challenge. Typically, the dominant selective marker genes will be of prokaryotic origin and will be selected from a group which either confer resistance to toxic drugs, such as puromycin (Vara et al. (1986) NAR, 14, 4617-4624), hygromycin (Santerre et al. (1984) Gene, 30, 147-156) and G418 (Colbere-Garapin et al. (1981) 150, 1-14), or comprise genes which obviate certain nutritional requirements such that their expression converts a toxic substance into an essential amino acid, for example the conversion of indole to tryptophan or the conversion of histidinol to histidine (see Hartmann and Mulligan (1988) PNAS, 85, 8047-8051).

A necessary requirement of the invention is that the dominant selective marker(s), if used, reside within the immunoglobulin heavy chain transgenic loci, so ensuring B-cell specific co-expression. Alternatively, the drug resistance gene maybe inserted into an endogenous or exogenous (transgenic) immunoglobulin locus using homologous recombination in combination with ES cells or nuclear transfer approaches (e.g. to Riele, Robanus Maandag and Berns (1992), PNAS, 89, 11, 5128-5132).

The same dominant selective marker gene may be incorporated within all heavy chain loci. Alternatively, different heavy chain loci or groups of heavy chain loci may comprise different dominant selective marker genes.

Hybridomas or B-cells, preferably long-lived plasma cells (Slifka et al (1998) Immunity, 8, 363-372), derived from transgenic mice of the invention expressing tetrameric antibodies may be selected for, free of cells expressing endogenous immunoglobulin, due to the co-expression of a functional dominant selective marker gene within the transgenic light chain loci. Furthermore, hybridomas or transformed B-cell lines or cultured B cells expressing antibodies derived from specific groups of V segments present on transgenic heavy chain loci may also be selected for due to the presence and co-expression of different dominant selective markers within heavy chain loci relative to the dominant selective markers incorporated within the light chain loci. For example, the inclusion of a puromycin resistance gene within the kappa light chain transgenic locus would allow selection of all cells expressing the kappa light chain transgene. Alternatively, the inclusion of the G418 resistance gene within a heavy chain transgenic locus comprising preferred V gene segments would allow the selection of all cells expressing the preferred V gene segments.

In some embodiments of the invention, the endogenous mouse heavy chain locus and/or the endogenous mouse kappa light chain locus may be disabled. Strategies for disabling these endogenous loci are known in the art and described in the examples herein.

In particular, the invention provides a method of producing an antigen-specific heterologous monoclonal antibody comprising:

(a) immunising a non-human transgenic mammal as described above with the antigen;

(b) preparing hybridomas or B cells, plasmablasts, memory B-cells or plasma cells each of which produces a monoclonal antibody from the B-cells of the immunised transgenic mammal;

(c) selecting at least one hybridoma or B cell, plasmablast, memory B-cell or plasma cell expressing the heterologous antibody by use of the dominant selective marker genes present in the transgenes comprising the heterologous immunoglobulin light chain and heavy chain loci; and (d) selecting at least one hybridoma or B cell, plasmablast, memory B-cell or plasma cell which produces an antibody which binds specifically to the antigen.

The invention is now described, by way of example only, in the following detailed description with reference to the following Figures.

EXAMPLES

In the following examples, transgenic mice are generated that express hybrid human/rat heavy chain and light chain loci as transgenes introduced by microinjection in fertilised eggs, a routine transgenesis procedure. The egg-donating mice can be modified to have no or very low expression of the endogenous mouse heavy chain genes and mouse light chain genes. For example, the mice can be μMTE mice as depicted in FIG. 7, obtained by homologous recombination of ES cells. The IgH locus can be inactivated by a strategy similar to that published by Kitamura and Rajewsky with the difference being that the stop codon is introduced into the $C_\mu$ regions at a position one amino acid before that described by Kitamura et al. (1991) Nature, 350, 423-426. Additionally, the mice can have the κ light chain locus inactivated as depicted in FIG. 8. The lambda light chain locus can also be inactivated, although it should be noted that the mouse lambda locus is used very infrequently.

Methodology used for the construction of heavy and light chain loci, the generation and screening of transgenic mice following antigen challenge are essentially as previously described (Janssens et al. (2006) PNAS, 10, 103(41), 15130-5, WO2006/008548, WO2007/096779, WO2009/13620, WO2010/070263 and WO2010/10965) excepting that the $C_H1$ domain is retained in all heavy chain loci. General methods for deriving vertebrates, including mammals, other than mice, which express functional heterologous immunoglobulin loci and/or have engineered endogenous loci are as described in WO2006/047367. In the examples below, recombination in ES cells is used and the modified ES cells are used to generate mice with the desired properties. However, the same procedures could be carried out in induced pluripotent stem cells (iPS cells) which are then used to generate mice (e.g. Boland, Hazen, Nazor, Rodriguez, Gifford, Martin, Kupriyanov and Baldwin (2009), 461, 7260, 91-4 and references therein). Alternatively, the modifications are carried out in somatic cells or somatic stem cells which are subsequently reprogrammed into iPS cells to generate modified mice. Also, modified hematopoietic stem cells could be transplanted into recipient mice lacking B cells to generate human or human hybrid antibodies.

Example 1

The most frequently and moderately frequently used $V_\kappa$ genes of the human $Ig_\kappa$ locus (FIG. 1, Vκ2-30, Vκ2-28, Vκ1-5, Vκ1-9, Vκ1-27, Vκ1-33, Vκ1-39, Vκ3-20, Vκ3-15, Vκ3-11, and Vκ4-1, assessed using the Ig database; http://imgt.cines.fr/) were amplified by standard PCR and subcloned between XhoI/SalI sites, as described previously for human $V_H$ segments. This allows the multimerisation of the $V_\kappa$ regions, keeping the multimer between XhoI and SalI sites.

Also, the 3' end of the mouse κ locus, including the 3' κ enhancer, and the rat constant ($C_\kappa$) region plus the rat 5' enhancer were cloned together. Next, the human $J_\kappa$ region and the region (17 kb) from between mouse $V_\kappa$ and $J_\kappa$ were cloned in to maintain the normal spacing between $V_\kappa$ regions and $J_\kappa$. Finally, the human $V_\kappa$ were inserted into the PAC by routine procedures (e.g. Janssens et al. (2006), supra).

Figure 1:
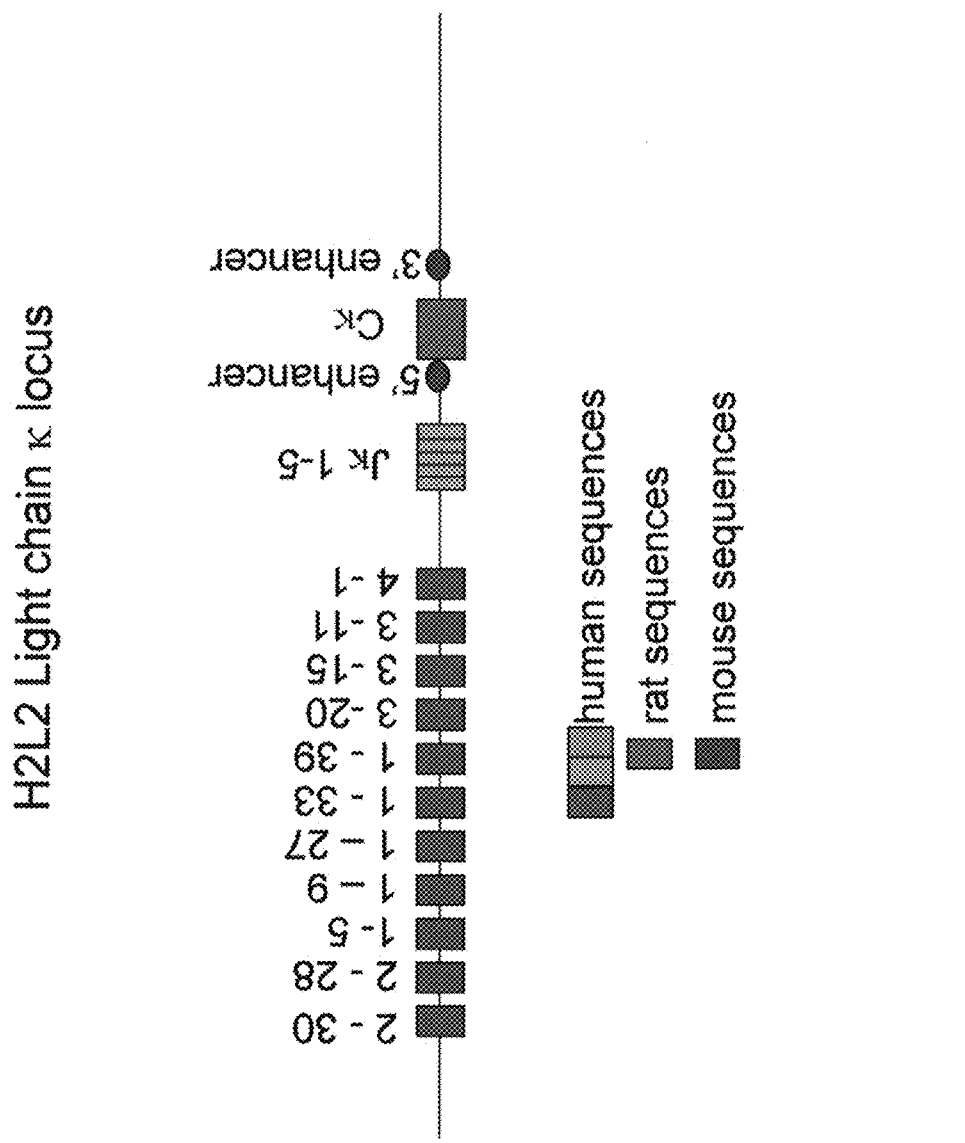
FIG. 1 depicts the composition of a hybrid human/rat $Ig_\kappa$ locus.

The $V_\kappa$ segments were multimerized and ligated into the PAC vector containing the human J regions and the mouse enhancers and rat $C_\kappa$ regions. This results in a human-rat hybrid locus comprising human $V_\kappa$ segments and a rat constant ($C_\kappa$) region (FIG. 1).

The hybrid loci inserts were subsequently isolated from the plasmid as large DNA fragments and injected into fertilized mouse eggs. All of this was done by routine methods (e.g. Janssens et al. (2006), supra).

Example 2

A hybrid human/rat IgH locus has been generated having 18 human $V_H$ segments and 5 rat constant regions (FIG. 2; human $V_H$6-1, $V_H$1-2, $V_H$4-4, $V_H$2-5, $V_H$3-07, $V_H$1-8, $V_H$4-b, $V_H$3-15, $V_H$1-18, $V_H$3-23, $V_H$3-33, $V_H$3-30, $V_H$3-48, $V_H$4-34, $V_H$3-49, $V_H$3-53, $V_H$4-59, $V_H$1-69). First, a central 70 kb DJ region of the human locus containing 21 D gene segments and all 6 J gene segments was extended at the 5' end with 8 kb from the mouse IgH intron to maintain the proper distance between $V_H$ segments and the D region. Next the first $V_H$ region (6-1) of 10 kb with an artificial SceI meganuclease site was cloned at the 5' end of the mouse intron sequences. In a separate plasmid, all the remaining $V_H$ regions were cloned together by slotting in XhoI/SalI $V_H$ segments. The $V_H$ multimer was cloned into the VH6-1DJ plasmid, after which the rat constant regions were added to complete the locus (Cμ, Cγ2χ, Cγ1, Cγ2b, and Cα and switch regions). These have been amplified by standard long range PCR from rat genomic DNA. Finally, the mouse heavy chain LCR was added. This regulatory sequence was amplified from mouse genomic DNA in three parts, subcloned together to restore the complete LCR and added to the 3' side of the rat constant regions. The resulting hybrid IgH locus thus contains human V, D and J regions and rat constant regions with mouse regulatory sequences.

The hybrid loci inserts were subsequently isolated from the plasmid as large DNA fragments and injected into fertilized mouse eggs. All of this was done by routine methods (e.g. Janssens et al. (2006), supra).

Example 3

The hybrid IgH and hybrid $Ig_\kappa$ transgenic mice were subsequently bred to obtain mice that are positive for the human/rat hybrid IgH and $Ig_\kappa$ expression. These mice were subsequently immunized to generate antigen-specific hybrid human/rat $H_2L_2$ antibodies by routine procedures.

Example 4

In this example, the diversity of the human/rat hybrid antibody is increased even further by the addition of a human/rat Igλ locus through breeding to the mice that carry human/rat IgH and/or Igκ loci described in the examples above. The human/rat hybrid λ locus was generated very much as described for the human/rat Igκ locus described in the previous examples (FIG. 3, Vλ3-19, Vλ3-1, Vλ2-8, and Vλ1-51). The difference is caused by the fact that Jλ and Cλ regions occur in pairs and hence 2 rat $C_\lambda$ regions were cloned onto 2 human $J_\lambda$ regions (FIG. 3). The spacing between the $V_\lambda$ and $J_\lambda$ segments was maintained by cloning the normal mouse sequences that occur in that position. In this example, 2 human $J_\lambda$ and rat $C_\lambda$ segments were used together with four human $V_\lambda$ segments. Together, these cover more than 80% of the human Igλ response. The regulatory sequences (LCR) were derived from the mouse to ensure optimal expression. As described above, the locus is isolated as a restriction fragment and injected into fertilised eggs to generate mice carrying the transgenic λ locus.

In all of these Examples, the complexity of the response will be enhanced even further by adding V segments as part of additional heavy or light chain transgenic loci present in the same mouse. Since all the loci are subject to allelic exclusion (see WO2007/096779), only the preferred rearrangement will be selected in vivo following antigen challenge, resulting in B-cell expansion and the accumulation of antibody in serum. The method could also be applied to other species using V segments specific for these species.

In all of these examples $V_H$, $V_L$, D, J and constant regions from different species can be used to generate other single species antibodies or hybrid species antibodies. It will also be apparent to one skilled in the art that, once an antigen-specific antibody has been identified, the $V_H DJ$ and $V_L J$ regions can be cloned onto alternative constant regions from the same species or from different species by completely routine methods.

The skilled person will appreciate that variations to this procedure may be made to generate the hybrid transgenic mice, such as the use of different vectors, different selection markers, different recombination positions to inactivate the mouse genes or variations in the actual (routine) cloning strategy of the hybrid loci. The same procedure can be used to generate any normal or hybrid locus using immunoglobulin DNA derived from any single mammalian species, or hybrid loci derived using DNA from two or more species.

The foregoing examples are meant to illustrate the invention and do not limit it in any way. Modifications within the spirit and scope of the invention are contemplated and included. All references cited herein are herein incorporated by reference in their entirety.

We claim:

1. A transgenic non-human mammal comprising an immunoglobulin kappa light chain locus comprising the sequence of SEQ ID NO:2, wherein the transgenic mammal is capable of expressing the Ig kappa chain encoded by SEQ ID NO:2 in response to an antigen challenge, wherein said locus is randomly integrated into the genome of said transgenic mammal.

* * * * *

UNITED STATES PATENT AND TRADEMARK OFFICE
CERTIFICATE OF CORRECTION

PATENT NO. : 9,980,470 B2  
APPLICATION NO. : 14/211130  
DATED : May 29, 2018  
INVENTOR(S) : Grosveld et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 736 days.

Signed and Sealed this  
Twenty-sixth Day of May, 2020

Andrei Iancu  
*Director of the United States Patent and Trademark Office*

SEQUENCE LISTING

```
<160> NUMBER OF SEQ ID NOS: 10

<210> SEQ ID NO 1
<211> LENGTH: 218449
<212> TYPE: DNA
<213> ORGANISM: Artificial Sequence
<220> FEATURE:
<223> OTHER INFORMATION: Hybrid immunoglobulin locus
<220> FEATURE:
<221> NAME/KEY: unsure
<222> LOCATION: 1379
<223> OTHER INFORMATION: "n" represents any nucleotide
<220> FEATURE:
<221> NAME/KEY: unsure
<222> LOCATION: 16903-16909
<223> OTHER INFORMATION: "n" represents any nucleotide
<220> FEATURE:
<221> NAME/KEY: unsure
<222> LOCATION: 35206-35211
<223> OTHER INFORMATION: "n" represents any nucleotide
<220> FEATURE:
<221> NAME/KEY: unsure
<222> LOCATION: 71895-71897
<223> OTHER INFORMATION: "n" represents any nucleotide
<220> FEATURE:
<221> NAME/KEY: unsure
<222> LOCATION: 158508-158516
<223> OTHER INFORMATION: "n" represents any nucleotide
<220> FEATURE:
<221> NAME/KEY: unsure
<222> LOCATION: 175598-175651
<223> OTHER INFORMATION: "n" represents any nucleotide
<220> FEATURE:
<221> NAME/KEY: unsure
<222> LOCATION: 175965-176009
<223> OTHER INFORMATION: "n" represents any nucleotide
<220> FEATURE:
<221> NAME/KEY: unsure
<222> LOCATION: 176101-176157
<223> OTHER INFORMATION: "n" represents any nucleotide
<220> FEATURE:
<221> NAME/KEY: unsure
<222> LOCATION: 176194-176251
<223> OTHER INFORMATION: "n" represents any nucleotide

<400> SEQUENCE: 1
atccctagct gaagcttctg atggaattag aacttggcaa aacaatactg agaatgaagt      60
gtatgtggaa cagaggctgc tgatctcgtt cttcaggcta tgaaactgac acatttggaa     120
accacagtac ttagaaccac aaagtgggaa tcaagagaaa aacaatgatc ccacgagaga     180
tctatagatc tatagatcat gagtgggagg aatgagctgg cccttaattt ggttttgctt     240
gtttaaatta tgatatccaa ctatgaaaca ttatcataaa gcaatagtaa agagccttca     300
gtaaagagca ggcatttatc taatcccacc ccaccccac ccccgtagct ccaatccttc      360
cattcaaaat gtaggtactc tgttctcacc cttcttaaca aagtatgaca ggaaaaactt     420
ccattttagt ggacatcttt attgtttaat agatcatcaa tttctcgatt tctcgactat     480
tcctttgccc tcggacgagt gctggggcgt cggtttccac tatcggcgag tacttctaca     540
```

```
cagccatcgg tccagacggc cgcgcttctg cgggcgattt gtgtacgccc gacagtcccg    600
gctccggatc ggacgattgc gtcgcatcga ccctgcgccc aagctgcatc atcgaaattg    660
ccgtcaacca agctctgata gagttggtca agaccaatgc ggagcatata cgcccggagc    720
cgcggcgatc ctgcaagctc cggatgcctc cgctcgaagt agcgcgtctg ctgctccata    780
caagccaacc acggcctcca agaagaagatg ttggcgacct cgtattggga atccccgaac    840
atcgcctcgc tccagtcaat gaccgctgtt atgcggccat tgtccgtcag gacattgttg    900
gagccgaaat ccgcgtgcac gaggtgccgg acttcggggc agtcctcggc ccaaagcatc    960
agctcatcga gagcctgcgc gacggacgca ctgacggtgt cgtccatcac agtttgccag   1020
tgatacacat ggggatcagc aatcgcgcat atgaaatcac gccatgtagt gtattgaccg   1080
attccttgcg gtccgaatgg gccgaacccg ctcgtctggc taagatcggc cgcagcgatc   1140
gcatccatgg cctccgcgac cggctgcaga acagcgggca gttcggtttc aggcaggtct   1200
tgcaacgtga caccctgtgc acggcgggag atgcaatagg tcaggctctc gctgaattcc   1260
ccaatgtcaa gcacttccgg aatcgggagc gcggccgatg caaagtgccg ataaacataa   1320
cgatctttgt agaaaccatc ggcgcagcta tttacccgca ggacatatcc acgccctcnt   1380
acatcgaagc tgaaagcacg agattcttcg ccctccgaga gctgcatcag gtcggagacg   1440
ctgtcgaact tttcgatcag aaacttctcg acagacgtcg cggtgagttc aggcttttc    1500 atggtggcgg ctggatcggt cggtcgaaag gcccggagat gaggaagagg agaacagcgc   1560
ggcagacgtg cgcttttgaa gcgtgcagaa tgccgggcct ccggaggacc ttcgggcgcc   1620
cgccccgccc ctgagcccgc ccctgagccc gccccggac ccacccctc ccagcctctg     1680 agcccagaaa gcgaaggagc aaagctgcta ttggccgctg ccccaaaggc ctacccgctt   1740
ccattgctca gcgtgctgt ccatctgcac gagactagtg agacgtgcta cttccatttg    1800
tcacgtcctg cacgacgcga gctgcgggc ggggggaac ttcctgacta ggggaggagt     1860
agaaggtggc gcgaagggc caccaaagaa cggagccggt tggcgcctac cggtggatgt    1920
ggaatgtgtg cgaggccaga ggccacttgt gtagcgccaa gtgcccagcg gggctgctaa   1980
agcgcatgct ccagactgcc ttgggaaaag cgcctcccct acccggtaga attcatcgct   2040
cgagcaattg gctagataac ttcgtataat gtatgctata cgaagttatc tagctctaga   2100
gtcgacgatt gaagagtgtg ataagtgccc agaccaagca gaacagaaat cagcatgtaa   2160
agatgatgat ctatggatat gatctaaaac catgtaaata cttcaaataa ttctatttaa   2220
tgcagtttga aataaaacac aaacttattc aaaatacaaa ttacttggta attattttgg   2280
gagctatgag ttcaccaaga aactcaaatt cctatttcta tttcaacccc tgattcctac   2340
tgtcaatggg agggaagtct cagaaccaat cacacatcag acggcaaatc tgtcaaccaa   2400
gagtctttcc actgaaggac ctgggaggtc aggaccctca ggaaagtgct ggggaccctg   2460
tcttgggagt gcccagcaga tctcagaact ctccatgggt cctgctggac actcatgtag   2520
ggtaacgagt ggccaccttt tcagtgttac cagtgagctc tgagtgttcc taacgggacc   2580
aggatgggtc taggtgcctg ctcaatgtca gagacagcaa tggtcccaca aaaaacccag   2640
gtaatcttta ggccaataaa atgtgggttc acagtgagga gtgcatcctg ggttggggt    2700 ttgttctgca gcgggaagag cgctgtgcac agaaagctta gaaatggggc aagagatgct   2760
tttcctcagg caggatttag ggcttggtct ctcagcatcc cacacttgta cagctgatgt   2820
ggcatctgtg ttttctttct catcctagat caggctttga gctgtgaaat accctgcctc   2880
atgcatatgc aaataaccct aggtcttctg agataaatat agatatattg gtgccctgag   2940
```

```
agcatcacat aacaaccaca ttcctcctct gaagaagccc ctgggagcac agctcatcac   3000
catggactgg acctggaggt tcctctttgt ggtggcagca gctacaggta aggggcttcc   3060
tagtcctaag gctgaggaag ggatcctggt ttagttaaag aggattttat tcacccctgt   3120
gtcctctcca caggtgtcca gtcccaggtg cagctggtgc agtctggggc tgaggtgaag   3180
aagcctgggt cctcggtgaa ggtctcctgc aaggcttctg gaggcacctt cagcagctat   3240
gctatcagct gggtgcgaca ggcccctgga caagggcttg agtggatggg agggatcatc   3300
cctatctttg gtacagcaaa ctacgcacag aagttccagg gcagagtcac gattaccgcg   3360
gacaaatcca cgagcacagc ctacatggag ctgagcagcc tgagatctga ggacacggcc   3420
gtgtattact gtgcgagaga cacagtgtga aacccacat cctgagagtg tcagaaaccc   3480
tgagggagaa ggcagctgtg ccgggctgag agatgacag gggttattag gtttaaggct   3540
gtttacaaaa tgggttatat atttgagaaa aaagaacag tagaaacaag tacatactct   3600
aattttaaga taaatattcc attcaagagt cgtaatataa gccaaattca cagagtggaa   3660
aaggccacac tctataacgt tgatacaaac attccatgaa ggtgctactg tgaacaagtt   3720
ttcaaattgg atgaatacat gatttggagc aaggttattt gatcatgtgg tgagactaag   3780
aatgctcgac tctggacttg agtgtcattg tccagccatg ttgcacaagt gtgtcctgtc   3840
agggaaggat cagagttcct tgtgctctca gagggaaggg gtcacagagt tcctctctgg   3900
ttcccaggaa aggtaatcgc actaatcttc atgatcttca tgagactatc ctccagtgct   3960
gacctgttat agagtttttg tctgaagttc tcactgcaat ccccaatcta catattttca   4020
atcagaagtg tttagaggcc aggacacatc ttcaaggtca cacattgaga aggatgtaga   4080
tatgtcccac taccttctcc tgagatctca gacagaatcc cagatttcaa aaggacacag   4140
aaggacagct ctcaggtgct tttaaaaaat gacccacttc cagggacagg gagcttccct   4200
ataaccatgg tggatgttct gaactacaat aaacattgga tggatccagg attgtttgaa   4260
gtcactgtca ttattacatt cagctgctgt ttcaatgtgt ctgaagtagt aaatgacaat   4320
ttagatgaca atttatatga atcttcaagg gtagaacaat attgaccata ttccaaaatc   4380
tgtccttgat ccatgatcac actcatctcc cagaccaggt ccttcagcac gtctctttac   4440
ctgaaagaag aggactctgg gcttggagag gggagacccc aagaagacaa ctgagttctc   4500
aaagggcaca gccagcatcc tactcccagg gcgagcccaa aagactgggg cctccctcct   4560
cctttttcac ctctccatac aaaggcacca cccacatgca aatcctcact taagcaccca   4620
caggaaacca ccacacattt ccttaaattc aggttccagc tcacatggga aatactttct   4680
gagagtcctg gacctcctgt gcaagaacat gaaacatctg tggttcttcc ttctcctggt   4740
ggcagctccc agatgtgagt atctcaggga tccagacatg gggatatggg aggtgcctct   4800
gatcccaggg ctcactgtgg gtctctctgt tcacaggggt cctgtcccag gtgcagctgc   4860
aggagtcggg cccaggactg gtgaagcctt cggagaccct gtccctcacc tgcactgtct   4920
ctggtggctc catcagtagt tactactgga gctggatccg gcagccccca gggaagggac   4980
tggagtggat tgggtatatc tattacagtg ggagcaccaa ctacaacccc tccctcaaga   5040
gtcgagtcac catatcagta gacaagtcca agaaccagtt ctccctgaag ctgagctctg   5100
tgaccgctgc ggacacggcc gtgtattact gtgcgagaga cacagtgagg ggaggtgagt   5160
gtgagcccca acaaaaacct ccgtgcaggg aggcggaggg gaccggcgca ggtgctgctc   5220
agagccagca gggggcgcgc ggggcccaca gagcaggagg cccggtcagg agcaggtgca   5280
```

```
gggagggcgg ggcttcctca tctgctcagt ggtctccctc ctcgccagca cctcagctgt    5340
ccccaggggt cctctttctt tattatctgt ggttctgctt cctcacattc ttgtgccaag    5400
aaagaaatga ggaagacaaa ttttcgtctg tagttgaagt ttcaccaatc tcgagacgat    5460
gcggatgtga tttaagtttc agaggaataa aaaaaaagat ttagggatta atttaattat    5520
tcaaaagttg attgaagtgc cgagtgaatg gctgcaaaca tagtctacat ttttcaaatc    5580
attccctata aatttgaatt aattatttat ttttatactt gaataaagca ataacaaaga    5640
aataaatgaa tattttgct aaaatggagc aataaaaga ctgatattga cagaagaaat     5700
atgactgact tctgaaaata cacacacatg agccgtggtt ctctctacat atttagataa    5760
attacagaaa gttgtcataa ctgatgggga atcctgcaga cttcactagg catagtccac    5820
actgccctgg agttgtctca ggggagctgc ctcctccagt ggttagagca caggcccagg    5880
taataggact cattttttta gatgtgtaat tttagacaca ctgcacaact gctgtgttct    5940
ctgcgcaaat tatctcctgt aaaatgcaac attgaaacct gccttaaata tattgtgtaa    6000
atatgtaaaa ataaaatcag attgtgagag ctaaatgcta atcaaggcgc aatcacgtaa    6060
tatacaatta tattttcctg aatgatggaa ttaataccaa tctcccccag gacacttcat    6120
ctgcacggag cccggcctct cctcagatgt cccaccccag agcttgctat atagtcgggg    6180
acatgcaaat agggccctcc ctctgctgat gaaaaccagc ccagctgacc ctgcagctct    6240
gggagaggag cccagcactg ggattccgag gtgtttccat tcggtgatca gcactgaaca    6300
cagaggactc accatggagt tttggctgag ctgggttttc cttgttgcta tttcaaaagg    6360
tgattcatgg agaactagag atatcgagtg tgagtgaaca cgagtgagag aaacagtgga    6420
tatgtgtggc agtttctaac caatgtctct gtgtttgcag gtgtccagtg tgaggtgcag    6480
ctggtggaga ctgaggagg cttgatccag cctgggggt ccctgagact ctcctgtgca     6540
gcctctgggt tcaccgtcag tagcaactac atgagctggg tccgccaggc tccagggaag    6600
gggctggagt gggtctcagt tatttatagc ggtggtagca catactacgc agactccgtg    6660
aagggccgat tcaccatctc cagagacaat tccaagaaca cgctgtatct tcaaatgaac    6720
agcctgagag ccgaggacac ggccgtgtat tactgtgcga gagacacagt gaggggaagt    6780
cattgtgcgc ccagacacaa acctccctgc aggaacgctg gggggaaatc agctgcaggg    6840
ggcgctcagg agccactgat cagagtcagc cccggaggca ggtgcagatg gaggctgatt    6900
tcctgtcagg atgtgggact ctgtcttctt ctgacggttc cccagggaac ctctctaagt    6960
ttagcattct gtgcctatga acgtcttctc taagtatttg aaagagatta ttttaatatg    7020
aagagcagtt ctcactcgtc gacctcttct gaaggaccat gaatgcctca accaaccatc    7080
tcccctgcct ccatgaccag aaatgcacca cgtgcccaca cggatattca ccctcatgg    7140 ggataagact ccattgatga ggctgactat tttatcatat aaaattacta aagactgatt    7200
taagggtttc aaaaactaat tgaactctgt tgttctatgt ccaccagaga ttacaaatct    7260
tccaatgatg ccttctttgt ttttgtctg cttgactttg tctcttcaac ttgttctgta     7320
ccccagagaa tctctttcag ctccctcagg tgcattcaat tgttttattt aactgacaat    7380
ttctaaatca gttaaagaca ttacgctaaa gactccatat tcctaggtcc atattccttt    7440
ttccatattc ctaggaaggc attgtgaccc agagtctggg catgaccttg tgagtgttcc    7500
tgaccctcct ccatatgaga tgctggtctg ggtgttcttg ccccttcc tggggtagag      7560 tcctcctgtt ttccccaggt gctccctccc acagctctag tgttctcaat cagtgtcatc    7620
accttccaga tcttctgccc tgccctgcag actaaggctc tgattccata agcaagatag    7680
```

```
gggagctgct cctcaataga tctttggtga ggatctctgt tcccatctca attcctgtag    7740
ggtggaacca gtgttcctag gattctggtt tcagtagctt gtccctgcag agtaaattct    7800
tagttctgta gggggattaa gggagttggg tctgaataca ttttagatgt cgaggatctt    7860
gttctctccc agaaagacac ttcgggaaag taagactttg gtaactgtcc cctttcttgg    7920
ggaaagggat tcaagaggat aggttgcttt tgggcatgtg gtcccttaaa atttcacact    7980
aaaaagcgtt tcccacactc aatttcaagc agcccaatat atatttgtat tttttcttgg    8040
aacagacaat attttatatt ccagactctg ccttaggtaa tttcaaaccc cggctttgtt    8100
actctctaca agaaattgct tctccataag cttcagattt gttgtgtgtt ttgaaatttt    8160
atcagaaata ttaagaaaaa ttggcaaaat tccatcctcc atgtttatct gttattgttg    8220
atgcagttgt aaaaaataag aaaaatatat tccttttttc tgtacatttc caagcttagt    8280
agcaaatttt tagtaacacc cagaataata aaaaattcaa atattgttta gctgcttaat    8340
aggaaaacaa attatagtaa atttgtttgc tagaatgcta cccagcattt ataataagta    8400
aacatttgat atacccaact acaaggtaaa atatccattt atgctaacta aaataagcca    8460
aacaaatgag aatatatact gttatttcat ttttataaat tctgaaaaat taaaatgaat    8520
ttgcagcaat gtaaagatca gtagttgcca gggaaatggt agaagaaaga aaggaaaagg    8580
agaaagaata cagaaaaaca aaaggaaatg ttaagaattc tcttgtccaa cttgataagg    8640
atgacggtta catcattttt atcaactgta atctttaaat atgtgaaagt ttattatccg    8700
taaactaaac gttataaact ttattacaag caaaaattga agttagaca acaaggagtg    8760 atagaaagag aaaatgtata ttaaatttca gaaatattta agaatgtatc tgcctgaacc    8820
ctagttctca ccatatcttt aggtgaatgc taaaatgcag caaaatcacg catgttctca    8880
ctacagaaag tgggttctac aaaccacact cggcacattt agctttgtcc tggagttggt    8940
gcagggagtt attggggcca gtgatgagga gcacaggcca agataccagc gattacttat    9000
cccaaacatg agctctaaca tacacactta gtccctttc cgtgtgtggt ttacttccac    9060
atctgtacat ggagagacca ctgactgaca aaatataatt tatacaaata tgtaaaatta    9120
aatagggtga tcagttcaag gtgtttatca cagcataatt ttacaataag acagcatatt    9180
tcccaaatac catcattgtc accaaactcc ttcaaggcac agtcatctta tctgggcccc    9240
gtcctctcct caggtgtccc accccagagc ttggtatata gtaggagaca tgcaaataag    9300
gccctccctc tgctgatgaa aatgagccca gccctgaccc tgcagctctg ggagaggagc    9360
cccagccgtg agattcccag gagtttccac ttggtgatca gcactgaaca cagaccacca    9420
accatggagt ttgggcttag ctgggttttc cttgttgcta tttttaaaagg taattcatgg    9480 tgtactagag atactgagtg tgaggggaca tgagtggtag aaacagtgga tatgtgtggc    9540
agtttctgac cttggtgttt ctgtgtttgc aggtgtccaa tgtgaggtgc agctggtgga    9600
gtctggggga ggcttggtac agccagggcg gtccctgaga ctctcctgta cagcttctgg    9660
attcaccttt ggtgattatg ctatgagctg gttccgccag gctccaggga aggggctgga    9720
gtgggtaggt ttcattagaa gcaaagctta tggtgggaca acagaatacg ccgcgtctgt    9780
gaaaggcaga ttcaccatct caagagatga ttccaaaagc atcgcctatc tgcaaatgaa    9840
cagcctgaaa accgaggaca cagccgtgta ttactgtact agagacacag tgaggggagg    9900
tcaatgtgag cccagacaca aacctccctg caggggcgca cagagccacc aggggcgct    9960 agggaccgac tgagtacggg acaggtccca ggagcaggtg caggggagg tttccttttt    10020
```

```
ccttggctgg aaaagtcacc tttatcttcc caggactcga cgatgagact atcctccagt    10080
gctgatgtac tatagagttt tcatctgaag ctgtcactgc tatccccaat gtacatcttt    10140
tcacacagaa atgtttagag gtcaggccat attctcaggg ttacacattg agaaggatgg    10200
agatatattc tactaccttc tcctgagatc tcacacacaa tctcaaattt caaaaggtct    10260
cagaagggca gctctcaggt actatttaaa aataacccac ttcctgggac aggtagcatc    10320
cttctaacca tgatggatgt tctgaactac agtacacatt gcatggatcc gggtttgtct    10380
caattcactg tgattattac actcagcagc tgtttcaata tgtctgaagg ggtaaatgac    10440
aatttaggtg acctgggtgt atggttggtg ttatatgaat ctttaaatgt agaacagtat    10500
taactgtatt ccaaaatctg tctttgatcc atgatcacac ttgtctccca gaccagctcc    10560
ttcagcacat ttcctacctg gaagaagagg actctgggtt tggtgagggg aggccacagg    10620
aagagaactg agttctcaga gggcacagcc agcatacacc tcccagggtg agcccaaaag    10680 actgggggcct ccctcatccc ttttttaccta tccatacaaa ggcaccaccc acatgcaaat    10740
cctcacttag gcacccacag gaaatgacta cacatttcct taaattcagg gtccagctca    10800
catgggaagt gctttctgag agtcatggac ctcctgcaca agaacatgaa acacctgtgg    10860
ttcttcctcc tcctggtggc agctcccaga tgtgagtgtc tcaggaatgc ggatatgaag    10920
atatgagatg ctgcctctga tcccagggct cactgtgggt ttctctgttc acaggggtcc    10980
tgtcccaggt gcagctacag cagtggggcg caggactgtt gaagcttcg gagaccctgt    11040 ccctcacctg cgctgtctat ggtgggtcct tcagtggtta ctactggagc tggatccgcc    11100
agcccccagg gaaggggctg gagtggattg ggaaatcaa tcatagtgga agcaccaact    11160
acaacccgtc cctcaagagt cgagtcacca tatcagtaga caagtccaag aaccagttct    11220
ccctgaagct gagctctgtg accgccgcgg acacggctgt gtattactgt gcgagaggca    11280
cagtgagggg aggtgagtgt gagcccagac aaaaaccccc ctgcaggtag gcagagggg    11340 cgggcgcagg tactgctcaa gaccagcagg tggcgcgcgg cgcccacaga tcccgaggcc    11400
gggtccggag caggtgcaag gagggcgggg cttcctcaac agctcagtgg tctgtctcct    11460
cgccagcacc tcagatgtcc ccaggactct ctttctttat tatctgtggt tctgcttcct    11520
cacatccttg tggcagggaa gaaaggagga agacaatttt tctgtttact gttgaggttt    11580
caccaattac ctcgacgtct tgttacactt catcaagaat taacctctgc tgtttcctca    11640
aagtgtttaa ttggataatg aatttgtcta taaattgaag agttgaaata catcaaatat    11700
taatttgtaa taatctggca caaattatct aagcaaattc aataactaga tgttttttca    11760 tttatttta tttaaaatca ggatctaagc actgacatgc tttaataaca tctgtgaccc    11820
tctcagcagt tttctcttct gagtatatga tctgctgtgg cagttttctt agcttcaatg    11880
ttacctcttt tggcaatgac taccgtcttt atatttgcca ggaatctggg ataagggagt    11940
gcttctaaga gttccctaac ttgcccattt tggtgggtgt tccagaacat atgagatgct    12000
ctgttgttaa caaagcatcc caaagccatg cactgcccta aaatgtgttt gtttcctagt    12060
ttgacaaatt ggaagttcta ataaatacaa tcacttctgc catctgggct gatttttacat   12120 cagatagagg gctgtattcc aaagaaaagc ttacattagt aatagcaatt ctagtcagaa    12180
acctagagtt ttatcattga ggtgcaattc ataacaaata atattaggtc gaggttctca    12240
gtggcagtgt ctaaatctct taggtgtaca gggtcttccc tgttaacatg aagcatttat    12300
aagcacagtc atagtttcca gctatgcttc tccctgtctc attatcacca caaactatgg    12360
cctcacctgg aacttgggtt aatttccaaa taagtaattt tttagtgttt atgcctctag    12420
```

```
attattatgt gagaaagtta acattcagta gaaagttaaa aagaacattt gaactgacta   12480
aacaacacag acaatcaaga ataaaattca aagcctagat gtgagaggct ccaggcctgg   12540
ataatgcaat agttcatgta tgcaggcagt ttctttgccc agttctacac tgatacaccc   12600
agaatgtcag cttcatgcca gatttgactc ctattatgta gagacatggc aatacattct   12660
caagggtcac atgaaataat atgaaaattg gtgggaatag gggaggagac aactctgcaa   12720
ttctcatctg aaggaccagg aaagcctgga cagaccatct ccccagcctc cgtgactgca   12780
ccacgtgccc acatggacgc tcatccctga tagggtaaga agactccatt gatggggctg   12840
agcattttat gatagaaatt actagagact gacgtggagg tttcaacaac taatatttat   12900
aaccaaaatt taattacccc cacattgtta ccattttctt cagtgaaaaa ttgcttgcca   12960
tgattaagtt ttaagtagat ttccaatgtt cacaactgag cttccaagag agtcttgaga   13020
acaaaaacaa tgagggcaga gaaatctacc tttctgcat tcaccactaa actcaagtgg    13080
actcagcact gcctttgatc actgctactt ctctgcagag ttcaggtttc tacttctcac   13140
aattctgaca cacattctac ctctcctcag atgtttggcc tctgcttctt gtaaggtcac   13200
cctctgttct taacttcttc tctgagtcat tttgtgaggt ggtcatgagc cattaaatgg   13260 atatttata ttttcccaac atgaatcaca tgagtggtca tgaattatac ttctgattat    13320
ggcagttgat ttttcttggc atgttcatga ctagtaatat ttgaagccat tcattcaaa    13380 tcttcgggc ttcgtttttg ttgctatgac attttttctt ctattgagtc tttccactag    13440
tattataaca tgacctagta tccaggctca gttgtcatta ataataacca catatgtcaa   13500
aaatcatgca ttcttttcac agcagacata atttcctctt ttctgcagat gaagacacac   13560
tgctgagcta cccccactta caagaatata tgcacaatta tgatatcttc atttatttga   13620
ctaataagct atatcattct cccttcaaat tctttacccc ccagaagtcc tggacaaatt   13680
tctgcatctg ctcaaacgat aaactcagaa ctacatggtg agtaaaagtc acctggttct   13740
ggatattggg tccatctctt cccctccaat gtcccagagc acctcagcac acccgtccag   13800
gttctatcaa gaaagagtag ctcctgcaca ctgaaggaaa caattgagtt aagagaggac   13860
ctgcagatga tagacaatat tgaaaactgt taatatgaca aaggattact accaagcatg   13920
tgaaataagc tcaacgggtg cggtggttca tgtctgtagt accagcaatt tgggaggcaa   13980
gttgcgcaga tcacctgagg ttaggagctc gacaccagcc tgaccaacat aaagaacacc   14040
ctgtctctac taaaagtaca aaattagccg ggcatggtgg catgcgcctg taatcccagc   14100
tactcgggag gctgaggcag gagcatcact tgaacctggg aagtggaggt tgcggtgagc   14160
tgagatggca ccattgcact ccagcctggg caacaagagg gaaactccat ctcaaaaaaa   14220
aaattacaaa aaattagctg agcgtggtgg tgggcgcctg tatacccagc tgctaggag     14280 actgaggcag gagaatggct tgaacccagg aggtgaaggt tgcagtgagc tgagattgcg   14340
ccattgcact ccatcctggg caacaagagt gaaactccat ctcaaaaaaa aaaaagaga     14400 cttgcaaagg gcaaatagat catagacaga cagatagata gatagaccta ttagtataca    14460
tacatacata tatatacact aatattcagg aaaatgcaaa ttcataatga gatgtctttt   14520 caccettcat ctctgctaga aagtttgtta tctgaaaaac aaatacatac atacatactt   14580
attaaaagct ggccaggatg cctagaaagt aaaactcata gaccactggt ggaaatgtaa   14640
attagtgcag ccatcaaggg aaaaaaatag aactaccata tattccagca atccaactgc   14700
taagtatata tctatttaaa tatttaaaag aaaaaactaa tattgaagag atacctgtac   14760
```

```
acccatgttt attgcagcac taatcacaat ttctaggata tgaaatcaac atatgtgtcc   14820
atcaacagat gaatggatac ataaaatgtg atatatttac acaatggaat attattcagc   14880
cttaacaatg aaattctgcc gtttgaagca acatggatgg aatgggacac ctctatgttg   14940
agtgaaatga gtcagacaca gaaaaataaa taccgcattt ctcagcgtta cttctagaag   15000
taaatagtag agtagtggtg atgagatgcc aggaatgaga gaaggctgag ataagaagag   15060
gtttgttaac aaacacacaa ttacaggtag acaggaggga tgtgctctag tgttctacag   15120
cacagtaggg tgactacagt taacaatata ttgtacgttt tctgtttaca agaagccaga   15180
agagagaatt ttctatgcta ccaacacaaa taaatgttag tgtctgaact gacgaatttg   15240
ctcattgttc tgattttagt cataccaagt ggcacacatg tattcaaata tcacactgta   15300
ccccataaac ataagcagtt attatgtgcc aaatttgaaa aatcctttaa ttagaaggaa   15360
ttatattggc gtacattaca aatgattcaa cacagagaca ggaataaata ccattttttct  15420 ttgaaatagt taattaacta acaatgtagt tacattcatt tgcaccaaat cgtgtatttg   15480
ataatggtat gcatagacag atttatgcat aggataatat ctttttaattt tagactacta  15540 cttaatacta taaatataaa taattttaaa acaactaagt aaaaagaata aagctgagaa   15600
aatgtgtgtg tggtgtgtga tgtgtgagct ttttcttgtg caccactgtg tccttggtgg   15660
atgtgtggtt catgtgtttg tttttattta ctctgtttgg ggttctcttt gcttctagga   15720
tctgtagttc agtttctttc acaaaattgg gaacattctt cgctattatc ttttcaaat    15780 agtttctgtg tatttataat ttctccttct cagatttaaa atatacacat actataattt   15840
tgatattaat gtttagtttc tttcttcact ctcttttcgt ttgcaattta ctttgtgaaa   15900
tttctaatga catactaatc acatggtttt attgaaaagc tgagccagct ctactgaggt   15960
gtgtgccaaa agattgctcg atgtttatac agcattgctt ttgatttctt atgcatttcc   16020
atttgattta ttcttagtat tttcatattt cagttcccta tctatgtcca cgatttcttt   16080
aagagattct tgcgtgtgaa ttatagttac tttacatatc ttgtttaatt agatatttat   16140
aacatctgtt tcatctacaa atctcatgct gatcatttgt ttattacaac tttggtactt   16200
ctcattaatg tatgtaataa ttgttgatag ccacagatac tgggatggac agtggatact   16260
ggccttatta tttcatttta tgcatttctg cctgtatttg accacacttt accttttgcca  16320 ggcctttact gtggaagtat ctgtgaatct tctcagaact atatttgaca ttcacttttg   16380
cagtggacat caaagttgaa gtctgttctt ctgtgtccac cagagacttc agttcctcca   16440
gtgatacctt gtttttcttt cctgcttggc tttgtctctt cacctgttcc ctcctccaga   16500
gaatcatgtt cagctccctc aggtggatta aaatgttatc taactgacaa ttgtgaaatt   16560 ggtgaaagc aatagaataa agggagattt tctgaccttt cttgggttca tattgtgaac    16620
atgagtctgg gtgtgacctt cccaatgttt ctgaacttcc tccagatgag atgttggtct   16680
gtgtgttctt gctcttttcc ctgctgtgga gtcctcttgt ttcccccagt tgttccctcc   16740
cgcagctcca atgttctctt ттттgтgттaт caccttacag atttgctgac tagaactgca   16800
gattagggct ctgattaaat aagaaggagg ggagatactt ctcaatggaa cttaggtgaa   16860
gacctctttt cccatctcag ttcttaaggg attgccccag tgnnnnnnna ctggttttgg   16920
tggcttgccc ctccaaaaaa ттттcтттgтт ctccagtggg gatatggaag gtgggtctga  16980
acacttttca gaagggtggg cactttttct ctcctagaca gacacaatgg gacagaacaa   17040

ttttggtgac тgтcccccатт ттgggggaaaa aggattcaat aggataggaa aactcttcag  17100
tctgtggtcc cttagaaatt caccctacaa cacatttacc acacttgact tcaagaaatc    17160
```

```
caatatatat gtgtgttttc atcttgtaat agcctacatt ttacatgcca tactctgcct    17220
cagttcagct cataccccag ctttgttact ctttacaaga acttgcctct ccctagattt    17280
cacatttgct gtttatctta aaacttcaag tatctaaagt attatttta aaaaatggcc    17340 agttgtggtg gctcacacct gtaatcccaa cgctttggga ggctgaggta tgtggatcac    17400
ctgaggtcag gagtttgaga ccaccctggc caacatggta aaacctgtct ctactaaaaa    17460
tacaaaaaaa aaaaaatagc ttggcatggt ggcaggcacc tgtaatccca gctactcggg    17520
aggctgatac tggagaatag cttgaaccca cgaggcagag tttgcaagtc gtaccattgc    17580
actccagcct gggcgacaga gtgagactct gtctcaaaaa aaaaaattcc aaaattccag    17640
ctcctctgtt tatctatttt tgttgatact gttgttgtaa acataagta aaatatatta    17700 ttcatctatg tacatttcca agctgtgtag aagaatttt aataagaccc agagtaaaaa    17760
aagaatgcaa atatgtaggg gccagcccta cagggtctgt ggatctttct ccccatgtgc    17820
agagatgaga gatcatagaa ataaaggcac aagacaaaga gatagaagaa aaaacagccg    17880
ggcccagggg accactacca ccaagacaca gactagaagt ggccccaaat gcctggctct    17940
gctgttattt attggataca aggcaaaagg ggaagggtaa ggagtgtgag tcatctgcaa    18000
tgattgataa ggtcatgtgt gtcacgtgtc cgccagacag agggcacttc cctgtttggc    18060
agccgaggcg gagagagaga gaggacagct taggtcatta tttcttccat tctcttctca    18120
gaaagatcaa agactttaat actttcacta attctgctac tgctatctag agggcggagc    18180
aagtgtacag agtggaacat gagagtgaaa caggagtgtg accgctgaag cacagcatca    18240
cagagagacg tttaggcctc tggagggctg cgggcaggtt tgactgatgt caggccttcc    18300
acaagaggtg gtggagcaga gtcttctcta actcccccgg ggaaagggag actcccttc     18360 caggtcttct aagtaatggg tgccttccca ggcactggcg ctaccgctag actgaggagc    18420
cctctagtgg ccctgtccgg gcgtgacaga ggctcacact cctgtcttct ggtcacttct    18480
caccgtgtcc cttcagctcc tattgctgta tggcctggtt tttcctaggt tataattgta    18540
gagcaaggat tgttataatg ttggaataaa gagtaatgct acagactgat gattaatgat    18600
attcatatat aaacatatct ataacctatt actagtacaa ctattcttat tttacatatt    18660
ctcttcatta cactggaaca gcttgtgccc tcagtctctt gcctcagcac ctgggtggct    18720
tgccgcccag acaaatattg ttaagcttct taatagaaaa acaaattatg gtaaatgtgt    18780
tcactggaat actacccgtc atttataata aattaatgcc tgatacacag agcaacaagg    18840
taaaatatct aagtatttat gttgagtaaa ataagctaaa caaataagaa tatatactat    18900
gtaatttcat ttttataaat tctgataaat aaaaatgcat ctgaagtaaa ataatgaaga    18960
taagtagttg cctggggaaa tggtagaaga agggaggggg agaggaggag gaatacagca    19020
gaacaaaggg aaaatgttga gaagaattca cttgtccact ttcttgataa tgatagcagt    19080 tacatcatt ttattagttg tacattttaa atatgtgaag tttatcatct ttcaattaag     19140
cctcataaaa tgtcttacaa gcaaacaaat ggaaacttag acaaggaaag agtaatagaa    19200
agatagaaaa aataagttca atgtcagaag tacctgaaaa ttaatgtgcc tggatcctag    19260
ttctctccat attttcagaa gagtgctgga gggcagcaaa accacacatg ctcttattac    19320
ggaaagtggg ttctgataaa aacactagac acatccagct ttgtcctgga gttggtttag    19380
ggggatgtca gagacagtga tgaagagcac agggccagat accggggttc actcatccca    19440
gacatgagct cctagatgca tacagagccc ccccatgtgt gggtttactt ccacttctgt    19500
```

```
aaatggagaa aatattgtct cctacagaac atagtttaca tgaatactta aaatgaaata    19560
gggtgattag tgcaaagtgt ttatcacagc acaatttcat aataagacag catatttcc    19620 aaatgcaatc attgccagca aacttctaca gggcaccgtc gtcttatctg ggtacagcct    19680
actcctcaag ggtcccaccc tagagcttgc tatatagtag gagatatgca aatagggccc    19740
tccctctact gatgaaaacc aacccaaccc tgaccctgca gctctcagag aggtgcctta    19800
gccctggatt ccaaggcatt tccacttggt gatcagcact gaacacagag gactcaccat    19860
ggagttgggg ctgtgctggg ttttccttgt tgctatttta gaaggtgatt cacggaaaac    19920
tagagagatt tagtgtgtgt ggatatgagt gagagaaaca gtggatatgt gtggcagttt    19980
ctgaccttgg tgtctctttg tttgcaggtg tccagtgtga ggtgcagctg gtggagtctg    20040
ggggaggctt ggtacagcct ggggggtccc tgagactctc ctgtgcagcc tctggattca    20100
ccttcagtag ctatagcatg aactgggtcc gccaggctcc agggaagggg ctggagtggg    20160
tttcatacat tagtagtagt agtagtacca tatattacgc agactctgtg aagggccgat    20220
tctccatctc cagagacaat gccaagaact cactgtatct gcaaatgaac agcctgagag    20280
acgaggacac ggctgtgtat tactgtgcga gagacacagt gaggggaggt cagtgtgagc    20340
ccagacacaa acctccctgc aggggtccgc aggaccacca gggggcgaca ggacactgag    20400
cacggggctg tctccagggc aggtgcaggt gctgctgagg gctggcttcc tgtcatggcc    20460
tggggcggcc tcattgtcaa gtttccccag ggaacttctc cagatttaca atcctgtact    20520
aatatttgat gtctctaaat gcaaccttt ttttccttt tgtgtctgtt ttttttttt    20580 taaaaacagg aggacacatc ctcacctcca cagaagccac agtgtcactt tggggcgga    20640 aataatcctt tcgtggtcaa cagggtgaga gttttgagga atcccaggga aacctgggga    20700
atgttttcca attagactca gggcagagac ctccatggga atccctgatt agaacaggct    20760
ttgagttctg atgggagcca aaagagaggc tcacccaggg tcagggttct taaaacctga    20820
tggttttcac agcaatcccc cttcatcttg tgaaactggg cacatctgac tcagactgat    20880
tcagttgacc ctctttctgc taatccattt tccttcccag tagacttgat tctcacagat    20940
ccctttcttc ttctctttcc tgaaaacaga ggatgtgttt tctgtagtcc tcgagccttg    21000
attgaagtgc tgagtaaatg gttgcaaaca taggtctaca tttttcaaat cattcaccat    21060
aaatttgaat tatttattaa ttacactcga ataaagcaat aaagaaactg atgagataat    21120
atttgactga attgcatcaa taaatagatc gatattaaca caaggaatat aactgatttc    21180
caaaaacata cacatgaacc gtggttcact ctgcgtattt agataaatta cagaaagttg    21240
tcataacaga tggggaatcc tgcagacttc actaggcatg ggccatgctg ccctggagtt    21300
gtctcagggg agctgcctcc tccagaggtt agagcacagg cccaggtaat aggactaaat    21360
ttttagatgt gttatcttag acacactgca caactgctgt gttctctatg taaattatct    21420
cctgtaaaat ataacattga agcctgcatt aaatatattg tgtaaatatg taagaataaa    21480
agaaagttat gagagctaag tgttaatcaa ggcacaagca tataagatat aactatattt    21540
tcctgaatga tggaattact accagtctcc cccaggacac ttcatctgcc ctgagcccag    21600
cctctcctca gatgtcccac ccagagcttg ctatatagtg ggggacatgc aaatagggcc    21660
ctccctctac tgatgaaaac cagcccagcc ctgaccctgc agctctggga gaggagccca    21720
gcactagaag tcggcggtgt ttccattcgg tgatcagcac tgaacacaga ggactcacca    21780
tggagtttgg gctgagctgg gttttcctcg ttgctctttt aagaggtgat tcatggagaa    21840
atagagagac tgagtgtgag tgaacatgag tgagaaaaac tggatttgtg tggcattttc    21900
```

```
tgataacggt gtccttctgt ttgcaggtgt ccagtgtcag gtgcagctgg tggagtctgg   21960
gggaggcgtg gtccagcctg ggaggtccct gagactctcc tgtgcagcgt ctggattcac   22020
cttcagtagc tatggcatgc actgggtccg ccaggctcca ggcaaggggc tggagtgggt   22080
ggcagttata tggtatgatg gaagtaataa atactatgca gactccgtga agggccgatt   22140
caccatctcc agagacaatt ccaagaacac gctgtatctg caaatgaaca gcctgagagc   22200
cgaggacacg gctgtgtatt actgtgcgag agacacagtg aggggaggtc attgtgcgcc   22260
cagacacaaa cctccctgca ggaacgctgg ggggaaatca gctgcagggg gcgctcagga   22320
gccactgatc agagtcagcc ctggaggcag gtgcagatgg aggctgtttc ctgtcaggat   22380
gtgggacttt gtcttcttct gacagttccc cagggaacct cttaaattta gaaaactgtg   22440
cctaacaatg tcttctctat gcatatgagg accttttctc cctggcacaa aatgcagatt   22500
gacgctgaca cggatggtcg acgctgctga cattcctaga taactgcagc tgtagttatg   22560
cctgctaagt tttgggcgca tggggcttgg cttttgtcag ctccctggga tttattttcc   22620
caaacaaaga aacctccagg ttaggggcac cctattcatt cccatcacct ggcatgattt   22680
aaaggataat tgcttagaat taaaatattg atccagattt tttatattcc ccatcgcttt   22740
ttgtttcttc tgggctgtag ccagagatca ttgattggcg ctcaggaata agcagagtta   22800
gtctaaaatg caggcaaata cttaaacaac tgaagagatt agaatttaaa gacaagtgta   22860
tgatatgttt tgaaatacaa tgtttctctt tccagttttg gttttgtca gcagcaaata   22920 atgataagac tgagttgttt gcaaaataaa ctttagtctt aaacttggcc tgattatttg   22980
cataaagtgc agcaagaata ttaataataa ttctgtagga aaagcctgca agcaccagga   23040
gcttcacagt ctaacactat gagcacgtgc atcctcacgc aactcactga atatgtccaa   23100
gtcagcctgt tccgatctta aatgccatcc agtggcatct gccccaggta cactaataca   23160
tgggtcctgc ttctctctgc agccgcctct ctcctcagat ttcaggtttt gtgtattgtt   23220
tgttttctct ctgacatcaa cacagatatg ttgaaggttt tctttttttt atttgtagtt   23280
gttcagcttt gttgttaatg aggtcagaat aagctcatag tttacacatt tttacattcc   23340
catgccgagt agctgctttt ctctatcaaa tccattaact gagagaacaa tcacatttcg   23400
ttacaggtga acagttaaat agtttggcat atatttctgt gctggaatct aatgcagctt   23460
gaaatcaagt catgcctcac tcattgaaaa aaacatggca aaattctcaa agaattgtgc   23520
tgagtgaaag aaactaagga atgaagagta aattttatat gatacatttg tagaaatttt   23580
agaagatgcc actattataa attaacatgg agaagattta agtgtttctg agaatatgct   23640
attgggagta atggggatgt gagttaaatt tcagaggaat aagagaaaga tttagggatt   23700
aattttttca aaccttgatt gaagtgctga gtaaatggtt gcaaacatag gtctacattt   23760
ttcaaatcat tcaccataaa tttgaattat ttattaatta cactcgaata aagcaataaa   23820
gaaactgatg agataatatt tgactgaatt gcatcaataa atagatcgat attaacacaa   23880
ggaatataac tgatttccaa aaacatacac atgaaccgtg gttcactctg cgtatttaga   23940
taaattacag aaagttgtca taacagatgg ggaatcctgc agacttcact aggcatgggc   24000
catgctgccc tggagttgtc tcaggggagc tgcctcctcc agaggttaga gcacaggccc   24060
aggtaatagg actaaatttt tagatgtgtt atcttagaca cactgcacaa ctgctgtgtt   24120
ctctatgtaa attatctcct gtaaaatata acattgaagc ctgcattaaa tatattgtgt   24180
aaatatgtaa gaataaaaga aagttatgag agctaagtgt taatcaaggc acaagcatat   24240
```

```
aagatataac tatattttcc tgaatgatgg aattactacc agtctccccc aggacacttc   24300
atctgccctg agcccagcct ctcctcagat gtcccaccca gagcttgcta tatagtgggg   24360
gacatgcaaa tagggccctc cctctactga tgaaaaccag cccagccctg accctgcagc   24420
tctgggagag gagcccagca ctagaagtcg gcggtgtttc cattcggtga tcagcactga   24480
acacagagga ctcaccatgg agtttgggct gagctgggtt ttcctcgttg ctcttttaag   24540
aggtgattca tggagaaata gagagactga gtgtgagtga acatgagtga gaaaaactgg   24600
atttgtgtgg cattttctga taacggtgtc cttctgtttg caggtgtcca gtgtcaggtg   24660
cagctggtgg agtctggggg aggcgtggtc cagcctggga ggtccctgag actctcctgt   24720
gcagcgtctg gattcacctt cagtagctat ggcatgcact gggtccgcca ggctccaggc   24780
aaggggctgg agtgggtggc agttatatgg tatgatggaa gtaataaata ctatgcagac   24840
tccgtgaagg gccgattcac catctccaga gacaattcca agaacacgct gtatctgcaa   24900
atgaacagcc tgagagccga ggacacggct gtgtattact gtgcgagaga cacagtgagg   24960
ggaggtcatt gtgcgcccag acacaaacct ccctgcagga acgctggggg gaaatcagct   25020 gcaggggggcg ctcaggagcc actgatcaga gtcagccctg gaggcaggtg cagatggagg   25080
ctgtttcctg tcaggatgtg ggactttgtc ttcttctgac agttccccag ggaacctctt   25140
aaatttagaa aactgtgcct aacaatgtct tctctatgca tatgaggacc ttttctccct   25200
ggcacaaaat gcagattgac gctgacacgg atgaaaattc ctcaaccatg gtcacaagga   25260
tcagagtcct gagtaacctc agggcttcct ggtgattctt ctccaatcag acccaggaca   25320
gggacctccg tgagattccc tgactggaac agtcttatg gatcctggtc acagacaata   25380
gagaggctga accagggtca gcgtcatgta gaacgtcaca gatttcacgt ctgatccttc   25440
tcctgacacg aaagtatgca aatcagtatc agcaccgatc tgctcgacga tggaaagata   25500
gataccaaca tgagaaatgt atgacactca agaaaataaa actgtaggaa acttgctttt   25560
ctttatattt gttaggtaat caccacagtg tgtacacatc acaccatgtt cccattacag   25620
agaaaaggtt ctgcgaacct cacgagctgt gaccctgtg tgctgggctt ggttcaggga   25680
gaagtcaggt ccagtggtga gaagcacagg cccagatgcc caggctcact ctgaccaaaa   25740
gtgagcactg gggacattgt aaaacccacc tgtgcttttg ctgataattt ttcatcttta   25800
acatggaaat aatattgata ctatatacca tggtttctct gcgtatgtaa aaataaaaga   25860
tgattggtgc taacttttaaa aatatgcagt ttatgtagat ctatggtacc tcaataaaac   25920
tgttttaaaa taaaaattac aaaattataa gattttttagg ttttaaggtt taagtttatc   25980
acaaaacaaa ctgacaatag gaaagcacaa tttcccaatg ctttcaatat cacagatctc   26040
cccgaggaca ttctgacatg ctctgagccc cactatctcc aaaggcctct cacccccagag  26100 cttactatat agtaggagat atgcaaatag agccctccgt ctgctgatga aaaccagccc   26160
agccctgacc ctgcagctct gagagaggag cccagccctg ggattttcag gtgttttcat   26220
ttggtgatca ggactgaaca gagagaactc accatggagt ttgggctgag ctggcttttt   26280
cttgtggcta ttttaaaagg taattcatgg agaaatagaa aaattgagtg tgaatggata   26340
agagtgagag aaacagtgga tacgtgtggc agtttctgac cagggtttct ttttgtttgc   26400
aggtgtccag tgtgaggtgc agctgttgga gtctggggga ggcttggtac agcctggggg   26460
gtccctgaga ctctcctgtg cagcctctgg attcaccttt agcagctatg ccatgagctg   26520
ggtccgccag gctccaggga aggggctgga gtgggtctca gctattagtg gtagtggtgg   26580
tagcacatac tacgcagact ccgtgaaggg ccggttcacc atctccagag acaattccaa   26640
```

```
gaacacgctg tatctgcaaa tgaacagcct gagagccgag gacacggccg tatattactg   26700
tgcgaaagac acagtgaggg gaagtcattg tgagcccaga cacaaacctc cctgcaggaa   26760
cgatgggggg gaaatcagcg gcaggggcg ctcaggaccc gctgatcaga gtcatccgca    26820
gaggcaggtg cagatggagg ctgtttcctg tcagggtgtg ggacttcatc ttcttctgac   26880
agtttctcta gtgaacctct ctaacctcag aattctgtgc ttactaatgt catctctacg   26940
tattttttaa aagatcattt taatatgagc acctattctc acacgcacca aatgcagatt   27000
gacgcttaca gagatgctcg accactggga ttcctaaggc caattcagta tttcaaaaga   27060
tggtgtgaga agcacaggct gtcactaaag gagaattctg agccagggca cagccacttt   27120
atacttggct ggggacactg gtaggaatat actctgtgag atcagacagg aacctccttg   27180
caggggcagg gcaggctgc aggggcgct caggacacac agagcacagg cttccgcccc     27240
agagcaggtg aaggaggctg gggaggggtt cctctcaggg cctgggactt cctttaaaaa   27300
atctaaaata agtatttcac aaggactgcc gatgtttata taaatatcct attcaattgt   27360
gagcatttat gaaactcgat gttgtaatga aaccacttt tacaatggga atttcaaact    27420
tccctagaca tcttaatagt aagcagctgg aggtcaggag gagatccttt cttataaata   27480
agtgcaattt ttggagaaac acactcattc ccaaaatagc acattcacat attaaggtct   27540
agaaatgatt cgagttgccc ctgagacagt caaatgtggg ttctaagtga ggtgcgtgtc   27600
ctgggggagc ttgttctcca gtgggggaag ctctgtcaac acagagttca gggatggata   27660
ggggatgcgt ggcctctaac aggattacgg ctttaacccct cagcttctac aattgtgtcg  27720
tccatgtgtc atgtatttgc tctttctcat cctgggtcag gaattgggct attaaatagc   27780
atccttcatg aatatgcaaa taactgaggt gaatatagat atctgtgtgc cctgagagca   27840
tcacccaaaa accacacccc tccttgggag aatcccctag atcacagctc ctcaccatgg   27900
actggacctg gagcatcctt ttcttggtgg cagcagcaac aggtaacgga ctccccagtc   27960
ccagggctga gagagaaacc aggccagtca tgtgagactt cacccactcc tgtgtcctct   28020
ccacaggtgc ccactcccag gtgcagctgg tgcagtctgg agctgaggtg aagaagccta   28080
gagcctcagt gaaggtctcc tgcaaggctt ctggttacac ctttaccagc tactatatca   28140
gctgggtgtg acaggcccct gaacaagggc ttgagtggat gggatggatc aacacttaca   28200
atggtaacac aaaactaccca cagaagctcc agggcagagt caccatgacc agagacacat   28260
ccacgagcac agcctacatg gagctgagca gcctgagatc tgacgacatg gccgtgtatt   28320
actgtgcgag agacacagtg tgaaaaccca catcctgagg gtgtcagaaa ccccagggag   28380
gaggcagctg cagtgaattt gaggagatta cagggcttac aatgtttaaa gttgtttaga   28440
aaatgagctg agcaactgag gaatgtaagt aatagaaaca tggatgcact ctatatagga   28500
aatgtttctt tcagctgtca ccctatatgc aaaattcaga gtggtaaaga cagcaatcag   28560
tgaggctgat gcaaagaatc ccatggaggc cttgtgcaga catataggtt ttaaaatcag   28620
atagataaat aatttggaac aagattgctg gtaacgtggc taagactact cgaccacctt   28680
ggtaactagg atggttacat caggtttatc aattgtacac tttaaatatg tgaagtttat   28740
tatcagtaaa ctgaaatttta taaatttat taccagcaaa caaatgaaaa cttgcacaag   28800
aaataagtga cataaagata gaaaaaatat taaatttcag aaacacctaa taatttatct   28860
tcgtgaaccc tagttctcac catatttta ggtgaatgct agaatgcagc aaaattacac   28920
atgctctcaa tacagaaagt gggtttcaca aaccacacta ggcatgctca gctctgtcct   28980
```

| | |
|---|---|
| ggagttgggt tagggagtaa tatagggcca gtggatgagg agcacaggcc tagatactgg | 29040 |
| ggctcactaa cctcaggtat gagctcttag atacatacaa agcccctcca cgcatgggtt | 29100 |
| tacttcccca tctgtaaatt gagaaaccat tgaccoctaa aaatatgatt tacacaaata | 29160 |
| tgtaaaaatg taagagagtg attagtgcaa agtgtttatc acagcacaat ttcataacaa | 29220 |
| gacagcaagt tttccaaaca gcatcattgt cattagattc ctgcagggca tcattccctt | 29280 |
| atctgggccc tgccctctgt tcaggcatcc caccccagag cttgctatat agtaggtgac | 29340 |
| atgcaaatag ggccctccct ctcctgatga aaaccagccc agtcctgacc ctgcagctct | 29400 |
| gggagaggag ccccagcctt gggattccca agtgttttca ttcagtgatc aggactgaac | 29460 |
| acagaggact caccatggag tttgggctga gctggatttt ccttgctgct attttaaaag | 29520 |
| gtgatttatg gagaactaga gagattaagt gtgagtggac gtgagtgaga gaaacagtgg | 29580 |
| atatgtgtgg cagtttctga tcttagtgtc tctgtgtttg caggtgtcca gtgtgaggtg | 29640 |
| cagctggtgg agtctggggg aggcttggta aagcctgggg ggtcccttag actctcctgt | 29700 |
| gcagcctctg gattcacttt cagtaacgcc tggatgagct gggtccgcca ggctccaggg | 29760 |
| aaggggctgg agtgggttgg ccgtattaaa agcaaaactg atggtgggac aacagactac | 29820 |
| gctgcacccg tgaaaggcag attcaccatc tcaagagatg attcaaaaaa cacgctgtat | 29880 |
| ctgcaaatga acagcctgaa aaccgaggac acagccgtgt attactgtac cacagacaca | 29940 |
| gtgaggggag gtcagtgtga gcccggacac aaacctccct gcaggggcgc gcggggccac | 30000 |
| caggggcgc tcgtgaccca ctgagggcgg gacaggtccc aggagcaggt gccgggagag | 30060 |
| gtttcctttc tcctcagctg gaaaagtcag gtttatcttc gcaggactct ggagtcttct | 30120 |
| aggctgtgct cgacagtgca atgatatagt ttagatgttt tcccttccaa atgtcatggt | 30180 |
| gaaatgtgat tctcaatgtt ggaggtggga ccgactggga ggttttgggt catggggaaa | 30240 |
| gatccttcag gaatggcttg ggaaccaccc catggcactt agtgaattct tgctgtgtta | 30300 |
| gctactatga gatctgattg ttaaaaagag tctggcaacc cttcttgcca ctcatgtccc | 30360 |
| agctctcacc atgtgacata gcctgttccc cctttgcctt ccatcatgat tgtaaagcag | 30420 |
| atcctggtgc catgcttctc acacagcctt cagaactgta agccaaatgt gcctcctttc | 30480 |
| tttgtaaatc acttggcctc aggtattaat ttataggaat gcaaagagaa ctaacacacc | 30540 |
| gtccaaagca ttacacagat tcaacactat ttttatcaaa tgaccaatat aattgattac | 30600 |
| atatttagaa aaaaaatact aaaattccta cagaatcaaa aaagagtctg aatagcaaaa | 30660 |
| gcaatcctaa gcaaaaagac cgaagctgga agcaccacat tctctgacct caaattatac | 30720 |
| tacatgaata taataagaaa gacagcatgc tactagtaga aaaaaacagc ccagaaagaa | 30780 |
| agccaaatat ctaaaaccaa ctgttgtttg acaaaactga caaaaatata cactggaaa | 30840 |
| acaaccctct attcaataag tggtgcaggg aaaattaggt ggcttatgtg gaagaataga | 30900 |
| acgagacttc catatcaccg tagacacaaa ttaactgaat atggattcag tgtttaaatt | 30960 |
| tataaactaa aactataaaa atacttgaat aaaatctaaa aagagtcctc tggacattgg | 31020 |
| tctaagcaaa caatatacga ctaagacttc aaaagcaaat gcaataaaaa cagaagtaga | 31080 |
| caaacaggat ttagttgaac taaaggtctt ctgcacagca aaagaaataa ccaacatggt | 31140 |
| gaccagacaa tctgcaaatg gaaaaaatat ctggaatcta ttcatcttgc aaagggctaa | 31200 |
| tatatagaat ctacaagtaa ctcaaataag tcaactaaaa attacaaaata acttcattaa | 31260 |
| agaatagaca taaacagaca tttatcaaaa gaatacacag aagtggccaa cacaaataag | 31320 |
| aaaatatact cagcatcacc aatcatctga taaatgtaaa ttagaaacaa cgtgatacgg | 31380 |

```
catcttccac cagtcagaat ggctgttatt acaaataaaa acagcaggtt tttgcagaca   31440
aacataggaa aaataatgat ttatatatgc ttggtgagaa tgtaaattag tacaacctcc   31500
atgaaaaaca acatagaaat ttctcaaaga actaaaatta gaattaccat ttcttccagt   31560
gagctgtccc agtaggcatg ttcctcccaa acttttatat cagagaatgt tgcctgcact   31620
catatgttta tttcaacacc attttcaata gaaaagtcaa ataatctaag tgtcaatcag   31680
tggatgatta gataaaatat gatatatgta aatcatggaa tactatgcag ccagtatggt   31740
atgaattcag tgtgaccagc ccctggacaa gggcttgagt ggatgggatg gatcatcacc   31800
tacactggga acccaacata taccaacggc ttcacaggac ggtttctatt ctccatggac   31860
acctctgtca gcatggcgta tctgcagatc agcagcctaa aggctgagga cacggccgtg   31920
tatgactgta tgagagacac agtgtggaga cccacatccc gagggagtca gaaacccga   31980 gggaggaggc agctgtgctg agctgaggca gtggtgcagc agtttctta acttccatat   32040 gatctcattt tgcatcatct tctactttta tattagctaa gaacttgggg tagacaggtg   32100
ctcctaagag atccttaact tgcccatttt gatggttttc cagaagacgt gagaagccac   32160
tttgttagca aagcatccca aatccatgcc ctgttctaga tacatgtgag cccatttcct   32220
ggtctttgct taactgacaa gctctcatca gtgcacctgg gctaatttca catcaggtag   32280
aggaacgcgt tataaggaa agctaatgtt gtaatggcaa ttcctgctta aaaaccttca   32340
gcttcattgt ttttgtgtaa tccatcagca aattatgtta gttcaaggtt ctcaatggga   32400
gtttctaata aatagaaagg ttgtatagag cttcccctaa ttaaaatgaa acaattgtga   32460
actcaacctc ggtattcagc catgtctcca cccttcacac ccttcgccac aaaggaattt   32520
tcacctctcc tggaagctgg gttcattttc aaattagtta tttttttcaa tgtaatatct   32580
caagattatc gtatatgact attttagcag aaagtgaatt atgggaactt gaactaaaca   32640
actgaaaaca aattcacaac taattaaaca agatgccaga atgtgattgg ctccaggctt   32700
tgtaattcag cagttcatgt acccagactg gaaatttaca tgtcttcttg ttaccttcac   32760
agcacagtca actcccatta tgtaagaaat ggtgactgca ttcccaaggg ttatgcatag   32820 atatgaaat agactgggta aggtgaggag ttgattgttt aaattcccct ctgaagaagc   32880
agcatcaact caacaaacca cctctcttca ctctgtgact agagctatgt cacaggccac   32940
atggacctaa atccttgatg gatataacat gactacataa attgggctga tcattttat   33000 gctataaaat taatagatga cactgcactc cagcctgcac aaccaagcaa gtcttcatct   33060
gtaaaatcta aaaagaaaa attagtaggt actgacttcg aaattttga taataatatt   33120 ttcaccaccc aaatttaatc acacccacat gttacctgca tcttcactga aaagttccca   33180
gtcacgatga gttccttcaa tgctccatgt gttcaaatct ggacatcaag agagtccaga   33240
gaataaaaca caatgacggc agtgaaactg atatatattc agcacctctt aactcaggag   33300
gactccatac accctggcac acagctgctt ttctaaatgg ctcacaatga ctccagctca   33360
ctcacagagc tcagacagaa acctcccttc agggtgggag ctgggtggca gggggcactc   33420
agtacccgca gaggtgaaaa tgagtttcag atggaacttc cctgtcacct caacatggaa   33480
tttattgttc catttcatta cctctctttc cataatggtt catttctttt ggcctgttca   33540
ttactgatat ttttcagagc aatctcactt gaatctttac tcttttgcat tttgtctcct   33600
tgacaatgtt gggaagtttt acctccagca tcataacatg atctagtgat ctgacacatt   33660
gtgcaaacaa tacctacaaa ttcagaacct ctttgttttt ctttccacaa aatataattc   33720
```

```
tttctgttct gtgtatgagc atgtcttagc aaccctgtac acacccacat agatgtctac    33780
aagcctatga attgttctct gtaaataaaa atttatctca aattccttca atgttcataa    33840
ttctgagagt gaggaaggtc cttctcaatc tgttcaaaca aaatgcccag agaccatcca    33900
gtaggtaagg agttcacctg gctctggtgt ggggtctgtc tctttccctc tgttgtccca    33960
caggtcagcc cagttgttca cgtcctaaca agaaagccca ggtttgtcct gattttaaaa    34020
cacatcaaac ttctgatgac tctcctgtta cccacatcca tggagataga ttatttatta    34080
tataattcag caaactaatg tcaaatgccc aagttgcaat accgcacatc ctagggtatg    34140
ttcatgcaat tcaatggagg agaaaatctt tcagagacag atggatctga atgataaat    34200 atgtgggtaa ggactctggg cttgagtatc attgtccagc catgtttcac aagtgtgtcc    34260
tgtcagggaa ggatcagagt tccttgtgct ctcagaggga aggggtcaca gagttcctct    34320
ctggttccca ggaaaggtaa tcgcactaat cttcatgatc ttcatgagac tatcctccag    34380
tgctgacctg ttacggagtt tttgtctgaa gttctcactg caatcccaa tctacatatt     34440 ttcaatcaga agtgtttaga gggcaggaca catcttcaag gtcacacatt gagaaggatg    34500
gagatatgtc ccactacctt ctcctacgat ctcagacaga atcccaaatt tcaaaaggac    34560
acagaaggac agctctcagg tgcttttaaa aaatgaccca cttccaggga cagtgagctt    34620
ccctgtaacc atggtggatg ttctgaacta caataaacat tggatggatc cagtattgtt    34680
tgaagtcact gtcattatta cattcagctg ttgtttcaat gtgtctgaaa gggtaaatga    34740
ctatttagat ggcctgggtg tgtggttggt tttatatgaa tctttaaggg ttgaacagta    34800
ttgaccctat tccacaatct gtccttgatc catgatcaca ctcatctctc agacaagctc    34860
cttcagcaca tctctttacc tggaagaaga gcactctggg cttggcgagg ggagccccaa    34920
gaagagaact gagttctcaa agggcacagc cagcattcta ctcccagggt gagcccaaaa    34980
gaccggcgcc tctctcatcc cttttcactg ctccgtacaa aggcaccacc cacatgcaaa    35040
tcctcactta ggcgcccaca ggaagccaca acacatttcc ttaaattcag gtccaactca    35100
taagggaaat gctttctgag agtcatggac ctcctgtgca agaacatgaa gcacctgtgg    35160 ttttcctcc tgctggtggc agctcccaga tgtgagtgtt tcacgnnnnn ngatatgaag    35220
atatgagaaa ctgcctctga tcccagggct caccgagggt ttttctgttc acaggggtcc    35280
tgccccaggt gcagctgcag gagtcgggcc caggactggt gaagccttcg gagaccctgt    35340
ccctcacctg cactgtctct ggtggctcca tcagcagtag taattactac tggggctgga    35400
tccgccagcc cccagggaag gggctggagt ggattgggag tatctatcat agtgggagca    35460
cctactacaa cccgtccctc aagagtcgag tcaccatatc cgtagacaag tccaagaacc    35520
agttctccct gaagctgagc tctgtgaccg ccgcagacac ggccgtgtat tactgtgcga    35580
gacacacagt gaggggaggt gagtgtgagc ccagacaaaa acctcctgc agggaggctg     35640 aggggaccgg cgcaggtgca gctcacggcc agcaggggc gcgcgagct cacgaaatac     35700 aaggccgggt caggagcagg tgcagggtga gcggggcttg ctcatcttct caaacatctc    35760
cctcctcgcc agcacctcag ctttccgtag aggtcctctt tctttattgt ctgtggttct    35820
acttcctcac atccttgtgc caggaaagaa aggagtaagg caattttcc tgttacaatt     35880 gaagtttcac caattactaa aaactttcct gcaagtacct gcacagccca ttatacctta    35940
tttatatata tatatattct aatgcttctc accatctctt gatttgtgtc atcaatttaa    36000 ttgtgcccctt tttgaaattc atatgctgaa actttaaatc caatggatct atatcggaat    36060
tttaatggta taattaacgt taaatgtggt cataagtgag accctaatgc aatagacctg    36120
```

```
ttgtctttat aagaagagga agagacacca gagacctctc acttctcaca tgcacacaga   36180
gaagaggcca cgtggagaca tagtgcacta gaaggtgggc ctctgcaagc caggaagaag   36240
ccgcaccaag aaccaaccct gccagcacct tgatcttcta cattcagact gcagaattgt   36300
aagaaaacca atatttgttg tttaagccac ccactccttt tgtcttctta cgaagaccca   36360
gacaggctaa taccacacaa ctctgttagc tccatctcct ggagggagaa gcagcccct    36420 gaggctgggc acatcgctca gattttcaca tgaattaggc aaaaacagta gctctcatat   36480
aaaaactgtc acgtccctgt tgggacaagg tcttctaaac aaccctggg gctttgtcac    36540 aaatgttgca tttatcctt tattaggact taactaattg acaatgagta ccagctggat     36600
ggaaactgac cactgaccat cttctgctgt ctccttatta tatcacagaa aaccacagca   36660
acattactct atgtcttcaa ctttctaaat ttgtactgaa tctattgcta aatgaggagc   36720
tacatggggt ctgagttttg ttatcttctc cccagtcttc cccaattacc aagcacagaa   36780
gatactttca gtgaaattta gctgtcaatg cccccaacac cacatcatgt tttaaggtcc   36840
aaggactttc tttgggggc tatttaaaaa cacttttgaa tggaaaatcc taaagcatac    36900
aacagctgaa agaatggccc ctgtgcacgt gaaggctgaa gggatggatg ataggggtacg   36960 ttcctccaag gtgttcctgg gcatgtgatg gttggatacc tcatgctcga cctatggatg   37020
tgaactacaa gtatgtaagt acttcaagta attctattta atggagtttg aaataaaact   37080
caaacttatt caaaacacta attacttggt atttattttg agatctatga gtttatcaag   37140
aaattcaaat tcctatttct atttaaactc ccgattccta ctctcagtgg gagggaaaac   37200
tcacagccaa tcacacatca caggacaaat ctgtaaacga agagtcattc ctctgaaggt   37260
cctgggtgtt caggactctc aggcaggtgc tgaggaccct gtcttgggag tgcccagcag   37320
atctcagaac cctacatggg gcctgctgga cactcatgtg ggataactag tcgccactta   37380
ttcagagtta ccagtgagct ttgactgttc gaatgggac cagcatggag tcaaggtgcc    37440
tgctcaatgt cagagacagc gatggtctca gaaacaatcc aggtaatctc taggccaata   37500
aaatgtggat tcacagtgag aagtacatcc tggaggtgga gcttgttctt cagtgggaag   37560
agtgctgtgc acagaaagct tagaaatggg gaaggggggtg cgtttcctca ggcaggatta   37620
gggcttcgtc cctcagcgtc ccactcttgt atggctgatg tggcatctgt gttttctttt   37680
tcatactaga taaggctttg agctgtgaaa taccctgcct catgaatatg caaataacct   37740
gagctcttct gaggtaaata taggtatatt ggtgccctga gagcatcact caacaaccac   37800
atctgtcctc tagagaaaac cctgtgagca cagctcctca ccatggactg gacctggagg   37860
atcctcttct tggtggcagc agctacaagt aaggggcttc ctagtctcaa agctgaggaa   37920 cggatcctg ttcagtcaaa gaggatttta ttctctcctg tgttctctcc acaggtgccc     37980
actcccaggt gcagctggtg cagtctgggg ctgaggtgaa gaagcctggg gcctcagtga   38040
aggtctcctg caaggcttct ggatacacct tcaccagtta tgatatcaac tgggtgcgac    38100
aggccactgg acaagggctt gagtggatgg gatggatgaa ccctaacagt ggtaacacag   38160
gctatgcaca gaagttccag gcagagtca ccatgaccag gaacacctcc ataagcacag     38220
cctacatgga gctgagcagc ctgagatctg aggacacggc cgtgtattac tgtgcgagag   38280
gcacagtgtg aaaaaccaca tcctcagaga gtcagaaacc ctaggggaga aggcagctgt   38340
gctgggctga ggagatgaca gggggttatca ggtttaaggc tttttttgaaa atgggttata  38400 tatttgagaa aaaaataaca atagaaacaa gtacacactc taattttaag agatatattc   38460
```

```
aattcaagaa ttgtagaagc cgaattcaca gtgggaaagg ccacactcaa taaagttgat    38520
aaaaacattc caggaaggtg ctactgctcg accctgtgtt tatctgttat gttgatgctg    38580
taaaacagta agtaaaatat actcctcatc tatgtacatt ttgaagctga gttgcaggtt    38640
ttttggtaag acccagagtc acagagaatt caaatattgt taagctgctt aatagaaaaa    38700
caaattatgg taaatgtgtt cactggaata ctacccatga tttataataa ataaatgcct    38760
gacacacaga acagcagcaa aaccacacat gctcttatta cagaaagtgg cttctgaaaa    38820
ccacaccggg cacgtacagc tttgtcctgg agttggttta gggggatgtc agagccagtg    38880
acgagaagca cagggccaga tggcagcgtt cactcatccc agacatgagc tcctggatgc    38940
atacagagcc cccccatgtg tgggtttact tccacttctg taaaaggaga aaatactgac    39000
tcctacagag cataatttac acattttta aaaaatgtaa tagggtgatc agggcaaagt    39060
gtttatcaca gcacaatttc ataagacagc atattttcca aataccatca ttgtcagcaa    39120
acttctgcag agcaccgtct tcttatatgg gtacagccta ttcctccagc atcccactag    39180
agcttcttat atagtaggag acatgcaaat agggccctcc ctctactgat gaaaaccaac    39240
ccaaccctga ccctgcaggt ctcagagagg agccttagcc ctggactcca aggcctttcc    39300
acttggtgat cagcactgag cacagaggac tcactatgga attggggctg agctgggttt    39360
tccttgttgc tattttagaa ggtgattcat ggaaaactag gaagattgag tgtgtgtgga    39420
tatgagtgtg agaaacagtg gatttgtgtg gcagttctg accttggtgt ctctttgttt     39480
gcaggtgtcc agtgtgaggt gcagctggtg gagtctgggg gaggcttggt ccagcctggg    39540
gggtccctga gactctcctg tgcagcctct ggattcacct ttagtagcta ttggatgagc    39600
tgggtccgcc aggctccagg aaggggctg gagtgggtgg ccaacataaa gcaagatgga    39660
agtgagaaat actatgtgga ctctgtgaag ggccgattca ccatctccag agacaacgcc    39720
aagaactcac tgtatctgca aatgaacagc ctgagagccg aggacacggc tgtgtattac    39780
tgtgcgagag acacagtgag gggaagtcag tgtgagccca gacacaaacc tccctgcagg    39840
ggtcccttgg gaccaccagg gggcgacagg gcattgagca ctgggctgtc tccagggcag    39900
gtgcaggtgc tgctgagggc tggcttcctg tcgcggtctg gggctgcctc gtcgtcaaat    39960
ttccccagga acttctccag atttacaatt ctgtactgac atttcatgtc tctaaatgca    40020
atactttttt tgtcctttt gtttctttgt tttttgcaa caggagtaca tatcctcagc      40080
tccacagaag ccagggctcg accatggtca gtgtcatata gaatatgggg accctcacaa    40140
gttttttgtc tgaccttct cctgacacta aattatgcaa attaataaca ctgatctggt     40200
gcttcttttg attctaattt attttatttt tagttgtcgt tctcactttt cctttggatt    40260
ttcctgctcc ctggaaaagg taaatgtggt ctccgtgacc tcaattcaag ggctgaagcc    40320 cttccctgt agctcagctg gggctcaggc tgtggctact gcagccatgt ggaagaggct     40380
gaagggactt tcttcactct ccttgctcag gaccatccac tgtattgtgt ataggcttct    40440
ctggaaatgc aagtggccat ttgtagtgaa agaaatatgt ttgtctggtt aaaatgggag    40500
gtggatgtag agttaattgg ctgctacata aactgtcctt ctccaccagt gcttttagga    40560
tgagattgtg aaatttgtaa gaatcaaaat ggagtcacat atgttaaaac cctgacaaat    40620
ggattcagga agtgtaggga gaattcttac acacatatcc ctgacaacaa gaactatcat    40680
aaaatagttc ttgcaaaaag accaacatga cctcataatc atgacttctg caaagacttc    40740
tactcagaat ctacttgccc agccttagat taatgccatc tgaattacac tgatcatgtt    40800
actatcactg ctcctcacca cagatgcaac accctcctga gtcctgaaac ctgactccat    40860
```

| | |
|---|---|
| cccatagagt agggcacaga tgaggggaat gcaaatctcc accagctcca ccctcctctg | 40920 |
| ggttgaaaaa gccgagcaca ggtcccagct cagtgactcc tgtgcccac catggacaca | 40980 |
| ctttgctcca cgctcctgct gctgaccatc ccttcatgtg agtgctgtgg tcagggactc | 41040 |
| cttcacgggt gaaacatcag tttctttgtt tgtgggcttc atcttcttat gctttctcca | 41100 |
| caggggtctt gtcccagatc accttgaagg agtctggtcc tacgctggtg aaacccacac | 41160 |
| agaccctcac gctgacctgc accttctctg ggttctcact cagcactagt ggagtgggtg | 41220 |
| tgggctggat ccgtcagccc ccaggaaagg ccctggagtg gctttcactc atttattgga | 41280 |
| atgatgataa gcgctacagc ccatctctga agagcaggct caccatcacc aaggacacct | 41340 |
| ccaaaaacca ggtggtcctt acaatgacca acatggaccc tgtggacaca gccacatatt | 41400 |
| actgtgcaca cagaccacaa agacacagcc caggcaccct cctgtacaaa acccaggct | 41460 |
| gcttctcatt ggtgctccct ccccacccttt gcagaacagg aaagtgcagc tgagatacgt | 41520 |
| tttcctgcca gggcctgcat ttcccatccc cattagactc agagcccgtg cttcctcctt | 41580 |
| cttctttaat aataaatggc atgactcctg ttaatagttc atagaagcag aagctgagtc | 41640 |
| ctgtttgtca acattcagc atgaaatgtt catgttacct gggccagatg catcactggt | 41700 |
| atgtggccgc cagctcgacg gtcacacatt gagaatgatg aagatatgtc ccacgagttt | 41760 |
| ttcctaaggt ctcagaaaga attccaggac tcaaaggtc tcagagggca gctcccagtg | 41820 |
| ccttaattaa aatggtggct caggcctgta atcccagcat tttgggaggc taaggcaagt | 41880 |
| ggatcacctg aggtcgggac attgagacta gcttggccaa catggtgaaa ccttatctct | 41940 |
| actaaaaata taaaaattag acggggtgg ttgtgcgtgc ctgtactccc agctactcgg | 42000 |
| gaggctgagg caggagaatc acttgaaccc aggaggcgga ggttgcggtg agccgagatc | 42060 |
| gggacactgc actctagcct gggcaaagga gcaaagttc atctaaaaaa tttattttaa | 42120 |
| tttaaaaatt ttgaaaaaat ggcccactcc ctagaacaga gagattccct ctaaacatga | 42180 |
| tggaggtccc gaactataca ttaagtgaat cctggtgtgt ctgaactcac atgattatta | 42240 |
| cgttaagctg ctgttccaat ctacttcctc acctgggaaa agaggagcca gggcatggct | 42300 |
| agttgaggcc ccaggaagag aactgagttc tcaaaggaca aagcaagcat cctcatccca | 42360 |
| gggcgagcct aaaagactgg ggcctccctc atccttttc acctctttat acaaaggcac | 42420 |
| cacctacatg caaatcctca cttaggcacc cacaggaaac caccacacat ttccttaaat | 42480 |
| tcagggtcca gctcacatgg gaaatacttt ctgagagtca tggacctcct gcacaagaac | 42540 |
| atgaaacacc tgtggttttt cctcctgctg gtggcagctc ccagatgtga gtgtctcaag | 42600 |
| gctgcagaca tggggatatg ggaggtgcct ctgatcccag gctcactgt gggtctctct | 42660 |
| gttcacaggg gtcctgtccc aggtgcagct gcaggagtcg ggcccaggac tggtgaagcc | 42720 |
| ttcggagacc ctgtccctca cctgcactgt ctctggtggc tccatcagta gttactactg | 42780 |
| gagctggatc cggcagcccc cagggaaggg actggagtgg attgggtata tctattacag | 42840 |
| tgggagcacc aactacaacc cctccctcaa gagtcgagtc accatgtcag tagacaagtc | 42900 |
| caagaaccag ttctccctga agctgagctc tgtgaccgcc gcagacacgg ccgtgtatta | 42960 |
| ctgtgcgaga gacacagtga ggggaggtga gtgtgagccc agacacaaac ctccctgcag | 43020 |
| ggaggctgag gggaccggcg caggtgcagc tcaaagccag caggggcgc gcggggccca | 43080 |
| cagagcaaga ggccgggtct ggagcaggtg caggagggc ggggcttcct catcagctca | 43140 |
| gtgctctccc tcctcgccag gacctcagct gtccccaggc ctcctctttc tttattatct | 43200 |

```
gtggttctgc ttcctcacct cgacgtcact gaaggagcat tctgagccag gcacagtca    43260
cttcctagtg agctacagag gctgagagaa aaatgctctg tgagacccaa tgggaagctc   43320
cctgcagtgc aaggtctggg tggcagggag cgctagggcc tcgcccagca caggctgcag   43380
ccctggagca ggtgcaaggg aggctgggga ggggttcctc ccagggtctg atgtcttcct   43440
tttctcggac aaacatgctt taataagtta aacaagactt tagtaaagac tattgatgtg   43500
tctttgtgtc tttcagtata cagttctatt tgtaggattt atctaaccta acaagtcaat   43560
gagaatcaca tgtaaaagga gaaatttcta ggattttcag atatcttaat aggtaggaga   43620
tggagaaaag ggatggtttt attaattcag tgcttgccaa tcttaacaga gacagtagta   43680
agacatgcag aaagcaaagc ccagaaaagt atgaaggtgt caaagtgcca tttaagtatg   43740
ggttcacttg gaggaccatg ttctgcggga acttgttttc agcagacaat ctatttagc    43800
agagttctgg gcatacaagg ggacacacat cattaaacaa ggattgggac agggacttca   43860
gcgtcccact gttgcatggc ccataaatta tgtgtgttct ctttctcatc ttggatcaag   43920
tctagagcta tgaaatagta tccctcatga atatgcaaat aacctgagat ttactgaagt   43980
aaatacagac ctgtcctgtg ccctgagagc atcacccagc aaccacatct gtcctctaga   44040
gaatcccctg agagctccgt tcctcaccat ggactggacc tggaggatcc tcttcttggt   44100
ggcagcagcc acaggtaaga ggctccctag tcccagtgat gagaaagaga ttgagtccag   44160
tccagggaga tctcatccac ttctgtgttc tctccacagg agcccactcc caggtgcagc   44220
tggtgcagtc tgggctgag gtgaagaagc ctggggcctc agtgaaggtc tcctgcaagg   44280
cttctggata caccttcacc ggctactata tgcactgggt gtgacaggcc cctgaacaag   44340
ggcttgagtg gatgggatgg atcaacccta acagtggtgg cacaaactat gcacagaagt   44400
ttcagggcag ggtcaccatg accagggaca cgtccatcag cacagcctac atggagctga   44460
gcaggctgag atctgacgac atggccgtgt attactgtgc gagagacaca gtgtgaaaac   44520
ccacatcctg agggtgtcag aaacccaagg gaggaggcag ctgtgctggg gctgagaaat   44580
gaaagggatt attattttta atgttgttta cagtatgtca ttaataaatt gaaaaaagt    44640
aacaatagaa gtatatactc taattatatg ggaactttgt tttttcagtt ttttcatttt   44700
tttttttttt tttggtttgt ttgtgacaga gtctcactct gccacccagg ctggagtgta   44760
acggcacaat ctcgacgagc atgtgcacat ttcattaaac ccactgtgta tgcagccct    44820
cccaagtgct ggcaggccac tgtacatgtg ggcagcccac tccaagggaa gaatcaaggg   44880
agaagaaata caaaccccag aaccatgtca atgtataaaa ccccaagtca agggccggac   44940
agagcactta gatctctcaa gtcgcccact tagccctctt ccaagtgtac tttacttcct   45000
ttagttccca ctttaaaact ttaataaaca tttactcctg ctctaaaact tgcttgggtc   45060
tctcactctt ctgtatgccc cttggccaaa ttctttcctc caaggaggcg agaatcaagt   45120
tgctgcagac ctgtatggat tcgctcctgc taacagatag ctggatgggt ggacagatgc   45180
atgaattagt ggatggacgt ttggatgtgt gggtggggtgg gtggattgtg ggatggctgg   45240
atgaatgcat ggctggatgg gtggacagat gcatgaatta gtggatggat gtttggatgt   45300
gtgagtgggt gggtggattg tgggatggct ggatgaatgc atggctggat gggtggacag   45360
atgcatgaat tcgtggatgg acgtttggat gtgtgggtgg gtgggtggat tgtgggatgg   45420
ctggatgaat gcatggctgg atgggtggac agatgcatga attcgtggat ggacgtttgg   45480
atgtgtgggt gggtgggtgg attgtgggat ggctggatga atgcatggct ggatgggtgg   45540
acagatgcat gaattcgtgg atggacgttt ggatgtgtgg gtgggtgggt ggattgtggg   45600
```

```
atggctggat gaatgcatgg ctgggtgggt ggatggatgc atggataagt ggtggacgga   45660
tggacgggtg agtggatggg tggatgtgtg tgtggatggg tggataggaa agccctctaa   45720
ttgattacag ggctcagtgt gtgcttcaac atcatgatgg catcatcaca ttggtccctg   45780
tatgaagcag tggggagga gagtgtacca ggggagcagg aatgactctt ctccagaatc   45840
gacctctccc accctgcagc ctgggctgtg caggccacat tggagaaggt gcggtcgact   45900
actcctaaat gttgttgtgt ccaatggctt tttgacgttg atgtaggaat gagcctacat   45960
ctccaccata gatggaactg tttgggtccc caaagcagaa agcctcttct gttgcaggtg   46020
ctgaagtttc catcttcttc tgcttatacg gaagctcacg catcccttgg atggcaggcg   46080
tcaggttcct gtgcgcactg agttccccc ttacatgctt tggacagaag tgtgagacac   46140
acaagattgc tgcaggaagt ccacctgtgg ggatgctgcg acttctccag caagaacacg   46200
agtctgctca ttgaccatca ccacacataa caaattaagt gtcccttttt tgataacacg   46260
tcattgtttc acagagtatt ctttaaagt gtataagttg actgcagtta ttattttta   46320 cttctgttac taatttactc ataattaggc acaatttaca cttaagaaat ttcttaatag   46380
ttttttcctc cttaaggtga actacagtca gataacatac ttatcaattg tctctagctc   46440
ttgtcagaaa agcatataga tgtgtgtgtg cgtgtgtctt ggcctttcca atgatgaatt   46500
aagatgtgca ttgagaaggc attcacttta tttgacgtta aggaagtacc aagaagacgc   46560
tctccacaga ccctgggaaa gccagcagct gcaccccgag gctgtgccag gcagggaaca   46620
aggaggcagc accacctgct gggcagggaa aatgtcctcc cagtccctgc cgcttctctg   46680
cagaggcaca aagagctgcc ccttctcctg ggccttctcc tgggctgatg agattgctcc   46740
ccgatatgcc aaatcagggt tgtgcatctg aggctctgtc tagactctca gctccttcct   46800
actcctgcaa agtgaagaaa acaatgccaa ggggtcctgg aggcgtctct accctggag   46860 agttttgact ctcttcaata gtctccacta ccctgccctc actccatgtc ctccgtttct   46920
ccctaaagcg gtgcccagtc tgattgcact gtggcaggga taacgagggg ccaggacatc   46980
aggggagaga agtttctacc tgagtcacag cagcggctgc cctgcagact cctgaagaca   47040
caagacacat ttccatccca gagacccagc gaaatgcaac ctcaggctag agacagccag   47100 ttatttttc ttgttctgtc ctggagaggc cactgagaaa gtcgagcccc ttgttgagga   47160
aaacatgaga tctctgtgtg tcgtcctctg cctgatggct gtacctccat gtgagtgtct   47220
cagagatttc agaacggggg ctgtgggctg tggtgtccgc ttgtgactca tctctttgct   47280
tcttgtccct gagtgtcctg catcagatgc agctactgga gtcatgccca gggctggtga   47340
ggtcctcaca gacctctggg cctggaccca gcagccctct gggaaggcgc tgggcacct   47400 cagctccagg ggcagcacac acttcagccc agcctttctg ggccaactct ccatctgtag   47460
agacacatcc aaggcccagt tatccctgca gctgagctcc gtgatggcca agggcagggc   47520
cgcacattcc cgtgggagac agaatgggga cctcagcgtg agcccagaca caaacctccc   47580
tgcagggaag cacaagacca ccaggcggcg ctccagacca cacagcggcc ccagaagcag   47640
gtttaggggg gcggggcaga cgtgtccgcg ttgagtcagg tcactggttt tacttttccct   47700 gaacaaacgg cctctgccaa ggactcactg cacctctcac cttcacagtt gttttttttt   47760 ttttttaat caccctgtag ggttttgcta gctaatttag atattgagga gtgcttcata   47820
cttccttggg cctctgcttg cagaaacata gcaattgtaa ggaggcacgt gggaaagccc   47880
cggctcggtg acccggggga tgctgctgta gccctggcaa gagggcgtcg ggccgcagta   47940
```

```
acaaaggtgc agacggctct cagcctgcgc ccgcggagta caacacataa gggctgtaac    48000
ctaacgaaaa aagaatcgca gtgcaactgt cctgcatttg agtttgtgat cagttttgcc    48060
ctttgtcttt aacaggttct aacataaaat tttgaatgct ggttcaagcc ctgtgggtaa    48120
aatgcactta cccacattcc ttaaacaaat agaacactga ggtggaaatg ttttgaaaaa    48180
gtagttttca gacatttgga aacaagcatc acaggatcat aaccccctgag aaagaaaaa    48240 caaatgaacg aatcctgcta ttgcctgaaa gcagctgcca ggacacacgg aaaggcttag    48300
tgagctgagc ggacagagag cagagttcaa ggcagcagca gcccgagggg aggagcaccg    48360
gggagcaggc tgctgtgcag ccaggatggg ccggggtggg gcgggggggag aacagctgga    48420 gacttgccgc agggagggggg atccctcagg tttggggctg agaactgact tatgcctgac    48480
ttatgcctgc atgaaaagaa actactcgat atcaggggga aatcaccaga aacctgtgga    48540
cccaaaacta cacagagcct acacaaggaa agcattgttt gtgttctccc agccagggtg    48600
gaaagacctt gagatatgta aagcttcaag caatcttccg aagtaatctc gtgagtagtg    48660
gtgccacatt aattcaggac taaagactgc tctgaactga acctaagaaa tgcttcaagt    48720
gtagcctgga gcccgggtgc agtggctcac acctgtaatc ccagcactgt gggaggccga    48780
ggcaggcgga tcacttgagg tcaggactt gagaccagcc tggccaacat ggcaaaacct    48840
gtctctacta aaacacaaa aattagctgg gcatggtggc agatgcctgt aatcacctcc    48900
cacctggacc cttccttgat acatcagaat tacaactaga gatgagattg gggtggggac    48960
acagagccag accgtatcac ataggaacct aaaaggataa taaagtagga aaacttccca    49020
catcagtaac cctttatccg atagtaatcc caatctgcaa agtaaaactg tgtgatttta    49080
ctaagataac ggaatcttct ctacagaagg acttttccagt gcaaaagctc cccaccctca    49140
ccatgaaatg cacgtgacca tttccaattt gtgtaaagtc ctcagttagt actgagactt    49200
cggaaggtta gaaatcccctt tgctcatgct gcatggtccg gatgagatgt aagaatcatt    49260
agctaataga catgcaacag ctttttgtgcg aaagatgtta tgagacattt aaggtatttg    49320
cttgtgctta ctaagcattc attgtatcat tggagcacat gtgctttat accctggaga    49380 aattccagta attgaattgc tgggttgaat gggattttga tttggattaa atttaaacta    49440
tagattttat ttagggaaaa ctggcatctt aattatgtta ttggggggcc cttgctccca    49500
gagctcccaa gatggtggca ggccgcttcc aaaatgaccg caggccactt ccaagatggt    49560
ggcaagcctc atgttctctg acctgggggtt cttggcctca cggattccaa ggaatggaag    49620
cttgggccat gcagtgagtg ttatagctct attagaagcc gtgggtcacg gaagagaacc    49680
gtggaaccca gtgactagtg ttcagctcga ttaggacgaa cccaggcact tagccgtgca    49740
ggaacaatgg cgagcatttg gcccgatcga gagtggcaat gggcgcctcg ccggatcagg    49800
agcacagcgg atatccctgat ggatccggag ggatggaagc cagcggtggg tctcccacgg    49860
gggcaaacag cagtggtgga cggtgagcga aagcgaagct cgagccgtaa caaacatgga    49920
ccagaagagt gcagttgcaa gatttagtag agtgaagaca gagctcccat acaaagggag    49980
gggacccaaa gagggtagct gttaccggct cgaatgcctg ggtttatatc ccgatcattg    50040
tccctcccgc tgtgctctca ggtgatagat gattggctat ttctttacct cctgcttttg    50100
cctaattagc attttagtga actctcttta ctatctgatt ggtcgggtgt gagctgagtt    50160
gcaagccccg tgtttaaagg tggaagtggt caccttccca gctgggctta gggattctta    50220
gtcggcctag gaaatccagc tagtcctgtc tctcaattac actgagtttt ccaatccatg    50280
catccaatat gtggtgtatc tcttcatatg ttcatagcct ctgagcaatg ttttacaatt    50340
```

```
ttctgtgtaa agaactccac atcgttttat gtttcttcta aggtatatcc tgattgcttt    50400
ttatgtcttc acaagttttt cccctttcaaa attaattttc caattgtttg gtgctaatat   50460
gctcaaatgt ccttgatttt cttagtttga acagtccgtt ttcgttttgg ggatttattt    50520 tttttcaga ttcttttaaga ttttctatgt ctataaccat ataatctctg aacagagaca   50580
gttttgcttt tcccttttcaa cttgaggtag ttttctggg tagttcagga cgcgcaggca    50640
ctgggtgggt ggtgttagca gctgcacgat gccttggaga ggacactctc ggggactgt    50700 ggccgctgct cagctgtgac tgttcttata gcaccagcag ctgcggccac cattcttatc   50760
caatttccaa agccacacca caggccctct caagaacgag gcgtggaggc tatgccctct   50820
cctggacaca tcatcattcc caagccccac gatgtgggcc ccatgggacg cacacctttg   50880
tctgtccaga cctcagcccc acctcctcat cctgcaccag aactcttcag agcccagtgc   50940
atgaaatggg ctaccaagga aatgagggta ggttcctgag aggaaactgg ccctgcattt   51000
gggagctaag agtctgctaa ttcgcctggc agccctgtgc agccctccgt ggctacagtc   51060
caccccgtgc ccatcagtgc ctccttcctg tgcaagcctg acctcgccc tgggctcagg    51120 atgggctgta gaccgagaat gcaggcggga aagtcgttgt ctatcggggc catagtcagg   51180
ttctacagtg agtcagggaa agacctgtgg aggtgtggat gaggacaatg ggtccaccat   51240
caacaggagg acacgggttc gacccccttgc agaggcacag tcccacatca ctgggaggca   51300
gccacactca ctgcctcgcc ctctcctcac acagtgcagt ttccacgttc acagcccag    51360 ccagtcacca ggaatgccct gggggcggcc tttcccagt gcaccccgag ccctccttg     51420 gctgtgcggt gagctccatg cccaggagat atccaccat agtcctccgg aaagcagctg    51480
acctgccatg ccctggaacc acaaatcccc acagatcagc cagcctgcag tgggccttgg   51540
atgtggtgag gagtggtggc accccgttc ccaccccaca gatgcaacgc ctgtgggtga    51600
cgcatgtgag tactgaggag tagagggtag aactgtaggc cccgagaacc acagaaactc   51660
gggtgttaca ctctggggcc atgtaaggag aaagtgtcac tggacagaaa caggcccctc   51720
ctagacactg tgtgcgccat agtcacctgt cattagctct cactcttgca gattcatgat   51780
tgaggtggtt aaaaaaaaaa aagctcctac tcacccatcc aacccccatcc tggggtgttt   51840 ccaccaccct tggggtttgg gatgagctgc ccttgcccac tgtgctctgt ggacctccct   51900
ttagaagctc acagctccct gcactcggct ccatcctgcc ccaccacaca gaagcaaaac   51960
ccctctcctt tccactgcag gcttttcctg gaccagaatg ctgacctgct gcccttcact   52020
cccgaagtgg tgggactgcc tggggtggtg tgggtgttga gccttcttac tctagggacc   52080
tggcacctgg ccccaggggc acaggatgg tgcatctgcc tagggatgcc tcctcatgcc    52140
agggggtggg ggttagtacc atcggccctc aggatttgtt gcatgaatga gtgaatgggt   52200
gaataaatga aggggatctg atctatgaat aagggtatat ggactttggt tgatgtagga   52260
cgccaaatgc tggaatttcg gagtcatcac acccaggggc cctgcctctg agctcctctt   52320
tgcatccaat ctgctgaaga acatggctct agggaaaccc agttgtagac ctgagggccc   52380
cggctcttca atgagccatc tccgtcccgg ggccttatat cagcaagtga cgcacacagg   52440
caaatgccag ggtgtggttt cctgtttaaa tgtagcctcc cccgctgcag agctgcagag   52500
cctgctgaat tctggctgac cagggcagtc acccgagctc cagacaatgt ctgtctcctt   52560
cctcatcttc ctgcccgtgc tgggcctccc atggggtcag tgtcagggag atgccgtatt   52620
cacagcagca ttcacagact gaggggtgtt tcactttgct gtttccttttt gtctccaggt   52680
```

```
gtcctgtcac aggtacagct gcagcagtca ggtccaggac tggtgaagcc ctcgcagacc    52740
ctctcactca cctgtgccat ctccggggac agtgtctcta gcaacagtgc tgcttggaac    52800
tggatcaggc agtccccatc gagaggcctt gagtggctgg aaggacata ctacaggtcc     52860 aagtggtata atgattatgc agtatctgtg aaaagtcgaa taaccatcaa cccagacaca    52920
tccaagaacc agttctccct gcagctgaac cctgtgactc ccgaggacac ggctgtgtat    52980
tactgtgcaa gagacacagt gaggggaagt cagtgtgagc ccagacacaa acctccctgc    53040
agggatgctc aggacccag aaggcaccca gcactaccag cgcagggccc agaccaggag     53100
caggtgtgga gttaagcaaa aatggaactt cttgctgtgt cttaaactgt tgttgttttt    53160
tttttttttt tggctcagca acagagatca tagaaaaccc ttttcatat ttttgaaatc     53220 tgttcttagt ctaatggaga ttctctgata tgtgacaatg ttttctctt gctgtttttg     53280 gaattctttg tcttgactt ttgacaactt gactttgac agtgtgcctc aaagaagttc      53340
tattttgggt tctgtgaacc tcctggatct gggaagtttt cagctatgat ttcattaaac    53400 gtgtttcta caccatttcc ctactctttt ggaatacca taatgcaaat atttgttcac      53460
ttaattgtgt cccataaatg ctggggattt tcttcattcc ttttactct tttttcttt     53520 ttattcatct gcctgaatta tttcaaaaga tctgtcttca acttcagaaa ctcttttgct    53580
tggcctagtc taatcttgaa ggtctcaatt gtacttttaa tttcattcat tgaattcttc    53640
aactctggaa tttctgttgg ttctttttta tgatacttat ctctttgttg aattcctcat    53700
tcaaatgata aattgttttc ctgatttcac tgaattttct atctgtacac tattgtatct    53760
ccctgagttt cttagagatt atcctttga attattttc tgacattctg tatatttcct     53820
tatgattggg gtctgctact ggagaatgac tgttgtcttt ttcaggtgcc gtgtttcctg    53880
gccttttcat gttttatgtg ttcctacgtt gatttctaca catctggcgg accagtcatc    53940
ccttgcaatt taatggagta ggttttgcag gaaaagactt cctagtacag acgggtctca    54000
gggtgtcagt gtggcgggc gtgctggctt tagttctagg ttgacgcagt agcgtagtct     54060
ccatgtcgtt tcttcagctg ccgtccacat tggtgacgtt tgcgagtgtc tcagtggcct    54120
gggctgagag gtttgtggca gtggaagtgc aacgttgcta gaggtggact caccaggctg    54180
tttctgaggt cgaggcacat gcatgcacat ggtggattga ccaacttggt gccaggctca    54240
ctagggttgg ggacatgggg ctgtttctca ggcccaggat gcaaacacaa gtctctttgg   54300
ctggcctggg ggtgtggctt ctgagggcaa tccacagggc tgtttctcag gttcaggaca   54360
caagtgcatg gccgctcaac tggcctgggc atgtgtctcc cagggccacc ccatgggctc   54420
tctctcagac ccaggacatg gccacatggc ttcctcagct ggcctgggtg tgtgtctgct   54480
tggggcctgc aggggcacag ggttattct caggccgggg tcatgggcgc acagctgctt    54540
gctggcttat aggagtgcct gccaggggtg gcccatgatg ctgtttctca ggcccgcgcg   54600
actgaataca taaacaggac acagcatttt gctgcataaa gcaaacacag cgttacttt    54660 ttttttctaa atgacatttt ttattagata ttgtctttat tgacatttca aatgttatcc   54720
cctttcctgg tttaccctct gaaatcccct atctcctccc cctccccctg ctcaccaatc   54780
cacccactcc cacttccagg ccctggcaat cccctatatt tgggcataga gccttcacag   54840
gaccaaggta ctctccttgc attgatgacc aactagtcca ttctctgcta caaatgcagc   54900
tagatctatg agtcccacca tgttttcttt tgttggtggt tcatgccag ggagctcttg    54960 gagtactgat tggttcatat tgttgttctc cctatgggt tacaaaaccc ttcaacttct    55020
tgggtccttt ctctggctgc ctcattgggg accttgtgcg aagtccaatg gatgactgtg   55080
```

```
agcatccact tctgtatttg ccaggcactg gcagagcctc tcagaagaca gctatatcaa   55140
gatcctggca gcaagctctt gttggtatcc acaaaagtgt ctggtggttg tctatgggat   55200
ggatccccaa aggggcagtc tctggatggt cattccttca gtctctgttc cacactttgt   55260
ctctttaact ccttccatga ctattttatt cctccctcta agaaggaccg aagtattcat   55320
actttggtct tccttcttga aattcatgtg ttttgtgaat tgtatctttg atattccgaa   55380
cttctgggct aatatccact tatcagtgag tgaatatcat gtgtgttctt atgtgattga   55440
gttacctcac tcaggatgat atcctccaga accatccatt tgtctaagaa tttaatgaat   55500
tcattgtttt taatagctga ggagtactcc attgtgtaaa tgtaccacat tttctgtacc   55560
cattgttctc ttgagggaca tctgggttct ttaaagcttc tggacattaa atataaggct   55620
gctatggaaa tagtggagaa tgtgtcctta ttacatgttg gagcatcttc tgggtatatg   55680
cccaggagtg ctattgctgg atcctctgat agtactatgt ccaatttctt gaggaactgc   55740
caaactggtt tacagagtgg ttgtgccagc ttgcaattcc accagcaatg gagaaatgtt   55800
ccccttcctc cacatcctca ccaacatctg ctgtcacctc aatttgttct tagtgattca   55860
gacaggtgtg aggtggaata tcaggttgt ttggcatttc cctgatgact agtgatattg   55920
aaaaaaattt taagtgtttc tcagccattc agtattcttc agttgagaat tcactgttta   55980
gctctgtact caggtttttt taatagggtt atttggtttt ctggagtcta acgtcttgaa   56040
ttctttctat atattggata ttagccctct gtcatattta ggattggtaa agatctttcc   56100
caatatgttg gctgccttt tgtgtccttt gccttacaga acttttttaa ttttatgagg   56160
tcccatttgc taattcttca ttttacagca aaagccattg gtgttctgtt caaaaatctt   56220 tcccctgaa cccatatctt gaggatcttc cccactttct cctctataag tttcagtgtc   56280
tctattattg tgctgaggtc cttgatccac ttgaacttga gcattgttca aggagataag   56340
aatggatcaa ttcgaattct tctacatgat aacagccagt tgagccagca ccatttgttg   56400
aaaattctct ttttttgcact ggatagtttt agcacttttg tcaaagatca agtgactatg   56460
gctcttcaac tatggctcat tccattgatc aacttgtctg tcactgtaca agcaccatgc   56520 aattttatt gcaattgctt agtattacac cttgaggtca aggatggtca ttccaccaga   56580
ggttcttcta tggttgagaa gagttttttgc tatcctaggt ttttgttatt ccagatgaat   56640
ttgcaaatgg ccctttctaa ctcagtgaag aattgaggtg gaattttgat gggaattta   56700 ttgaatctgt agattgcatt caacaagata gccatttata atacattaat cctgccagtc   56760
catgagcatg ggagatcttt ccatcttccg agatcttctt cgatttcttt cttcagagac   56820
ttgaagtttt tatcatacag atctttcact tccttagtta gagtcacacc aaggtatttt   56880
atattatttg tgactactgt gaaggttgtt gtttccctga ttcttcctc agcctgttca   56940 tcctttgtgt agagaaaggc cactgattta tttgagttaa tattgtatcc agctaattca   57000
ctgaagttgt ttatcaggtt taggagttct cttgtggaat ttttggaatc acatgtgtat   57060
actattatat catctgcaat tagtgatatt ttgacttctt cttcccaaa ttgtatccct   57120 ttgatctcct tttgttgtct aattgcccac actaggactc gggcagcctt agtgcctagt   57180
ccctgatttt agtgtgattt gttcaagttt ctctccactt agtcggatgt tggctactga   57240
tttgctgtat attgcttta ttatgtttag gtatgggcct tgaattcctg atctttccaa   57300
tacttttatc atgaatgggt gttgaatttt gtcaaatgct ttctcaacac ctacaaagat   57360
gatcatgtag attttgtctt tcagtttgat tatatagtgt attatgttga tggatttcca   57420
```

```
tatattaaac catccctgca tccctgggat gaagcctact tggtcatgat agacgattgt    57480
tttgatgtgt tcttggattc agttagtgag aaatatattg agtatttta catcgatatt    57540
cataagggaa attggtctga agttctcttt ctttgttggg tctttatgtg gtttagttat    57600
cagagtcatc gtagcttcat agaacaaatt gagtagagta cctctgtct ctattttgtg    57660
gtatagtttg aggagatttg gaaatatgtc ttcttgggac gtctgagaga attctgcact    57720
aaacccatct gatcctgggc ttcttggggg gggggggact attaatgact gcttctattt    57780
ctttagggga aatgggactg tttagattgt taatatgatc ctgaatagaa atctgatctg    57840
atctagaaaa ttgtccatt tattcaggtt ttccagtttt gttgagtatt gccttttgtg    57900
gtagggtctg atgatgtttt ggatttcctt aggttctgtt gttatgtctt cttttccatt    57960
tctcattttg ttaattagga tactgtccct gtgtcctcta gttactctgg ctaagcgttt    58020
atctatctta ttgattttct caaagaacca gctcctggtt tggttgattc tttgtatagt    58080
tcttttttgtt tccacttgat tgattttctgc cctaagtttg attgtttcct gctgtctact    58140
cctcttgggt gaatttgctt cctttttgttc tagagctttt aggtgtgctg tcaagctgat    58200
agggtatgct ctctctagtt tcttttttggc ggcactcata gctaggagtt ttcctcttag    58260
cagtgctttc attacgtcct gtaagtttgg gtatgttgtg gcttcatttg cattaaattc    58320
taataagtct ttaatctctt tccttctttc ttccttgacc gagttatcat tgactagagt    58380
gttcatcagc ttccacatca atgttggctt ttaattattt atgttttttat tgaggatcag    58440
cctttgtcgg tggtgatctt ctaggatgca cgggaaattt tcaatatttt tgtatctatt    58500
gaggcctgtt ttgtgaccaa ttatacggtc aatttttggag aaagtaccgt gaggtactga    58560
gaagatggta tatcttttttg ttttaggata aaatgttctg tagatatctg ttaaatccat    58620
ttgtttcata acttctgtta gtttcactgt gtctctgctt agtttctgat tccagaatct    58680
gtccaatgat aagagtaggg tattaaattc tcccactact attgtgtgag gtacaatgtg    58740
tggtttgagc tttaaaagag tttccttaat gaatgtggat ggccttgcat ttggagcata    58800
gttattcaga attgagagtt cctcttggaa gattttacct ttgatgagta taaaatgccc    58860
ctccttgtct tttttgatac ctttgggtta gaagtggatt ttattcgata ttagaatggc    58920
taatccatct tgtttctttg agatgtttgc ttggaaaatt attttcctgc cctttactcg    58980
gtggtagtgt ctgtcttagt ccctgaggtg ggtttcctgt atacagcaaa atgttgggtc    59040
ctggttatgt agccagtctg ttagtctgtc tttttatcag gtaattgagt ccattgatat    59100
taagagctat taaggaaaag taattggtgc ttcctgttat ttttgttgtt agacttggga    59160
ttctgttctt gtggctatct tcttttaggt ttgttgaagg attactttct tgctttttt    59220
agggtgtaat ttccctcttt gtgttggagt tttctcttta ttatccttg aagggctgga    59280
ttcatggaaa gatgttgggt gaatttggtt ttgtcatgga attctttggt ttctccatct    59340
ataattgaga gttttgctgg gtatagtagc ctaagctggc atttgtgctc tcttagtgtc    59400
tataacatct gtccaggatc ttctggcttt cataatctct ggtgagaagt ctggtgtaat    59460
tctgataggc ctgcctttat atgttacttg accttttttcc cttactgctt taaatattct    59520
atcttcattt agtgcatttt ttttctgatt tttatgtgt caggaggaat ttcttttctg    59580
ctccagtcta ttcggattct gtaggctact tctatgttca tgggcatctc cttctttagg    59640
ttacggacgt tttcttctat aattttgttg aagatattta ctggcccttt aagttgaaaa    59700
tctccattct catctatacc tattatcttt aggtttggtc ttctcattgt gtcctggatt    59760
tcctggatgt tttgagttag gatcttttttt gcattttgca ttttttttta ttgttgtgcc    59820
```

```
catgttttct acggaatctt atgcacctga gactctctct tctacctctt gtattctatt    59880
ggctgatgct tccacctatg tttctcgatt tctttcctag gatttctatc cccagagttg    59940
tctcccttg tgatttctt attgtttcta cttccatttt tagattttga atggttctgt    60000
tcgattccat cgcctgttgg gttgtgtttt tctgtatttc tttgagggat ttttgtgctt    60060
catctttaag gtcttctacc tgtttaggag tgttttccta taattctttg agggatttt    60120
gtgttttctc tttaagggct tctagcaatt tagcagtgtt ctcctgtatt tctttaagtg    60180
agttattaat gcccttctta aaatcctcta ccaacatcat tagatatgat tttaaatccg    60240
aatcttgctt ttcaggtgtg ttggggtatc caggactcac tgtgggggga gtactgggtt    60300
ctgatgatga aaactggtct tggttttat tagtaagatt cctacttttg ccttccacca    60360
tctgataata tctgttgtta gatattctag ctgtctctgg ctggagcttg ttcctcctgt    60420
gattctgtca gcctctgtca gcactcctgg gagtacaact cttttctgag tcccaatgtt    60480
cagagcattc tctgcaggca agctctcctc tggcaggtaa ggtgcccaga gctcttgagc    60540
tcagctccac ctcctgactg cagatgaaga cccaaaggga ccctgtccaa taagctctgt    60600
tgcttctgcc acccacatgc tctcctgtgc gaactggtct ctgagagacc cgggatacaa    60660
gatggtactc tcacctgaat cccagggtca aagccctccc tggaggctga ctctcctctt    60720
gtgggaaggt gcacagaggt ctggagctca gctctgcctc ctggctgaag atgaaggccc    60780
gaagggaccc tgtccaagaa gctttgttgc ttctgggacc cacatgctct cctacatgga    60840
ctggtctctg agagaccagg gattcaagat ggtgctctca cctgagtccc agggtcagag    60900
ccctctctgg aggccaactc tcctcagtga tcctaagatc ctgggtatgc tagggtgcct    60960
atggcatgga gagtcctctg aggaatgtgg gactgtctgc tgagtttcca cccaaggtgg    61020
tgctgggctg gctccagtca gaatgaaccc agactctggt tgggcaggtt tccagtcctg    61080
ttggcccaag cccctctggg ttgttttaga acagatgttg ctttccactc accagtgatc    61140
ccaagatcct gggcgtgcta gggtgcctgc tatgtggaga gtccactggg gaccttagga    61200
gcatacatca agttcacacc catggtggca aggagctggt gcctaccaga acaaaccccg    61260
ggcacttta ctgacccttt aagttgaaaa tcttcattct catctatacc tattatcctt    61320
aggtttggtc ttctcattgt gtcctggatt tcctggatgt tttgacttaa gatcttttg    61380
catttgcat ttttttgat gttgtgtcca tgttctctct ggaatcttct acacctgaga    61440
ttctctcctc tgtatcttgt attctgttgg tgatgcttgc atctattgct cctgatctct    61500
ttcctagggt ttctatctcc agagttttct ccctttgtga tttctttatt atttctactt    61560
ccattttag atcctagatg attttgttaa attccttcac ctgtttggtt gtgtgttcct    61620
gtaattcttt aagggatttt tgtatttcct ctttaagggc ttctacctgt ttagctgtgt    61680
tctactgtat ttctttaaag gacttatgaa tgtccttctt aaaaacctct accagcatca    61740
tgagatgtga tcttaaatgt caatcttccc tttctggtgt gttggggtat ccaggacttg    61800
ctgtggttgg agttctgggt tctggtaaac ctgccttaga gggtcaccac agagtaatga    61860
tagcactact tttaaacagg ggaagatgat gaaataattg ctgtgggaaa atgcaaggaa    61920
ggctccaaca catgtaggca tctatgaagg tctcaaatct tcaaaatcca aaccaccaa    61980
gaaagaaaga aagaaagaaa gaaagaaaga aagaaagaaa gaaagaaaga aagaaagaaa    62040
gaaagaaaga aggaaggaa ggaaggaagg aaggaaggaa ggaaggaagg aaggaaggaa    62100
ggaaggaagg aaggaaggaa ggaagattct aaaagtagtc acctgcacca ggtgcctggg    62160
```

| | | | | | |
|---|---|---|---|---|---|
| gagtcactca | gcagccctag | actgagaaag | cttgaagaaa | gtagaaatag | agaaagtgta | 62220 |
| cagccagtat | cctctagcta | ctcacatcca | aacagggcct | cctgactgct | ctgagcctgt | 62280 |
| cctaagaaca | gcaatgatgc | cacagaaatt | tttagagtga | accctgaagg | aacttgaggc | 62340 |
| cgatatgaga | aagccagtcc | cagaggaaag | gaaaacccgt | agagagaaaa | caggtgagtt | 62400 |
| agtgcattaa | aggggctgag | caggcaacgc | gccgtcgacc | ggaggagttt | cttccctgtg | 62460 |
| cggagtccac | gggcctcctg | tgagtgtgtg | catgggcaca | agtgtgtgtg | tggctctgct | 62520 |
| gtgtgtctgt | acacacatat | gttttgggtt | tttttgtgtc | tcagaccaca | gagtctgccc | 62580 |
| ctcccaccaa | agcccaggca | gaaggatgaa | cccacgcccc | tggggcccag | gcctcagcag | 62640 |
| cctctgcggg | atcattgttc | ccagttgtca | cttgcctttg | ccacagccct | atttctccac | 62700 |
| aattccttaa | agtcctcaac | atgcatttaa | ggcacaaagg | tgaaactgcc | cagaaacatc | 62760 |
| tgactccgcc | gtggaaccca | ggagcaagct | gggttagcta | aggagcgggg | ccgttggcag | 62820 |
| aggctgggga | tccaggctga | actttggagg | aggcatgtcc | cagcatgggc | tcctgactat | 62880 |
| gtcctcctgg | gacaaaccca | aacccactct | ttgaatatgg | gagggacttt | gctggccccg | 62940 |
| gccctgaccg | cagcacttgg | aaactgagga | gtggtcgcct | cctccgtgtc | acagctgccc | 63000 |
| gttcaccatc | atagaagcaa | ctctgtcacc | tccatgggcc | cctctgtggc | tgctgcctgg | 63060 |
| gtccaagctg | agcccagctg | cccaggccca | gaaggaaagc | ccaggccagg | tgcccagcac | 63120 |
| agaggcagtc | acataccccg | gggagagcca | cagcaagcag | ccaatattgc | ccaggagagg | 63180 |
| agtagctgac | aaggcagaac | gtgagctgcc | atcggctcga | gaggctttgc | tggtcctcct | 63240 |
| ggggctctgg | acatgaccag | gaggagcgag | ggaagaagtc | gcatggtggt | cccatcctgg | 63300 |
| gtggggcctg | atggcagctg | gccacccgtc | ccagagtggc | agccagatgc | cagcgccatt | 63360 |
| cccacagtca | catcattggt | cacagaatgc | aggacataga | gtgtcttctt | tccatcacag | 63420 |
| tgctgtccag | acccatagcc | tagggtagac | ctggaagatt | caatgtccac | acccggggct | 63480 |
| ggagcgtagc | catgagccac | gcccctgcc | cgtgcatgga | aagccagccc | aagctctgct | 63540 |
| ccatccctag | ccaaagtcag | tgtccttttcc | ccttctccca | agtgagctct | agccacctgc | 63600 |
| ctaccctgcc | atctgaggat | gacagccttc | attccattgg | aacctggctc | tgccaccagc | 63660 |
| aggcttgcag | tcctgggcag | actccgtcac | ctctctatgc | ctcagccttt | ccatctgcac | 63720 |
| aggaggaaga | tgatgatggt | ggtgatgatg | atggcgatgg | tttccttttg | catctgaggc | 63780 |
| aaggactaat | tgagatgata | cacatcaggc | actgggtatg | gtgctggtcc | ttcctgagca | 63840 |
| ctcaatctat | gtgagctgtc | cttgtgaaat | gggtgtcacc | acatttcccc | acgcagaaca | 63900 |
| tcctttgtct | gccatacttg | aaacgtctgc | cccaatacta | acagctcctc | atggaagatg | 63960 |
| tgcccaccca | cccaccctca | tactcccaaa | ggtgcccgtg | ctttatcaag | ccaaagtcca | 64020 |
| gccaggaact | ttacagcagc | atccctttcc | ctctccaagc | accaaggagc | aaggcaaagc | 64080 |
| actacatctt | ccatctggag | gcaatgccac | cctcttctcc | catttcact | gccatcccta | 64140 |
| agaggcagtg | cttccccaaa | aggttccata | gcagcctgcc | tacagcaact | ctgttcacac | 64200 |
| gagtttcagc | atccttgcag | tggctcccct | gccatgctgt | ggctcttcat | tcaccctctt | 64260 |
| ctcctgctcc | ccgtgacagg | catagattct | gagtgatctg | gatacattgc | tttgtttaat | 64320 |
| aacattacag | cttctgtgct | gaaaaagata | cagcagatag | agaaggcaat | tgttgaacac | 64380 |
| aaaatagtga | cagcagagat | gacggcaagt | tggcattttt | cttttctagc | aataaaactt | 64440 |
| aaagctgact | caaggagaaa | tggaaatcat | aattggaaca | gtaatcctca | agaaagcatt | 64500 |
| aagattatta | ataattgcc | ctcacagatg | acttcaggcc | aagatggctt | tatgggtgaa | 64560 |

```
gtttagactt tcacaaaact aatcagttcc cataagaact gctccaggat ttggaggaac    64620
atgggaaagt ctattaaagg gatcacaatt cacagtcccc agagtaaaac atgggctaac    64680
ttgcattttg gcaaagagcc aaatgttata aatgacatcc tagaaggcca aattctgtcc    64740
atctcgttga acaaggactt acaccaggaa tttagaacta tttatagctc atcccaccac    64800
tcaggccaat gatgacccat gatcatctca ccagaaatgg aaagactcag atgattaata    64860
gagtctcaat ttctctgaga catctaagag cccagcccaa gcccagaccc aggagggcac    64920
ccaggcctgg acagagaaca ctgatatcac accagccctc cagagggaag cagagactcc    64980
ttcaagctct ggaaacacag gcccagacag ctgcccaaag ttgggcaggc ttcactgcaa    65040
acccaaatca tgaagctagg taacaccttt acagattctt tacatttaaa aatcatcaaa    65100
acaagagtaa ataataaact caaataatat taatctaata tgtaaaggtc ttgtaccatt    65160
attatgcaaa caacatacat aagctaataa gaaaaagaac aaatcccttta agaaatcagc    65220 aaaaaggata taacacaatt tctaaaagaa aacaaatggc tagcacacat aaggaaaaca    65280
ctttgtgaac agacattctt cagaacatta tttataatta taaaatagtt gaaagcaaga    65340
tagtgcctga agaaattatg gtgcatacat tagtgggact attctgcaaa cattcccaat    65400
tatacttgtc acatatctgt gataacgtga cagccagcat tcatggggtg acctcatttg    65460
gtaaaagggt gcaaagctca acacgcattg tgagatgact gtggtgtaaa attagtggga    65520
ttattccgca acattccca attatactta ccgcatatct gtgataacat gacagcattc     65580
atggggtgac ctcatttggt aaagggtgc aaagctcaac acgcattgtg agatgactgg     65640
tgtaaataca aagaccaaac tgtgaaaagg agtccatcaa ttaatcgatg cttaccttca    65700
gttttgggct aattttttaaa gtatgctata agcatatgct cctgttataa cagaatggag    65760
ggattatgag agatgatgca ggtgtgtcct gggcctcccc tggcccactg ggccctagag    65820
atgccttccc aggcatcgct gtcagggctt ccctcagagg gagtcctgta ttgacctcac    65880
caccaaggtc tggagcaggg gatccttaga tattggttgg ggttatctca ccttaggtct    65940
gaatatgggg ttgtcttaga ctgttttgtg ctgttagaat agaatacccca agactgggaa    66000 atttatactg aacggaaatt tatttctcac agttctagag gctgtgaagt ccaagagcac    66060
aggtgccaga gcaagtccaa gagcaaggga aagtccaaag caagtccagg agcatctggc    66120
gaggaccttc ttgctgtgtc atcacatggc ggaaggcaag aaagagagca agaggggcc    66180 gaactcaccc ttttataaca gcaccaatcc caccccatgag gtggggacct tatgacctaa    66240
tcactcttca tactgttaca atggcaatga aatttcaaca tgagttttgg aggagagaag    66300
cattcaaacc acagcaaggg tgctcctacc tcctctctca gggcatctgc agaaagagct    66360
gcaactgcac gtccttcctc cgtccatcct ccatcccttc ccaatgtccg tgcatatcct    66420
gtgacccagg aggtctggca taggggtgc tcctgcctta ggtctgaggc cctgtctgaa    66480
gaggggtagg tgaggaggcc atctgatggt ctgggccaag acagtcacag gacgcatcat    66540
ttatcatcaa ggaggctgag ggttgagtct ccaggtccag ggaactcccc acaaagtggg    66600
aaccctgccc agctccacac agcctctgct gggggaccct gctctggtgc agagcctggg    66660
gacaggtctt gagctcagcc agagtctgcc tccctgtcat ttaggaacta aaccaagcgg    66720
caggatgctg gagcccagcc cccatctgac cttacagggc caaggctggg gccctgggtt    66780
cccctcaagg cacagcagga ctggagcccc aggcagtgca ggagtggcca aagctggggc    66840
ttcctccaga gcccccaagc atcatggcac caagaagggt aggaccctgg cctgaggaat    66900
```

| | |
|---|---:|
| tggcaccaaa gccccagaaa ctaccctgga caccatggag agaggcttgg aggggaagca | 66960 |
| ccaggcactg cctcccttc tgatcccacc tgaggtggct gccaagccca gagagccgct | 67020 |
| ctgatgtccc ccagccctgc agcccaggga tacctgtact gtgccctgg ggaccctg | 67080 |
| gccagtctgt gcaaagaagt caccacccta cactcagaga cagtgggggt cctcgtccca | 67140 |
| catcctcaga gcatggcccg gctgctgcag ggatggtctc cttgtcctca gagcatggcc | 67200 |
| cggctgctgc agggatggtc tccttgtcct cagagcatgg cccagctgct gcagggatgg | 67260 |
| tctcctggag gccccccagt gctctattgt cagggctccc tccacccccc cgcaccaaga | 67320 |
| gagagccaga cccagcaag gcttccagtg gcttcaggtc acacccctag gctgacccca | 67380 |
| gccccattaa cacctgcctg agaaagctcc acgcaccaga actgaccgtc tgctccaact | 67440 |
| cttgacctcc cgttctcagg gcgtctgctg aaaaggctgc aactgcacat ccttcctccg | 67500 |
| tccgttcccg atgtccgtgt gtctcctgtg gccaggaagg tctttctcgg gacctgagag | 67560 |
| ccgctccctg aagtgtcccc attgggaagg atggggcctg tgtctccagg ctctgggagg | 67620 |
| acagaatcct gacctcaaca gtggccggca cggacacaac tggcccate ccggggacgc | 67680 |
| tgaccagcgc tgggcaactt ttcccttccc cgacgactga gccccgagca ccctccctgc | 67740 |
| tccctacca cctcccttta caaggctgtg gcctctgcac agatgataat ggagcttggc | 67800 |
| tcattcccct agagtcggta gggagttaag gacaaaactc agtttcctcc acctgaactc | 67860 |
| aagtctgcct atgtttacct aatcacacct ggtggacagt ttggacaaac ttgcacactc | 67920 |
| agagacacag acacttctag aaatcattat ctccctgccc cggggacccc actccagcag | 67980 |
| aagtctgcta ggcactggcc tgggccctcc tgctgtccta ggaggctgct gacctcctgc | 68040 |
| ctggctcctg tccccaggtc cagagtcaga gcagactcca gggacgctgc aggctaggaa | 68100 |
| gccgccccct ccaggccagg gtctagtgca ggtgcccagg acaagaaaga ttgtgaatgc | 68160 |
| aggaatgact gggccacacc cctcccgtgc acgcccctc ctgccctgca cccacagcc | 68220 |
| cagccccccg tgctggatgc cccccacag cagaggtgct gttctgtgat cccctgggaa | 68280 |
| agacgccctc aacctccacc ctgtcccacg gcccaaggaa gacaagacac aggccctctc | 68340 |
| ctcacagtct ccccacctgg ctcctgctgg gaccctcaag gtgtgaacag ggaggatggt | 68400 |
| tgtctgggtg gccccctagga gcccagatct tcactccaca gaccccaacc caagcacccc | 68460 |
| cttctgcagg gcccagctca tcccctcct cctccctctg ctctcctctc gtcgcctcta | 68520 |
| cgggaaatcc gggactcagc agtaaccctc aggaagcagg gcccaggcgc cgtttaatag | 68580 |
| gaggcttcct cacaatgaaa cttttagaaa gccttgacta caatgatgac cttggtgtgg | 68640 |
| ctgtgaacac tgtcagctcc cacagctgct gcagcaaaaa atgtccatag acagggtggg | 68700 |
| ggcccggggt cgtctgctgt cctgctcagc ccacagcacg catggaggat ctgaggtgcc | 68760 |
| acacctgacg cccaggccag aacatgcctc cctccagggt gacctgccat gtcctgcatt | 68820 |
| gctgagggga caggggcagc ctatgaggat ctggggccag gagatgaatc ctattaaccc | 68880 |
| agaggaaaac taacaggacc caagcaccct ccccgttgaa gctgacctgc ccagaggggc | 68940 |
| ctgggcccac cccacacacc ggggcggaat gtgtacaggc cccggtctct gtgggtgttc | 69000 |
| cgctaactgg ggctcccagt gctcacccca caactaaagc gagccccagc ctccagagcc | 69060 |
| cccgaaggag atgccgccca aagcccagc cccatccag gaggcccag agctcagggc | 69120 |
| gccggggcag attctgaaca gccccgagtc acggtgggta caactggaac gaccaccgtg | 69180 |
| agaaaaactg tgtccaaaac tgtctcctgg ccctgctgg aggccgcgcc agagagggga | 69240 |
| gcagccgccc cgaacctagg tcctgctcag ctcacacgac ccccagcacc cagagcacag | 69300 |

```
tggagtcccc actgaatggt gaggatgggg accagggctc caggggtca tggaagggc    69360 tggaccccat cctactgcta tggtcccagt gctcctggcc agaaacgacc ctaccaccga    69420
caagagtccc tcagggaaac gggggtcact ggcacctccc agcatcaacc ccaggcagca    69480
caggcataaa ccccacatcc agagccgact ccaggagcag agacacccca gtaccctggg    69540
ggacaccgac cctgatgact ccccactgga atccacccca gagtccacca ggaccaaaga    69600
ccccgcccct gtctctgtcc ctcactcagg acctgctgcg gggcgggcca tgagaccaga    69660
ctcgggctta gggaacacca ctgtggcccc aacctcgacc aggccacagg cccttccttc    69720
ctgccctgcg gcagcacaga ctttgggtc tgtgcagaga ggaatcacag aggccccagg    69780
ctgaggtggt gggggtggaa ggccccagg aggtggccca cttcccttcc tcccagctgg    69840
aacccaccat gaccttctta agataggggt gtcatccgag gcaggtcctc catgagctc    69900 ccttcaggct cctccctggt cctcactagg cctcagtccc ggctgtggga atgcagccac    69960
cacaggcaca ccaggcagcc cagacccagc cagcctgcag tgcccaagcc cacattctgg    70020
agcagagcag gctgtgtctg ggagagtctg ggctccccac cgccccccg cacacccac    70080 ccaccctgt ccaggcccta tgcaggaggg tcagagcccc ccatgggta tggacttagg    70140 gtctcactca cgcggctccc ctcctgggtg aaggggtctc atgcccagat ccccacagca    70200
gagctggtca aggtggagg cagtggcccc agggccaccc tgacctggac cctcaggctc    70260
ctctagccct ggctgccctg ctgtccctgg gaggcctgga ctccaccaga ccacaggtcc    70320
agggcaccgc ccataggtgc tgcccacact cagttcacag gaagaagata agctccagac    70380
ccccaagact gggacctgcc ttcctgccac cgcttgtagc tccagacctc cgtgcctccc    70440
ccgaccactt acacacgggc cagggagctg ttccacaaag atcaacccca aaccgggacc    70500
gcctggcact cgggccgctg ccacttccct ctccatttgc tcccagcacc tctgtgctcc    70560
ctccctcctc cctccttcag gggaacagcc tgtgcagccc ctccctgcac cccacaccct    70620
ggggaggccc aaccctgcct ccagccctt ctcccccgct gctcttcctg cccatccaga    70680
caaccctggg gtcccatccc tgcagcctac accctggtct ccaccagac ccctgtctct    70740 ccctccagat acccctccca ggccaaccct gcacatgcag gccctcccct tttctgctgc    70800
cagagcctca gtttctaccc tctgtgcta ccccctgcct cctcctgccc acaactcgag    70860
ctcttcctct cctggggccc ctgagccatg gcactgaccg tgcactccca ccccacact    70920 gcccatgccc tcaccttcct cctggacact ctgaccccgc tcccctcttg gacccagccc    70980
tggtatttcc aggacaaagg ctcacccaag tcttccccat gcaggccctt gccctcactg    71040
cccggttaca cggcagcctc ctgtgcacag aagcagggag ctcagcccct tcacaggcag    71100
aaggcactga aagaaatcgg cctccagcac cctgatgcac gtccgcctgt gtctctcact    71160
gcccgcacct gcagggaggc tcggcactcc ctgtaaagac gagggatcca ggcagcaaca    71220
tcatgggaga atgcagggct cccagacagc ccagccctct cgcaggcctc tcctgggaag    71280
agacctgcag ccaccactga acagccacgg agcccgctgg atagtaactg agtcagtgac    71340
cgacctggag ggcaggggag cagtgaaccg gagcccagac catagggaca gagaccagcc    71400
gctgacatcc cgagcccctc actggcggcc ccagaacacc gcgtggaaac agaacagacc    71460
cacattccca cctggaacag ggcagacact gctgagcccc cagcaccagc cctgagaaac    71520
accaggcaac ggcatcagag ggggctcctg agaaagaaag gaggggaggt ctccttcacc    71580
agcaagtact tcccttgacc aaaaacaggg tccacgcaac tcccccagga caaaggagga    71640
```

```
gcccctgta cagcactggg ctcagagtcc tctccaacac accctgagtt tcagacaaaa    71700
accccctgga aatcatagta tcagcaggag aactagccag agacagcaag aggggactca    71760
gtgactcccg cggggacagg aggattttgt gggggctcgt gtcactgtga ggatattgta    71820
gtagtaccag ctgctatgcc cacagtgaca cagcccatt cccaaagccc tgctgtaaac    71880
gcttccactt ctggnnnggg tgtgtaagag gggatgcggg cagagcctga gcagggcctt    71940
ttgctgtttc tgctttcctg tgcagagagt tccataaact ggtgttcgag atcaatggct    72000
gggagtgagc ccaggaggac agcgtgggaa gagcacaggg aaggaggacc agccgctatc    72060
ctacactgtc atctttcgaa agtttgcctt gtgcccacac tgctgcatca tgggatgctt    72120
aacagctgat gtagacacag ctaaagagag aatcagtgag atggatttgc agcacagatc    72180
tgaataaatt ctccagaatg tggagcagca cagaagcaag cacacagaaa gtgcctgatg    72240
caaggacaaa gttcagtggg caccttcagg cattgctgct gggcacagac actctgaaaa    72300
gccctggcag gaactccctg tgacaaagca gaaccctcag gcaatgccag ccccagagcc    72360
ctccctgaga gcctcatggg caaagatgtg cacaacaggt gtttctcata gccccaaact    72420
gagagcaaag caaacgtcca tctgaaggag aacaggcaaa taaacgatgg caggttcatg    72480
aaatgcaaac ccagacagcc acaagcacaa agtacaggt ttataagcga ctctggttga    72540
gttcatgaca atgctgagta attggagtaa caaagtaaac tccaaaaaat actttcaatg    72600
tgatttcttc taaataaaat ttacaccctg caaaatgaac tgtcttctta agggatacat    72660
ttcccagtta gaaaaccata agaaaaccaa agaaaaggat gatcacataa acacagtggt    72720
ggttacttct gctggggaag gaagagggta tgaactgaga tacacagggt gggcaagtct    72780
cctaacaaga acagaacgaa tacattacag taccttgaaa acagcagtta aacttctaaa    72840
ttgcaagaag aggaaaatgc acacagttgt gtttagaaaa ttctcagtcc agcactgttc    72900
ataatagcaa agacattaac ccaggtcgga taaataagcg atgacacagg caattgcaca    72960
atgatacaga catatattta gtatatgaga catcgatgat gtatccccaa ataaacgact    73020
ttaaagagat aaagggctga tgtgtggtgg cattcacctc cctgggatcc ccggacaggt    73080
tgcaggctca ctgtgcagca gggcaggcgg gtacctgctg gcagttcctg ggcctgatg    73140 tggagcaagc gcagggccat atatcccgga ggacggcaca gtcagtgaat tccagagaga    73200
agcaactcag ccacactccc caggcagagc ccgagaggga cgcccacgca cagggaggca    73260
gagcccagca cctccgcagc cagcaccacc tgtgcacggg ccaccacctt gcaggcacag    73320
agtgggtgct gagaggaggg gcagggacac caggcagggt gagcacccag agaaaactgc    73380
agacgcctca cacatccacc tcagcctccc ctgacctgga cctcactggc ctgggcctca    73440
cttaacctgg gcttcacctg accttggcct cacctgactt ggacctcgcc tgtcccaagc    73500
tttacctgac ctgggcctca actcacctga acgtctcctg acctgggttt aacctgtcct    73560
ggaactcacc tggccttggc ttcccctgac ctggacctca tctggcctgg gcttcacctg    73620
gcctgggcct cacctgacct ggacctcatc tggcctggac ctcacctggc ctggacttca    73680
cctggcctgg gcttcacctg acctggacct cacctggcct caggcctcac ctgcacctgc    73740
tccaggtctt gctggagcct gagtagcact gagggtgcag aagctcatcc agggttgggg    73800
aatgactcta gaagtctccc acatctgacc tttctgggtg gaggcagctg gtggccctgg    73860
gaatataaaa atctccagaa tgatgactct gtgatttgtg ggcaacttat gaacccgaaa    73920
ggacatggcc atggggtggg tagggacata gggacagatg ccagcctgag gtggagcctc    73980
aggacacagg tgggcacgga cactatccac ataagcgagg gatagacccg agtgtcccca    74040
```

```
cagcagacct gagagcgctg ggcccacagc ctcccctcag agccctgctg cctcctccgg    74100
tcagccctgg acatcccagg tttccccagg cctggcggta ggtttagaat gaggtctgtg    74160
tcactgtggt attacgatat tttgactggt tattataacc acagtgtcac agagtccatc    74220
aaaaacccat gcctggaagc ttcccgccac agccctcccc atggggccct gctgcctcct    74280
caggtcagcc ccggacatcc tgggtttccc caggctgggc ggtaggtttg ggtgaggtc     74340 tgtgtcactg tggtattact atggttcggg gagttattat aaccacagtg tcacagagtc    74400
catcaaaaac ccatccctgg gagcctcccg ccacagccct ccctgcaggg gaccggtacg    74460
tgccatgtta ggattttgat cgaggagaca gcaccatggg tatggtggct accacagcag    74520
tgcagcctgt gacccaaacc cgcagggcag caggcacgat ggacaggccc gtgactgacc    74580
acgctgggct ccagcctgcc agccctggag atcatgaaac agatggccaa ggtcaccta     74640 caggtcatcc agatctggct ccgaggggtc tgcatcgctg ctgccctccc aacgccagtc    74700
caaatgggac agggacggcc tcacagcacc atctgctgcc atcaggccag cgatcccaga    74760
agcccctccc tcaaggctgg ccacatgtgt ggacactgag agccctcata tctgagtagg    74820
ggcaccagga ggggaggggct ggccctgtgc actgtccctg ctcctgtggt ctctggcctg    74880
cctggccctg acacctgagc ctctcctggg tcatttccaa gacagaagac attcctgggg    74940
acagccggag ctgggcgtcg ctcatcctgc ccggccgtcc tgagtcctgc tcatttccag    75000
acctcaccgg ggaagccaac agaggactcg cctcccacat tcagagacaa gaaccttcc    75060 agaaatccct gcctctctcc ccagtggaca ccctcttcca ggacagtcct cagtggcatc    75120
acagcggcct gagatcccca ggacgcagca ccgctgtcaa taggggcccc aaatgcctgg    75180
accagggcct gcgtgggaaa ggcctctggc cacactcggg cttttttgtga agggccctcc    75240 tgctgtgtga ctacagtaac taccatagtg atgaacccag tggcaaaaac tggctggaaa    75300
cccaggggct gtgtgcacgc ctcagcttgg agctctccag gagcacaaga gccgggccca    75360
aggatttgtg cccagaccct cagcctctag ggacacctgg gccatctcag cctgggctgg    75420
tgccctgcac accatcttcc tccaaatagg ggcttcagag ggctctgagg tgacctcact    75480
catgaccaca ggtgacctgg cccttccctg ccagctatac cagaccctgt cttgacagat    75540
gccccgattc caacagccaa ttcctgggac cctgaatagc tgtagacacc agcctcattc    75600
cagtacctcc tgccaattgc ctggattccc atcctggctg gaatcaagaa ggcagcatcc    75660
gccaggctcc caacaggcag gactcccgca caccctcctc tgagaggccg ctgtgttccg    75720
cagggccagg ccctggacag ttcccctcac ctgccactag agaaacacct gccattgtcg    75780
tccccacctg gaaaagacca ctcgtggagc ccccagcccc aggtacagct gtagagacag    75840
tcctcgaggc ccctaagaag gagccatgcc cagttctgcc gggaccctcg gccaggccga    75900
caggagtgga cgctggagct gggcccacac tgggccacat aggagctcac cagtgagggc    75960
aggagagcac atgccgggga gcacccagcc tcctgctgac cagaggcctg ccccagagcc    76020
caggaggctg cagaggcctc tccagggaga cactgtgcat gtctggtacc taagcagccc    76080
cccacgtccc cagtcctggg ggccctggc tcagctgtct gggccctccc tgctccctgg    76140
gaagctcctc ctgacagccc cgcctccagt tccaggtgtg gttattgtca ggcgatgtca    76200
gactgtggtg gatatagtgg ctacgattac cacagtggtg ccgcccatag cagcaaccag    76260
gccaagtaga caggccctg ctgcgcagcc ccaggcatcc acttcacctg cttctcctgg    76320
ggctctcaag gctgctgtct gtcctctggc cctctgtggg gagggttccc tcagtgggag    76380
```

| | |
|---|---|
| gtctgtgctc cagggcaggg atgattgaga tagaaatcaa aggctggcag ggaaaggcag | 76440 |
| cttcccgccc tgagaggtgc aggcagcacc acggagccac ggagtcacag agccacggag | 76500 |
| cccccattgt gggcatttga gagtgctgtg cccccggcag gcccagccct gatggggaag | 76560 |
| cctgtcccat cccacagccc gggtcccacg ggcagcgggc acagaagctg ccaggttgtc | 76620 |
| ctctatgatc ctcatccctc cagcagcatc ccctccacag tggggaaact gaggcttgga | 76680 |
| gcaccacccg gcccctgga aatgaggctg tgagcccaga cagtgggccc agagcactgt | 76740 |
| gagtaccccg gcagtacctg gctgcaggga tcagccagag atgccaaacc ctgagtgacc | 76800 |
| agcctacagg aggatccggc cccacccagg ccactcgatt aatgctcaac cccctgccct | 76860 |
| ggagacctct tccagtacca ccagcagctc agcttctcag ggcctcatcc ctgcaaggaa | 76920 |
| ggtcaagggc tgggcctgcc agaaacacag caccctccct agccctggct aagacagggt | 76980 |
| gggcagacgg ctgtggacgg gacatattgc tgggcatttt ctcactgtca cttctgggtg | 77040 |
| gtagctctga caaaaacgca gaccctgcca aaatccccac tgcctcccgc taggggctgg | 77100 |
| cctggaatcc tgctgtccta ggaggctgct gacctccagg atggctccgt ccccagttcc | 77160 |
| agggcgagag cagatcccag gcaggctgta ggctgggagg ccaccctgc ccttgccggg | 77220 |
| gttgaatgca ggtgcccaag gcaggaaatg gcatgagcac agggatgacc gggacatgcc | 77280 |
| ccaccagagt gcgccccttc ctgctctgca ccctgcaccc ccaggccag cccacgacgt | 77340 |
| ccaacaactg ggcctgggtg gcagccccac ccagacagga cagacccagc ccctgagga | 77400 |
| ggtcctgcca gggggagcta agagccatga aggagcaaga tatggggccc ccgatacagg | 77460 |
| cacagatgtc agctccatcc aggaccaccc agcccacacc ctgagaggaa cgtctgtctc | 77520 |
| cagcctctgc aggtcgggag gcagctgacc cctgacttgg acccctattc cagacaccag | 77580 |
| acagaggcgc aggcccccca gaaccagggt tgagggacgc cccgtcaaag ccagacaaaa | 77640 |
| ccaaggggtg ttgagcccag caagggaagg cccccaaaca gaccaggagg tttctgaagg | 77700 |
| tgtctgtgtc acagtggggt atagcagcag ctggtaccac agtgacactc acccagccag | 77760 |
| aaacccccatt ccaagtcagc ggaagcagag agagcaggga ggacacgttt aggatctgag | 77820 |
| actgcacctg acacccaggc cagcagacgt ctcccctcca gggcacccca ccctgtcctg | 77880 |
| catttctgca agatcagggg cggcctgagg gggggtctag ggtgaggaga tgggtcccct | 77940 |
| gtacaccaag gaggagttag gcaggtcccg agcactctcc ccattgaggc tgacctgccc | 78000 |
| agagagtcct gggcccaccc cacacaccgg ggcggaatgt gtgcaggcct cggtctctgt | 78060 |
| gggtgttccg ctagctgggg ctcacagtgc tcaccccaca cctaaaatga gccacagcct | 78120 |
| ccggagcccc cgcaggagac cccgcccaca agcccagccc ccacccagga ggccccagag | 78180 |
| ctcagggcgc cccgtcggat tccgaacagc cccgagtcac agcgggtata accggaacca | 78240 |
| ccactgtcag aatagctacg tcaaaaactg tccagtggcc actgccggag gccccgccag | 78300 |
| agagggcagc agccactctg atcccatgtc ctgccggctc ccatgacccc cagcacgcgg | 78360 |
| agccccacag tgtccccact ggatggggag acaagagctg gggattccgg cgggtcgggg | 78420 |
| caggggcttg atcgcatcct tctgccgtgg ctccagtgcc cctggctgga gttgacccctt | 78480 |
| ctgacaagtg tcctcagaga gacaggcatc accggcgcct cccaacatca accccaggca | 78540 |
| gcacaggcac aaacccaca tccagagcca actccaggag cagagacacc ccaatacccct | 78600 |
| ggggaccc gacctgatg acttcccact ggaattcgcc gtagagtcca ccaggaccaa | 78660 |
| agaccctgcc tctgcctctg tccctcactc aggacctgct gccgggcgag gccttgggag | 78720 |
| cagacttggg cttaggggac accagtgtga ccccgacctt gaccaggacg cagacctttc | 78780 |

```
cttcctttcc tggggcagca cagactttgg ggtctgggcc aggaggaact tctggcaggt   78840
cgccaagcac agaggccaca ggctgaggtg gccctggaaa gacctccagg aggtggccac   78900
tccccttcct cccagctgga ccccatgtcc tccccaagat aagggtgcca tccaaggcag   78960
gtgctccttg gagccccatt cagactcctc cctggacccc actgggcctc agtcccagct   79020
ctggggatga agccaccaca agcacaccag gcagcccagg cccagccacc ctgcagtgcc   79080
caagcacaca ctctggagca gagcagggtg cctctgggag gggctgagct ccccacccca   79140
cccccacctg cacccccac ccaccctgc ccagcggctc tgcaggaggg tcagagcccc   79200
acatggggta tggacttagg gtctcactca cgtggctccc atcatgagtg aaggggcctc   79260
aagcccaggt tcccacagca gcgcctgtcg caagtggagg cagaggcccg agggccaccc   79320
tgacctggtc cctgaggttc ctgcagccca ggctgccctg ctgtccctgg aggcctggg   79380 ctccaccaga ccacaggtcc agggcaccgg gtgcaggagc cacccacaca cagctcacag   79440
gaagaagata agctccagac ccccagggcc agaacctgcc ttcctgctac tgcttcctgc   79500
cccagacctg ggcgccctcc cccgtccact tacacacagg ccaggaagct gttcccacac   79560
agaacaaccc caaaccagga ccgcctggca ctcaggtggc tgccatttcc ttctccattt   79620
gctcccagcg cctctgtcct ccctggttcc tccttcgggg aacagcctg tgcagccagt   79680 ccctgcagcc cacaccctgg ggagacccaa ccctgcctgg ggcccttcca accctgctgc   79740
tcttactgcc cacccagaaa actctgggt cctgtccctg cagtccctac cctggtctcc   79800
acccagaccc ctgtgtatca ctccagacac ccctcccagg caaaccctgc acctgcaggc   79860
cctgtcctct tctgtcgcta gagcctcagt ttctccccc tgtgcccaca ccctacctcc   79920
tcctgcccac aactctaact cttcttctcc tggagcccct gagccatggc attgaccctg   79980
ccctcccacc acccacagcc catgccctca ccttcctcct ggccactccg accccgcccc   80040
ctctcaggcc aagccctggt atttccagga caaaggctca cccaagtctt tcccaggcag   80100
gcctgggctc ttgccctcac ttcccggtta cacgggagcc tcctgtgcac agaagcaggg   80160
agctcagccc ttccacaggc agaaggcact gaaagaaatc ggcctccagc accttgacac   80220
acgtccgccc gtgtctctca ctgcccgcac ctgcaggag gctccgcact ccctctaaag   80280
acaagggatc caggcagcag catcacggga gaatgcaggg ctcccagaca tcccagtcct   80340
ctcacaggcc tctcctggga agagacctgc agccaccacc aaacagccac agaggctgct   80400
ggatagtaac tgagtcaatg accgacctgg agggcagggg agcagtgagc cggagcccat   80460
accatgggga cagagaccag ccgctgacat cccgagctcc tcaatggtgg ccccataaca   80520
cacctaggaa acataacaca cccacagccc cacctggaac agggcagaga ctgctgagcc   80580
cccagcacca gccccaagaa acaccaggca acagtatcag aggggctcc cgagaaagag   80640 aggaggggag atctccttca ccatcaaatg cttcccttga ccaaaaacag ggtccacgca   80700
actcccccag gacaaaggag gagccccta tacagcactg ggctcagagt cctctctgag   80760
acaccctgag tttcagacaa caacccgctg gaatgcacag tctcagcagg agaacagacc   80820
aaagccagca aaagggacct cggtgacacc agtagggaca ggaggatttt gtggggctc   80880 gtgtcactgt gaggatattg tagtggtggt agctgctact cccacagtga cacagaccca   80940
ttcccaaagc cctactgcaa acacacccac tcctggggct gaggggctgg gggagcatct   81000
gggaagtagg gtcagggggt gtctatcaat gtccaaaatg caccagactc cccgccaaac   81060 accacccccac cagccagcga gcagggtaaa cagaaaatga gaggctctgg gaagcttgca   81120
```

| | |
|---|---|
| caggccccaa ggaaagagct ttggcaggtg tgcaagaggg gatgcaggca gagcctgagc | 81180 |
| agggcctttt gctgtttctg ctttcctgtg cagagagttc cataaactgg tgttcaagat | 81240 |
| cagtggctgg gaatgagccc aggagggcag tctgtgggaa gagcacaggg aaggaggacc | 81300 |
| agccgctatc ctacactgtc atctttcaaa agtttgcctt gtgaccacac tattgcatca | 81360 |
| tgggatgctt aagagctgat gtagacacag ctaaagagag aatcagtgag atgaatttgc | 81420 |
| agcatagatc tgaataaact ctccagaatg tggagcagta cagaagcaaa cacacagaaa | 81480 |
| gtgcctgatg caaggacaaa gttcagtggg caccttcagg cattgctgct gggcacagac | 81540 |
| actctgaaaa gccctggcag gatctccctg cgacaaagca gaaccctcag gcaatgccag | 81600 |
| ccccagagcc ctccctgaga gcgtcatggg gaaagatgtg cagaacagct gattatcata | 81660 |
| gactcaaact gagaacagag caaacgtcca tctgaagaac agtcaaataa gcaatggtag | 81720 |
| gttcatgcaa tgcaaaccca gacagccagg ggacaacagt agagggctac aggcggcttt | 81780 |
| gcggttgagt tcatgacaat gctgagtaat tggagtaaca gaggaaagcc caaaaaatac | 81840 |
| ttttaatgtg atttcttcta aataaaattt acaccaggca aaatgaactg tcttcttaag | 81900 |
| ggataaactt tccctggaa aaactacaag gaaaattaag aaaacgatga tcacataaac | 81960 |
| acagttgtgg ttacttctac tggggaagga agagggtatg agctgagaca cacagagtcg | 82020 |
| gcaagtctcc aagcaagcac agaacgaata cattacagta ccttgaatac agcagttaaa | 82080 |
| cttctaaatc gcaagaagag gaaaatgcac acagctgtgt ttagaaaatt ctcagtccag | 82140 |
| cactattcat aatagcaaag acattaaccc aggttggata aataaatgat gacacaggca | 82200 |
| attgcacaat gatacagaca tacatttagt acatgagaca tcgatgatgt atccccaaag | 82260 |
| aaatgacttt aaagagaaaa ggcctgatgt gtggtggcac tcacctccct gggatccccg | 82320 |
| gacaggttgc aggcacactg tgtgcagggg caggctggta catgctggca gctcctgggg | 82380 |
| cctgatgtgg agcaagcgca gggctgtata cccccaagga tggcacagtc agtgaattcc | 82440 |
| aaagagaagc agctcagcca cactgcccag gcagagcccg agagggacgc ccacgcacag | 82500 |
| ggaggcagag cccagctcct ccacagccac caccacctgt gcacgggcca ccaccttgca | 82560 |
| ggcacagagt gggtgctgag aggaggggca gggacaccag gcagggtgag cacccagaga | 82620 |
| aaactgcaga agcctcacac atccacctca gcctcccctg acctggacct cacctggtct | 82680 |
| ggacctcacc tggcctgggc ctcacctgac ctggacctca cctggcctgg gcttcacctg | 82740 |
| acctggacct cacctggcct ccggcctcac ctgcacctgc tccaggtctt gctggaacct | 82800 |
| gagtagcact gaggctgcag aagctcatcc agggttgggg aatgactctg gaactctccc | 82860 |
| acatctgacc tttctgggtg gaggcatctg gtggccctgg gaatataaaa agccccagaa | 82920 |
| tggtgcctgc gtgatttggg ggcaatttat gaacccgaaa ggacatggcc atggggtggg | 82980 |
| tagggacata gggacagatg ccagcctgag gtggagcctc aggacacagt tggacgcgga | 83040 |
| cactatccac ataagcgagg gacagacccg agtgttcctg cagtagacct gagagcgctg | 83100 |
| ggcccacagc ctcccctcgg tgccctgctg cctcctcagg tcagccctgg acatcccggg | 83160 |
| tttccccagg ccagatggta ggtttgaagt gaggtctgtg tcactgtggt attatgatta | 83220 |
| cgtttggggg agttatcgtt ataccccacag catcacacgg tccatcagaa acccatgcca | 83280 |
| cagccctccc cgcaggggac cgccgcgtgc catgttacga ttttgatcga ggacacagcg | 83340 |
| ccatgggtat ggtggctacc acagcagtgc agcccatgac ccaaacacac agggcagcag | 83400 |
| gcacaatgga caggcctgtg agtgaccatg ctgggctcca gcccgccagc cccggagacc | 83460 |
| atgaaacaga tggccaaggt caccccacag ttcagccaga catggctccg tggggtctgc | 83520 |

```
atcgctgctg ccctctaaca ccagcccaga tggggacaag gccaacccca cattaccatc    83580
tcctgctgtc cacccagtgg tcccagaagc ccctccctca tggctgagcc acatgtgtga    83640
accctgagag cacccatgt cagagtaggg gcagcagaag ggcggggctg ccctgtgca     83700 ctgtccctgc acccatggtc cctcgcctgc ctggccctga cacctgagcc tcttctgagt    83760
catttctaag atagaagaca ttccggggga cagccggagc tgggcgtcgc tcatcctgcc    83820
cggccgtcct gagtcctgct tgtttccaga cctcaccagg gaagccaaca gaggactcac    83880
ctcacacagt cagagacaaa gaaccttcca gaaatccctg tctcactccc cagtgggcac    83940
cttcttccag gacattcctc ggtcgcatca cagcaggcac ccacatctgg atcaggacgg    84000
cccccagaac acaagatggc ccatggggac agccccacaa cccaggcctt cccagacccc    84060
taaaaggcgt cccaccccct gcacctgccc cagggctaaa aatccaggag gcttgactcc    84120
cgcataccct ccagccagac atcacctcag cccctcctg gagggacag gagcccggga     84180 gggtgagtca gacccacctg ccctcgatgg caggcgggga agattcagaa aggcctgaga    84240
tccccaggac gcagcaccac tgtcaatggg ggccccagac gcctggacca gggcctgcgt    84300
gggaaaggcc gctgggcaca ctcagggggct ttttgtgaag gcccctccta ctgtgtgact   84360
acggtgacta ccacagtgat gaaactagca gcaaaaactg gccggacacc cagggaccat    84420
gcacacttct cagcttggag ctctccagga ccagaagagt caggtctgag ggtttgtagc    84480
cagaccctcg gcctctaggg acaccctggc catcacagcg gatgggctgg tgccccacat    84540
gccatctgct ccaaacaggg gcttcagagg gctctgaggt gacttcactc atgaccacag    84600
gtgccctggc cccttccccg ccagctacac cgaaccctgt cccaacagct gccccagttc    84660
caacagccaa ttcctggggc ccagaattgc tgtagacacc agcctcgttc cagcacctcc    84720
tgccaattgc ctggattcac atcctggctg gaatcaagag ggcagcatcc gccaggctcc    84780
caacaggcag gactcccgca caccctcctc tgagaggccg ctgtgttccg cagggccagg    84840
ccctggacag ttcccctcac ctgccactag agaaacacct gccattgtcg tccccacctg    84900
gaaaagacca ctcgtggagc ccccagcccc aggtacagct gtagagagac tccccgaggg    84960
atctaagaag gagccatgcg cagttctgcc gggaccctcg gccaggccga caggagtgga    85020
cactggagct gggcccacac tgggccacat aggagctcac cagtgagggc aggagagcac    85080
atgccgggga gcacccagcc tcctgctgac cagaggcctg ccccagagcc caggaggctg    85140
cagaggcctc tccaggggga cactgtgcat gtctggtccc tgagcagccc cccacgtccc    85200
cagtcctggg ggccctagc acagctgtct ggaccctccc tgttccctgg gaagctcctc     85260
ctgacagccc cgcctccagt tccaggtgtg gttattgtca gggggtgtca gactgtggtg    85320
gatacagcta tggttaccac agtggtgctg cccatagcag caaccaggcc aagtagacag    85380
gcccctgctg tgcagcccca ggcctccagc tcacctgctt ctcctggggc tctcaaggtc    85440
actgttgtct gtactctgcc ctctgtgggg agggttctct cagtgggagg tctgttctca    85500
acatcccagg gcctcatgtc tgcacggaag gccaatggat gggcaacctc acatgccgcg    85560
gctaagatag ggtgggcagc ctggcggggg acagtacata ctgctggggt gtctgtcact    85620
gtgcctagtg gggcactggc tcccaaacaa cgcagtcctc accaaaatcc ccacagcctc    85680
ccctgctagg ggctggcctg atctcctgca gtcctaggag gctgctgacc tccagaatgt    85740
ctccgtcccc agttccaggg cgagagcaga tcccaggccg gctgcagact gggaggccac    85800
cccctccttc ccagggttca ctggaggtga ccaaggtagg aaatggcctt aacacaggga    85860
```

```
tgactgcgcc atccccaac agagtcagcc cctcctgct ctgtaccccg cacccccag    85920 gccagtccac gaaaaccagg gccccacatc agagtcactg cctggcccgg ccctggggcg    85980 gaccctcag ccccccaccct gtctagagga cttgggggga caggacacag gccctctcct    86040
tatggttccc ccacctgcct ccggccggga cccttgggt gtggacagaa aggacacctg    86100
cctaattggc cccaggaac acagaacttc tctccaggga cccagcccg agcacccct    86160 tacccaggac ccagccctgc ccctcctccc ctctgctctc ctctcatcac cccatgggaa    86220
tccggtatcc ccaggaagcc atcaggaagg gctgaaggag gaagcggggc cgtgcaccac    86280
cgggcaggag gctccgtctt cgtgaaccca gggaagtgcc agcctcctag agggtatggt    86340
ccaccctgcc tggggctccc accgtggcag gctgcgggga aggaccaggg acggtgtggg    86400
ggagggctca gggccctgcg ggtgctcctc catcttcggt gagcctcccc cttcacccac    86460
cgtcccgccc acctcctctc caccctggct gcacgtcttc cacaccatcc tgagtcctac    86520
ctacaccaga gccagcaaag ccagtgcaga caaaggctgg ggtgcagggg ggctgccagg    86580
gcagcttcgg ggagggaagg atggaggag gggaggtcag tgaagaggcc cccttcccct    86640
gggtccagga tcctcctctg gaccccgg ctcccatccc ctcctggctc tgggaggaga    86700
agcaggatgg gagaatctgt gcgggaccct ctcacagtgg aatatcccca cagcggctca    86760
ggccagaccc aaaagcccct cagtgagccc tccactgcag tcctgggcct gggtagcagc    86820
ccctcccaca gaggacagac ccagcacccc gaagaagtcc tgccagggg agctcagagc    86880 catgaaagag caggatatgg ggtccccgat acaggcacag acctcagctc catccaggcc    86940
caccgggacc caccatggga ggaacacctg tctccgggtt gtgaggtggc tggcctctgt    87000
ctcggacccc actccagaca ccagacagag gggcaggccc cccaaaacca gggttgaggg    87060
atgatccgtc aaggcagaca agaccaaggg gcactgaccc cagcaaggga aggctcccaa    87120
acagacgagg aggtttctga agctgtctgt atcacagtgg ggtatagcag tggctggtac    87180
cacagtgaca ctcgccaggc cagaaacccc gtcccaagtc agcggaagca gagagagcag    87240
ggaggacacg tttaggatct gaggccgcac ctgacaccca gggcagcaga cgtctcccct    87300
ccagggcacc ctccaccgtc ctgcgtttct tcaagaatag gggcggcctg agggggtcca    87360
gggccaggcg ataggtcccc tctaccccaa ggaggagcca ggcaggaccc gagcaccgtc    87420
cccattgagg ctgacctgcc cagacgggcc tgggcccacc ccacacaccg gggcggaatg    87480
tgtgcaggcc ccagtctctg tgggtgttcc gctagctggg gcccccagtg ctcacccac    87540 acctaaagcg agcccccagcc tccagagccc cctaagcatt ccccgcccag cagcccagcc    87600
cctgccccca cccaggaggc cccagagctc agggcgcctg gtcggattct gaacagcccc    87660
gagtcacagt gggtataact ggaacgacca ccgtgagaaa aactgtgtcc aaaactgact    87720
cctggcagca gtcggaggcc ccgccagaga ggggagcagc cgccctgaac ccatgtcctg    87780
ccggttccca tgaccccag cacccagagc cccacggtgt cccgttgga taatgaggac    87840 aagggctggg ggctccggtg gtttgcggca gggacttgat cacatccttc tgctgtggcc    87900
ccattgcctc tggctggagt tgacccttct gacaagtgtc ctcagaaaga cagggatcac    87960
cggcacctcc caatatcaac cccaggcagc acagacacaa accccacatc cagagccaac    88020
tccaggagca gagacacccc aacactctgg gggaccccaa ccgtgataac tccccactgg    88080
aatccgcccc agagtctacc aggaccaaag gccctgccct gtctctgtcc ctcactcagg    88140
gcctcctgca gggcgagcgc ttgggagcag actcggtctt aggggacacc actgtgggcc    88200
ccaactttga tgaggccact gaccttcct tcctttcctg gggcagcaca gactttgggg    88260
```

```
tctgggcagg gaagaactac tggctggtgg ccaatcacag agcccccagg ccgaggtggc    88320
cccaagaagg ccctcaggag gtggccactc cacttcctcc cagctggacc ccaggtcctc    88380
cccaagatag gggtgccatc caaggcaggt cctccatgga gccccttca gactcctccc     88440 gggacccac tggacctcag tccctgctct gggaatgcag ccaccacaag cacaccagga     88500
agcccaggcc cagccaccct gcagtgggca agcccacact ctggagcaga gcagggtgcg    88560
tctgggaggg gctaacctcc cccccccca cccccatct gcacacagcc acctaccact      88620
gcccagaccc tctgcaggag ggccaagcca ccatgggta tggacttagg gtctcactca     88680
cgtgcctccc ctcctgggag aaggggcctc atgccgagat ccctgcagca ctagacacag    88740
ctggaggcag tggccccagg gccaccctga cctggcatct aaggctgctc cagcccagac    88800
agcactgccg ttcctgggaa gcctgggctc caccagacca caggtccagg gcacagccca    88860
caggagccac ccacacacag ctcacaggaa gaagataagc tccagacccc agggcgggac    88920
ctgccttcct gccaccactt acacacaggc caggagctg ttcccacaca gatcaacccc     88980
aaaccgggac tgcctggcac tagggtcact gccatttccc tctccattcc ctcccagtgc    89040
ctctgtgctc cctccttctg gggaacaccc tgtgcagccc ctccctgcag cccacacgct    89100
ggggagaccc caccctgcct cgggcctttt ctacctgctg cacttgccgc ccacccaaac    89160
aaccctgggt acgtgaccct gcagtcctca ccctgatctg caaccagacc cctgtccctc    89220
cctctaaaca cccctcccag gccaactctg cacctgcagg ccctccgctc ttctgccaca    89280
agagcctcag gttttcctac ctgtgcccac cccctaaccc ctcctgccca caacttgagt    89340
tcttcctctc ctggagccct tgagccatgg cactgaccct acactcccac ccacacactg    89400
cccatgccat caccttcctc ctggacactc tgaccacgct cccctccctc tcagacccgg    89460
ccctggtatt tccaggacaa aggctcaccc aagtcttccc catgcaggcc cttgccctca    89520
ctgcctggtt acacgggagc ctcctgtgcg cagaagcagg gagctcagct cttccacagg    89580
cagaaggcac tgaaagaaat cggcctccag tgccttgaca cacgtccgcc tgtgtctctc    89640
actgcctgca cctgcaggga ggctccgcac tccctctaaa gatgagggat ccaggcagca    89700
acatcacggg agaatgcagg gctcccagac agccagccc tctcgcaggc ctctcctggg     89760
aagagacctg cagccaccac tgaacagcca cggaggtcgc tggatagtaa ccgagtcagt    89820
gaccgacctg gagggcaggg gagcagtgaa ccggagccca taccataggg acagacacca    89880
gccgctaaca tcccgagccc ctcactggcg gccccagaac accccgtgga aacagaacag    89940
acccacagtc ccacctggaa cagggcagac actgctgagc cccagcacc agccccaaga     90000 aacactaggc aacagcatca gagggggctc ctgagaaaga gaggagggga ggtctccttc    90060
accatcaaat gcttcccttg accaaaaaca gggtccacgc aactccccca ggacaaagga    90120 ggagcccct gtacagcact gggctcagag tcctctctga dacaggctca gtttcagaca     90180
acaacccgct ggaatgcaca gtctcagcag gagagccagg ccagagccag caagaggaga    90240
ctcggtgaca ccagtctcct gtagggacag gaggattttg tggggttcg tgtcactgtg     90300 agcatattgt ggtggtgact gctattccca cagtgacaca acccccattcc taaagcccta   90360 ctgcaaacgc acccactcct ggggctgagg ggctgggggga gcatctggga agtatggcct   90420
aggggtgtcc atcaatgccc aaaatgcacc agactctccc caagacatca ccccaccagc    90480
cagtgagcag agtaaacaga aaatgagaag cagctgggaa gcttgcacag gccccaagga    90540
aagagctttg gcaggtgtgc aagagggat gtgggcagag cctgagcagg gccttttgct     90600
```

```
gtttctgctt tcctgtgcag agagttccat aaactggtat tcaggatcaa tggctgggag    90660
tgagcccagg aggacagtgt gggaagagca cagggaagga ggaccagccg ctatcctaca    90720
ctgtcatctt ttgaaagttt gccctgtgcc cacaatgctg catcatggga tgcttaacag    90780
ctgatgtaga cacagctaaa gagagaatca gtgaaatgca tttgcagcac agatctgaat    90840
aaatcctcca gaatgtggag cagcacagaa gcaagcacac agaaagtgcc tgatgccaag    90900
gcaaagttca gtgggcacct tcaggcattg ctgctgggca cagacactct gaaaagcact    90960
ggcaggaact gcctgtgaca aagcagaacc ctcaggcaat gccagcccta gagcccttcc    91020
tgagaacctc atgggcaaag atgtgcagaa cagctgtttg tcatagcccc aaactatggg    91080
gctggacaaa gcaaacgtcc atctgaagga caacagacaa ataaacgatg gcaggttcat    91140
gaaatgcaaa ctaggacagc cagaggacaa cagtagagag ctacaggcgg ctttgcggtt    91200
gagttcatga caatgctgag taattggagt aacagaggaa agcccaaaaa atacttttaa    91260
tgtgatttct tctaaataaa atttacaccc ggcaaaatga actatcttct taagggataa    91320
actttcccct ggaaaaacta taaggaaaat caagaaaacg atgatcacat aaacacagtg    91380
gtggttactt ctactgggga aggaagaggg tatgagctga gacacacaga gtcggcaagt    91440
ctcctaacaa gaacagaaca aatacattac agtaccttga aaacagcagt taaacttcta    91500
aatcgcaaga gaggaaaat gcacacacct gtgtttagaa aattctcagt ccagcactgt    91560
tcataatagc aaagacatta acccaggttg gataaataag cgatgacaca ggcaattgca    91620
caatgataca gacatacatt cagtatatga gacatcgatg atgtatcccc aaagaaatga    91680
ctttaaagag aaaaggcctg atgtgtggtg gcaatcacct ccctgggcat ccccggacag    91740
gctgcaggct cactgtgtgg cagggcaggc aggcacctgc tggcagctcc tggggcctga    91800
tgtggagcag gcacagagct gtatatcccc aaggaaggta cagtcagtgc attccagaga    91860
gaagcaactc agccacactc cctggccaga acccaagatg cacacccatg cacagggagg    91920
cagagcccag cacctccgca gccaccacca cctgcgcacg gccaccacc ttgcaggcac    91980 agagtgggtg ctgagaggag gggcagggac accaggcagg gtgagcaccc agagaaaact    92040
gcagaagcct cacacatcca cctcagcctc ccctgacctg gacctcacct ggcctgggcc    92100
tcacctgacc tggacctcac ctggcctggg cttcacctgg cctgggcttc acctgacctg    92160
gacctcacct ggcctcgggc ctcacctggc ctgggcttca cctggcctgg gcttcacctg    92220
acctggacct cacctggcct gggcctcacc tgacctggac ctcacctggc ctgggcttca    92280
cctggcctgg gcttcacctg gcctgggctt cacctgacct ggacctcacc tggcctgggc    92340
ttcacctgac ctggacctca cctggcctca ggcctcacct gcacctgctc caggtcttgc    92400
tggagcctga gtagcactga ggctgtaggg actcatccag ggttggggaa tgactctgca    92460
actctcccac atctgacctt tctgggtgga ggcacctggt ggcccaggga atataaaag    92520 ccccagaatg atgcctgtgt gatttggggg caatttatga acccgaaagg acatggccat    92580
ggggtgggta gggacagtag ggacagatgt cagcctgagg tgaagcctca ggacacaggt    92640
gggcatggac agtgtccacc taagcgaggg acagacccga gtgtccctgc agtagacctg    92700
agagcgctgg gccacagcc tccctcgggg gcctgctgc ctcctcaggt cagccctgga    92760
catcccgggt ttccccaggc ctggcggtag gtttgaagtg aggtctgtgt cactgtggta    92820
ttactatgat agtagtggtt attactacca cagtgtcaca gagtccatca aaaactcatg    92880
cctgggagcc tccaccaca gccctccctg cgggggaccg ctgcatgccg tgttaggatt    92940
ttgatcgagg acacggcgcc atgggtatgg tggctaccac agcagtgcag cccatgaccc    93000
```

```
aaacacacgg ggcagcagaa acaatggaca ggcccacaag tgaccatgat gggctccagc   93060
ccaccagccc cagagaccat gaaacagatg gccaaggtca ccctacaggt catccagatc   93120
tggctccaag gggtctgcat cgctgctgcc ctcccaacgc caaaccagat ggagacaggg   93180
ccggccccat agcaccatct gctgccgtcc acccagcagt cccggaagcc cctccctgaa   93240
cgctgggcca cgtgtgtgaa ccctgcgagc ccccatgtc agagtagggg cagcaggagg    93300
gcggggctgg ccctgtgcac tgtcactgcc cctgtggtcc ctggcctgcc tggccctgac   93360
acctgagcct ctcctgggtc atttccaaga cattcccagg acagccgga gctgggagtc    93420 gctcatcctg cctggctgtc ctgagtcctg ctcatttcca gacctcacca gggaagccaa   93480
cagaggactc acctcacaca gtcagagaca acgaaccttc agaaatccc tgtttctctc    93540 cccagtgaga gaaaccctct tccagggttt ctcttctctc ccaccctctt ccaggacagt   93600
cctcagcagc atcacagcgg gaacgcacat ctggatcagg acggccccca gaacacgcga   93660
tggcccatgg ggacagccca gcccttccca gaccctaaa aggtatcccc accttgcacc    93720
tgccccaggg ctcaaactcc aggaggcctg actcctgcac accctcctgc cagatatcac   93780
ctcagccccc tcctggaggg gacaggagcc cgggagggtg agtcagaccc acctgccctc   93840
aatggcaggc ggggaagatt cagaaaggcc tgagatcccc aggacgcagc accactgtca   93900
atggggcccc cagacgcctg gaccagggcc tgtgtgggaa aggcctctgg ccacactcag   93960 gggcttttg tgaagggccc tcctgctgtg tgactacggt ggtaactccc acagtgatga    94020
aaccagcagc aaaaactgac tggactcgca gggtttatgc acacttctcg gctcggagct   94080
ctccaggagc acaagagcca ggcccgaggg tttctgccca gaccctcggc ctctagggac   94140
acccgggcca tcttagccga tgggctggtg ccctgcacac cgtgtgctgc caaacagggg   94200
cttcagaggg ctctgaggtg acttcactca tgaccacagg tgccctggtc ccttcactgc   94260
cagctgcacc agaccctgtt ccagagagatg ccccagttcc aaaagccaat tcctggggcc   94320
gggaattact gtagacacca gcctcattcc agtacctcct gccaattgcc tggattccca   94380
tcctggctgg aatcaagagg gcagcatccg ccaggctccc aacaggcagg actcccacac   94440
accctcctct gagaggccgc tgtgttccgc agggccaggc cgcagacagt tcccctcacc   94500
tgcccatgta gaaacacctg ccattgtcgt ccccacctgg aaaagaccac ttgtggagcc   94560
cccagcccca ggtacagctg tagagagagt cctcgaggcc cctaagaagg agccatgccc   94620
agttctgccg ggaccctcgg ccaggccgac aggagtggac gctggagctg ggcccacact   94680
gggccacata ggagctcacc agtgagggca ggagagcaca tgccggggag cacccagcct   94740
cctgctgacc agagacccgt cccagagccc aggaggctgc agaggcctct caggggggac   94800
acagtgcatg tctggtccct gagcagcccc caggctctct agcactgggg gccctagca    94860 cagctgtctg gaccctccct gttccctggg aagctcctcc tgacagcccc gcctccagtt   94920
ccaggtgtgg ttattgtcag ggggtgccag gccgtggtag agatggctac aattaccaca   94980
gtggtgccgc ccatagcagc aaccaggcca agtagacaga ccctgccac gcagccccag    95040 gcctccagct cacctgcttc tcctggggct ctcaaggctg ctgtctgccc tctggccctc   95100 tgtgggagg gttccctcag tgggaggtct gtgctccagg gcaggatga ctgagataga    95160 aatcaaaggc tggcagggaa aggcagcttc ccgccctgag aggtgcaggc agcaccacag   95220
agccatggag tcacagagcc acggagcccc cagtgtgggc gtgtgagggt gctgggctcc   95280
cggcaggccc agccctgatg gggaagcctg ccccgtccca cagcccaggt ccccagggc    95340
```

```
agcaggcaca gaagctgcca agctgtgctc tacgatcctc atccctccag cagcatccac    95400
tccacagtgg ggaaactgag ccttggagaa ccacccagcc ccctggaaac aaggcgggga    95460
gcccagacag tgggcccaga gcactgtgtg tatcctggca ctaggtgcag ggaccacccg    95520
gagatcccca tcactgagtg gccagcctgc agaaggaccc aaccccaacc aggccgcttg    95580
attaagctcc atcccctgt cctgggaacc tcttcccagc gccaccaaca gctcggcttc     95640
ccaggccctc atccctccaa ggaaggccaa aggctgggcc tgccaggggc acagtaccct    95700
cccttgccct ggctaagaca gggtgggcag acggctgcag ataggacata ttgctggggc    95760
atcttgctct gtgactactg ggtactggct ctcaacgcag accctaccaa aatccccact    95820
gcctcccctg ctaggggctg gcctggtctc ctcctgctgt cctaggaggc tgctgacctc    95880
caggatggct tctgtcccca gttctagggc cagagcagat cccaggcagg ctgtaggctg    95940
ggaggccacc cctgtccttg ccgaggttca gtgcaggcac ccaggacagg aaatggcctg    96000
aacacaggga tgactgtgcc atgccctacc taagtccgcc cctttctact ctgcaacccc    96060 cactcccag gtcagcccat gacgaccaac aacccaacac cagagtcact gcctggccct     96120
gccctgggga ggacccctca gcccccaccc tgtctagagg acttgggggg acaggacaca    96180
ggccctctcc ttatggttcc cccacctggc tcctgccggg accttgggg tgtggacaga     96240 aaggacgcct gcctaattgg cccccaggaa cacagaactt ctctccaggg acccagccc     96300 gagcacccc ttacccagga cccagccctg ccctcctcc cctctgctct cctctcatca      96360
ctccatggga atccagaatc cccaggaagc catcaggaag ggctgaagga ggaagcgggg    96420
ccgctgcacc accgggcagg aggctccgtc ttcgtgaacc cagggaagtg ccagcctcct    96480
agagggtatg gtccaccctg cctggggctc ccaccgtggc aggctgcggg gaaggaccag    96540
ggacggtgtg ggggagggct cagggccctg caggtgctcc atcttggatg agcccatccc    96600
tctcacccac cgacccgccc acctcctctc caccctggcc acacgtcgtc cacaccatcc    96660
tgagtcccac ctacaccaga gccagcagag ccagtgcaga cagaggctgg ggtgcagggg    96720
ggccgccagg gcagctttgg ggagggagga atggaggaag gggaggtcag tgaagaggcc    96780 cccctccect gggtctagga tccacctttg ggaccccgg atcccatccc ctccaggctc     96840
tgggaggaga agcaggatgg gagattctgt gcaggaccct ctcacagtgg aatacctcca    96900
cagcggctca ggccagatac aaaagcccct cagtgagccc tccactgcag tgctgggcct    96960
gggggcagcc cctcccacag aggacagacc cagcaccccg aagaagtcct gccagggga     97020 gctcagagcc atgaaggagc aagatatggg gaccccaata ctggcacaga cctcagctcc    97080
atccaggccc accaggaccc accatggggtg gaacacctgt ctccggcccc tgctggctgt   97140
gaggcagctg gcctctgtct cggacccca ttccagacac cagacagagg gacaggcccc     97200
ccagaaccag tgttgaggga cacccctgtc cagggcagcc aagtccaaga ggcgcgctga    97260
gcccagcaag ggaaggcccc caaacaaacc aggaggtttc tgaagctgtc tgtgtcacag    97320
tcgggtatag cagcggctac cacaatgaca ctgggcagga cagaaccccc atcccaagtc    97380
agccgaaggc agagagagca ggcaggacac atttaggatc tgaggccaca cctgacactc    97440
aagccaacag atgtctcccc tcagggcgc cctgccctgt tcagtgttcc tgagaaaaca     97500
ggggcagcct gaggggatcc agggccagga gatgggtccc ctctaccccg aggaggagcc    97560
aggcgggaat cccagccccc tccccattga ggccatcctg cccagagggg ccggaccca    97620 ccccacacac caggcagaa tgtgtgcagg cctcaggctc tgtgggtgcc gctagctggg     97680
gctgccagtc ctcacccccac acctaaggtg agccacagcc gccagagcct ccacaggaga   97740
```

```
ccccacccag cagcccagcc cctacccagg aggccccaga gctcagggcg cctgggtgga    97800
ttctgaacag ccccgagtca cggtgggtat agtgggagct actaccactg tgagaaaagc    97860
tatgtccaaa actgtctccc ggccactgct ggaggcccag ccagagaagg gaccagccgc    97920
ccgaacatac gaccttccca gccctcatga cccccagcac ttggagctcc acagtgtccc    97980
cattggatgg tgaggatggg ggccggggcc atctgcacct cccaacatca cccccaggca    98040
gcacaggcac aaaccccaaa tccagagccg acaccaggaa cacagacacc caatacccct    98100
gggggaccct ggccctggtg acttcccact gggatccacc cccgtgtcca cctggatcaa    98160
agaccccacc gctgtctctg tccctcactc agggcctgct gaggggcggg tgctttggag    98220
cagactcagg tttaggggcc accattgtgg ggcccaacct cgaccaggac acagattttt    98280
ctttcctgcc ctggggcaac acagactttg ggtctgggc agggaggacc ttctggaaag    98340
tcaccaagca cagagccctg actgaggtgg tctcaggaag accccagga gggggcttgt    98400 gcccttcct ctcatgtgga ccccatgccc ccaagatag gggcatcatg cagggcaggt    98460
cctccatgca gccaccacta ggcaactccc tggcgccggt ccccactgcg cctccatccc    98520
ggctctgggg atgcagccac catggccaca ccaggcagcc cggtccagc aaccctgcag    98580 tgcccaagcc cttggcagga ttcccagagg ctggagccca cccctcctca tcccccaca    98640 cctgcacaca cacacctacc ccctgcccag tcccctcca ggagggttgg agccacccat    98700
agggtgggcg ctccaggtct cactcactcg cttcccttcc tgggcaaagg agcctcgtgc    98760
cccggtcccc cctgacggcg ctgggcacag gtgtgggtac tgggcccag ggctcctcca    98820 gccccagctg ccctgctctc cctgggaggc ctgggcacca ccagaccacc agtccagggc    98880
acagccccag ggagccgccc actgccagct cacaggaaga agataagctt cagaccctca    98940
gggccgggag ctgccttcct gccaccccatt cctgccccag acctccatgc cctcccccaa    99000
ccacttacac acaagccagg gagctgtttc cacacagttc aacccaaaac caggacggcc    99060
tggcactcgg gtcactgcca tttctgtctg cattcgctcc cagcgcccct gtgttccctc    99120
cctcctccct ccttccttc ttcctgcatt gggttcatgc cgcagagtgc caggtgcagg    99180
tcagccctga gcttggggtc acctcctcac tgaaggcagc ctcagggtgc ccaggggcag    99240
gcagggtggg ggtgaggctt ccagctccaa ccgctccact agccgagact aaggaagtga    99300
gaggcagcca gaaatccaga ccattccata gcaaatggat tcattaaaag ttaccagact    99360
tcagtgtaag taacatgagc cccatgcaca acaatccctt atgaagggga agtcagtgtc    99420
gcctcggatt tcttgaaaaa cacaaaaact tatcaatgcc tgtaaaagtc tgttggaaag    99480
aaaatatgat tcaagaatgt tatgcccaac aaagctggca tattttctac ccggacacac    99540
tcagggaatg tggtcccttg agtgcttctc tcactgcgta aatcctacgt ggtgtttaag    99600
catattcata aatgtgtatg tctattttta tgtgtaagat ggttcatttt tatttattt    99660 attcaatatg tacaataaag aatattgaca aataggctgg acatggtggc tcccacctgt    99720
aatcccagcc ctttgggagg ccgaggcggg cagatcacct gaggtctgga gttcgagacc    99780
agcctggcca acatgatgaa aacccatctc tactaaaaat acaaagatta gccaggcatg    99840
gtggtgcatg cctgtaatcc cagccactca ggaggctgag acaggagaaa tgcgtgaacc    99900
cggaaggcgg aggttgcagt gagccgagat cacaccactg cactccagcc tggcgacaga    99960
gcaagattcc atctcaaaaa aaaaaaaaga caaagaaatt tgttttttg aataaagaca   100020 aatttcatca cacgaagata aagatgcaaa gctccagaca ggaaggcacg gacagcacag   100080
```

-continued

```
tgaagcccgg agcgggcgct ggggggccag gggcatggcg ggggtgccag cgtctctcgg    100140
tgcctaccat ggccactcca gcctgtgttc tcacgaggat ggctgtgcaa tgctaggagc    100200
gtgttcgaag ctctagggca accactggaa gtgaggctga ggagcagagc ccagaggccc    100260
gtggagctga tgaaaagaaa gctggagaaa gtgtttgctg cctcccaaca tggtaagaaa    100320
agatagaaag agagagcaca cggcaaaggg agcttgctga gggactcttt acaatggctt    100380
gcacagagct caggggg tct gggaggctag ggccctgcgc agggcagtca ccccagcctg    100440
ctgaccaagg tttgctgcag gcagctctgg gggtggttga ggcgcggtcc ctggagccac    100500
ccctcaaggg aacgaggcag cagagtgggc caaggcccag gtcggctgca aggctgccca    100560
ggacttgggg tccttacatc agcagccact gatgcagctg cccagagag aggcgccgag    100620 caggttgcct ccaggggaca aaccaggtcg gagagggtga ggcagtggat ggagccacaa    100680
caaccccggg cacgggtgac acgcacgttc atgcacatct gacccttcct ccctcaccaa    100740
acaggtcccc ctgccttccc catggttgcg aaaaagcaaa atgtagacgt tttttctttt    100800
ttaattcatg ttttaattga caaatgaagc cgtatatatt tattgtgtac aacatgatgc    100860
tttaaaatat gtatacatcg tggaacagca acgttgagct aatttaacac gcattacttc    100920
acatacttgt catcttttgt ggcgagaatg cttaaaatcc actctcttag tattttttaa    100980
gaatgcaata cattgttgtc aactgtggtc accgtcatgc atagccaagc tcccgacctc    101040
accctcctgc cagctcaggc tgtgcatcct ttcaccagca tccccaccc cggccctgg     101100 ccctggtaac taccactcta tactctacgt atgagttcag ctttttaaga ttccacagat    101160
gaatgagatc atacagtatt tgcttcat gcctggctta ttttagttaa cacactgtcc       101220
tccagatcca tccgttgttg caaatgacag ggtttcattc tttttaaagt ctaaagagta    101280
ttccattgtg tcaatggacc tcatttgctt tatccatgca tcaactatgg acatttaggt    101340
tgattccatt tcttagctgt tgtggatggt gctgcagtaa acatggggct gcagatgtct    101400
cttcaacata ctgacatcat gtcctttgga taaataccca gtagtgggat cgctggatca    101460
caatgtacag tttgttttt aatggaaact ttcattttt ggtgaaatta ggaaaacaga      101520
taaaacccac agaatccaaa atatatgtga agatgccaaa aacagttgac attgggcaga    101580
ggtcacatgg aaggaagtga atacatgacg gggtgtgagg gcccagaggc agctgaaata    101640
cgctttctaa acacaaggac ctcttctgag agggcagaag ttttatcctg cacatgcaat    101700
gaccagcaca gctaaaatac actttctaaa catgaggacc tcttctgaga gggcagcttt    101760
atcctgcaaa tgcaatgacc agcacaggac ccagaataaa gagagttgcc agcggacgcc    101820
tggtgtccat gtgtccaggt gagttcgaga tgcggacggc gctggccagc cagtcacacc    101880
ctaagtcaat ctgctgcatg catttgtcct tgccacagca gaaaacgaga aagcctttgg    101940
gctgcaaagc ttcacaggct cctcttctcc cgactccatg gaaacagcta caagagcag    102000 gcccagtaga gcttaattca tgaaaatgag taataaactt gaactggaac agtatcgact    102060
ttttagaaac ggcagcaaag tgtataaaaa atattcacca gaacaatatt tccaaacgat    102120
gagatgagaa tttcagccaa gtaatcctcc atggatagaa aataatgaag ggattggatt    102180
tatgaaggaa aatcatggag ctcaaataca agagaagaga atcaaaaatg aacaggagga    102240
gataaaatat ggtttggcca agttacaaa ataaattttt taaaaccct tcatcatggc       102300 aagtagaaag agcgagagga aaacagatc ccgtggaaga cacaaatagg acatggggag     102360
aaaaatgaat gagatgaaac agagcagaaa taaaattta cggaactaaa gacaagtgat     102420
ctgaacctgc ctggggcctg ggggacctcg ccaccctgaa gggaaagaac atgcctggct    102480
```

```
ggctttgcca cctgctcatt gcagagcccc acagcttgca acaaacatag gcggtagcca   102540
gggagtggtt acagcaggcc ttgagcaaga cccagtgttg tgctgacttc aggtctgacc   102600
cagcactgtc atagtggtgg tgtccatagt ggtagtgggg gtgcttgtgt cactccaccc   102660
ccatctccag gaggctcaga acagacagag agagactcca tttgtttggg agaaagtaag   102720
ggatgagaac aagagtctct gcctggtaat ccagagaatt attctagatc ttggccaaga   102780
ttatcaaagc agtacctcta tgagtctttt gggcttggag tcccctaaa  gcagatatag   102840 ctaagatcac aacacccaag tccttttgaa tatgtgggaa gacttcccaa ggacaggagc   102900
aaacaaacaa gcccagactg caaaaaaaca agcccagact gcaataaaca cctcactctt   102960
caatgcccag gcactgaaga acatctccta gcagcaacac catccaggaa aacatggcct   103020
caaccagtga actaaataag gcaccaggga ccagtctcgg agaaatagag gtatgttatc   103080
tttcagagaa ttcaaagtag ctttgttgag gaaactcaaa gaaattcaag ataacacagt   103140
gaaggaattc agaatcctat ccgataaatt taacagagat tgaagcaatt aaaaagaatt   103200
aagcagaaat tatggagctg aaaaatgcaa ttggcatact gaaaaatgca tcagagtatt   103260
ttcatagcct cttatatcaa gtagaagaaa gaattagtga gcttgaaaac aggctatttg   103320
gaaaagcacg ataaaaggag acaaaagaga aagaataaa  taacaatgaa gcatatctac   103380
aggatctaga aaatagcctc aaaaggccaa atctaagaat tattagcctt aagaggagg   103440 tagagaaaga gggatggaga gtttattcaa agggataata acagaaaact tcccaaacct   103500
agagaaagat atcaatatcc aaatgcaaga aggatgtagt acaccaagga gatttaatgc   103560
aaagaagact acctcaaggc attcaatact caaactccca tatgacaagg actttaaaaa   103620
gatcctaaaa gcagcaaaag aaaagaaatg aataaaatac tatggagctc caatatgtct   103680
ggcagcagac ttttcagtga agactttata tgccaggaga gagtgtcata atggatttaa   103740
agtgctgaag gaaaaaactt ttaccctcga acagtatagc tggtgaaatt atccttcaaa   103800
catgaaggag aaataatttg tttccagaca aatgttgagg gatttcatga acaccagacc   103860 tgtctttaa  gaaatgctaa agggagtact tcaatcagaa agaaacacgt tagtgaacaa   103920
taagaaatca tctgaaggca caaaactcac cggtaatagt aagtacacag aaaaacacag   103980
aatattataa cactgtaact gtggtgtgta aactcctttt gtttgtttgt ttgtttgttt   104040
gtttgttttt gttttagac  gggagtttgc tccagcccag gctggagtgc aatggcacaa   104100
tctcagctca ctgcaacttc cacctcccgg gttcaagcaa ttctcctgcc tcagcctccc   104160
aagtagctgg gattacaggc atgtgctacc atgtccagct aattttgtat tttagtagag   104220
acggtgtttc accatgttgg tcaggctagc cttatcttga gtagaaaaac taaatgatga   104280
agcaatgaaa aataataact acaacttttc aagacatagt acaataagat ataaatcata   104340
acaaaaagtt aaaaggtgga gggatgaagt taaggcaaag agtctttatt agttttcttt   104400
ttacttgtct gtttatgcaa acagtgttaa gttgtcatca gttaaaata  atgggtcata   104460 agatactatt tgcaagcctc atggtaacgt caaaccaaaa gcaatacaac agatacacaa   104520 aaacaaaaa  gcaagaagct aaattacgtc atcagagaaa atcaccttca ctaaaaggaa   104580
gacggagaaa agaatgaaga gagagaagac caaaagcaaa tagcaatatg gcaggagtaa   104640
gtccttactt atcaataata ccattgaatg taaatggact aaactctcca atcaaaagac   104700
atagagtggc tgaatcaatt aaagaaaaaa caagacccat tgatctgttg tccacaagaa   104760
acacacttta tctataaaga cacacataga ctgaaaacaa agggatggaa aaagatactc   104820
```

```
cacgccaatg gaaaccaaag aaagagcagg agtagctaca cttatatcag gcaaaataga  104880
tttcaagaca aaaactataa gaagagacaa ggtcactaat gataaacagg tcaattcagc  104940
aagaggatat aacaattgta aatatatatg cacccaatgc tggagcaccc agatatataa  105000
agcaagtatt tactagagct aaagagagaa atagactcca atgcaataat agctggagat  105060
ttcaacatcc cactttcaac attgaacaga tcctccagat agaaaatcaa caaagaaata  105120
ttggacttaa tctgcactat cgaccaaatg gatctaacag atatttacag aacatttcat  105180
ccaacagctg cagaacacac attctttttcc tcagcacata gatcattctc aaggatagac  105240
catatgttgg gtcacaaaac aagttttaaa atattcaaat acattgaaat aatatcaagc  105300
atcttctgtg accacaatgg actaaaacta gaaatcaata acaagaggaa ttttggaaac  105360
tatataaata tatggaaatt aatgaatgct gagtgggtca atgaagcaat taagaaggaa  105420
actgaaattt ttcttggaac gaatgatcat ggaaacagaa aataccaaaa cctatgggat  105480
acagcaaaag cagtactaag agggaagttt acagctacaa atgcttacat taaaaaagaa  105540
gaaaaacttc aataaaaaaa cctaacaatg catcttaaag aactagaaaa gcaagaggaa  105600
atcaaatcca aaattagtag aagaaaacag taaaggtcag agcagaaata agtaaaattg  105660 aaaatgaagaa aacaatacaa aagatcaata aaacaacagg ttgttttctt gaaaagttaa  105720
acaaaattga caaacccttta gccagactaa gaaaaaaaga cagaagatcc aaataaaataa  105780 aatcagagat gaaaaaggtg acattacaac ttacaccaca gaaattcaaa ggatcattag  105840
tggctactat aagcaactat atgccaataa attggaaaat ctagaagaaa tgcagaaatt  105900
cctagacaca tacaacctcc caagattaaa ccaagaagaa attcaaaacc tgaacagact  105960
gataacaagt aatgagatca aagccgtaat aaaaagcctc ccagtaaaga gaagcccagg  106020
acccgacggc ttcactgctg aattctacca aacatttaaa gtagaactaa taccaatcct  106080
actcaaacta ttccaaaaaa tagaggtgga aggaatactt caaaactcat tatacgaggc  106140
cagtattaac ctgacaccaa aactagacaa agacacatga aaaaagaaa actacaggcc  106200 aatatgtctg atgaatattg acacaaaaat cctcaacaaa atactagcaa accaaattca  106260
actacacatt agaaagttca ctcatcatga ccaagtggaa tttatctaac ttgggatgca  106320
aagatggttc aacatatgca aatcaatcaa tgtgatacat catatcaaca gaatgaacaa  106380
caaaaaccat ttgatcattt aattgatact gaaaaagcat ttgataaaat tcaacattcc  106440
ttcataataa aaattctctt ctatactagg tacaaaagaa acttacctca acataataaa  106500
gccatatatg acagtcccac agtatgatac taaatgagga aaaactgaga gcctttcctc  106560
tacgatctgg aacatgacaa agatgcccac tttcatcact gttattcaac atagtactgg  106620
aagtcctagc tggagcgatc agacaagaga aagatataaa agacatccaa attggaaagg  106680
aataagtcaa attatcctca tttgcatatg gtatgatctt ctatttagag ctaactaaag  106740
actccaccaa aaaagttat tagaactgac gaacaaattc agtaaagctg caggatacaa  106800
aatcaacata caaaaatcag tagcatttct atatgccaac aatgaccaat gtgaaaaaga  106860
aattaaaaag taaccctatt tacaataacc acaaataaac acctaggaat taaccaaaga  106920
ggtaaaagat ttctgtaatg aaaactataa aaaactgatg aaagaaattg aagagtacac  106980
caaaaaatgg aaagcaattg catgttcatg gattagaaga atcagtgttg ttataatgtc  107040
catactatcc aaagcaatct acagattcaa tgcaatcctt atcaaaatac caatgacatc  107100
attcacagaa atagaaaaaa aaaatcctaa aatttacgtg gaaccacaaa gacccagaat  107160
agccaaagct ctcctaagca aaaagaacga aactgtagga atgacattgc ctgtcttcaa  107220
```

```
attctactac agagctatag atagtaacca aaacagcgtg gtactagcat aaaaacagac  107280
acagagacaa acagaacaaa atttaaaaac ccagaaataa atccacacac ctacagcaaa  107340
ttcatttttg acaaagttgc caagaacata ctctggggaa tagataatga tatctcttca  107400
ataaataatg tggggaaaac tggatatcca tatacataac agtgaaacta gacccctctc  107460
tctctcacta tatacaaaaa tcaaatcaaa attgtttaag gacttaaatc taagacctca  107520
tactatgaaa ccactgcaag acaaccttgg cggaaactct ccaagacatc agtccaggca  107580
aagatttctt gagtaatatc ccacaagcac agacaaccaa agcaaaaatg gacaaatggg  107640
atcacatcaa gttaaaaagc ttctgcacag taagggaaac aaccaacaaa atgaagagac  107700
aacccacaga atgggagaaa atatttgaaa atacccatc tggcaaggga ttaaaaacca  107760
gaatatatgc agaatatata aggagctcaa acagtgctat agaaaaaaaa atctaataat  107820
ctgatttaaa aatgggaaaa atgttagaat agacatttct taaaataaga catacagatg  107880
gcaaaccgac atgaacggt gctcaacatc atggattatc acagaaacac aatcaatcaa  107940
aactaaaact aaaatgtgct atcatctcac cccagttaaa atggctgata tccagaagac  108000
aggcaataac aaatgctggc aaggatgtgg ggaaaaggga gcccccatac actgttgctg  108060
ggattgtaaa ttagtacaac cactgtggag agcagcatga aagttcctca aaaaactgaa  108120
agaaagctac cataggatcc agcaatccca ctgctgtgta tatactacaa aagaaaggaa  108180
gtcagtatat gaagaggtat ctgcactccc atgtttgttg cagccctgtt cacaacagcc  108240
aagatttgga agcaacctaa gtgtccatca gcagttgaat gtataaagaa atgtggtgc  108300
atatacacaa tggagtatta ttcaataata aaaaggaatg agattgagtc atttgcaaca  108360
acatggatgg aactggagat cattatgtga agtgaaataa gccaggcaca gaaagacaaa  108420
cattacaatg ttcttactta ttaatgagat ctaaaaatca aaacaattgc acccatgttc  108480
ataaagagta aaaggatggt taccagatgc tgagaacggt ggtgggggga tagggaaagg  108540
tggcagtggt taacgggtac aaaaaaatag aaagaatgaa taagacttac tacttgatag  108600
cacagcaagg tggctatagt cagtaattta gttgtatatt tttaataatg aaaggtgtat  108660
aattggattg tttctaacac aaaggataat gcttaagagg atggataccc cattttccat  108720
gatgtgatta tttcacattg cacgcctaga tcaaaacatc caatgtaccc cataaatata  108780
tacatcttct atgtacccat aaaaattctg taaaataaaa tatataaaaa gaggtgacag  108840
atatggaaga caggcaaaga agagacgaca tccacataat ccgagtacct aagaaagaat  108900
ggagtccagt gcatctcagg agccaccatt ctaagccaat tttctctggt tctctcagtc  108960
accctaccaa tacgtgggca atcttgtttt atttcaggat agagttttg aaattataga  109020
tttaagtatg ctttctgttc tattactttt ggtaattaat tttagaaaga actaatttgg  109080
gcacaaattt gaaaaaattc taaatccaaa aaaaaaaga aaaaacaca cacacaatca  109140
tctataaggg ggatgatgac cagtcctaga tttctcacca gccacattca agatcagtaa  109200
atggtaggac aaaacctgta gggtccttaa ggggaaaga agtagtggat agtccagagt  109260
ctatatacag ccaactgttc ttgaagaaaa aaggctgctg aaaaggagtt ccaaacattc  109320
tataatccat aatctcatga tgaaactact agaggaagac caccagccat caaaaggtgc  109380
ttggagaacc cagggccaag aaccaaaagt aaatattaag tgtccttaac tgcgagacta  109440
agatagaaat gactgtgggg gaccatgtgg cctcaacaga ggtgaaatgg tgtctgcctg  109500
acaaagtgga cattttacaa tgatcaaaac acagaatatg agatagagag cacttctgaa  109560
```

-continued

```
ttactgcctc actccaaata actctcagcc aaaggacttc agtaaaacca aattgggcat    109620
attagacagt acaaacaaat tctaagaaaa taatattact gattacaatc acatgatgct    109680
agagatggag gggaaaagga agaggaaacc aggtaatttc atactcgtat atagtaaaga    109740
actaaagtac attgtccaaa gaagaacaaa gaatattttg gaaagttata aaggtagcca    109800
ctacacatag aagatagcaa agaacaagaa aacttaagat ggaaaacttt ttggaagcat    109860
aaaaatagaa aatataaact actaagataa gattgaagcc aaacagatct atgaaaacaa    109920
caaacatcaa tggccttaac ttgcctatta aaggaagag actttcaaat tggaccacaa     109980
gataaaaccc aactctatat agcatatgag tattacacac aaaatgggaa aagctgaaaa    110040
aacttgggca aaattcaccc caagcaaatt ccactgtttc ctttgggaca aaatgccaag    110100
ctccatgcca gggaagatga ttctcctcag accttctcct cactctccca gtcctcttag    110160
ggaaggaatt gggtgttaga ggaggagac tctgtcgatt atcagctgaa gcagtggtgt     110220
gctcctgcgt tgcttctgac ctgggaaatg aagcagcaag actctttctg ctgtgtcttt    110280
gcccagaagg gccatccccc cagagcagag tacccaggcc ggcaggagca gtggtggaag    110340
cgtggaaacc acgtctccta cagcagagac catcagaagc ggagcctcgg gtataaggga    110400
aacaacgcgt tctccctaac ctgggagtga cagacagcgt cattcctcac agtgataccc    110460
tgtgttctag ccatctggcc catgacagag ccagcccaga ccagcccag agccagcccc     110520 tgaccatcct ggagcctggc cagctcgcca agctgcacca taggcctgga aggcgtggag    110580
acctgcggca gtgccctgtc ctcccgtgag gcctgccatc cctgccaggg gtcgcctctg    110640
gcttctcctt ctccaggacc gcacggtcca gaggctcagt gcctggagta ggtgttgcct    110700
ccctgcttct aggcccagac cctcccttgt tcctgacccc gggccttcc ctctggcttg     110760 gacatccagg gccctgtctc agctggggag ctgctcctgc tcaaggactg tcttccgcgg    110820
gatcgaaagg ccgcgtcctg aacaatgcgt gggccacgtg agcggagcag gctctaaagg    110880
ccgcgtccta aacagtgcgt gggccacgtg agcggagcag gctctaaagg ccgcgtccta    110940
aacagtgcgt gggccacgtg agcggagcag gctctaaagg ccgcgtccta aacagtgcgt    111000
gggccacgtg agcggagcag gctctaaagg ccgcgtccta aacagtgcgt gggccacgtg    111060
agcggagcag gctctaaagg ccgcgtccta aacagtgcgt gggccacgtg agcggagcag    111120
gctctaaagg ccgcgtccta aacagtgcgt gggccacgtg agcggagcag gctctaaagg    111180
ccgcgtccta aacagtgcgt gggccacgtg agcggagcag gctctaaagg ccgcgtccta    111240
aacagtgcgt gggccacgtg agcggagcag gctctaaagg ccgcgtccta aacagtgcgt    111300
gggccacggg agcggagcag actctaaagg ccgcgtccta aacagtgtgt gggccacgtg    111360
agcgaagcgc cctctccact gccctcgggg ccgcagctcc cagctcagct cccagccctg    111420
ctcagggcag ccaggccagg aggtaccatc caggctaagt gaccctcagg ggggacaggt    111480
gccccaggag atgccagctg ttgggagagg ctggggacc aactcgacct ggcctgtggg     111540
ccctgccctg gccacccatt gtaggatcca gccgccacgc ctgtgacact cgtgtgctttt   111600 ccctggtgtg tgcttgtggc aggtgggggc agagggtcct caggccagag agccactccc    111660
ccagcgccag accaccctct tcctcactcc cccacctcac cccctcacag gtgcctccca    111720
ggccatcagg gcccaaccac ccctaaacaa atgggttctc ggcccctcgt ggctggaggt    111780
gggttctctc accattccca gcctaagact ccatccccat gctggcagct gttcaaccat    111840
gtctagagag atccactgtc ccagacagca cctcagggtc cccgtcctg cctgaaccc      111900 tgtaggaaac tccacaaacc gccgccattc tgtccacacc cctacaggag ccccaaccct    111960
```

```
ctccccacat ccaggcttcc ctcccagacc cctcatccct gcccgcacgg tgcctgaggg 112020
ggccttcttg ggcagcgcct aagcaagccc ccagcaccct tcggccccCtt caaggcacac 112080
aggccccctt tccacccagc ctcaggaaac cacctgtgtc ctccaacgac aggtcccagc 112140
ctcccagcct ttgccttgcc tgttcctctc cctggaactc tgccccgaca cagaccctcc 112200
ccagcaagcc cgcaggggca cctcccctgc cccagacac cctgtgcccg tcagttcatc 112260
cccagcagag gccctcacca ggcacacccc catgctcaca cctggcccca ggcctcagcc 112320
tccctgaggg ccccacccag cccgcgtctg gccagtggtg cgtgcaaagc ccctcaccca 112380
gactcggcga aaggcagcca gtgcaggcct ggggagggc tctccttaga ccaccttgca 112440
ccttccctgg cacccaccat gggaagagct gagactcact gaggaccagc tgaggctcag 112500
agaagggacc cagcactggt ggacacgcag ggagcccacg ccagggcgcc gtggtgagtg 112560
aggcccagtg ccacccactg aggcctcccg ttcagtggga cgacggtgaa caggtggaac 112620
caaccaggca accccgccg ggccccacag acgggatcag agcaggaaag gcttcctgcc 112680
cctgcaggcc agcgaggagc cctggcgggg gccgtggccc tccaggcgag gaggctcccc 112740
tggccaccgc caccccgggcc tctctgctgc tgggaaaaca agtcagaaag caagtggatg 112800
agaggtggcg tgacagaccc agcttcagat ctgctctaat ttacaaaaga aaaggaaaaa 112860
cacacttggc agccttcagc actctaatga ttcttaacag cagcaaatta ttggcacaag 112920
actccagagt gactggcagg gttgagggct gggtctccc acgtgttttg gggctaacag 112980
cggaagggag agcactggca aaggtgctgg gggcccctgg acccgacccg ccctggagac 113040
cgcagccaca tcagcccca gccccacagg ccccctacca gccgcagggt tttggctgag 113100
ctgagaacca ctgtgctaac tggggacaca gtgattggca gctctacaaa aaccatgctc 113160
ccccgggacc ccgggctgtg ggtttctgta gcccctggct cagggctgac tcaccgtggc 113220
tgaatacttc cagcactggg gccagggcac cctggtcacc gtctcctcag gtgagtctgc 113280
tgtctgggga tagcggggag ccaggtgtac tgggccaggc aagggctttg gcttcagact 113340
tggggacagg tgctcagcaa aggaggtcgg caggagggcg gagggtgtgt ttttgtatgg 113400
gagaagcagg agggcagagg ctgtgctact ggtacttcga tctctgggc cgtggcaccc 113460
tggtcactgt ctcctcaggt gagtcccact gcagccccct cccagtcttc tctgtccagg 113520
caccaggcca ggtatctggg gtctgcagcc ggcctgggtc tggcctgagg ccacaccagc 113580
tgccatccct ggggtctccg ccatgggctg catgccagag ccctgctgtc acttagccct 113640
ggggccagct ggagccccca aggacaggca gggacccgc tgggcttcag ccccgtcagg 113700
gaccctccac aggtagcaag caggccgagg gcagggacgg gaaggagaag ttgtgggcag 113760
agcctgggct ggggctgggc gctggctgtt catgtgccgg ggaccaggcc tgcgctttag 113820
tgtggctaca agtgcttgga gcactgggc cagggcagcc cggccaccgt ctccctggga 113880
acgtcaccc tccctgcctg ggtctcagcc cggggtctg tgtggctggg acagggacg 113940
ccggctgcct ctgctctgtg cttgggccat gtgacccatt cgagtgtcct gcacgggcac 114000
aggtttgtgt ctgggcagga acagggactg tgtccctgtg tgatgctttt gatatctggg 114060
gccaagggac aatggtcacc gtctcttcag gtaagatggc tttccttctg cctcctttct 114120
ctgggcccag cgtcctctgt cctggagctg ggagataatg tccgggggct ccttggtctg 114180
cgctgggcca tgtggggccc tccggggctc cttctccggc tgtttgggac cacgttcagc 114240
agaaggcctt tctttgggaa ctgggactct gctgctgggg caaagggtgg gcagagtcat 114300
```

```
gcttgtgctg gggacaaaat gaccttggga cacggggctg gctgccacgg ccggcccggg    114360
acagtcggag agtcaggttt ttgtgcaccc cttaatgggg cctcccacaa tgtgactact    114420
ttgactactg gggccaggga accctggtca ccgtctcctc aggtgagtcc tcacaacctc    114480
tctcctgctt taactctgaa gggttttgct gcattttggg ggggaaataa gggtgctggg    114540
tctcctgcca agagagcccc ggagcagcct ggggggctca ggaggatgcc ctgaggcaac    114600
agcggccaca cagacgaggg gcaagggctc cagatgctcc ttcctcctga gcccagcagc    114660
acgggtctct ctgtggccag gccacccta ggcctctggg gtccaatgcc caacaacccc     114720
cgggccctcc ccgggctcag tctgagaggg tcccagggac gtagcggggc gccagttctt    114780
gcctggggtc ctggcattgt tgtcacaatg tgacaactgg ttcgacccct ggggccaggg    114840
aaccctggtc accgtctcct caggtgagtc ctcaccaccc cctctctgag tccacttagg    114900
gagactcagc ttgccagggt ctcagggtca gagtcttgga ggcattttgg aggtcaggaa    114960
agaaagccgg ggagagggac ccttcgaatg ggaacccagc ctgtcctccc caagtccggc    115020
cacagatgtc ggcagctggg gggctccttc ggctggtctg gggtgacctc tctccgcttc    115080
acctggagca ttctcagggg ctgtcgtgat gattgcgtgg tgggactctg tcccgctcca    115140
aggcacccgc tctctgggac gggtgccccc cggggttttt ggactcctgg gggtgactta    115200
gcagccgtct gcttgcagtt ggacttccca ggccgacagt ggtctggctt ctgaggggtc    115260
aggccagaat gtggggtacg tgggaggcca gcagagggtt ccatgagaag ggcaggacag    115320
ggccacggac agtcagcttc catgtgacgc ccggagacag aaggtctctg ggtggctggg    115380
tttttgtggg gtgaggatgg acattctgcc attgtgatta ctactactac tacggtatgg    115440
acgtctgggg ccaagggacc acggtcaccg tctcctcagg taagaatggc cactctaggg    115500
cctttgtttt ctgctactgc ctgtgggtt tcctgagcat tgcaggttgg tcctcggggc     115560
atgttccgag gggacctggg cggactggcc aggagggac gggcactggg gtgccttgag     115620
gatctgggag cctctgtgga ttttccgatg ccttggaaa atgggactca ggttgggtgc      115680
gtctgatgga gtaactgagc ctgggggctt ggggagccac atttggacga gatgcctgaa    115740
caaaccaggg gtcttagtga tggctgagga atgtgtctca ggagcggtgt ctgtaggact    115800
gcaagatcgc tgcacagcag cgaatcgtga aatattttct ttagaattat gaggtgcgct    115860
gtgtgtcaac ctgcatctta aattctttat tggctggaaa gagaactgtc ggagtggtgtg  115920 aatccagcca ggagggacgc gtagccccgg tcttgatgag agcagggttg ggggcagggg    115980
tagcccagaa acagtggctg ccgtcctgac aggggcttag ggaggctcca ggacctcagt    116040
gccttgaagc tggtttccat gagaaaagga ttgtttatct taggaggcat gcttactgtt    116100
aaaagacagg atatgtttga agtggcttct gagaaaaatg gttaagaaaa ttatgactta    116160
aaaatgtgag agattttcaa gtatattaat tttttttaact gtccaagtat ttgaaattct    116220
tatcatttga ttaacaccca tgagtgatat gtgtctggaa ttgaggccaa agcaagctca    116280
gctaagaaat actagcacag tgctgtcggc cccgatgcgg gactgcgttt tgaccatcat    116340
aaatcaagtt tattttttta attaattgac gcgcgtctta tcatggttgt cgcaatgtga    116400
caattggttt gcttactggg gccaaggcac tctggtcact gtctcttcag gtgagtccta    116460
acttctctca ttctaaaatgc atttggggga actttgagca ttccggacca agactccctg    116520
caaatgggag ccaagattcg accccttttgt cccatattga gacacgggtc tgggtcaggt    116580
atctctacct gctggtctgt ggttatacca gaactggagt gtgatgaagg gtctgccaga    116640
actgaggctt gaagtctggg gcagactcct gtccagagtc tattggactc ttatgagaat    116700
```

```
tagggggctga cagtttataa taataattcg agagtcagtg actgtctttt tttctcagag  116760
gtgaggctgg aatatgggtc acattaaagg ctaaaaaggg gtccagggac ctttctgccc  116820
aggcagggaa cagagtatgg gacagtgatt taaatggttg attattgtat gacactagga  116880
gacagcacgg tgtcttgagt tgcccagggg ttattctagt cattctctgg ggtttttgtg  116940
gggtatgaag ggaaaatcca ctattgtgat tactatgtta tggatgcctg gggtcaagga  117000
gcttcagtca ctgtctcctc aggtaagaat ggcctctcca ggtctttatt tttaatcttt  117060
gcctatggag ttttcagagt attgcatact aaccccggag atgtgtcaag ctggccggga  117120
gaagctaggg actaaactgc ctaggggatc tcagagcctt ggggataaac taagaatctc  117180
tttgatggtg ttggtagagt ccctaaatga tggagcaggg atttttggagc ctcatttgag  117240
ggagatgcta aaaagattcc atggctaaag ggatagtttg ggctgtggtt ggagattttc  117300
agtatttaga gtaatagtgt tagctgagaa atataattca ggaccctctg agacagcatc  117360
tgtacagtat ctgatgcaca gggacaaaga gtggagtggg acactttctt cagatttgtg  117420
aggaatgttc tgagtagatt gtttaaaaca tcatttgttg aaaagagaac ttttagtgaa  117480
tcaatcaagg aaggaaggaa ggctcagtct caaaagggta gctgatatcc agaggaatct  117540
ggataagcct gcaaaagtct agctttcaaa ggaatgcaga agtatgcatg tggaaaatta  117600
gaagattttt tttaccctt aaagtggttc ctatgatagt tagaatactg tgactttact  117660
atgtgagaga gttttcaagt attcactttt ttttttaaat gtccaagtac gaaaaaattt  117720
tgtcagtttg aagtcaggtt tgtacagaat tgatattgtt gaaagtttaa ccaaagaatg  117780
ggaatgaggc tcttttcacac cctattcaga actgactttt gacaataata aattaagttt  117840
aaaatgtttt taaacaaatt gagcaatgtt gagttgcagt caagatggcc gatcaggacc  117900
aggacacctg cagcagctgg caggaagcag gtcatgtggc aaggctattt tgggaaggga  117960
aaataaaacc actaggtaaa cttctagttg tggtttgaag aagtggtttt gaaatgctct  118020
gtccagccac gcagaactga aagtccaggc tgagaaaaac aacacctgga taatttgcat  118080
ttctaaaata agttgaggat tcagtcgaaa ctggaaaggt cctcttttaa cttagtgagt  118140
tcaatctttt aattttagct tgagaagttc tagtttccct caaacttaag tttatcgact  118200
tctaaaatat attcattttc aaaattaagt tatgtaaaaa aattgaagga cttcagtgtc  118260
tttaatttct aatgtattta gaaaactttt taaagttact ttattattct tccctctgat  118320
tattggtctc tgttcaattc tttttcccagt acccaaagca tttacagtga ctttgttcat  118380
aattttttt aagttagttg ttttctgcct tactattaag actttagcat tctggtcgaa  118440
gtggcttcat aaatctttt caaggccact ttttaggaga aagacatctt tttttttaatg  118500
aatgcaatta tctagaatta tttcagttaa acatgttagt tggtggttga gaggacactc  118560
agtcagtgca gaaggtctgt aagccagtcc acagagacat tcctgggtga actccctctg  118620
gccctgcttc ttgttggaga actggccaga ggtctgagac caggctgctg ctgggaaggc  118680
ctggactttg gtctcccagt accgcccaga cctggggatg tatggttgtg gcttctgcca  118740
cccatccacc tggctgctca tgaaccagcc agtcttgatg gctttgaagg aatgattcca  118800
cacaaagact ctggacctcc ctgaaaccag gcactgcaaa cggtaagcca gcgccagcca  118860
cagctgtggc cgctgtcctt aaaccttgta attgtttctg cttgattgag tcttaagtca  118920
ttgcttagg aggagaaaga gacatttgtg tcttttgagt accattgtct gggtcactcg  118980
catttaactt tccttgaaaa acttataaga gaaaacgtt gcctgttaac cattaactac  119040
```

```
agggctcgtg atactttgag aaaatcttag aaaaaaatgt atacagttgt ctggaattat    119100
ttcaatgaag tgtattagtt ggggtactgg cgctgtctct acttcagtta tacatgtggt    119160
tttgaatttt gaatctattt tgtctcttct taagcaccaa gtatagatac agtggataca    119220
ctcactggtt tttaacggtg gttttaatct agaaggaatt taaactggag gctaatttag    119280
aatcagtaag gagggaccca ggctaagaag gcaatcctag gattctgaaa gaaaagatgg    119340 ttttagttttt tatagaaaac actactacca ttcttgatct acaactcaag acggtctaat    119400
gaattttgaa gttactggta aatatacttc ctggttgtta aggaatgatt atcaaatgga    119460
tcagtgcttg gatctgaggt cagtgtgaga ggacagggcc tgggctgtgg atatacagaa    119520
ggaaggccac agctggatag aattgaaaaa gaatggagac ctgctgctga ggcaagcaga    119580
tcagccggac tctttccagc catagcaaag aaccagatta ataaagaaa ggccagatta    119640 ataaagcttg ctgagcaaaa tttagtgaac aaggttgaca gcctggctag gaagctaggc    119700
tctagttaag cacagttgga ctgagatgtg taggcttccc tgagcccttc aaaaatgtgc    119760
taagctgaga tgattactct gaggtagcca aagctggact tgagcaggaa cgaggtagac    119820
tgcaatgagc tgaattgagc taggccggct aagctaaact aggctgactt aaccaagata    119880
gccaaattgg aatgaattgt cttgatctgg gctgattgga gctaaactct actgactgc     119940 tctgaactga gctgtgttgg gctgtgttgt gctggggtga gctgagctag catgagctac    120000
tctgtggtag ctggggtgag ctgggatgag ctgagctggg tgagctgagc tgggtgagct    120060
gagctgggtt agctgagctg gggtgagctg gggtaagctg gggtgagctg agctgggtga    120120
gctgagctgg gtgagctgag ctgagctggg tgagctgggg taagctgggg tgagctgggc    120180
tgacctgagg tggttgagct gagctgggtg agcagagctg aggtgagctg agctgagctg    120240
ggtgagcaga gctggggtga gctgagctga gctgggctgg ggtgagctga gctgagctgg    120300
gtgagctgag ctgggtgagt tgagctgagc tgggtaagct gagctgagct gggtgagcag    120360
agctgggggt gagctgagct ggatgagctg ggctgaactg gggtgagctg gggtggggtg    120420
agctgggtga gctgagctgg gctgagctgg gctgagctgg ggtgagctga gctgggatga    120480
actgggctga gctgggctga gctgagctgg gctgggctga gctgagctgg gatgagctgg    120540
gctgggctgg gctgggctgg gctgagctga gctgggctga gctgggctga actggggtga    120600
gctggggtgg ggtgagctgg gtgagctgag ctgggctgag ctgggctgag ctggggtgag    120660
ctgggtgagc tgagctgggc tgagctgggc tgagctgggc tgagctgagc tgggctgggc    120720
taagctgagc tggactgagc tgggctgagc tgggctgagc tgagctaggc tgggctgggc    120780
tgggctgagc tgggctgagc tgggctgagc tgagctggga tgagctggga tgagctgaac    120840
tgggtgagat gagctggggt gagatgagct gaacagggct gaactggggt gagctgagct    120900
gggatgagct ggggtgagct gagctgggtg agatgagctg ggtgagctga gctgagctgg    120960
gctgagctgg gtgagctgag ctgggtgaga tgagctgggg tgagctgagc tggggtgagc    121020
tgagctgggt gagctgggct gagctgggct gggtgagctg agctggggttg agctgagctg    121080 ggctgagctg ggctgagctg ggctgagctg ggctgagctg ggctgagctg agctgagctg    121140
ggatgagcag ggctgggatg agctgggctg agctgagctg ggatgagctg ggtgagctga    121200
gctggggtga gatgagctgg ggtgagatga gctgggatga gctgagctgg gatgagctag    121260
gtgagctgag ttggggtgag ctgagctggg tgagctggg ctgggtgaac taaactaggg    121320
tgagctgggc tgagctgatc tggttgagct gggctgggtg agctgagctg ggtgaactga    121380
gctggggtga gctgaactga gctgggtgag ctggggtgag ctgagctgag ctgggtgaac    121440
```

```
tgagctgagt tgagttgggt gagctgagct gggtgagctg aactgagctg gactgagctg   121500
gggtgagctg gggtgagctg ggctggatga gctgagctgg gtgagatgag ctgaacaggg   121560
ctgaactggg gtgagctgag ctgggatgag ctggggtgag ctgagctggg tgagatgagt   121620
tggggtgagc tgaactgagc tggactgagc tggggtgagt tgggctaggt gagctgaact   121680
ggggtgagct gagctggggt gagatgagct gaacaggtct gaactgggat gagctgggat   121740
gagctggggt gagctggggt gagctgagtt gggtgagctg agctgggtga gctgagctgg   121800
ggtgagctga gctgggatta gctggctgag ctgggatgag ctaggtgagc tgagttgggg   121860
tgagctgagc tggggtgagc tgggctgggt gaactaaact agggtgagct gggctgagct   121920
gatctggttg agctgagctg gggtgagctg ggctgagctg ggctgggtga gctgagctgg   121980
gtgaactgag ctggggtgag ctgaactgag ctgggtgagc tggggtgagc tggggtgagc   122040
tgagctgagc tgggtgaact gagctgagtt gagttgggtg agctgagctg ggtgagctga   122100
actgagctgg actgagctgg ggtgagctgg gtgagctggg gctgggtgag ctgagctggg   122160
tgagctgagc tgggctgagc tggggtgagc tgagctgagc tgggctgggt gagctgagct   122220
gggtgagctg agctggggtg agctgagctg agctgggtga gctgggctga gctgagctga   122280
gctggggtga gctggggtga gctgggctgg gtgagatgag ctgtgctggg ctgggtgagc   122340
tgagctgggt gaactgagct gagctgagtt gggtgagctg agctgggtga gctgagctgg   122400
gctgagctgg ggtgagctga gctgagctgg ggtgagctgg ggtgagctgg gctgggtgag   122460
ctgagctggg tgagatgagc tgtgctgggc tgggtgagct gagctgggtg aactgagctg   122520
agctgagttg ggtgagctga gttgggtgag ctgagttggg tgagctgagc tggggtgagc   122580
tgaactgagc tggactgagc tggggtgagc tgagctggct gagctgagct gggtgagctg   122640
agctgagctg agctgaactg agctgagctg ggctgagctg ggctgggtga gctgggctga   122700
gctgggctgg gtgagctggg ctgagctggg ctgggtgagc taagctgggt gagctgggat   122760
gggtgagctg gcctgagctg ggtgagctga gctgaaagga tctgggttgg agtcagcttt   122820
gcttgggtga gctgagcagg gtttagctga gctaggatga gttgagttgg ctgggctgag   122880
ctgggatgaa gtaggctaaa taagctagct tgagctaaat agagctgggg tgagctgtac   122940
ttaaatgagc tgtgattgaa gtgggctggg atgagctcag ctgaactggg ctagctgatg   123000
tggatgatgg tgaggctgag ttaggatgag catgactgag ctggtttgga catgaatgag   123060
ctggacccgg ctgacttggg ctggttgagc tttgcaagat gatgtggact aaactgggct   123120
agctggcagg atgagagagg ttgaactagg ctcagatgag ctaggctgag cagggcttag   123180
gtgaggtggt ttgggatgag ctgggataag ttgggctcag atgagctacc atgaactggg   123240
ctgaggtggc ctgggagaac atgaatcgag ttgcactgag tacagccagg atgaactggg   123300
ataaactggg ctaaactggg ttgggctaag aatggactgc ctgagttatg ctaagctgag   123360
ctgggatgaa ttggggattg tcaagactta aatgagccag actgaactgg ttggacttgg   123420
gtgagctgag gggacctgct gcagggccgg catagctgag ttgaatttag atgaggaagg   123480
gtgagctaga ctgagcaagg ctagactgct tatgctgagc tacactaacc tggcctgagt   123540
tgggccaggc tttgttggcc atgtctaaac tgagttaaga tcaacaggga gtctagaggg   123600
gtaggggatg aactaagatg aattacacta gctgagctga attgagataa ggtatggtaa   123660
cctgagctga actggaaaga gatgtactgg ataaccttaa ctgggctgag atgagctagg   123720
tctacccagg cctggatcag cttaattagg gtaggctaga ccaaactgta gcagtatgta   123780
```

```
ttagcctgtg ccaagctggg ctacattaaa ctaaactgga cttagctagg ctcagattag   123840
tttcgctact ctagaatggg taagttgggc caaactggga tgaactaatt taactagcct   123900
gagatgggca gatctgaagt gtagcaaaca cagccagggt gaactgaatg agtttgacca   123960
ggcctggacc agttaggcta aggaccttgt cctgggcaga ccgtgtgcta tggtggagtt   124020
tcatgatgat gccataagag ttcccccacc ataacccacg tttctcctac cccatatacc   124080
tgtctggtgt gtaaacctaa tctttgtgtg ctgatacaga agcctgagcc catccccctt   124140
ccaccaccac ctacctattg ctttggaatg agcaaggtta tctcagcgaa tgtctcaaag   124200
ggaagccggg acctaggcct gtccctgaga gcagatgttc atgcccctgg agtggctgcc   124260
ggtggctgaa gggccagaac cacctactct agaggcatct ctcgctgtct gtgaaggctt   124320
ccaaagacat tcctgtggtt agaaggcagc cctgctgtgg ctctgtccca tagaccaaac   124380
ttacctacta tctagtcctg tcaaccttaa gagcagcaac atggagacag cagagtgtag   124440
agagatctcc tgactggcag gaggcaagaa gatggattct tactcgtcca tttctctttt   124500
atccctctct ggtcctcaga gagtcagtcc tccccaactg tcttcccct cgtctcctgc    124560 gagagcccct gtctgatgag aatttggtgg ccatgggctg cctggcccgg acttcctgc    124620 ccagctccat ttccttctcc tggaactacc agaacaacac tgaagtcatg cagggtgtca   124680
gaaccttccc aacactgagg acaggggaca aatacacagc tacctcgcag gtgttactgt   124740
ccgccaaaaa tgtccttgaa ggttcagatg aatacttggt atgcaaaatc caccatggca   124800
acaaaaacaa agatctgcat gtgccgattc caggtaagaa ccaacccttc ccgaggggat   124860
ggggagaggg ggcaggccca ggcatggccc agagggagca gtggagtggg tcctaagcca   124920
gcctgagctc acacctcaac ctttcattcc agctgtcgtt gagatgaacc ccaatgtgag   124980
tgtgttcatt ccaccacgtg atgccttctc tggccctgca ccccgcaagt ccagactcat   125040
ctgcgaggcc accaacttca gtcccaaaca gatcacagta tcctggctac aggatgggaa   125100
gcctgtgaaa tctggcttca ccacagagcc agtgactgtc gaggccaaag gatccagacc   125160
ccaaacctac aaggtcataa gcacactgac catcactgaa agcgactggc tgaacctgaa   125220
tgtgttcacc tgccgcgtgg atcacagggg tctcaccttc ttggaagaacg tgtcctccac   125280 atgcgctgcc agtgagtagc ctgtgctaag cccaatgcct agccctccca cattagagca   125340
gtcctcctac ggttgtggcc aatgccaccc agacatggtc atttgcttct tgagccttgg   125400
cttccaacag tggccaaggc caaggatgag cagtaggcag caggggggatg agagtcagat   125460 ggagggaatc agcatcttcc cttaagcaga tttggaagat ggagactgag cttttatcca   125520
acttcacaac tagacacatc acaacctaac acagtgttct cttgactgca ggtccatcta   125580
cagacatcct agccttcccc atccccccct cctttgctga catcttcctc accaagtctg   125640
ctaagctgtc ctgtctggtc acaaacctgg caacctatga caccctgaat atctcctggt   125700
cttccaaaag tggtgaacca ctggagacca cactaaaat catggaaagt cacccccaatg   125760 gcaccttcag tgctgtgggt gtggctagtg tttgtatgga agactgggat aacaggaagg   125820
aatttgtatg cactgtgact cacagggacc tgccttcacc acagaaaaaa ttcatctcaa   125880
aacccaatgg taggtatccc cctttccttc ccctccaatt ccagagcata ccctgtacct   125940
cacagggagg gcaggtcccc ttctacccta tcctcactat tatctttgct tacagaggtg   126000
gccaaacatc cacctgctgt gtacctgctg ccgccagccc gtgaacaact gatcctgagg   126060
gagtcggcca cagtcacctg cctggtgaag ggttttctctc ctgcagacat cttttgtacag   126120 tggcttcaga gagggcaacc cttgtcctca gacaagtatg tgaccagtgc cccaatgcca   126180
```

```
gagcctgggg ctccaggcct gtacttcacc cacagcatcc tgactgtgac agaggaggaa   126240
tggaactccg gagagaccta cacctgtgtt gtaggccacg aggccctgcc acacatggtg   126300
accgagagga ccgtggacaa gtccactggt aaacccacac tgtacaatgt atcgctgatc   126360
atgtctgaca caggtggcac ctgctattga ccatgctagc gctcaaccag gcaggccctg   126420
ggggtcgagt tgctctgtgt atgcaaacta accatgtcag agtgagatgt tgcattttat   126480
aaaaattaga aataaaaaaa aatccattca aatgtcactg gttttgattg tccgatgctc   126540
atgcctgctg gggcaactgt tgtgttatgc ttgtcctgca cacaccctgt atacttgcct   126600
ccaccttggc ccttcctcta ccttgccagt tacatccttg tgtgtgaact cagaaaggct   126660
tacaacagag tgtgagcatg ccattcctcc agctacttct agatatggct taaagcttgc   126720
ctaccctggt gcaggcagca ttcaggcaca tccacagaca cacagagaca gacatgcatt   126780
tatacataga tctagagatg aacatgtata gatacatgca cgaatatgta ttcatagaca   126840
cacagataga ggttccgcat gcgtgcatgg acaaatacaa ataccttcag agacaaatat   126900
gcacagacac acaaccacac atggaaacag gcacaaacac acatgatcat gtgtgcacca   126960
aaacagaata taggcaaata tagacaagtg aactacatag acatgaagac atgcatacac   127020
agacatgtaa agaaacatct tgaaatgtgt acactaacat gtggacagac atggcacaca   127080
gttacacctg gtctctgacc aggaccataa tctccagggt tcagggctca gagagtccat   127140
actaggctgg gtggcactga tactcctcag ggtcccactc tatgattagg ggaaatagcc   127200
cgaggagcaa aatgtgcatt tttggctcaa caccatgggg cagaagatac cccactaacc   127260
acccatgaca gaaaattagc cttggttgtg tctccattaa tagaatacct caggagatca   127320
atgagagagc gcttgaccca ctcacttccc agtccagatg cagaagacac aatgcaattg   127380
tccaaaagaa ttgtacacac acacacacac acacacacac acacacacac acaccaacaa   127440
aggaacctct ataaggagtc accacccaat aacattgcct ctttggattc acatcctgga   127500
cattcttcat attcatatcc atttgggacc tgggctttag aaatcccaa gggctcatct    127560 ttacagaggt cagagatccc aataaatgcc ctggtcccac agcctctcta tctcttggta   127620
ccaagaccca acactgctgg cagggtaga acaatcaaca cacaggaact ctgatcaaag    127680
agaggcatga gatgcctggg tccttcagga agtaaggagg gataacctct gatatgccta   127740
ctcttattcc caaagcccag gagaagggaa acctgctctg aattctcagt ctaacagccc   127800
cgatggtgcc acctgctcag agaaagtcca aagaacacaa aaatcattat gccacatttc   127860
ctgagtctgc ctttacccat gtccgtatgt tgcatctgcc ttgcttgctc tgctgcccca   127920
gagttcctgg gacaaggccc caagttagtg cctcctccag tttgacctgt gctttgtctc   127980
tgtctagctt gagctattag gggggccagt caatactcca gaaccagcag aacacccca    128040 accctgaggc aaatgttcaa tcaccccaag gcttggcttg accctccctc tgtgtgtccc   128100
ttcacagagg gggaggtgaa tgctgaggag gaaggctttg agaacctatg gaccaccgcc   128160
tctaccttca tcgtcctctt cctcttgagc ctcttctaca gcaccactgt caccctgttc   128220
aaggtagtgt gtgtggtggg gctgaggaca cagggcagag acaggagtc accactcctc    128280 actgccccta cctctactct gtaaaaggga acagcaattc acactgtctc tgtcacctgc   128340
aggtgaaatg actctcagca tggaaggaca tcagagacca agagaccctc ccacagggac   128400
actacctctg ggcctggggt tcctgcctgt atgactagta aacttattcc cacatctttc   128460
ctgtgttgcc ctccagcttt gatctctgag acgggcttct ttctagactg gccaaagact   128520
```

```
ttgtccactt gtgcaacctg gaacaatgtc tggaaccaca gacagctgtg ctgtatacaa    128580
atgtcacttt gaaataaata cttcaccttg cgaacccact ctattgtgaa ggaatttgtt    128640
cttgttttca aacttttcct gtggtgttga catcccaaat actctctaaa tagagcctgg    128700
gaacttgaag tgaacagtct gatggggctt aagagtgaaa gagggaaagg aggtgtggaa    128760
gaagagagag agagagagag agagagagag agagagagag agagagagag agaaaccacc    128820
ctgacagcaa agtatagcac aggcagccaa tgggtagcag tctggtttat ccaccctgat    128880
agaagaaagt agggcagaga aaactccagg cctgatctca caaaagcaac cgaatctgaa    128940
aagtagcctc tagcctgggg tgtctgctcc atccctcagc ccaccacttt gggctggcgt    129000
tgcttccagc tagtgcaata ctttggtgtt agccaaacct ttgtggtatg tggggtgtgc    129060
cttgggagag ttggctgaga tctctaggat gtttgtatcc cttctgcaac atgacaagcc    129120
ctaggggtta gcccataact tgaggactca aaccctctgt ctataacaac tgctgtggtc    129180
actggagaag gacagctaaa ggcctgctca cacagcagga aggaaaggg aggtaggtca    129240
tgtacttcag ctcagaggag gaagcacagc agatacaagg tgagggcagt gctaggggtt    129300
ctgctgttca ccgtgtggat ggctggagga acctcacaga ggtgggacta gctggttaca    129360
ttgagagcag gacctgggag cagggcataa gaaagaatat cagacagtgg gagggaactg    129420
tgtagatgcc agggtccggc gcgcggagtc aagctctata ccaagtggac agctaaactt    129480
tgcattatta attatatggc tatggcttta gagtcatgaa ggatacatga gtaaagggac    129540
tgtaggatct tcctctgtgc tgaagagttc atgaggccaa gtgtgtgacg ggctccctgt    129600
gtggagtcac tggtaggcca ttggataaag ttataaaagg ctacaggatt tggagttttc    129660
tccgcttggc ttcactcttg ttttggttga gtatttcctc aatatgtccc cattcctcac    129720
ttttggaatg gtaatatatt tttcagtatc actgtatgat aaaagtatgt aatttttcttt    129780
agtactttat ggggcttacg ataaagacat tgccttgagt ctcagaagag actttggatt    129840
ttggactttt aaattgtgct gagaatttaa agtctacag gacttctat cacagggctg    129900
aatgtatagt gcactctgat atggccagga acacacgagg gccaggagcc tatctggtgg    129960
tttaaataag aatgatcctt ttagactcat atgtttgaat acttggtcca cagttggaaa    130020
ggattaggag ctgtggcctt gttggaggga ctgtgttacc ggcaataagt tttgatgttt    130080
caaaaatcca taccattccc agttagttct ctgtgcctca ggcttgtgga tcaagatgta    130140
agttctcagc tactatttga gtttcctgcc tccctacctg ctgtcatgca ctgtgccata    130200
acagtcatga actctaaccc tctgaaacaa tcaacccca atgaatgctt tcttttatac    130260
gttactttag acgtgatgtc ttatcccaac aaccacaaag caacttagcc ggtgtgtggc    130320
ccgatgagtg gtgcctgctc tcagttccca tgtgctcttc acaaactcag gtccatgacc    130380
ttggtcatgc aggctaagcc ttcagagttg ggtttgagct aaagagagtg aacaaatccc    130440
actcctaggc tcctgactct gagtctgcac tggctgcacg atgcccatgg gacacttcct    130500
cagcctgcgg gctacttcaa ttcctaaatc tgggctctgg gctctgcttg accttggtac    130560
tcttgaatc ttcttccttg acttctgagg ttcagcaagc ctgtcatgaa gcttcccagc    130620
atgggcatcc ctggtctgcc ctgtcctgat ttctctggat gtctctgtgc ttcttgtcct    130680
ctgcagcgtg ttttttctaat ggaaatctaa tgagctcagc tctagttccc ctactgcctc    130740
ttctcttatc ctgaaccccca cacttacccc tgccttctcc tgtgtcactg gtgctgctgt    130800
ctctactccc aaggaaccct ctctttccag gaaccctcag ccttcaaatt tagagtctac    130860
caccattctt gaagaagatg gccatattcc tatcccttgt gatcctggtg catccccttc    130920
```

```
agtcccagaa ccctgcagac cttgcccccc tcttctaacc tgcacttcac cctctgacac   130980
atgcctgtct ggttctatga catcatccct cccttctccc catgcaatcc actgccctgt   131040
gcacaccaca ttgctgtacc agttttctc tttcctttcc ctgtctcagt gtattccctg    131100
tcctctggac aggccatatt agccagcccc agggaccttc cctgcctagg tcttctcaaa   131160
gtataaccaa aggcccctcc tggccactag cacaggttcc ttctgtagct atgctattcc   131220
tgaatgtgag ctgaagtctt taacacgttc tggtcaccat caggctcata ctctgtgttc   131280
tatccacctg ctgtcagccc ccattctctt tcctaaacca cagattggtt gggattcccc   131340
taaggaagca ctgtctggag agaactggga gacactgcca ccatatttgg actttaacct   131400
gaataaaaag cctccctatg cagagagatg ataaaggcag agaacagact cagccagccc   131460
aggaacctaa ggaggctatg aacacagaga agcaggtaag ggccaggctt cctgatttct   131520
cccctgggtc tcaatggtac tacctcatcc accccaccc atccacgtga tgcagcttcg    131580
acctgatcta ggctcccctt atccctgac acagaaaccc ctaaaaaagg ggaacttag    131640
atagtacctt ctgacaccta gtttcaatcc tgttcttagc cttgcagaga tgggtatggg   131700
gtggcattca gacctttgtg acaatttggt tgcagctcct gagaggaagg atcccagagc   131760
taagctcctg gcggacatgg gccaaagcaa gaaaagaggc agtcactttt atattgccca   131820
cgcaagagtt gtatcagccg agaaaggaga gtacagtggg aggtctgggt cagtggtgaa   131880
tatcagcaga acggaacaac caacaaccca tggaagagtg ggaaggagtt gagatacaag   131940
actgtggagg ggttccatct gctgtatagg taagacagtc tgaagaacat tgaccagaca   132000
ggggtctagg aatgccacag ggtggaacat gggccagtgg atctgaacac acacacacaa   132060
caataactac tactaatact cccaccacca ccagagtcag cctcaaggag atgatgggct   132120
acatcaggag gcctgtgaga tgaacttggt ctgtctggaa gcttatagga ccacatcagc   132180
taaatcagca gagaggaggt gtccagagga gccagagctc tgcagcagaa atctttaggg   132240
ctgacaaagg tgagttgata gttcatccaa gagggacact aaggcgtgct ggcaaagcca   132300
agagtggtat ccctaaggtt tgggaatcaa gctcagtgtg aagagatga gaagcagagg    132360
caaacttgag ctgaaatagg ccaagattgg caggaagaag tctaagaaac tcctaggatc   132420
aggtgagtca gctacaggtg agctgtgaaa gctggacatt tgggaggaca aagacagact   132480
cagaagctct gggaattatg aaacagcaga gaggaattga ggtacctaag attttaaggt   132540
accagattga gcagccacag gagagctggg gcaggtggga gcttagggga cctgaataaa   132600
ccattatgta ggagccgagg tagctggaaa tatgggaaaa tagactgacc agctacggga   132660
gaactagagg agaatgaact taaggaaact gagtgagcag ccatagtggg gctgaggaag   132720
ctgggtgggt gggagaccaa gctgagaggc taaaagataa cagggatagg tgagagtgtg   132780
tggtaccagg atgagagcta aaggagattt gggcaggtac caatatgggg aaccaagctg   132840
agaatctaca gggagccagg tggcagttcc acagcttcag gacagtccta ggagtttagg   132900
aaaacaggat gagatgttac ctggacactg aagtaagtgg gaactcggac aaccagactg   132960
aacacctcca gggatcccag aggtattcgg tgagggggag ttgggaggga gggtggtcat   133020
ggagctcagg aaaacctgag caccaacagc agtgctgagg cagcactggg gagctggggt   133080
aggtgtggct gtgggaccag gctgggcag ctctggggag ttggggtagg tgtgactatg    133140
gagaccaggc tggcagctc tggggagctg gggtaggtgg gtgtgtgagg accaggctgg    133200
gcagctctgg ggagctgggg taggtgggtg tgtggggacc aggctgggca gctctgggga   133260
```

```
gctggggtag ctgggtgtgt ggggaccagg ctgggcagtt ctggggagct ggggtagctg    133320
ggtgtgtggg gaccaggctg ggcagctctg gggtgctggg gtaggtgggt gtgtggggac    133380
caggttgggc agctctgggg agctggggta ggtgtggctg tgggaactag gctgggcagc    133440
tctggggagc tggggtaggt gtggctgtgg ggagcaggct gggcatctct ggggagctgg    133500
ggtaggtgag gctatgggga ccaggctggg cagctctggg gagctggggt aggtgtggct    133560
gtggggacca ggctgggcag ctctggggag ctggggtagg tgggtgtgtg gggaccaggt    133620
tgggcagctc tggggagctg gggtaggtgt ggctgtgggg accaggctgg gtagttctgg    133680
ggagctgggg taggtgaggc tgtggggacc aagctgggca gctctgggga gctggggtag    133740
gtgtggctgt ggggaccagg ctgggcagct ctggggagct ggggtaggtg ggtgtgtggg    133800
gaccaggctg ggcagctctg ggaggtaggg gtaggtgggg gtatgggggac caggctgggc    133860 agctctttgg aagctggggt tggtgagata tggggaccag gccaagtagt cctgggagtg    133920
ctgtgatatg tggggggtgtg gggaccaggc tgggtagttc tggaggagct gggataggtg    133980
tgactgtggg gaccaggctg ggcagctctg gggagctggg ttaggtgtgg ctgtggggac    134040
caagctgggc agctctgggg agctgggtag gtgggagtgt ggggaccagg ctgggcagct    134100
ctggggagct ggggtaggtg ggtgtgtggg gaccaggctg ggcagctctg gggagatggg    134160
ttaggtgtgg ctatggggac caagctggga agctgtgaga agctgggtta agcaaggctg    134220
tggggaccag gctgggcagc tctggggagc tggggtaggt gtgactatgg agaccaggct    134280
gggcagctct ggggagctgg ggtaggtggg agtgtgggaa ccaggctggg caactctggg    134340
gggctggggt aggtgggaat gtggggacca ggccggggaag ctctagggag ctggggtagg    134400
tgggtgtgtg ggaccaggc tgggcagctc tggggagctg gggtaggtgg aatgtgggg    134460 accaggctgg ggagttctgg ggagctgggg taggtgggt tgtaggaacc aggctgggca    134520
gctctgggga gctggggtag gtgggaatgt ggggaccagg tagggcagct ctggggagct    134580
ggggtaggtg gggctgtgcg gaccaggctg gcagctctg gggagctggg gtaggtgggt    134640
gtgtggggac caggctgggc agctctgggg agctggggta ggtgggtgtg tggggaccag    134700
gctgggcagt tctggggagc tggggtaagt gggtgtgtag gaagcaggct gggcagctct    134760
ggggagctgg ggtaggtggg tgtgtgggga ccaggttggg cagctctggg gagctggggt    134820
aggtgtgact atggggacca ggctgggcag ctctggggag ctggggtagg tgtggctgtg    134880
gggaccaggc tgggcagctc tggggaggta gggtaggtgg gggtgtgggg tccaggctgg    134940
gcagctctgg gagtgctgtg atatgtgggg gtgtggggac caggctgggt agttctggag    135000
cagctggggt aagtggaagt atatgatatc aagctgagag tagctgcagc tgagctgggg    135060
taggtggagt gtagggacca ggctgggcac ctctggggaa ctgaggtggg tagaaatgtg    135120
aataaccttt ctgatgagcc acagggagc tagggctgtc agatcacagg tcccaggtta    135180
tacagcttct gagtcagggt agggggtaat tcttgagcag aggaaccaag caggtaggat    135240
agattgagca gccacagggg aatgggttgg taggaattgg agggaccagg ctgagtatgt    135300
acaaggtgat tggaaacgt cgaagtttgg ggtggggacg gggcgcagat caagcacttg    135360
ctaaggttct ggggcagatg ggagtgtggg aaagtggact gtgttgttac agggaaccag    135420
gacatgtggt tgtgtgggaa gccagtgtga atgaccacag tgtactgagg caggttttag    135480
tgctaggata ccagatcaag cacaggaaca cagtagttct agccagggcg actaggagtg    135540
ctgtggcagg agagtaaaca tgaaccagcc cagggccttt gaagaccgta gatgagtcag    135600
gaggtgacag ttgagggctt gggaatccag tgaggcgaga ggacaggaga cagcttaggg    135660
```

```
aaactggtca tctcacctcc ctgctgtgtc agcgctccta tagccgctct gcacctcgta    135720
tctgtatata cctattagca agaaaatagt aagagctggg tttggatata ggactgtgag    135780
caaggactag atggagggg aaatgatgga gaaagagaaa gggaaagtgc ccggggcctg    135840
tctaactcac aggcaagaga gaatcgataa tgagggacaa gaagggcctt ggctaagcag    135900
ggcagggaaa gtccctgcag ctaacaattt ccgaggaaca atatagatag cagttctcaa    135960
ctgggggccc attttagctt ctggagatga agaggaacat accgtaggaa ggtcaaactc    136020
ttacagaagt taggtataga gttggatgca cagggcgggg gcgggggca tatcagggta    136080
tgagcagtag gagccagcag ctatggttaa aagaaggatg atcctgaagc taagagaagg    136140
agacctgggc tggagagaat gtagcctgac aaccagtttc ctcgtgaatg gcagcatatc    136200
ctaaactcag gggctcaaag cttctagaaa gaaaaggggg actcgttggg atctggagac    136260
actggcgcca gtgacacagg agaaggcagg gatgagtgtg gggttcagga taagagaaga    136320
ggcagtaggg gaactagagc tgagctcatt agatatccat tagaaaaaca cgctgcagag    136380
gacaagaagc acagagacat ccagagaaat caggacaggg cagaccaggg atgcccatga    136440
tgggaagctt catgacaggc ttgctgaacc tcagaagtca aggaagaaga ttcaaagagt    136500
accaaggtca agcagagccc agagcccaga tttaggaatt gaagtaaccc agaggctgag    136560
gaagtgtccc atacatcgtg cagtcagtgt agactcaaga gtcaggagcc taggagtggg    136620
atttgttcac tctctttagc tcaaacccaa ctctgaaggc ttagcctgca tgaccaaggt    136680
catggacctg aatgtgtgaa agacctgaga ccagggccac aaattaaaaa caaggcctat    136740
taaaaacaga tgccagacac ataagctggc accagtgaca caggagaggg agcaaaggaa    136800
caccaggaca gcaagaggca gcatagcagg acaggcagag ccagggaagg caatgaagac    136860
ccactgaagg gaaacacgaa tgacgtgcac agcctcaaga cacagatgca agaggctcta    136920
gagcgggaca taggaaacac atggagaact catccaccag ctttctgaaa atgcatttgg    136980
aatagagctg tgctcagaag ttcaactggc caagcctagc tggtgatcct ggggtggaga    137040
gggtctaagg taaggcagtt ggaaccgtca aggtgatgcc ttggtctagg tgatatgcat    137100
gctcttttgca gaagcctggc atccttgtag gaccaaggac agaactcctc caggtgcctg    137160
gatccagccc tgtctgataa gctcacacat cttcctatct tgcagccaga caacagccc    137220
catctgtcta tcccttggtc cctggatgca gtggcacatc tggatccttg gtaacactag    137280
gatgccttgt caaaggctat ttccctgagc cggtaaccgt aaaatggaac tctggagccc    137340
tgtccagcgg tgtgcacacc ttcccagctg tcctgcagtc tgggctctac accctcagca    137400
gctcggtgac tgttccctcc agcacctggt ccagccagac cgtcacctgc agcgtagccc    137460
acccagccac caaaagcaac ttgatcaaga gaattggtaa gagggtgacc aagggagata    137520
atatttaatc aggaggtcag gctggggtca accccttgta tagaacaacc aaactgaaca    137580
gaccttggca gagagacaac accaatcagg gcagtgggct tcctttgtgt ctacctccta    137640
gaaacttctt tttgtgttcc tcacactcag aaagtggtcc tctggaatga ctaccagtag    137700
ctcacatcag ggacacacag aagtggacat gggtctcaac ttgtaaatgg tcatatccag    137760
gaacaccttg gcctgagaca acactagggc catcgttctc ctccccagac tattgccttc    137820
tcccttccag gccccattaa tgcccagtct tttctctgca gagcccagaa gacccaagcc    137880
cagacccccc acagatatct gttcatgtaa gtcatttaag tatcctttag ttccaagaca    137940
tgatcgtccc aaacagccaa atgatggagg acagttgctg acccacccta tctctctcca    138000
```

```
ccaggtgatg acaacttggg tagaccatct gtcttcatct tccccccaaa gcccaaggat    138060
atactcatga tcaccctgac ccccaaggtc acctgtgtgg tggtggatgt gagcgaggag    138120
gagccagacg tccagttcag ctggtttgtg gacaacgtac gagtattcac agctcagaca    138180
caaccccatg aggagcagct caacggtacc ttccgagtgg tcagtaccct ccatatccag    138240
caccaggact ggatgagcgg caaggagttc aaatgcaagg tcaacaacaa agacctccca    138300
agccccatcg agaaaaccat ctcaaaaccc agaggtggga acttcaggct gacttcatgg    138360
gggctgggat gggcgtaaga ataaatgcct gcgtggacgg ccatgacctc tgtgtctgct    138420
tctaacccca caggaaaagc ccggacacct caagtataca ccattcctcc acctcgtgaa    138480
caaatgtcca agaataaggt tagcctcacc tgcatggtca ccagcttcta ccccgcatcc    138540
atcagtgtgg agtgggaaag gaatggggag ctggagcagg actacaagaa cacccctaccc   138600 gtgctggact cagatgagtc ctacttcctc tacagcaagc tcagtgtgga cacggacagt    138660
tggatgcgag gagacattta tacctgctct gtggtgcacg aggctcttca taaccaccac    138720
acacagaaga acctgtcccg ctctcctggt aaatgagcac agtgcttagc cacacccag    138780 gtcttacaag acactgacac cagccctaac ccctgatcct ataaataaag cacccagaga    138840
tgggaccctg tgagattagc ctggttcttt atatggtata tagttcacga tatgcctcag    138900
ccacaggctg tggggtctgg ccagggttca aggtgtaagt taccctccaa gaaagaacaa    138960
ggtcttacac tgccagaccc agagcatgca agtgtacctg ccttgccag atcctccc      139020 tctctggata ctaagtttgg cccaaggggc cctctccata ctcttcccca caaccagcaa    139080
ctgttctgtg atgggactgg aaataactat agaaaatatc ccaaaaaaat cagcataggg    139140
aatgcctccc acctcaacac aaaccccacc ttcgtctgtc tgtccttccc tctaccacaa    139200
ctcacctatc ttgaccaagg aggtcttgtg tgcattacat aggcaagctg tgacactgac    139260
agagtcttag tcatacatga agtccattca tctcggccag acctccagag atagggatag    139320
ggatgacttc tctgaaggac actacctccc atatgacatc cgttcagacc taagctccaa    139380
gacactgaga cctgtgactc tagctgctcc caaggaagtg gctactcaga tacccacata    139440
gaactattag aaccagcctg ctaagcatca ctcaaacctc atggtacctc caagcataca    139500
ttcacccatt gatacctcac ctaggcaacc tgtatagcca ccaagtccat cttagtgtcc    139560
ggatatactt aaacactatc taaatgtcca catttggacc agtgcagatg aaagatctct    139620
catggacacc taaccatta cccctaacac acacaagtac ccctaaaccc agtttgaccc    139680
tctatcccta tttccctatt ttcatcccctt aaagttaaca ctctcccata gctgtataac    139740
caggctcact tcccaatgtg gaccttctag gaagcccagg catcaccaaa cacgggctct    139800
accctcactc tggccctctg aattcagtca ccaggagaca ggcagtagat caggcaggat    139860
gcagagcttc tacctacagg ggtctcaaga cttgactcag cctagccagg ctcagaactg    139920
aaggtgggga cacacagaat gacctactgt acaggccaga ccaccatcat gtccagggtg    139980
tctggtgagc tcaggacaa aactgcagca ctttggggag ctggagtttc tgatctagag    140040
agaacagaaa agaaagatgg ccccagggag ggtctgctgg accagtcagg ctgcagcttt    140100
ctcctgggtc tacacacagc ctcctgtcac acaggaatg gccctagccc cactttgttg     140160
gggcaaggac tgactgccct ctctgtgcag agctggaact gaatgaaacc tgtgctgagg    140220
cccaagacgg ggagctggac gggctctgga caaccatcac catcttcatc agcctcttcc    140280
tgctcagtgt gtgctacagc gcctctgtca cactcttcaa ggtcagcccc atttccccca    140340
ccatccccac aatatctaca ctatacccaa gccatcccca tagtgaccca tgatgtccct    140400
```

```
acctgtccca taccgtctca agctctctct catcatcata tgatatcttc cacaaagtca   140460
tatgctgtac tcatgccact ccctccttgt ccctctgttc tatattgtaa ccacattgtc   140520
catgttgtct ctaatttgtc ttgatgctcc cccaagttgt cacccaccct atccttacac   140580
tgtctccaat actcgctgca cactgttcct gtggctgatc cccactctac acctggtcct   140640
caccagatcc ctatgctgtc cctacaatgt ccccttgct atagctataa gccatcccaa    140700
aactccactc acagcacgcc ctgtgatctc actgttttat cctcactcta gatgtatgac   140760
accctaagat tggggactgc cctgtcttgg tgtacaagac ggaggagagt gaggtcaggc   140820
acataacatc tcacttttgc acctcgcagg tgaagtggat cttctcctcg gtggtgcagg   140880
tgaagcagac gatggtccct gactacagaa acatgattgg gcaaggtgcc tagcttgtct   140940
ctacagaagg cgccagagct tgctagccct ctaggaccaa gcccatgctg ctgaacaacc   141000
agacacacag gttatactgc cttctcatct cagcattctt tgatcttatg gctctcactc   141060
tgctatcaac atcccttcca cattggaagg agcatgtgga gagcaggctt taccacagac   141120
ggtagccaac aggacccaag tactactacc acagccagaa caatggatag gccaaaattg   141180
ctgtgtttct tctacatggt gtctagctct cagccaggca ctctcccagg aggggttgca   141240
tcacctgcat gcatttagaa gcagatgagc cttagagcca atcctgtcta cacagtcctc   141300
tgaaaaaaca tgcttctctg ggagaggagg actttccata tatctctgag actgagaagg   141360
ccccaaaggg acctctctgg gaaagactac caaaggtgat tctaacggcc ttcacccgac   141420
cagtgccttg ccatgttttt ctctgacacc taagtgaact ctcacttctt ggactgtaag   141480
atggggctcc ttgtgaagat gcctcttcct gccatccatg cgatgtgatg aattcccaga   141540
tataaaatcc catcggagac actgctgact ccacagcttg aagaccctgt tacctcacca   141600
gatgatctag agagatactc agcttcatag tctctgttgg gccctagcag gtgcaggagc   141660
ccctgagcag tggctgagca acacagaaaa gtctgtagga gaagagcatg atgaacacac   141720
cctgatcagt ccagaaggtg gtccaggagc aacatggggg aaaagagagg atgctttgaa   141780
agccaggcag gagtgggctt ttcctgcagc ccggcatcca gattgggcca ctgacagcag   141840
agaacaccaa ttagagtaaa catccaagga gagagcccag gcctggggca ctgaggctga   141900
ctgaccgctg gcattggaga ggcgccgtga ctgtttctcc atttcatatc aaggcaaatg   141960
ccaggccaga gttccccaac aaagtcaaag gagaaactct ggaaggaaag cggggggtgg   142020
ggggcttggg gggagttctt ggcgcttagg ggactccaag agatattcac tgacctgaag   142080
cttagctttg ccagctttt ctttaaattt tctggagtcc agtcatgtct ttaaggtccc    142140
tgttcatctt tttaaaataa taataaaaca tccttcaaca ttgtacaact cgctctgttc   142200
ttcctgtgtg gaccagcccc cactctcctt atacaaaaat cacacacaca cacacacaca   142260
cacacacaca cacacacaca aatatataca tgcacatgta cacaaacaca ctcacacatg   142320
catacataca catgtacaca cacactcaca catgcataca tacacacaca cacacacaca   142380
cacacacaca ccacacacaa aacatgctaa cattcccaaa gcacaaacca ctcagctcaa   142440
gtcccctcca actatcccat aatcaagtgg ggatgatcta tggttgggag tcattctgaa   142500
tttgcaggcc atggtggcca tgagggaggg atagtcagga agcaaagat aggaaccacc     142560
catatgagag gaacagatgc tgtagcttga gtgagggtta tagcctgata acttgcagta   142620
gagaagacag tctggtggaa atggcctcca cttgcgctgg tacagggtaa cagacttct    142680
gaggcagatc gggggctgg ggaaagaaag atggagctca gtagtgtcag ggtggtctgt     142740
```

```
tctcactgca ttcccaaggc gtagttttgt agctggaaca tcctaagatg caggtctaca  142800
taggccctgg cagaggagtg tggtggagac tcagggactg gactagccac aaaatctggt  142860
gcagttgcag cagcagtgtg gacctggcta gcaatgcaac tgcagcttct gctgttgtgg  142920
gagaagcgtt ctacctggga ctgagaagca tctgattcct gtaagtggca tttctgcttt  142980
gggagccaca caatgacagg caataaagtg tgccatttga ctcataacca gtacctacgg  143040
cgcgttgact tagatcacac atgaacaaga ggcccagagg ctatgaaccc tctccaatga  143100
gctggtcagg aaagagtggg cataatcact cagcctcagc cagctcaggg acccagaagg  143160
cccaggtgca cagagtagga gcacatccag gcttcctacc ttgtcccctg agtctcaaga  143220
gtaccacatc aactactccc acacatccac atgaactaat ctcagtcagc tttggactcc  143280
ccctcatgtc cagatacaga aacctcccca gaataaaggg gaacctcagg aaataccttta  143340 tgccacccac tgtcaatcat gttcttactc aatcataggg tggaaatagg gtggcattcg  143400
catctctgga acaaaggctg tgactctggg aaagacaaga gaaagccagg aacaaataca  143460
tctgctttca cagcttccac atgtcaaagg ggtcagcact aaatgaagct gcagaagaag  143520
aggacctcac agacagccag catctgtagc ccttccagat ctttgagtca tcctatcaca  143580
ggagattgag aaggagttga cggaccagcc caagcagagg aagcctgtgt gttcaacagt  143640
aaatgtgttt gccagcagcc tgatgtcaac tgagaagact gtggcgagtg cttgggagac  143700
aatcacgggc agctagagct gcacaacccc atagacaaca agcctgaaac acaaggagat  143760
gatgaaatat atccagaaga ctgcggaatc agtttggcct ggaccacagg ttgatagaac  143820
caaggcagct gagccctgtg gtaagtgacc aggagggcag agggagggag cttccaggag  143880
catgcctggg aatgccttca ggccttctga gaagcagaaa gtaggcactc tggggttcca  143940
ggaaccatcc cagcactcaa gagttactaa gggaatagaa gcaaacctga gctgaaggag  144000
agaaagaaaa gtggagggaa gcccaagcca ctcaaagtaa caggcaggac aacttccagt  144060
gagctgagag aataggagtg ctggagaagg cagagcaagc ccagcagatc aggagaacct  144120
gcataggagt ctggatgact agagaaaccc agaaggtgag agaacaggct taacagctgt  144180
catggactta gggatatgca agcctggggc accaagctga tctgcataga gggcaagggt  144240
aagtgggaat ccaagagatc taagaatgac cagcgctggg cagagaggtg gcctgggaga  144300
agatggctgg tcttccccat gagtccaata gcaagattgt cggaataggt tatcctatga  144360
cagatggcag tatcagtgac caaatgaaga cgctatggaa gaattggacc atgtgggagt  144420
tgagagttga ggacacaagg ctgacctgcc catgggaact acagctgata aaagtgctgt  144480
gattcagggc atttctggaa gctctgtgat ccaggttgca gtacacaagt aaactgggac  144540
agacgggagt tctgggggtt cagttcagat actaggaact taggaaactg ggaaaaggga  144600
agttggggct gatggcagaa ctatgagaag gcactggaat tctgaagacc agaccttcta  144660
atcaactata gaggaaatgg agtgggtagg agtggtggat acagctgagc atcacagggg  144720
acctggggat tggggacagc tatactgggg ctagcagtgc aaacacagaa attggggac  144780 caaagggga attgaggatg accttgggta gatagaaatg ctggatgcct aaggtacctc  144840
caggagctta gggaacctcg cagagcagct acaaagctgg tggtgttagt gacactttca  144900
gaaccagatc gggcaggttg gcatgtagaa atggggttaa tggagaccca ggacagtggc  144960
agattcagaa taaatacaa acaaccgaaa gagttatgtg ccctgtaaga agttgatctg  145020
acacccacag cagagacatc taaggtctca cagcccacat caaacaggct tctgatctaa  145080
ggacagcaca aaaggaagga ggcatcaaac catcctgggg aagacagtgc agtagtagcc  145140
```

```
agaagtgtaa gcccaacagc agtgggactg gtgtagcagc cagggacagg gtccctgcca   145200
agatgagcct caggggagct gagcagctga gaaactcacc agctgagaag ctcaggggaa   145260
tcagggtaag tggaggttcc agagaatcag gggaagtcag gagctcagaa cccaagaagg   145320
ggcacctgca aaagagctaa ggcctatgag agtgtgggga cactttaag cagctttagg    145380 ggagccaaga caggtagaag tgtggggacc caaacaggga agctccaggg gagctaggaa   145440
aggtggaact gtgggaatcc aggcagagca gcacctgggg agcaaggaaa gaagtgtggg   145500
gatccaggca gagcaggtcc aggggagcca aaaagtggag gtgtggagac acaagcaggg   145560
cagcatctgg ggaaccagga caggtggaag ggtagggacc caggcagagc agcaccaggg   145620
gagccaggac aggtggaact gtggggatcc aggcagagta gcaccagggg actaaggaaa   145680
gaataagtgt ggggatctag gcagaacagg tccagaggag tcaaaaagta gaagtgtgga   145740
gagccaagca gggcagcatc tggggagcca ggacaggtgg aagtgtgggg atccaaccag   145800
agcagcacca ggggagccag gaaaggtggt agtgtagggt cacaggcaga gtcgaaccag   145860
ggaaccaaag aaagaagaag tgggggggacc aggggagcca ggacaggtag aagggtgggg   145920
acccagacag agcagctcca ggggagccag gacaggtgga agggtaggga tccaggcaga   145980
gcagcaccag ggaagccagg acaggtggaa gggtagggac ccagacagag cagctccagg   146040
ggagccagga caggtggaag ggtaggggcc caggcagagc agcaccaggg aacgcgggac   146100
aggtagaagg gtggaaaccc aaacagggca gcaccagggg agcaaggaaa ggttgtactg   146160
tggagatcta ggcagagtaa taccaggaa gccaagacag gtagaagtgt ggggacccag    146220
acagagcagc tccaggggag ccaggacagg tggaagtgtg gggacaaaaa tggggcggct   146280
tcagtgtgtc tggggagcaa ggaaaggtag aagtggagag acccaggcag agcaatacca   146340
ggggctaaca aggtagaagt gtggggacca gaacagagca gcaccagggg agccaggaca   146400 ggtgggggatg tggggacccca ggcagggcag ctcaagggga gccaggacag gtggaagggt   146460
agggagccag acagagcagc tccaggggag ccaggacagg tggaagggtg gggaccaagg   146520
cagagcagct ccaggggagc caggacaggt ggaagtgtag ggaccaggc agagcagcac    146580 caggaaagcc aggacaggtg gaagggtagg gatccaggca gagcagcacc aggggagcca   146640
ggacaggtgg aagggtaggg acccagacag agcagctcca ggggagccag gacaggtgga   146700
agggtagggg cccaggcaga gcagcaccag gaacgcggg acaggtagaa gggtggaaac    146760
ccaaacaggg cagcaccagg ggagcaagga aaggttgtac tgtggagatc taggcagagt   146820
aatgccaggg aagccaagac aggtagaagt gtggggaccc agacagagca gctccagggg   146880
agctaggaca ggtggaagtg tggggacaaa aatggggcgg cttcagtgtg tctggggagc   146940
aaggaaaggt agaagtggag agacccaggc agagcaatac caggggctaa caaggtagaa   147000
gtgtggggac cagaacagag cagcaccagg ggagccagga caggtgggga tgtggggacc   147060
caggcagggc agctcaaggg gagccaggac aggtggaagg gtaggagcc agacagagca    147120 gctccagggg agccaggaca ggtggaggtg tggggaccca ggcagggcac caccaatggc   147180
caacaaggta gaagtgtggg gacccaggca gagcagctcc atgggagcca ggacaggtgg   147240
aggtgtgggg accaaggcag agcagctcca ggggaggcag gacaggtgga agggtgggga   147300
cccaggcaga gcagctccag gggagccagg acaggtggaa gtgtgggggac ccaggcagag   147360 cagctccagg ggagccagga caggtggaag ggtggggacc cagacagagc agcaccagga   147420
gtgtcaggag aggtggaagt taagtagtta taggggaaca ggggcagaat agaatgaggg   147480
```

```
atgcaggctg agaggataca ggggaaatgt ggcaagtgga agggcaggaa gagaggcaga    147540
gtggctacag ggaagttgag gcaggtaaga ctgtctgttc caggtcaaaa aacactgaag    147600
gccagtagaa aggaaactgg tgcatgtggt agtgggggat tcttagctta gcagtcacag    147660
ggaaagtgag ccaagtagga atgcaggcat ggggggcagg cacagctgag caaacactaa    147720
agagctgtag ctgaagggtt ataaggtacc aagctgagaa gctgctggga atctggagct    147780
aatggggtgt gggggagcag gctgagcaac tacacaggat cagggatagg taactgtgta    147840
aggaggcagg ctgagcatct ccatgacagc tggagctact atgaatgtta agctccagac    147900
tgagcacctg cagggaaaca gaggcaagag ggagtgtggg gatccaggct gagtaggtcc    147960
agggaagctg tagtaggtgg aggtggaggc ccaggctgag gagctacagg agagatggga    148020
cactagggag ggcagggatc atggccaagc ggatactcag tagctgagat agatgtgggg    148080
aatcagctta agcagcagac acaggggagc aggatctagt cagcttctag ggatccaggc    148140
tgtgtagaca tggagggact gggggagcta taagtaaata cactaggcat aaaattacag    148200
ggaaacggag gccagtggga acgtgggcct cctaccgaac aagtaacaga gagccagaac    148260
tgacgggttg aagaggaacc aggctgatga gctccaggaa atctgtgggg actcggtcaa    148320
tgggagaaca gggtgagcag ctatagagga tcagggatag gcaaagacgt atggagtcag    148380
gctgagcagt tacatgagag ctggagccct agttatgtgg aggtccaggc agaggggctg    148440
gagggtagct gagggaaatg tgctagaga atcaggctag gcagacacag gggagcaggt    148500
tctagtctac atatgagtgg ggatccagga tgtgtagaga aaggatagca aaggtcatgg    148560
aggattccag gcttaggggt cactgggaaa ctaagactgg tggaagtggg attgtcctaa    148620
gtgaacaaat tccatgaagc tagagccagt gggtgtaaag gtagcagact gaaggactat    148680
agagtatctg ggggtggatg ggaatgtggg gaatcgtgct gagccactac aaggacagtg    148740
tggctagcag gctgtaggag accaagctga gtatctgaag ggaaaccaag ggaagtggaa    148800
gtgtaggatt ccagaaatga gcaaatgcag ggcacttgag gcaggtatca gtgtagggaa    148860
cgagactgag cagttcacag gtcacccagg gtaggtaaga gttctggatc atcagagaag    148920
cctctggaag ccctaagcac ctacagtaga cctaaggcag gtgggggtgca gggaataagt    148980 tgtgcagctc ctgaggagga ggacaggttg gagtagaggg ggttctgact aaagagttga    149040
atgggagcag ggcaggtggg aatgtagagg aactagctag acagaagtcc agatgagatt    149100
gagggccaca tgatgccctg agccgatgag ctggccttag aaatcacttt gctgggacca    149160
gggccagggg tttgaggaac aaggctgagg tgaaatggta gcatgacagg gaggcaatgg    149220
cagagaggaa ggagaaggca tgcttaattc atggtggagt gcagggaggg aaagagccag    149280
gaggtctagg ctggagctga tccagctttc tgcactgatg agaggggcgg gactgagttc    149340 tttggctcc aggagccagg gcaacaagac aaaggcgcct agcatagcaa ggacacatct    149400
ggatctaaga ccaggagaag agggcaagac cgaaagttca ggaggtcatg ggagggagcg    149460
ggaaatctac aagggactgt ctttagaaaa gagtaagtgc ccagtggagg gagtgcccaa    149520
gcaacaagtc cagtgttggg agagatcggg gtgggcaaag gctgtatgtg cagtaggcag    149580
gcccaagtcc ccaggaagga aagaagaagt gcataggaaa acgggtcagg tctagcagga    149640
gccaaccgag gtgctcagga ctgagaggca gagcccaaga cacaggaatc gctgagctca    149700
tgcaggtacc aagaataact gagagctaag agaaaaatta tctagggaat aggggacat     149760 gaggaaggac tgttggctga gaagggaaag ggacaggag aatcctaagg gttggctag      149820 acaaaggaaa cacacaggct ttgggttgtt agtccggggc tctgcatatg atccaccgag    149880
```

```
attgtggaaa cagaagagca ggaagatcaa atctgtccca actatacagg gacacacggt   149940
cgacctacaa aaggaaggag atgtgaggat caggggccga gcagtgagga ggtgtgtgga   150000
ggtgttagag ctcaggtgca gcagagacta gcatggccct ggggatagag ggaaggaccc   150060
aagggacagt agggacagga gggcgaggtg aggtgatgac cagcattata caaatggtgg   150120
cgctgtccaa cttctagggc cctgtgctac tgagaaagga aagggacttc cgaggtttgg   150180
caatacaagc cccgtgcaaa ggcagaaccc agggcactgt gaagacaaca ctgcaagaca   150240
ggagaagcca aggctgagtt caccgaggtc acattagtga aatacactg cgaggagagg    150300 ggaggcgctg agcacccagc cacaccagac aggcccatgc tgagtccctg gacagtgggg   150360
gaggggagca cctggtgacc tgtaagaact gtgagactgg aggagaacca aggtaaaagg   150420
tgtgtcaaag gacacatgtt tagcaggctg ggccgactta atgcaggaca cacgtggtgg   150480
caaagccaag agggctgcgt atgagccaca agtgaatcct gacccaagaa tagagagtgc   150540
taaacctact tacatcaaag ccaactgaaa ggacaaggcc agcaaaacga agctaaggcc   150600
agagatcttg gactatgaag agttcagaga acctaggatc aggaaccatt agtgaacaga   150660
caaaggcagg taaagcagcc taggagtgga caaagacagg agaatacaga agacggcagg   150720
gatgacccga cttcagtttg ggcttcactg ttgtccaaac tgtgtgcaga ttatggccca   150780
tgggtaagag gtttagcatt agaacacaga tacccacatt ggacaatggt ggggaacac    150840 agatacccat actgcaaggc tcttcgagcc ctttcctaaa agtgtactag gagtgggact   150900
gggctcaaag ggattaggtg tgatctggcc tggtgaggct gacactgaca agcccaatgg   150960
ttgggtgttg catcctccat ttatacagcc agggacttgg ggagggtaca aaatggagga   151020
cttgtaggag cttgggtcca gacctgtcag acaaaatgat cacgcatact ttttcttgta   151080
gctgaaacaa cagccccatc tgtctatcca ctggctcctg gaactgctct caaaagtaac   151140
tccatggtga ccctgggatg cctggtcaag ggctatttcc ctgagccagt caccgtgacc   151200
tggaactctg gagccctgtc cagcggtgtg cacaccttcc cagctgtcct gcagtctggg   151260
ctctacactc tcaccagctc agtgactgta cccctccagca cctggcccag ccagaccgtc   151320
acctgcaacg tagcccaccc ggccagcagc accaaggtgg acaagaaaat tggtgagaga   151380
acaaccaggg gacgaggggc tcactagagg tgaggataag gccttagact gcctacacca   151440
accagggtgg gcagacatca ccaggagggg ggcctcagcc cgggagacca aacattctcc   151500
tttgtctccc ttctggagat ttctatgtcc tttacaccca tttattaata ttctgggtaa   151560
gatgcccttg catcatgaca tacagaggca gactagagta tcaacctgca aaaggtcata   151620
cccaggaaca acctgccatg atcccacacc agaaccaacc tggtgccttc taacctatag   151680
acaccaataa cacacagcct tctctctgca gtgcccagaa actgtggagg tgattgcaag   151740
ccttgtatat gtacaggtaa gttactaggc cttaaattcc agccccaggt ccaacaaatg   151800
tcctctgagg cccatgttgg aggatattgg catatttcca cctttcttct tcatctacag   151860
gctcagaagt atcatctgtc ttcatcttcc ccccaaagcc caaagatgtg ctcaccatca   151920
ctctgactcc taaggtcacg tgtgttgtgg tagacattag ccaggacgat cccgaggtcc   151980
atttcagctg gtttgtagat gacgtggaag tccacacagc tcagactcga ccaccagagg   152040
agcagttcaa cagcactttc cgctcagtca gtgaactccc catcctgcac caggactggc   152100
tcaatggcag gacgttcaga tgcaaggtca ccagtgcagc tttcccatcc cccatcgaga   152160
aaaccatctc caaacccgaa ggtgggagct gcagggtgtg tggtgtagaa gctgcagtag   152220
```

```
gccatagaca gagcttgact taactagact tctgccctct tactgacctc catgctgacc   152280
actctctgta tccacaggca gaacacaagt tccgcatgta tacaccatgt cacctaccaa   152340
ggaagagatg acccagaatg aagtcagtat cacctgcatg gtaaaaggct tctatccccc   152400
agacatttat gtggagtggc agatgaacgg gcagccacag gaaaactaca agaacactcc   152460
acctacgatg gacacagatg ggagttactt cctctacagc aagctcaatg tgaagaagga   152520
aaaatggcag cagggaaaca cgttcacgtg ttctgtgctg catgaaggcc tgcacaacca   152580
ccatactgag aagagtctct cccactctcc gggtaaatga ccccagagtc agtggcccct   152640
cttggcctaa aggatgccaa aacctacctc taccacctttt ctctgtgtaa ataaagcacc   152700
cagctctgcc ttgggaccct gcaaaaatgt cctggttctt tctgagatac agagtccagc   152760
gaggtcatgg gctgaggggc gtccagggtt tgaggcctga ggtttgacta aggaaaaagg   152820
gtgatctaca ctgccagaca cagcactttt gatttgctgg catgaacaga atttacctct   152880
cactgaaaag tggaggcttt atcccgaggc aatccctctt gctttctctt cctctaccta   152940
atacatctat agtgggcaca gaatatatca tgaaagtaag gacgacccaa actccacctc   153000
cctagtccac ctttacccct cttcctagcc aaggatccca ctgaaggcac tcaatggaca   153060
catatggtca cagacagacc cttgctattc caccactcaa tgcaagaagc gttccagaga   153120
ctaagtctaa tgtaacgatg cacatagctg tcactgctct ctcactgccc atgagaatca   153180
acatggaccc attagacaca acctgatgag caacactgag ggcaaaaggc ccatatgtat   153240
gcatgcacac acatcttcaa atgcacagca cagtgacaca cacacacaca cacacacaca   153300
cacacacaca cacacacact ggaacctcac atgggcatcc tgtgcagtac tcccagatga   153360
aaagaaacca ggtctacaca caggatcatc ccaacattca caagtgggcc agctgagaca   153420
gatacaactt ttctctgcct tggatgccca cagacatctt catgcacaca tgagtttcct   153480
ggggtcaatc tgtccctgac cctgggatgg tgccccaacc tcacacagtt ggcacccatc   153540
cgaaactgta taacttactc acttcccact gtggatctta actgcagtcc tagcatcatg   153600
gggaatcagc tctgcaatcc ctctggccct cagttctcgg tcatcagcag atacaggatc   153660
aggcagacca cacagacact acccatgaga ggcacaggcc ctgactcagc ctagccaggt   153720
tcagaactca aggctggagc acacacagaa tgacctagtg tataggccag gccaccatca   153780
ggtccagggt gtctggtgag ctcagggaca aaactacagc actttgggga actgaagttt   153840
ctggtccaga gagagatcag aaaggagaga tggcctcagg gagggtctgc tggcccagtc   153900
aggctgtaac tttctcctgg aactccacac aaccccatct gacacaggga atggccctag   153960
tcacgccgtg ttgggataaa caaacgctga cttccctctc tgtccaggga tggaagtgga   154020
cgatgcctgt gctgaggccc aggacgggga gctggacggg ctctggacaa ccatcaccat   154080
cttcatcagc ctcttcctgc tcagcgtgtg ctacagtgca gctgtcacac tcttcaaggt   154140
cagccacgcc atctccacag tgtccacacc atcctcacac tgttcctcat actgtctctg   154200
tgatcagcta tgcccacac tgtcccatgc tattgacctg tcttacatgc tgggcaatgc   154260
cacctaacct tctctatgat acagtctcac agtgtcccat gcagtctccc taattcccca   154320
agatgtccgc actctattgc tgtgttgcct catgctgccc ccacactgtc catccctccc   154380
tggtatgcta tcccaggctg ttgtctctat tttcatgctc tcctcacact gtccctagtg   154440
tctcatactg ccaatgttgg ctcccacatt gtcccacac tctgcacaca accggacaat   154500
aaaccctgct gtcccataat gttccctgtg gtccccaact ctatccctgc acatttgtct   154560
atgttccctg aattctcatg ttgtttgcac actgttagtg tctaacgaac tctctcccag   154620
```

```
gtgtaccttc ttccatgctg tctcacctca tctcccattc tgtccttgta ctaaccccac  154680
tctatcacga cactgtccct attcactgtc cctatgaagt gcccatgctg tctgcattct  154740
gtcccatgtt gtatcctcat cccggtctca tgcagttcag atctatctga cactattccc  154800
actctatgca cacatttccc cctataccat ccctgtctga tcaacatgca atcctctaga  154860
cacccatgta gcaggttaga gactctaggg atgggtacct gcctgactga gctacctctc  154920
ttggtgggag aggaaacaca ggtgagagtg cagtcctgat cttatcttat tcacccagtc  154980
ccacaggtaa agtggatctt ctcctcagtg gtagggttga agcagacgct ggttcctgaa  155040
tacaagaaca tgattggaca agggccctaa gccacctcct ataatggcaa aggattcccc  155100
acgccctaga ggaccctgtc caatgtgcca agcagtctga ctcagatcac actgtctgct  155160
cacttcacta tcttctgtct atgagaccca acctccctca attcttctct ctctggagga  155220
ctatgtggac attagatttc caaaagccac agcctccagg acctaaaata ccatcacagc  155280
agcagccagg acactagata gggtcagaag gaccatagtt tcctgactag tttatccaat  155340
ctgttgggac agaagaatca ctgaaaaagt gacaagtgcc caagttgcct gtgttcagct  155400
tggaagggac caaccttgga accagtcctg tcagcatcat cttctaaaac acaagaattg  155460
agtatgtaaa tggcagattt tggatcccca gggtaagaca gacttcaacc aggccacgac  155520
ctggacaatc atgcccagc tgaagttgac tgaattattc cagtggcctt cacatcgtct  155580
tgccaggttc cttcttacca cttccatgaa ccctgggata cagaaaagaa ctgtgcttct  155640
cgggatcttg ggacagaact gtctaattgg tgggatcctt aggtagatct ttcttccagt  155700
cacgggtata atacaataca ctagattctc acataaagga aaaaattcac acacaactcc  155760
ggccagtcct gaggcctaga caccaccacc tctctggaat tctgagctct atgctggagg  155820
cacaagagag gaaggcctgg acttcatggc ctctgtgtag ccctagtagg tgcagaggcc  155880
cctaagccgg ggttgggtga ccagcaagga cctcctggag agggatctga tgagtagatt  155940
ccacctggga cagaaggaaa aagatgaaaa gcaacagagg tggaagggca ctggagagag  156000
ccatggtata gcaggtttat cttgcagacc tgacatctgt ccatgactct gagacttagc  156060
taatgacagc tgggggcagca gtccaaggaa ttaccatgcc ccctaacacc aggctcctgg  156120
agtgtggagt gggtctactc cagagctcca atacctgttt ctccatcact tctcagccaa  156180
tgagaaatcg gtttccagac aggaagaaaa atgaaggcag gaaggaaaag tgggcacctg  156240
ttcttctgtg agtggcagga agttctcaaa agactcagga ctttggcttc taacttcctg  156300
tggatcattg atgtctctaa ggtctctgtc tgctttgttg gttttgtttg tttttggttt  156360 ggttttttt tttttttttt tttggtcaat aaaacgtttt ttcaaacatt ccacaatctc  156420
tgtgttcttc ctatgtgaac cagccctggt acttagaaac agcactgtta aagccgcgcg  156480
aggaccactt cacctacccc tacaggaggt aacccagacc atgtctggac tcccctggt  156540 ctcccctac cccaaacact gaaaccaaca gaagaaagag gaacctcagg aagtgtcccg  156600
tgtcacccag tttcgatcct gttcttagtc tgtactgggt tgggagaagt gtgatgttca  156660
cacctctggg gcaaggactg tgaatcctgg aaggatgaga cagatctcag agctgggctg  156720
ttagcagccc agcaccaatg caaaaagagc agcagtcaca aggttccaca cgtgaatgta  156780
gtcagcagag aagctggaga aagccacagc ctagggagag cagtgagctt ttccagacct  156840
aatagacggc agaacacagg aggatgagga gttgacagat cagcccccaac agaggggcct  156900 gtctgttgca aagaaaaggt gcctacctgc aacctggtgc caaccaggca gacaccagac  156960
```

```
tttccacgga cagaagccaa gaccactaaa gccgtgccca cctacagaca accagagtaa  157020
gcctcaagga gttaatggga tagacccgga aacctgaggg tctagccagg cctagaggcc  157080
ggtggaccca ggacagctga accaacagag aaaagaaaac ccagtggagc aagggcagag  157140
gcatacagaa ttgagagagt tggtaaagag gggatgggga acgttcacct gggaggactg  157200
atacacctat tagaaagagc tagagtcaga gtggatgccc ttgtgactcc cggcattgga  157260
tagcagatcc caagaacaaa gctgaaagaa ggtaaatttc tcaagagaaa gtcttccaga  157320
ggaactatgg gtaccaggca ataagtagta catccgtagg agggaaccag acagtagtac  157380
atctgtagga ggggaccagg cagtacagct gcaggtaggg accaggcagt atatctgtag  157440
gagaggacca ggcagtatat ctgtaggagg ggaccaggca gtagtatacc tgtaggaggg  157500
gaccaggcag tatatctgta ggagaggacc aggcagtagt atatctgtag gagaggacca  157560
ggcagtatat ctgtaggaga ggaccaggca gtagtatatc tgtaggaggg gacaaggcag  157620
tacagctgca ggtaagctaa ggacagtaag agtagtagag agccatggtg actccaaaag  157680
ctcagaagac ctggcagagc agctacaggg aatccgggc tggtggagtt gggaggacca  157740
agccaaagag ctataggtaa gccgaggctg gtgaaggcac aaaaacaagc taaggagcta  157800
cagggggggc aagggctgtg gcaggtgtgg ctaagagagg tccagggcac ccccaggaac  157860
cagaaagagc tttacaggag ttctagagga ggaaggagtt ggggagacag gctgggtatc  157920
tgtaaagata aggtagcagt tgtcacagtt tgggtctcag agctgcccag gggattaggg  157980
gaaaattctg agaagctgtg ggagagtagg ggatggtagg aatgtggagg accagtccta  158040
gcagctgtgg ggaagctggg gatggtagga atgtgggggga tcagtcctag cagttttggg  158100
gggagctggg gatggtagga atgtggggga ccagacctag caattttggg gggagctggg  158160
gatggtagga atgttgggga ccagtcctag cagctatggg aaagctgggg atggtaggaa  158220
tgtgggggac cagtcctagc agctatgggg ggagctggga tggtaggaat gtgggggacc  158280
agacctagca gttttttgaga gctgggaatg gtagcaatgt ggggtccagt cctagcagct  158340
atgggagagc tgtagatggt aggaatgtgg gggaccagtc ctagcagctg tggggaagct  158400
ggggatggta ggaatgtggg ggacaagacc tagcagctat gggagagctt ggaatggtag  158460
aaatgtgggg gaccagtcct agcagctgtg gggaagctgg ggatgggnnn nnnnngggag  158520
gaccagtcct agcagctatg ggggagctgg ggatggtagg aatgtggagg accagtccca  158580
gcagctatgg gaagagctgt gaatggtagg agtatggggg accagtccta gcagctatgg  158640
gagagctggg gatggtagga atgtggggga ccagtcctag cagctatggg agagctgggg  158700
atggtaggaa tgtggggggac cagtcctagc agctatggga gagctgggga tggtaggaat  158760
gtgggggacc agtcctagca gctatgggag agctggggat ggtaggaatg tgggggacca  158820
gtcctagcag ctatgggaga gctggggatg gtaggaatgt ggaggaccag tcctcacagc  158880
tgtggggaag ctgggggatgg taggaatgtg gaggatcagt cctagcagct atgggtgagc  158940
tggggatggt aggaatgtgg gggaccagtc ctagcagcta tggagagct agggatggta  159000 ggaatgtgga ggaccagtcc tagcagctat gggagagctg ggatggtag aatgtgagg  159060 gaccagtcct agcagctatg ggagagctgg gaatggtagg aatgtggggg accagtccta  159120
gcagctatgg gagagctggg gatggtagga atgtggggagg cctgtcctag cagctatggg  159180
agagttgagg atagtaggaa tgtgggggac cagacctagc agctatggga gagctgggga  159240
tggtagtagt atgggggacc agtcctagca gctatgggag agctgggaat ggtaggagtg  159300
tggaggacca gtcctctcag ctgtggggaa gctggggatg gtaggaatgt ggggggcctg  159360
```

```
ttctagcagc tatgggagag ctgggaatgg taggaatgtg ggggaccagt cctagcagct  159420
atgggagagc tggggatggt aggaatgtgg aggaccagtc ctctcagctg tggggaagct  159480
ggggatggta ggaatgtggg aggcctgtcc tagcagctat gggagagttg aggatagtag  159540
gaatgtgggg gaccagacct agcagctgtg ggggagctgg gaatggtagg aatgtggggg  159600
accagtccta gcagctatgg gagagctggg aatggtagga atgtggggga ccagtcctag  159660
cagctatggg agagctgggg atggtaggaa tgtgggggac cagtcctccc agctgtgggg  159720
aagctgggga tggtaggaat gtggaggacc agtcctctca gctgtgggga agctggggat  159780
ggtaggaatg tgggaggcct gtcctagcag ctatgggaga gttgaggata gtaggaatgt  159840
gggggaccag acctagcagc tgtggggag ctgggaatgg taggaatgtg ggggaccagt  159900
cctagcagct atgggagagc tggaatggt aggaatgtgg ggaccagtc ctagcagcta  159960 tgggagagct ggggatggta ggaatgtggg ggaccagtcc tcacagctgt ggggaagctg  160020
gggatggtag gaatgtggag gaccagtcct agcagctatg ggtgagctgg ggatggtagg  160080
aatgtggggg accagtccta gcagctatgg gagagctagg gatggtagga gtgtggggga  160140
ccagtcctag gagctatggg agagctgggg atggtaggaa tgtggggggac cagtcctagc  160200 agctatggga gagctggtaa tggtaggaat gtgggggacc agtcctagca gctatgggag  160260
agctggggat gataggaatg tggggggacct gtcctagcag ctatgggaga gctgggggatg  160320 gtaggaatgt gggggaccag tcctagcagc tatgggagag ctggggatgg tgggaatgtg  160380
ggggaccagt cctagcagct gtggggagc tggggatgat aggaatatgg gggacctgtc  160440
ctagcagcta tgggagagct gggggatggta ggaatgtgga agaccagtcc tcacagctgt  160500
ggggaagctg gggatggtag gaatgtggag gatcagtcct agcagctatg ggtgagctgg  160560
ggatggtagg aatgtggggg accagtccta gcagctatgg gagagctagg gatggtagga  160620
atgtggagga ccagtcctag cagctatggg agagctgggg atggtgggaa tgtgggggac  160680
cagtcctagc agctgtgggg gagctgggga tgataggaat atgggggacc tgtcctagca  160740
gctatgggag agctggggat ggtaggaatg tggaggacca gtcctcacag ctgtggggaa  160800
gctggggatg gtaggaatgt ggaggatcag tcctagcagc tatgggtgag ctggggatgg  160860
taggaatgtg ggggaccagt cctagcagct atgggagagc tagggatggt aggaatgtgg  160920
aggaccagtc ctagcagcta tgggagagct gggggatggta ggaatgtgag ggaccagtcc  160980
tagcagctat gggagagctg ggaatggtag gaatgtgggg gaccagtcct agcagctatg  161040
ggagagctgg ggatggtagg aatgtgggag gcctgtccta gcagctatgg gagagttgag  161100
gatagtagga atgtggggga ccagacctag cagctatggg agagctgggg atggtagtag  161160
tatgggggac cagtcctagc agctatggga gagctgggaa tggtaggaat gtggaggacc  161220
agtcctagga gctatgggag agctggggat ggtaggaatg tgggggacca gtcctagcag  161280
ctatgggaga gctggtaatg gtaggaatgt gggggaccag tcctagcagc tatgggagag  161340
ctggggatgg tgggaatgtg ggggaccagt cctagcagct gtggggagc tggggatgat  161400 aggaatgtgg gggaccagtc ctagcagcta agggagagct ggggatggtg ggaatgtggg  161460
ggaccagtcc tcgcagctgt ggggagctgg ggcaggtggg aatgtgagaa acaatccctt  161520
gagctatgga ggagctgggg atggcaagga tgaaaagggg caaatcctag cagctagagg  161580
gaagctgggg caggtgaggg cgggtgtaag gaaccagacc tagaaactat ggggaagtg  161640 gagcaggtaa aaatgtgata aaccagttat gcagtccaga ggctggtagg agtgtaaggg  161700
```

```
agcagacata gtggctatgg ggaactggga tatatgggag tgtaagggac cagattcagt   161760
agctatggtg gaacttggga gtgtagatga gcacgctgaa aagctatggt gcaactgcaa   161820
caggttgtca gggtgtaaag aaccagaccc agcagccatg ggaaacctgg ggaaagtagc   161880
gatgtggggg accagatttg gcacctataa gggagctggg gcatgtggac atatgagggg   161940
ccagaagcag cagttatagg gaaactttga aatataggca agtgtaccaa gaagccgtag   162000
tggagctgaa acagatccta ggtcctatgg aggagctgaa gaaggtggga gtgtgaggga   162060
ccaggccgag catctgtgga agggctgagg cagggctctg ggtcggatgg gagtggcacc   162120
ccagagaagc cctagaagct ctggcgatgg agctgagcag ttacagtgga cttggggctg   162180
gtgggatcgt aggagaccat gtagctgcag aagagctgga gaaaacagga gtatgaaaga   162240
cccagccaag tagccactga agagctgggg tgttattggg gtgtgtgggg acacagtccc   162300
agcaggttta tagaggttgg agccttggca gtatgtgcag taccaaaccc agcagcttgg   162360
ttcaggggct tgagtagagg caggctaatg gggtccacgg taaccctagg cacttagggg   162420
actggattgc gaatcttcag gggagctgga acaggcaaag ttaaaaggaa tcaagcacct   162480
ggaagaaagc aaggaaagat aggattgatg gggatccaag aaactcccag gaagtaaccc   162540
cagcagggac atctgggagc tcagttcaga cactgaatca aaagcacaga ggaaggagag   162600
gtggtaggtt tccaagctat cctgtccagg ccaatggagc agccaggaag gagggaagga   162660
gaccaacagg aatggggcag ctgtagccag cagggtgtga gagacaggga tgaggctagg   162720
tggctagcaa gaagggcaac ttagtgggag aggggtgaat taaccaccct gacctcatgc   162780
tgacaggggc tgagcaacag acaaaagaat aagaaagcca agagctcatg gctggaacta   162840
ttctggctgt ctgctctgac tgtgttgaag gggctaagca cctgttagct aatgaggcta   162900
aaacagttaa atgagcaaag tagagcaaaa agctctcaca gcggagagca tgggagaacg   162960
ggagactgtg agatcctcgg ggggtctagg agtttatctc agagtgaaga acagtgaaaa   163020
gctctgcttg ggagttcttt ggggaatggc gatcatcctg ggaactccct tatagacctc   163080
atggcatgga ggagagcagg agctcaggca gacagagtag ctgtgtgtga gctggataag   163140
aaagaaaaga gacaacaggg agagaagaga aaagggatgg gaaaggactc agggctctac   163200
tgaattcagg cagaagagct tggcttcagg atgctggggg ccaaggaagg tgtctgattg   163260
agtaggaaca tagtcaggaa aagaccctgg tgctcacatt cccagacaaa tcttacaggt   163320
taaagttcta gtatcagaac ccctcgctca gatcctaggg gcttatggga acataagaca   163380
ggaagtgaaa cctcttagga cagcacgaag tagcctgtgt tggcccacag aagaagagca   163440
aggtaactct cagagtttga gcaggggatt gaggaaggta gtgtacagga gaggcagaaa   163500
gaccagaaag gtccccagag taagaatgaa tcaagaattt atgtgtggtt tggttcgatg   163560
aaggcaaagg cagggaagat agatgagaaa ctgatcctct ttcacaacca agaactcatt   163620
gttcagtgtg agttttgata tatagaaggg ggggaatgt gctattaaaa gtaaaaaaga   163680
atgaaccaga ttcaaaaggg aaaggggact aaatgtcttc ctgaataatg cagcatacat   163740
tcctatttca agagctaccg gcaagagaaa gggacacttc tgggatgtgc ccagtaacat   163800
tagcactgtc agagagaacc cagggcagtg cgaagggtga ggtgggggag gaaggtgtct   163860
gcactcatca gcgtctcatc aggggcact gagctgtgta aacaagagt ggccagctag   163920 gtcaagacag aaaggatgcc cacacacaga aggtgtaggg tagagggttg gtagtaatcc   163980
ccaggaagca gggagcaagg tccaaggaga gctaaagtca cggatagaga cctagggcac   164040
agatttagga gccagagttt gcgtaatgtt agtagattca gtaggggctt ctgaagggcc   164100
```

```
tcatcactga aagatcaagg ctcctagggc tggagagttg gctcagtggt tgctgctctt 164160
ccagaggacc caagtccagt tcccaacaac cacatggcat cttacaacta tctgtaagaa 164220
actccagttt ctcgagattc aatacccctct tctaacagca caggcatcag gcacacacat 164280
agtacacata gtcatacatc taaaataaaa tacctaaaaa aaaattaagg tcagagtgca 164340
gggtctagaa gtggaagctg ctgacaccac ttaccccaga gcaacttgag aagacacagt 164400 cttttagag caaagctaag gccagagcct ctccaaatat ctgaggccac gcatgttgga 164460
aaagctcaca ctccctcctc tcttgcagcc caaacaacag ccccatctgt ctatccactg 164520
gctcctggat gtggtgatac aaccagctcc acggtgactc tgggatgcct ggtcaagggc 164580
tatttccctg agccagtcac cgtgacctgg aactctggag ccctgtccag cgatgtgcac 164640
acctttccag ctgtcctgca gtctgggctc tacactctca ccagctcagt gacctccagc 164700
acctggccca gccagaccgt cacctgcaac gtagcccacc cggccagcag caccaaggtg 164760
gacaagaaag ttggtgagag gacaaccagg ggacgagggg ctcactagac gtgaggataa 164820
ggcattagat tgcctacacc aaccagggtg ggcagacatc accagggagg gggcctcagc 164880
ccgggagaca ctgtctctgc ctccctcctg gaggcctcct ggaggcctct gcctatggcc 164940
acccaccccc taagacatga tcctctggta tagatgtctg tgtcatgcat aggatcatac 165000
cagggacaaa ctttcctctc tggtttggtg ccttctctcc ttgaaaaccc agtaacatcc 165060
agtcttctct ctacagagcg cagaaatggc ggcattggac acaaatgccc tacatgccct 165120
acatgtcaca aatgcccagg taagtcacta gacctggacc ccagctccac aatgatggca 165180
agagctgtaa gcatccagc actgcaggat aagccacgta ctgacccatt tctatctctc 165240
ctcatcagtt cctgaactct tgggtggacc atctgtcttc atcttcccgc caaagcccaa 165300
ggacatcctc ttgatctccc agaacgccaa ggtcacgtgt gtggtggtgg atgtgagcga 165360
ggaggagccg gacgtccagt tcagctggtt tgtgaacaac gtagaagtac acacagctca 165420
gacacaaccc cgtgaggagc agtacaacag caccttcaga gtggtcagtg ccctccccat 165480
ccagcaccag gactgatga gcggcaagga gttcaaatgc aaggtcaaca acaaagccct 165540
cccaagcccc atcgagaaaa ccatctcaaa acccaaaggt gagagctgca ggccgactgc 165600
ctggggactg ggataggtat aagaatgaat gcccgtgtgg acggccatga cctctgtgtc 165660
tgtttctatc cccacagggc tagtcagaaa accacaggta tacgtcatgg gtccaccgac 165720
agagcagttg actgagcaaa cggtcagttt gacctgcttg acctcaggct tcctcccctaa 165780 cgacatcggt gtggagtgga ccagcaacgg gcatatagaa aagaactaca gaacaccga 165840 gccagtgatg gactctgacg gttctttctt catgtacagc aagctcaatg tggaaggag 165900 caggtgggat agcagagcgc cttcgtctg ctccgtggtc cacgagggtc tgcacaatca 165960
ccacgtggag aagagcatct cccggcctcc gggtaaatga gcacggcacc cagaaagctc 166020
tcaggtccta agggacactg acacccatct ccacccttcc cttgtgtaaa taagcaccc 166080 agcactgccc tgggaccctg caaaactgtc ctggttcttt ccggggtata gagcctaggt 166140
cacgggcttt aaggtctggc tggggtttaa ggccagagtt gtcttcagga agagagtgag 166200
gtttccacac tgccagactc agagctcatg agtcatcagg gcctggagtg ttgggctta 166260 gctttaggaa gtgcctattc cttgacttca aactaaccag cagctgccag acggagagat 166320
acacctagga aacctccaag ggaagaaaca cacaaactcc accaccctct gcctgttcct 166380
atccccatgt cccactcctc tgcctatggg tttctctgag tctattgcac acatggccat 166440
```

```
gggcgtgcca gagacccttg ctatccctac actcaactaa acccaggcag cttttcatgg   166500
gctaggtctg cacacccata cagactgccc actcatgcct gtgccacgtg agactgaggc   166560
agatggctct tgccgcccaa agggagggtc tgttagccac atgcatactg aatcctgacc   166620
cattcaaatc agcctgccga acatcatcca gtccgtatag cacatgtatc cacgtgcaca   166680
tgtgcacaca catttaacac accaggactc cgcctgtgtg ccctgcacag cacctacacc   166740
cagcagtgta tcaggatacc acaaccacc acttgagtgc ccacgtttct gccatcacaa    166800
ccagacacac ctttcccctt ctaaggtcac tgcattctag gctcagcaca gtcctctga    166860 agccagatcc gtctctggta cctcagggtc acgcttcaac cccacatgaa ttatacaacc   166920
cagagccata atggtctgag tcacttcaca ctctggaatt ttctcaagtt caggcaagac   166980
caggcacagg ctccgctggt gattgaggga caggtaaagg gtcagaccag ctgtatagcc   167040
actgtccact ggggtcacag gccctgctga cccttcacct tctcctgtac tgcaaacaga   167100
gagggccctt gcacaatcca ggccgccatg aggtccactg tgtctggcaa accccaaggc   167160
cttatccaac tcagccggag ggaacttaga ctgatgtccc agagggaaaa gaaaggaaag   167220
tagggagtag aaagtctccc agggagactc tgctggccca gcccaaatgg agctttctcc   167280
tctgccacat ggggaattgc tcccagcccc ccactttatt gggacaaatt ctgactgccc   167340
tctctgtcca gggctagaag tggatgatga ttgtgctgag gctcaggacg gggagctgga   167400
cgggctctgg acgaccatca ccatcttcat cagcctcttc ctgctcagtg tgtgctacag   167460
tgcctccatc acactcttca aggtcagcca caccatcccc caccatctgc tgtgatgcct   167520
gtgtcaaccc tgcgatgtcc tcacactcct ctcctgacgt agtaggatgt ccccttgctg   167580
tccccactct gccccacaca ccattcccac cgttccctga gccgtccac attgctctgt    167640 gtggctaccc atggcgtcca tactgtctga cattctatct ctcttgctgt cctatgtgat   167700
ctccatactg tcttacgaaa cctccttgca tgccacacta cccttcatga cgtccctgct   167760
atctaccatg ctacccctct gggtgtcccc atcagcctca ccatgtattc tttgagctat   167820
cctcatacca tctcaacctc aactcccacg atgtctccac accggctcct agtctatgtc   167880
accctgaccc cttgccatcc ccagtctcct gcctgtatga aaggaactgc aggagggacg   167940
ggcctctgtc ttgcccacag ggctgaaggg cctaagcatg ggtgtgttct ctgacttact   168000
cccacctccc cacaggtaaa gtggatcttc tcctcagtgg tggagctgaa gcagacaatc   168060
tcccctgact acagaaacat gattggtcaa ggagcctagg ccacttcctc tgggatgagc   168120
ttcctgggcc ccgcacaacc ccatccatcc tactgtgcag cctaatgtgg aggccacact   168180
gccgtctgac agtgccaccc tctagccctg tgactctgat ccagaactct agactgtctt   168240 cctttggag gatcatgtgg acaatgagct atacccaga cccaaacagc acctccacag     168300
cagttgccag gaaactaact ggttgggacc agaagaacca tctctaggat gtttgcctca   168360
gaggagctgg gagtccacgg tgcctgagtc gagctccatg ggaatcagcc gtgtctgaaa   168420
tgggtcttcc cagaaagagc aatgtttca gatccttgaa aggaaacatc tgctaggaag    168480
accatggtcg ccacagcccc aaagagtcac ttcactctgg tagcctttga accagttata   168540
tctggacacc ttctttcccg gtacttctgt gaaccctggg ctgagtaagg ggtttatgtt   168600
tctcaaactg ttgggatgag cctccccgag atgaagctcc ttgtgcagtc ttctcttccc   168660
gaaacccact caacatgctg gactcttggg ttcaggatcc gatccgaaga caccattgac   168720
gacgcaacct caagacaagg ccactgtcac ctccatagag actccatcca cactctgcag   168780
ggacaggagg actgctttgt gtaacctccg caaagcccta gcagggacaa gtgcacagac   168840
```

```
cactgagtat tggtgaggtg accaggcagg aaaacctcca ggagagggcc ctgatgagaa   168900
gattcatatt gggctcaaaa aatgggatgg ggggagggg gcgggtggga aagaacagtg   168960
ggcagggtgt gaacagatga ttagaagaca gtcacagtgc cgcagatctg ccctgcaggc   169020
ctgctttcca gactggacca cttacagcag aaaacaacag ttacagtaag catctaggag   169080
agtggacctg gaataccagg gctgctgtgg ccagtggaga gtagccctgc atctacttct   169140
ccattacctc tcatggccaa taagaagcca gagcatccag gcagaaagaa agagtgtgcg   169200
tttctgtgac tggtaggaaa tgcttagaga acttggatct ttaaaacagc tttttctag    169260
actgtgaatg tctttaagca ctctctttcc tctccattcc ctccctctct ctttctctct   169320
ctctctctct ctctctctct ctctctctct ctctctctct ctctgtgtgt gtgtgtgtgt   169380
gtgtgtgtgt gtgtgtgtgt gtgtgtgcac tcacacacac tgttgttttg gcattttaaa   169440
caataaaaca ttcttttaac attttgtatc tcatggtgtc ccttcttaat ggattagggc   169500
gcgtgcacca gagttggtga gatgtcaaca tgtagaaggt gcggcttggg gcagcaatgt   169560
gggctgtccc gcatggatac tttgagacag gactttgaag agcctcaatt tgacctatca   169620
aatgctggtc acccaggtct ttcagcatca gggtcactcc atattgactg aataaccaca   169680
aaagcacaag aacccagagc ctagagtccc cactaggccc cacctagagc acagagtcaa   169740
agctgggaca ctcagaatca acccaaagtc cagaccctcg ctcctcagaa ggaatcctgc   169800
cccactgctt ccagacagac ctctggccta ggcagatcgt cctactgcca gataaggagc   169860
ctcccacagg gcagcagcag actcaagctc tgaggcccca tcaaccccag ccccagcctg   169920
gcagtcctac tttgtctctg gtctctttag taaagttctt ttccataact cctgagagtg   169980
ctttgagaag gtatttaagg ctaccattat ggtgatgaca ggtcccaaga acatggacaa   170040
ggaccagatg ataagagcct ggggattaaa catccacctc tatgccatcc tcctcaaacc   170100
acagagttct gccccagtct ccatccggtc catcattcct gctgaccaga ctcacctccc   170160
aggggaattg aggtggaatc agggctgggc ccccgggaac ctggctgcag gtcactcttc   170220
aagaccacaa tctgcccacc cagtaagtgc agactgacag gccagtcccc tgacccaagc   170280
tgggacacta gagggactag gtaacagcac gcaagtgtac aagaaccatc cagaatgggt   170340
tgtgccatcc tcaagacatg atctcacatg acaaaagaca ggcttctctc atatataatg   170400
attgctcagg gactaagaag aaaggcctct tcatgggacg gaaaaaccag cagtcactgt   170460
tttttttcctg aagaaaatgc ttcaatggtg agaacacttc tagaaagaag gatgttaggg   170520
tgagtgtggc cctgctgggc cctgggtaaa gaaaggcatg agaactactt agaccatttt   170580
gagggtcagt tggccaaaca ctcttgtcat cacaagtgac agtcccacaa agaggtccac   170640
actggggtgt caagctcagc accagggac tttgggggaa ctaagatagg gataaaccag   170700
ccgggatcag gccatagtcc acaggcatct gagccctctg ctgctgagtc cggcttctac   170760
gggccttgga gtagggccca gatggcaaag acacagaaag ctacccctcc tgggtgcaga   170820
agacccagga ctgggagaat gactgttctg atgagaaaag aggctctgtt taggatgtgt   170880
cccaagccat tagtgtggcc agcttactaa tgtgcattca tgctgcaaac cattgctcac   170940
aatcaaatgt ataccacgca cacagtcacg tagtttgcgc agaccactc atgtggcaca    171000
tgcctgtggg cacatgggac cacacataca cgtgatgctt taaaacacag atctgcacgg   171060
tcttgtactt agacacacat tgtctcagga agcccaggtg tggaccaccc tgtcctcctg   171120
ccacattctc ctaagccata tcccctgcca agctgaggcc taggtgcctc ttcctcaacc   171180
```

```
agctcctaga ccaacatccc tgaggcatag ctcagtgtct tcttctaatc actatccctc 171240
caagccacga gaccccatag acactggaca cgggcagcaa gggttcagct caaagaacac 171300
ggtgtggcag gaactcctac caaatcccaa ctagaaggaa ggaaagtccc acagagagct 171360
agactcactc tagacaaccc agacagtgac cctggcttct acataccatg aatgaatgac 171420
cttctgagac taagaggtcg cttctttctc tattcctaca ttatcagtcc accatggagg 171480
gctacatgga aaaccccaaa agacataacc acattttgga acccataaat gtagcctctt 171540
gggaatagtt cttcatcaat gtgaccaagg taactatctc aagacgaggt catcaaggac 171600
tagctagtgg actttaacct ggtgacaaga gtcataagag acagaagcag gacctggggg 171660
gtaaacaggg cctgcattct ccaaaatcaa cgtgtcaaaa cagaaatatg gcagcaaaac 171720
agaagtaccg tgcccaacac tggtcaagac caatggggga ggctcatgag gggttgccta 171780
acaagagcag gcacaagtgc ttagataaaa ccacaaccta cactcggcca ccgtaaccct 171840
acatagaaaa tgtacctatg ggacgtcagc tcaacgtcag tcccacctcg ttgctgtgcg 171900
cagacagctg cagcctgaat aacctgtcca agtgtgcatg tcacatcctt gatgacacac 171960
tgtaaccagt gatgccatgt tagcacgatg tcctgtgagg gtgtctgctg actcgggatg 172020
gcaaacccta agaccaaaag gaggtgcttg gttcacgaga gcggcctcgt ggctggacac 172080
atggcgttaa atgagcctct gtggactagg aagcagcttt aaccagaaag actataccag 172140
caccctgctt cacgttttcca cctttgagcc tctactgact aagccactgg cagccactca 172200
gtctgtggta ttctctaacg gcaacagaaa tgactaagac aggcaaccac aatgtccccc 172260
actgctgatg gctccagggc attcttggcc tgatgacagg acctccagag cctccttgag 172320
acaggcagat ctctggaggg caggaccaag cttcctcctc tctacctccc caacatcttt 172380
gactagcttc acagataaaa ggctaggggg acatcagttt attccacact ttctaagtct 172440
gatgcaggag cccttcctct gcgaagtatc tatccaagaa cccagaaaag gctaacttcc 172500
ccaactcaac acttagcacc actgacacac ctgaccatac ccactgattt acaaccttc 172560
tcccagacag ggccattcct gggcaaagac tgtggtgtga gggcccagag tcctattgtt 172620
gtataaatga ggcacagtgg cagaggcaag ctacaaagag tgacattgtg gagagaggac 172680
actggggaca gtcggatgtg tagaggatca tatgaagggt ggagccctac cctgacaatc 172740
tacaaagagt gacattgtgg agagaggaca ctggggacag tcggatgtgt agaggatcat 172800
atgaagggtg gagccctacc ctgacaatct tcaagaggct ccataggtca aaggcccatc 172860
ctgagaaagc tgtgatagga aattgactca gggcagatgg gatccaaatg agggtagcac 172920
ctaactgtga cctacagacc tccatgttgg tcctcaagtt ggggcaccca ctttctcatg 172980
gacgtagcca tggaggtagc cacagctcgt gaaaagccat tccagacact tgcctcaccc 173040
cgttgtcaac cctgtgacct caaagctctt ctctgaggcc cccctcagct tagggacccc 173100
tctggagtag ccctgttact ttggctcctt gacaacaagc tctcaggtct cccttctacc 173160
cctaattgtc ctctccctct ccatctctgc cttggagtct ctgagaaact agatgttcat 173220
ttcattccct cctgcatctc ctgcccaacc tacccctgtg gccatgcatg tggagtcctg 173280
gccccatcca ggcccgtgtg gtcagacaca cctgtctcca ccacagccag accacaggcc 173340
agacatgacg tggaggtaag cggccacaat gtggaggtgg aacaggaagt gggtgaggga 173400
ccccatccag gggccagaca cacagtcgtg cagcccctc accgctcagt ctgacccatc 173460
cacaggcaac cacacacaga gaaaaccagt ttccagccaa ggcttcaccc agtcctaagc 173520
tctctccggt agggcagacg gcctttagcc atgagaatgg accttcaggg tggaccacc 173580
```

```
tggccatggg aggcctggct gttcccctat gaatgacact caacaacctt gagcaggtgg    173640
gtcccggtac catctggact gctctgctcc ttggtgcact ggggaatctc aaccaggcca    173700
gacctgagaa cataaggcag agaagcatta gcaaggagaa ggtgattcgg agagcaagaa    173760
ccagaggaat acaggacatg aacacaggca cgaggcgggg tcatggtctg agctgcagag    173820
aagagagaaa aatggatgaa actcagcttc ctggaaagca gcaacaagag actcccaggc    173880
tagactgagg caaggataag gaggcatcaa caaagaatgg gggtgactcg ggctgccatg    173940
gctcagccga gctggattta gccaggctga gctgaactaa gcttagctga ggtgaatggg    174000
actgagctga gctgagctgg gacaaggtag gccaagttgg gctgactgag ctagtctaga    174060
ctggtctggg ctagtctgat ctggactggt ctgagctgaa ctgagctaag ttgagctggg    174120
ataaactggg ctgaggtggg ataagatggc ctgacttggg taactaagcc agtctagaat    174180
tggataaact gaactagact ggtccaaact ggactagact gagccggact gagttagaat    174240
gaggtggact gggctaaact gggctgagct gggttaagct agggtggact agaatgctga    174300
tttaagatgg cctggggtgg gaacgctagc taagccagac caagctgggc taggctgggt    174360
taagttgagt tgagctacag taaactagcc tgggctgtgc tgaccttact acaccaggct    174420
gggtttggtt ggcatgaatg gagctgattt gagctgggct agaccaggtt agtatgagct    174480
atgctgtcct ggtctaagta gactgggtga ggctgagaaa attcgagatg gaaactggac    174540
tgagatggaa aaagataggc ttagtgttgg cttactgaac cagtctagaa tgagctgaac    174600
tggacttgga atggcctgaa ctgggcttag cttatctagc ctgggcttgg ctaggctggc    174660
ctaacctagg ctgagttgat ctgaactggt gtaggctggg ataggcttgc tgaaatggac    174720
taggtcaagc tgggctggag tggggttagc taaaataggt ggactaggct gagatgagtt    174780
aggatgacct gagctatatt taggggatgg atgggatggg atgggctatc ccaagctaag    174840
ctgggctaga atgggctagt gtaagctaaa ctggctgggt tggaatgtgc tgggctgtgc    174900
taagctagaa taaactagag tggactggcc aaaatcggct gggacggtct gtactgaacc    174960
aggctgggct gggctaactg agctagaccg gtctgaggtg agctaatctg ggatggggcg    175020
gacagagctg ggataggcta gattaagctg ggatgagcta ggctaggctc actgagctag    175080
gctggaatag accggtctaa gataggctgc ctgagctaaa ctagactgag atgaactgta    175140
atgagctggg atgagctaag ctaatctggg atgatctggg ctaggctgga atggactgag    175200
ccgagctggt ctcagctggg ctgggttgtg ctgaatgggg gtaaaccaga ctaggctacc    175260
cagactaagc tgggctgtgc tgggccaagc tgggctgagc tagggtgggt tgggctcgat    175320
ggctgggcta atccaagcta ggctgagctg agctggactg agctgggctg gacggagcta    175380
ggatgggatt gactgagctg agctggactg aaatgggctg gctgagcta ggctgagatt    175440 cgctgagctg ggctgagcta gactaggctg gactgagctg aactgagctg gactgagctg    175500
ggctgggctg agctaggctg agattcgctg agctgggctg agctgggctg agctgggctg    175560
agctgagctg agctgaactg agctgagctg ggctgagnnn nnnnnnnnn nnnnnnnnnn    175620 nnnnnnnnnn nnnnnnnnnn nnnnnnnnnn ntgagctggg ctggtctcag ctgggctggg    175680
ttgtgctgaa tggaggtaaa ccagactagg ctacccaaac taaactgggc tacgctaggc    175740
tgggctggac tgagctgagc taagctggac agagctgggc tgggctgggc tgagttgagc    175800
caggctaact tgagctgagc tgaactgagc tgagctggac tgagctagac tgagctgggc    175860
tgagctgagc taggctgggc tgagctgggc tgagcggggc tgagctgagc taggctgggc    175920
```

```
ttggctgagc tgagctgagc tggactgagc tgggttagct gaacnnnnnn nnnnnnnnnn   175980
nnnnnnnnnn nnnnnnnnnn nnnnnnnnnt gagctgggct gagctgggct gagctgagct   176040
aggttgagct tggctgagct gagctggact gagctgggct gagctggact gagccgagct   176100
nnnnnnnnnn nnnnnnnnnn nnnnnnnnnn nnnnnnnnnn nnnnnnnnnn nnnnnntga    176160
gctgtgatga gctgagctgg gctgggctaa gctnnnnnnn nnnnnnnnnn nnnnnnnnnn   176220
nnnnnnnnnn nnnnnnnnnn nnnnnnnnnn ngagctgggc tgagctagac taggccaggc   176280
tgagctggaa tgagccgagt tgagctgagc tgagctgaga taaacttagt aaggctagaa   176340
tgaattgagc tgagctaggc tgggccgacc taaagttgct ctgaggtagg ttagacatgg   176400
ttgtctgagc tgggctgagt taggctagct ataccgtctg ggctgaccta atatgcccat   176460
attagttgta atgacgtgac ctaggttgac acgggcttgc tgatctgggc tggactgggc   176520
caaactggag ttagtctagc ctgggctgac ttagtgtagc ctgggcagag ttagactgga   176580
atgggctaca ctgagctgaa ctaggatggg atgggaaggg ataggctgaa ctgactgagc   176640
tgggttcagt tggccttgct gggctgagct gggctggata gtctagctgg gctggccaga   176700
atgaggcaga gctaggctgg aattaggcta aacttggttt ggctggttaa gatgagctaa   176760
cataaattag gctggctgaa ctacactgga ctgtaagcta gctgggtga gttcgcatgg    176820
ctggacgcct tcacagctct agtctgagtt ttactggttt gttctcctca gtgctgaggt   176880
aatagaaaga ctttggagta aatgtgaacc aactcttgtt tcatgggtcc agactgtggc   176940
ctcagtttgt cttatatgaa cggagccacg ccactcagtg tccaattctc atgccctctt   177000
ctccttccct gattacctgg tggaaactca catgtacctg tagatagtgc ctacatggac   177060
agaaccactg ctcagattta gtcctctggc cttttggtcc actgcttgct gggtggatgg   177120
gcaggtggct ggagtggtgg gtctgaagcc aggacaaggc aagtataaag taaaaacaca   177180
acaaaatggc ccccaccccc cagtgtaacc tccaagccag ctgttcccca accattcctg   177240
ccctgtgctg gctgaggttg gccgtccctg ctcaggccca ccagttctgg acctcctaac   177300
ctgggactga gaacacggct ctacccactg cccaagcagg agtggggctc agaaatctgg   177360
ggcgctagac tgctcaggag catagccatg tttacaaaga cactcacagt gcgtacaagc   177420
cctgctggag gcatctagcc agatccttga aaaagacaac ctgcaggtca cgttcaaaat   177480
ctatgcagcc agtcggtcag ctccaactgc gggtacatga tgcaacccct atgtgatact   177540
gggcctaggt tctccggtat aaagaagaaa aaggcatggt cctttctcca gagattgtct   177600
caagatgggc agtgtgagga ctactatctc actcatgttt tatgttccag agtccgcgaa   177660
agatcccacc atctacccac tgagaccccc accatctccg tcaagcgacc cagtgacaat   177720
cggctgccta attcagaatt acttcccatc cggaactatg aatgtgacct ggggcaagag   177780
tggaaaggat ataagcgtca taaacttccc acctgcccca gcctctgggc catacaccat   177840
gtgcagccag ttgacattgc cagctgcaga gtgcccaaaa ggaacatctg tgaaatacta   177900
tgttcaatat aacacaagcc ccgtcagaga attgagtgtg aatgccctg gtaaagaagg    177960
ttggggggt ctgggtggg ctaagtccta ccttaacctg gtatctggac ccatataccc     178020
ctctgaagca cacatcccac tcagaaacct cccatggggg atgggggag ggggtgtgaa    178080
caggcagagg gagcagggc ctcagaacat ccagaaaagg ggacagcaaa ggagaaaagg    178140
agactattct gatttgctaa aacttctatg ttacaggtcc aaaaccctcc ttagtctgcc   178200
gccctcgcct gtcactgcaa cggccagccc ttgaggacct gctcctgggt tcagaggcca   178260
gcctcacatg tactctgaga ggcctgaaag agcctacggg agccgtcttc acctggcagc   178320
```

```
ccaccactgg gaaggatgca gtgcagaagg aagctgtgca ggactcctgt ggctgctaca    178380
ctgtgtccag cgtcctgcct ggctgtgccg agcgctggaa caatggagag accttcacat    178440
gcacagctac ccaccctgaa tttgagaccc ccttaaccgg cgaaattgcc aaagtcacag    178500
gtgggcccaa atgcatacct gggacattgt atgatgttcc ctgcttgcgt acctgctttc    178560
ttcctctaat acagatgctc agctgctcag gcccttgtgt cacagaggga aactggagct    178620
atccaaagaa ctgcccagaa gggaagggca gagaggtctc tgctctcctt gtctgagcca    178680
taactcttct ttctaccttc cagaaaacac cttcccgccc caggtccacc tgctaccgcc    178740
gccgtcggag gagctggccc tgaatgagct cgtgtccctg acatgcctgg tgcgaggatt    178800
caaccctaaa gatgtgctgg tgcgttggct acaagggaat gaggagctgc cctctgaaag    178860
ctacctagtg tttgagcccc tgagggagcc aggcgaagga gccatcacct acctggtgac    178920
aagcgtgctg cgtgtgtcag ctgaaacctg gaagcagggt gcccagtact cctgcatggt    178980
gggccacgag gccttgccca tgagcttcac ccagaagacc atcgaccgtc tgtcgggtaa    179040
acccaccaac gtcaacgtgt ctgtgatcat gtcagaggga gatggcattt gctactgagc    179100
caccttgcct gcccctactc cttaaataaa ctctgtgctc atccaaagta tccctgcact    179160
tccatccagt gcctgtccat catccttagg gtctacaaaa cactgggagg ggtcagggcc    179220
cagggaagga ggaaccccca ccacctgagc ttgtaaggcc tcagagactc tgaaggacct    179280
acatgcctag agtatatgtg tatgcatgta tacgtattag tgagtgcctt tgcgtgtgta    179340
cctgtgtgta acaagagagg agtgagtttg tgcgtgccta cgggtttata taggtatgta    179400
tatgggcata agtgcatacg cctttaagtg tgagcatatc tgtgtccccg tgagcacatg    179460
tgtgtctgtg tatgcctatg agtgtgcacg tatctgtgta tgctcatgtt ggtggaaaca    179520
tgtgtgccta tagtgtgtgt acctgccagg tggatgtgca atgaaaggga ggtgagaatg    179580
ggggtgaagt ccgagatgag cagattcagc caagacaggc aaacctcagg ggagagtccc    179640
aagagcagtg ggttgctgca gaggtactct gaatggtact tctggatggt ggtgtggctg    179700
tctgagtata agattacagc ttttgtccca aacaagaaag ggatagatgg agcaagagag    179760
tagcaagacc aaggctggta ctgcctggga gtcccaatag gaacggtaga ggagtgagga    179820
gatgaatcca aggggcactg ggaagaagat gccacccacc ctcagtgggc cagccctgaa    179880
tggaggcgtg catagccact cagggtgacc actgactcat gagaaagaga cataacatgg    179940
cacagacagc cctcagcagc accctgctct gcatatatgc acatgggcat acacctggt    180000 ctgcatacag atacatgggc atacacgcac atacatttgc acactcacac agacccgaac    180060
cctggaggag gacgaagttc acagcccaca cgcagcttct ggaaagcaat gggagtcccc    180120
tcccaagccc aaccatgaca actcatggac aagtctataa gctcctccag gtggcccctt    180180
tctaacctaa gtctcccttc ccatcctgag cccaagtata acaaaccaga aacagggtat    180240
gtggcaagct gggaaaagac aggagcaggc catagagacc actctcacac aggccttggc    180300
ctcctccatg ggcacccta gaacacaaag ttctacaacc aggtacactt ggcacccaga    180360
tgcccacaag agggcagtgg ggcccctgct cctgtctcac gggccttcag aacctctcca    180420
ggggcctggt ttctagcaac ttccctctgc tgtcagagca aggcccatgc acaccctgga    180480
taccctccag cttgaaagtc cacttccccg aggatagcaa aagcgacagg ccagctttgg    180540
aaacctgacc cagaaaagcg cgatagccac ccatggaacc caaggcctgg tccaaaacag    180600
aattctagta aggaggagcc aataggtgaa agactgaaca cacacaggga gagaagacag    180660
```

```
aggagcacga tagtcgagag agggggggctg gtgggtgagg cgatgagtga gtgactggaa   180720
caaggttggg tggatatgca gatgaatgat gggaatggtg gatggactga tggatggctg   180780
cagtgacaga aatatgagtg actgagtatc ggcacacagt ccctacctcc acttaaaatc   180840
aaagttctat gcgcggagac tctgagggca gtggggttgt ctctaccggg agactttagt   180900
gttggttaac ccccccccaa gttctttata atgcaacaga atcctctgac cacatgtcca   180960 cccccttggta ttccaacctc ggcccagaaa tcaccttggc ctgtatctgt ttgagagtgt   181020
ccgatcttac cgaaccctag tacccaggcc aagttcaacc taagaactgg ggcttttgtg   181080
aggtgttgct aaatgtctag agaggtctga gacaagtggc cttgggctca aactcttctc   181140
agagcctcaa agacagaaac aactctctta ccatgatagt tctctaatta agatcccctg   181200
agggaaagag agagagtcag gtcttggggg gcatctcaag aacttcaagg attccagccc   181260
cttacctggg accctgcctt ctcattatcc cagaacaagt cccttctcag agataaggaa   181320
cccctgccac caccgtcccc aaagcccaag ggggcataga aacagaggcc ttaagcctga   181380
gcccccatcc ccatgggttt ggatctagaa ggtcatctat gtcttacaga atgccaagag   181440
ccaccttcct acgtgatact ggaccagtca caagacatcc tggaggaaga gaccccgggt   181500
gccagtctgt ggcccaccgc tgtgaccttc ctcaccctct tcctactgag cttgttctac   181560
agcacagcac tcaccgtcac aactgtacga ggcccatttg gcagcaaaga ggtcccccag   181620
tactgaccag gagccagcca caggtggctg tcatggagac ggtggggtac agggtggggg   181680
caggggcctt gaggatttac tcagcccctc cacatgtggc cttgcaaccc ttcacagaca   181740
tcaaggaagt ggaaggaagt agaaggaaat tatggcagca cttcctgggt ttaacccagt   181800
cttccagaag ccaggctgag acctcagcaa aagcaaagac ataacccaac tccaggatcc   181860
tcccctctgg ctgaccactt gtgtctttgc acggatgaag cttggagaaa gtccggcgct   181920
caaatcttcc agaagccagg ctgggacctc agcaaaaggg aagacataac ccaactccag   181980
gatgccctgt ggctgatcac tcttgtcttg gcggggatga aggttggaga aaggcctcca   182040
cgtctcagag ctaagaccga cgtgacaact tcccagccca ctcacagact ttcctgagca   182100
ataaattgat acaaaaccac aaattcctac tctcaaaaac aaacattaac aaaggattgg   182160 gggaggggggt caggggtagt atggtggcgt tgggcagggt aaaactcaggg tacccattgt   182220 ctaatgtctg agacataact tgaacatatg tgtagctgca gccaaagatg aacaagtgat   182280
ggtatttgtg tcctcttcag acccgatacc aggtcattaa gcttgagatc tggacctgat   182340
ttctaaacat ttggcctctg tgagcaccct tggcaaatac tgaacagcaa accctggtcc   182400
tggctgtgaa ccttggtcct gatcactgag ccctatattg gtaactgaac cgtgatcctg   182460
atctctgacc tcagtcatgg tcatgaggcc ctggtcctgg ccactcattc taataactgg   182520
tccctagtcc tgagccctga accttggtcc aggtcactga atcctagtca tgatcactgg   182580
gtttgatcct cattactgag cctagtcttg atcaccgatg actggttttg atcatagcaa   182640
ttaacctgat cactagtccc cgttcctcat cactgggcca tgatactggt cactgggtcc   182700
tgatcctgat cactaaatcc tgtttctaaa caatgtgtag tggaatgtat agtgaagcct   182760
ttgtgtctgg ctctgggtga aatgtctcag cagagccttt gctaggtttg ggttaatcag   182820
ttggggctga gaaatgtttt tgaggctgtt tgaacttcaa aagaagaaat gtctccctgg   182880
acaatctgca catttgcagc tgcgcaaacc ttcatcctaa aacttaactc ctggcaaact   182940
tagaattctt acttttaata atggctaacc atggttgaaa gggactgaga tgtctgtggg   183000
tggatggaac cttcccagc tccaagtaac tctgtatact gtttgaataa agtaactgaa   183060
```

```
gtgagctagc tggggtcaat cttctttcca aggagaataa agccctccgc tcctccagaa    183120
aatgaaggct tagctccttg gttagcttct ctctctactg cggcacctac aaccaactca    183180
gcagtcctag gttcctgtca ccagatccag tcctgatagc taagtgtcaa tcctcgtcat    183240
taaggcctga cccttagcaa tatgcctggg gtctgataat cagactgaca ttctgataac    183300
tggacccaga ttcttatcac tgggtctttg tcctggtcat gggcatttga ccctagtcta    183360
cagcactgag ttctgggcat ggaccctggg tcccagttct agatactgag ttctggttct    183420
aataactggc tcctgtactg atcgatgggt cctgacctag tcattgggcc ctgatcctca    183480
acattgactt caaaacctga actctagccc catgcctcat tcacattagg aggatcccta    183540
caggggattc ctgcagaaga ttccagaatc cccacaacac tgttcacaca ctgggctgca    183600
actgggacag tgaccccttt gctcatagga cttgcccagg ctcagatgca ctgaatggag    183660
acaaagcaag cccaggccct gggagatgga gcctctggcc tggggtctac agatgtgggg    183720
tcagcatcat agggaggttt gcagggcagg tgtgggcag gcagaagtg gtcatgcttg     183780
tagatactat ttttctctcc tctggagcct cctttgtcta tcacctgctg tcctgggatc    183840
tctatctggg gtcaacaatg tttgcagtac aggtgtgggg gtagggcagg atgttcaca    183900
ttagcaactt gttttctct cttctgaagt ctctgttgtc tatcacctgc tgaaacattc     183960
aaagcagctc tgagctgagg gcagctgagt catcctgagc ctgtctcagc acaggtgccc    184020
caaaccagag ctactgttct gagaatcaca ccacactgga ccaggccagg tgggcctggg    184080
gcctggatga ggggtgggag ccaggggagc cctgccaggg gctgaggagg ccccaaccccc   184140
catcacccaa ggccatccac actcgtgcct taatgaggcc atgttctgtc ccaatgagaa    184200
caagtccaat taagattaag tatggtcttc ccagggtcat ccagagtcaa ggggtgtcag    184260
ccaggggacaa cccagaccag cctgaggtca gccagcatca cccaaggcca cacagctatt   184320
ttggcagagg actagaatag tcagctcatc gaggccctgg agatgcagaa tggagagttt    184380
atccctgcca gacagggttc ctcggatagg caggtccctc accacacatg acctccctga    184440
atatttccca gagtccagtt ggttctagac tatcacaata gtcttctgta ttcctgataa    184500
gcatgcagaa agctaacagg atgacaagaa attttatgca gaaaacagaa gcatctcag    184560
gatagaacag aggagaatag atactggaag tctgctggag accccagtgg agtctctttg    184620
tagagtcaag ccgtaagatc aaacctgcac tgagcctcaa gattgagtca agtacagagg    184680
caaccttcag gaccctaaag accttacagg caatggacag gatggagtcc aggcagacaa    184740
gtaaacgggc agtcatatgt aacataatga accatgtcaa cagagggtac tgagccaagg    184800
aaggctctgg gacacttgtg gataatctgc cactggatct cttgatgtat ataccaggtg    184860
atcagatgac agttcagtgg cgccatcgcc gttacagtgt taggtgttgt cctcgtcatg    184920
ggttcacgtg agaatgtgac acctttttag ttggatgtgt acagtaagct ctcaggcctg    184980
gtgttcctgg tatgatttta atgatccatg tgttcctata tctttaataa gtttataggg    185040
tgacattaag cttggggata agttgtttat caggctgtgc ctttagaagt tgatgtgcag    185100
ggattgttgt ttacaccaag atgcccagtc ttcctccagc ttccaaacgg agtcaaaggc    185160
catttgaaaa tgtgaaacct ctcagggcaa ggtacaatct ttttttttt taaagccact    185220
acctcacaca acatggagta atttaaagca gggcacagct tgatcgaaac acacacacac    185280
acacacgcat acacacaatg taagataccg agaagggat caaggacac agaagtagag      185340
agagaatgag acagttcagg gatgtagaga tgagaggtaa ctagaggaaa ggagaaacac    185400
```

```
aaggactgga gggtaaagag ccagggacag aaagatccat gcaagcaaga cagacagaca   185460
caaggaaggg aaaggtggga agagacagac agacaaggtg cagcaatgta gcccacctga   185520
gactcccatg aaagtctggc acccactctc agatgaaagc caagtaccta cagacacgta   185580
cccacagcac ccacacagag cacctgcctg cctaactcaa gcccacctac ccatcgcctc   185640
tcctccaggc ctctgtcctc aggaagcaca ctgagggtaa ctcagtctgg acacttctaa   185700
ctatggctta gtgaacagcc tgagaggctc tggatccaca ggtcactacc acttgctggc   185760
cctgtgctcc atgccatgct tcagggggga attcactgaa tgcatgaacc atagtctggg   185820
gtcaacatgt actaagggat aggatcctat caggatttgt ccaaataagg tccaaacaaa   185880
gtgaagaagg tgataggcga aacagctgg cagctgagag aacgctggcc agttcttagg    185940
ccagagctta gggacaattt ccagacctag cctttcatct caactctagg tcatgggtaa   186000
cttcccagat ctctattttg ttcctggtaa ctatgcatgc tggtacaagt ctaagaacct   186060
cggtgagaca cagaaccagt aagatgaaag catccgtgga taaggaagaa aggaggagag   186120
tagaagggac aggaccctgg acacatgaga ttcccacacc caggaactgc tcatccagcc   186180
cgagaaacgg tatcccccta gcacacagaa agaaaacagt accacaggtc taaaagagta   186240
gagtcagtgg aaggggtac tactagggcg cctcctgcct ggtccaggag cagaggctgg    186300
gaaggggcac taaacagggg ggagcatgga gacaggagag tgaaggagcc tttgggactg   186360
catggtggga actagactgt tctctgaatg agcctgtgtg tgtggcagct gcctgagagg   186420
gaagacaccc agaggccagg cagaggaaaa gagtaatcag ggctgagggg actggggtgg   186480
gggtctgagg aagtcaaggt agctatcgcc catttatcag ggccatgaca tgcacttcat   186540
gggcacatat ctaaaaccag acctggccct cacctacact cagacaatgt cccttttgtg   186600
gatttaggga tttcagtact tcatcccatg gcctctcaaa ctggaagatc catctaaaag   186660
gctgatgttg tggtatcagg gcccaggact agagaatggg acactgagtg gcagaggtgc   186720
agaggacaca tacactcact cagatgaaag caatgcacaa gaagacagag ccatgtatga   186780
acactcctca gactcagacc cacagcactc acacccagct ccccacagac acacacagcc   186840
cctgcctgcc tgttccaaaa atcaaaccca tctaccccact ccctctcctg caggccttg    186900 tcctcagagt ggcacactga aggtagctca gcctgaacac ttcccatggg acctggtgaa   186960
cagcaggagc ctctggtcca cactccccac ctcttgttag ccttgtagtc tatgtgatgc   187020
tgttgagaac agggtacatg gcctctgcct ggtacagtct ggggtgcagg cttcaggtga   187080
ggcccaagtg tgaagagtgc agaagacagt gggcagagct gagagactgc tagccagttt   187140
tgttcaaagg actgtgatgg ctgctccagg ctactgaaca ttccaggact gcttcctacc   187200
ctcctcaaag atgctggaac acaaccaatc ctcaacacaa tccaatgtag ttgcctgtag   187260
cagggcatgc ctctgtacag cagggagtca cacagagcca catgagactc tagacctggg   187320
gactgcagag gggaaggcat gtccaagacg gcctcctcct tgttacccta ggttttcagg   187380
cctcaggata accactgaac aacatatgct gagtcctgtt ccccaggatg ctgatggaca   187440
ccaggtcaca gggctagagg ccaggagggc tagagcctgt gggcaggggg gctatattca   187500
ttcttcctgt gcttgcccag gagcaggtgc tgggcagggg cacaggacag ggtgaggcag   187560
ggagacaggg gcatgaaggg gcctctggga ccacaaggtg ggaactaggc tgtgcctgac   187620
tgagcctgtg tgtgtgacag ctgattcatg gggaagacac ccagagacca ggcagaggaa   187680
aagagtaatc agggctgagg tgactggggg ttggaggtc tgaggaggta gaggcagcta    187740
tgtcccattt gtcagggtat ggggacatgt acttcataga cacagatcta agaaccaggc   187800
```

```
gtggttccca cctacccca gacagtgtcc ctcatatggg cttagggatt tcagtacttc    187860
atcccacggc ctcacaccctt ggaagatcca cctcaaaggc tgatgttgtg gtgtgggggt  187920
ccaggactgg ggccagggac actggttggc agaggtgccc aggacataga gtgctcagag   187980
tgtagttggg gacatgctga gcactgttcc tctgtgaggg gacaggctga gacagggact   188040
gaagtccatc cataggctca gcacatacca ggctctggat gggaacactg agctctgcca   188100
ccctccaaca tctggcacag cagcctcctg tgccagggaa gctagtcagc agggacagag   188160
ttcctgtccg ggctggatgg agtcttctct gctagcatcc aaaataagtg catcttcagc   188220
aataaggtcc agtcatggtg gacggccagg aacaaaggca gtaaacagcc tggtttgtgt   188280
ttggttatct acagtctctc tcactaaagc atcaagactt cttttaataa atttagaagt   188340
tgttttcttt tgaaacacgg tctctctatg tagtcctggg ggtcctggaa ctccctgtgt   188400
agaagaccag actgtcttca aacttaagga gatcctcctg tctctgcttc ctgaatgctg   188460
ggattaaaag catgtgccac cacacccaac ctaacccttt cctctgagag caacatgcat   188520
acaatttccc ctcttatttc cccagatttt caatccttt atccacactt aaatctttaa    188580
tgctaaaatc tccctccctc catttccaag ctgcatgtgt tctactattc cctcaaatta   188640
tttttccttg tgtgcaggtt ttagatttga atgcaggaag ccttcactct ggcaaagcct   188700
cccccaaccc agcctttccc atttccacac ctcctaacac gtgatttagc ccacatcccc   188760
tcatgtgtat ggtgtttccc ttcagtctga ggtattaccc ccagtgtccc cttacagctg   188820
cctatggtca caaataccctt tcatctgttt ttgctgtgga aagcgtttat ttccccttga   188880
attttaatag ctttctgggt atactaccct gggttgagag tttagatttt tcagatcttg   188940
gaatatgtct ttctagacat ctagccttaa atgtttctac tgggggctac agaaatggct   189000
tggtggttga caacacatga tgttcttgca gaggagtggg ttttgattcc tagtacccca   189060
tatcagctaa gagctatgga agacacaaat ggaagagggg actctgagat tctgagaaaa   189120
gcctcatggt taagggtaca ctgagatact gagagagaaa gacagagaca ctgagaaaga   189180
cagaagcaca gaccactaaa agagacaggg aaacagagag agacagtgat gagatgcagg   189240
gacagagcaa cccagagaga cagacagaga catagacact gatagagaca caaagaagag   189300
aggggtcgtg gaagttttga gagaaactgg taggaggtga gagagacaca gagccaatac   189360
agacacagaa agacagagac tccagagaga cagagactga gagagacaga gactgggaga   189420
gacaaagata ctgagacagt cagagacacc aatgggtgct tttccagggg atccagattc   189480
aattcccagc acccacatgg cagctctcta ctgtaatccc agttccaggg tgccctgaaa   189540
aatccttcat gcatgtgaag cttagaagct cacacacaaa cacacagaca gacagacaga   189600
cagacagaca gacagacaca cacacacaca cacactcaaa tgaagagtgt ggttctcttt   189660
ctctctctcc gatgaaagcc atgcaccaga agacagagcc atgtgtgaac actcctcaga   189720
ctcagaccca cagcactcac acccagctcc ccacagacac acacagccct gcctgcctgc   189780
ctgttccaaa actcaaaccc atctacccac tccctctcct gcaggccttt gtcctcagag   189840
tggcacactg aaggtagctc agcctggaca cttcccatgg gacctggtga acagcaggag   189900
cctctggtcc acactcccca cctcttgtta gccttgtagt ctatgtgatg ctgttgagaa   189960
cagggtacat ggcctctgcc tggtacagtc tggggtgcag gcttcagggg aggcccaagt   190020
gtgaagagtt cagaagacag taggcagatc tgagagactg ctaaccaatt ttgttcaaag   190080
gacagtgatg gctgctccag gctactgaac atcccaggtc tgcttcctac cctcctccaa   190140
```

-continued

```
gctgttggag cacaaccaac catctttgta attgcccagt tgtttgttat tgcctatagc   190200
agggcatgcc tctgcacacc agggagtcac acagagccac atgagactct agacctgggg   190260
actgcagagg gaaaggcatg tccaagaggg cctcctcctt gggacactgg gattccaggt   190320
ctcaggataa ccactgaaca acatctgctg agtcctgttc cccaggatcc tgatggaccc   190380
caggaggtca cagagctaga ggccaggagg gctagagcct ttgggaaggg ggaatgttag   190440
ggtttctccc atcctggtcc aggagctgct cacctgacag tgatacagga cagggtaagg   190500
cagagacagg gggatgaagg aaactttggg agcacatggt gggagtgtag gttgtgcttt   190560
tgcttagcct gtgtatatag cagctgcatc attgggaaga cactcagagg cccgacagag   190620
gaagagtaat caaggctgag gggacagcag tgtctaagga agtggaggca gctatggtcc   190680
atttgtcata gtattgggac atgtacttca tgaacactga tctatggacc aagcctggtt   190740
gtcatctgcc ctcagtcagt gtccctcatg tgggtttagg aatttcagta cttcatccca   190800
aaagccagtc acattggaac ataaatgaaa tgctgatgct gtggtgctgg ggcccaggag   190860
tgcggggtta gtatactggg tgacagaggg tgtccagtaa atagattgct tagagtgtag   190920
gtggggacaa gctgtgcagt gttcctccat gaggggaaag actggtacag gttttgacat   190980
ctctttcgta tccataggcc ctgccatact gcccttgtcc atggtccctg tggggtcaca   191040
tacttagtgt caagtaaacc ataccacaaa ctggaagggt ctacactatc cttgtaggtt   191100
ctacactctc catgacttct cccaactcac acagactgtt ccaatacact actctcttca   191160
gtgggcaatc atgccatgaa cagagagtgg agggttatgg ttgccctata ttctgacaca   191220
tccaacagtc ttgtgcattt gactctcatg tgtacaagcg tgctcaggcc tgctgtagtc   191280
ccctcgagac agtgatgcct tccttgagag ccgattctca ctgtcagcat ctcctcagac   191340
caaagcccta tagatccagc ccctttgagg agctaatgta gtcagtcaca gggcttgatg   191400
ttggtggcta tagctgctgt ccccatggct gccagagatg cttgaccacc ataatcccag   191460
acttgagcat aggaataacc tggaatcaac agcatccaga cactgtaggg actgccaga   191520 gatgtgcata gaccctatgt catgtgacca agacctcttt ttctagtatc ttatttcatg   191580
aaagtctaca aaatacgatc ttctattcct tttattcctc tttgcctgct aacatggagc   191640
cttctaggaa gagggtcccc tctctgtcta ctgactgtga agatagatcc tgtaggtgtg   191700
atcacagagt aatgtttcat ttcttggcca gcctcaagcc aggggactca gggagagaga   191760
caggagaagg agagatgggg agagagacag aaagacagaa aaacaaagca agggagagac   191820
agaagcaggc agacctggag actgggtgct taggaaagag ataaatgtgg atacaggag   191880 tgaaagatag ggaattgaag acagaggtgg agataaagac cagaatatgg gagtcagaga   191940
cagacaagag acatagagat caatataggc aaacagagac tgagaaagac agtgatgaga   192000
cagagagaca tggagacaga caaggagaca gacatggaga cagacaagga gacagagata   192060
gaaataggga gagaaaataa tacataatta gtggttgatt aaggaagaga taatgaatgg   192120
caagaaggga cagaggcagg gagagacata tacaggtaga gaaaaagatg aagacagaca   192180
gagagagact gaaagaggga gaaagataca gagagaagag agactatgaa acaggcagag   192240
atataaagac agtgagagaa aaacagagag acagagatgg aagagagaca gagagacagg   192300
gagatagaga aatgggaaga caggaggacc aagagaagag acacacggcg aggcaagatg   192360
tagtagagag acctctgatg gaatcggcat aggtggaggc aaacatagat agaccctctc   192420
caactgcagt tgacagactg agcagagaga ataccattca gagagaaaca gaggctaagg   192480
ctaggaaagg caagagtagc cagaggagac agagttgagc ctgtgggaca ggaccagacg   192540
```

```
ccatcttgga agaggcagtg acaagccagg gaggtgacag gctggcacag tttctatccc   192600
acagtccaca ggctggtgtc acaggcctgt ctcctcgtgg ccacagtcta tccctgcctg   192660
ccaagcctgt ctgtggaggg atggggggggg gggggctgg gctgaggcag gccaggactt   192720
ttccagtgga gtggccaggc actgggctga gggcatgatc cctgcccacc atcccagtgg   192780
gtctgggtaa tggatggcct tgattatttt ccttcgtgtt tagggtggaa cctgcttaga   192840
ggcagctagg gctctccatg atggcctagc ctgtggtgag ttaatgaacc cctaagggta   192900
gttcttccac atgggctagg gttacaatct gggggttggg ggctcagata tcagtaccag   192960
aaacaaggct tactcccaac atgtcacact cgcacacaca cagctgccga gttactcatt   193020
ctgtgcagag ttggctcaca agggcacatg caaaaggatg tttgtttcat acagaaaaac   193080
atgtttctca ctttctgagg ttgttttccag aaatagcatc agtgactccc ccacctgcag   193140
ctgcaggttc accccaacct ggccaggctg accagccttg gggatggggg actcccagca   193200
taggccactg ggactggggg tccatgaccc ctattgatga cgttgaattc agtgtttccc   193260
agttatcacc actgctggaa tctgacccac caagaggaca tgacaggaga tgggcaagga   193320
tgggtggctc aacaccccag ggaagtgaga gaggcaggaa ggctgtaggt gtgctccaga   193380
tcctgggtct acccagaacc atgggaatgg tgggcagtga tcatgccctc agcccagtcc   193440
ctggccactc cactggaaaa gtcttggcct gcctcagccc agacccctc ccccacccct   193500 tctcagacag acttggcaga cagggagcta gcctgtggcc acatggagac aggcctgtga   193560
ctccaacctg tggactgtgg gatagaaact gtaccagcct gtcacctccc tgcttgtcac   193620
tggctctttc aagatggtgt ctgaccctgg ctccatctct ggccaaccct gccttttccca   193680 gccttagcct ctgcctctct ctctctctct cagtgtgatt cttgctcagt ctgtccctca   193740
gttactgtct ctccgtctct aacaaaacat aagagttgtc tctattaaca ccttgtctct   193800
cctctttctt cttctccttc tccttctcct tctccttcct ctctctctct ctctctctct   193860
ctctctctct ctctctctct ctctctctct ctctctctct ctctcatctc tgcttgtgcc   193920 cccctttctct aggtgcacat ctcctaccct tgtctgtcta tctgtgtctc ttccttctgt   193980
catctcctct ctatcattct ttcagtcttt ctctatgtct cttttctgtt gacgtctgtc   194040
tttgtgtgtc tctctctcca tcccattcct tttatgactc tggctcccct tatctctctg   194100
tctgtatttc tgccccactt ctctgtcttc ctatctttttt gtcttttctc tgtttctgat   194160
ttttctctcc atgtctttct ctccactttt ctctctccct ttctgagtct cctgcatct   194220 gtctcattgc ttctcccatct cgctctctct ttctctgttt tctgtctctg ttcttgtatc   194280
tctgtgtgcc tctccatgtc tctctgctgt ctctttttct ccatacagca atttactaaa   194340
agaacaaaca tcaaggcagg aaagtatata tatttcaaat aaaagttctt caaattgcta   194400
tgtcctatac tccaagaagc atttccaaag tatagattaa tttaacccctt ttaaatgaaa   194460 agatacattt ttaacttcta aagtgtctcc acaaagaaat gaatgttttt aattaagaaa   194520
tgttgtaatt tagtgttggg ctcctgtctt ataatgtaca cttccttata aatctagcca   194580
tgtggcttat atccatttgg tatgctcgga gctttatgta ataaacgtct tcccgatagg   194640
tgcaaggatt ggtgttttgt actgcttact acatacatgc ttttaatcat tccaggacat   194700
accgtccctc tgctgctgct tctcaccgtc tttgcctttc tctcaccctg tccatctttc   194760
tctctcccca tctctctgtt tctgtccctt cctgttccag tctctctcca atctcccttgt   194820 gtttctctct ctctctctct cctgatgtct cttttctctgt gggcttgtct ccccatctgt   194880
```

```
cctcttcatt tctgtatttc tccttatctt tctatctctg tccatgactc tgtctctttc   194940
tgcctcgttc atcccctgcc ccctgaagg cacaatgaca cttttatcag ggtttaatag    195000
gaaagtttca gggcaggaaa gttgtaagac tcaagcagct gccccgagga ggccagtggg   195060
ggagattggt aaaaagccat gacatctaat ctgacatgga ggtcaggcac atgtcccaca   195120
agcagccaca tggcgagaag ggggcagtta gagaacaagt aagaaagccc agcatgttgg   195180
ggaggaagcc aaggtgttaa ggaaaacttg ctcagaggga gacagaaaga aggaagctac   195240
aattctgtga attcagaaag gaagctgact tacagcccca catggctata gccctaagc    195300 ttctggccct tccccttctg tctcttcctg ttctctgtca ccctgtttc tcctattct     195360 ctgtcacacc tgtctctgtg ctcccattaa tctctctctg tctctacaca tctccacctc   195420
tgcctccttc atctctgtct tttccggaac cctgtctgtc tctgtcaggc ttctccttgt   195480 ctcccctgc agacttgcag tttctccctt tgtcttcctc tgtcttacct ttattatgtc    195540
tccccgtctt tcctaccttc ctgactttct gtctcttacc ctgagtcccc tggcctgaaa   195600
ctggccaaga aggaaaacat cagtctgtga tcactcctac agggtctgtc tccatagcca   195660
gcagagaggg gaccctcttt ctagaaggtt ccctgttcgc aggcaatgaa gaataaaagg   195720
aatagaagat cccgttgcat taaggtttca tgagataaca tactaggaaa agagacctag   195780
gtctacgtag aagtctggtc agtccctgaa gtgtctagac gcacttgatc cctaggccat   195840
cactatgtct gaggtcatgg tggtcaagca tctctggcag tcacagtgaa agcagctgtg   195900
gtcaccaaca tcaagccctg tgactacaat agctcctcaa agaggctggg tctgtggggt   195960
tttgttttga gggtcagcta gaaatgggag tgagtccaag gaagacccac tgccccgcc   196020 cccgagagat aggggaatga gcatgcttgc acacgtggac atgaaaggca caagagtgtt   196080
gtatgtgaca gtttgaggtg accacattct gccctctctg tgcctgtcat ggttacaact   196140
gaggacagtg gtggatttgg gcagagtctg tgtgagctgg gagaagctgt ggagagttgc   196200
aagcatggca tgtagatatc agaagccctg gtcttccagc agtcctcatg gtgatggttc   196260
agtaggacac tggatgtgtg gcccatgcta gggtcatggg caaggctggt atgggttgac   196320
tctatggctg gacaaagagc tttaacctcg tcagcttccg caatatggag gaacactgca   196380
cagcttgccc ccacctgcac tctgagcact ctgtacactg gacatgctct actacccagt   196440
gtctcagact ccagtcctgg gccccagccc catagcacaa ccatgtttat aatccctcca   196500
gtgtgagagg ccatgaaatg ttgtggagct cagtctgaag gcaggtggga gacaggcatg   196560
cttttggatc catgtccatg aagtatatgt ccacattcca tgacaaagga gccgaagcca   196620
cctctatttt ctcaaggacc ccctcagtcc tcattactct tcctctgcct ggcctctgga   196680
tgtcttcccc atgaatcagc tgtcacaaac acaggctcag tcagagcaca gtctagttcc   196740
caccttgtgg tcccaaaggc tctttcacgc cagtgtctcc ctgccttacc ctgtcatgca   196800
cctctggcca gccagctgct cctgggcaag gacgagaaga agccaagtag ttcctcttct   196860
cacagactct agtcctgctg gcctctaact ctgtaacctt ctggtgtcca tcaggatcct   196920
ggggccacat cactctgagt gtgtttatca ccggcaatcc tgagggctaa gatttcagat   196980
tctaaaggag gaggccccg tggacatgcc ttccctctg cagtccccag gtctagagtc     197040
tcatgtggct ctgtgtgact ccctgatgta cagaggcatg ccctgctaca ggcaattaca   197100
atggattggg tagagggttg gttgtgctcc aacatctttg aggagggtag gaagcagacc   197160
tgggatgttc agtagcctgg agcagccatc actgtccttt gaacaaaact ggccagcact   197220
ctctcagctc tgcccactgt cttctgtact cttcacactt gggcctcacc tgaagcctgc   197280
```

```
accccagact gtaccaggca gaggccatgt accctgctct cagatgatgt ttcatacaga   197340
ttacagagct aacaagaggt gtggtgtgtg gaccagaggc tcatgctgtg tagtcaccca   197400
tggtcctgct gaaaagcagg ctggggctaa aaagagaata gagtatgaga cacaccaaga   197460
caaatgctga tcaaagccca atgtttacta aaaatctgtg cttatataaa aggaaagccc   197520
ttctcctgca gatccacttt tgatgtctgt tgccagcctg taagcaattt gtctgacagc   197580
actagtttga caagaaggtg tcaatcactg ctgtctttgg aatctctcag cctctcagca   197640
ggtatcagtg tcttggagaa gaagagcaat ggtgacagaa caatagaatc atctaggtgg   197700
gaaggctcta ccccaggtgg tctcattctc agtggcagca aggtctgagc cagcctgctc   197760
aaggctgggg gaggctacaa tgttattcaa caggtcccat gggaagtgtc caggctgagc   197820
tactcagtgt gccactctga ggacaaaggc ctgcaggaga gggaatgggt agatgggttt   197880
gaggtttgga acaggcaggc aggggctgtg tgtgtctgtg gggagctggg tgtgagtgct   197940
gtgggtctga gtctgagggg tgttcacaca tggctctgtc ttctggtgca tggctttcat   198000
ctgagagaga gaaagagaac cacactcttc attagagtgt gtgtgtgtgt gtgtgtgtgt   198060
gtgtgtgtgt gtgtgtgtgt gtgtgtttgt atgtgagtct gtctgctgtc tgtgtgtaaa   198120
tgtgagcttc tatgcttcac atgcatgaag gatccttcag ggcaccctgg aactgggatt   198180
acagtagaga gctgccatgt gggtgctggg aattgaatct ggatccctg gaaaagcagc    198240
cagtgctctt aatccttttg gtgtctctgc ctgtctcagt atctctgtct ctctcagtct   198300
ctgtctctct ggagtctctg tctttctgtg tctgtactgc ctctgtgtct cccacacctc   198360
ctaccagttg ctctcaaaac ttccacgtcc cccctcttct tcatgtctct atcagtgtct   198420
gtgtctctgt ctgtctctct gtgtctctct gtccctgcag ctcatgactg tttctctcta   198480
agtgtttccc tgtctctttc agtggtctgt gcttctgtct ttctcagtgt ctctgtcttt   198540
ctacttcaga atctcagagt cccctcttcc atttgtgtcc cttcttgggc tcattcactc   198600
tgcctccagt gtcatcactt gtgagaccag aacctactat gagtccagag gactgtcctt   198660
catggtctgt gaccagctgt gatctgggga acactgggga aggcatgaac agggagggac   198720
ctgcctgtct gtggagccct gcctgtcagc atgaactccc cattctgcac caccagagcc   198780
ctgctgagct gactattcca caccacctcc agaaagggc attgaatcct gtggaaccga   198840
tggctcttag ctgatacggg gtactaggaa tcaaaaccca ctcctctgca agaacatcat   198900
gtgttgtcaa ccaccaagcc atttctgtag ccccacagta gaaacattta aggctagatg   198960
tctagaaaga catattccaa gatctgaaaa atctaaactc tcaacccagg gtagtatacc   199020
cagaaagcta ttaaatttca ggagaaaata aaaaagcttt ccacagcaaa aacagatgaa   199080
aggtatttgt gaccatagac agctgtaagg ggacactggg ggtaatacct cagactgaag   199140
ggaaacacca tacacatgag gggacgtggg ctaaatcacg tgttaggagg tgtggagatg   199200
ggaaaggctg ggtgggggga ggctttgcca gagtgaaggc ttcctgcact caaatctaaa   199260
acctgcacac aaggaaaaat aatttgaggg aatagtagaa cacatgcagc ttggaaatgg   199320
agggagggag atttttagcat taaagtttta agtgtggata aaaggattgg aaatctgggg   199380
aaataagagg ggaaattgta tgcatgttgt tctcagaaga aagggttagg ttgggtgtgg   199440
tggcacatgc ttttaatccc agcattcagg aagcagagac aggaggatct ccttaagttt   199500
gaagacagcc tggtcttcta cacagggagt tccaggacac ccaggactac atagagagac   199560
cgtgttcaa aagaaaacag tttctaaatt tattaaaaga agtcttgatg ctttagtgag   199620
```

```
ggagactgta gataaccaaa cacaaaccag gctgtttact gcctttgatc ctggccctcc   199680
accatgactg gaccttattg ctgaagatgc acttattttg gatgcagagc aaagaagact   199740
ccatccagcc tggacaggaa ctctgtccct gctgactagc ttccctggca cgggaggctg   199800
ctgtgccagc tgttggaggg tggcagagct tagtgttccc atccagagcc tggtatgtgc   199860
tgagcctatg aatggacttc agtccctgtc tcagcctgtc ccctcacaga ggaacagtgc   199920
tcagcatgtc cccaactaca ctctgagcac tctatgtcct gggtacctct gccaaccagt   199980
gtccctgacc ccagtcctgg accccacac cacaacatca gcctttgagg tggatcttcc   200040
aaagtgtgag gccgtgggat gaagtactga aatccctaag cccatatgag ggacactgtt   200100
tgggggtagg tgggaaccac gcctggttct tagatctgtg tctatgaagt acatgtccca   200160 atacccctaac aaatgggaca tagccgcctc tacctcctca dacccccaa accgcagtcc   200220 cctcagccct gattactctt ttcctctgcc tggtctctgg gtgtcttccc catgaatcag   200280
ctgtcacaca cacacaggct cagtcaggca cagcctagtc cccaccttgt ggtcccaaag   200340
gccccttcat gcccctgtct ccctgcctca ccctgtcctg tgcccctgcc cagcacctgc   200400
tcctgggcaa gcacaggaag aatgaatata gtccccctgc ccacaggctc tagccttcct   200460
ggcctctagc cctgtgacct ggtgtccatc agcatcctgc acaacaggac tcagcatatg   200520
ttgttcagtg gttatcctga ggcctgaaaa cctagggtaa caaggaggag gccctcttgg   200580
acatgccttc ccctctgcag tccccaggtc tagagtctca tgtggctctg tgtgactccc   200640
tgctgtacag aggcatgccc tgctataggc aactacaatg gattgtgttg agggttggtt   200700
gtgtttcagc agcttggagg aggggtaggaa gcagacctgg gatgttcagt agcctggagc   200760
agccatcact gtccttttgaa caaaactggc cagcactctc tcagctctgc ccactgtctt   200820
ctgcactctt cacacttggg catccctga agcctgcacc ccagactgta ccaggcagag   200880
gccatgtacc ctgctctcaa cagcatcaca tagactacaa ggctaacaag aggtggggag   200940
tgtggaccag aggctcctgc tgttcaccag gtcccatggg aagtgtccag gctgagctac   201000
cttcagtgtg ccactctgag gacaaaggcc tgcaggagag ggagtgggca gatgggtttg   201060
aggtttggaa caggcaggca ggcaggcagg ggctgtgtgt gtctgtgggg agctgggtgt   201120
gagtactgtg ggtctgagtc tgaggagtgt tcacacatgg ctctgtcttc tggtgcatgg   201180
cttccatctg agggggtgtg tgtgtgtgtg tgtgtgtgtg tgtgtgtgtg tgtgtgtgtg   201240
agcttctaag cttcgcatgc atgaatgatc cttcagagca ccctggaact gggattacag   201300
aggtgagctg ccatgtgggt gctgggaatt gaatctggat cccctggaaa tcagccagtg   201360
ctcttaatcc ttttttgtgtc tctgcctgtc tcagtatctc tgtctctctc agtctctgtc   201420
tctctggagt ctctgtcttt ctatgtctgt actgcctctg tgtctccctc acctcctacc   201480
agttgctctc aaaacttcca tgtcccccccc ttctctgagt ttctatcagt gtctgtgtct   201540
ccgtctgtct ctctgtgtct ctctgtccct gcagcccatg actgtttctc tctaagtgtt   201600
tccctgtctc tttcagtggt ctgtgcttct gtctttctca gtgtctctgt ctttctctct   201660
cagaatctca gtgtccctc ttccatttgt gtcccttctt gggctcattc actctgcctt   201720
cagtgtcatc acttgtgaga ccagaaccta ctatgagtcc agaggactgt ccttcatggt   201780
ctgtgaccag ctgtgatctg gggaacactg gggaaggcat gagcagggag ggacctgcct   201840
gtctgtggag ccctgcctgt ccgcatgaac tccccattct gcaccaccag agccctgctg   201900
agctgactat tccacaccac ctccagaaag gggcattgaa tcacgtggaa cctaagaaca   201960
ccgtgttgtc aaccaccaag ccatttctgt agccccacag tagaaacatt taaggctaga   202020
```

```
tgtctagaaa gacatattcc aagatctgaa aaaaatctaa actctcaacc cagggtagta    202080
tacccagaaa gctattaaat ttcaggagaa aataaaaaag ctttccacag caaaaacaga    202140
tgaaaggtat ttgtgaccat agacagctgt aaggggacac tgggggtaat acctcagact    202200
gaagggaaac accatacaca tgaggggacg tgggctaaat cacgtgttag gaggtgtgga    202260
gatgggaaag gctgggtggg gggaggcttt gccagagtga aggcttcctg cactcaaatc    202320
taaaacctgc acacaaggaa aaataatttg agggaatagt agaacacatg cagcttggaa    202380
atggagggag ggagatttta gcattaaagt tttaagtgtg gataaaagga ttggaaatct    202440
ggggaaataa gagggaaat tgtatgcatg ttgttctcag aagaaagggt taggttgggt    202500
gtggtggcac atgcttttaa tcccagcatt caggaagcag agacaggagg atctccttaa    202560
gtttgaagac agcttggtct tctacacagg gagttccagg acacccagga ctacatagag    202620
agaccgtgtt ttaaaagaaa acagtttcta aatttattaa aagaagtctt gatgctttag    202680
tgagggagac tgtagataac caaacacaaa ccaggctgtt tactgccttt gatcctggcc    202740
ctccaccatg actggacctt attgctgaag atgcacttat tttggatgca gagcagagga    202800
gactccatcc agcctggaca ggaactctgt ccctgctgac tagcttccct ggcacgggag    202860
gctgctgtgc cagctgttgg agggtggcag agctcagtgt tcccatccag agcctggtat    202920
gtgctgagcc tatggatgga cttcagtccc tgtctcagcc tgtcccctca cagaggaaca    202980
gtgctcagca tgtccccaac tgcactctga gcactctatg tcctgggtac ctctgccaac    203040
cagtgtccct gacccagtc ctagaccccc acaccacaac atcagccttt gaggtggatc    203100
ttccaaagtg tgaggccgtg ggatgaagta ctgaaatccc taagcccata tgagggacac    203160
tgtctggggg taggtgggaa ccacgcctgg ttcttagatc tgtgtctatg aagtacatgt    203220
ccccataccc tgacaaatgg gacatagctg cctctacctc ctcagacctc cccaaccccc    203280
agtcccctca gccctgatta ctcttttcct ctgcctggtc tctgggtgtc ttccccatga    203340
atcagctgtc acacacacac aggctcagtc aggcacagcc tagttcccac cttgtggtcc    203400
cagaggcccc ttcatgcccc tgtctccctg cctcaccctg tcctgtgccc ctgcccagca    203460
cctgctcctg ggcaagcaca ggaagaatga atatagtccc cctgcccaca ggctctagcc    203520
ctcctggcct ctagcccgtg gacctggtgt ccatcagcat cctggggaac aggactcagc    203580
atatgttgtt cagtggttat cctgaggcct gaaaacctag ggtaacaagg aggagcccct    203640
cttggacatg ccttcccctc tgcagtcccc aggtctagag tctcatgtgg ctctgtgtga    203700
ctccctgatg tacagaggca tgccctgcta taggcaacta caatggatta tgttgagggt    203760
tggttgtgtt tcagcagctt tgaggagggt aggaagcagt cctggaatgt tcagtagcct    203820
ggagcagcca tcactgtcct ttgaacaaaa ctggccagca ctctctcagc tctgcccact    203880
gtcttctgca ctcttcacac ttgggcatcc cctgaagcct gcaccccaga ctgtaccagg    203940
cagaggccat gtaccctgct ctcaacagca tcacatagac tacagggcta gcaaagaggt    204000
ggggagtgtg gaccagaggc tcctactgtt caccaggtcc catgggaagt gtccaggctg    204060
agctaccttc agtgtgccac tctgaggaca aaggcctgca ggagagggaa tgggtagatg    204120
ggtttgatgc ttggaacagg caggcagggg ctgtgtgtgt ctgtggggag ctgggtgtga    204180
gtgctatggg tctgagtctg agggggtgttc acacatggct ctggtgcatg gctctcatct    204240
gtgtgtgtgt gtgccacagg ctccatttga gtgctcggtt ggctccattg ctgtacctct    204300 gtccccttg ttttctatct gtctgtcctc cctgtctgtc tgtctctcct ttcctatgcc    204360
```

```
tcctcctcat atccacgtct gcatctcttt ctatcagtct ctatccctgt gaccctggt    204420 ttccatttct gtctttctgc atatctttcc atctttctct ctgtgtgtct gtcctcatct    204480
cttccagtgt ccgtgtttct gtttccctct gttcccatgc ggaggtatgt tctcacaatc    204540
cttaagttcc ctggtcccct gtccccatt tcttgtcata ttatccatc agtgtctctg     204600 tgcctctctg tctgtgtctc tgtgttgtct ctgtgtgtgt ctctcagtat ctctctctct    204660
ctctctctct ctctctctct cagtatctgt atttctttta gtaactttgc tatcttttta    204720
agtatctctg tctttcttca tctctgtctc tcttgaggtc tctgtctttc cgcatgtcta    204780
atgtttctgt atctctctca cctcatctct gcctctctca atattcagta gatccatgcc    204840
cctttattct ttgtgcctct gtctctgttt gtctctttct ctgtctctct gtctttctct    204900
ctctcagaat ctgtgtccct catgttattt ctcaaaatgc ctccctaact ctttcaataa    204960
cagtttctgc ctcttctttc tgggcctggc tcaatcttcc ttcttggacc tcagtttcat    205020
tggttgtgag accataccct gctatgagtc cagaggactg tcctccatag tctagaacca    205080
catgctatct aagggatatt ggggcaatac atgtgtagtg atatacctgc cttctgatg     205140 agccctgtct ggcagggata aattctccat tctgcatctc cagggccttg ctgagctgac    205200
tattctagtc ctctgccaaa atagctgtgt ggccttgggt gatgctggct gacctcaggc    205260
tggtctgggt tgtctctggc tgacaccct tgactctgga tgaccctggg aagaccatac     205320
ttaatcttaa ttggacttgt tctcattggg acagaacatg gcctcactaa ggcacgagtg    205380
tggatggcct tgggtgatgg gggttggggc ctcctcagcc cctggcaggg ctcccctggc    205440
tcccacccct catccaggtc ccaggcccac ctggcctggt ccagtgtggt gtgattctca    205500
gaacagtagc tctggtttgg ggcacctgtg ctgagaaagg ctcaggatga tcagctgcc    205560 ctcagctcag agctgctttg aatgtttcag caggtgatag acaacagaga cttcagaaga    205620
gagaaaaaca agttgctaat gtgaacatcc ctgccctacc cccacacctg tactgcaaac    205680
attgttgacc ccagatagag atcccaggac agcaagtgat agacaaagga ggctccagag    205740
gagagaaaaa tagtatctac aagcatgacc acttctgccc tgccccacac ctgccctgca    205800
aagctcccca ggatgctgac cccacatctg tagaccccag gccagaggct ccatctccca    205860
gggcctgggc ttgctttgtc tccattctgt gcctctgagc ctgggcaagg ccaatgagca    205920
aaggggtcac tgtcccagtt gcagcccagt gtgtgaacag tgttgtgggg attctggaat    205980
cttctgcagg aatcccctgt agggatcctc ctaatgtgaa tgaggcttgg aatagcaaag    206040
ggacgtcttg taaaataccca ctgattcctt gggcctcaga caatggattt gagatgagga    206100
ccaaggtcca gggccagtgt tggtaagcag aatttggggc tagagttcag gcttagaagt    206160
caatgatgag ggccagggcc cagtgactag gtcaggccc attgatcagt acaggaccca    206220
gttgttagag ccggagctca atgatctgga ccaagtcaca aggccaaatg atcaggatca    206280
gtagccagtt accaggaccg agatccaggt ttcacagcca aagccaggtt accccaacca    206340
gagaccattc atcggaatct gggtctgttg atcggagccc aagcacgctg ctgtaaacca    206400
gagctgctct aaagcagaac tcagtgctga gcaccagaga taagtgatga gaccaggatt    206460
cagtgattaa ggaaacaaaa ccaaaggtca ataggatatt atgtgagag aggggagaga     206520 gagagagaga gaggacagag agagaaagag cggtaggttc aggactaagt ctcagtgagg    206580
agggtcagga gtcagtggtt tgaacccaga cacactgccc aggtccacag ttcaacggtg    206640
agagccaggg gtcagctatc agaaccaggt ccagtaacta caaccaaaaa ccagtggccc    206700
caaccaaaaa ccagttacta aaacccgaat agaatagaaa ctagccaggc agtgatagct    206760
```

```
ttaatcccaa tactcaggag tcagaggcag gtggatctct gagttcaagg tcagcctggt 206820
ctacacaatg agttctaaga cagccagggc tacacagaga aaccctgtct ggaaaacaag 206880
caaaagccta gaaaccgtgg actcagtggt cagtggcagt tcttggtgac taagaccatg 206940
gtcaagaggt caagcaggac tcagcggtta gaatcagggc atgggtgatg acagcctgtt 207000
ccagggatca gaaccaggtc taagggcaaa ggccatgact gagtcatcaa acagtgtctc 207060
ttcataagtc ctagccaggc ccaaccaggc ctagggtgtc agatcaggca agactgatgc 207120
ggtatgtgtg aggtggtatg acaatacatc tcagtatctc tgggacccca ccaccatctt 207180
ccctgcctcg gtccactcac aaatctctgg ctctctcact gtctttgtct cattcttgtc 207240 tagcttttcta ccgtgtcccc tctccccaca tttgtctctc ccagtatctg tctctctgaa 207300
agtctctgtg tcccctctga ctttctcagt gcttatgttc cctgcccctt gatcatttga 207360 gaggggatg gtgagtagag aattatggaa cagtgagtgt gtgtctctat atgtgtgtgt 207420
gtgtctgtgg ggctggcagt gggtatgtgt gagtatgtgt gtgtctgtgt gagtgtgtgt 207480
ctgtggggtg acagtatgta tgagtgtcag tgtgtgtgtg tgtgtgtgtg tgtgtgtgtg 207540
tgtgtgtgtg tgtgtgtctg tgtgtctgtg tgtctgtgtg tctgtgtgtc tgtgtgtctg 207600
tggggtggca gtgtacatgt gtgagtgtgt gaatcaaaat gtgtgagcat gtgtgtgtgg 207660
aggtggtaat gtatgtatgt atgtctgtgt gtatgagtgt gtgtctacgg gagtggcagt 207720
gtatatgtgt gagtatattg tgtattgtgg gtacgggtgt gtgtctgtgt gagtgtgtgt 207780
ttctatgtgt ctgtggaggt aacagtgtgt atgtgtgagt gtgtgtctat atgagtgtct 207840
gtatgtgtgt gtgtatgaga gagagagaga gagaaagaga gagtgtgtgc agggtgatag 207900
tgtatatatg tgagtttgtg tgtatgtgag tgtgtgtttg tgtgtatgaa tgtgtgtgtt 207960
tatggggtga cagtatgtat gtatgagtgc atgtgtctgt ggggtagcag tgtgtatgtg 208020
tgagtgtgtg tgtgtgtgtg tgtgtgtgtg tggtatgtgt gtgtgtgaga gagagagtgc 208080
agggtgatag tgtatatatg tgagtgtgtg tgtctgtttg tgagagtgtg tgtttgtgtg 208140
tatgagtgtg tgtgtctatg gagtgacact atgtatgcat gagtgcatgt gtctgtggga 208200
tagcagtgta tatgtgggag tgtgtgtgtg tgtgtatgtg cagggtggta gtgtatatat 208260
gtgagagtgt gtgtttgtgt gtatgagtgt gtatgtctat ggggtgacag tatggatgga 208320
tgtatgagtg cctgtggggc agcagtgtgt atatgtgagt gtgtgtgtgt gtgtgtgtgt 208380
gtgtgtgtgt gtgtgtgcag ggtggtagtg tatatatgtg agtgtgtgtg tctgtgtgtg 208440
tgagtgtgtg tgtttgtgtg tatgagtgtg tgtgtctatg ggatgacagt atgtatgtat 208500
gagtgcatgt gtctgtgggg cagcagtgtg tatggtgagt gtgtgtgtga gtgtgtgtgt 208560
ctgtgtgtgt gtgtgtgtgt gtgtgtgtgt gtgtgtgcca cttccctaat 208620
atgttctctt ccagctatgg cttctgcttc atccttcact caaggccaga cctcactggc 208680
cagtccacag cataatacca gccatgcctc tacccaataa ttgtatgtgt cagggagcca 208740
agaggatgga cagggatctt gttcttgggg tgagaatgtg agaacttttg gggagccctt 208800
ccacacaccc atgcagtagt agacacctct gcaaagctat gcatatcctc acactagcac 208860
actgcacaac catgcactct ctgcagactc actgttcacc atgaacccag ctagtcagat 208920
tcatatgtga aactcatatc agcctctgca cacacataca cacatattac acccatgcac 208980
acacatgtac acatacatac acatgtacac atacatgtgt acacacacat atagagaagg 209040
cattggtggg gaaaacatta ggccatggct acagtacagg gcacaaggat ggtggtacag 209100
```

-continued

```
aatgaggtca ggctgggtca gcataacaag aacacttgga caaagtgagg gtagtgtgtg    209160
tgtgtgtgtg tgtgtgtgtg tgtgtgtgtg tatatgtgtg tgtgtgtaca cgttgaaagt    209220
cttcagtaga ctggtatcac tagccctgat atgggcaaca cagcaagcct gggtcacact    209280
caagctgagt atcagggtaa ccagggcctt ctaaccaagg gtagatgcag cctgtgttcc    209340
gtttactgac cagtgagaag ccatgagctg aaccagacca gaagacccttt actgttccca    209400
cccaacccc acccagttta gtctcagcaa gaccctgtac tgtgggccac agctctcccc    209460
cacaccccac ctgtagcaca aacactattt gcaaacattt ctaaaaatga tgagaacagg    209520
aaccacagag cagaggggg gactggcgtg gaaagcccca ttcacccatg ggactgaaac    209580
tcggggaacc agaaccgtaa ggagatctgc atggtgctgg gggaggttgg ccctggatca    209640
gtgagcccag agagttactg gtttctcact tccatcaggt caacctcctc aaccccaa     209700
aatggccagg cctaggctat ggatgagttt caatgaccag gccctaagga cgagtcacag    209760
aggacttcct ggtgggctca ggcagcagac ctgcccagat ggattgcaga accaggggga    209820
gccatggcca ggaaggccag acgccttagg ggtgtgctgt ctctgcatcc tttgccctct    209880
ctgctcctca cagtccatct gccatctcac aatccctcct gtcgctctgg ggcccagacc    209940
tggccagtct gggtacctgt ggaatacacc caaagaagca atcccagcc tcaggaccca    210000
caactacttc ccctacagac atgagtgatc tcagcccaca tgtctggggg ccacagaagc    210060
ccctaagacc ctactctgct aataggccct cctcccacca gccaagacaa tacacaggca    210120
aggtgatgtg gatgagtcac cccatgggta cctgtgtctg agatacaccc tgtgggtatc    210180
ctggccagaa tctggtgacc aacccaacct gtgtccctag aggagaactc cgtgcctgca    210240
ctcacctacc cacctaactc caagcttggt atgatgcaga gccctgtgt agacctaaaa    210300
gtcagccata ggacagggtc aagaatgact cttcctacac ataaagtctt ctactaagac    210360
agtaaggtag acacacaaac atacccggat gcagagacac acaggcatgc agagaaggca    210420
tgtagacaca aacgcatgca taaacgcaca aacatacaga tatatgctga caaatataca    210480
cagcaactta caagtacaca gacacacaaa cagacaaaca tgcacagaca gaaacacaca    210540
gagctcaaaa tcaagtatac acagacaaat ttacacagag acttacagat acacagatat    210600
atgagacaca cccaaacaga cacacacatg ggggcacaga aaaacataca agcagacaca    210660
tgcagactta aagacccaca agacatggag agatacaaaa acacacaaca cagacacaga    210720
gatatagaga cacacagacc cacaaatatg aacagacgca gagacaccca gaaacaaaaa    210780
cacactcagg cattccactc ccaatgggcg tacacatggg catacacagc ccagtcacac    210840
agacaaacat aacacataca gaagtgcagg catacatatc acacaataca cgctggtatt    210900
cacacacagg tgtgctcaca aacccccacac actcacacat aaaagttgac actggcactc    210960
ccactccgag gcacatgctt agccacagcc ggctgacact gcacacccca cacacgttcc    211020
agagactccc acagaactgg aagctcaccc aggcccaccc aggctctcag gccacacaca    211080
tgggacatct cagaggcatg tgggatacag ttgctcacag gtttcatgag gactcacagg    211140
cctgtccttg aacattcccc tgagcagggg ctcccttctt aaagcacagg gatcccattc    211200
tttacagata agcacccaga cagaggcact accaggccca gaccacacta gacacacaca    211260
gctctgcatt gtcccacact caaacacagc tctgtcgcct gagctcatgc cagtcacaca    211320
gaacacagac atgggctcgt gtgctagaga gacataagca atggtagcca aggtgctcac    211380
atcatgccca tacacacaca cacacacaca cacacacaca cacacacaca    211440
caccctgtga acaggcctgc agtcctgact gaagccctgc tctacccaat ttagtgagtc    211500
```

```
ctgcacctga accctcttac cctcacagcc cctgacctct ccctgtgtgc tgctcagcta 211560
tggcccctcc ccattcctaa cgtgccaccc taagatgtcg gttccgtgca tcaccgcaca 211620
catgctcttg ggataaggcc ttagaaggct ctgtaccatc tgcagctcat gccactgcct 211680
tccctggtaa ccctctcctg catacaaggg ctgcaagggt caatgatatg aatccatcca 211740
tgctctgacc ccagcttggc ccagggcagc catgatggga ggacaacccc tgacccagc  211800
ctaagatagt tgttgcacag agcagtccct taacgcagga taactgttgg aggtaggcag 211860
cacttgaccc ctgcccaagc tagatgatgg gagaggatag gtccagccat tgacagctgc 211920
tgtagcaagg caggccctgg tcccaggtta actcaaggct gctgcttagg caaccccctga 211980
ctccagctcc agaagtctgc tggggtgta tcctctggct acaggagctg aacaaatggc 212040
gcgccgcggc cgctcgacca attctcatgt ttgacagctt atcatcgaat ttctgccatt 212100
catccgctta ttatcactta ttcaggcgta gcaaccaggc gtttaagggc accaataact 212160
gccttaaaaa aattacgccc cgccctgcca ctcatcgcag tactgttgta attcattaag 212220
cattctgccg acatggaagc catcacaaac ggcatgatga acctgaatcg ccagcggcat 212280
cagcaccttg tcgccttgcg tataatattt gcccatggtg aaaacggggg cgaagaagtt 212340
gtccatattg ccacgtttta aatcaaaact ggtgaaactc acccagggat tggctgagac 212400
gaaaaacata ttctcaataa acccttttagg gaaataggcc aggttttcac cgtaacacgc 212460
cacatcttgc gaatatatgt gtagaaactg ccggaaatcg tcgtggtatt cactccagag 212520
cgatgaaaac gtttcagttt gctcatggaa aacggtgtaa caagggtgaa cactatccca 212580
tatcaccagc tcaccgtctt tcattgccat acggaactcc ggatgagcat tcatcaggcg 212640
ggcaagaatg tgaataaagg ccggataaaa cttgtgctta tttttcttta cggtctttaa 212700
aaaggccgta atatccagct gaacggtctg gttataggta cattgagcaa ctgactgaaa 212760
tgcctcaaaa tgttctttac gatgccattg ggatatatca acggtggtat atccagtgat 212820
tttttttctcc attttagctt ccttagctcc tgaaaatctc gataactcaa aaaatacgcc 212880
cggtagtgat cttatttcat tatggtgaaa gttggaacct cttacgtgcc gatcaacgtc 212940
tcattttcgc caaaagttgg cccagggctt cccggtatca acaggacac caggatttat 213000
ttattctgcg aagtgatctt ccgtcacagg tatttattcg cgataagctc atggagcggc 213060
gtaaccgtcg cacaggaagg acagagaaag cgcggatctg ggaagtgacg gacagaacgg 213120
tcaggacctg gattggggag gcggttgccg ccgctgctgc tgacggtgtg acgttctctg 213180
ttccggtcac accacatacg ttccgccatt cctatgcgat gcacatgctg tatgccgta  213240
taccgctgaa agttctgcaa agcctgatgg gacataagtc catcagttca acggaagtct 213300
acacgaaggt ttttgcgctg gatgtggctg cccggcaccg ggtgcagttt gcgatgccgg 213360
agtctgatgc ggttgcgatg ctgaaacaat tatcctgaga ataaatgcct tggcctttat 213420
atggaaatgt ggaactgagt ggatatgctg ttttgtctg ttaaacagag aagctggctg 213480
ttatccactg agaagcgaac gaaacagtcg ggaaaatctc ccattatcgt agagatccgc 213540
attattaatc tcaggagcct gtgtagcgtt tataggaagt agtgttctgt catgatgcct 213600
gcaagcggta acgaaaacga tttgaatatg ccttcaggaa caatagaaat cttcgtgcgg 213660
tgttacgttg aagtggagcg gattatgtca gcaatggaca gaacaaccta atgaacacag 213720
aaccatgatg tggtctgtcc ttttacagcc agtagtgctc gccgcagttg agcgacaggg 213780
cgaagccctc gagtgagcga ggaagcacca gggaacagca cttatatatt ctgcttacac 213840
```

```
acgatgcctg aaaaaacttc ccttggggtt atccacttat ccacggggat atttttataa  213900
ttattttttt tatagttttt agatcttctt ttttagagcg ccttgtaggc ctttatccat  213960
gctggttcta gagaaggtgt tgtgacaaat tgcccttttca gtgtgacaaa tcaccctcaa  214020
atgacagtcc tgtctgtgac aaattgccct taaccctgtg acaaattgcc tcagaagaa   214080
gctgttttt cacaaagtta tccctgctta ttgactcttt tttatttagt gtgacaatct   214140
aaaaacttgt cacacttcac atggatctgt catggcggaa acagcggtta tcaatcacaa  214200
gaaacgtaaa aatagcccgc gaatcgtcca gtcaaacgac ctcactgagg cggcatatag  214260
tctctcccgg gatcaaaaac gtatgctgta tctgttcgtt gaccagatca gaaaatctga  214320
tggcacccta caggaacatg acggtatctg cgagatccat gttgctaaat atgctgaaat  214380
attcggattg acctctgcgg aagccagtaa ggatatacgg caggcattga agagtttcgc  214440
ggggaaggaa gtggtttttt atcgccctga agaggatgcc ggcgatgaaa aaggctatga  214500
atcttttcct tggtttatca aacgtgcgca cagtccatcc agagggcttt acagtgtaca  214560
tatcaaccca tatctcattc ccttcttat cgggttacag aaccggttta cgcagtttcg   214620
gcttagtgaa acaaaagaaa tcaccaatcc gtatgccatg cgtttatacg aatccctgtg  214680
tcagtatcgt aagccggatg gctcaggcat cgtctctctg aaaatcgact ggatcataga  214740
gcgttaccag ctgcctcaaa gttaccagcg tatgcctgac ttccgccgcc gcttcctgca  214800
ggtctgtgtt aatgagatca acagcagaac tccaatgcgc ctctcataca ttgagaaaaa  214860
gaaaggccgc cagacgactc atatcgtatt ttccttccgc gatatcactt ccatgacgac  214920
aggatagtct gagggttatc tgtcacagat ttgagggtgg ttcgtcacat ttgttctgac  214980
ctactgaggg taatttgtca cagttttgct gtttccttca gcctgcatgg attttctcat  215040
acttttgaa ctgtaattt taaggaagcc aaatttgagg gcagtttgtc acagttgatt   215100
tccttctctt tcccttcgtc atgtgacctg atatcggggg ttagttcgtc atcattgatg  215160
agggttgatt atcacagttt attactctga attggctatc cgcgtgtgta cctctacctg  215220
gagttttcc cacggtggat atttcttctt gcgctgagcg taagagctat ctgacagaac   215280
agttcttctt tgcttcctcg ccagttcgct cgctatgctc ggttacacgg ctgcggcgag  215340
cgctagtgat aataagtgac tgaggtatgt gctcttctta tctccttttg tagtgttgct  215400
cttatttaa acaactttgc ggttttttga tgactttgcg attttgttgt tgctttgcag   215460
taaattgcaa gatttaataa aaaaacgcaa agcaatgatt aaaggatgtt cagaatgaaa  215520
ctcatggaaa cacttaacca gtgcataaac gctggtcatg aaatgacgaa ggctatcgcc  215580
attgcacagt taatgatga cagcccggaa gcgaggaaaa taacccggcg ctggagaata   215640
ggtgaagcag cggatttagt tggggttct tctcaggcta tcagagatgc cgagaaagca   215700
gggcgactac cgcacccgga tatggaaatt cgaggacggg ttgagcaacg tgttggttat  215760
acaattgaac aaattaatca tatgcgtgat gtgtttggta cgcgattgcg acgtgctgaa  215820
gacgtatttc caccggtgat cggggttgct gcccataaag gtggcgttta caaaacctca  215880
gtttctgttc atcttgctca ggatctggct ctgaaggggc tacgtgtttt gctcgtggaa  215940
ggtaacgacc cccagggaac agcctcaatg tatcacggat gggtaccaga tcttcatatt  216000
catgcagaag acactctcct gccttctat cttggggaaa aggacgatgt cacttatgca   216060
ataaagccca cttgctggcc ggggcttgac attattcctt cctgtctggc tctgcaccgt  216120
attgaaactg agtaatggg caaatttgat gaaggtaaac tgcccaccga tccacacctg  216180
atgctccgac tggccattga aactgttgct catgactatg atgtcatagt tattgacagc  216240
```

```
gcgcctaacc tgggtatcgg cacgattaat gtcgtatgtg ctgctgatgt gctgattgtt   216300
cccacgcctg ctgagttgtt tgactacacc tccgcactgc agttttcga tatgcttcgt    216360
gatctgctca agaacgttga tcttaaaggg ttcgagcctg atgtacgtat tttgcttacc   216420
aaatacagca atagtaatgg ctctcagtcc ccgtggatgg aggagcaaat tcgggatgcc   216480
tggggaagca tggttctaaa aaatgttgta cgtgaaacgg atgaagttgg taaaggtcag   216540
atccggatga gaactgtttt tgaacaggcc attgatcaac gctcttcaac tggtgcctgg   216600
agaaatgctc tttctatttg ggaacctgtc tgcaatgaaa ttttcgatcg tctgattaaa   216660
ccacgctggg agattagata tgaagcgtgt cgcctgttat tccaaaacat acgctcaata   216720
ctcaaccggt tgaagatact tcgttatcga caccagctgc cccgatggtg gattcgttaa   216780
ttgcgcgcgt aggagtaatg gctcgcggta atgccattac tttgcctgta tgtggtcggg   216840
atgtgaagtt tactcttgaa gtgctccggg gtgatagtgt tgagaagacc tctcgggtat   216900
ggtcaggtaa tgaacgtgac caggagctgc ttactgagga cgcactggat gatctcatcc   216960
cttctttct actgactggt caacagacac cggcgttcgg tcgaagagta tctggtgtca   217020
tagaaattgc cgatgggagt cgccgtcgta aagctgctgc acttaccgaa agtgattatc   217080
gtgttctggt tggcgagctg gatgatgagc agatggctgc attatccaga ttgggtaacg   217140
attatcgccc aacaagtgct tatgaacgtg gtcagcgtta tgcaagccga ttgcagaatg   217200
aatttgctgg aaatatttct cgcgctggtg atgcggaaaa tatttcacgt aagattatta   217260
cccgctgtat caacaccgcc aaattgccta atcagttgt tgctcttttt tctcaccccg    217320
gtgaactatc tgcccggtca ggtgatgcac ttcaaaaagc ctttacagat aaagaggaat   217380
tacttaagca gcaggcatct aaccttcatg agcagaaaaa agctggggtg atatttgaag   217440
ctgaagaagt tatcactctt ttaacttctg tgcttaaaac gtcatctgca tcaagaacta   217500
gtttaagctc acgacatcag tttgctcctg gagcgacagt attgtataag ggcgataaaa   217560
tggtgcttaa cctggacagg tctcgtgttc caactgagtg tatagagaaa attgaggcca   217620
ttcttaagga acttgaaaag ccagcaccct gatgcgacca cgttttagtc tacgtttatc   217680
tgtctttact taatgtcctt tgttacaggc cagaaagcat aactggcctg aatattctct   217740
ctgggcccac tgttccactt gtatcgtcgg tctgataatc agactgggac cacggtccca   217800
ctcgtatcgt cggtctgatt attagtctgg gaccacggtc ccactcgtat cgtcggtctg   217860
attattagtc tgggaccacg gtcccactcg tatcgtcggt ctgataatca gactgggacc   217920
acggtcccac tcgtatcgtc ggtctgatta ttagtctggg accatggtcc cactcgtatc   217980
gtcggtctga ttattagtct gggaccacgg tcccactcgt atcgtcggtc tgattattag   218040
tctggaacca cggtcccact cgtatcgtcg gtctgattat tagtctggga ccacggtccc   218100
actcgtatcg tcggtctgat tattagtctg gaccacgat cccactcgtg ttgtcggtct    218160
gattatcggt ctgggaccac ggtcccactt gtattgtcga tcagactatc agcgtgagac   218220
tacgattcca tcaatgcctg tcaagggcaa gtattgacat gtcgtcgtaa cctgtagaac   218280
ggagtaacct cggtgtgcgg ttgtatgcct gctgtggatt gctgctgtgt cctgcttatc   218340
cacaacattt tgcgcacggt tatgtggaca aaataccttgg ttacccaggc cgtgccggca  218400
cgttaaccgg gctgcatccg atgcaagtgt gtcgctgtcg agcggccgc               218449
```

<210> SEQ ID NO 2
<211> LENGTH: 87862
<212> TYPE: DNA

<213> ORGANISM: Artificial Sequence
<220> FEATURE:
<223> OTHER INFORMATION: Hybrid immunoglobulin locus

<400> SEQUENCE: 2

```
gtcgacagcg acacacttgc atcggatgca gcccggttaa cgtgccggca cggcctgggt      60
aaccaggtat tttgtccaca taaccgtgcg caaaatgttg tggataagca ggacacagca     120
gcaatccaca gcaggcatac aaccgcacac cgaggttact ccgttctaca ggttacgacg     180
acatgtcaat acttgcccectt gacaggcatt gatggaatcg tagtctcacg ctgatagtct    240
gatcgacaat acaagtggga ccgtggtccc agaccgataa tcagaccgac aacacgagtg     300
ggatcgtggt cccagactaa taatcagacc gacgatacga gtgggaccgt ggtcccagac     360
taataatcag accgacgata cgagtgggac cgtggttcca gactaataat cagaccgacg     420
atacgagtgg gaccgtggtc ccagactaat aatcagaccg acgatacgag tgggaccatg     480
gtcccagact aataatcaga ccgacgatac gagtgggacc gtggtcccag tctgattatc     540
agaccgacga tacgagtggg accgtggtcc cagactaata atcagaccga cgatacgagt     600
gggaccgtgg tcccagacta ataatcagac cgacgatacg agtgggaccg tggtcccagt     660
ctgattatca gaccgacgat acaagtggaa cagtgggccc agagagaata ttcaggccag     720
ttatgctttc tggcctgtaa caaaggacat aagtaaaga cagataaacg tagactaaaa     780
cgtggtcgca tcagggtgct ggcttttcaa gttccttaag aatggcctca attttctcta     840
tacactcagt tggaacacga gacctgtcca ggttaagcac catttatcg cccttataca     900
atactgtcgc tccaggagca aactgatgtc gtgagcttaa actagttctt gatgcagatg     960
acgttttaag cacagaagtt aaaagagtga taacttcttc agcttcaaat atcaccccag    1020
ctttttctg ctcatgaagg ttagatgcct gctgcttaag taattcctct ttatctgtaa    1080
aggcttttg aagtgcatca cctgaccggg cagatagttc accggggtga gaaaaagag    1140
caacaactga tttaggcaat ttggcggtgt tgatacagcg gtaataatc ttacgtgaaa    1200
tattttccgc atcagccagc gcagaaatat ttccagcaaa ttcattctgc aatcggcttg    1260
cataacgctg accacgttca taagcacttg ttgggcgata atcgttaccc aatctggata    1320
atgcagccat ctgctcatca tccagctcgc caaccagaac acgataatca ctttcggtaa    1380
gtgcagcagc tttacgacgg cgactcccat cggcaatttc tatgacacca gatactcttc    1440
gaccgaacgc cggtgtctgt tgaccagtca gtagaaaaga agggatgaga tcatccagtg    1500
cgtcctcagt aagcagctcc tggtcacgtt cattacctga ccataccgga gggtcttct    1560
caacactatc accccggagc acttcaagag taaacttcac atcccgacca catacaggca    1620
aagtaatggc attaccgcga gccattactc ctacgcgcgc aattaacgaa tccaccatcg    1680
gggcagctgg tgtcgataac gaagtatctt caaccggttg agtattgagc gtatgttttg    1740
gaataacagg cgcacgcttc attatctaat ctcccagcgt ggtttaatca gacgatcgaa    1800
aatttcattg cagacaggtt cccaaataga aagagcattt ctccaggcac cagttgaaga    1860
gcgttgatca atggcctgtt caaaaacagt tctcatccgg atctgacctt taccaacttc    1920
atccgtttca cgtacaacat ttttttagaac catgcttccc caggcatccc gaatttgctc    1980
ctccatccac ggggactgag agccattact attgctgtat ttggtaagca aaatacgtac    2040
atcaggctcg aacccttaa gatcaacgtt cttgagcaga tcacgaagca tatcgaaaaa    2100
ctgcagtgcg gaggtgtagt caacaactc agcaggcgtg gaacaatca gcacatcagc    2160
agcacatacg acattaatcg tgccgatacc caggttaggc gcgctgtcaa taactatgac    2220
```

```
atcatagtca tgagcaacag tttcaatggc cagtcggagc atcaggtgtg gatcggtggg    2280
cagtttacct tcatcaaatt tgcccattaa ctcagtttca atacggtgca gagccagaca    2340
ggaaggaata atgtcaagcc ccggccagca agtgggcttt attgcataag tgacatcgtc    2400
cttttcccca agatagaaag gcaggagagt gtcttctgca tgaatatgaa gatctggtac    2460
ccatccgtga tacattgagg ctgttccctg ggggtcgtta ccttccacga gcaaaacacg    2520
tagccccttc agagccagat cctgagcaag atgaacagaa actgaggttt tgtaaacgcc    2580
acctttatgg gcagcaaccc cgatcaccgg tggaaatacg tcttcagcac gtcgcaatcg    2640
cgtaccaaac acatcacgca tatgattaat ttgttcaatt gtataaccaa cacgttgctc    2700
aacccgtcct cgaatttcca tatccgggtg cggtagtcgc cctgctttct cggcatctct    2760
gatagcctga gaagaaaccc caactaaatc cgctgcttca cctattctcc agcgccgggt    2820
tattttcctc gcttccgggc tgtcatcatt aaactgtgca atggcgatag ccttcgtcat    2880
ttcatgacca gcgtttatgc actggttaag tgtttccatg agtttcattc tgaacatcct    2940
ttaatcattg ctttgcgttt ttttattaaa tcttgcaatt tactgcaaag caacaacaaa    3000
atcgcaaagt catcaaaaaa ccgcaaagtt gtttaaaata agagcaacac tacaaaagga    3060
gataagaaga gcacatacct cagtcactta ttatcactag cgctcgccgc agccgtgtaa    3120
ccgagcatag cgagcgaact ggcgaggaag caaagaagaa ctgttctgtc agatagctct    3180
tacgctcagc gcaagaagaa atatccaccg tgggaaaaac tccaggtaga ggtacacacg    3240
cggatagcca attcagagta ataaactgtg ataatcaacc ctcatcaatg atgacgaact    3300
aacccccgat atcaggtcac atgacgaagg gaaagagaag gaaatcaact gtgacaaact    3360
gccctcaaat ttggcttcct taaaaattac agttcaaaaa gtatgagaaa atccatgcag    3420
gctgaaggaa acagcaaaac tgtgacaaat taccctcagt aggtcagaac aaatgtgacg    3480
aaccaccctc aaatctgtga cagataaccc tcagactatc ctgtcgtcat ggaagtgata    3540
tcgcggaagg aaaatacgat atgagtcgtc tggcggcctt tcttttttctc aatgtatgag    3600 aggcgcattg gagttctgct gttgatctca ttaacacaga cctgcaggaa gcggcggcgg    3660
aagtcaggca tacgctggta actttgaggc agctggtaac gctctatgat ccagtcgatt    3720
ttcagagaga cgatgcctga gccatccggc ttacgatact gacacaggga ttcgtataaa    3780
cgcatggcat acgattggt gatttctttt gtttcactaa gccgaaactg cgtaaaccgg    3840
ttctgtaacc cgataaagaa gggaatgaga tatgggttga tatgtacact gtaaagccct    3900
ctggatggac tgtgcgcacg tttgataaac caaggaaaag attcatagcc tttttcatcg    3960
ccggcatcct cttcagggcg ataaaaaacc acttccttcc ccgcgaaact cttcaatgcc    4020
tgccgtatat ccttactggc ttccgcagag gtcaatccga atatttcagc atatttagca    4080
acatggatct cgcagatacc gtcatgttcc tgtagggtgc catcagattt tctgatctgg    4140
tcaacgaaca gatacagcat acgttttttga tcccgggaga gactatatgc cgcctcagtg    4200
aggtcgtttg actggacgat tcgcgggcta ttttttacgtt tcttgtgatt gataaccgct    4260
gtttccgcca tgacagatcc atgtgaagtg tgacaagttt ttagattgtc acactaaata    4320
aaaaagagtc aataagcagg gataactttg tgaaaaaaca gcttcttctg agggcaattt    4380
gtcacagggt taagggcaat tgtcacagac aggactgtc atttgagggt gatttgtcac    4440
actgaaaggg caatttgtca caacaccttc tctagaacca gcatggataa aggcctacaa    4500
ggcgctctaa aaagaagat ctaaaaacta taaaaaaat aattataaaa atatccccgt    4560
```

```
ggataagtgg ataaccccaa gggaagtttt ttcaggcatc gtgtgtaagc agaatatata    4620
agtgctgttc cctggtgctt cctcgctcac tcgagggctt cgccctgtcg ctcaactgcg    4680
gcgagcacta ctggctgtaa aaggacagac cacatcatgg ttctgtgttc attaggttgt    4740
tctgtccatt gctgacataa tccgctccac ttcaacgtaa caccgcacga agatttctat    4800
tgttcctgaa ggcatattca aatcgttttc gttaccgctt gcaggcatca tgacagaaca    4860
ctacttccta taaacgctac acaggctcct gagattaata atgcggatct ctacgataat    4920
gggagatttt cccgactgtt tcgttcgctt ctcagtggat aacagccagc ttctctgttt    4980
aacagacaaa aacagcatat ccactcagtt ccacatttcc atataaaggc caaggcattt    5040
attctcagga taattgtttc agcatcgcaa ccgcatcaga ctccggcatc gcaaactgca    5100
cccggtgccg ggcagccaca tccagcgcaa aaaccttcgt gtagacttcc gttgaactga    5160
tggacttatg tcccatcagg cttttgcagaa ctttcagcgg tataccggca tacagcatgt    5220
gcatcgcata ggaatggcgg aacgtatgtg gtgtgaccgg aacagagaac gtcacaccgt    5280
cagcagcagc ggcggcaacc gcctccccaa tccaggtcct gaccgttctg tccgtcactt    5340
cccagatccg cgctttctct gtccttcctg tgcgacggtt acgccgctcc atgagcttat    5400
cgcgaataaa tacctgtgac ggaagatcac ttcgcagaat aaataaatcc tggtgtccct    5460
gttgataccg ggaagccctg ggccaacttt tggcgaaaat gagacgttga tcggcacgta    5520
agaggttcca actttcacca taatgaaata agatcactac cgggcgtatt ttttgagtta    5580
tcgagatttt caggagctaa ggaagctaaa atggagaaaa aaatcactgg atataccacc    5640
gttgatatat cccaatggca tcgtaaagaa cattttgagg catttcagtc agttgctcaa    5700
tgtacctata accagaccgt tcagctggat attacggcct ttttaaagac cgtaaagaaa    5760
aataagcaca gttttatcc ggcctttatt cacattcttg cccgcctgat gaatgctcat    5820
ccggagttcc gtatggcaat gaaagacggt gagctggtga tatgggatag tgttcaccct    5880
tgttacaccg ttttccatga gcaaactgaa acgttttcat cgctctggag tgaataccac    5940
gacgatttcc ggcagtttct acacatatat tcgcaagatg tggcgtgtta cggtgaaaac    6000
ctggcctatt tccctaaagg gtttattgag aatatgtttt tcgtctcagc caatccctgg    6060
gtgagtttca ccagttttga tttaaacgtg gccaatatgg acaacttctt cgccccegtt    6120 ttcaccatgg gcaaatatta tacgcaaggc gacaaggtgc tgatgccgct ggcgattcag    6180
gttcatcatg ccgtttgtga tggcttccat gtcggcagaa tgcttaatga attacaacag    6240
tactgcgatg agtggcaggg cggggcgtaa ttttttttaag gcagttattg gtgcccttaa    6300
acgcctggtt gctacgcctg aataagtgat aataagcgga tgaatggcag aaattcgatg    6360
ataagctgtc aaacatgaga attggtcggc ggcccgcgca ccccaatgtc gagcagtgtg    6420 gttttttgcaa gaggaagcaa aaagcctctc cacccaggcc tggaatgttt ccacccaatg    6480
tcgagcagtg tggttttgca agaggaagca aaaagcctct ccacccaggc ctggaatgtt    6540
tccacccaat gtcgagcaaa ccccgcccag cgtcttgtca ttggcgaatt cgaacacgca    6600
gatgcagtcg ggcggcgcg gtcccaggtc cacttcgcat attaaggtga cgcgtgtggc    6660
ctcgaacacc gagcgaccct gcagccaata tgggatcggc cattgaacaa gatggattgc    6720
acgcaggttc tccggccgct tgggtggaga ggctattcgg ctatgactgg gcacaacaga    6780 caatcgctg ctctgatgcc gccgtgttcc ggctgtcagc gcaggggcgc ccggttctt    6840 ttgtcaagac cgacctgtcc ggtgccctga atgaactgca ggacgaggca gcgcggctat    6900
cgtggctggc cacgacgggc gttccttgcg cagctgtgct cgacgttgtc actgaagcgg    6960
```

```
gaagggactg gctgctattg ggcgaagtgc cggggcagga tctcctgtca tctcaccttg   7020
ctcctgccga gaaagtatcc atcatggctg atgcaatgcg gcggctgcat acgcttgatc   7080
cggctacctg cccattcgac caccaagcga acatcgcat cgagcgagca cgtactcgga    7140
tggaagccgg tcttgtcgat caggatgatc tggacgaaga gcatcagggg ctcgcgccag   7200
ccgaactgtt cgccaggctc aaggcgcgca tgcccgacgg cgaggatctc gtcgtgaccc   7260
atggcgatgc ctgcttgccg aatatcatgg tggaaaatgg ccgcttttct ggattcatcg   7320
actgtggccg gctgggtgtg gcggaccgct atcaggacat agcgttggct acccgtgata   7380
ttgctgaaga gcttggcggc gaatgggctg accgcttcct cgtgctttac ggtatcgccg   7440
ctcccgattc gcagcgcatc gccttctatc gccttcttga cgagttcttc tgaggggatc   7500
ggcaataaaa agacagaata aaacgcacgg gtgttgggtc gtttgttcgg atcctctaga   7560
gtcgagacag ttcctattcc gaagttccta ttctctagaa agtataggaa cttacgtgcg   7620
agcaatgagt cagaaaggag aagacagaga aagtggccaa aaaattttg gagggatgac    7680 aaaagctttc aagaagcaat gaaactcatt cgtctataga taaaagaaat tgaaagaact   7740
tattcaggac aaacacaatg atacacataa ctatacatat tataattaaa atgctgaacc   7800
agcgacaagg aggaaatcgc aaatgcacaa aaataaaatg actctctata tacagaaata   7860
cagtgataaa gccatcagct aactttcat cgtgcccaaa ggaggctaga aaacagcgga    7920
atgacatatg taaatgcagg gaaacaaaac aaaacaaaac ctaggattca atatccagtg   7980
aaagtatgca ttcaaaataa aagtaaagta aaaacatttc ttgataaaca aaatgaaga    8040 gaaataatta cttaaagaca tgctgtataa caatttatct aggaaattct tcagattcac   8100
aaaaaatgac agcagacagt aacttgaatc tgtaaggagg aaggaaggcc tcaaaagtac   8160
taagggaaca aaaaaagagc tagaccaaac caacatgttt acttccgttt atatgaggtt   8220
tcgtataggg aaagccaatc tatttggaca gatgtcagaa tgccagtttc cttgattggg   8280
atggggaaac agctgtttcc tgaaaggtag gtacatgagg gaagaatctg gagattctgc   8340
agtattctac agtttaatct cggtggagaa tatatgtaaa actttattcg gttgcacttt   8400
ttaacatttc tgtcttttac tttgtgtgtg ttttatttaa atttttaaaa aattgaaagg   8460
gccaaatctg aactctttta aacaaaaatg aacaaaaaca taagaattag taaatatttg   8520
tggaaacatg gccttattaa caagaagcat aaaatgtgcc tgggagagta ctatgaaaca   8580
agaaatctgt tagggaagac agaaggaaat acttaaattt ctccaacata gacagcatag   8640
attttatgcc tattcgtttc cctccaaaca gagaagatat ttaagtcatt ttgctcacaa   8700
gagaggctcc taccctcccc ttggctcttt ccaccccact gcacccacca ggtgatttgc   8760
atattatccc ttagtgaaga cttccttgt gagtctgaga taaaagctca gctctaccct    8820
tgccttgact gatcaggact cctcagttca ccttctcaca atgaggctcc ctgctcagct   8880
cctggggctg ctaatgctct gggtcccagg taagggtaga agggagatga gggaggagaa   8940
tggcatggaa cggtgagttc tggggcccca ctgcctctaa caacagtgat ctctggggt    9000 ctcactacac tcctatgtgt gttccttttcc tgtattggac atgcacatgt tgtcctccag   9060 agtgggcat gtgatgatca gatctgtgag agtgaggaag attcaggcag aaacaaggat    9120
ctgtgctctg gggaagactg acacagaaag gggatggtgt ggggtcttct ggagacccct   9180
ttgagccttg gatcccttga gttccatttt gaaactgtgt attttgaaa tatgaacaaa    9240 tacatatata gcctgaaata aacaacaaat caaaattat gaaaattaca cataaacttt    9300
```

```
atacataacc ttgctcttct ttctatttat ttcaggatcc agtggggatg ttgtgatgac    9360
tcagtctcca ctctccctgc ccgtcaccct tggacagccg gcctccatct cctgcaggtc    9420
tagtcaaagc ctcgtataca gtgatggaaa cacctacttg aattggtttc agcagaggcc    9480
aggccaatct ccaaggcgcc taatttataa ggtttctaac cgggactctg ggtcccaga     9540 cagattcagc ggcagtgggt caggcactga tttcacactg aaaatcagca gggtggaggc    9600
tgaggatgtt ggggtttatt actgcatgca aggtacacac tggcctccca cagtggtaca    9660
gccctgaaca aaacctccc tgtggagtgg cccagctgcc acatgtggt gcttgtctgg      9720 ggagcagctc agcagggtct cagaatctgt gtaagaggaa gatgctggag aaccagggaa    9780
caattcacat ctgaggactc tggactttga gagcccagcc cacctcagg caccactcct     9840 ttatgccctg ccagttgcca ccaccttgac tgtcataagc agcaggagaa tgaggggtcc    9900
aagtgccctg tgagtaaaca agcaagatgg aaggggagg agaatgaaag ctcaccctaa     9960
ctctccctac cttgtgtcca tttgttaatt aaatgtaatt agcagagcag ccaggccatt   10020
gacacagatt gtgactatcc atgttggata catctttggg tttagcagtt tttggcatat   10080
cgttcagagg acatttgata atatttaatg ttggtatttt gccagttttc taacttcctg   10140
cttccccttt tctcccactc ccaaaataga gtagagacag cattctatac cagttatcct   10200
aagcggaagc tggctgagga cagtcagtaa aaatcttgat tttggagtat caaatagatt   10260
tttgtaaatt catagaagat acaagatcct aatgctaaaa ctgtttagtt agccttagtt   10320
acctcttaat gatagaaaaa aggagtacct gaaattccag aagttgtttt caaaaataaa   10380
aagcatatac tggaaaatgt agagtatata attttcccca tagaaaactg gaaaagtaca   10440
gaatgatgtg aacgttttta tttccaaatg ttaagaattt aagattgggc agacattagg   10500
gatgaaagca tgaaggaaac ccaggagagg tcagcttcaa ttaaactacc cttggccttt   10560
ggtaggtagg gatgtggatg gtggtggagt tggcagttca tgatgtggac ccaggaggcc   10620
tgatgtgttt cttgtgaaga atcacagagt tgaaggcacc actacctggc ttcctgggtg   10680
gagcctgcat cactgcgaat tttctgggaa ataatgctt tgggaagggt tttagatctg    10740
taatcaccaa aggcttagtg aaatcccgt gcaggagac ctgaggtcat gtcactcata     10800
tcttgtcaac cccacacagc caaacagagc atctgaaact cattctgtcc ctagagactg   10860
ctggttgggt ctggagatgt cacaagcact gacatgctga gcagaaggcc cagcagggtc   10920
tacaccagca gggggcgcag tgggatgga gaccagtgtc catgattcag acatgtattc     10980
gggatacatg tatctgtgta gccttgggga ttggggagc atgctgaatc tgtgaagtt     11040 ttatgtcctt gtagcccagc acctccatcc ctgcctgctg actcagacct caacatgtgt   11100 cccatgaaa gcacgggcca cttatagagg ctgccctgtg caaccccaa ggctcagctg     11160 gattcccctt tcccaggaga gctcctctgc ctgtaccaag tcagagcttg tttccacagg   11220
cgaacttggc ggctatggca gaaggacaaa aagtcaggtg agcatcagct caacaatgaa   11280
aggttctttt tactatggaa ttttagatca tgcattcctt attccttcca ctactttcta   11340
aagtcattta attctaactt tggtattcta ttgttttaaa tggtttgtac cttttgcagt   11400
ggttgttttg gcctttccac ttctatctac attgctgtac ctgggaatga agattccctt   11460
catttttttt taaacacaaa taaagtttta gaagtgacta tgttggtact atttagtcaa   11520
aaaaagtaaa acatttttaa acaataaatt aatgtattat tttcactgta ccttgtcagt   11580
acttggacat aaacctgatt cccacattct aacaatagta atataaaaaa tgtatgcttt   11640
ccatagagtc aatttaaaat agttctctat gaatatttgt gaattagtaa tgagcctgtg   11700
```

```
atttacgtcc tatagtgtgg tatgactaaa gtaaacaat  gttgcaatca acaggataaa   11760
gtaatccaga tttagattaa agaaatatgt tacattcgag ataattttct attaaagata   11820
atgtattcca tgacaagcat aattaaatct gtagttttaa ccagacagac aacatataca   11880 gtaaaatt   ggtttatagc aagtggtgta taagacaaaa ttaataacaa gtctccagag   11940
tatattttta cacataccaa aaagtaagga cacacataca atcaaaattt tattcatttc   12000
ttcatcacag gcaccagttt ggagcctgga gatgctgcac gttctcctgt gagcagaaaa   12060
ctcaccaggt cgagctctga accaagtgga cctaatagac atctacagaa ctctccatcc   12120
caaatcaaca aaatatacat tcttctcagc agcacatcgc acttattcta aaattgacca   12180
caaatgcctt atgtaaatga cgagttgatg ggtacagcaa acccatatgg cacatgtaca   12240
cctatgtaac ctgcaagttg tgcacatgta ccccagaact taaagtgtaa taatacaaaa   12300
aaatgacatg tgactagtag tatcttatct agaatcttca ttctaagata ctcaaggacg   12360
cataaagggg accctaagta gtcttttcat acatatatat gcatatatat atgtatgaaa   12420
agcagtcttt tcatcaacta gagaaaccct caggacagcc cttaataccc ttggtgatac   12480
atttcagatg agtaaactgt tatcagagcc cgtagttgaa actattcaac agagatggtt   12540
tgcccaaaga tatgtggtca gcaattgtca gggctgagct tggaacccag gtctgcataa   12600
ccttaaatat gttgcttcca catggccacg tttggttcat atacgattga atggcccttta  12660 aattcaaaga agagacaaag ccagaagagt ggtgtgaaat tctcaacaca agctccctgc   12720
tacctctaca ccttaccgtg attactccaa ttataaactc aggccctcat gcagttttgt    12780
ctacaaagca aaacttcctc aaagtctta caaatactaa atgtctttct ttcagattcg    12840
agggcaagag cacatcttgc attgccctga acactttgca tcttttctac cattctcatc     12900
tttctgtccc agtccttcct tctcaaatga tgtcctgtaa atctgatttc tcccccaata    12960
tgaaaacaaa tgaacaaata ttcccctact tttctcatat ccagaggata caagagttaa    13020
tcacatatcc agagagtacg agagttaatc aagggattta tgcaagagtg tttacacata    13080
acaaggattc tggtgctagc catcttcaca gtgaaatttt ctgtgtgtct tgctaaaatt    13140
gacactaaaa aatgacaaga taaaaatatt tggaagaaca gagggcaacc atgcccttaa    13200
ggaggcaaaa gacacccctg ccccttgtgt tagtttccta ctcctgctgt aacaagttat   13260
cagaatctta ctagtttcat acaacacaaa tttattatca tacagttctg gcagtgagaa   13320
gtctcactga tttataatca aggtatccgt agttctatat tccttctgga agttccaggg    13380
gagagaatct gattctcagc tttttcatctt caaagatagc cccatgttcc gggctgcctg     13440
gcccctttct ccatcactga agcatccctg tccattgtcc ctattcctct ctgactgtta     13500
cccccactcc tccctattat aaagacccct ctgatgacgc tgtctttcct agataattca    13560
gctgtttcct aaattttctg aatatcccta tgcatgaaaa aaaagaatt  ggcaagtatt    13620 cagactatac tttccaagaa tgaggatttg tccactgttt taggttggat ctttcaggga     13680
caatgatgcc catgcaggca gcatatttat aatgcacagt aaacactagg aggaaacaag    13740
gcagtgagag aggaaagaga gcagcgatac cgaaaatgtc ctcagcgaga agctaccaca    13800
gaggatgaat ggagatcaag cccacgtgga aacatggaaa aatgtctcag tattttcca     13860 cctaagaagg gagggagatg gggtatgtat acacctccct gtcctcactg attgagggct    13920
ttccgagagg atgctcattc caggtgctgt gataggccat gtgtacaggc agggctgcct    13980
tctccagctt cagatagagc agtgaggaaa agatatggcc atggggggtc agcagaagta    14040
```

| | |
|---|---|
| cagcaaaggg aaaagggaaa gggtagcaag agtgacaact atattcaccc cccccacaca | 14100 |
| cacacacaca cacacgaaat tgtgtattgc aatccagaac tgcttctctc tgaacctaaa | 14160 |
| tcttagcaag cagtttacca gtaactgccc ttgaaattca ggcccctgga aaggagcagg | 14220 |
| gggttgtgta caggctatac cacagcagtc tgcccaccct tagtgatgca tgagtaatgc | 14280 |
| tccctggact ccccaggttc tagtcttctc atgtcgatgt agttgattcc acttcccttg | 14340 |
| ctgcacaacc aggctgggat gcctgggcag aggcagacat gtgaggtata ggggttcaaa | 14400 |
| tctgttttcca agttttatcc agcttcaaag catttctccg tgtacatgag cggtggcttg | 14460 |
| acaggagatg gagactctct ttcctggatg tgaggcaagg aggcaggcgt ctgagtcagg | 14520 |
| atgatgtccc tactcactgc taaagagaaa agtggctttg atggtgcagg gcagggaaat | 14580 |
| gcactgagtg gtcgccaccc tcacagaaga gaaagtgttc actgacctgg cctttcccca | 14640 |
| gggcctctcc ctcccattgc tttccagaaa gccatgattt tgagagcca cacctgaaca | 14700 |
| ctcacaaaca ttatggtggg aaaagcagat cagagcatta ggcaagttgc attaccttgg | 14760 |
| ccttcttcct ttggagacaa ttgatgtggg gttctagatt gacccagagt ttcaagttta | 14820 |
| tcctgattca ggcttcaaca gctggaggaa gaaacagaga tgttttttga agtaaacaga | 14880 |
| tctagcatta ctaatcaacc cttcatactg atgacctatg ggaaataata cccaagggca | 14940 |
| gaaaaatggg cagaataagg ggagccccaa accaagacga agctgctgcc cattgagacc | 15000 |
| ctgggtatta cagagaccta tagctctgga taatggaaga tctatgagtg gcacaggcgc | 15060 |
| tgaggaatca cagcatcatt atcgtgcatc tgcagggaat tgcttgtaaa tatactggta | 15120 |
| attacaaatg tttaaggtca ctacaaatac tttggagtgt attaaatatg cttctgataa | 15180 |
| agactgtttt tctcacatga aacaatggga accatgtgac aatcacagag gtgttgttac | 15240 |
| tatagcaaaa gggattgtta ctctccacat ccctttaagt aacttgaagg cctgatagac | 15300 |
| ccaccctcta agacttcatt agacattccc tacgaatggt tatactctcc tgtatactcc | 15360 |
| caatacaact ctaaaatata ttattccata tagtccttag gtttgtatta aagtttgact | 15420 |
| ttttccttc aaaatatctc ttgtcacaac agcggctcta gagagaaata cattccttcc | 15480 |
| aggcaaatct atgctgcgct ggtctgacct gggaccctgg ggacattgcc cctgtgctga | 15540 |
| gttactaaga tgagccagcc ctgcagctgt gctcagcctg ccccatgccc tgctgattga | 15600 |
| tttgcatgtt ccagagcaca gccccctgcc ctgaagactt ttttatgggc tggtcgcacc | 15660 |
| ctgtgcagga gtcagtctca gtcaggacac agcatggaca tgagggtccc cgctcagctc | 15720 |
| ctggggctcc tgctactctg gctccgaggt aaggatggag aacactagga atttactcag | 15780 |
| ccagtgtgct cagtactgac tggaacttca gggaagttct ctgataacat gattaatagt | 15840 |
| aagaatattt gttttatgt ttccaatctc aggtgccaga tgtgacatcc agatgaccca | 15900 |
| gtctccatcc tccctgtctg catctgtagg agacagagtc accatcactt gccgggcaag | 15960 |
| tcagagcatt agcagctatt taaattggta tcagcagaaa ccagggaaag cccctaagct | 16020 |
| cctgatctat gctgcatcca gtttgcaaag tggggtccca tcaaggttca gtggcagtgg | 16080 |
| atctgggaca gatttcactc tcaccatcag cagtctgcaa cctgaagatt ttgcaactta | 16140 |
| ctactgtcaa cagagttaca gtaccccctcc cacagtgtta caagtcataa cataaacctc | 16200 |
| caaggaagca gatgtgtgag gacgagccac cccagatgct cctcctggtg cctccatctg | 16260 |
| ctgagagcat ttctcaaact cagtcaggtt tgaaagtca ttgggagact tttgtagagg | 16320 |
| ggaccaggga ggctcctctg aactctaagc ctctttttgcc cctatcccca ggagaaaaga | 16380 |
| tgtgacaatg cctgtcctga ttgaataagg aagagataca agtccacctg aggagtctgt | 16440 |

```
gttatgggat aattggaatt tacacagcaa aagagaagct attctcggta tttcaaggag   16500
aaattgttca agttgaataa attagagtct aaactagtct ttttgaagcc tacggtatgt   16560
tattcgtgaa gcagccacta gagacagggg attctcagat gctcctgcag aagtcagagt   16620
gcacctgccc ctggtggtat gtgctgagta ccgtgtgatg atcctcagac ctgtctggga   16680
agccgagggc tggggtgctg atgctctcag ctgcctgcag cacgtctcca ggtgattctc   16740
cagtccacaa acaattccac atgttttact tcagatgtca gagtacatga atccaccact   16800
ctgacttccc aatctcatgg gagtgcctct cattaagcaa ctctaaagaa accatagaga   16860
gaaaaggagt tttggaaaat gtgcgtccag aagtgatagt agcgatgggg aattgacagc   16920
tgacaggtca gtaaggttgc tctttccaca aggctcaaaa ctttgccagt tacagattgt   16980
cccagaatat actcgaatgt gctatcacgt cttacgagca actctgggtt catagcaaga   17040
aaacttcatt aagtcataga tgaaacagaa aaatcaggaa actgtatgaa atacattata   17100
aggctgtgtg tggtagctca tgcctgtaat tcccagcact ttgagaggct aaggcaggag   17160
aattgcttca tcctaggagt ttgagattgg actgggcaac ataggaagac tctgtctcta   17220
caaaaaacaa aacaaaacaa aaagataaat agatagttat aacaatcgtt tgacaacctt   17280
tttccttgac aaaaaggaaa acaagagaaa atcctaaaca tggatgtagc attttttcctc   17340 ttaatatgaa agtcctctgc tactcaaaac tatccagaat ccagtagcac cttagcaata   17400
ctgagagggt gccttgcaag atacatagca ggcccacctc aaattacctg aaagagaatc   17460 ttcatttaa cacggtaaca agtgatctac ataaagctta acaaggtatg ttttaggtga   17520
tattttagct aaagagattt attttttttct caatgaggat atttaagaaa atttcaatgg   17580
agagtcacat gttgaaagca cacccagctt tactttcaaa ttgatgcaac attgcatttg   17640
aaaacatttt gaagattaca aaggttgaaa atcataatta tatatgtcca tagaattatc   17700
aaataacttc atgtttaaat ggagtaaaca tttttagaaa ctttaataat taccaagtga   17760
aagaatcaat taaagttgtg tgtacctatg ttagagattc tcgggcttaa ttgtatcagg   17820
tcagcttggt ttgggatttg tctactcctg cgaccctgcc atgagaatct tctgccctga   17880
gtagtcagtg cccttcaggc ttggcctcag ataaatgcaa tccataggct ggagacaagc   17940
tcgattccct gcagccgaac caaccagctg agccctgcct tgggatcagc caactgatta   18000
ttaaaatgaa cattcaggaa tatgaaaata aatacttagt gttaataaga cactaagagt   18060
ttaagtggtt gattgtcaat aattattgtg caaaaactga ccaatacagt atttatacat   18120 ctacctatt agatagatgc attttattaa aattgatggc ataaatatga atatttatta   18180
atccatatat agagatacta agacaacatt taaaacatta aaacttaata ccaataaaaa   18240
ccatgaaatt gatgtcattt ggggaaaata catatttgag tgtatataac atacatattg   18300
gtgcatttat atttttgaaa aattattggc tgcatatacg tatatgtaca catatttatc   18360
tttaaataag tctatttaag tatatttata tatccatata gaagtaacac atgcatattt   18420
acaaaacaat tatgtaaaaa tgaaatctgt gaaggtgatt tcagtttccc cccataagaa   18480
cactggtgcc cgagacctgg tgtagtatct gctgtggcta cagaaagttc ctttataacc   18540
tttagttata aaatactcac ctaatgggta tttcacacctt aaaatatttt tctaactcaa   18600
gtggaggggt aaagggtatg aatggggata actgcctact gttaaaaatt aatcatttca   18660
tcctatggaa gtccaatcat gcatatgctg ccaatgatgc catgctggat ggagttctca   18720 taactggggtg ctgtattgat gttataccac tgccatggta aaggataccc tgggagacta   18780
```

```
gcagtcacaa gagtgggcaa acccgaaggg tgaagtcacc gtacactttg caaagaggga    18840
ttagcaattc cataacattg gctattggtt tggagagatc accaggtcga gcattcacca    18900
ggtctgacac gagcatagta ctgcaatcta ttacgttggc tctccccaga tgttttctct    18960
ccaggacagt gcgtgtcctt gtgaagggat ctgatgtagg cacaatcttt caagagctgt    19020
tcaactcaat cttgagcata tcattgacaa acaaatagtt ggattgtttc cctgttttca    19080
tgatcagctg tgtggtagat tgacatctct gagctgtgat cgtctttaca tgaaagctca    19140
ggaaaatgcc agtcatgggt aatggtgacc atgagacagt aaagctgtgg atccagttcg    19200
tgctcttctt acatagagaa tttccactcg aattgtgaac tcatggctgt ggctgcacca    19260
cttacaggcc caggggacac tcagatctca cttggtagtt gacgaaaaac tggaagtcct    19320
gataggacct cattccacat gatgaggaag actgtgggaa gagcttttgt taacaccatt    19380
cagaaaaaca tagtgcaaag ttagttttttg ttctttctat ataattatcc tagaaaagtc    19440
ttcccttaat aaatccttct ggttaatctg gcatatgtga gatgattatg atgggatata    19500
taccagattg aacaattggt caccaggaat tttatattca ctgcctgagg aataaattgt    19560
ttcccacttt cctcttacct gcactgggct cttgaatcta aatatagaga cccacattat    19620
tttccctatg aggcccttgg acagagcgct cttatgggc tcactcacca ggtgccaggg    19680
gagggtagat tccaacactt gctatgaaca ttcttgaaca gttatcctgg aaaccgcaga    19740
taccagacca ctcttgaact ggctcaagac tatgttttat ttgtaggctg tctgctcatc    19800
agtgcttgta ggaaagggta acgtttcctt ttttagatta gctgggaggg agccaagaag    19860
aatggcattc atccatattc attctagaca tatctctaca ttgttagggt tgttatgctt    19920
tcctagagtt gcatatccta tacaatggga cctacccaag atccaaactg tcacagtcag    19980
atccttcctc ccattttata tcacattgct cacaggagag acatatcccc tgcccgcctg    20040
ccccattgac tctttccaca ccactgcatg caccagggga tttgcatatt gtcccacagg    20100
gaggaccttc ccttgtgagt ctgagataaa agctcagctg taactgtgcc ttgactgatc    20160
aggactcctc agttcacctt ctcacaatga ggctccctgc tcagctcctg gggctgctaa    20220
tgctctgggt ctctggtaag aaaagaagga gatgaggaag gagaataggg tgggagggtg    20280
agctctaggg ctccacagca tcccatgatc ccatgtttag tcttaccctg tgttagagga    20340
gtataatctg tgctgtagaa aagggaactt gatattttgc tctgtgaata attagaagcc    20400
tcataagaaa tatgacgtct ggtgctctga ttaagatctt caaaatataa aggtctctta    20460
tactttacaa aaaattgaatt catttttagaa tgtgtatttt tatggcataa atcactattt    20520
tttaaaatta agtttaaata aatgacataa gataaattat gaaaattgct cattaggttt    20580
gtacataact ttgcaattca ttatttcagg atccagtggg gatattgtga tgactcagtc    20640
tccactctcc ctgcccgtca cccctggaga gccggcctcc atctcctgca ggtctagtca    20700
gagcctcctg catagtaatg gatacaacta tttggattgg tacctgcaga agccagggca    20760
gtctccacag ctcctgatct atttgggttc taatcgggcc tccggggtcc ctgacaggtt    20820
cagtggcagt ggatcaggca cagattttac actgaaaatc agcagagtgg aggctgagga    20880
tgttgggggtt tattactgca tgcaagctct acaaactcct cccacagtgg tacaaccccc    20940
aacagaaacc tcctcctggg gttgcctagt tgctcacatg tgctgcttgt ctggagagca    21000
gctcagcagg gtctctgagt ctgcagaaga ggaggctgtt ggagacctca gggcagaggt    21060
tgctgctgag gactctggct catgatagcc tcagctgtac ttcagtccca catgttaagg    21120
ccccattagg tgaaaaataa atgattccaa aaactgagat gaaataccaa ggagaatcag    21180
```

```
agtacaatta aggctgttac aaagaagcct caaaatatgg tggactaaat gtgacatggt    21240
ttctgtgtct gttgcctgac agtgcagagg caggtggtcg agcgatctct gcatagctgc    21300
cctttccccc ccgggctctg acattagcaa cagtgtcctc caccctttgtg actgtcctgc    21360 tcatcctcat ccagctgtga tgtcctgcat aagtgggagg aggggtcttg catcctgcac    21420
acccaggtag ggatacttgt ctctgctaac tatagcttca acgcccaggt gggctttcct    21480 ctacaccca caacacgggt gcactttcta tactgtgtag gctcagtatc tcatacaatt    21540
ccctggcttt ttgttgcata gttttctttc tgaacctgct cggatcaagt gccctaaacc    21600
cagtcactaa gaactgtttt ctcttaggag ctggaagaga ttggtgattt ggaaatatgc    21660
aggtataaga aacagagtag tcacagggat agagggtgac aacttggttt agaggacacc    21720
tcagcttctg aaggggaatg gcttggataa agaaataaa aggcataaat aaaattcagg    21780
gagcacaggg aaatatctag catgagactg taggatggca tacagagcta gaatatagct    21840
gagaactttc agaagtaaag ggagaaaatt tatcatgttg gctggcccag ctgaaagagg    21900
taggaaagaa cattcagata tggaggataa caattatgtg tctggagatg ggagattagc    21960
tatgccagat agccagtggc aggacccttc cttgctgtgg cactattttc aagtattagg    22020 tttttttaa gttttttatt tcttttttaa tgagcaaatc tatctatcta tctatctatc    22080
tatctatcta tctatctatc tatcattcat gattatacct taatgcatcc attgttggta    22140
gcactgacaa tttacagcac tggtggttcc agggaattgg accaaaaagg aagtctctct    22200
gaccttaata gtactcatct gtatcaaatg caggaaactt ctaaaatgtc ttgagtttct    22260
agagatgttt ttccctagca gaccttgtca taaatagaaa gctagcaaga gaagcatgtc    22320
atgaaacatg aagagagcaa aagaacactc cacatatagg acagtaggct gattctgtcc    22380
tgtagcctgc agggagaaac acatgctctg cagactttgg acacctggga ggcactgggc    22440
ctgtgcagtg ttattgagat aagacatctt tgcagctgtg cagatttgca tgtcccacag    22500
agcaacgcct actgccctga acatttatca ataggctggt gacatcctgt gcagaagtct    22560
ctctcagtca ggacacagca tggacatgag ggtccctgct cagctcctgg gactcctgct    22620
gctctggctc ccaggtaagg agggaaacaa caaaaatttt attcagccag tgtagccact    22680
aatgcctggc acttcaggaa attcttctta gaacattact aatcatgtgg atatgtgttt    22740
ttatgttcct aatatcagat accagatgtg acatccagat gacccagtct ccatcctccc    22800
tgtctgcatc tgtaggagac agagtcacca tcacttgccg ggcgagtcag ggcattagca    22860
attatttagc ctggtatcag cagaaaccag ggaaagttcc taagctcctg atctatgctg    22920
catccacttt gcaatcaggg gtcccatctc ggttcagtgg cagtggatct gggacagatt    22980
tcactctcac catcagcagc ctgcagcctg aagatgttgc aacttattac tgtcaaaagt    23040
ataacagtgc cctcccact gtgatacaag cccgaacata aaccatggag ggaagtagat    23100
gtgtgagtct gggctgcccc agctgctcct cctggtgccg ccctctgctg acagcagttc    23160
tcagatgcag ccaaggtttg aagctccctg ggaagttttg gtagaagggg tcagggaggc    23220
acatttacat tctatctctc tttatcctca gctccatcag ctgatatgca agtatctctc    23280
ctgattatta ttaataaagg acaaagaaaa ttaaacctag gaggtctaga ttgcagcaaa    23340
agtcagactt atacagaaaa ggagaaggta ctctacatat ttttaaagaa ttttttttga    23400
tacaggggat tagagtctaa attatgacct ttcaaagatc agacataagt acatacacat    23460
ataagtatgt tcagccaaca acatatcaga taaacatatt gcacctatat gtatactgta    23520
```

```
aacatttatg ctccgatccc accttcttcc gtcgagcagt actgtgtact aagtgaagaa   23580
taagacatta cctgttttt tcaagacttg ctacaaatag attaaaatgt tacatagtcc    23640
cctgtcacca tggagcaact cagtttggcg gggcaaaaag actttagggg aacagagact   23700
aacgatggac tatttcacgt tgaatgctaa ggccacttgg acaggaaacc aaggaaggat   23760
agcagatata gttaaacatt gttggtacta gcagcaacca ttaataaagg acaacagctg   23820
gtaggcttct ttgagtattg gtaacagcat aaacctctct ggggtgggct ttcagtcccc   23880
ttagtcaaaa tcaaaatcac aaacaaaacc accaaccttg aacagagccc tttgcaacag   23940
cagccttgga agaagttcaa caggacatgg tccaaacact tcttttagac ctttagagcc   24000
tgttagcctg atggaagttc aggtgtccac agtctctatg tatgctgact gtagtatgtg   24060
gcaacagaaa attgtcactg agtgagccag cctctcagat actgaacaca aaccagctga   24120
agcagccacc agatgtccct cttggcata gcaactcctt gcttgctatg ggaaactgac     24180
agggactgga catcttgggg ctgagcacca agtgtggcgc tgctgggtga actgctcctt   24240
ttcacttggg tgcctaaaat ccaaccagtg aaactgagca ggctcaatag agctgcgtta   24300
tcaaatggaa atggtgtatt cagaatcagg cccagccagc aacccgtggg atccaaaggc   24360
tccataaaca aatggcgagc ttgctagaag ggactaaatg acccatgggg gatggtttgg   24420
ctctgctttt ggctacccga agtccaagat tcagagacat gccgacatcg gtatggcatg   24480
gttcacttag ggctctgcaa aacatgtaga ctggggtgg ctaccatcta gccagtggat    24540
gactattttc tttcctgaga ctgataatgg tcattccacc caatggtcca aactacatgc   24600
agtggtaatg gtcatgcagg cctttctgcc acctcttgct atatttttac caactcatgg   24660
gccactgcca acagtctagc tatctgatca ggaaaatagc aaccgagtga ctggactatt   24720
aaagcatccc ctctgtggag aaaaggacta tggcaacagc ttgccaccta taagagacaa   24780
atatgtcact cagctggatg ctgggtctac catgaccacc cttgagatga acttatgcca   24840
tgtttttgga tgcccactga gactttgctt tgaccaagga aagttcttta ctgcccaaat   24900
gacgtcaatg gacacactct catgggacat gatggatttt ccatacacct tgttatccaa   24960
aggccaatgg atctatttaa tgctagaaca gctgactcac acggcaactg aagagtgtac   25020
atcagggcaa cctgctagta gggtggtacc ccatctgact acagcaattg gacattaaac   25080
actgcactgc agagcaaggg aaagacggca cggaggtgca ggttgaaaaa cactgagttg   25140
agtgaggaag aagttgggca aggccagttt cctgatagac gctgccactg tgaaatccca   25200
aactcagtgt ttccaatcat ttttttcctt ttatagtgat gttcttgggg gtgttgcagt   25260
ttaggccacc atgataaccc agacaggcct cctaactcta attggatgga atgattcccc   25320
tgggtgcctt ctatgggttc cacaggatca agaaatatca gggtgttaat ttccttctgc   25380
tggtaggagg gtcatctgat tcctccatta gggtggatga cgttattaga catgtcaatt   25440
ttctacagta cttgacctgc cttctagaac tggacaaccg agggtgaaag gactggatca   25500
agcaacaatg gcaatgggtg cccaaagagg tagtagtctc agaacaggga gagacagact   25560
gagtccctcc actaactcag cccaacacct gtggatgagt aggggatgcc tgagatcctg   25620
gggtggatgg gaggtgggc actgatctgt caatctgctt tttcttcaag gatcaggcag   25680
cagagaccca gaagcttcat gtctttgtaa ggctcttcca agccaacaca gataatttga   25740
caaaacactg tatctgcatc ccagacctca ccctgtcaca gactgaagtg gttgtttcat   25800
cctactaagg gtaaactata ccagctatac agaataaaag gactggatag tttagaggat   25860 caccccaagaa atagttcttt gcctgcatgg acaaaaccat cttctgtctt tagggaaatg   25920
```

```
gtatcactac cctgaggatt tggagcccag gtctcactta tctgtgcagt tgtgaaagtc   25980
ctcacaccca cagtgctgag gttaattgaa tgttactctt ttaatttctg caaagaatga   26040
gacagcttct ggaccctcag gaaagatcac taacaagtaa atacaagtat atccggaaga   26100
taaagttgta atagactctt cctttcaacc tgatccatca tgcatttagg gagctgactg   26160
ggcacaagtt ggagcagaaa gagaaaaatg aaaccacagc cttctatttt gtttctaaca   26220
gacttgtacc aaacattctg tggctcaatc taggtgatgg tgagacaaga ggacacaggg   26280
gttaaattct gtggccgcag gggagaagtt ctaccctcag actgagccaa cggccttttc   26340
tggcctgatc acccgggcat gggctgctga gagcagaaag gggaggcaga ttgtctctgc   26400
agctgcaagc ccagcacccg ccccagctgc tttgcatgtc cctcccagcc gccctgcagt   26460
ccagagccca tatcaatgcc tgggtcagag ctctggagaa gagctgctca gttaggaccc   26520
agagggaacc atggaaaccc cagcgcagct tcttcttcct cctgctactc tggctcccag   26580
gtgaggggaa catgggatgg ttttgcatgt cagtgaaaac cctctcaagt cctattacct   26640
ggcaactctg ctcagtcaat acaataatta aagctcaata taaagcaata attctggctc   26700
ttctgggaag acaatgggtt tgatttagat tacatgggtg acttttctgt tttatttcca   26760
atctcagata ccaccggaga aattgtgttg acgcagtctc caggcaccct gtctttgtct   26820
ccaggggaaa gagccaccct ctcctgcagg gccagtcaga gtgttagcag cagctactta   26880
gcctggtacc agcagaaacc tggccaggct cccaggctcc tcatctatgg tgcatccagc   26940
agggccactg gcatcccaga caggttcagt ggcagtgggt ctgggacaga cttcactctc   27000
accatcagca gactggagcc tgaagatttt gcagtgtatt actgtcagca gtatggtagc   27060
tcacctccca cagtgattca gcttgaaaca aagacctctg caagaccttc attgtttact   27120
agattatacc agctgcttcc tttacagata gctgctgcaa tgacaactca attttagcat   27180
ctcttctctg cttgggcatt tggggatct taaaaaagta atcccttgat atattttga   27240 ctctgattcc tgcattttc ctcagaccaa gatggacagc caggtttaag cacagtttca   27300
cagtaatggc cactgatca gatttacatc agtggatgtc agtaaaggtc ccaaccagag   27360
ccataaggca acaacaatag caacaaataa tcaaaattgg aaaagaagaa ttaaagctgt   27420
cataattcac tgatgaagga ttgtgtgcag ataaaattca aatttgtcta cagagaaact   27480
actaaaattg acatgagaaa tagaaaatca ttagattcaa gatcaattta ttaattcata   27540
gattcaaaaa tcaatttcat ttctgcataa taaaaaatgc taaaaattaa cattataaaa   27600
caaacacacc atttacaaaa acatcaaagt atcaattatt taaaaaaaat agactaaata   27660
cactgacgtc tccagaatat tattttgaaa aataaaagaa aacctaagta aatagaaatt   27720
cagttcaaag actgaatgtc tcagtactat aaaaatgtca attcttcaaa gattaaaata   27780
ttgattacat ataagaaaaa tcaaaatcct aaagtatact ccaatttaaa ttaagaagct   27840
aatctaaata ttatatggga atgtcaagga tgtagaatag ccacagtgaa cctgaagaaa   27900
caccaaaatg agaacttcca gtgcctgaat acctggaata tagtgtgggt gccagtatgg   27960
tgatggtgag atcagaagtt taaaaatttg caaacgtgct tatttttgga aataatcact   28020
acgcagatgt agccaaaccc tcttcaactg tgccaccaga atctcagatt tccagaatta   28080
gtttctcaca gtgtgattct taacatgaca tcaataattc tcagtctccc cagtaaacgc   28140
agctcagtgc atggtgcagc tatccatttg acttctacaa atattttaaa aggtagaaaa   28200
ttatatttat ccaactaatt gactcagtaa cagctgttca tttgcagaga ggtactctgt   28260
```

```
tttaataaat aacaaaacta agaaagttag tgaatgacca agtaggaaga gtgataggaa    28320
cagctgtctt agctttgtca aaggcttcct tccaaaagga atttcactgg tcactttcat    28380
ttatcaccac caataattta ttataactta ttgtaatgtg gtttattgaa tattatatga    28440
aagtgaaaaa cagagtagtt gtaccagtac tggaagcact gtttctactg aatacaaata    28500
attttcacac tattgtaaag tcaaaacatc ttaagtgcaa ccaccatgaa ctagggactt    28560
actgtaagtt cagggaagta actataaaga aactcacaaa tttcaagaaa atagaaatat    28620
attcctgata gtggtacagg aatatattat ctaaaatata cagttttcca ttaaaaaatc    28680
ctgcaaagaa acagaaaagt atgatcaata ttgagggaac aaaacaaaac aactgcagca    28740
agaaagcaca gtcaatgaaa gctgattctg acttgtcctg aatatcagct ttagcaaaga    28800
ctacaaagcg attattatat agatgtttaa ataattattc ttaaaactac gatcatatag    28860
ttttaaagat ataagagga aaatataaag acaatgactc agcaaatgga aactcttaaa    28920
aaatagaaac tatggaaaag aatcaagtga gaattctaga aacaaaaagt acaataactc    28980
aactgaaaaa tatattacat aagtccaaca tcagtttaag atggcaaaag attcagtgaa    29040
cttaaaaata gatgtacaga aattattgaa tctaaataaa gaaggagtt taagaaaaaa    29100 tgcgcaagac ttgacagaat tacagctcag gttgaaagat accaacaagt gtgtaaaacg    29160
agtcacaaaa aaagcagaga gagagagaaa gtgatcaaaa aatacttgga aaagtaatga    29220
caacagcttt tcaaaaataa tgaaccacaa aggtaattta atctatagat gaaagaaact    29280
caatgaaacg ctttcaggat ataatacaag attaataaca aaatacatta actttaaaa    29340 tgttgaaaga caaagagaaa ttcgtgaatg tgtcaggact aaaagctgac tctacatatg    29400
gagacacaat aataatgcca ttggctaagt tttcattagg accgagggag gctggaagag    29460
attggaatga gatctttaaa tactaaaagg aaatgaaaga ggacaaccag caattttgtt    29520
tctggtgaaa atattcttca gaactaaaaa tattccttga taaacagaat aaattcatta    29580
atagcagctc tgccttataa gaaattcaag atgaaatctt tcagaatcac agaagattac    29640
agcaggcggg attttgagcc cacagcctat aatgaaggac tcaaaagtag taaacaataa    29700
gaataaagct agaaaaaagc acacaattca atttatatga cattaaagac ataaaaaccc    29760
aaattactgt gttcgatgtc agaatgacaa ttaccttggt tgagatgggg aagcagctac    29820
tgaagaggaa ggtgcatgga ggaggcatca gcagaaggta aatattctgt agttccatct    29880
ggccaatgaa tacacaaaaa ctattcagtt acaatttgaa gatgtgtgcc ctttgtgccc    29940
tctgggtgtt ttatcactta aaataatacg taaaaatacc atatagaata gaaaatatt    30000 atgaaaactc agcctattaa agaccaatgt aaaatatgcc tgggaaaggg aaaaataatt    30060
agaaacctct tagagaaaac agaaggtat taaaaaatat gtcccctcgg ccgggcgcgg    30120
tggctcacgc ctgtaatccc agcactttgg gaagccgagg cggggggat catgaggctt    30180 aagatccagg tctggaaggt cgagcgacag cagctagaag gtttgatact catacaaata    30240
gtactgtagc tttctgttca taattggaaa aatagacaag acccaatgta atacaggctt    30300
tccttcagcc agttagcgtt cagttttttgg atcaccattg cacacatata cccagcatat    30360
gtctaatata tatgtagaaa tccgtgaagc aagagttata atagcttgtg ttttctattg    30420 tattgtatt tcctcttata tcatcttctt cttcgttcat tataaaaaaa acccgttcaa    30480
gtaggtctaa attaattatt ggatcataag tagataaaat attttatttc ataacacatt    30540
gacccgatga atatgtttct ttgccagaca tagtcctcat ttccaaggta acaagcctga    30600
aaaaattata ctggagcaag tcaacaggta atgatggtag cttttcctta ttgtcctggg    30660
```

```
gcaagaataa gacaaaagat aacagggtag aataaagatt gtgtaagaaa gaaggacagc    30720
aacaggacat gggaacctttt tatagagtaa cattttgata atggatgatg agaattaatg    30780
agttagacag ggatgggtgg gaatgattga aggtgtgagt actttagcac agattaagac    30840
caaatcatta ggatttaaag agttgtgtag agttagtgaa ggaaaagcct tagaattaaa    30900
tttggctgtg gataaaacat tcttggatta gactgaagac tcttttctgt gctaagtaag    30960
tatatttatg ataatgatga tgactgtagt gctgaatatt taataaataa aaacaaaatt    31020
aattgccgca tacataatgt cctgaatact attgtaaatg ttttatctta ttttctttaa    31080
actgtctaca gcactataag gtaggtacca gtattgtcac agttacacag atatggaaac    31140
cgagacacag ggaagttaag ttacttgatc aatttcaagc aatcggcaag ccatggagca    31200
tctatgtcag ggctgccagg acatgtgact gtaaacagaa gttttttcact ttttaactca    31260 aagagggtat gtggctgggt taatggaaag cttcaggacc ctcagaaaac attactaaca    31320
agcaaatgaa aggtgtatct ggaagattaa gttttaacag actcttcatt tccatcgatc    31380
caataatgca cttagggaga tgactgggca tattgaggat aggaagagag aagtgaaaac    31440
acagcttttt atattgttct taacaggctt gtgccaaaca tcttctgggt ggatttaggt    31500
gattgaggag aagaaagaca caggagcgaa attctctgag cacaagggag gagttctaca    31560
ctcagactga gccaacagac ttttctggcc tgacaaccag ggcggcgcag gatgctcagt    31620
gcagagagga agaagcaggt ggtctttgca gctgaaagct cagctcccac cccagctgct    31680
ttgcatgtcc ctcccagctg ccctaccttc cagagcccat atcaatgcct gggtcagagc    31740
tctggggagg aactgctcag ttaggaccca gacggaacca tggaagcccc agcgcagctt    31800
cttcttcctc ctgctactct ggctcccagg tgagggaat atgaggtggt tttgcacatc    31860
agtgaaaact cctgccacct ctgctcagca agaaatataa ttaaaattca atgtagatca    31920
acaattttgg ctctacttaa agacagtggg tttgattttg attacatgag tgcatttctg    31980
ttttatttcc aatttcagat accactggag aaatagtgat gacgcagtct ccagccaccc    32040
tgtctgtgtc tccaggggaa agagccaccc tctcctgcag ggccagtcag agtgttagca    32100
gcaacttagc ctggtaccag cagaaacctg gccaggctcc caggctcctc atctatggtg    32160
catccaccag ggccactggt atcccagcca ggttcagtgg cagtgggtct gggacagagt    32220
tcactctcac catcagcagc ctgcagtctg aagattttgc agtttattac tgtcagcagt    32280
ataataactg gcctcccaca gtgattcaac atgaaacaaa aacctcaaga agaccatcag    32340
tgtttactag attataccag ctgcttcctt tacagacagc tagtgtggtg gccactcagt    32400
tttagcatct ctgctctatt tggccatttt ggagctcaag ttctcaagtc caaaattact    32460
tatgttagtc cattacatca taccatttca gtgtggctat tacattcatt taaacgcatt    32520
tcagaaggca tctctgttta tggcatcaca aagagtttaa taaatctgtg caagaataaa    32580
caacaaacac acctataaat ataaagctga aatatcaaaa ctatttcagc actctgaaaa    32640
ttggcaaagc ataaaataat taaggatgca tatttttttat agaaaaaaaa agtactagtg    32700
ctttgagtaa ggacagaaaa tgtctgtagc cttttgcctg tgacagcacc cttctattcc    32760
cagctcagtc aatatgaatt gcagaactgg agttttaccc atgtaaggat agcaaataaa    32820
actggcagct tgctgccaaa gtgggtggac ttgagtaaag ccaaggagtg ggaaataatt    32880
cttcagtgtt tccagctaaa cagggagaac accataggaa atgaacgtcg agaagcaaga    32940
gtcataatag ctagcatttg atattgtatt gtatttttcct cttatatcat cttctccttt    33000
```

-continued

```
tcgtccttaa aaaaaatctg ttcaagtcag tctaaattaa ttattggatg ataagtagat    33060
aaaatctttt atttgataac acattgaccc aatgaatatg tttctttgca agacatagtc    33120
ctcacttcca agataacaag cctgacaaaa ttatactgga gcaagtccac aagtaatgat    33180
ggtagctttt ccttattgtc agtcctgggg caaaaataag acaaaagata acaaggtaga    33240
ctaaagatta tgtaagaaag aaggaaagca gcaggacatg ggaaactttc ataggataac    33300
attttgataa tggatgatga gaattaatgc gttagacaga gatgggcggg aatgattgaa    33360
ggtctgagca ttttagcaca gattaagacc aaatcattag gattttaaga gttgtgtaca    33420
gttagtgaag aaaaagccct agaatttaat ttgactgttg ataaaacatt cttggattag    33480
attgaagact ctttctgtg ccaagtaagt atatttatga taatgatgat gactgtagtg     33540
ctaaatattt aatcaataaa aacaaaaata attgccgcat acataatgtc ctgagtacta    33600
ctgtaaatgt tttatcttat tttctttaaa ctgtctacag cactgtaagg taggcaccag    33660
tattgtcaca gttacacaga tatggaaact gagacacagg gaagttaagt tagttggtca    33720
atttcaagca atcggcaagc catggagcat ctatgtcagg gctgccagga catgtgactg    33780
taaacagaag ttttaacttt ttaactcaaa gagggtatgt gtctgggtta atggaaagtt    33840
tcaggaccct cagaaaacat tactaacaag caaatgaaag gtgtatctgg aagattaagt    33900
tctaacagac tcctcatttc catcgatcca ataatgcact tagggagatg actgggcata    33960
ttgaggatag gaagagagaa atgaaaacac agccttttat attgttctta acaggcttgt    34020
gccaaacatc atctgggtga atttaggtga ttgaggagaa gaaagacata ggaatgaaat    34080
tctctgagca caagggagaa gttctacact cagactgagc caacagactt ttctggcctg    34140
acaaccaggg tggcgcagga tgctcagtgc agagaggaag aagcaggtgg tctctgcagc    34200
tggaagctca gctcccaccc agctgctttg catgtccctc ccagctgccc taccttccag    34260
agcccatatc aatgcctgtg tcagagccct ggggaggaac tgctcagtta ggacccagag    34320
ggaaccatgg aagccccagc tcagcttctc ttcctcctgc tactctggct cccaggtgag    34380
gggaacatga ggtggttttg cacattagtg aaaactcttg ccacctctgc tcagcaagaa    34440
atataattaa aattcaaagt atatcaacaa ttttggctct actcaaagac agttggtttg    34500
atcttgatta catgagtgca tttctgtttt atttccaatt tcagatacca ccggagaaat    34560
tgtgttgaca cagtctccag ccaccctgtc tttgtctcca ggggaaagag ccaccctctc    34620
ctgcagggcc agtcagagtg ttagcagcta cttagcctgg taccaacaga aacctggcca    34680
ggctcccagg ctcctcatct atgatgcatc caacagggcc actggcatcc cagccaggtt    34740
cagtggcagt gggtctggga cagacttcac tctcaccatc agcagcctag agcctgaaga    34800
ttttgcagtt tattactgtc agcagcgtag caactggcct cccacagtga ttccacatga    34860
aacaaaaacc ccaacaagac catcagtgtt tactagatta ttataccagc tgcttccttt    34920
acagacagct agtggggtgg ccactcagtg ttagcatctc agctctattt ggccattttg    34980
gagttcaagt tgtcaagtcc aaaattactt atgttagtcc attgcatcgt accatttcac    35040
cgtggctatt atgttcaact aaatgcattt tagaaggcat ctctgtttat ggcatcacaa    35100
agagtttaat aaatcttcgg tgcaaaaata aacaacaaac acacatttaa atataaagct    35160
gaagtatcaa aactatttca gcactctgaa aattggtgaa gtataaaata attaaggatg    35220
catattcttt atagaaaaaa aaagtaccag tgctttgagt aaggacagaa aatgtctgta    35280
gccttttgcc tgtgacagca gccttctacc cccagctcaa tcagcatgaa ttacagaact    35340
gaagttttac caatatgagc gtagcaaaaa aaactagcag cttgctgcca aagtgggtgg    35400
```

```
acttgagtaa agccaaggag tggaaaaaaa attattcagt gtttccagct aaacatgcag    35460
aactccatag gaaatgtcga gaaggaagaa ggaaagtgta gcaggaaata gaagatgggt    35520
ggcaaaagtc tccccctaaaa gccacttaac tcttaggatg actgaagctt catcccatgt    35580
ggaaatatcg ggacaatgcc tctgggctat tccatctgag gggagagagc tggggtatgt    35640
tatcatactc ctgttatcat ctactgatag tgtctctctt agtctgctgt gtcttggtat    35700
aacagaatgc ctgaaattgt aactgataaa gagcagacaa ttattctctc acacttctgg    35760
aggatgggaa gtctaagatc aaggaactgt cagattagga atcagtttat ctactttcaa    35820
gatggcacta tgactcccga gtcctccaga aggaaggaag tccatgtcct agcatgactg    35880
aagagcagaa aagagagaga gagaaaccct actcccacaa atgggaaaga gcaaggactc    35940
actctcagga gcctgcaacc cccacacccc aagcatggaa agaatagaaa atcttgactc    36000
tcttcaaagg aaattccaag cacctaccta gccttaagac gtaagtaagt aacgtgataa    36060
gcaaggaagt aaaaacagcc taaaatggcc aaataagcta gactcagaag atggtgggtt    36120
cccctataga aaccgaaggt gacattttag tatatgtctc tgaggtgttt ttgaggaaac    36180 aagacccct ccaaatgaat ctgccagcac atagatctca caaagggag aactggggac    36240 tgagctctga ccatggtact ttgttctaaa tatcttacag aggggtctgg taaaagtcat    36300
atccataaac ctgagctaat tcgtctcttc tgctgaaccc aaatgtttaa acaaagcttt    36360
tcttcctcag ccaattgtaa attagaaatc ttgtaatcca cccttgatct gtaagcccct    36420
gtttcaagat atcctgccct tttaggccaa aaccaatatg tgacctccat gtattaattt    36480
tcaatttgac ctgtaacttc tgcttttcctg aaatttactc ctgccttaaa aaacccttac    36540
ctgcaagcca tcagtgaggc caggatttga atcttagctg cctgattctc tttacctgat    36600
gccctacaaa aaaacaaaca aacaaacaaa caaacctttta ctttctcctg ctgcaaactc    36660
agtgtgaata tctgatctga ctgagctgag tgagtggact ccagttcggt tccacagcac    36720
aagctctgtt tatagtggca tttatccact catgagggca gagctctcat gacttcaaca    36780
cttcccatta ggccccacct cccaattctg ttgctttgag ataaatttaa aaacagatgg    36840
gttttgaagg acacagtgaa accataacac tgcccaaaga gagggccatt cgagcccctg    36900
tggtctgcta tgcatgcagg cagagctgcc ttctccaggt tcagaaagag caatgagggg    36960
catagatggc cattggaagt cagcagcagt acagcgaaag ggaaaggcat agcctgtaga    37020
cagggattgc aatcttgata tatttctat ttagtttcct ttctaaaaac agaataattt    37080
catgctaaca gaagtgttgt aagtacagca caaagtgctt tttttccaatt aagtgcatat    37140 tgtattttt aaaaaataat ctccatctcc atacacgaat aaaatacatt actccatcta    37200
gtcctcagga atatttcaaa ttttgacaat taactcaaaa aagttctttg taaccaaaca    37260
gcctccagga agaaacactt atttacggac aaatctgtga tgccctggtc cgacctggga    37320
cactggggac attgctccta tgctgagtta ctgagaagag ccagccctgc agctgtgccc    37380
agcctgccct atcccctgct gatttgcatg ttcgcagagc acagcccct gccctgaaga    37440 cttattaata ggctggtcgc accctgtgca ggagtcagtc ccaaccagga cacagcatgg    37500
acatgagggt ccctgctcag ctcctggggc tcctgctgct ctggctctca ggtaaggaag    37560
gataacacta tgaattttct cagccagtgg gctcagtaca gcctggctct tgacggaagc    37620
cttcctataa tatgactaat agtatgaata tttgtgttta tgtttctaat cgcaggtgcc    37680
agatgtgaca tccagatgac ccagtctcca tcctccctgt ctgcatctgt aggagacaga    37740
```

```
gtcaccatca cttgccaggc gagtcaggac attagcaact atttaaattg gtatcagcag   37800
aaaccaggga aagcccctaa gctcctgatc tacgatgcat ccaatttgga aacagggqtc   37860 ccatcaaggt tcagtggaag tggatctggg acagatttta ctttcaccat cagcagcctg   37920
cagcctgaag atattgcaac atattactgt caacagtatg ataatctccc tcccacagtg   37980
taacaagtca taacataaat cacccagggg agcagatgcg tgaggctcag ctgtcccaga   38040
tgccccttct ggtgccttcg cctgctgaga atgtttctca aattgcagtc acactttgaa   38100
gttcactgga gagtttttgt aaaagggcca tgaaggccca cttcatcgta gctgtctttc   38160
cttgtcctaa tccccagtat catagacagg gcaatgcctc tcctgatttc attgagaaga   38220
aatggttaca cctgaggggt ctgagttgta gcatcagttg gaattcatgt agcaatagtg   38280
agccactcta ggtattccaa gtaggatttt ttttaaatac aagatgtgag aatctaaact   38340 acagccttt aaaggtttgc aagtatagta gtcaaagacg caaatactag agaagaggaa   38400
ttctcttctg gaatccagaa tgcatctgat agagaaggta caactgccaa tcatgtggtc   38460
ctcagacctt tctgagaagc ccatgggtgg gggtgcagat gctctcagct gcctagagga   38520
cttcatcagg tgcttctgca gtcctcacct cggtccatat gtcttgctgc aggtgttgat   38580
ggatagtatt gaatcctcct cttcttactt ctcaatctca gggcaggccc cacactgggc   38640
aactccacca aaaccagag aaggcatagg gtttctggca aatgtgcttc cagaataata   38700
gtgatgatgg ggaagtgaca gctgacatcg tagtgtggtc atgtatctcg actctcagga   38760
ttttttcagt gaagtgatgg cctcagaata cacttggatg tacttccata cactatgagt   38820
aagtttgaaa tcatagcatg aaaatgatat ttagtcatat gataaataga actacatggc   38880
tacattaatc aaaatagcat agtgctggta caaaagata cacagacaaa tggaacagaa   38940
tagggaactc agaaataatg ctggagacct acaaccatct gatcttcaac aaccctgaca   39000
aaaacaagca atggggaaag tactccctat ttaatagata atgctgggag aactggctag   39060
tcatatgcca aaaattgaaa ctggaccct tccttacacc ttacacaaaa atgaactcaa   39120
gatggattga agacttaagt gtaaaacccc aaactataaa aaccctagaa gaaaatctag   39180
gcaataccat ttaggacata gacacgggca gagatttcat gacaagaatg cccaaagcat   39240
tgcaacaaaa gcaaaaattg acaaatgtga tctaattaaa ctaaaagcc tctgcacagc   39300 tgaagaaact atcatcagag cgaacagaca acattaagaa tgggagaaaa ttttgcaat   39360 ttattcatct gacaaaggtc taatatccgg agtctataag gaacttaaac aaatttacaa   39420 gaaaaaaaa caaccccatt aaaaggttgg caaaggacat gaacagacac ttaaaagagg   39480
acatacatga ggccaataat catatgaaaa aaagatcaac attactaatc attgaagaaa   39540
tgcaaatcag aaacacaatg agatactatc tcacaccagt gagaatggcg attattaaaa   39600
agtcaaaaaa caataagtta ggcaacgtga ctcacacctg taatcctagc cctttgggaa   39660 gccgggqtaa gtggatcact tgaggtcagg agttcaagac tagcctggcc aatatggcga   39720
aatctcatct ctactaaaaa tgcaaaaatt agctggaggt ggtggtggat gcctgaaatc   39780
cctgttcctt gaggggctga ggcacaagaa tcgcttgaac ctggaagaca gaggttgcag   39840
tgagctgaga tcatgccact gcactcaagc ctgggtgaca gaatgatatt ccttctcaga   39900
tataaaaaaa aaatcaaaaa acgacagatg ctgcggaggt tgtggagaaa taggagtcga   39960
gcattaaaga gacttatagc tctggacaat gcaggaactg tggatgtcat atgctttaag   40020
gaatcccaat atcatcttct ttgtcaatct gcagtaaacc tcttcagctt agactggtaa   40080
taacattggt ttagggccat tacaaaatgc ttttgagaac attttacttg ctcatgacta   40140
```

```
agtgttcttt tttacttaaa aaaagatcaa tttcatgctt acaaaaatgt agtatgtatg   40200
tcacaaagta tcgctcccaa ctggaacaat ttcacagtgt gttgaagacc tgatagcccc   40260
actctctaag actttattaa gaattctcta caaacaagga tattctccta cttatgccca   40320
atacggcatt gaaatatatt attccatcta gttctcacaa ccacttcgag atttgccaat   40380
aaatgctcaa aaatgtactt ggtaacaaaa tatcctttag gaagaaacat tctctgcagg   40440
caaatctagg tgccctggtc tgacctggga cactggggac actgcccctg tgctgagtta   40500
ctgagataag ccagccacgc agctgtatcc agcctgcccc accccctgcc gatttgcttg   40560
ttcccagagc accaccccct gccctaaaga cttcttaata ggctggtcac acctgtgcag   40620
gagtcagtcc cagtcaggac acagcatgga catgagggtc cccgctcagc tcctggggct   40680
cctgctgctc tggctcccag gtaaggaagg agaacactag gaatttactc agcccagtgt   40740
gttccgtaca gcctggctct tgagggaagt tctcttacaa catgattaat tctatggaca   40800
tttgtgttta tatttccaat ctcaggtgcc agatgtgaca tccagttgac ccagtctcca   40860
tccttcctgt ctgcatctgt aggagacaga gtcaccatca cttgccgggc cagtcagggc   40920
attagcagtt atttagcctg gtatcagcaa aaaccaggga aagcccctaa gctcctgatc   40980
tatgctgcat ccactttgca aagtggggtc ccatcaaggt tcagcggcag tggatctggg   41040
acagaattca ctctcacaat cagcagcctg cagcctgaag attttgcaac ttattactgt   41100
caacagctta atagttaccc tcccacagtg ttacaaacct gaacataaac ccccagggaa   41160
gcagacatgt gaggccgggc tgccccagct gctcctcctg attcctccat cagctgagag   41220
tgttcctcag atgcaggcac actctgatgg tgttggtaga gggggatgtg aagtcacctc   41280
tgcatcccaa tttcttttte tttctcagca ccaggtgcac agacataaca gttcctctcc   41340
tgatttaaaa aaggcaggga tcatgacacc tgaggagtct agtttatggc ttcagttgga   41400
attcaagtaa cagagaaaga agccactata gatattctaa gcaggaattg tcttgataca   41460
gagaaataga gtataaacta tggaagtcta aataaaaata tagagatgaa tctcaaattt   41520
catgttttat ttgctaagaa atatttgcta aatggggcat acagaaaaac tcaatggtct   41580
tcaatatgtt ggtcgagcag gctgcttaca aagcagcaga aatgtttgtg catgggctgc   41640
agcactgtga ttttgctccc ctagtcaggc atcagtaaaa ttttgtggag cccgaggctg   41700
cagcccactg atgctgatgt ggttacatcc acttcccctg ctactgagtc aggctgggac   41760
gttcagggta cattagagat atgagatata atgaatgcaa atccatgtcc agtttcatct   41820
ggatccaact gatttctcca tgtacataga caattgcttg ataagagatt gagtatgttt   41880
ttcctaaagg tgttaacagg gaggctggtg tctgggtcag gatgatgtcc ccatgcactg   41940
ataaaaagta taagaagaaa gtgtcattga tggtgcatgg cagggacatg ctccgtgcag   42000
tggccaccct cactaagaca gatgaacttt gggaaataat acccaatggc agaaaagaag   42060
gtagactatg aaggtaccca aaacaagaat aaggtgcacc tcatttagtc tctgggtatt   42120
aaagagacct gcagttcttg atagtggtgg atctgtgagt gctgcatgca tggagacaac   42180
acggtatcat ctttgtatat ctgtaataaa ttgcttgatc taatactagt aagaacaaag   42240
gcataacacc attacctaat acttacaaat atatagcatc atgccgatac attttatttt   42300 taatttttt tagaaaggaa caatgttaaa ctcacagaaa tgttgcaggt atagcacaat   42360
tacccccttc cctacccgga atcttatgag agtcttttga agacttgaga atcctaccat   42420
ctaacatttt actatgtgtt tcctacaaac aagaatattc tcctaaataa tcctgataca   42480
```

```
ccaatgaaat acattactct atcggctcct gaggaatatt taaaattctc aaaaaaatac    42540
ctaaaaattg tttctcataa taaaatagtc cccagtagaa acacattctc tgcagacaaa    42600
tttgtgctac cctggtctta cctgggacac ctggggacac tgagctggtg ctgagttact    42660
gagatgagcc agctctgcag ctgtgcccag cctgccccat cccctgctca tttgcatgtt    42720
cccagagcac aacctcctgc cctgaagcct tattaatagg ctggtcacac tttgtgcagg    42780
agtcagaccc agtcaggaca cagcatggac atgagggtcc ccgctcagct cctgggctc     42840 ctgctgctct ggctcccagg taaggaagga gaacactagg aatttactca gcccagtgtg    42900
ctcagtactg cctggttatt cagggaagtc ttcctataat atgatcaata gtatgaatat    42960
ttgtgtttct atttccaatc tcaggtgcca aatgtgacat ccagatgacc cagtctcctt    43020
ccaccctgtc tgcatctgta ggagacagag tcaccatcac ttgccgggcc agtcagagta    43080
ttagtagctg gttggcctgg tatcagcaga aaccagggaa agcccctaag ctcctgatct    43140
ataaggcgtc tagtttagaa agtggggtcc catcaaggtt cagcggcagt ggatctggga    43200
cagaattcac tctcaccatc agcagcctgc agcctgatga ttttgcaact tattactgcc    43260
aacagtataa tagttattct cccacagtgt tacacacccg aacataaacc cccagggaag    43320
cagatgtgtg aggcagggct gccccagctg ctcctcctga tgcctctatc agctgagagt    43380
ggtcctcaga tgcagccaca ctctgatggt gttggtagag ggggacatgg agtcacctct    43440
gcaccctaat tcttttctct ttctcagccc caactgcaca gatctagcaa tgcctctcct    43500
gatttaataa agacagagat catgacacct gaagagtcta gtttatggct tcagctggac    43560
tttatataac agagaagagg ccactataga tattcaaagc aggaattgtc ttaatacaga    43620
caattagagt ctaaactact gaagtctaaa taaaatgtag atgaatct ctaaatttaa     43680 tgttttacgt gcaaagaaat atttgccaaa tggggcatac aggaaaactc agtggtcttc    43740
aatatgttgg aagaacaaag agaaggttag agttttacga aaaagggaac atgttaccta    43800
tggctctttg agaaagttca tgggcactag gaagggttgg gagctggcaa gctcagactg    43860
ggaagcagtg gtggacaaag tgaatcctac agttatatca agttatctca gaagttgtgg    43920
ataaatttga tttcaggtta caataagcca aaggcagtgt cgagcatcag gagcatcaat    43980
ggctattcaa tatcctattt atgtaccata gtttataaat gtattgacat ttaagtgata    44040
atttattatg gttttttgct attataactt attgaattga tgaaatgaca tactttttatt    44100 aactgatttt tctaatatta atttctagtt ccatgaggct ttccactttg gatggtaaaa    44160
agggagatag catttctact tatatgcata aattaattct aggtagtgaa ttttatttat    44220
ctgggaataa ttttttagata tggcaactct cattcatttt gacaagaaaa atctaaagct    44280
cataaaccct gaatcctata tgcttactct cacaaaaatc tctaatgtcc tgctgggatt    44340
tatccacagt ttagattaga cctggaatac atatggtcat gcaacaatga tcttagaaca    44400
ggactttaac ttggctttag gaactgaggc tgagagtaat agaattgatt ttttttgtgtg    44460 tgtgtgaagc tcctattata ataatgagaa tactttgatt cactcagtta aagttttccc    44520
ctgatttatt gtgtacatac aatgaaggat caagaaagag aaattttttaa atggaagcat    44580 tagccagaca agtttgacct cacagttta ctagggata tatcacctag ttttggatct     44640
atttctaaca tcttaacatt gtgaaagag tcttgggaaa ctggttaaat cccaaagaat     44700
gctgcaatag gaggtggcc cttatgagtt atttaatatc ttgagctgcc ttcggaaaat     44760
gttgctgagc aggcattgaa gagtatcgat aaaatttatt gagaatttgt ttattatgat    44820
taacagaggt aaaagccagt atattactga ttaatatagg taaaaggcag ttaagaaatt    44880
```

```
gggaatgctt tctcttctgc tttcttctac gatgcacaag gcgtttcaca tttatgcccc   44940
tatgaaaatt actaggctgt cctagtcatt agatctttca gcagtttgta gttttagagc   45000
ttctaagttg acttctgtct tttctattca tacaattaca cattctgtga tgatatttt    45060 ggctcttgat ttacattggg tactttcaca acccactgct catgaaattt gcttttgtac   45120
tcactggttg tttttgcata ggcccctcca ggccacgacc agctgtttgg atttataaa    45180 cgggccgttt gcattgtgaa ctgagctaca acaggcaggc aggggcagca agatggtgtt   45240
gcagacccag gtcttcattt ctctgttgct ctggatctct ggtgaggaat taaaaagtgc   45300
cacagtcttt tcagagtaat atctgtgtag aaataaaaaa aattaagata tagttggaaa   45360
taatgactat ctccaatatg gatccaatta tctgctgact tataatacta ctagaaagca   45420
aatttaaatg acatatttca attatatctg agacagcgtg tataagttta tgtataatca   45480
ttgtccatta ctgactacag gtgcctacgg ggacatcgtg atgacccagt ctccagactc   45540
cctggctgtg tctctgggcg agagggccac catcaactgc aagtccagcc agagtgtttt   45600
atacagctcc aacaataaga actacttagc ttggtaccag cagaaaccag gacagcctcc   45660
taagctgctc atttactggg catctacccg ggaatccggg gtccctgacc gattcagtgg   45720
cagcgggcct gggacagatt tcactctcac catcagcagc ctgcaggctg aagatgtggc   45780
agtttattac tgtcagcaat attatagtac tcctcccaca gtgcttcagc ctcgaacaca   45840
aacctcctcc ccatacgctg ggccggtagg tctttgctgc agcagctgct tcctctgcac   45900
acagccccca acatgcacgc ttcctctgtg tgttggggag gtcactctct tgatttattc   45960
gttggagggt ttgcagggcc caggattaaa ttaagagact tgacttttgc tggatctctt   46020
tttgtagaag attattaaag caaaatgttg taaagatccc ttagagacat tgtcaggagt   46080
ttttgtgttg caggaacctg catgtttcac atggacacat cacatgaccg agccaaatag   46140
atttatcttt actctctaga acagggtcca ctcagttta cgcacagatg ggtcaattct    46200
ttcctctatg tgcctccttg actctggaaa gtttctactt ggattcctaa ttctcttttt   46260
tctttcttca tctgcaatcc ttcccaatat taaaccttga tccttcctat tcatagcctc   46320
ccacatagaa ggtagtgtcc ctctgtagct ttttccttcc agagaccctg tttctttcca   46380
tcatattaat actttcatag gcaatttct aattctttat tactctagaa atatgtgaca    46440
gcatttcgtc gagaaatatt tggcgcgcat cctcctttga cttccagtc actaaggatt    46500 taccatctct tatttacaat atcaaatata tagaaagaac tcaagaagtt gaactccaaa   46560
aaaccaaata accctattaa aaaattgggt gtagagccaa acaaagaatt ctcaactgag   46620
gaatactgaa tagatgagaa gcacctaaag aaatgttcaa catccttact catcagggta   46680
atgcaaatca aaacaaccct gaaattcctc acgccagtca gaactggtac caacagaaac   46740
cactaagatc aaaaactcag gtgacagcag atgctggtga ggatgtggag aaagaggaac   46800
actcctccat tgctggtggg attgcaagct gatacaacca ctctgaaat cagtttggcg     46860 gttcctcaga aaattggaca tagtattacc tgaggatcca gctataccac ttctgagcat   46920
atatccaaaa gatgttccaa catataacaa ggacacatgc tcccctatgt tcacagcagc   46980 atttttttata gtccaaagct ggaaacaaac cagatgtcct tcaacagagg aatggataca   47040
gaaaatgtgg tacatttaca caatgaagta ctactctgtt attaaaaaca atgaatttat   47100
gaaattttta ggcaaatgga tggatctgga gggtatcatc ctgagtgaag taacccaatc   47160
acaaaagaac tcacatgata tgtactcact gataagtaga tattagccca gaaactcaga   47220
```

```
ataccgaaga tacaattcac aagccacatg aaactccagt ccttcttaga atggggaaca    47280
aaatgcccat agaaggagtt acagagacaa agtgtggagc agagcctaaa ggaaagacca    47340
tccagaaact gccccacctg gggatccatc ccatatataa ccaccaaacc attgtggatg    47400
ccaccaagtg cttgctgaca ggagcctgac atagctgtct cctgagaggc tctgccagag    47460
cctgacaaat acagaagtgg ttgttcacag ccatccattg gacggagcac agggtcccca    47520
atgaaaaagc tagagaaagt acccaaggag ctgaaaggat ttgcagcccc ataggaggaa    47580
caatatgaac taaccagtac ccctgagct ccctgggatt aagccaccaa ccaaagaaaa    47640
cacattgtgg aactaatggc tccagctgca tatgtagaag aggatggcct agttggtcat    47700
caatgggagg agaggcccctt ggtcctgtga aggctctatg ccccagtgta ggggaatgcc    47760
aggaaggaaa aatgggtgga ttggtgagca ggggaagggg ggagaggata gggggttttc    47820 ggagggggaaa ccaagaaaga caataacatt tgaaatgtaa ataagaaaa tatctaacta    47880 aaaagaaaa gaatcttcac aaaagcaaaa aaaaaaagaa atgcaaataa agaaaatatc    47940
taataaaaat taagctttga tacgcaaaaa ctgaaagaat taagtataaa taaaaccttc    48000
tcaaagggaa taaaaattac ctgaatgggg tgaacatgtc aagtcactct tggggtgaga    48060
atgggcagga agaatagtca agaatatgat gtctactctc taaagtgtga atagaaaaca    48120
aaggctctga gtctatagac aagccactca aacagcacca gacaagataa aatctgctgt    48180
aattctagga gaaatccaga aatatggagg tgagtgagtt ccttcaacac cgtcaatgac    48240
tgaaaaatgc catcatagca tagaatgtat atttaaaagt ggaattaaca gtgttggtta    48300
agtatgaata tatatgacta tatatgacta aatatgaata tatgaccagg aaacaggaaa    48360
agtatctttg cctggcagat tagaagtatg ttttgagaat gagtactata ttagctacaa    48420
ataagagaaa taaacttatg aatgaaaaac aataactagg gcctagagag atagcttatc    48480
agttaagagt tcttgctgct tttctggaag acccaaattt tattcacagc accccttgctg    48540 ggcacctcac aagtacctgt aactccagct tcatgaaatc tgatgccctc ttctgacctc    48600
tgtgggcatc tgtatgtatg tgtagcattc atgcatacac atacacataa ataagataa    48660 tcttgacata agagaaaata agtggataag ctttgactat aatttcataa aattgcattt    48720
actttaaaaa aaccaagtga taaagatgta agatgtttat acgataattt tctaactaaa    48780
accgggtgaa aagaagaaat tatattagaa ttatttatat tatatatgtg tatatatgaa    48840
gtgaccacat ttaaaatgtg tggtagtatt caaatgtaaa tatcagtatt ccagtgatta    48900
tgtgttattt attcatgcat tcagaaaaca agcgtgcaca tagatagagc aactgttcaa    48960
ttaaggacat agaaatggaa agacaaacct atgaaaagca aataaaacat cataaagaat    49020
aaaagcagaa ccaccaacag attggaaaag gatctttacc tatcccgaat cagataggg    49080 acttatatcc aatatatata aagaactcaa gaaggtggac tccataaaat caaataaccc    49140
cattaaaaag aggctcagaa ctgaagaaag aattctcgcc cgaggaatac cgaatggcag    49200
agaagcacct gaaaaaatgt tcaacatcct taatcatcag ggaaatgcaa atcaaaacaa    49260
ccctgagatt ccatctcaca ccagtcagaa tggctaagat gaaaagttca ggtaacagca    49320
gatgctggcg aggatgtgga gaaagagaaa cactcctcca ttgttggtgg gattgcaagc    49380
ttgtacaacc actctggaaa tcagtctggc ggttcctcag aaaattggac atagtactac    49440
tggaggatcc agcaatacct ctcctgggca tatatccaga agatgtccca accggtaaga    49500
aggtcacatg ctccactatg ttcatagcag ctttatttat aatagccaga agctggaaag    49560
aacccagatg cccctcaaca gaggcatgga tacagaaaat gtggtacatt tacacaatgg    49620
```

```
agtactactc agctattaaa aaggatgaat ttatgaaatt cctaggcaaa tggatggacc    49680
tggagggcac catcctgagt gaggtaaccc aatcacaaag gaactctcac aatatgtact    49740
cactgataag tggatattag cccagaaact taggatacee aagatataag atacaatttg    49800
ctaaacacat taaactcaag agaacaaagg ccaaagggtg gacactttgc cccttcttag    49860
aatagaaaac aaaacaccca tggaaggagt tacagagaca aaatttggaa gtgtgatgga    49920
aggatggacc atctagtgat tgccatatcc agagatccat cccatgatca gcttccaaac    49980
gctgacacca ttgcatacac tagcaagatt ttgctgaaag gacccagata tagctgtctc    50040
ttgtgagact atgccagggc ctagcaaaca cagaagtgga tgctcacagt cagctattga    50100
atggatcaca gggcccccaa tggaggagct agagaaagca cccaaggaac taaagggaac    50160
tgcaacccta caggtggaac aacaatatga actaaccagt accccggagc tcttgtctct    50220
agctgcatat gtatcaaaag atggcctaat aggccatcac ttgaaagaga ggcccattgg    50280
acttgcaaac tttatatgcc ccagtacagg ggaatgccag ggccaaaaag ggggagtggg    50340
tgggtagggg agtgggggggg gtgggtgggt atggggact tttggtatag cattggaaat    50400
gtaaatgagc taaataccta ataaaaaaat ggggaaaaaa gaataaaagc agaaactaat    50460 gaaaatgtg gttataaagt gaataaaact gtgattgaaa tatctttctc ttgaaaagga    50520
tcattaaaac agatgaatat tgagctattt aaaggtaaaa catgccaaaa atcatgttat    50580
gaaggagcaa agagaaaaca actgtatcta tagctcctga agagcttaag tttggaggag    50640
tgtgtcctgc ttttaaagag gcagaaccat gctgtagatg aagcccatga tgttctgtgg    50700
aaagagaagt aaccctgact ccagaagatg tgttcaactg gaaagatca ataatcaaag    50760 atcgtaaaac aattgggaga gacccaccat cccctcctct gtgggaaagt tcaaggtcat    50820
tttcttgaaa agttctagca tatgttttg gagtagtagt agttgttgct gttgttgttg    50880
ttgatgatga tgatgatgat gttgttgttg ttgttgttgt tatataaacc ttctttggag    50940
catagaaaac tacaaaaaca gaaacaaaaa aacacaaaaa aaatatctat ttcagataac    51000
ctatattcaa tacagctgca ttaatgaggc aatttatcat caatgaagca tcacctattg    51060
ttgatttgtt aaagattatt tatcttcaat ataagtaaaa gcctgataac tggccctgtt    51120
gactgtggct tttactgctg tttctctgtg ctgaaactat ccatacaaaa tagaaataaa    51180
gtctgaaaag tcaaaaaaaa cacaatgttc tgatagttgg aaaccgtgtg tatatgtggg    51240 gtggggagg gggtaatgct cataaatgtg tgacagagag ataggggaag aggagaaaga    51300
cagatcttct aaaaacaaca gtctggtccc attatggggg tggagacctg gccaaattga    51360
gatctctgct tttgtttgca ggacagttct gtgacccatg actgggcctc tgtagacttg    51420
ccgcttatac aacactgcca tctgctgata cagcattagc accctgactt gctctggtga    51480
taaactggag gcactgtgag atcatttcct tgtcactgtt tcctgtgcca cacccattca    51540
tatgtactag aaatagtctg agaagaaaaa gacgttcaga taggaaggga gcatgtaatg    51600
tacctatata tctacataga tacttactca agggagggga gggtttggtg tgtgtgtgtg    51660
tgtatctccc gtgcacacac acacgcgcga aaaagttgga gaggaaagat ttttttttta    51720
aacaacagtc tgatcccatt atagaggtgg agacctgaca agattcagat cactggcttt    51780
gtttgcaggc cagctcagtg acccatgatc gggcctccgt aggctcactg cttatacagc    51840
actgccatct gctgacacag cttctctgtt gacacagctt ctgcccctg ccatgctcag    51900 ataatgagct gttcattggc tctgtgagat cgattccttt tcattgcttt cattttgat    51960
```

-continued

```
atctaaacaa tgtttctaca attcagagac acaaacaaat tgtataaata acttcaatttt    52020
tacaagttaa catttttccac cttttactgg tatcaaacgg cttgccgtgg ttctgacctg    52080
ccaagatagg gagtaaagct ctctttggtc tctagtccca ggccttggag ttccaaaagc    52140
ctgggtttgg agggagtccc agaagtttac agctccaagc cctgagagct agaggcctac    52200
tgttccaggt tttgaaatcc aacaggatga ctagggagag gtggctcagt ggttaagatg    52260
tgccctgctt tttcagagga tgtaagttca gttcctagca cccatatcag gcagctcaca    52320
tgcagttaca tataaccagc ctgtaatttc atctccaagg atctgaacat ctcttctggc    52380
ctcctcaagc actgtgttca catgcatgca cagtgtgtgt gtgtgtgtgt gtgtgtgtgt    52440
gtgtgtgtgt gtgtgtgtgt actatatata cacacatata tagtagagtg agttgagctg    52500
gtagcctggg gtgtctgaca ccttggccct tgacagttc cttagaaatc tcccagtacc     52560
agggccagaa gtttcttgtc ttcagcagct gtctctattg cctctgctcc tcctcatctc    52620
taccacagcc ttttgatgtc actgccgatg tcaccaagga cacttccttc accactgaca    52680
ttgccttcat tgtccctgct tccttccttt cctcatgtta ccagctcaac tcactctact    52740
aatgataaaa cgcaaaaata ggcaagaccg ggcctttat tgcaacttaa tgcttcagct     52800
tcaacaccag agagcaacat ctagctggta tctccaggtt aacttgcaga gtgaaccaag    52860
cagagcactt atatagccag agtgggagtg tgtccagtgt gtgtgcacgt ggcagtacat    52920
cacaccaatg aagaacagta ttctcaccaa gcatgaaggg ctgcacctgt cccaatcaca    52980
gcagtccctc agacactcag aatgaagtca cacaccttca gactgccttc ttgactgata    53040
ttccttcatt caaggccata catagctcca taggatgaag cagtcttaat ttaccattca    53100
aatcatccaa gctatcagga aaattgacat taagaaacac atctacaata aagttgtcat    53160
tcacagtgat ttaacaatag gttaagaatg catagctcct gcctcagtga tcccatgagt    53220
aatgggcctc ctaatatgac tgttttactt atcccaccat ccaaccaccc ttggcaacca    53280
ccacacacat ctctttgaca tgtgtgcatg agatatttta atcatattca aggctgatta    53340
ccttctctta tctccctcac attctaacta catccctgct aactttgtgt ccgttttaa     53400
ggtttatttt tatttatgtg tatgtgtgtg tgtctgttat ggaccatgag aatgtgtcca    53460
atcgcctgga cctggagtta caaacagttg tgaattgcct gctgtgggtg ctgggaatca    53520
aattcaggcc ctctgcagga gcgtcaagtg ttcttggccg ctaagccacc ttcccacaac    53580
cccacacact ttttgataac ccgttagctg aggtaactta cataaactcg ggttaggggt    53640
tatttaacaa agcatgatca acttagcagt gggtatatca ctgaagaaac ttttgttccc    53700
tcccctagca actattaaca gccaaaagct gtttagaaaa gggtaggggc cttaaaagcc    53760
ccaattaacc taattagaag tccttaactg actataaatc ttaaaggaaa agaagagcct    53820
cataagcccc tgccctgccc gtgatggaat attggcaggc cagatcttct ggttgtgaga    53880
aagtaatcaa gctgctctga gtccgtgagt gcaaccagcc atgtctgatt cccaaggatg    53940
gtgcacaaag ccccttccc tccaccaact ctgtgttctt tctaccccctt ctcctgcagt    54000
gtactctgaa ccttgtatgg tgatgacata aacgaaccat tgatgactga gcactcaatc    54060
atcccttatt ttcagcgctt tgacccgtta taagtctctg cataaaacac acacacacac    54120
acacacaagg gaggagggtc tgagcaacac taatctatag gttttcaacc tagcaatatt    54180
tacaaggcca ttcaaaaaac aaaccatgtc catttagtga aacaacagca gtaagtttcc    54240
cactagggcc tttaaccaca cccccataag ccttttaacca ggtttacagt agcaggaatg    54300
aatactgtgg agtggacctc aaacccaatc agaaaatggt tggttacccc cattctagcc    54360
```

| | |
|---|---|
| ataccactat tgctccagtg ggcatatctt accctgccgt ggggtcgatc caatagggca | 54420 |
| cagggtctat agctaaatgc aactgctgac tagctccttc acccagaaga ctgtgcacca | 54480 |
| tcgtctggca ctgtgaaatc cacccagctg aaaggaagcc tccaatcggc tccatctggg | 54540 |
| cttttccatg gtctacaacc aggagcatgg tgtatccagc aatagggtct tagcatctag | 54600 |
| aaattagcta tggtaattgc ctatattgtt tgaaggacct taaggacctc aatgaccaac | 54660 |
| atatagcatg gaatctcacc cctggcacca ggatttttat ttaataacct atggcttccg | 54720 |
| ggagcagctt tatcctccca tgcagggtac ctcacaccaa ctccttttta ttaattgtac | 54780 |
| gttaaatcac ttgcaaagta gtattcttcc ttacggcttt ttcatgcacc ctcacgcagc | 54840 |
| tttgaatggc catctctccc ccctctcctc tttcccattt ttctgcacta cattcctact | 54900 |
| tcctacaaaa tttgtcctaa acagtttttc ctttctctcc accattgtcc cttccaagat | 54960 |
| tcctagattt tggttacctt aaatgccaac aaggtacaat tttcagaggc tttacagtaa | 55020 |
| cagaaaaaaa agaggttaca aggtactttt caaatttatt gatgggcaca ggagtgcagg | 55080 |
| ttaaagcaaa gtggggaacc tctgctacag acctcggatg ctatctgacg gtcccagtgt | 55140 |
| ttgccgtgag gatgctgctc ggccaacaac tcaagtcagg atgagttggg atctgttctt | 55200 |
| gtattccaaa ggatttacct aacagtcaca aagatgatag gtcacagacg gcagtaaatg | 55260 |
| gcctcaagta gcagttaatg gccacttgag ggagctaaag ataacttgtc tctgggcctg | 55320 |
| cacagattcc accctccac agtcactgaa gttctttatt atcattattg ttgttgctgc | 55380 |
| tgttgttgtt gttgttttat atccataaat gttgccgccc ccgcccccag cctccctttg | 55440 |
| cagatttctt ccccaacacc cccttagctt ctaagagggt accccaccc cagtcatccc | 55500 |
| gcttccctca ggcatcaagt ctttacagga ttagctcatg ctctcccact gaagccaaac | 55560 |
| aaatatgtct gctacatatg tgcggggggag gacggggggg ggggggggga ctcggaccag | 55620 |
| cccatatatg ctctttggtt gctggatttc tctctgggag ctctcagggg tctgggttag | 55680 |
| atgacactct tcatcttcct atagagttgc catcccttcc tttccttcag tccttcccct | 55740 |
| aagtccttcc cctaactctc ccataggggt ccccgacttc agttcaatgg ttggcagtaa | 55800 |
| atatctgtct cagtcaaggg ctggtagagc ctctcagagg acagtcatcc aggctcctgt | 55860 |
| ctgcaagcac aacgtagcat caataatggc gtcagggtcc taatcggtga ttcagccttt | 55920 |
| gtaaagtggt caacgtaagg tgcaggttct tggggaggga cttgaagggg acacgaggac | 55980 |
| tttaattcac atggataaaa tagaagactg cctctatgag aaaggtgagt ctgtggacta | 56040 |
| aatggattct ttcccgcaga gagaaataga ggaagaattt cagatgctca tttttaaagat | 56100 |
| aaaagaatac ttgaaaagaa gggggggtgg gaggaaagta tgacagagaa atcagctaaa | 56160 |
| tgctgccccc agcttacact tccttagaag ggaaagggaa gggaaagcta ctcctgaaag | 56220 |
| aaaagctaac cgaagcagag cagtcccacc ctcaagacag gcacagagct agctctcaca | 56280 |
| tgctaaagta cagatgcaga aacctcttgc attgggatca gccttggata aaataagtc | 56340 |
| ggtgaaagac agactgcaaa gctcaatgtg gccagcagag gcccctagtc agcaacaagg | 56400 |
| aaaactctca cgctaaccag acaaacaata cagactcagc aaaaacataa acggaaggat | 56460 |
| gtgcccacaa gttcacctga ccctcttcct ccgtgagtgt gcttttctga agaggcagct | 56520 |
| ccaacactgc ctcacatctt cctctctatt gttttctttg tgtattcccc cacaatactc | 56580 |
| gcttagcagg attttactg tatgtatttg gggtggatat atgtgtgtgt gtgtgtgtgt | 56640 |
| gtgtgtgtgt gtgtgtgtgt gtgtgtgtgc atgtgtgtgt gtgtgtgtgt gtgtgtgtat | 56700 |

```
tgttatctct tttcatacaa tcatttaatt ttgttcgtgc gttttttcag tttagagcag   56760
gtttttttcc ttagtttctt tcttttttcc ttgtttactc ctgtgtccct tacacataca   56820
cacacgcaca cacacacaca cacacacgta ttcatacttc taattgtttt atactttct    56880 taagttttac cttttttctct tctagttttt ggttgtcaac gctttcatta ttgttaagtc   56940 tttttttttcc ctacttttcc tttttcccaa gtctagaaaa agaaacagac agtgaaataa   57000
aaaaggaatt gagaactcta aacagacttc acaagagaaa atcctcttca ctccatttta   57060
taatcagaaa attaaaaaaa aaaatgttaa agcaaagaac aaatgttagg aaccgtaggg   57120
ggacaccagc tcatgcacgg gacacaaatt ccagagcaca caaatcctcc cctctgcggt   57180
cctaaaagcc aggaaagtac gaaatgatgc ccttcaattc ggaaagtaaa taccatctaa   57240
ccacgcttta aattgatagc aaagctactc gtgtaacaag caatctataa gtgagttcgt   57300
gactgccaag actacactac aagatagttt ttaaaattct ttacagaaaa ggaagaatga   57360
caccggccat cacagaggca caggaaagac tgggtttcat gagaggaatc tatgtcctgg   57420
attgggagaa ataacgtgtg aaatgttgta ctaaaaaaca caatcttcag atttaatgct   57480
atcaccatca tggttctagt gacattcttt acagaactag aaagataata ctaagcttgt   57540
atggaaacac aaaagaccat gagtaggcta agcaggacaa accctacatc acatcacatc   57600
acatcacatc actgaaactc acattatccc acataagtgt aatgacaaag agagtaaggt   57660
gcatccacaa aagcagacag agaacaatga actggaagag ggcccataac ctgcacttct   57720
gtggacagat aatttctgac aaacgtgtta aaaacataaa tgaaaaaaaa aaaacaagtt   57780
gcaaattgga catccacaag gactacattg gatccatatc tatcatcctg cacaaaaatc   57840
aattcaaagt tgggtcaaag gctttgattc aaaacatgaa aagttgaaac tgcacaggaa   57900
aaaaaaaact ttgaagtgta agaactggca agaactttct gaacagaacc tccatatcac   57960
tggaaatatt ctcaagaatt gataaggagg attatataaa actaaatgtc ttctgcacag   58020
taaaagaaac catcaacata acaatagtcc agctacagag tgaaaagaa ttgctttact   58080 ttaacgaggg attggctcct agaatataca aagaactgca aaaattaaac accaaaagta   58140
taaaatgtcc aatcaataaa tgagataatg gactgaataa agaaatatag atagacaaaa   58200
tatgatataa tcaggaagtt gcagataaaa actaaaataa tagtatgtat atcactctag   58260
tcagtatggc tattattaag aaaacagctg ataaccccctg gcaatggata aagggacacc   58320
ttggtggtgg tggtgttctt ctatcagtca ggggcagagc agatggcatg gcagtccttt   58380 gttcaccta gcttgatggc tggctcagtg gcctaagctg ttttatgcct gggagacata   58440
aaaatcaaat caaatccagg cagtgcagtg caagaggagg aagacagagt tctgcaacac   58500
tatgtggggc aggtcctcca ccctacagca tgggagggcc gaagatgcac aggggcctgc   58560
ctaccaccta cccaacacag tccggaagaa ggaaggccga gacctgaaga ccgcaatgcc   58620
acccacaaac cctcaggtgc gtggcataga cagccaaaaa caccacttgc tgccacacca   58680
cgcagtgccg agaatgtcac ctaggggccc gtctatatca ggagcctcca caatgcacga   58740
gtgagtggtg ggcagatgag agagaaagag aaatgcagca gctggacagc agcctgttgt   58800
gaggccatgg tgagatccca gcctcagctt ctgctgagag tcgggtctga ggctgaggct   58860
acacagagta gcggcagggt gtgggttga tatccgaggc tcacattgcc acctgagaac   58920
atggggacat ccctgatctg agcagccact tttgtcgaca tgaatgtcca ggggctgtgc   58980
agaactgtcc ctgcccctca ctggctgcag ctctcttaaa gagatagtcc cgcctctcac   59040
catggcagca cttaggagag caggccctgc acctcgccca gctagcaccg tggagcgggc   59100
```

```
cctggtggca agtgagcaag ccccatgagt gtgggagagt tgacccctcc ttcttctgca    59160
gtgggctggc acaggtgcag gggtgatgcc cctcccacc cctcactacc tcagcagtca    59220
gaaaagtaac cacagggtca ggagagttgg aggacacaac agagttgacc ttggtggtgg    59280
ggacacagat gagccaccac caagatctga gtccaccaca agtctgctac aaggtggtat    59340
atgtacatgg ttgatgtccc ctccacacct cccctcaac gccttcagta gtcaggaaag    59400
aaaatgaaga tgtgtggaca gagggacata ctttggaaca cactgtgaca cactacagct    59460
tccatgatga gatttctatg cttctgttct ctctctctct ctctctctct ctctctctct    59520
ctctctctct ctctctctct ctctgtgtgt gtgtgtgtgt gtgtgtgtgt gtgtgtgtgt    59580
gtgtgtgtgt gtgtgtgtag gagggggggag gttgcaaggg caaagggcag atatgagggt    59640
aaagggacat tagtgggact gggtgtatg atgggaaact caaaaaatta attaaaaggt    59700
ttttttttaat taaaagaaaa gaagtgacaa caaatgctga tgaagatgaa ggaaaagagg    59760
agtcgttatt cacaggtggt gtgagtgtaa gctggtgtgg ccaccatgga aataagtata    59820
actttcctca aaagattaaa cacaaaacta ccataaaacc tatttatatc attcctggac    59880
ttgtgtacaa agggctatat tttactagag aaccttatac attcatgttt attgatgttc    59940
tagacacaaa acttaagaag taatatcaac ctgatgtcca caaactgatg aataaatcat    60000
gaaaatattg tatgtaaaca ctatagattt tatccagtcg tataataaga taggaaaata    60060
agtggaatgg ggggcggggg acattctctg tcatgagtag atcccagctt ccaaattttg    60120
tgtatgagta tttatgtggg agtttagaca ggggtcagga gcctagagac cgtgaactat    60180
agaagtaaat aaaagtactt taaaagaaga ggtgaggagg taggggaggt gatatgcagt    60240
atgaaagggg aaagtggaat actaaaagta caagcagagg tggaaggcag ggagatgagg    60300
ttgtagcctg gtgggtccat agacctcagc caatctctac attcttcttc aatttcttca    60360
gtccccaggc ttcactggca gtagttatac aaccaacctt tgcccagagc atgcgtgtgg    60420
acagaagtgt ttctctggtg gtttccacag ccctcgctgg aataccttga tgcagttagg    60480
ctccatgcct tgttattcct gcgtggaaaa aatattttttt agcttaataa gcttatgtac    60540
agatcgtgtc tcttatgcta gggtgcatgc agttgtattt ttgtacaatc cagtgactac    60600
tgctagagct ccctgtagat tgatcttcat atttaattcc tctacttagc acaataacct    60660
tacaagtcta tggacaagac aaaacatctt caaactagct agcttaccac cttcttcctc    60720
aatgatctat ccaaagaagg ccattcaatt ctagcacaca tatgccaaat tacatcacct    60780
ggggaacaaa actggaatgg taaaaacaac caagcacaat atgtcagtgg tagacacatg    60840
ggggaaggca gagagctcag aattcagttt atcacacgta tagagtaagc tggaacccac    60900
aacagccaat atgtaaattt cagaggctta gcccctctga ggttagtaaa ccctgatcca    60960
cttactgttt tctctttcat gtggagtgaa atggctgtag cctaatgtcc ttctgaaatc    61020
aagagacaca tcttcacttt ccagactggg accagacttt tgtgccacgt tgtgacatgc    61080
acacatgcac acacaggaaa ggacttggct tgtgcccaca tgcctttctt cagggacaag    61140
tgggaatgga cataaggagc gtctcatcct tacgtggcct cctttgtctt cctccttcct    61200
ggccaagacg gtgatttact gcccaaagac aagtccatct gaagcaagaa ctgactatcg    61260
aggactctgt agtgactgat aaactgggaa gagaaaattg gaccagagac ttcaaggcag    61320
ctctcagaca agaatattcc agtgccaggt agggaagcca acaaccttca aactttgcag    61380
agaacaaaat tgtttctgac atgcaggata atcctctctg ttactaatat gggaaaaaaa    61440
```

```
aaactcccctt aaaagactgt ttaatgatgg aaaaattact tagcaacagc aacaaaaaaa   61500
aaaaaaaaag tttctggaat tgttatatct aaagatgtca ctaatgtagt ttgtgaagta   61560
tgtttggaat aatttaaaga tgtgttttta tgcttactgg ctcccttttcc ctctccctcc   61620 ttttccccat ctcccttttct ctccacaaac aggttagaaa ttactctgag gattgccttt   61680
ggtgagggtg aagtgggaag caacattaag aatgaattta ttgaggtgct tcccccagaa   61740
ttctattctc atcactctag tgagttaagt ccaggaacca cagggattgt cttatagata   61800
cttagccttt cctcaataga ccaatcaata cccaacatgg acactctaca gggtcataga   61860
tcccagaaga gcctcatcaa tgctcctgac acattctttg tctgcaaata atgaatccca   61920
aattaaaggt ttcaaccact tctagagtag agatcttagc ccatatccat caaccactac   61980
tgtatgacca aacacggctt cataatgatc tagttcaaac cagatcttgt ttcctccaaa   62040
atgtttctct tatgctgcca actcatgcag tccactccca tgttatagtc cctcattctc   62100
tgtttggaaa aaaattatct cctgtgcaga accagagagg cttttaccgt tttttaactc   62160
tgtttaaaga tattttaaaa aattaattga ggaaaaagaa aagggtaatt tcagaattca   62220
catttttgat ggtgtagtct ctacacacca aacaactgaa aatggtttct gaaaactata   62280
aaatgaatgt ataaaatgaa ctattataaa agaaacaaat ataacaatca gccaatatgc   62340
catgtaaaca cacatatata atagatagga ggacagtatg tgtccttact gcccttgagc   62400
tgccccaggg gaaacctcta agcacagctt gtgcagcctc ctagaagaag cctgtactac   62460
agcatccgtt ttacagtcag accatacacc gtatccagtg ccccatattt taacaaaaac   62520
atctagaaac atatttcctt ttattaactg atttgtgttc gttgtggtct acataaacta   62580
gtttatccaa actcctatcg atggatattt ggtattccta ttcttttttac ctttttaaaaa   62640 atagtgtagt ctctacagac atctgagcac acttagctct catttcccac cccaggatgg   62700
cctaaggggt tcctcttcct cctactccag tattctctct cttacatgca tgctgctcct   62760
attcggtaat tttgtccctc gtgtctactc taataactgt gcactaagtg cataaacagc   62820
agatttaagt ctaagctttg ttctttaatg tcacagacaa acaatattaa tttctagttc   62880 atagagttttt atggatagct aaatataatg agccatatat gatgtctggc atttttataag   62940 ttctcaacaa acatcaattt ttatggttga tatcgcttcc ataactacag agaaaaatca   63000 ctttttcattc tctttatgat ccatgttaat tgagatcatc agctacttta catagttaag   63060
ttttattgac aatttctctt ttctttctat ttcctacttg attcttttct ttctccatct   63120
tctggtgaaa cacatgtaga atctgccatt ccagattagc aaaaccctaa taacataaac   63180
aagtagacct ctctaatctt ggttagagtt gcaattttttc taagaaagtt gattcttgta   63240
gaggtcagta ctaacctttt gtctgttgta gattactatc actgatctat actattggct   63300
tttttttatt gcttttttttt catttattct gcaaatgtct gatgagtgct tgtcaattaa   63360
aaataaatgg accagaattc ccaaaatcct agctaataaa ataacaaaca tcttactatc   63420
tcagagcaaa tgggttctac aggcctaaca acctatctat aaagccaact tggtggtaga   63480
aagaatctct tgagctgaat cttgaatgac agctcaaggg atagggagga cagggtgttc   63540
agaagcagag aagatgcctt gtaaatgtgg aaggctgtgg caggagttgg aaggactttg   63600
gggtggtagg aaggggatgg gaatgggtgg ttacaagaga aacaagactg tagtaaataa   63660
agctgaaact caaagcaagc tttcagcatc tttaattgga gacacaaact tcaaaggtat   63720
catgaatgtg gttgatcttg gtgaaagttg agcttcacct gtcctaacaa cagaccaatc   63780
catgagtgaa agcttatctt tctcctttat taatggttgc tgttgtatcc ataactcaat   63840
```

```
tccaaggat atgaaccttaacatatagat ataattttgt gtaccttcta tgaaacagca    63900
ttaaagcaaa gaagttcaaa tagaaagact ggcttagtta ttattaacta agagatgcta    63960
gtgagttcta aattaatacc atttaaaatt tataatttgc agaattacca ccaccgccac    64020
cactcagccc aggaaaagtt acaagaact ggctatccaa tttgtttgtt ttcctccttt    64080
ttagagttct tttatttatg tgtgagtgaa tgccatgtac ttatggatgc agaggctgtc    64140
agattccttg cagctggagt aatagacagt tgtgagctac ttatagtact agaactaaga    64200
tcctatggaa gagcagcgag tgccactaac tgctgaggcg cgcagtccag atgtggcaag    64260
ttgctaaaga aaggaaccat caggccatag acgtaaatat attctcttct tggattttag    64320
gtcttaccta agaaaataaa cacatgctat gtcagagaag cctcagggtt tccacacctg    64380
ctcgaaaagg gagttgagct tcagcagctg acccaggact ctgttcccct tggtgagaa    64440
gggttttttgt tcagcaagac aatggagagc tctcactgtg gtggacgttc ggccaaggga    64500
ccaaggtgga aatcaaacgt gagtagaatt taaactttgc ttcctcagtt gtctgtgtct    64560
tctgttccct gtgtctatga agtgatctat aaggtgactc tgcaatcagc ctctgatatc    64620
cttcagggaa aggataaaga taagtctgta gtcaaactcg agaattgatt gcacattttc    64680
tttgaagagc aagcaagatt cagtcattgg gtgagaataa cttgtctaag taatagcttc    64740
agaaatgtcc tggggaacat aacatgttct ggacagagcc ttggtcaatt gtcagaaagg    64800
gagttttgt ataggaggga agttaagagg aaccattgtg tgtacacttt tggccagggg    64860
accaagctgg agatcaaacg taagtacttt tttccactga ttcttcactg ttgctaatta    64920
gtttactttg tgttcctttg tgtggatttt cattagtcgg atgccaggga tctaacaaac    64980
ttcattcccg ggttaggtac agaggagggg aaattgttcc acaggacgct agcttgtggc    65040
taatttttaa gatttctaaa tcaaataac ttcattgggg gaaagaggct tgctgagctt    65100
tcagggaggt ttttgtaaag ggaaaagtta agacgaatca ctgtgattca ctttcggccc    65160
tgggaccaaa gtggatatca aacgtaagta cgtctgtctc aattattcgt gagattttag    65220
tgccattgta tcatttgtgc aagttttgtg atattttggt tgaataaacc tggtgaccca    65280
gaagtaaata gcaggacacc agaaaatgaa cttaaaaagc tgagcaaata gacgaatcat    65340
tgggtttgag aggagaatag gattcatggg ggaaatgggg aagaaatagc tagatttttc    65400
tctgaacaag cagcctatct catatgattg gcttcaagag aggttttgt tgaggggaaa    65460
gggtgagatc cctcactgtg gctcactttc ggcggaggga ccaaggtgga gatcaaacgt    65520
aagtgcactt tcctaatgct tttcttata aggttttaaa tttggagcgt ttttgtgttt    65580
gagatattag ctcaggtcaa ttccaaagag taccagattc tttcaaaaag tcagatgagt    65640
aagggataga aaattagttc atcttaagga acagccaagc gctagccagt taagtgaggc    65700
atctcaattg caagattttc tctgcatcgg tcaggttagt gatattaaca gcgaaaagag    65760
attttgtta agggaaagt aattaagtta acactgtgga tcaccttcgg ccaagggaca    65820
cgactggaga ttaaacgtaa gtaattttc actattgtct tctgaaattt gggtctgatg    65880
gccagtattg acttttagag gcttaaatag gagtttggta agattggta aatgagggca    65940
tttaagattt gccatgggtt gcaaagtta aactcagctt caaaaatgga tttggagaaa    66000
aaaagattaa attgctctaa actgaatgac acaaggcgc gctgcagata gcgttgtctt    66060
ctagaagttt aactgggaga tttgggggg gatgaggaat gaggacactt caagataaaa    66120
gagggctaaa gtcaagatca gctgcataaa tggatgtgga agcaaagttt ttgagataaa    66180
```

```
ctgaatgact cagaggaaga aaatgtgcag atgaaaatag gggcttggag ctctgagaac    66240
agaagtaagt tgagtttcca caaatattgt gttgagcttt gtattaaatg tgggatagca    66300
ttgttgattg aggagagcct tagactgttt tctctcttct gtctcctaat tatttgacga    66360
ctacaaaact cagtattatt ccctgaaata aaaatcagta aaatgtttga agtatgact     66420 gtttgccacg tagaaatggt ggcttactaa ataatcagaa gaggcgcgat tcttagagtc    66480
taaaatctgt cacaaatgtc aaatgagag actctgtagg aacaagttct gtacagacag     66540
ctcagggtct ttttggctc atttctacat gaatgtaaat ttgaaatgat ctctttatt      66600 acgacactag aaatacaatt tgggtgtat aaattatgtg ttttaatggc cacgatttta     66660
taagacatcg gcccttcact ttcccagtta ttaatcgctt gtgttttac gccgccagca     66720 aggggctgaa atggtccgca acctcttctt tacaaatggg tgacttcgcg gccacgccag    66780
ccatttagag ttcacccttc cctgccgcta acggccatgt gaaccccgct gtagggcctt    66840
ttgctccacg tggaccactt tcctgaggca cagtgatagg aacagagcca ctaatctgaa    66900
gagaatagag atgtgacaga cactacacta atgtaggaaa aacaagggta acttattgga    66960
gatttcagaa ataaaatgca tctatcatta tattcccata tcttaatttt tcattaggga    67020
attagaaaag gcttaaaact gttttagcca gtgttatatt aaaagtttta tgcatgtagt    67080
cttttggagg taaaatctac aaccagcaaa agtcacggta aacctacttt gactgaaccc    67140
tcattaaact ctgtttaaaa attatatttc atattaactg gttaaaataa gataaatttg    67200
tgacatggtc ttaactggtt aggtaggata ttttttcttca tacaaaaaat atgactaata    67260
aaaatttaat ataaattcct aatactttaa ttctgtgata gaaaaatgtt taacttggct    67320
actataatcc cataattttg aaaactgttt attaatttgt ttctgtggtt gaccttccc     67380 tagctaaagg caactgttta aggacccttt aaaacccctta aaactacttt agagtctttt   67440
aagttattta accacttta actactttaa aacaatgtca actctgtttc aaactattaa     67500
tttctttaaa ggggaaaaac agctggtcat aattctgttg ttttttcttgg taaaggactc   67560 tcagttttca ttttttactac cactctgtca ctcaagggtt ggcatctcaa cagaggggc    67620 tttccgagaa gccatctggc agctgcttaa ggtcagaagt gaagccagcc agttcctccc    67680
aggcaggtgg cccagattac agttgacctg ttctagtgtg gctaaaaatt gtcccatgtg    67740
gtatcaaacc attagaccag ggtctagtta gcgctcagaa tgtttctgga catccaccca    67800
aacacatacc ctgacttaag gccccatcca tagagtaagt ttagcttggc cacaccaaag    67860
gaagccatag agaggctgat atcagagtat tcttggaata ggcaggagaa aatgaaagcc    67920
aacctctgct cctaccttac atgtttgtgt taggggtgtc agataaactg gtctggtatc    67980
tctgtctgat gcatggaact attgtagctg aagaagaaca tagtttcagg gaagaaaggc    68040
aatagaagga aggctctgaa tagcttcaaa gggtcagacc caatttactt tctaaagtag    68100
ctagggacta gggaataact caaaacccac aagactgtgt acatgtgtcc tggcttcatt    68160
gttcctaatc tgtagggata agtgtgcttt tctgtgtgtc tgtgtgtctg tctataacat    68220
gtctataaca tgcataatgc actgatttc cttgttactt cataccatcc tctgtgcttc    68280
cttcctcagg ggctgatgct gcaccaactg tatctatctt cccaccatcc acggaacagt    68340
tagcaactgg aggtgcctca gtcgtgtgcc tcatgaacaa cttctatccc agagacatca    68400
gtgtcaagtg gaagattgat ggcactgaac gacgagatgg tgtcctggac agtgttactg    68460
atcaggacag caaagacagc acgtacagca tgagcagcac cctctcgttg accaaggctg    68520
actatgaaag tcataacctc tatacctgtg aggttgttca taagacatca tcctcacccg    68580
```

```
tcgtcaagag cttcaacagg aatgagtgtt agacccaaag gtcctgaggt gccacctgct    68640 cccagctcc ttccaatctt ccctcctaag gtcttggaga cttccccaca agcgacctac     68700
cactgttgcg gtgctccaaa cctcctcccc acctcatcct ccttcctttc cttggctttg    68760
atcatgctaa tatttgggga atattaaata aagtgaatct ttgcacttga gatatttgtc    68820
tttcttacta aatagtggtt aacagttatt tatcctgtaa cctggtttct cttctaaaga    68880
agttaaatgt ttagttgccc tgaaatccac cacacttaaa caacaaataa aactctcccc    68940
cttgccctac ttggttgccc actacatggc agtcctctct aaagttcaca agtactattc    69000
atggcttatt tctctgggcc atggtaggtt agaggaggca tacttcctag ttttcttctc    69060
ctacgtcacc aaagtcctga aggaggacag tgtttacaag cacatattct gtaatctgtt    69120
tcaacctttc cagaaaccctt gacaaagcaa tggggagtca ttatcacagg aaggggagac   69180
aacttaaatg accaagcaac cgaaaaacac gttgaagccc ataatagtac ctgggcttca    69240
tcagctctta ggctagcatg agctggctcc tatctgccat tggcaaggct gggcactacc    69300
cacaacctac ttcaaggacc tctataccgt gagattacac acatacatca aaatttggga    69360
aaagttctac caagctgaga gctgatcacc ccactcttag gtgcttatct ctgtacacca    69420
gaaaccttaa gaagcaacca gtattgagag actcatttat gaaagtctaa aactggatac    69480
aaccaaaatg tccaccaaca gttaaattat gacatgttca caattgagct attacttaat    69540
aaggagaatt aataaaataa aacttaagag catagtttaa tctcataaac aagataataa    69600
gcaaaacaaa acattttttc atccatgtaa gtttaaaagc aggtaaaatt taaaattaag    69660
agagacataa gttttgaggt agcaagatgg aaactctggg gcttggggaa tgttctgtct    69720
ctctgtatgg gatgtgaaag ttactattgt ggaattggga tctatgttct tcctgtatat    69780
attgtatact tcataataac ttcacctaaa gaaatatcta atacccagtg catacataaa    69840
agaggataca aggaatgaat catacgtcaa ggccagaaag acaataaagt agggggatcca   69900 ggatcaaatc tcccacaacc ttgagccttc tactattctg ccttccagag ctcaaagtac    69960
aaaacacata attcaaacac atgatccctc cttggggtct cttccttcat gcatcgaatt    70020
agaaatagcc atgtataaaa tgagatagaa gagaccttca tcaacaggtc aaagaatata    70080
ggtaattttg tctgggtatg aagagcccac gtatcaaagg ttacattagg aaggaagag    70140 gacactaaca gtgactttca ttctccccct cttcctggag gccctgcat ttagtccctc     70200 gtgggctcat ccactcagca cacatttact aagcatcttc tcagcctaca ctctgaaggc    70260
agtgcagaat aatgttagtg tcccttcccc cagttaatat gcagtccagt ttccctgctc    70320 cttcccttc tcagtccaca taaggatgat gggaaaggac agtcaccaaa taggagaggg    70380 caacccttg cctcctacc tcttgagaat gtacattatt atccactttt tgaaacttct     70440
tttaattgct ttttttaat ttgtcttttc aaatagcata accttgttca tccatttctg     70500
ggaaccaaat ttatcaatca acagtgcctc taatctggct attaatacaa aaatgcctcc    70560
tcaaaatata tatgttcgag tcttatctaa aacagaaccc acaataaaaa agaagaaaga    70620
atacatataa gcatttatat aattctgagc aaccttgtgc tttgtgaaaa aaatataatc    70680
taatgtcaca tgctgtattc ttttttattta acactggtga aattatacca ttagagagaa    70740
agaggacaga tcactgatcc taggatctag ggatgttaca gataagaaaa caaatgtgac    70800
aaagagctgt cacaaggagg atcttcaagg tcacagaatc actgtcttga tttcagtggt    70860
ggttacatac atttaaatat gtgataaaat gttgttgaac tatattcata tattgtacca    70920
```

```
acgtcaaatg cttaattttg gctctatagt ataattatgc actaaataac tatttggaca   70980
aagaaaatga tgtttacatc aaaggtgagg ccatatttgt taggaacata acttaaaaac   71040
cattttggat aactaatgaa aagccatttt gtgtgccttg gcatatcatg cctaagctgt   71100
caccagatag atctaataag acctaagcct cagaagcaag cccctgccca gcaagcaggc   71160
agcacagata agagctaaac ccaggacagg ccatgatatg ccaatgaact accttcaagg   71220
tggtgttgct gacctagtga accagcccca agctgtgagc cccaatagca caaagctact   71280
gcccaaagaa attatacaaa aattggaact ttgggaatgg tgtgcaggat cgctctgctg   71340
tatgcctgga acacagcttc tctatgtttt gtattgatac cagtctagaa gcttccaaaa   71400
ctttctcact gaagaagatt ccccatgtgg gacccctaca gactcttttg cccaaacaac   71460
tgcttccctc ctggtgtgat atctgttttg cttttatgtt agcataatat tataaggaat   71520
gtttgtgtga ataaaccaaa catattttaa aagcaaatat tgtatgcaca tcctaattgc   71580 taaaagttt acagctaata gtcccatgct ctccacaata ctggatccaa ataagtccta   71640
atttcaatgt tgggcatcct tacagagaga aagacattaa aaatgaagag acatgcagag   71700
agtgcaccat gccatcgtgg agacagactg aagtgacaca actgttagtc aaagaggatt   71760
aaggacttcc agaagccacc aaaggaagga ggtatgaagt ggtttctccc tcagagtatc   71820
cagaggagac taaaccaacc aacacctttt tgcttaagac ttcttgcctt caggactgtg   71880
agaaggtagc ttcctattgt tctaagcccc agtatgtggc attttgttaa ggtagagtca   71940
agaaaccaat aaaatgcaga cagacaaaag gatagctgag ttttccaggc ccttccttct   72000 tattttggt tttgttggtg gtggtggtgg tggtggtgat ggtggtggtt ttgtttatgt   72060
tttgtttggg gagttttttg gggttttttt gggttttgtt tttgttgttg ttttgggggt   72120
ttttgttgtt gttgttgttt gcttttttgt ttttgttttt ttgtttttttt gagacagtgt   72180 ttctctgtat agccctggct gtcctggagt tccttctatc tctaatgtct acatctcaga   72240
ggggatcctc taatttcaaa tgagcagtag ctctccattt ttagctctta tttattcatt   72300
tatttactta cttacttatt gtctgtagat gaaagaattt tggagtggga aagggttcat   72360
gagcccccag caactaatga ggagctacag acaattgatg tttctgggga aaggagactc   72420
agtttctttg agagtatagc ttctgacggg tcaaccatgt tcctgtggct gatgtcacac   72480
ccaggagtat gcagacaaca gaaactggag ttaatgagtt gttttaaaaa taaaaagggg   72540
catgaagctt gggatagaaa ttaaggataa atacaattaa atacaggaaa ttctgaaaga   72600
attaataaaa acatttcttt ttttaaaaaa aaatccagaa ttagctatgc ttcttcaaaa   72660
ttgcttctgg agaactttac aagttaaata agttatattg tagaaaaggt agagaggaga   72720
atagtggaag agagagatga ggagacttca aaaggagtgg agggagatag aggaggagaa   72780
agcagaagca atggctgata gacacaggat aagagggaac agaaaggaga aagaggaagc   72840
caggatgggg atttctttgc ctatctgtga cttgcacatg gtcttggcaa ttattgatga   72900
gttcaaggct taattcttca cttgtgccaa ctcaacagag tctttctttc ttataaccag   72960
gcccccagta tgctcatgta tgtatcaggt cctcttatct ccttatagca atcctgttta   73020
taactgggta actttgtgaa gggaaggaag tgcacactga gatgtgctac aactttttaa   73080
tacaaaattt tgaagagttt gtacaatgta tgtataatta ataattaata ttatgcactt   73140
tagattttga tttcaactca agatactaat tctatatata tgggttaaat caatatatta   73200
ataagtttaa tttcacatgc ttattttat cgtggttttc gagacagggt ttctctgtat   73260
agccctggct gtcctggaac ccactttgta gaccaggctg gcctcaaact cagaaaccct   73320
```

```
accctgcctc tgcctctgcc tctgcctctg cctctgcctc tgcctctgcc tctgcctctg   73380
cctctgcctc tgcctctgcc tctgcctctg cctctgcctc tgcctctgcc tctgcctctg   73440
cctctgcctc tgcctctgcc tctgcctctg cctctgcctc tgcctctgcc tctgcctctg   73500
cctagtgctg gaattaaagg tttgcgccac cacgcccggt gaaatttta aactttatat   73560 atgtctcatt ctatttctat cagataggac tgtgtaaact gtgctaaact aataaatgtg   73620
ccctcaaaag taatcgcaag ttgtattgtt gttgttttgc tttgctttgc tttgctttgc   73680
tttgctttgc tttgctttgc tttgctttgc tttgctttgc tttgctttgc tttgctttgc   73740
tttgctttgc tttgctttgc tttttgttt tgggttttt tccgggggag ggagggtgga   73800
gaaagaatct tactatgaag ctctgactgt cctgggaact cactatatag atcaggcttg   73860
attcaactca tagagatctg ccttcttctg cctcccaagt gctgggaata aaggcataca   73920
cctccatgcc cagatagtga tcccaagttt tagcaaaagt ttctagactt gacattaatc   73980
gatggagata gacatgaatt acacaaagaa ctaatgtgga gtttacctga atcatactct   74040
atactttatc agagattaaa ttaacattta ataatccagt gccaggctag aggcaccatt   74100
caatggcagt gtttgccatc atgcataggc ttagtcttca gtgctgaaag gcattggggg   74160
caatattact cattatacag atgagaaact gggaaagact tgcctcagat tctctactga   74220
aaggctgagt ttgtggcttc tagaaaatcc tttactttca atattttaa tgtataattt   74280 ttttatttcc actgatttta ttttttattt ttaacattta taagaaataa atgcaataaa   74340
ccaaatacat ggacaaaaaa atacaagaat catatgatca cctcaatgga aggaaaaaaa   74400
aagaaagaaa aagtctttga taagattcaa cattcattct tttttatta gatattttct   74460 tcatttacat ttcaaatgct atccccaaag cccctatac cttcccctgc cctgctcccc   74520
aacccaccca ctcctgcttt ctggccctgg cattcctctg tactgaggca tatgatcttc   74580
aaaaaaccaa gggcctctcc tctcattggt ggccgactat taggccatct tttgctacat   74640
atgcaactgg agacacagct ctgggggtta ctggttagtt catattgtta gtcctcctat   74700
agagttgcag accccttag ctccttggat actttctcta gttccttcat taggggccct   74760
gtgtcccatc caacagatga ctgtgagcat ccacttctgt atttgccagg cactggcata   74820
gcctcacgag aaagagagag ctatgtcagg atcctgtcag taaaatcttt ctggcatatg   74880
caatagtatc tgggtctggt ggttgtatat gggacggatc cccaagtgga gcagtctctg   74940
aatggtcctt ccttccatct cagctccaaa cttttgtctct ataactcctt ccatgggtat   75000
tttgttcccc attctaagaa ggagtgaaga atccacactt tggtcttcct tcttcttgag   75060
tttcatatgt tgcatcttgg atattctaag tttctgggtt aatatccacg tatcagtgag   75120
tgcatatcat gcgtgttatt ttgtgattag tttacctcac tcaggatgat atcctccaga   75180
tgcatccatt tgcctaagaa tttcattaat tcactgtttt taattgctga atagtactcc   75240
gttgtgtaaa tgtaccacat tttctgtatc cattcctctg ttgagggca tctgggttct   75300 ttccagcttc tggctattat aaataaggct gctatgagca tagcggagca tgtgtcctta   75360
tcaagttgga acatcttcta ggtatatgcc caggagagga attgctggat cttccggtag   75420
taccatcaac atgcattctt aataaaagcc ctagaacaag gaggactgta ggaaacatat   75480
tccaacataa taaaggttat gtatgacaaa ctcatgacca atatcatcct aaatgaatga   75540
aaccattaat aagctccatt aaaatcagag gactgcccac tatccctact tctcatccat   75600
aatgagattg aagcattagc tggagcaata aggcaagaga agggatacaa atgggaaaat   75660
```

```
attaagtcaa attgttttca attgaagatt atattatctt atacccaatg acctcaaatt    75720
ttgactagaa aaattgtaga aattatcaat aatttcagca aagtgttatg atgcaccaca    75780
tccttattct tctccccagc ttctgcttgc ttctctcttc ttgctcttca tcctttctgt    75840
ccttccatct gcctgcactc ttgtctcaag actgagtgca gcgtgtaact ctcctgtgac    75900
tgagtatctc acaaaacgtt ctacctgcca aacctggatg agccctttgt ctttctgaag    75960
ctatgaggct ctctacatag actcaagaag gaaatgacag ggaggaggta ataatgaagt    76020
ggggaaggct gacattagca ttgctcctgt gtggctcctt aatttctcat acttcacact    76080
gagatgttat taactgtgac tcataggtga agaagccaga gctaaggttc tcatatttga    76140
gtgttataga atgagtagag cagtagttct caaactaagg gtcatgactc ctttatgggt    76200
caaactaccc tttcacacag gttgcatatc agatatccta attttatata catatatata    76260
tgcatatgta tatatatata tttcacaaca gtaggaaaat tatttagtaa tcattttata    76320
gttgtgggtc atggcaacat gaggaactgt attaaagggt tgcagcatta ggaatgttga    76380
gacccactgt aatagagaat gaggcttaag gcagggctat aaagcccaat ggaccatgtg    76440 cctttttccaa catttgccac atggtaagct ctgtatagac ttttttaaaga acattggttt    76500 gtaatttttaa atggataagg gtcttcactg tctatcaccc atctatataa taaatacata    76560
agttttgatt ccaccatgga ttcaaatgca aaaatcctca acctaagaca tagcagtgaa    76620
acattgatga ccaaatagga aatccatgta gagaccttct atcttctgat ggctccacag    76680
gcaccatctt gcaacagagt tctactttgc taccagtaat gaatacagtg tctcaactcc    76740
tgccattgaa tcttcaggaa gcccctgaaa tgacttgtac tacaccattt cttaaagaca    76800
gaaaagctaa gactagagg gaataaatgt catgcctgag atcatgcaac caattaagtc    76860
caacttggcc tgatcaagag gcacaattca aaagcaatgt tgttccttca ctagctcttg    76920
tgtatggttg ctgattccgg aagcaaagta tcagtgaata tccctagtgg aaaagactt    76980 ggaaatcaaa tgtctcattt aacagattag gagatgaaac ggtagactct gtgtagtgt    77040 acacccctgt gatcccatcg ctaggaagac tgaggcagga agtcctcgag ctcaaaccag    77100
cttaggctac acagagaaac tatctaaaaa ataattacta actacttaat aggagattgg    77160
atgttaagat ctggtcacta agaggcagaa ttgagattcg aagccagtat tttctacctg    77220 gtatgttta aattgcagta aggatctaag tgtagatata taataataag attctattga    77280
tctctgcaac aacagagagt gttagatttg tttggaaaaa aatattatca gccaacatct    77340
tctaccattt cagtatagca cagagtaccc acccatatct ccccacccat ccccatgcc    77400 agactggtta ttgattttca tggtgactgg cctgagaaga ttaaaaaaag taatgctacc    77460
ttattgggag tgtcccatgg accaagatag caactgtcat agctaccgtc acactgcttt    77520
gatcaagaag acccttgag gaactgaaaa cagaacctta ggcacatctg ttgctttcgc    77580
tcccatcctc ctccaacagc ctgggtggtg cactccacac cctttcaagt ttccaaagcc    77640
tcatacacct gctccctacc ccagcacctg gccaaggctg tatccagcac tgggatgaaa    77700 atgataccc acctccatct tgtttgatat tactctatct caagcccag gttagtcccc    77760 agtcccaatg cttttgcaca gtcaaaactc aacttggaat aatcagtatc cttgaagagt    77820
tctgatatgg tcactgggcc catataccat gtaagacatg tggaaaagat gtttcatggg    77880
gcccagacac gttctagaag tacctgagag tggcaaaaaa tagttgtgct aaatagtttg    77940
gccatcttta ggctgagaga ctaggaaata cagcgatgga ctatatcagc attgcaggat    78000
agttgtcagt aaacacccca caacccataa cagaagtatt ctcttctttc tatatccctt    78060
```

```
ttccatccat gtagatggct gtcttcatat ttgttctaga cattggttct actcaagtca   78120
aggcaagtca tctgaccttc accaagaaag tccagcatcc aggaaaggaa attgtatgtt   78180
tggatatgtg agtagtcact tttattcatc ttgtgggtgg tttttggggc agaatctcac   78240
tatgaagcct aggtttgtct caaacccttta atcctcccat ttaagatggt tataactata   78300
tacaaccatg ctggacttca ttccaatcat tggtatctcc atgcacctac ttctgaattc   78360
tgttctacaa ataatatagt ccatgataag aagttccagt gtcaaggtgc ttccagtcta   78420
aggtagacac aatcaaccag aagttgcaac atggaatagg tgggtatgtg tgacttatat   78480
tgacagttct aaagaaccaa gctacaaaaa gggcacacat catgtattga aggtcaaaga   78540
aggtgtatac ccgcatccac ctgtcaaatg ttagtcaaac taggaactaa ctggcgccaa   78600
ggacaatcct cacagaccat tccaatgctt cagccctctg actaggaatg ggtcatgtga   78660
gagttcatca attacaaact tatttgctct tcctttgtct ttagttctct gtctatatta   78720
aagcaatacc tacaagatct ctacttcatt gtcactctga acaataaatg aaatactaca   78780
tatagtctac ttattataag acatggtatg tcttgtatat gctcacacct ttttatagtg   78840
tcttttttat ttaactgttt ggttgacaat ttgattttg tggctgttgc tgttgctgtg    78900
cttatttggt ttttgagaca aagccttctt ctagatagcc ctggctgacc tggaactcac   78960
tgtgtagaac aaagtagcct caaatttgca gtgatccttc tgcctccacc tcccaagtcc   79020
ttaccacata ctaccatgta ttgctcatat ttttaattat taacacagtt tcttggacac   79080
catcctgagc ccagtagata ttcttccagc agtaacccca caaggaatcc tgcagtttag   79140
actgaaatat ttttttcttcc aatatgcaaa aacacattta gcaatgtaac aggtaaaaaa   79200
aaaatctcac aattgggaag atagagaaaa tgaggcacac agtgaagata ttgtttgcca   79260
atcctgtatc tcaccctagg cctagggagc taggtcagat ccacatagtt tcccccatcc   79320
acaccatcca gttccataaa gaaatttagg aaatgttaca aggtacatgt gtatctcaaa   79380
agactaatat tttatactga agaataaaag aaatgtactt tctaatcgtg agcaaagagt   79440
ttcacgagat ccaacaatcc agctgcctcc tctcaccagg acactgagtt gacggtgtgc   79500 tctttacccct tgttagagag agagagagag agagagagag agagagagag agagagagag   79560
agagagagac cctggatact gaaatatatc acagtcattg gcctacaaac caagttagac   79620
ctgccttcag ttcacagtca gggagtgatg atgaatttta tatttttggc ctttcgtgat   79680
acagagattt ttttttataa ggggaaagaa ctaacattgt aaatagagga gaattaaaaa   79740
caaacaaaaa cataacaaac aaaactaaca accaaaaata tatatgac cttggggaat     79800 taagacatag ttgacaccga aattataaga gattgtaact ttatgccccc acaggtaacc   79860
tgaattgttc agtcctatag atgtgacttg cccattaaaa tcagaggaag actgggtaag   79920
gtactccagg accagcagga tatggcaagc cctgcccatc tggtgcagga gcatgaccca   79980
catgtgatca ggactcacct tccttccagt cagagcctca ggctctgcac aaagactcaa   80040
atgtgctgcc tgggaaggag gaagggagg aggagggctt ctgacctatt actacttggt    80100
ccacaatggt ctctcagagc cctaaggatc tgcacgtggg ctccactgca cagcttcctt   80160
tgttatcaac caaaaacagt aatgtagaca tgaggaaatt ctggaataag gttcaccgtc   80220
ctgacactaa atggaacacc ctctacagct gcccaacccc tcccctctc catctccctc    80280 tccctctctc tctctctctc tccttcccc tttccctctc ctccttcccc atccatggct    80340 gggggtgggggg gcttctggtt tagttttttgt ttatttggat ttactgagac atgatttcac 80400
```

```
aatctaccca agttggcctc aatctcacaa tcctcctgcc tcaacctcct gagtgctaga   80460
attgtaggta tgtgtcccac tgtctccaat ctttctctca tccttccttt ctttctttct   80520
ctctttcttt ctttctttct ttctctcttt ctttctttct ttccttctga agcaattgag   80580
aatacttcat gggtatagat aagagtattt atgaagtatt ttatttaaca aattaaaatg   80640
tttgtgcttt agttccataa tatgcccaat taaaaattta ataactctg tggaaaagat    80700 ttttttaagc tggggaaaaa gtagagaaaa aactatgaat taaaaaaagg aaaacactgg   80760
gaggttgcaa tggctggagg aacttgactg tgtgtgtcta ggaatgaggt tgtgtgttgc   80820
aatgcttgtc acctagtctg ccactccata ttccaggatc cattgttaaa tgacatgctt   80880
ttggagactc caatggtgat gttaaccaaa gcagctcaca ccaataatga aagagtcccc   80940
tggattatgg caatagaaat ataacccact gcagccaaaa gactagaagg tcccgtgctt   81000
cccagccctg caatgccttg cttttttattt acatctaccc tccattccag gcatccttta   81060
ggactataaa tgttaaagat acagacagga acttctaaga ataactacca ataaaaggag   81120
caaagtccta gaagcaaagc aggcatatgt gacaaatggc agcacacagt ccccactgct   81180
gccaccctag cataagtgca tacaagcata aacatattct ttgtccagac tgctcatcag   81240
tctcctactg actctctcca ctctcaacct cactgtggct ttttaacaca ttgatgttca   81300
gaaatacagt gaaatacagc atttcttctt tccagtccta tacattgttg caatagatgt   81360
taagtgacat taaacaaatt ccaagcattt gtttcactga cctgcttgat acaaccatgg   81420
caaagaacat tatcacccct gttgtcagat atcagataca tgtaatgggc ctggagaaat   81480
gactcagcat ttaaggcatg gactgttttgc tcttctagaa gaagtgagtt tgcttcccag   81540
attcgtgtaa tgtcccaaaa tactgagaca taaatgtctt aactgtgaca ctatcaaatc   81600
tgttaacctg aaaactccta tgacctgttt cccttcaagc atgtctgaac aatgaaaact   81660
tggctctact tccatctgac ctgaagaaat ttcatctttc ctgaaatggg tatctcctac   81720
tctccacccc acactaaccc tcttcgattt tctacgtcac aagatttact aaatgccacc   81780
tatcatatgt gtatttgact tgtgcaagtt tctgggtcta gtagcacaac ctcaaaatct   81840
cagcaacttg ggaagctgag gcaggaggat ctcatgttta agacttgcca gggctgtggt   81900
gcaaacttga agctagtctg gttaagttag tgaaaccctg cctcaaaata tctatatagc   81960
ttgggatgta attccatggc agagtgcttg cctaacatgt ataaggcccc aaatttaatc   82020
cccagtacca caagacaata atgtacataa ctataataaa ttttacatag taaactttta   82080
taagtatatt tcacaaatat tttcacaata gacagaatct attgtccaat aagcaaaacc   82140
tgatagtttc cttgaaaact gtgcgctaaa agcatttaat gattgtaatc atagaaaact   82200
tagaggaagt catccttgat ttccatgcct cagtgtataa tttactacca ctcattggaa   82260
acaggatttt tcaaaccttg aaccttagtt aattgtattg ttgttctgtt attgttgttg   82320
ttgtggagtt tgttacaaag catagcacct tggtctgacc agcatctgtt gaataaatga   82380
ctagatgagc aaatgtgttg ttgatggcag atgagtatgt ttgtccatgt ttaaagggta   82440 gttttttttct gtaagcatgg gtgtgtttgt tttctggata cactgactga cagagtgtga   82500
cattattacc ttctgtttac aggtgaagaa gcagaactgt ctagagactt gctcaagtgg   82560
aagtcacctc tcacacctgc cctatgcagt caggccttct gtgcacacaa tcaattgcct   82620
ggattaatgt cacaggaaat ccactctgtg tgtattttc tttgtgtcat atttctgcat    82680
tgtaacctga agctccagaa atgttccctg taaggacagc agactccacc ttctgggcc    82740 agacagctag cacaaatttt tctcattctt gactctggat aatccagtcc tattccacca   82800
```

```
gcactaccct ccacccagta ccgtggccac attgtgaata tacatggtca tttactgtta   82860
gtgtcaagag agcgagtcta cactggggtc gagtaatttg gtcccgtgta agagttcatt   82920
aagttggcag ggaaagaatg cttagtcac tctgattgct ttagaattac tggagtttca   82980
caagtggaag aggggtgtgt gtgtgtgtgt gtgtgtgtgt gtgtgtgtcc agacaaattt   83040
ctcaaacaac ctcatttaat aagaagaata aatcttttaa aagacttttc aacatttact   83100
gcaatatata catacataaa aatgatctat aaacattcaa tttatttta aaaactgacc    83160 acttttcact tgagttaaaa ccattttgca gacatgagaa agactctaaa ggttagaggc   83220
caggtgtgtg tgccttacgg cagtagcctg actcactcta ccttgttagt agctaacatt   83280
aaaacaagat tagaagtcag gtctcaggac tttccattct gctcttcctc tacactcgta   83340
acctaactta gaccaggaga ccctaagagg ctgtccagta gcatgaggga tgagtgtacc   83400
ctcagtgaga gaaaggccag agcatgtcag ccaccctgtt taactctaac tcagacagga   83460
atttggtcac tacactcact ggcactaaca ctcatgaact tagagaatgc ttgcattggg   83520
caagctctcc tggactggct taggtaaaac ttccacctat tagtgtgact tgaatcacaa   83580
atgtgattca atcacagttg tgttgtgtgg tctcaggttc ctctcctcgg gcaagaaccc   83640
agttcaagtc ccagaatagg aagcattgct agctacagta taaagtgcta catggaatct   83700
gcacatagct gaagaaccaa agcttttatt ggataaggtg ttctttccag aataaagcct   83760
ccatcagcca agaaagatgt agagatgggg aaatgcccca gcagttaaag cactcacatg   83820
aacccaagca ggaggacctg agttcagatc cccacaaaga accggacaca ggaggacaca   83880
tctctaattg cagcacgcct acagggacaa gagaggtgga aactaaacaa tcgctggaag   83940
gaagtatgca ggccaagcac cctggaatgt ttaatggcaa acaagagacc ctctctcaaa   84000
cgaagtgaag tgaggatcag tgcctctgac ttccacacaa agcagcatgt gactgaactc   84060
acatccaaat acataaatta tacacataaa acatgcacac atgtgcacac acacacacac   84120
aacttcgaaa agacaatgta aaccccctgc cctgctgtct acttggcaag ctgacaatta   84180
cttaccatac tcctttcact ttttacttt tttttaaggg atttgtactt ctatcggttt   84240
ttagaagaac tgggtagttt tcccaacgaa cagtaggaca aatccctgaa gcctgacatc   84300
agagctacca gagcctcccc ttcctttgga ctcaatacta ggttataagt atgtgggaag   84360
acagagccca agcaagacaa acaggagagt cccattgccc gctgtgtgtg ttatatctca   84420
cactctttaa gaaaaccatc cactcaaagc taagacacaa accagaaagg aagttctggc   84480
ccagagatgg atggaatccc tcaggtgggg accacttgat cattcaacgc agtcattatt   84540 caatatttt aaaaggtatc tatgtcaatt attaaataga aagtctttta aatccacctg    84600
taaatctcta accctagcat ccatctcttt cagttgtcac attgtgttct tttctgaaat   84660
gtatcggcat actccatgca tagcccctgg atcagccaca aaatcgcaac ttgatgtgca   84720
gctctgtgca ctcagagcac ttgtttctcc cttggacttg gaacactgta cattattctc   84780
attcctggct gacttggtct ctctgtcatt acagctcata tctgtggtct taacttttc    84840 ctagactgat cagctgtgct ggctctccac agtctccatc gttgtgagga tccatctgct   84900
ctccctgggg taggtttgat ccaaatccat caattgttca tttcctaaca atctgtgctg   84960
tgattgtttc acctgtattc attgggtctc atgaaaacaa atctagcgtg ggttgaagta   85020
gtgaagatct caccggcaca cccaaggcct tgaacttgat cacccaata acaacaacaa    85080 acaaataata aaattgctta gttgagatgc gagggctcat cttaaacatt ttctagaccc   85140
```

```
atagttaatc catgagctgg tgctcacagc agaggaaaca gagccaaggg tttgacccag   85200
agtgatcatt ttcttgatgc tcagccagac acttgagtag tactatgact tcgctcattt   85260
aatttccacc tggtattgtt agtagagcct ggccctcaat gtattcttat taaatgaata   85320
atgataccct tttcttggag tagtagtaga aattagtaaa ttttaataaa taccaatgct   85380
tgacagtata atctctcaag atgttgagct ccgaagaaga agaacattta ctgtttaagc   85440
aaaaaagtat gaacagttgt catggaaagg cctgtcccaa attttaaatt gaatcatctc   85500
caatttctg tgattcaaaa tgtacacaag agtccttgat caagcttctg ggtgtatctg    85560
atcgttttag aatgactgtg aacaggctaa acatcatatc aaaatggtga gacaagacat   85620
tttaaatatc aaaagccatc gttagcccca gctgtccttg ccagaacagc atgactggga   85680
gaatcaaaca agatgaagag aattctaaaa cagtcctaat cagaagcaca ggcacaggga   85740
atcaaaggca gaaggaagct tgacaccacc aagatcaagt cctgttacaa acggagaaac   85800
tagagaagcc aaatgagaaa cgaaaggtct catagaagcc agggaaatgc cacagagaag   85860
ggacagatca ccatttcgtt aatctgaaca tgaggtaatg aagtcagggg ggtttccact   85920
gtgccacatc acacagaaca aagttttctat tttaagagtc cagccctgca cctgtgcagt   85980
gcagatggac ttggcaaaag aagaaatgaa acagattttt ctcactgccc agctggcctg   86040
aaggtgcagg gcacaggcta gatgagcaac cgtgaagggg ccaagtgtcg cagcatggag   86100
accatccaga tgtggagaca tttgccctaa gattcccagt ttttctctac cctagcttga   86160
gccccaacac caagggagaa aacacggcag agtcagagga aagaatcgtt gctatcctgg   86220
cttgtatgta gtcccactgt ctgctgctta agcaaaaaga atgggaaatt aaattaaaga   86280
gggaacagca ctgccattgg ccataagtaa gggcctaggg ttccatgctg tctgctccac   86340
agcccaggga aaggaaacag gcctcggaat gatttgtcaa taaaggcagg aaatatctca   86400
tcatgtcttc agtatactaa caaaactgca gtgggaaaat gacaagctgt aaagctagcg   86460
aacctgatta tgaccctagc tccttctcaa cctggttggt tggccttgac taaactgcta   86520
acattaccta gacttcatct ccccacttgt aactttttaa tatctaacaa accacacttc   86580
tgggtgtgat tatcactgta ctgacaacag ctcctaggga aggatcaaag gaaggtaaat   86640
tgttttgcta tttttttatat tgttcacttg tctgcataca catgcattca tgtgtacaca   86700
cacatatgca caaacacaca cacacgcaca cacacatgca ccgagagaga catacacaca   86760
tccctgagtg taccatagca tacatatgaa ggtaaagggg ctttggggag gaattagttc   86820
tcttcttcta ccatgtaagt tctagggctt ggattcaggt tgtcagactt ggtagcaagt   86880
gccttcaccc actaagccat tttccaggcc tgtattctta gtgttatcaa tacatgtgaa   86940
cactgctgag caaactccaa agctcagact agaggctcca ctcttctgtg tctctacacc   87000
agaacatgag ccataattcc atctgtagca tcttactagt tatgcaaaag gccaggttgt   87060
actaccttcc ttcttctgag gatctgccat tcaaattgaa agacttatca aagtttagct   87120
taaaccatgc cattagatca tctttctcta gtaaaacctg ataatttaag acttactgtg   87180
tacagttttt aaatatcttc aaagtcaatt tctttagcaa agaaagaaaa aaggaaagaa   87240
agaaagaaga gagagagaga gagagagaga gagagagaga gagagagaga gagaagaaga   87300
gagagagaga gggagggagg gagggaggga gagggaggag gaggaaggaa ggaaggaagg   87360
aaggaaggaa ggaaggaagg aaggaaggaa ggaaggaaat caagaggctg ggagagggc    87420
tcagtgagta aaacacttgc tgggcaagca tgagggacta gttcaaatc cccaggaccc    87480
cacataaaaa atatgaaatt taaaaattcc aatcccaggg ccagagggtg gctctgagcc   87540
```

-continued

| | |
|---|---|
| tgaaagcact gctgctcctg cagaggagcc agaacccaca tctggtggat cacaattacc | 87600 |
| tgtaactttc tacaggatct gactccctct tggggcctct acaggaattc acacacgtgg | 87660 |
| cataaacata caaacagata cacacatata cacataactg tttttcatct caatccagag | 87720 |
| cttggattat agctcagtaa gaagagtgct tgccttgtat gttcatcccc agatcctgtg | 87780 |
| taaaaataac cagaaacagt gacacacact tgtaatccca ggattggaaa ggcgcgcctg | 87840 |
| tacagcggcc gcaattgtcg ac | 87862 |

<210> SEQ ID NO 3
<211> LENGTH: 56567
<212> TYPE: DNA
<213> ORGANISM: Hybrid immunoglobulin locus
<220> FEATURE:
<221> NAME/KEY: unsure
<222> LOCATION: 43223
<223> OTHER INFORMATION: "n" represents any nucleotide
<220> FEATURE:
<221> NAME/KEY: unsure
<222> LOCATION: 43291-43299
<223> OTHER INFORMATION: "n" represents any nucleotide

<400> SEQUENCE: 3

| | |
|---|---|
| cgcgccgcgg ccgctcgacc aattctcatg tttgacagct tatcatcgaa tttctgccat | 60 |
| tcatccgctt attatcactt attcaggcgt agcaaccagg cgtttaaggg caccaataac | 120 |
| tgccttaaaa aaattacgcc ccgccctgcc actcatcgca gtactgttgt aattcattaa | 180 |
| gcattctgcc gacatggaag ccatcacaaa cggcatgatg aacctgaatc gccagcggca | 240 |
| tcagcacctt gtcgccttgc gtataatatt tgcccatggt gaaaacgggg gcgaagaagt | 300 |
| tgtccatatt ggccacgttt aaatcaaaac tggtgaaact cacccaggga ttggctgaga | 360 |
| cgaaaaacat attctcaata aacccttag ggaaataggc caggttttca ccgtaacacg | 420 |
| ccacatcttg cgaatatatg tgtagaaact gccggaaatc gtcgtggtat tcactccaga | 480 |
| gcgatgaaaa cgtttcagtt tgctcatgga aaacggtgta acaagggtga acactatccc | 540 |
| atatcaccag ctcaccgtct ttcattgcca tacggaactc cggatgagca ttcatcaggc | 600 |
| gggcaagaat gtgaataaag gccggataaa acttgtgctt attttctttt acggtcttta | 660 |
| aaaaggccgt aatatccagc tgaacggtct ggttataggt acattgagca actgactgaa | 720 |
| atgcctcaaa atgttcttta cgatgccatt gggatatatc aacggtggta tatccagtga | 780 |
| tttttttctc cattttagct tccttagctc ctgaaaatct cgataactca aaaaatacgc | 840 |
| ccggtagtga tcttatttca ttatggtgaa agttggaacc tcttacgtgc cgatcaacgt | 900 |
| ctcattttcg ccaaaagttg gcccagggct tcccggtatc aacagggaca ccaggattta | 960 |
| tttattctgc gaagtgatct tccgtcacag gtatttattc gcgataagct catggagcgg | 1020 |
| cgtaaccgtc gcacaggaag gacagagaaa gcgcggatct gggaagtgac ggacagaacg | 1080 |
| gtcaggacct ggattgggga ggcggttgcc gccgctgctg ctgacggtgt gacgttctct | 1140 |
| gttccggtca caccacatac gttccgccat tcctatgcga tgcacatgct gtatgccggt | 1200 |
| ataccgctga agttctgca aagcctgatg ggacataagt ccatcagttc aacggaagtc | 1260 |
| tacacgaagg ttttgcgct ggatgtggct gcccggcacc gggtgcagtt tgcgatgccg | 1320 |
| gagtctgatg cggttgcgat gctgaaacaa ttatcctgag aataaatgcc ttggccttta | 1380 |
| tatggaaatg tggaactgag tggatatgct gttttgtct gttaaacaga gaagctggct | 1440 |
| gttatccact gagaagcgaa cgaaacagtc gggaaaatct cccattatcg tagagatccg | 1500 |

```
cattattaat ctcaggagcc tgtgtagcgt ttataggaag tagtgttctg tcatgatgcc   1560
tgcaagcggt aacgaaaacg atttgaatat gccttcagga acaatagaaa tcttcgtgcg   1620
gtgttacgtt gaagtggagc ggattatgtc agcaatggac agaacaacct aatgaacaca   1680
gaaccatgat gtggtctgtc cttttacagc cagtagtgct cgccgcagtt gagcgacagg   1740
gcgaagccct cgagtgagcg aggaagcacc agggaacagc acttatatat tctgcttaca   1800
cacgatgcct gaaaaaactt cccttggggt tatccactta ccacggggga tatttttata   1860 attattttt ttatagtttt tagatcttct tttttagagc gccttgtagg cctttatcca   1920
tgctggttct agagaaggtg ttgtgacaaa ttgccctttc agtgtgacaa atcaccctca   1980
aatgacagtc ctgtctgtga caaattgccc ttaaccctgt gacaaattgc cctcagaaga   2040
agctgttttt tcacaaagtt atccctgctt attgactctt ttttatttag tgttacaatc   2100
taaaaacttg tcacacttca catggatctg tcatggcgga aacagcggtt atcaatcaca   2160
agaaacgtaa aaatagcccg cgaatcgtcc agtcaaacga cctcactgag gcggcatata   2220
gtctctcccg ggatcaaaaa cgtatgctgt atctgttcgt tgaccagatc agaaaatctg   2280
atggcaccct acaggaacat gacggtatct gcgagatcca tgttgctaaa tatgctgaaa   2340
tattcggatt gacctctgcg gaagccagta aggatatacg gcaggcattg aagagtttcg   2400
cggggaagga agtggttttt tatcgccctg aagaggatgc cggcgatgaa aaaggctatg   2460
aatcttttcc ttggtttatc aaacgtgcgc acagtccatc cagagggctt tacagtgtac   2520
atatcaaccc atatctcatt cccttcttta tcgggttaca gaaccggttt acgcagtttc   2580
ggcttagtga aacaaaagaa atcaccaatc cgtatgccat gcgtttatac gaatccctgt   2640
gtcagtatcg taagccggat ggctcaggca tcgtctctct gaaaatcgac tggatcatag   2700
agcgttacca gctgcctcaa agttaccagc gtatgcctga cttccgccgc cgcttcctgc   2760
aggtctgtgt taatgagatc aacagcagaa ctccaatgcg cctctcatac attgagaaaa   2820
agaaaggccg ccagacgact catatcgtat tttccttccg cgatatcact tccatgacga   2880
caggatagtc tgagggttat ctgtcacaga tttgagggtg ttcgtcaca tttgttctga   2940 cctactgagg gtaatttgtc acagttttgc tgtttccttc agcctgcatg gattttctca   3000
tactttttga actgtaattt ttaaggaagc caaatttgag ggcagtttgt cacagttgat   3060
ttccttctct ttcccttcgt catgtgacct gatatcgggg gttagttcgt catcattgat   3120
gagggttgat tatcacagtt tattactctg aattggctat ccgcgtgtgt acctctacct   3180 ggagttttc ccacggtgga tatttcttct tgcgctgagc gtaagagcta tctgacagaa   3240
cagttcttct ttgcttcctc gccagttcgc tcgctatgct cggttacacg gctgcggcga   3300
gcgctagtga taataagtga ctgaggtatg tgctcttctt atctcctttt gtagtgttgc   3360
tcttatttta aacaactttg cggttttttg atgactttgc gattttgttg ttgctttgca   3420
gtaaattgca agatttaata aaaaaacgca aagcaatgat taaggatgt tcagaatgaa   3480 actcatggaa acacttaacc agtgcataaa cgctggtcat gaaatgacga aggctatcgc   3540
cattgcacag tttaatgatg acagcccgga agcgaggaaa ataacccggc gctggagaat   3600
aggtgaagca gcggatttag ttggggtttc ttctcaggct atcagagatg ccgagaaagc   3660
agggcgacta ccgcacccgg atatggaaat tcgaggacgg gttgagcaac gtgttggtta   3720
tacaattgaa caaattaatc atatgcgtga tgtgtttggt acgcgattgc gacgtgctga   3780
agacgtattt ccaccggtga tcggggttgc tgcccataaa ggtggcgttt acaaaacctc   3840
agtttctgtt catcttgctc aggatctggc tctgaagggg ctacgtgttt tgctcgtgga   3900
```

| | |
|---|---|
| aggtaacgac ccccagggaa cagcctcaat gtatcacgga tgggtaccag atcttcatat | 3960 |
| tcatgcagaa gacactctcc tgcctttcta tcttggggaa aaggacgatg tcacttatgc | 4020 |
| aataaagccc acttgctggc cggggcttga cattattcct tcctgtctgg ctctgcaccg | 4080 |
| tattgaaact gagttaatgg gcaaatttga tgaaggtaaa ctgcccaccg atccacacct | 4140 |
| gatgctccga ctggccattg aaactgttgc tcatgactat gatgtcatag ttattgacag | 4200 |
| cgcgcctaac ctgggtatcg gcacgattaa tgtcgtatgt gctgctgatg tgctgattgt | 4260 |
| tcccacgcct gctgagttgt ttgactacac ctccgcactg cagttttcg atatgcttcg | 4320 |
| tgatctgctc aagaacgttg atcttaaagg gttcgagcct gatgtacgta ttttgcttac | 4380 |
| caaatacagc aatagtaatg gctctcagtc cccgtggatg gaggagcaaa ttcgggatgc | 4440 |
| ctggggaagc atggttctaa aaatgttgt acgtgaaacg gatgaagttg gtaaaggtca | 4500 |
| gatccggatg agaactgttt ttgaacaggc cattgatcaa cgctcttcaa ctggtgcctg | 4560 |
| gagaaatgct ctttctattt gggaacctgt ctgcaatgaa attttcgatc gtctgattaa | 4620 |
| accacgctgg gagattagat aatgaagcgt gcgcctgtta ttccaaaaca tacgctcaat | 4680 |
| actcaaccgt tgaagatac ttcgttatcg acaccagctg ccccgatggt ggattcgtta | 4740 |
| attgcgcgcg taggagtaat ggctcgcggt aatgccatta ctttgcctgt atgtggtcgg | 4800 |
| gatgtgaagt ttactcttga agtgctccgg ggtgatagtg ttgagaagac ctctcgggta | 4860 |
| tggtcaggta atgaacgtga ccaggagctg cttactgagg acgcactgga tgatctcatc | 4920 |
| ccttctttc tactgactgg tcaacagaca ccggcgttcg gtcgaagagt atctggtgtc | 4980 |
| atagaaattg ccgatgggag tcgccgtcgt aaagctgctg cacttaccga aagtgattat | 5040 |
| cgtgttctgg ttggcgagct ggatgatgag cagatggctg cattatccag attgggtaac | 5100 |
| gattatcgcc caacaagtgc ttatgaacgt ggtcagcgtt atgcaagccg attgcagaat | 5160 |
| gaatttgctg gaaatatttc tgcgctggct gatgcggaaa atatttcacg taagattatt | 5220 |
| acccgctgta tcaacaccgc caaattgcct aaatcagttg ttgctctttt ttctcacccc | 5280 |
| ggtgaactat ctgcccggtc aggtgatgca cttcaaaaag cctttacaga taaagaggaa | 5340 |
| ttacttaagc agcaggcatc taaccttcat gagcagaaaa aagctggggt gatatttgaa | 5400 |
| gctgaagaag ttatcactct tttaacttct gtgcttaaaa cgtcatctgc atcaagaact | 5460 |
| agtttaagct cacgacatca gtttgctcct ggagcgacag tattgtataa gggcgataaa | 5520 |
| atggtgctta acctggacag gtctcgtgtt ccaactgagt gtatagagaa aattgaggcc | 5580 |
| attcttaagg aacttgaaaa gccagcaccc tgatgcgacc acgttttagt ctacgtttat | 5640 |
| ctgtctttac ttaatgtcct ttgttacagg ccagaaagca taactggcct gaatattctc | 5700 |
| tctgggccca ctgttccact tgtatcgtcg gtctgataat cagactggga ccacggtccc | 5760 |
| actcgtatcg tcggtctgat tattagtctg ggaccacggt cccactcgta tcgtcggtct | 5820 |
| gattattagt ctgggaccac ggtcccactc gtatcgtcgg tctgataatc agactgggac | 5880 |
| cacggtccca ctcgtatcgt cggtctgatt attagtctgg gaccatggtc ccactcgtat | 5940 |
| cgtcggtctg attattagtc tgggaccacg gtcccactcg tatcgtcggt ctgattatta | 6000 |
| gtctggaacc acggtcccac tcgtatcgtc ggtctgatta ttagtctggg accacggtcc | 6060 |
| cactcgtatc gtcggtctga ttattagtct gggaccacga tcccactcgt tgtcggtc | 6120 |
| tgattatcgg tctgggacca cggtcccact tgtattgtcg atcagactat cagcgtgaga | 6180 |
| ctacgattcc atcaatgcct gtcaagggca agtattgaca tgtcgtcgta acctgtagaa | 6240 |

```
cggagtaacc tcggtgtgcg gttgtatgcc tgctgtggat tgctgctgtg tcctgcttat    6300
ccacaacatt ttgcgcacgg ttatgtggac aaaatacctg gttacccagg ccgtgccggc    6360
acgttaaccg ggctgcatcc gatgcaagtg tgtcgctgtc gagcggccgc tagggataac    6420
agggtaatac gcgttattaa ttaagggcgc gcgagtatat caggaataga gattcctccg    6480
aggtgaaaaa ttagaggcag agggaggggc aaatgggcaa ggaagcttgc accaagtcgg    6540
gagtgatcca gtgtaggctg agagaaaaaa ggtcttaaaa tcagccttgt agctgaaacc    6600
aaaaacacac aagatggttg gtgttctgag catcattaac aaatgataaa tgaagttgaa    6660
cttttaaatg tattgcaaat ttttataaag caagtagatc gttaaactca gaatgcaaca    6720
atggaataaa gaagagagtt tgagatgttt ttaaaattta tttatttatt tattttttgag    6780 atggagtctc actctgttgc caggctggag tgcagtggca aatcgcggc tcactgcaac    6840 atccacctcc cgggttcaag aaattctcct gcctcagcct cccaagtagc tgggattaca    6900
agctctcgcc atcatgccag ctaattttt gtattttttg tagagacatg gtttcacaat    6960
gttgaccagg atggtgtcaa tctcctgacc tcatgatcca cccgtctcgg cctcccaaag    7020
tgctgggatt acaggcatga actaccgtgc ctggctgagt ttgagatttt aactgtaagt    7080
cctccaacta agttgccatg acaagaacag ggatgatgag agtggaaata tgttatcctg    7140
caaattatcg ttttatgtaa aagaatattt tccctctttt aggtaaagga agcatcttct    7200
ggagcaccTT ctctctgact atcaaagcac cattaagcca caaataaact gtaacatgaa    7260
gtaggaaaca actgcccttt tatataacca ttgagaggtg gctttatatg cataccaaaa    7320
tgttgatgct caatgctaaa attggattta gtaatttaat atgcctacaa gaattaatt    7380 ttctttggat tatattattt ctgtgtacga tttatcttag ttaacttgga aatattctgc    7440
tctaaaaaca actcttgttt tttgggttat atttctgta tcaactatag ctcttttcca    7500
aatgctgtca gagatagccc atggctactg atcacaaaat tcaatttat ggcatttaaa    7560 ttattctata ctctaaatta ttttaaaagt gcacagatgt gaatttttca catctgactc    7620
aaaaatgttg ctgatgttga ctcacttttt tatttcaatc ttattgaagt aggagtttac    7680
ttttctggaa cctggatgat aacaggagac tggagaggaa accccccaaa ttgttttcct    7740
ttaaaccctc aggatgaatc atcctggata atcacccaca cttgatttgg gtgatatcta    7800
aatgagagtt gggtcttaga gtaggtgctg agttagttta ggacttgcgc tgttggaatg    7860
agttgaatgt ttttacaagt gagaaagaca tgagtttttt ggagtccaga gggtgggggg    7920
ttattggctg aattaagtcc cccaaaatgt atgcattgaa gctgtaacac acaatatgtg    7980
actgaaattg tgcatagggt cttttaaagag gtgactaagt gaaaatgaaa aaattagggt    8040
ggattcttct caaattggac tgatgtcctc ctaggaagaa gaaatttgca cacacagaaa    8100
tgaggcacca gaggtgagcg tgcagagaaa agaccaggtg aggattcagc aaggaggtag    8160
caacctgcaa gccaaggaga gagtcctcag gggaaaccaa acccactacc acctttatct    8220
tgggttttcc agcttcagaa ctgtgagaaa atatgtttct gccatttcgg tcactaattc    8280
tttcctatct tcttgtggga gctctagcaa aaacaagagg gaccccaaag accttggatg    8340
agggagaagg aggagatgga gcagggtgca ggaggcggtg caggaagggg ctggaaggtc    8400
gggctctgag gtgcatctcc tgggtggaat cttgactcca ctccctattg tctggaggac    8460
ttgggaaaaa catttaacct cctaatattc actcactaat aaagatgggc ttgaagcaca    8520
aggctcccca tcatcctatt ctatattaca aaagtcttct tgaggtaaca cttgtaaaac    8580
tctcgctaat gcatctggca tgtattatgg actcataagt agcccttctg agtgatctag    8640
```

```
tgatgtgcag aaaatggcat tcatgctgtg tgcaccaggg ggcactgtga ggtttagtct   8700
gaggccccta atgagtccaa gcccctagta atgctcaagg gcgaagagcc tgactgttgc   8760
ttcctatgag gccccttcta gtgggtaaat ctgaaaatgc acttggccct tcttctgatc   8820
ttgagaaatt actcagagaa ggccatcagg ctcagggctc agacaagaac caggacaaat   8880
gttttaggga atggagaaca gatttgcatc cactgctcac cagagccacc taacgacgac   8940
acaagaataa aggaagtaga tttgcatgaa gagacttccc ttcctatgat aagagaggcc   9000
tggaggttcc tccttagctg tgggctcaga agcagagttc tggggtgtct ccaccatggc   9060
ctggacccct ctctggctca ctctcctcac tctttgcata ggtgctgcct cccagggctc   9120
aaccccatat tatcatgcta gctgtgccaa cctggccctg agcttcggct caacacaggg   9180
agtagtgtag ggtgtgggac tctaggcgtg aaacccttat cctcacctct tctgtcctct   9240
tttgcaggtt ctgtggtttc ttctgagctg actcaggacc ctgctgtgtc tgtggccttg   9300
ggacagacag tcaggatcac atgccaagga gacagcctca gaagctatta tgcaagctgg   9360
taccagcaga agccaggaca ggcccctgta cttgtcatct atggtaaaaa caaccggccc   9420
tcagggatcc cagaccgatt ctctggctcc agctcaggaa acacagcttc cttgaccatc   9480
actggggctc aggcggaaga tgaggctgac tattactgta actcccggga cagcagtggt   9540
aaccatctca cattgacaca gacagatggg gaagtgagac agaaacccct tcactatctg   9600
tgtcatcctc tctctccagc cccagcagga ctgtgaacaa agccataaac agggctggcc   9660
cagttcacct gcatctgaga cctccaggct gcctttccct ccattcctcc aggtaggctc   9720
tgcagaaggt gggtcaggat gatgtgaggc ttgaaggacc aggctgttct gctgttgttt   9780
agactgagtg tgccttgcct caagatgacc tgaatggaag gaccacaaga aggagatggg   9840
cagctgttga gtggtcatga tccctggagt tcctcttgtg tggtgactgg atctaacaca   9900
atgcctgtac tttgtggccc aaatgccctg gattattggt ctgaactccc catgtttaac   9960
tgagaccctc aagccccagc tccatgcatc ctgatgttct gaacaggaaa gtcttttcta  10020
gtgagcactg tggcatccct tggcatccca gcttcacaca gcaattcccc accaaaaaat  10080
gcctttgagt gcaaagaacg gcttcatgca aagatgtgcc tccttcagaa tgtagttcag  10140
gagcaataac tacctgatgc cttaatccca aagccatatt ttaatttaga atgaccttga  10200
aatgccttct agctgagcag tcagttgtaa cacattccca gtcacgcctc ccacacttct  10260
ttcctgacag tatgtcatga aaccctactg catggaatcc tgcctcttag agtaggattc  10320
cagggatctc aaaaattgtt tagaaatgaa caaaaacagt ctagttggaa gagtatcaaa  10380
gaggaggcag ttgcacatgc agagaactct gaggtctgca aatatacatg aactgatgag  10440
cacttgtgtg taaagaaaca cctccgaaag agaaagaaac cacgcaaaga ctcttgaggg  10500
aacacctcac agagctcact cccacacaca cccacccacg cactcacaga cactcacaca  10560
ctacagtcac agaggaaagg cctgacttac agggcatgag gttgactcat cagaagagct  10620
ttgcctcagt actggggaaa aagtcaccct agacaaaatg ctgctcaggt ctcaactatg  10680
aaagtgtaaa agcaaacaga aaactcaaac tgttttctg aacagtaaag taactttact  10740
gaattcaaca ataaaagaca gaaatagaga atgaactgca aagaattct caacccagca  10800
ggaaaaatgc acaatgcctt catcctgtca atatttcctg caaggtaacc agaaaatata  10860
tgctatatca aacagagaag tgaatcaatc ccaaatggca ataaaattgc acacatgata  10920
gaccttgtag gcaaggatat gaaagaaatt cttataactc tattctattc tacttgttct  10980
```

```
tgaggatata agattgaaaa atcatattaa gtggatacat aaaacatata aagacagacg    11040
caagttatac tcttataaat gatccataat atgtctgcaa taaaaaatac actgaatgag    11100
actgattgca gattggattc tgtgaaagaa tagatgagtg aacttgaaga tatggcaatg    11160
gcagctattc aagacgaagc acaaaagcgt aaacagagta tcagtgagtt ttaggacatc    11220
ttcaactgcc taaattggta taatgaaagt cattaaagga ggtaagattg gacagggaag    11280
agaaaaggca gaaaaacaat ttaaaggaac aatgaccaaa atttcccaaa ttttgtgaaa    11340
actagaaacc tcctattcca aaagtttaa catgtcccaa agacacacac acacacacac    11400
acacacacag agagagagag agagagatag agagagagag agaaagagag aaagggagag    11460
agagagatac aggtgaacaa caaaatgaca agaacaaatt tggtttttaa aaatttttt    11520 aattttagtg gcttcatagt aggcatatat ttttattggg tacacgagat gtttcaaaac    11580
aggcatgcgg cgcgctctgt cagtcctgac agcagttcca gagacacttc cccattaaga    11640
tgtccccagg ctcttataat acaacctgtc tgttattttc tgcctaaatc tttttaatta    11700
tccccatagc atttacaact gtaggaatct ttgcctattg ttaattttat taattgattg    11760
gtgttaaata tttacttaat tggtcatgga tgctttttta ccacagaatc acacataaaa    11820
aacagacaca aacagctaag ggtgtatttc tcgctgcaat aatacccacc actttcacga    11880
agacaccagg gtcttctca cttttttgtcc caccatccct atgatattgg ctttattttc    11940
atccctgctg atgtgtgacc tcagggtggc tgctgcagct ccagctatca ctcccatatt    12000
caaggagaaa agggcctcat gaatctagtg ctctttcaca agagcaaagc tttcctaaga    12060
agaatttcac ccactgatct cacacccac tgatcaggcc tgagtcacat ggtcaatccc    12120
agctgagcag gacctgggaa tcacaggcac cagtcttttc ggtgaatata aagacagtg    12180 ctcaggtgga aggtgacagg gactgtctgc tgggtctgca aacccagttt ccccgcacag    12240
ccaaaccagc acgatgaaca actcacttca agaaggctgt gtcttgttcc tgctgaattc    12300
accgcatgga acgtgtccca gaccacagtg ggtctggatt aacatttgat gggtggatgt    12360
tcttctgtct ctgactttgg tgcaggagtc accactgtac gctggtcctg catccacagc    12420
ggggaccagt aagagccagt ccctgagtcc tgtgatcccc gccctgcatg ccaagccctg    12480
gtattacccc catgaccacc caccgcccag acacatgtgc aggcagcctc agatggacct    12540
tcctcctcct cttccaaata ttcatgttca tattgtcatg agtaatctgc acccctcgca    12600
cctggtattg aggcaggcat gagtcacaaa gagaagagaa aaatttcctc cattggcacc    12660
agcagtctgc agaccaggga atcagggacc tgaacagaag attttaatta tacacccgga    12720
cccaggaggc ccttgagcct ccagcagcca gtatggagca gccaccaggg gacagaacag    12780
agtcacctgg caaagtcact tggagatagg gtagacctgg gtgacaagga gatgctgaca    12840
tgcagggagg gtcagtgacc acaacctgag atctagaaag gtgtcgtttt tctacagcat    12900
catccttaac atcgagtaca aattctccag gctttgtgtt tctcagcttt gtctctggcc    12960
aatgttgcat atttgacaca ggtgcagaca ctttgcttcc ccctacacac tggcccactc    13020
ttctgtgcta aaacgctgtc attgccacaa acgccatcct cccctgtggg cacatgtgtt    13080
tcatcaccct cctgtttgct ctgagagccc cctcattctg ctacacagca agttttctt    13140 tcagcatcta agctgtacct gaccatgacc acatactggg ggtacatagg cacagcacct    13200
gtgccctacc ctaggagctc acagccaagg ccaggaactt acagcatctc ctgagtcttt    13260
caacactccg tgtgcacatg acaagggtga agtttgattg tggaaagcac cactcagaag    13320
caatggcagg tccctgcatg tgtgccagcc ttacggtgtc acctgtagag tggggtcatg    13380
```

```
agggtcactg cactgggttg aaaagtgccc tccagagggg gagctagaac cacacctaac    13440
ttctggattt tgccacaaaa tatttaggga caggacaccc ctggagtcct caattaccca    13500
agttattctg agccagtatt caacagagga agtaccttag atctcagaat aatccctcag    13560
tcgccattgt aagtcagtcc ctggccatct ccacgcagga caaggaatgg ccacatgggc    13620
aggacatcat actacctgga aaacgcacaa agaattcctc tcagagttct gcatggccag    13680
atcagctcag gagtgaggcc ataacacaac ctacagtgac gatgtcaacc cagatgatgg    13740
gaccagaagg agaatgagaa ttctgtgtgc tgagggtggg tctttagggg cccctctct    13800
ctctgtccct tggggctgag cccttctctg gaaaccacac agctcctcct gcagcagccc    13860
ctgactgctg atttgcatca cgggccgctc tttccagcaa ggggataaga gaggcctgga    13920
agaacctgcc cagcctgggc tcaggaagc agcatcggag gtgcctcagc catggcatgg    13980
atccctctct tcctcggcgt ccttgcttac tgcacaggtg ctgcccctag ggtcctagcc    14040
actggtccag tccagggct ctgggtccag cctggccctg actctgagct cagcagggcc    14100
cccgcctgtg gtgggcagga tgctcatgac cctgctgcag gtggatgggc tcggcgggc    14160
tgaaatcccc ccacacagtg ctcatgtgct cacactgcct tagggctctt tcatccctgg    14220
atctgtgtcc aggccaggca cgtgggaaga tttacttgga gttcagctcc tcagtttcaa    14280
gccttttctc tcccgttttc tctcctgtag gatccgtggc ctcctatgag ctgactcagc    14340
caccctcagt gtccgtgtcc ccaggacaga cagccagcat cacctgctct ggagataaat    14400
tgggggataa atatgcttgc tggtatcagc agaagccagg ccagtcccct gtgctggtca    14460
tctatcaaga tagcaagcgg ccctcaggga tccctgagcg attctctggc tccaactctg    14520
ggaacacagc cactctgacc atcagcggga cccaggctat ggatgaggct gactattact    14580
gtcaggcgtg gacagcagc actgcacaca gtgacacagg cagatgcgga agtgagacag    14640
aaaccagcca cctcggcctg gctcacaaga cccttccctc tctcctgccc tgtcacactg    14700
agcaggaggg agccttccat gtggaatgga agtttccagt cctatccctg cccttatgtt    14760
cctgagagac gggagcaagt tcctgcccac ctctaggctc agcttatccc agaataaact    14820
gagctagtca ttttgatgat caaatgccag ctcccaaaag accccagaaa ccctgatatc    14880
taagtagcac cgactctatt agtatcaagg gagactagcc ctagggtgga atcattttag    14940
tgtctcagaa ggcacagggc aatggaaagt gtttatgagg tttcaggata tgcacgtgag    15000
cagttaaagg caggtcttac aaggaaggaa cctactagaa ttggggccca tctgtgacat    15060
catagcacag cctggtggac acagagaagg gaaggtcctg aatcaagtct tgatcagtaa    15120
atatttattg gataagtgag caatttacat aggtgagaac tgtgtgctct cttgagcaga    15180
acacttacct ggataattgg ttttcaggaa ttccctgaag caatgagtga cattctttat    15240
tgttttcacc ctcatccacc tgggaaagag tatcctggaa ccagcagtta acattgacac    15300
agctggtctc ggtcctcagc acaaacattc attgcaggct gaaaagtgac aacgaaagag    15360
aaaggagttt attaaatccc tagacacaaa caaatccata agcagagatg agagatgcgg    15420
gctcagctgg cccagtccca caggggtcat tcctcttgtg atggaaatga ccacatgagg    15480
gtcccccaag cggtgtttgg gggcagtcat ggggaactgg cctcccaggg ctacctgctg    15540
cttgggctgg gcagaggtta gagggatgga agtctggtcc agtccttccc agcagcatct    15600
ccaggctcct cctccctcta ctggggcttc ccctccactc cccagaacca tcattgcttc    15660
ctcatctcct gtcctctccc tgccccaagg ccctcccgt gctcaccctg gctcctcccc    15720
```

```
ctgctccatg cccagcctct gcagagcagc ccaggcccag agacttgggc agaagcttcc   15780
gtcccaccag ctgcagaacc ttccctacag aaccaggcca gtccctgtgt ctcatatttg   15840
tagagatccc aatcaccctc agagatgacg ggtgggaaac cagcccacag tgacctaggc   15900
tgttgggcat atggccttca agctggcctt caagcccact tggctgcatc tccttggcca   15960
actccaacat ccaggctggg agtctggaat cctagttccc ctggcccatt cactcccact   16020
agggttgctt ctaaactccc tgggcctcag cttcctagtc tgcccactgg aagcagcgac   16080
aggcattttc cagggctgcg gtaagggccc tggaacaccc tctctcaccc tctctctccc   16140
tttctctctc tctctctctc tctctctctc tcccccctccc cctcccccctc cctcccctc   16200
tctctctctg cctctgtttc ctcctcagta gtgggaagac cccctgtcag gtgggccagt   16260
ccatgacatc tacagaggga gcaggaacct ctcctatttc ctggaggaga gctggggtgg   16320
aggctgcaac ccaggatcat cagaggagct ggggtcttca aggttcctag ggacccctta   16380
agcggggtc agagtggctt cagcggtctt attgctcggt ccagacagaa gatgtttcca   16440
gttgtgaaaa acgacttcag ggacaacaaa aacagagatt cgcctctcca gacaccagtg   16500
gttggtgtgc ctggagtact cctcgtacca ggcaggggag agagtcctag acagaggagg   16560
ttctaagtgt cacctagatt tcgggcctcg gggcctgtat tgggtaggtg atgtcacagt   16620
gagttgaggc gcgctggtgc agaaaacaga ctcctccagg tctatgccct ttctcagtga   16680
ggttagattt catgactgcc tgaggccgag ttctcgactc tgcctcaata taggaagacc   16740
tgaaaatcct cccagctcca cagctctctg taggaaagac ttgagacctc aatgagggtc   16800
agggtctcct gcccagggtt gcctccctca cctcctttca catcctctgt gcatgcaatt   16860
cctcatctca gagtctgctt ccagggaacc caattaagat caccagccat ccccaacatg   16920
ggccatgtgg gacttcagga ggccactgta tgctggaaag cacctgtttta ttcctaaatt   16980
agcactgtga gtatccacac gcccaatgag atctgagtgt ttcttgcatt tgcatggaat   17040
gagaagggag cctgactcgc caggtgctct ggggtctaag ggagagttgg agtcagatct   17100
ccctgcaggg aaacctgggg caggaggagc agccttaccc catgcaggga ccacagatgc   17160
acccacaggg tgagcttaag tatggacact gcctacctcc accctccaca tcctgtgtaa   17220
aaaatcattc tttccacccc tcctccagcc tatcaaagtt gacacttaaa aagccaccac   17280
aacccacccct tgtcaacagg aaacccattc acatctccat cagccacaca atctccacat   17340
aaagattctt caaaaaataa taacaatagc catgcaaagt atatgatata tatcataaat   17400
aattgtactt agattatata tgaaaatgat actcttttttg atatgctagg taaataaaat   17460
acattattta aactcattga cttcttctct ttgtatttat aacatgatga ctagacagtg   17520
ggattcccat gaggctcaca tcacattgtg attgaacaag gctggtctgc agggcttcag   17580
gttacagggg ctgtggagtg acctggtgca ggaagccccg tctccatcca taggacatca   17640
gtgtgaaccc agggagaggc gctggtataa gagagatgag aacacaggtg tgaaccacct   17700
gcttgtgcag gggactgagc cttcactttg agccaaataa gttttctttc ccaagttcga   17760
tcctgaacaa gagggctttc tggacttctt tttgttttca ggtttgtgcc ccttcaggtt   17820
tggggctgtc tggagtccca gccaggggac agtgaggaaa tccagcagtc tcacactgac   17880
tctgttgtat ttcatctgct ggggccatcc caaactgctg cgtaccattt cctttcctgg   17940
tgctcaaata gctgctccat gcacttgtca tggttttata gctcaatcta gatgggaaga   18000
caggatagtg tatgttacaa tatttaaata gaacctgaat cccttaatag ttatttaat   18060
atggaacatt aaaagagttg catcataggc aatgggaaa gatgaagaaa gattaaacgc   18120
```

```
atttggagga aaaactaaaa atgtctttat tgaatgtctg tgtgtcttca gtgtcgaagg   18180
gttgagagag gtcagcttta ggttgtcctg aggatgtgct cagatggggg aaagtaagaa   18240
agccggaaac gtgcatctct gtgacctgac acataaatca cagtaaaatg gaagtaaatc   18300
tttcaataaa cctttcaaga taacatcact ctggtgcaca tagaaaggcc tgttagcaaa   18360
ctttcccttt tccctgctgg ctcatatccc catggatcac ctgtatgcag aacggactct   18420
gtggtctcca tttatcaggc tgagaaccag aggctgggaa ggacaagtca cctgctcatg   18480
agtgggaggg gcaggattgg gagcagcgga ctcaggctca ggactgtggc cctggttggt   18540
gctccttgtt cccttcacag gtccccaccc acatgtgccc gtgtggatgt gggtgcactg   18600
cctggggtgg ctgatgtgct ccagggattt gatggtgcag atgcttcagg acaaagcatg   18660
ggagtgggga tgggacgagc tgccgctggg cagaccaggg accaacgcca cccagcagag   18720
gcttccagtg gggttgggca gccccatttc ctgagaatag agagaacctg gcaatgagtg   18780
ccagaaagag gttacttcga ggtgtgccca ggcctggagg gtcacagaga cacaggcacc   18840
acacagcaga gacactgagg gccaagagct cactcaggtg aggggcttca gcagattttt   18900
ctctcctgag caaatcacgt gcaaagaaat caacttcctg tcatcagaat agacaatcag   18960
gactttagtc tccttggctg agccccgctg tcaagggaag cagaagtctc taagcccagg   19020
cccaagtgag ggtggggtga gaagaggagc tcaggatgca gatttgcatg gaggtcccgc   19080
ccttctctga ggcagaggga taagacaggg ctgggggcag gcccagtgct ggggtctcag   19140
gaggcagcgc tctcaggacg tcaccaccat ggcctgggct ctgctcctcc tcaccctcct   19200
cactcagggc acaggtgatg cctccaggga aggggccaca gggacctctg ggctgatcct   19260
tggtctcctg ctcctcaggc tcacctgggc ccagcactga ctcactagac tgtgtttctc   19320
cctttccagg gtcctgggcc cagtctgccc tgactcagcc tccctccgcg tccgggtctc   19380
ctggacagtc agtcaccatc tcctgcactg gaaccagcag tgacgttggt ggttataact   19440
atgtctcctg gtaccaacag cacccaggca aagcccccaa actcatgatt tatgaggtca   19500
gtaagcggcc ctcaggggtc cctgatcgct tctctggctc caagtctggc aacacggcct   19560
ccctgaccgt ctctgggctc caggctgagg atgaggctga ttattactgc agctcatatg   19620
caggcagcaa caatttccac agtgttttaa gtcaatgagg aagtaagatc aaaacctgcc   19680
ctgggctctc aggcccottc ttgctctgca gatgcttcct cacgctgtat aagggtttcc   19740
tgcaggatgg ccttgacaat tctcctctct cagctcctct cctttcccac catgaggtct   19800
aaaaggaaac ctgctcgtga tttctcgttc aggactgtgg caacttcctt ttgcttgtgt   19860
gctctggtcc cttaacgtgc aactattcct agctcttcaa tgcagggacg tagggacaag   19920
gagtttactg cttggtgcag tccctcctgt tttcaggaac atcctcattc taaatgcatc   19980
ccccatctgt cacactatgc agatcaatct ggacagaagc catcaggggg atggcttcta   20040
gtttccagga attgcatctt gttccactct gtgtccacca cgctctaatg aagatggccc   20100
tcctagctta aagtgaccac tttaagaaga cttgaagatg ttttttgaggg attaagaaca   20160 aagaggatgc tgctgttttt cttttttattg ctcctgctct ttgccgaaat tcctcaggtt   20220
gctgagctgg ggagattttg agtgacaggc tcagtgctct cgcagaattc tcctcccctc   20280
acatcgctga ggccctgtcc tggaaactcc tcacaagtgg acggtcttcc cataggatgg   20340
gggattccaa aatggctcca caggaaagag ttaacctgag tccacctccc ttcctcatgg   20400
acatcgagca tttctaattt tcatggctgt caatactttt gtacctggaa tccctaataa   20460
```

```
tctaatggtg agaattgatt tagaacacat tcggacatta gctgggtcca atatttaaat    20520
tttctgagcc agttgttaaa tacagctatt atcatatata gtttaggctc cttaaacttc    20580
gattatacag attatattta aaacaaagta actagtttac tatatatatt tacaaagtaa    20640
ctactatata acatcatgtt gtgtacctga aatataaaca ctaaaattta tttcaaaaac    20700
caaagtgtat tgtctattga tgcataaaaa aacactcaca aaacttagca cactaagaga    20760
acacatgtct gtgaccttgt gacttggatg cacctagaat tgggagtagc ttagtttggt    20820
cattctcgct cctggttaat cacgaggttg cagccaagct gtcaggccag gctgcattca    20880
ggctacatct gccaaagagg ttaggaactg tggaagcctc cctctggctg tggaagcctc    20940
cctctggctg tggaagcctc cctctggctg ggagacttcc gcagttccta acctctttgg    21000
cagatgtaga tcatctcaag gataaaggag agagtggagt gaaggcccct gtccttgtcc    21060
tccatgtaaa agaccatccc atgcatgcac tatttttttat tctttgctga gacatcctag    21120
gcatagagca ctgccccatt cattcaaagg ttgtagagta ttctatggta gaattttagc    21180
caactcactt ttaatggtta ttatcactat tttgatctta taaataacac tgcagcgaac    21240
atccttatgt agactccttt gattttatat gtagacatga ccatagaata aatttctaga    21300
agtcaaattg ctgagtcaaa aggatgtgtg cttgtaattt tcactcactg tcctcagatt    21360
ctcctctaga ggggttatct acaaattcgc aatgtcagcc ataaatattc gaacagagta    21420
cactggggaa agtttaaatg ttttttcaacc tagcagattt aaaaatgtta tttttttttag    21480 ttttgctttc tcctgttctg cttgaagttg agcatttttct ctaatacttc agtgctattt    21540
atttttataa tttggtaaac attttcttaa atgtccagat aagaaggatt ttggtctgtg    21600
gggcgcgtta ttaattaagg gcgcgcgtca tacaatggtg gtgtacaatg tcgcaccatg    21660
gacactaggg ggcgcctgcg caccattcct gagaagactg ggtgtgatga gagcaggacc    21720
agcgccacct gtcctgcttg gtgccctatg cttagggctc acagatgtca actctccacc    21780
ccctgggacc acacagcccc accccctggca ctctctgaca tcctcaggca gaggagcttg    21840
acccagggcc cagggtggga tcagaaagct ggagggtctg atttgcatgg atggaccctc    21900
cttctctcag agtataaaga ggggcaggga gagacttggg gaagctctgc ttcagctgtg    21960
agcgcagaag gcaggactcg ggacaatctt catcatgacc tgctcccctc tcctcctcac    22020
ccttctcatt cactgcacag gtgcccagac acagggtcag gggaggggtc caggaagccc    22080
atgaggccct gctttctcct tctctctcta gaccaagaat caccgtgtct gtgtctctcc    22140
tgcttccagg gtcctgggcc cagtctgtgt tgacgcagcc gccctcagtg tctgcggccc    22200
caggacagaa ggtcaccatc tcctgctctg gaagcagctc caacattggg aataattatg    22260
tatcctggta ccagcagctc ccaggaacag cccccaaact cctcatttat gacaataata    22320
agcgaccctc aggattcct gaccgattct ctggctccaa gtctggcacg tcagccaccc    22380
tgggcatcac cggactccag actggggacg aggccgatta ttactgcgga acatgggata    22440
gcagcctgag tgctggcaca gtgctccagc ccaatgggga actgagacaa gaacccccctt    22500 cttcctcccc caggagggtg agtgccgcca gctgctgctc acgcctgacc tgtagcttct    22560
gctgctgcag gttctcccat gggccacggg gcagccaggg ccctgcctag gagtggaggc    22620
tccaccactt ttgtcctcag agtcaggaac agggactcca ggaatgagaa tatcctgctc    22680
ctgcagcttg ggcgcgttat tacgcgccca gctattcatt gtgggcatct ttattcccca    22740
atcagaatta atttagtggc agggtcacag aggctatgtg aagactctag gtcttgtagg    22800
cctacactta gccttgcaat atacagtaaa agacaaagca attcaacaat tcccccagtt    22860
```

```
agtccaataa atggctcttt tctctcagat ataaattaaa cacaattata acaattatgc    22920
aaattataag atgtgatata cacttataat atccaggcaa tcatatttca cactttagaa    22980
taagtattct atcatctatc tataatttaa tgagttataa ttctgtacct aaatcatgtt    23040
tgatttcaac atgtattacc atctgaaacc atcctttcaa atctagagca tcttctttaa    23100
tgctgaacaa ctaaggttta attgtgagac tatgaatatc taatcttcac cccaatcaga    23160
gatttgaaaa ggaattaaat attacctgag tatgtagaaa gcacaaaggc acaggttcca    23220
aaacttaaac aattggagga gacagctgat tgcctggaaa ctccccaatg gtccatataa    23280
cattggaaca tctcatctat cttctgcctt ctagcctaaa acatcagaca gaccttaact    23340
gaaatagcaa ttatgaagga ctagctaact tgcttttggc agagcttagc aattgactgc    23400
cctatgtcca tttgtccttt ttatatagca ttctttctgc agataaaatt aggacatatc    23460
ttctgcagtg gatagtttgc cccaattgaa gcaactccat atggaattat ttatactcaa    23520
tatcttcttt gaagtggaat gggcatagta ttagaagcag acatgtcttg tagtcaaaag    23580
atcttttaat aatgaattcg cattgaatgc catattcggt agatctctga tgcttttat     23640 ctatatagag cctaattgaa tcaacaaaca tcaattgatt ttagctattt actttatgaa    23700
taagcttgaa acattcggt tgtaattaac tgaataagaa tctaatatga acatgaaaat     23760
gaatatctga ccattaactg gtaatattaa cttaattatt ccaaatactt tttaataaca    23820
gccaataaaa gaattggatc taatctttgt attcttatat gagttgaata ggttcaatgc    23880
ctatctaaga gtaaaaaaat aataatttta aattttatat taatttacaa agatttatac    23940
caatgataac cttaagtatg tatcactata attcttgtac taatgtaaga aaatatagct    24000
tcaattctgc atgaaaatat agagatttct attgatgtaa cattatggct ataaatgatt    24060
tgtttataaa ttataaaaaa gtaaatttat gaattaatcc ccatttatct aatgtcttgt    24120
aatattatta tatcccttt tttttctttt caacccccctt cccttaccct aagaaataaa    24180
gagagagaag aggaaaggaa atatataaat cactgagtct aagctctctg tttagtttac    24240
tacctgtcca agacaataat tattttaaat tatcctttaa aatgatagca tatttataat    24300
tcataaaata atcaaaatta tttaccccaa ttaaaggacc agagcaatga ttttccatga    24360
tttcttcctg ctgttttgaa taaagaattc ccttttaggt gatggcaaga aaattagaaa    24420
aaatttgtta gtcttaagaa tggatgaatc ttcaccaggt tgccttttgc tgtttcattc    24480
tgtactatat gaaccttatg actaatattt agttttatat acatatttgt atggattgtg    24540
caaggtcaca ggtcagttaa ggatgaattt tgttcctta tttcagcaag taaaagacca     24600
tgatgtgctc ccaagcaagc cattgcaggc ctaacatttg ctttccactc tatacagaca    24660
ccccactgct gtggttctgc tcctctattg ttatttctct acaggtttaa atccataaaa    24720
gaagagcagt gcctgctgcc agagttccag cagagacaac accatctgct gagacctgca    24780
gacaaccaag ctgccttcct gcagacacct catctgactg aagattccca agacagatgc    24840
tgagatccag agacaggtgc tgaacctcac agaggacaga tttggtacct tccagctaca    24900
gttgaactcc tttgccaaag tcaaatggct actgaacttg ggggaagtta catgatagta    24960
aggaaaacat gatttatcta gattaatcaa gtgctgtata aaactgacat tattaccctc    25020
aaactgtatt acccatggag caattaattg attcagtgga ccctgcctt cccaaaccct     25080 attcttaaca ctccttacca cattgcctta gttgtgttac ccatttgggc tgtacagtgt    25140
tttcttttga tactgcctcc ccacccagaa ttttaccac aaatgacaag gtcactccag     25200
```

```
tgaccoctct ctttgaaaaa agtaaaaggg ggagttgtgg ggtggtgaat tgtgcccaga  25260
catcctggtt acccagttga gcacaggcct ggaaccccag agacctggtg ggctgtgact  25320
tccccattca tgggatgaga ggagtttgac caggcctcct atgcctctgg ctcttgttgc  25380
agctacagac tcccacagcc cccttcacag aggtgtgtgg ccatcagtca cacaggcaat  25440
gccttaagct cctggtattc tgcctggact ccatacccac agttacctgg caacagccag  25500
gtatgctcct ccacacagtt acctagcaaa agccaggatg gcacagacaa ctaaaaaagg  25560
agctgcttgc cccctcctct ctttcttgct ctcttactct cttgcttctc tcttgccctc  25620
ttgctccccc tttacccatt ccctttcctc ctctctccat gtgtccatgg tcagtctctc  25680
cttccccact ctctccctct ctctgccttt ctaaaataaa caccttaaaa ccatgggcca  25740
tctctgctta tcaggaactg ccatgctgga acagtggagt aggtttccct ctaaagagct  25800
gtgtgtctaa cctaccgcca ggaggcctcc cttctctcca accatggctg ccagccaacc  25860
cagcccaga accagctgcc tgagctagcc agacttcctc caccctgcag taacctgcca  25920
cagctctcct cctaccttt cccttcagtt cccaggccag agtctgcctg agggtccggt  25980
ctcagcaatt ctgcaacaaa cagcagggtc tgggatatcg gagagcgaga acctgtcatc  26040
cctggcctct gtgcaaacca gggaccccag aactggctct tccacaatgc ccagtggtct  26100
atggtgccca agagttggag cccgactctg gcagttctga agggactcca gactgtgccc  26160
tttcctcacc caaggagtgg gatcccgcag cttcccacag ttcaatggct gcccagcagt  26220
tccgtagggt ctgagcacag tcagacttcc tgagacagac tccccatgtc caccttgccc  26280
agcggcccta gcccagagca gacgttggac ccccccccca ttttttttg acctgcagga  26340
ttccactgat ggattgtttc ctatgttgaa ccatgcctga atccctggat gaagcttact  26400
ttatcaggtg gatgatgatt ttgatgttat ttgatttgat tggtgagtat tttgaagaga  26460
atatttgcat caatattcac aagggaaatt agtctaaaaa ttctttcttt gttgagtctt  26520
ttgtggggtt taggtatcat ctctgagatt gttgtctcag agaatgagtt tggcaacatt  26580
cttcctgttt ctattttgtg gaatagtttt gtggaatagt ttgaggagga ttgatattat  26640
ttcttcttta aaagtctggt tgaattcaac tttaatacct tatgtccctg gacttatttt  26700
tggtggtgag acttttactg tctgctcctg gttgcttagg agtatagctc tatttaagtt  26760
gttttcttgg agttgattta acttcggtaa gtgttgtatc cattttattt agattttca   26820
attttatgga gtacaggttt ttagagaaag acttaatgat tctttggatt tcctcagtgt  26880
ctgttgttat gctcctcatt tcaattctga ttttctaact tgcatattct ctctctggtt  26940
aagagttttt atctgtgttg ttgttttacc tcatagattc aactctagag tctgttgctt  27000
ttctgtatta ttctctttgt ttttaattta ttgatttcag catgaatttg attatttcct  27060
tttgcctact cttctttggt atatttgcct cttttttatt aatttaatta attaaatttt  27120
acactccata ttttattccc cccagccacg tcaaccctcc tactgctcaa taccctacat  27180
ctcctctcaa tccctgtcct ccatgtggat gtacccaacc ccatgccac ctgacctcta   27240
aactgtctgg ggtctccagt atcttgaggt ttaggtgcat catctttgaa tgaacccaga  27300
cccatcagtc ctctgctgta tgtgtgctgg tggcctcaca tcagctggtg tatgctgcct  27360
gtttggtgtt ccagtgtttg agagatctca ggcctccaga ttaattgaga ctgctggtcc  27420
tcctgcaggg tcaccctcct cctcagcttc tttgagtctt tctctaaatc aacaacaggg  27480
gtttagctgc ttatgtccat tgggtgcaag tatctgcctc tgactctttc agctgcttgt  27540
tgggtcttcc agagtgtgat catgctagat ccctttttgt gagtgctcca tagcctcagt  27600
```

```
gatagtgtca agccttggga catctatttg agctggatca gtctttgggc cagtcactgg   27660
accttctttt cctaaggctc ttctccattt ccatccctgt gttagacatt atgagatatc   27720
atctatttct ttatgaaggc acttagtaat atgaactttc ctcagcaatt ctttcagtgt   27780
gtctcataag tttggccata ttgtgcccct atttacactg agttctagaa aggctttaat   27840
ttctttattt cttccttgac tcagtggtct ttgaatacga aattatttag tttacataag   27900
tctctaggct ttctgttgtt tctgttgttg aagaacagct ttaatagttc ttggtctcgt   27960
aaaatacagg aggttatttt aactttcttt tatctgttga gacttgctct ttaacaaatt   28020
atatggacaa atttagagaa gatttcctaa gatgctgaga agaaggtata ctcttgtatt   28080
tgagttaaat ttctatggtt atctcttagg tatttttgat tcataacatc cactaccttc   28140
cttatttttc tgttagtttc tgtctagaca acttgttcat tggtgacagt ggggtgttta   28200
agtttcccac tgttaatgtg tggggtttga tgtgtaattt gatctttagt agtatttctt   28260
ttactactaa atgaagtgtg tatgcccttg catttgggc atatatattg aggattcaga   28320
catcatctta gcatatttt cctttgatga gtatgaaatg tcattctcca tctttttga   28380
ttatttttca tttaaagtct attttattaa atattagaat agaatacaaa tttgattctt   28440
ggctctgttt gcttgaaaat ctgttttaga ccttaactct gaggtaatgc ctatcttgga   28500
tgctgaggtg tgtttattgt atgcagtaga atgagtaatg tgattatgta tccattctgt   28560
tagcctgtga tatttcatta atcaatgtat ttattctgat cttgatagat gtcctctagt   28620
cacctttaa cagactctcc cccatcctct tatcctctga gagtgggaga cacccctgag   28680
aatcactata cccttaaagc cattgtcttt gattgaggac ttgagaccat tgatattgtg   28740
agatactaaa gaaagaccaa caattgttat ttcctaatat tttgatgttg atggtggtgt   28800
gtgtgtgtgt gtgtgtgtgt gtgtgtgtgt gtgtgtgtgt ctaagggtga ttatgtgggt   28860
gtgtgcatgt ttctattctt ttggtttcac tagtgtggaa ttatttattt tctgtgtttt   28920
ggagtgtagt taacctcctt ttcttgcaat gttggcgcgt aagggcgcgt tattacgcgc   28980
tgccctgcac atattttta acatggtctc cacatgacct caaaactatt cagcagccgc   29040
tgactacttg tcaagctgaa ggatgtcatt cttcacatat aattcaatta ttagaattca   29100
taagcattga tttaaacaca gtggaggatt ataagccaca ggcacaggca taaatcctca   29160
ataatgtttt gatttggtag gaagatgatt atgagtaatg tgaactttgg actgagagaa   29220
attgaaactc aggtgtatca ttgaatgtgg atatgttaca aggagatgga acattctcac   29280
tgcctgttga atggctcctg ggcccaccca gtactttgac tgatcttatc acttgtgtgc   29340
cctaagatct tagaaagctt ttccctcttc aagggacaca cacgtttcaa agacttgagg   29400
ctgggaccta ctaagccttt tattaaatgt ctgactttag tacaaagttt cattgaacgg   29460
aaagtgaagt gttctgaggc atctcccatg ctggtgctcc agcagagatg caaagggtgc   29520
taggtctgtt aaagaactcc cctctggata actgaatcct aatgtgtcta gaaatacagg   29580
ctcagacgaa tatcactgat gtcactgcag aagttctaac agcggtctta aagacttatt   29640
cctcctattg tttgtgtcaa acaagggaga attttgagag tgcctgatgc aggggggaaaa   29700
aaggtgaatc caaaaagcaa tctactaagt gtcccaaatt tcacaagggc aatcaattat   29760
aaattgaaat gtgatgggga tggtcttatc ctgtttctt taaactccta agggacaacc   29820
tttggccctg cctacaagag ggtctttctc caaagaaacc atttcaaatt aaatggttgt   29880
gaaataggtc acaatctaaa gtttactgga ctgtactaac tgagtcagta aagcctcaga   29940
```

```
tgaatagata ttgggaagga aaaccatata aggcaattaa agttacaggg gcagatgtct    30000
ccattattag ggcaaaagag gcaccctctg tgtgggttct aacagcagat cttactgtgg    30060
agggtattgg taatccaagc tgttctaaaa cacctttgac ctttcttata tggaaggact    30120
cttacggaca cactgaaaaa gttaagccct taattcttga aggcttatct aataatctct    30180
ggggaaaaga tacattagaa ctggctgaaa gcacttttaa tactagtgat caagcctttc    30240
aaaatggtct agagctcatg aaagagaaat tacatcttca cttccaatat taggggctat    30300
tgtttcactt cctgagcctg taaaatttca atagaaaaca gatgaaccta taattggtaa    30360
agagaaacta aaacattctc agggattaat agaacaaaaa caagtagaac atgttgaacc    30420
aagcatcagt gattggaact ctcctatctt tgtcattcag aaaaaaggta aaaaaaatgg    30480
agattataac ataaatttaag agtcattaat ttgcagataa acaagaggcc tttataacct    30540
ggtctccaca aggccctgta attgttatta aacacaaatt atattcatgt atattaaaga    30600 ttattttat tctatcctat tataccaaga agatggggaa agcttttctt cttttatgcc    30660
tgtgccaaac aatatatatt ctgctcaaag atagcaatgg aaagtgttgt gtcaaggtgt    30720
gaaaaacagt cctactatgt attaatatta tgtattttag gccttgaatc ctttgtaaaa    30780
taatctctct ataacattta tttattacat gaatattttc cttgctgatt aggattctag    30840
caaattagaa gttttttcaac tggctttgaa aaatttgaac aatataggggc tcaaagttgc    30900 ccctgaaaaa tacaagtaat cttttccttt ttacttttctgg aatctgttat aatcctcaag    30960
gtcaagctgt attggagata gtgtacatat aacctaaagc acaaattgat aaatacaggg    31020
gagggaatat tggtctgaat atgactcatc ctcaacatct tactaatatt catcatttac    31080
tttaaatttc ctgaaaacgg ataagagaaa tactgcagtt cattaacact gggtaccttt    31140
gtcagggact atgaagtcac ctctggtggc ctggaaagtt gtaataaaag ataaatgaca    31200
atgacaatca ccagccctat tacttaacat tggaaaaggt tttgtttgtg tctttccagg    31260
acatggacca cagcctatct ggatcctaat gtggctcacc ataccctgga cagctaatac    31320
cagcaatgaa gcaaaaaagt tgagcagatg acagagaaga tagcaagacc ttcttctgtt    31380
ggcttagagc ctgactccaa ataattcctg tgctgaaaaa tatcaggcac tggtacataa    31440
ccctctcttg atattaggga agaaggacag aggactttgt cctcagctgt ttacaaactc    31500
caaccaattt tctgatatag gtcccataag agaagtttct aaaatttgga atagcaccat    31560
tcccatgact agataccctc tttgctttca taaccattac aatctacttt cctattctac    31620
tatcttttca cttataatat attggttggc atagtctact tattgatcag aagactctgc    31680
tctccagaaa gaaaattata tagaggcaag atctatatga gaaaacgctg gcttgacctg    31740
gcattcagcc tacctagcac acggaatata caatttttaaa ttagaagcat ggcatacaat    31800
gctcctgagt attcacagaa gtcagaatac tgaattctga gatagcatga gaagcctgga    31860
tctagcctgc tgatatgtct acaatctcca catctccttt tatgtgcttc ttcatagaga    31920
cacatgtggt attagtgctc actgtccaat ctgagataat gtgctaactt atcacaattg    31980
ataggttccc tataaataaa atagttgctt atagaagtaa aacagacaca gttatgtaaa    32040
accctctcga gcagttttc tccatatcct tttctgaccc acaaggtatt atgttcttct    32100
caggggatgc cccagttatt actgcaatta caaaaatagg gctgacacag atacacacag    32160
ccaatacaca acacaggcac agtagataaa caactggtag acaacatagg cacaacagaa    32220
aagaaacata caacacgtag gtacaaaata caggcacaca aacatacatg acaaatagaa    32280
aagaggtaaa gaccgatagc agggagagg ggtgtaaaat taaaatttta gttcattctt    32340
```

```
agaaagatat tttatctatt cttttttttc attttctaat gtgacatgat gaattttgct   32400
accctctctg aggtttcttt aatgtataat cagtgcccaa taggatagat aaacacacca   32460
tcaggagtga agataaacag acaaaatact aagtttcctt cttctaagct attttgggtt   32520
tttaaccttg aacagataaa catggtccat atttagatga agtatgttct gtttcaaaaa   32580
gtatgatcaa ggaacttctt cataagtgtg gcaagtagtt tgtgttttag ttgattttat   32640
atgctgtcaa tttaataaca aagattagct atggaatatg cagagccaac cgttgggtaa   32700
gtaccctgag agattcaata ccctttgatc tttatccaag atttctaaaa gaggaaataa   32760
aaagaggtga aaatatttgg tgatttgtgc aggcaagctg actcagtgag tcaaggtatt   32820
tgtggaaatc ctgataatct gagtttcatc ccaggaactt gcatagtagg agataaccaa   32880
ctgctgccag atatcctctg acatccacat gggcatcaca cacacacaca cacacacaca   32940
cacacacaca cacacaaaca cacaaacaca aacacacaaa catacacacc actaaccaaa   33000
acataggttg aataattaaa tgtaacattt aaaattaatt gtatttattt tggggaatgt   33060
gagaagtgga aagagaaaca gtgaacctac aaagagaagt atactctagc tgcagaaaaa   33120
gactctaaca gttgtgatgg agagtggtta ggagctattt aggaggaacc cagagaagcc   33180
tgtctcacac tagagttgat aaaaagattc tgggtaggag acttccctaa cctggaagaa   33240
aaagtctagg tgacaaaggt cttgaacaca gagtcagctc aattgcacct atcttcacaa   33300
gtttgacttg attcagcact caacccattt tagtccagag gagcacagtc tgggcagaca   33360
aaccttaaac tatatgatgt ggaaatccct agtatccttc cagatatgaa catacatacc   33420
tacactctga ggatttgttt tgtggtctgt gatgaaatgc atacccagaa aacatgacaa   33480
atgcagagcc ttggaggaga gcaactaatg ttgctaaatt taggaacagt cccctttttc   33540
ataagacaat cgactgtccc tgaggagact tcatattctg ggctctgaac catgaaacac   33600
acatgttcat acgatgatgc tagggaacct tcagtcacca aggaccaaag gagtccaatg   33660
tcagaggcaa gacagtgccc aagacacaat ggagagaaac ttgaatagat cagaggcttc   33720
ataggtcacc ctcacactaa taatggtgcc cacaccccta cttgattaga agcatgcgaa   33780
tttagaaaat tggggtatat ggagtgattt ttttaaccta acctttagca ccagacctgg   33840
tcatcagaag ttgcctaagc agttttgtac agtgacaata tatagcctga agagccaggt   33900
aagctgatct tggagaaata aaaaccgatt aatccttgat cactatcctt aaattcatat   33960
tttcttattc caattgtctt agtcagggtt tctattcctg gacaaaacat catgactaag   34020
aagcaagttg ggaaggaaag ggtttattca gcttacactt tctaaattgc tgttgatcac   34080
caaaggatgt caggacagga actcaagcag gtcaggaagc aggagctgat gcagaggcca   34140
tggagggatg tttcttactg gcttgctttc cctggcttgc ctagcctgct ctcttgtaga   34200
acccaagact actagtccag agatggtgcc ccccccacac acacacacaa ggggctcttc   34260
cccccttgatc actaattgag aaaatgcccc acagctggat ctcatgaagg cacttcccca   34320
actgaagctc ctttctctgt gataactcca gcctgtgtca agttgacaca caaaaccaac   34380
cagtacacca atattaccat cattattggg agctgaaaaa ggtgtaggac tgttctctac   34440
tgttctagca agctatgtca gttctggagt tacaggtaaa agatatggaa ttttggatca   34500
gagaacaaga acagcttatc agttgcagaa atacatgtac cagcattttta gtacaaattc   34560
cacaagacaa tgcgaagaga acattgtctc tgcacagcca acattggaaa tgtcatcttt   34620
ttgacatagt tttatggtgt ctatacattc caagtgcggt cacatttcaa acaacctcag   34680
```

```
tagggtaaat acagaacaaa agcaatcatg cctttgctaa agacacttga gcagattctt  34740
cctagaagtc acaatagtta taagtgaaat gaaatgctgg acaattttc  agtccctgaa  34800
ctccatgaaa atatatacac tggtttgcag caaacatatt aaaaagtaaa ataagtaagc  34860
atgtatctga tctaaaagag ggccaaaata ctcaagtggc caggaattc  attttgctat  34920
gtcctgagtg gtgcttgcta taactgttga aatgaaatat caaaaccaga agcatatcaa  34980
agatcacaaa gaactgcaac tctgaactta agcagattag tttaatgtgg gcgcgttatt  35040
attacgcgct gtgtatgaga gcttgagctt atgtgtgttc actatgttat tgcagttgct  35100
tgtgaggcct tatggtgtcc gatgccctgg actggagtta ctggtggttt tgagccacct  35160
cctgtaagaa acctaggact tttccaatag cagtatacat tttaaactgc tgtgccatct  35220
gactatcaca ttttttttct ttcttcagag atagagtggc cctctggtgc caagctcagt  35280
tggttttgca atcctgggat taggtgatgc tcttccatca gtctccagta gtctactgct  35340
aattcacaca ccatgttttt ttgctttata cagagtattt tgagtcttcc caagacagaa  35400
aaaaatagta aatgttggtg aatttgtcaa aaaccttggt caaattgtaa attgtagaca  35460
agcactgaca tatcacatac actccattaa taggtatact tgacgttaat gtcataaaag  35520
tctatgtgaa agcttttgag ataactcagt agtcttgcac ttatgcctca agatacccaa  35580
cagtagggtg agggaaaata tagtgcccac ctacagcagg aagacaggac atcaagtgag  35640
ggatgggtt  gctatttcaa agtcacatct ctgacccata attgttcctg tctgaaataa  35700
ttacaagaat gaaatggag  aggagcctga ggaaagaag  gtccagcaac aggcccaaag  35760
tgggatcctg ttgtgcccac cttggccggc aaggaagtca caacacagtc ggattcttct  35820
taacagcctt taaggcagga atgcctggat gcaccccagg gagcaggaca ccgagggagc  35880
actgcttata tgcaccccag cacaggagaa ggctccgtgg cccctggga  ttggtcagtt  35940
tgccagcacc taatttgtat gcacccgctt gggaggggtt ggcgccagat tcaagctagc  36000
acctgtgcag tggtgttgtt taccacaaag gcacaccgga aaccggcgcc atcatagagt  36060
tggcttccta catctccctc ttttttgttt aataaaatga ggctggtcta ggcctgagca  36120
aatctgtcta ttggccacag ctcctgtctt aggtcgatcc tctagcatca cagcctttcc  36180
catcataagg ttaccctatc gcctccaggc cccttgtctt aggttggtct gtgcacgagg  36240
aaagttgccc gcctctgaat accatggatc tgtgtgacta caagtgccaa atgacctagg  36300
gcaaactctt aatttttaaa agaggccagc caaatattag gagatgtgcc atcttcaatt  36360
gccaacaaag cttggtagac cactgcttta tgctgagcat gctctctttt tagtggacac  36420
aatagccaga tgcagaagac acacccagg  aggaccactg ctccccaggc caacatttct  36480
tcccactgct taaaaaagga gaaggcattg gtgatccagg aggtgaagtc tcccagggtg  36540
acagggtaga gttgagtgcc attgagtttg gcaatctgga ggagcaactt tctggacagc  36600
tgctctacct tagctgacca atttccttta agataagcaa ttttcatgtc agcctttctg  36660
gtacccaaat cggatgttct ttatcctgtg gaaaacaca  aacagctccc ctagatctcg  36720
aaataacggg atctgggcca taccatttac cagttaagac atcgttccat tttacatcat  36780
gttgaattac aggtgaggtc atggcaagcc tgtctgcagc cgagcgacca tgatcaccca  36840
aaatttaaaa atttaaggtt aaataaagct aaagataatt gttctttggg tgctcgtccg  36900
taggcaatac cttttttgt  ttttgttttt gtaacagttc tttcaaggtg tgatgtgctc  36960
tttccgcaat accttggcct tgtgggttat agggaaggcc agggtatgac taacttgcat  37020
agtttcgcag aagacttgga aggatgttga tgtatatgca ggtccattat cagtttttaa  37080
```

| | | | | |
|---|---|---|---|---|
| attagctggt | tttccccaag | ctgcccatgt | gtctaagcaa | tggctaataa cattgtgggt | 37140 |
| tttttcacca | gacataggtg | aggcacacat | gatacctgaa | caggtgtcaa tagaaacatg | 37200 |
| gacatatttt | agttttccaa | aagctggaaa | ttgtgtaaca | tccatttgcc atatttttag | 37260 |
| agggatcaat | ccatgagggt | taatcccaac | atggggatgg | tgatgaaact gcacgcattg | 37320 |
| tgggcattgc | aatacaacag | ttcgggctga | agcacggaaa | atattaaatt tttgctgtaa | 37380 |
| tgtggcagca | gggacatgat | acaattgatg | aaaacctttt | gcaagctcta atggagtaac | 37440 |
| atgaaaaatg | aattccatat | gggtacttgc | atctaccagg | gcattccttt cagtcatagg | 37500 |
| gcctggcaga | gtagaatgag | cccgaatatg | ctgaataaaa | aatttacttt tcctattcca | 37560 |
| aatcaagttt | tgtaattcta | agaaaatggc | acatacaggg | ctggtagatt tgatgggtcc | 37620 |
| tgcaacttcc | aatgctttta | ctacattcac | tacatatgct | gaatcagaca ctaaattaaa | 37680 |
| ggaaatttca | agcctcttaa | atacttctaa | tacgatttta | cattcaacta gttgtggggt | 37740 |
| accaggatca | tattgaaata | aaacagggtt | ttgagaatta | atcacataag caccaacatc | 37800 |
| tgttttagaa | ccatctgtat | aaatatccaa | tgcacctggt | atgggtttag atgctgtaac | 37860 |
| ctttggaaaa | gtcactggat | gttcagtaaa | aaattgtaat | aagggatctt tatgataatg | 37920 |
| attatctaat | tccccatcat | aactacaaag | taacagagcc | cattcatcaa ctaaagagct | 37980 |
| cagggtttgt | atttggttag | catcatatgg | tgtaataatt | tttttggggg gggctccaaa | 38040 |
| atgttgaatg | catgacttaa | tgcccaagat | tgctaaatgg | gctacagcgg tgggataata | 38100 |
| ttcaagagtt | ttattaggag | acacatgagg | ataaatccac | aatagttgac ctgatttcca | 38160 |
| cactactccg | gttggttggc | gaaacatctt | caggacacac | aaatgtatgt cctctccttc | 38220 |
| tttccatcta | cataatttag | ctttttctaa | gcacctctct | acctttccta aggcaactcg | 38280 |
| ggcctcagga | gtgagggcac | gggggggaatg | acaattaagg | gtcacctttc agcatatcaa | 38340 |
| agagtggagt | taattcagaa | ttgggtagcc | tcacatatgg | gcgtatccaa tttatatcac | 38400 |
| ctaacaattt | ctggaaaatca | tttaatgtttt | ttaaatgatc | tttgcgcaat tcaatctttt | 38460 |
| gaggtgctac | ataatgcgaa | gtaacttggg | tacctaaaaa | ctctcctaaa tttcccatct | 38520 |
| gaactttgtc | aggtgctaca | aataatcatt | tcttttctaa | ttcttttact aattctatat | 38580 |
| aagctttatc | taaactttct | ttattattag | aagcaaggag | gatatcatcc atataacgca | 38640 |
| ctatcctcac | ttttggaaat | gcatcatggg | caggctgtaa | ggcttctcct acaaaaagtt | 38700 |
| gacacataat | agaactattg | gccatgcctt | gaggtaaaat | gaccccttga taccgtttat | 38760 |
| caggctcttc | attatttaca | gaggggagaa | taaaagcaaa | gcactcgcta tcacacaatg | 38820 |
| caagggggaat | agaaaaaaat | ccttaatatc | aattattatt | ataggccaat cagcaggcag | 38880 |
| gctagagagc | aggggcaggc | ctctttgtat | tgggcccata | atttgcattt gactattaat | 38940 |
| agctctaaga | tcatgtaaaa | gcctccattt | acctgatttt | tttcttgatt acaaatatag | 39000 |
| gggtattcca | tagtgactgg | gagggtttaa | tatgtcctaa | ttccaattgt tcccttacta | 39060 |
| attccctggc | tgctgccaat | ttttcagagg | aaagaggcca | ttgaggaacc catacaggtt | 39120 |
| cctctgtttt | ccaagtaatg | ggtatactgc | cctaaacggc | ccctaggaaa aacccagttt | 39180 |
| tttttttatct | agtttaaact | tggttggtac | tggcatagta | ctgccttgta atgactttcc | 39240 |
| caatcctttta | cctagacata | atttctcgag | cttgtgggga | atactcatta gttaatctaa | 39300 |
| gatccatctt | ggttaagaca | tccctgcccc | ataggtcac | aggtatgtcc acaatgtagg | 39360 |
| ggaggaattt | tcctgactta | gcttcctcat | ttttccatgt | caattcctta gtactaataa | 39420 |

```
gaggggcagt ctcataaccc agaccacgca ggctttgaga tgatgtctgc aagggacact   39480
ttgacggcca atcatgagtg gagataatac tgcgatctgc accagtgtct aataatccta   39540
aaaggatcat ccttcaatct ctaaagctaa catgaggcga tctcctaatt ccattgataa   39600
gaaagtgaac cgagaacctg tagaacctag tctgctctct cctcttattt tattatttgc   39660
tgggaaatat ttatgtaaac tgggtaatag caacaattga gcaattctat ctcctgggga   39720
gatagctgag atgccagcag gggaggctac caaaacctttt acaattccag tatagtccag   39780
gggttatctg taatccttttt aaagcagaag atgagcggcc aagcaatagt cctacagtat   39840
ctttgaaaag ggggcccttta aaatctgtat ctatgggctg tacccccatc tgtggggtta   39900
atacgagtct ggtggtggag tggaggtcca atcctgcaga gcaagtagtg gctctcggtg   39960
gtctctcgga tgatggagag gtggccaagg tttcttctag tcattctgaa gagccccata   40020
tatttaaggg ccctggggac gtgggccctg ctgtccatttt tttggcctgg tgccaccata   40080
tcctgcttat aatggtcggc cttctatatc ctttgtagat ctgcattcat tagcccaatg   40140
ttttcccttc ctacatttgt ggcataagcc cgactgtcta ggtttatcta atgcagcccg   40200
tttttcattt tcagggcagt ttcttctaaa atgtcctctt tggccacact tataacaagt   40260
atcattatta gatctaacca attgcactac agctgccgct aggcctgcat tggttaacgg   40320 gcccctagt tctctgcaaa ccttcatcca tacttctaaa cctttatgtt tatagggtgt   40380
aatggctgct ctgcattcct tagtgcattg cttatatact agctgtttga ctaaaggcat   40440
agctgtatca gggtcaacaa agattctagt agctgcctca actaggcatg ctacaaagtc   40500
tgaaaatggt tctgtgggac cctgcaagat ttttgtaaga ttgcctgaga ctgtgccttt   40560
gtttggcaat gccttccagg ctttggtagt tacctcatttt attgggcat agactgcttt   40620 aggataattt gtttgatcta aagcaaaacg tcctaaaccc agcagcatgt ctgcatccca   40680
atgtctctga ggatcttgtc ctgtagctaa attggccgct gcctgactat ttgcatattc   40740
ataagtcaag gacttccagt ctaaatattg cccggacgac aagcaagccc gagccacatg   40800
gcgcgtaagg gcgcgttatt aattaagggc gcgcgtcatg cccagcaggc tcctgctcca   40860
gcccagcccc cagagagcag accccaggtg ctggcccccgg gggttttggt ctgagcctca   40920
gtcactgtgt tatgtcttcg gaactgggac caaggtcacc gtcctaggta agtggctctc   40980
aacctttccc agcctgtctc accctctgct gtccctggcg cgcgatctgc tctcctcaga   41040
cataaggact gattcctgaa atttctccag ggtagaggag gtagaccatt tgaaggaag   41100 aaccagaaga gtggaatcag ctggccatag gttctcatag atacattctg atctcagggg   41160
cgtcagttag ggtctagcca gagttaagag ctccactctt gtactcaaga agattaataa   41220
tttgggaccc tgggccaagt ctaaaaaggg ggcactagga ttttcatggc gcatacaatg   41280
tctttctggg ttgtcaaaag ttacatctag aggtgttagt ccaacttcca gagactgaca   41340
ttatctaaat tggaatccac agaatcatag tgacagagta gtcttgtaat gtgttcagat   41400
atctgttctt tatactgggct gctgaagtcc tatgagcata tagatagctc tgactagtag   41460
atctggtggt cctggtcatc tcaggattat ctctagagtt aatcagggat tctgtctaca   41520
aagctccata accgtgggtt tcgctgttttc atgtttccat tgccagcttc tcgttttcct   41580
taaatggcct gttatatgca ggaggtcagg aatgagagac aaacttgggg tttcagaata   41640
ctaattgact gtcagtcaat actaatgctg ctgcagtgag caagtggctg cgatgctcta   41700
cctcctaggg gaagaaacct ctagaatata ctgaagggta ttgtgatcag atcaaaatgt   41760
actgtgggca ccagtcccag agtagcctca gatctttttct ggatggaaac cactacaaat   41820
```

```
tagaaaaact gagtggattg atatagagaa tttgctgcat ataataagct cagtgtcccc   41880 gggggtgctgg agacaaagaa ggaacttcct caatcaaaat gcagtctgca aagcaaggtg   41940
gaatgtaccc tgtttaccag agagctctga tcaccacagg gacaaagggg aaataactgc   42000
cctggggaag gtgatcagat gcagttcaaa tccaagttag attataaaca ataggggtgga  42060 taaagcacag ttatacctgc tgacagtgga attgaggcag aaaggaagcg tcaaggatat   42120
gtaagttggg agactatttt gaaaaaggat aatgagaagg ctatctgtac tcaaccaggc   42180
tcaatggagc agttgagaaa aaacaaaatg ccaggtaaaa gcatgaccaa acttgagaag   42240
ttactgaaat tttgatattt tatatagtct cctgaatcag tcccttctt ttattgacac     42300 aggtcagccc aagtccactc ccacactcac agtatttcca ccttcaactg aggagctcca    42360
gggaaacaaa gccacactgg tgtgtctgat ttctgatttc tacccgagtg atgtggaagt    42420
ggcctggaag gcaaatggtg cacctatctc ccagggtgtg gacactgcaa atcccaccaa    42480
acagggcaac aaatacatcg ccagcagctt cttacgtttg acagcagaac agtggagatc    42540
tcgcaacagt tttacctgcc aagttacaca tgaagggaac actgtggaaa agagtctgtc    42600
tcctgcagag tgtgtctagg agcccaggtt tctccttagc ctgggaaccc tgcagctgta    42660
gacccagagc agggtctctt ctctctacta gctaccttat cccttctccc ttgcccactg    42720
aatattaaat aaaatgtcat tagctgatca aaagtactgt tttgcttcat ttgttctcat    42780
tatatattta atttttcaacc tttgaaacta caatgtgggt aggttggatc atggtcccca   42840
gtgagaaatt agttcacatt taaaacacgc tgacggtacc acccccaacag tgacctttcc   42900 cctgttctgt gctgttctct gggccttgcc atgcagggac acccatttag aatgcatctc    42960
aggtaagata ttgtgtttca gagttaaaca attatataga aagtccccaa atgtgtgagt    43020
tcttgcaata aatttagaga atttcattgt atgcttcaga acattggtgt tcatggtcat    43080
ctatactgag acatgagaca ggataaaacac tcaagcataa taactgtgtc tagtgagaaa   43140
tacacccaac ttgagactag aaagggatat caaataattg tgcataagaa gtggtttcaa    43200
agtgaacagc tctcacttga gcntcttgtg ggtgatgggt gactcctgaa agcagaactt    43260
gcatccacat tgttagagct aaattcaagc nnnnnnnnnt ggggaaactt acatgtaata    43320
aacacctatt ttactgaccc aagtcctctc atgtatggca ccccagtgtg cattttacag    43380
tgatgccaac cacagtctttt gaaattgaca ttcaagctcc tgtggtcctg cttctatcca   43440
ggtcaatatg tacttagtat tcagggttg aggacatcat cttctatacc tcacaacatg    43500
gacactgagt acattcataa ctctttgctg gatcatacag ttccatagca ttgtcttcaa    43560
aatcgaaaat attcttcaaa aatgaggcat aacaacagtt gacaacatag actgggatct    43620
tagacaccta tattcctagg aggaatattt gggatctgtg ccctgcattc catttctgat   43680
gataggccat gatataatct gtccctaata aatggaagta aaaattctgg gtaccctcac    43740
agcaatgttc catgctgggg acacagccaa cactcatcta tcccatttta ttttttcagag   43800 actcataggc ttgtttcaag ttttcactga caagtttgat cagaaaaatt aggaaacaca   43860
gaaatagtaa tacccccata tccccaccaa gcagactctt aacaacattt tacccagatt    43920
ttgattcaca actacaacta taattaacta tatctataac tttataatta taactagagt   43980
atacctataa ctttaactat aacagaaaat tcttccctat atatgttaag aaagctgatt    44040
ccagaactca catcttgtta gctaaaatta ttccttcagag tttaaaaaaa agaatgccta   44100
ggtattattt caaacctcaa aagaagttat tacttctatt tcttcataac atagtcaaca   44160
```

```
aacatgtcat catcttacag tgtttattgg taatgaatga ttctaaagtg taggaagatg    44220
agatgtacat tgatactgat ggttatgtgt gttctctatc tgctctctcc tgaagggcct    44280
caggcatttc tctttgcctt tttccaggca tgagctgcaa agattgagtt agtggtctct    44340
caacactttg catagactct atacagctgg tggtttcctc aagccctcac tggggactct    44400
tctctgttcc ttcttattct gtgaagagct tcttatatac agagtatgga aaatccatgg    44460
atgaatttct ggcaaggctg gctaagggga catatagatc ctgggaagaa gaatcttttcc   44520 gtgatgtggc gcgttattaa ttaagggcgc gcgaaattca ctccttagcg acactaatgc    44580
cctctaataa attcaatcct gggcctgagt gatggttggt gcaaaaaaca aattcaagat    44640
cccagtgtcc tccagaagcc tggatttcca gggatcctgc tgtgggtcac aggatgtcac    44700
cggtcccctc tctctgtggg ttgagtgtgg gggccatgtg gactccctca tgagcagatg    44760
ccaccaggac cactggtccc agcttcctcc ttcacagctg cagtggggc tggggctagg     44820 ggcatcccag ggagggtttt tgtatgagcc tgtgtcacag tgttgggtgt tcggcggagg    44880
gaccaagctg accgtcctag gtgagtctct tctcccctct ccttcccgc tcttgggaca    44940 atttctgctg ttttgtttg tttctgtatc ttgtctcaac ttgtggtcag cctttctccc     45000
tgcatcccag gcctgagcaa ggacctctgc cctcccggcg cgcgaattct gtattctagt    45060
tcatgtctaa ccctaactct aggtaaataa tctccttctt ctctagattc tgtgtctcat    45120
ttcagactac tccctgtagc ctttcatgtc taatctcaaa gacatggggg ctgaaacaga    45180
taaacatcaa tgtctgtcta taattatgtt aggatatgta gcactttgat aagtactcca    45240
ttgtgctatc acctttaat gtctatttt ctgataaact ttgtgaggaa taaatttaat      45300
tgccatctca tggagaagga aaaccagggg catagaggga gacacagctg ttgaatttag    45360
agagcacagt cattcagcac ggaggcttgg gaaggctaat aacctgggca atggaactca    45420
agattaagtt cctaggacag ctgggagata gaatgaaccc cagagccttc atggaaagac    45480
acgaacagag caccatccaa gctatgactc aggaaattta attaggagtc aaaagggag    45540 ggagctctgg ccacagaaat tcaagagaag agagatatct gttgggaatc tgggctccta    45600
ggattctcta aaagactgct tagaagacac agcaactaag ttcacataca tctggtcctg    45660
atgcatgaaa atcatgtaac tcatccagag atgtgaatat tccgtcattc tgtaggatga    45720
gacaaaggtc aagcaagtac atgctctgcc tgtactcagg aggaataaac tcaggtgaga    45780
acaaactcag gagttagagt ttaagctcag aataatgttc ctacatcaga actgtcctca    45840
gggtgggtca ggaagactgt agatactcat agagtgaagg gaggatacag aaggggtca    45900 ggtgtctgtg gtgaaggtca atggtacagg tgtgtcaggt gaagcagtgc acaaatgtgt    45960
agatttataa ttcctaggca catagggagc agatagaaga aattcataca ccctcttctg    46020
tctaagctca aggaccctt acacactact gccaggactg ctactgaaag atcaagattc     46080
tgatcttcct ttttctctat cctgcagacc aacccaaggc tacgccctca gtcaccctgt    46140
tcccaccttc ctctgaagag ctcaagactg acaaggctac actggtgtgt atggtgacag    46200
atttctaccc tggtgttatg acagtggtct ggaaggcaga tggtacccct atcactcagg    46260
gtgtggagac tacccagcct ttcaaacaga caacaagta catggctacc agctacctgc     46320
ttttgacagc aaaagcatgg gagactcata gcaattacag ctgccaggtc actcacgaag    46380
agaacactgt ggagaagagt ttgtcccgtg ctgagtgttc ctaggtcatc tgactttcat    46440
cttacccaca gagacttgga tcagaaacat gtccaagtgt acctatactg cttttgccta    46500
ccatagccct tctccctatt ctcggcgcgt tattaattaa gggcgcgcga caaccgcctg    46560
```

```
attcacagtt tctagtccca cacatatttc gctgtcaaat cctaaatgga aaaagcgccg   46620
ggttagcact gttccaaact taacccatat ccttccgcat ctccagcaac acttttaaaa   46680
aatgaagttt aaagccaacg ctcgcataaa tacctgttgc tcaccgagcc caataagatt   46740
ctctgattct ttcattccct tggagctcca tacaagatgc gattccctcc gggttttccc   46800
accgttccca agatccctgt ctcggacagc aatctgttgt atgtcagccc gcggcctact   46860
tgaactgggt acacctggga ggcaggttgg ggctgaaaaa gacttagatg gcgagagaga   46920
taatgaagcc aaaatgattc tctgttcaag gctcaagaat ttactaagag agtgtgctta   46980
taagggggaa ggcccatctc ccaccagtcc attcttggtg tctggagcca gtctgcaggc   47040
gacgtgcagg ataggatgtt cctctggaat atctcagggg cctctcagca ggtagcagtg   47100
tcttggagga gagcagtggc aggtgacaga acaatagagc catctaggtt ggaaggctcc   47160
acccgaggta atctccttag tggcagcaag gtcaagtctg aatcagcctc ctcaaggctg   47220
ggggaggcta cattattgca gatgccaaaa agttttttgct gacaggagcc tgatatagct   47280
gtctcctgtg aggctctgcc agtgcctggc aaaaacaaaa gtggatgctc acagtcatct   47340
attggatgga acacagggtc cccaatgaag gagctagaga aagtacccaa ggagctaaag   47400
agatctgtag ccctatagga ggaacaacaa tatgaactaa caagtaccccc cagagctccc   47460 ttggactaaa tcaaaccaca aatcaaagaa aatgcatggt ggcactcatg tctctagctg   47520
catatgtagc aaaggtggga ggagaggctt ctggtcctgt gaaggttcta tgctccagta   47580
tatgggaatg catggccagg aagcaggagt tgttgggttg ggaaacaggg gcaggggtga   47640
gggaatagag gaatttctga gaggaaacta gcaaggggga taacatctga aatgtaaatt   47700
taaaaaatat ctagtaaaaa aatttttaaaa agaaagaaaa tggcaaaaaa aagaaaagaa   47760
atcatattgt actatgtcaa gtgatttttt agcatcaatc aagatgatta tgtggtttct   47820
gtccttaact ttgtttatat gatatattac atttattgat ttacatatgt tgaatcaatc   47880
ttgtctttct gagaaagaac actcctgatt ataatgtata attttaacat atttttctta   47940
attgtgtttt caaatgcttt gttgagaatt tttgaatctc tcttcaccaa agaaattgat   48000
ctatttattt gttgttgtat ctttatctaa tttggcaatc aaaataatat taaccacatg   48060
tagagaattt gttactttgt attttaaaga ataagttaaa aagaattggt attatatcat   48120
tttatagcct gttatatttt aacaatgaat ccacattaac ctctgtttct gggggggggg   48180
gggtcttttg attacagatt tgattccatt taaggaatca ttaaggtcca tttaagttat   48240
tcatagtttc tgaatttaac aaattgtgct gtcaagactg tatctacttg cagaagaatg   48300
aaagtagatt catatctttc acctcatacc aaaatcaatt ttaaaatgta tcaataaact   48360
taatttgaaa cctaatgtgg taaagtttgt aaaagaaaac atagagggta cccctccaaat   48420 ttggagtagg caagtacttt ggaacagaat aataattggg cagacattaa tctcaagact   48480
gctcagatgg gactacaaga aaataaaaca tttctacaag caagagaagc tatcgttaga   48540
gcaaacaatc tacataaagg gagaaaaatc tttgaaacaa aaaactaata tccagaattt   48600
taatagaatt tcagaaattg tatatcaagt aaatagatca gccagccagc aaatgagctc   48660
atgaatttga tgtttttttga agagagaaac acaaccacca ataactattt ttcagagtgt   48720 tcaatacccct tagacactgg gggaaaaaaa caaataaaaa actattttga gacagcactt   48780
caccaagtgt gaggaaagaa aggagtaaga tgatgtaact ctatttcaat taaagtatgt   48840
tataaaaatc tttaaaaatt aagaatagaa gtggcataat gtgtaatcat ttcactcctg   48900
```

```
aaaatatcct actgtaagga aatttatacc ctcatacata ttgatgcttt attcactata   48960
gtgaaaagac aaaaccaaaa tagttgggta tcaacagatg aatagatgat taaaacctgg   49020
cacatatgta aaatagaata cagttcagct ctgaaaagga atgtaataag aacttttcag   49080
gtaaatttat agacataaaa tggacaattt tctaagtgag gttatacaat ctcagaaaga   49140
aagaattcgc attctctctt acatatgaat cccagattat gccaaattat tttagtgctt   49200
tataatatta aaacttatgt attatatatg taaacaagta tatatgtggg aacattataa   49260
tatctagaaa ggagaacagg aaaggttaaa tagtaggcag tgaggaagaa ctcaatatag   49320
gttatgaaca tgatcaggaa acgatataaa gctactttt tcatggtttt agctcggtaa    49380
ctgattttta gattttttg gagattggca agcgtgtaaa atgtatttga tagtgtaggt     49440
gtaaaatcca gtgtgtggat cagcaccttt ggtctatcta ctcttgctgc aggatgtgtt   49500
tttaatttgt aagctcttta taataaagtt tttattaaaa tgctgttgat aatttagaaa   49560
gaaaacagtc ttataaacaa tactatgaaa tatgtttata atgaaatcat gtcatgattg   49620
cttagtgact aagcacaaca aatgttactg tgacactttt cttctgcttt tttactctgt   49680
gtgaagctgg acagtgcatc acataaacca actcataatc tgctttataa aacaaaaacc   49740
ctttggatga aaataaagat atgaaaagat tttaacgtaa ttgtataagt gtaggaatag   49800
acttttcact ttaaacattt caaaagctat aaaaatcaca tttgtagata ccagtaagac   49860
attaaacaaa ctccctctca ttatttgggg ttggaccctg agactttaat atggtaagcc   49920
agagtttatc tctgactttc atctcaagac ctatgcttta cttttattgt gagacagtat   49980
gcttgataca ttgcttaagc tggccatgaa ctccctctgc ttcagctttg gcttccaaag   50040
tacctggggg tgtatacaag cactgacatg cccagctgta agtctgtctt gagagttcca   50100
cgctcacact atgggtatat gctactgttc atttcttact aaatgacaat ctggctttat   50160
attgcctcat ccttaatttc tcttctgctt gatgaatcaa gagcccagtt atttctgacc   50220
aggggtctct ggaaataacc cattgtgtac aaccagaaat acaaagctgc atctttgatg   50280
tccagtgtca tcccaactgt tgtccatgta cttaacattt cacccaaacc ttaggctcta   50340
tgctctacag tagggttcct tttaaactta aatagattgt caagtttctg tttgtgcctg   50400
ttcttaaatt ttttaagtaa tacaactaag gaccctaaga ggggaacctc aatttcccag   50460
cgtcatactt ggattcctca atatttctag taacaaagtt tctggtaact aattctttaa   50520
ttagcagaga aaaaggaccc atatctgcac ctctgggtag catctgtatc attcccaaca   50580
acatttctac aaaatcccta agaatcagat atttcaaagg ttgcacatga ggtcctcagt   50640
gagatgatat acggaaacca aactcctgtg aagatatctt gaggaatttc agacaaggct   50700
tggaaacaca agtacagaaa cacggtgtac agtagcctga tcaaggtcat acttgtttga   50760
gttctctgaa aagtcacaag gtcaatgagg actacaaacc tattgatttt tctaggaagt   50820
ccacataatc cctctaaaga acaacctcgg ctagtgtcct ttaaacatta tgaccccaa    50880 aaaaaactct ttattttggg gacattctca gtttatgcc tgccatattg ctccatctc     50940 cttcttcctg ttcttggaac tcatgtatct gtgacatgtc tcaaattgac aatcctccta   51000
ttttcaacta tttagtgctg gccttaaaag actgaagaaa atataaaggt caggaagact   51060
gatcagtgac tgagggaagg ctattgtcca caaccccaa agttatgccc tgatatgatc     51120
tgtgcagcaa acaaaaacaa aaaaattgta ggacaatccc caacaatctc agaaatcctg   51180
tgtgccctga gacatccaag agcagttatt atgtggaagg gctcagccag gtgaaactaa   51240
tcgcatgtgg acaacatatt cacatgaggc aatcccataa tagaatcaga tattaagagc   51300
```

| | | | | | |
|---|---|---|---|---|---|
| acctgttaag | ttacaagcgt | atagcaagtg | tgggacaatc | tagtgttatc | aggcttagaa | 51360 |
| tacagaaacc | taaaagataa | atatgtctaa | gagataagtg | cacaatatca | cctaagacag | 51420 |
| aggggattat | tttgtggaga | aataaagtat | gtatagtatg | aaggggctgt | aataacgcca | 51480 |
| actagggttt | cccaaagata | atgttctaat | agccaaagt | aaatagaaac | ttacttttga | 51540 |
| ctatgtttag | cctcagtttt | ctctctgtgc | agcaggatga | taataataga | cactttgttc | 51600 |
| tatgcataga | aaggaaagga | gatcagatga | acaatgagat | tctcatcatt | atccaaaaca | 51660 |
| caaagctcca | aggttttaca | ttgttctcat | cttccctgaa | gttggtccaa | ccaccagaca | 51720 |
| gtgtttcatt | tgatccagca | agcccttcat | ctagtttctg | ccaacctcac | cactcaggta | 51780 |
| ctttatgagt | tttatgtatc | ttggtgatac | caatgttggc | tttgtgtctg | tgctacccag | 51840 |
| tattcacaac | aggatcctta | aataaggagc | aagacctgca | aaaacaggag | actctgcttc | 51900 |
| ttaaaatcaa | tcaaccatta | tctaaatatt | ctgactacct | tcaaaatgag | aaatggtgct | 51960 |
| gagggcagat | agcaacatag | tgaagggcgc | gttattaatt | aagggcgcgc | gtgctgaggg | 52020 |
| cagatagcaa | catagtgaag | ggtcttgaaa | ccatttccaa | gctaagactg | caagctggat | 52080 |
| ttgccctaaa | tctacccaca | gaggtaaaag | cacctgatgc | caggcctggg | tctggctgaa | 52140 |
| gtttctcaac | taattttgac | ctctgagatt | cttaagctcc | accagtccaa | ctgcacgaga | 52200 |
| tgagaaatca | ggccttcagg | gactcaagct | aggacagaag | gattgatcca | tatgcagcag | 52260 |
| aggttgtggc | agcctgagat | taacaactaa | catgtaaaca | gcaaagtctc | catgtttcaa | 52320 |
| tatccaccct | tcctttcctc | caagaaatga | aagtccattg | acatcacttt | agttttatga | 52380 |
| gaagtgcttc | cactttacct | tccaccagac | atggccaccc | atgagtctgc | gaaagtttgg | 52440 |
| ctctctactt | aactatgaac | atcacctaat | acttccaatg | tgtgctcaaa | agtgtttcct | 52500 |
| ccaatttgca | ttctggaagc | tagctgatcc | tatgatgcaa | gagcttacac | tacagaacaa | 52560 |
| atctgctatg | gcattggtat | attgtaggtc | atgtgtggtc | ataacaagat | cctagagcag | 52620 |
| agcccaggag | ttataccccca | agactacaag | gcaaatgtat | gaagggcaac | ttgggtgact | 52680 |
| ggcctggcca | cggaaataga | gggtgagtac | tatggactt | ctctctgcag | cctgagcagt | 52740 |
| gaattcaaca | tcattttacc | tctatcccac | aatcttatgt | cccactgttc | ctgacctacc | 52800 |
| accctactct | ccacacagaa | agtccctaaa | ctctgagtac | tatggctggg | tggtgctaag | 52860 |
| aactaggcca | catgtgggaa | aggaaagaga | ggagagcaga | gatgtgagcc | ctattgcaag | 52920 |
| gagaaagagt | aattcaacac | agttaaagtc | tgcacaggga | gactgagcaa | aagctcttca | 52980 |
| tttgaggcag | ctccagggaa | gaggtttggc | tactgatgag | gaactaaatc | ttgaatgtaa | 53040 |
| tttctagttt | gggacaggaa | ccagagattt | acaaatctca | cagcccagga | tatttgtgac | 53100 |
| accagggcct | agatcaaaag | gcctgaaata | gaggcaataa | aagtttcatt | ctggccatat | 53160 |
| ctaccaattt | gaaaggtgtc | aatgtcttga | gctttactgt | cttctatacc | atttacaaaa | 53220 |
| cttgaacat | tcaaaatcag | aacaggcatt | tagtaatcct | atgaagccaa | tacctaggac | 53280 |
| cttcattcca | ctgcagtgaa | atctccagaa | tcaggcagaa | tgggctccta | tccatctttt | 53340 |
| tttaagacac | attccatatt | ttatttaaat | tttaagacta | actttcatat | taaaatcaca | 53400 |
| tatccataca | ctgatttcct | ttttgttaac | tccacttaaa | acatctaagc | atgtttact | 53460 |
| aaacaaagac | tgtaaaaaaa | ttatcatgtc | tgttacaaat | gttacaaata | ggaacagctt | 53520 |
| ttaacagaaa | ttcaaaaccc | caaacatctt | ttattataaa | tacaggtatc | aaaacaatcc | 53580 |
| tgaacatatg | tttaagacta | atagtagtca | gcacccacac | cacttcaaga | attaacacaa | 53640 |

```
ttgttgacta atcattgtat cttctatttt aaacaatttc aactgcagct ctaaatatga  53700
taaagcatgc catttctgtt cttcttgaga ctttactttc cagaaaaaca gatgtttcca  53760
tggccatctg acactctttt gtcatgcttt tgtattgaaa gcctgaattc cattttgagt  53820
acttcaggtt catgtttaat tgacagtgat ttaagaagag aaaggaaagg gactggtgag  53880
atggctcaat gggtaagagc acccgaccgc ttcttctgaa ggtcctgagt tcaaatccca  53940
gcaaccatat ggtagctcac aaccatctat aggggatctg actacctctt ctggagtgtc  54000
tggagaaagc tacagtgtac ttatatataa taaataaata aataaatcta aaaaaagaa  54060 gagaaagaaa aattgtgctg cacgtctctt gttacctgaa aacataatag gtgtgcatat  54120
attaaatata ttcttgcaac tgtccaggtc atgtttacca gctgcaatct tttacttatt  54180
gtgtgactat tgtgcatggt gatatttaat caagacatta acatgagtat aaggttgcag  54240
atttaagaca agtttgagat ccactaaaat tagttgttgt acatctgtcc ttctggtggc  54300
ttcatatttt ctttggacct cataagacat cttagctctt gaggtatgac tttaattcta  54360
tagaaatttt gccattttgc taatactggt atgctctgtg catccaccat tccactggaa  54420
ttattgatcc cattcatatt aattttgtt ataaatctaa ctgatggagg aacttctggg  54480
tatttagatc cacattctac tttcaggcta tatattctgt tttcatagtt tgtccttggt  54540
ggcccaataa tcatgcctgt ccaccatgta ggtgtcatgt ctccatcatc ttcaaggccc  54600
cagctaacag tactatcacc tactcctttt tgtccttctt caagttcttc caacaagcga  54660
aaattatgag gaactcctgt ggagaccgtc atcttctcct gctaccagat gcaccaccca  54720
actcctatct atcttcaatt ctattccaga acctttcatt atgaaccaag gaaacatatt  54780
cattggagta agacacctgc ctgtgctcac acagtatgga gtgctgcctc cttccaggca  54840
atggacactc tcacatagag agattttat tcatcatgct aaagtgagca gagcaaaaat  54900
caaccagcaa tgacagctga cattgaggag aagctgacat acaggtacta tgatcaacca  54960
tctacaagaa gctaagggtg tggctagaca gcaacaaaga atcaagcaga gcctagatac  55020
gtgttttata gaagactcaa ggtgatatac aggggtagct gctacttgct cattctttat  55080
cagaacttca ccctgagaaa ttaacttccc ctctgtgaac ttcagtttcc ctgtcttcac  55140
tagggagtgg ttatcaatct gttcaggaaa gtgtggggtc atagattaat tgaggagatg  55200
cttagagtgt ctctggtcag tggagatcct cgctaatctc tagtttccac tatcatctcc  55260
tgagatgtta cataggcctg ccatagaagg gtaacttccc ttccctggag cttcagattc  55320
ctatgaccaa tgagcagtta cacgataaat gtacactatt gggaagcaat agatttacta  55380
tatgatggaa ttggccagga aaatcggttc tacacttggt aaagcagcaa tgcttgaagt  55440
gtgatatata gtaatagtaa gaagacatta caagctctgt ggaggaggtt gggaaagaga  55500
gatgaaccta gttgctttac tgagctcgct atgactgcag ctgccaccct tgagagtcca  55560
caagctaaaa ttaaatctgt gataactgaa acaaaaactc atggtcacag aaaaagagaa  55620
ataataggaa ctgaaaccaa gtccattagc agcaaggcat ggcaagtagg ggtaggtgtg  55680
tcattggagg gtcagggggcc agttttgaaa gtgtaggttg tgcatctaaa tgttagggac  55740
aacagagccc cctttatacc tcatctgtac tttcattcac attctttgtg atgctaaccc  55800
ttggctgcct ccatatacca agctcaatat taaacacttg aatcctggaa ggtcatgtcc  55860
caaagatctg tgtgaccaga cagtagtggt catgtgggtt atcagagcac aaaggagtaa  55920
gcaacttagg tagagcacaa ggttctcacc tgaacagaaa caggtgattg aataagcaag  55980
caccagtctc acttcttcag aatctgtggt tcagaggtat attatctagc ccttcaggca  56040
```

```
cactgacttt gttccttatg tctagaaggt tgtaaacacc cttcctatta tccaaaaata    56100
tttattttgg caatcaatca tgaagcaatc acagaaccag catgtggaaa catagacgag    56160
agttcattgt tttggtggga catgttatgg atgactaggg tacatgtggt ttcagtggct    56220
tgcagaatga cctggacggg tatcaacaga agggaacact gtcctacaga cccaggaaaa    56280
gatctcactt ttgtttaaag acacgatttc ctctggataa tagtctaaat agatccataa    56340
aatgtactct caaagttctt cccagtagaa atgagccttt gagctttccc gtgttttctg    56400
atttgtcagt gaatgactac aggctttcta cctaaggaag aaatgaatgg gctgatgtaa    56460
gaaacaagat tctctacaaa tactctctga gaagaaatta aaatacattt gtaaaatggt    56520
atacagaata tttcttcaaa gaggtccaaa gatttgagca gggcagg                  56567
```

<210> SEQ ID NO 4
<211> LENGTH: 6
<212> TYPE: PRT
<213> ORGANISM: Mus musculus

<400> SEQUENCE: 4

Glu Glu Gly Phe Glu Asn
1               5

<210> SEQ ID NO 5
<211> LENGTH: 37
<212> TYPE: DNA
<213> ORGANISM: Mus musculus

<400> SEQUENCE: 5
gaggaaggct ttgagaacta gtcgagaagt tcctatt                              37

<210> SEQ ID NO 6
<211> LENGTH: 11
<212> TYPE: PRT
<213> ORGANISM: Mus musculus

<400> SEQUENCE: 6

Glu Glu Gly Phe Glu Asn Leu Trp Ala Thr Ala
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Lox site insertion

<400> SEQUENCE: 7

Ile Thr Ser Tyr Cys Ile His Tyr Thr Leu Leu Cys
1               5                   10

<210> SEQ ID NO 8
<211> LENGTH: 60
<212> TYPE: DNA
<213> ORGANISM: Artificial Sequence
<220> FEATURE:
<223> OTHER INFORMATION: Lox site insertion

<400> SEQUENCE: 8
ggataacttc gtatagcata cattatacga agttatgctg atgctgcacc aactgtatcc    60

<210> SEQ ID NO 9
<211> LENGTH: 8

```
<212> TYPE: PRT
<213> ORGANISM: Mus musculus

<400> SEQUENCE: 9

Ala Asp Ala Ala Pro Thr Val Ser
1               5

<210> SEQ ID NO 10
<211> LENGTH: 26
<212> TYPE: DNA
<213> ORGANISM: Mus musculus

<400> SEQUENCE: 10
gggctgatgc tgcaccaact gtatcc                                              26
```